US012485183B2

(12) United States Patent
Cemerski et al.

(10) Patent No.: US 12,485,183 B2
(45) Date of Patent: Dec. 2, 2025

(54) MULTIMERIC T-CELL MODULATORY POLYPEPTIDES AND METHODS OF USE THEREOF

(71) Applicant: Cue Biopharma, Inc., Boston, MA (US)

(72) Inventors: Saso Cemerski, Boston, MA (US); Ronald D. Seidel, III, Boston, MA (US); Rodolfo J. Chaparro, Cambridge, MA (US); John F. Ross, Boston, MA (US)

(73) Assignee: Cue Biopharma, Inc., Boston, MA (US)

( * ) Notice: Subject to any disclaimer, the term of this patent is extended or adjusted under 35 U.S.C. 154(b) by 658 days.

(21) Appl. No.: 17/900,636

(22) Filed: Aug. 31, 2022

(65) Prior Publication Data

US 2023/0139456 A1 May 4, 2023

Related U.S. Application Data

(63) Continuation of application No. PCT/US2021/031707, filed on May 11, 2021.

(60) Provisional application No. 63/041,451, filed on Jun. 19, 2020, provisional application No. 63/023,834, filed on May 12, 2020.

(51) Int. Cl.

*C12N 15/62* (2006.01)
*A61K 39/00* (2006.01)
*A61K 47/64* (2017.01)

(52) U.S. Cl.

CPC .... *A61K 47/646* (2017.08); *A61K 39/001114* (2018.08); *A61K 39/001153* (2018.08); *A61K 47/642* (2017.08); *A61K 47/6425* (2017.08); *C07K 2319/30* (2013.01)

(58) Field of Classification Search

None
See application file for complete search history.

(56) References Cited

U.S. PATENT DOCUMENTS

| | | | |
|---|---|---|---|
| 5,635,363 | A | 6/1997 | Altman et al. |
| 6,197,302 | B1 | 3/2001 | Hirsch et al. |
| 6,211,342 | B1 | 4/2001 | Hirsch et al. |
| 6,268,411 | B1 | 7/2001 | Schneck et al. |
| 6,322,789 | B1 | 11/2001 | Vitiello et al. |
| 6,600,012 | B1 | 7/2003 | Agrawal et al. |
| 6,696,304 | B1 | 2/2004 | Parker |
| 7,098,306 | B2 | 8/2006 | Economou et al. |
| 7,186,804 | B2 | 3/2007 | Gillies et al. |
| 7,432,351 | B1 | 10/2008 | Chen |
| 7,670,595 | B2 | 3/2010 | Gillies et al. |
| 8,435,494 | B2 | 5/2013 | Gelfand |
| 8,992,937 | B2 | 3/2015 | Hansen et al. |
| 9,284,349 | B2 | 3/2016 | Tsunoda et al. |
| 9,359,424 | B2 | 6/2016 | Maoult et al. |
| 9,494,588 | B2 | 11/2016 | Springer et al. |
| 10,059,750 | B2 | 8/2018 | Davis et al. |
| 10,272,042 | B2 | 4/2019 | Daftarian et al. |
| 10,501,521 | B2 | 12/2019 | Georges et al. |
| 10,927,158 | B2 | 2/2021 | Seidel et al. |
| 10,927,161 | B2 | 2/2021 | Seidel et al. |
| 11,117,945 | B2 | 9/2021 | Seidel et al. |
| 11,370,821 | B2 | 6/2022 | Seidel et al. |
| 11,377,478 | B2 | 7/2022 | Seidel et al. |
| 11,380,821 | B2 | 7/2022 | Jia et al. |
| 11,479,595 | B2 | 10/2022 | Seidel et al. |
| 11,505,588 | B2 | 11/2022 | Seidel, III et al. |
| 11,505,591 | B2 | 11/2022 | Seidel, III et al. |
| 11,530,248 | B2 | 12/2022 | Seidel, III et al. |
| 11,708,400 | B2 | 7/2023 | Seidel et al. |
| 11,739,133 | B2 | 8/2023 | Seidel, III et al. |
| 11,767,355 | B2 | 9/2023 | Seidel, III et al. |
| 11,851,467 | B2 | 12/2023 | Seidel, III et al. |
| 11,878,062 | B2 | 1/2024 | Cemerski et al. |
| 11,905,320 | B2 | 2/2024 | Seidel, III et al. |
| 2001/0021516 | A1 | 9/2001 | Wei et al. |
| 2002/0006664 | A1 | 1/2002 | Sabatini |
| 2002/0031520 | A1 | 3/2002 | Economou et al. |
| 2002/0123108 | A1 | 9/2002 | Edwards et al. |
| 2002/0165136 | A1 | 11/2002 | Baserga et al. |
| 2003/0100074 | A1 | 5/2003 | Yu et al. |
| 2003/0190614 | A1 | 10/2003 | Presta et al. |
| 2003/0229023 | A1 | 12/2003 | Oliner et al. |
| 2003/0235536 | A1 | 12/2003 | Blumberg et al. |
| 2004/0038349 | A1 | 2/2004 | Hilbert et al. |

(Continued)

FOREIGN PATENT DOCUMENTS

| | | |
|---|---|---|
| CN | 1791675 | 6/2006 |
| CN | 101384621 | 3/2009 |

(Continued)

OTHER PUBLICATIONS

Schmied, et al.; "Analysis of the functional WT1-specific T-cell repertoire in healthy donors reveals a discrepancy between CD4+ and CD8+ memory formation"; Immunology; vol. 145, No. 4, pp. 558-569 (Aug. 2015).

Zhang, et al.; "Engineering CAR-T cells"; Biomarker Research; vol. 5, No. 22, pp. 1-6 (2017).

Bresson, et al; "Anti-CD3 and nasal proinsulin combination therapy enhances remission from recent-onset autoimmune diabetes by inducing Tregs"; The Journal of Clinical Investigation; vol. 116, No. 5, pp. 1371-1381 (May 2006).

Casares, et al.; "A Peptide-Major Histocompatibility Complex II Chimera Favors Survival of Pancreatic β-Islets Grafted in Type 1 Diabetic Mice"; Transplantation; vol. 85, No. 12, pp. 1717-1725 (Jun. 27, 2008).

(Continued)

*Primary Examiner* — Michael D Pak

(74) *Attorney, Agent, or Firm* — James J. Diehl; Bozicevic, Field & Francis LLP

(57) ABSTRACT

The present disclosure provides T-cell modulatory multimerit polypeptides that comprise an immunomodulatory polypeptide and that comprise an epitope-presenting Wilms tumor peptide. A T-cell modulatory multimeric polypeptide is useful for modulating the activity of a T cell, and for modulating an immune response in an individual.

1 Claim, 108 Drawing Sheets

Specification includes a Sequence Listing.

(56) References Cited

U.S. PATENT DOCUMENTS

| | | | |
|---|---|---|---|
| 2004/0132977 | A1 | 7/2004 | Gantier et al. |
| 2004/0161817 | A1 | 8/2004 | Benton et al. |
| 2004/0209363 | A1 | 10/2004 | Watts et al. |
| 2004/0234531 | A1 | 11/2004 | Casares et al. |
| 2005/0003431 | A1 | 1/2005 | Wucherpfennig et al. |
| 2005/0009012 | A1 | 1/2005 | Holzberg et al. |
| 2005/0100926 | A1 | 5/2005 | Hedley et al. |
| 2005/0142142 | A1 | 6/2005 | Burrows et al. |
| 2006/0034865 | A1 | 2/2006 | Hildebrand et al. |
| 2006/0269515 | A1 | 11/2006 | Deniz-Mize et al. |
| 2007/0036752 | A1 | 2/2007 | Gillies et al. |
| 2007/0148162 | A1 | 6/2007 | Bhardwaj et al. |
| 2007/0286843 | A1 | 12/2007 | Pfizenmaier et al. |
| 2008/0199485 | A1 | 8/2008 | Kundig et al. |
| 2008/0219947 | A1 | 9/2008 | Linette et al. |
| 2008/0269070 | A1 | 10/2008 | Ramseier et al. |
| 2010/0159594 | A1 | 6/2010 | Hansen et al. |
| 2010/0190720 | A1 | 7/2010 | Hollingsworth et al. |
| 2010/0226854 | A1 | 9/2010 | Schøller et al. |
| 2011/0002956 | A1 | 1/2011 | Weiner et al. |
| 2011/0268737 | A1 | 11/2011 | Favier et al. |
| 2011/0318380 | A1 | 12/2011 | Brix et al. |
| 2012/0003220 | A1 | 1/2012 | Chen |
| 2012/0121577 | A1 | 5/2012 | Weidanz et al. |
| 2012/0177595 | A1 | 7/2012 | Wong et al. |
| 2012/0264161 | A1 | 10/2012 | Scholler et al. |
| 2013/0017199 | A1 | 1/2013 | Langermann |
| 2013/0066055 | A1 | 3/2013 | Lerchen et al. |
| 2013/0149305 | A1 | 6/2013 | Ostrand-Rosenberg |
| 2014/0046026 | A1 | 2/2014 | Garcia et al. |
| 2014/0162293 | A1 | 6/2014 | Springer et al. |
| 2014/0242077 | A1 | 8/2014 | Choi et al. |
| 2015/0071987 | A1 | 3/2015 | Selvaraj |
| 2015/0224186 | A1 | 8/2015 | Nakagawa |
| 2015/0232532 | A1 | 8/2015 | Ostrand-Rosenberg |
| 2015/0344586 | A1 | 12/2015 | Georges |
| 2015/0352201 | A1 | 12/2015 | David et al. |
| 2015/0374788 | A1 | 12/2015 | Paulsen et al. |
| 2016/0011204 | A1 | 1/2016 | Almo et al. |
| 2016/0083477 | A1 | 3/2016 | Klein et al. |
| 2016/0090407 | A1 | 3/2016 | Hosse et al. |
| 2016/0114019 | A1 | 4/2016 | Li et al. |
| 2016/0152725 | A1 | 6/2016 | Cheung et al. |
| 2016/0175397 | A1 | 6/2016 | Umana et al. |
| 2016/0304580 | A1 | 10/2016 | Ellmark et al. |
| 2016/0362465 | A1 | 12/2016 | Nishimura et al. |
| 2017/0044229 | A1 | 2/2017 | Garcia et al. |
| 2017/0044259 | A1 | 2/2017 | Tipton et al. |
| 2017/0058015 | A1 | 3/2017 | Seidel, III et al. |
| 2017/0304421 | A1 | 10/2017 | Wang et al. |
| 2017/0334951 | A1 | 11/2017 | O'Reilly et al. |
| 2018/0044404 | A1 | 2/2018 | Oda et al. |
| 2018/0064795 | A1 | 3/2018 | Sugiyama |
| 2018/0086832 | A1 | 3/2018 | Vogelstein et al. |
| 2018/0127481 | A1 | 5/2018 | Santamaria |
| 2018/0208626 | A1 | 7/2018 | Scheinberg et al. |
| 2018/0282392 | A1 | 10/2018 | Seidel, III et al. |
| 2018/0339030 | A1 | 11/2018 | Scheinberg |
| 2019/0046648 | A1 | 2/2019 | Seidel, III et al. |
| 2019/0119375 | A1 | 4/2019 | Abrams et al. |
| 2019/0119377 | A1 | 4/2019 | Spirig et al. |
| 2020/0172595 | A1 | 6/2020 | Seidel, III et al. |
| 2020/0317747 | A1 | 10/2020 | Seidel, III et al. |
| 2020/0369745 | A1 | 11/2020 | Seidel, III et al. |
| 2021/0284709 | A1 | 9/2021 | Brandt et al. |
| 2021/0393693 | A1 | 12/2021 | Seidel, III et al. |
| 2022/0008467 | A1 | 1/2022 | Seidel, III et al. |
| 2022/0079985 | A1 | 3/2022 | Seidel, III et al. |
| 2022/0143063 | A1 | 5/2022 | Seidel, III et al. |
| 2022/0162314 | A1 | 5/2022 | Yeung et al. |
| 2022/0251202 | A1 | 8/2022 | Djuretic et al. |
| 2022/0409732 | A1 | 12/2022 | MacDonald et al. |
| 2023/0117521 | A1 | 4/2023 | Seidel, III et al. |
| 2023/0126199 | A1 | 4/2023 | Hanayama et al. |
| 2023/0139456 | A1 | 5/2023 | Cemerski et al. |
| 2024/0025964 | A1 | 1/2024 | Seidel, III et al. |
| 2024/0034770 | A1 | 2/2024 | Suri et al. |
| 2024/0067700 | A1 | 2/2024 | Seidel, III et al. |

FOREIGN PATENT DOCUMENTS

| | | | |
|---|---|---|---|
| CN | 101418309 | | 4/2009 |
| CN | 101448951 | | 6/2009 |
| CN | 101688213 | | 3/2010 |
| CN | 105121715 | | 12/2015 |
| CN | 108431022 | | 11/2016 |
| CN | 106456733 | | 2/2017 |
| EP | 2998740 | | 3/2016 |
| EP | 3157552 | B1 | 10/2019 |
| EP | 3596118 | | 1/2020 |
| JP | 2000515363 | | 11/2000 |
| JP | 2004501364 | | 1/2004 |
| JP | 2005506058 | | 3/2005 |
| JP | 2007530021 | | 11/2007 |
| JP | 2009537175 | | 10/2009 |
| JP | 2010524506 | | 7/2010 |
| JP | 2012516854 | | 7/2012 |
| JP | 2015537043 | | 12/2015 |
| WO | WO1994/000150 | A1 | 1/1994 |
| WO | WO 1996/004314 | A1 | 2/1996 |
| WO | WO 1997/028191 | | 8/1997 |
| WO | WO 2001/090747 | | 11/2001 |
| WO | WO 2002/072631 | | 9/2002 |
| WO | WO 2002/087613 | | 11/2002 |
| WO | WO 2002/093129 | | 11/2002 |
| WO | WO 2002/102299 | | 12/2002 |
| WO | WO 2003/048334 | | 6/2003 |
| WO | WO 2004/029197 | | 4/2004 |
| WO | WO2004040262 | A2 | 5/2004 |
| WO | WO 2004/111190 | | 12/2004 |
| WO | WO 2005/012493 | A2 | 2/2005 |
| WO | WO2005017148 | A1 | 2/2005 |
| WO | WO2006073941 | A2 | 7/2006 |
| WO | WO 2007/136778 | | 11/2007 |
| WO | WO 2008/019888 | | 2/2008 |
| WO | WO 2008/113970 | | 9/2008 |
| WO | WO 2008/116468 | | 10/2008 |
| WO | WO 2008/134461 | | 11/2008 |
| WO | WO 2009/023270 | | 2/2009 |
| WO | WO 2010/037395 | | 4/2010 |
| WO | WO2010037514 | A2 | 4/2010 |
| WO | WO 2010/085495 | | 7/2010 |
| WO | WO 2010/091122 | | 8/2010 |
| WO | WO 2011/066342 | | 6/2011 |
| WO | WO 2011/066389 | | 6/2011 |
| WO | WO 2012/007951 | | 1/2012 |
| WO | WO 2012/127464 | | 9/2012 |
| WO | WO 2012/175508 | | 12/2012 |
| WO | WO 2013/003761 | | 1/2013 |
| WO | WO 2013/079174 | | 6/2013 |
| WO | WO 2014/083004 | | 6/2014 |
| WO | WO 2014/093118 | | 6/2014 |
| WO | WO 2014/145806 | | 9/2014 |
| WO | WO 2015/007903 | | 1/2015 |
| WO | WO 2015/112541 | | 7/2015 |
| WO | WO 2015/142675 | | 9/2015 |
| WO | WO 2015/164815 | | 10/2015 |
| WO | WO 2015/195531 | | 12/2015 |
| WO | WO 2016/000619 | | 1/2016 |
| WO | WO 2016/014428 | | 1/2016 |
| WO | WO 2016/025642 | | 2/2016 |
| WO | WO 2016/029043 | | 2/2016 |
| WO | WO 2016/030350 | | 3/2016 |
| WO | WO 2016/141357 | | 9/2016 |
| WO | WO 2016/154246 | A1 | 9/2016 |
| WO | WO 2016/164937 | | 10/2016 |
| WO | WO 2016/168771 | | 10/2016 |
| WO | WO 2016/186177 | A1 | 11/2016 |
| WO | WO 2016/198932 | | 12/2016 |
| WO | WO 2017/008844 | | 1/2017 |
| WO | WO 2017/023779 | | 2/2017 |
| WO | WO 2017/029389 | A1 | 2/2017 |
| WO | WO 2017/059819 | | 4/2017 |
| WO | WO 2017/120222 | | 7/2017 |

(56) References Cited

FOREIGN PATENT DOCUMENTS

| | | | |
|---|---|---|---|
| WO | WO 2017/123644 | | 7/2017 |
| WO | WO 2017/129737 | A1 | 8/2017 |
| WO | WO 2017/151818 | | 9/2017 |
| WO | WO 2017/151940 | | 9/2017 |
| WO | WO 2017/167217 | A1 | 10/2017 |
| WO | WO 2017/201131 | | 11/2017 |
| WO | WO 2017/201210 | | 11/2017 |
| WO | WO 2018/052947 | A1 | 3/2018 |
| WO | WO 2018/119114 | | 6/2018 |
| WO | WO 2018/129270 | A1 | 7/2018 |
| WO | WO 2018/165631 | | 9/2018 |
| WO | WO 2018/170168 | | 9/2018 |
| WO | WO 2018/170475 | | 9/2018 |
| WO | WO 2018/185564 | A2 | 10/2018 |
| WO | WO 2019/005886 | A1 | 1/2019 |
| WO | WO 2019/038230 | | 2/2019 |
| WO | WO 2019/051091 | | 3/2019 |
| WO | WO 2019/051094 | | 3/2019 |
| WO | WO 2019/051126 | | 3/2019 |
| WO | WO 2019/051127 | | 3/2019 |
| WO | WO 2019/139896 | | 7/2019 |
| WO | WO 2019/162937 | | 8/2019 |
| WO | WO 2020/053398 | A2 | 3/2020 |
| WO | WO 2020/071551 | A1 | 4/2020 |
| WO | WO 2020/132297 | A1 | 6/2020 |
| WO | WO 2020132138 | | 6/2020 |
| WO | WO 2020/180501 | A1 | 9/2020 |
| WO | WO 2020/181062 | A1 | 9/2020 |
| WO | WO 2020/205778 | A1 | 10/2020 |
| WO | WO 2020/243315 | | 12/2020 |
| WO | WO 2020/247843 | | 12/2020 |
| WO | WO 2020/257191 | | 12/2020 |
| WO | WO 2021/055594 | | 3/2021 |
| WO | WO 2021/081232 | | 4/2021 |
| WO | WO 2021/081239 | | 4/2021 |
| WO | WO 2021/127495 | | 6/2021 |
| WO | WO 2021/172596 | | 9/2021 |
| WO | WO 2021/209759 | | 10/2021 |
| WO | WO 2021/230247 | A1 | 11/2021 |
| WO | WO 2022/015880 | | 1/2022 |
| WO | WO 2022/087458 | | 4/2022 |
| WO | WO 2022/099156 | | 5/2022 |
| WO | WO 2022/125694 | | 6/2022 |
| WO | WO 2022/125711 | | 6/2022 |
| WO | WO 2022/226058 | A1 | 10/2022 |
| WO | WO 2023/081718 | A1 | 5/2023 |
| WO | WO 2023/097188 | A1 | 6/2023 |
| WO | WO 2023/137156 | A2 | 7/2023 |

OTHER PUBLICATIONS

Durinovic-Bello, et al.; "DRB1*0401-restricted human T cell clone specific for the major proinsulin73-90 epitope expresses a down-regulatory T helper 2 phenotype"; PNAS; vol. 103, No. 31, pp. 11683-11688 (Aug. 1, 2006).

Gojanovich, et al.; "The Use of Peptide-Major-Histocompatibility-Complex Multimers in Type 1 Diabetes Mellitus"; Journal of Diabetes Science and Technology; vol. 6, No. 3, pp. 515-524 (May 2012).

Li, et al.; "Suppression of Ongoing T Cell-Mediated Autoimmunity by Peptide-MHC Class II Dimer Vaccination"; The Journal of Immunology; vol. 183, pp. 4809-4816 (Sep. 14, 2009).

Lin, et al.; "Reversal of type 1 diabetes by a new MHC II-peptide chimera: "Single-epitope-mediated suppression" to stabilize a polyclonal autoimmune T-cell process"; Eur. J. Immunol.; vol. 40, pp. 2277-2288 (2010).

Michels, et al.; "Islet-Derived CD4 T Cells Targeting Proinsulin in Human Autoimmune Diabetes"; Diabetes; vol. 66, pp. 722-734 (Mar. 2017).

Preda, et al.; "Soluble, dimeric HLA DR4-peptide chimeras: An approach for detection and immunoregulation of human type-1 diabetes"; Eur. J. Immunol.; vol. 35, pp. 2763-2776 (Aug. 16, 2005).

Sang, et al.; "Long-term silencing of autoimmune diabetes and improved life expectancy by a soluble pHLA-DR4 chimera in a newly-humanized NOD-DR4/B7 mouse"; Human Vaccines & Immunotherapeutics; vol. 10, No. 3, pp. 693-699 (Mar. 2014).

Tan, et al.; "Type 1 diabetes induction in humanized mice"; PNAS; vol. 114, No. 41, pp. 10954-10959 (Oct. 10, 2017).

Woodham, et al.; "In vivo detection of antigen-specific CD8T cells by immuno-positron emission tomography"; Nat Methods.; vol. 17, No. 10, pp. 1025-1032 (Oct. 2020).

Zhang, et al.; "Monoclonal antibody blocking the recognition of an insulin peptide-MHC complex modulates type 1 diabetes"; PNAS; vol. 111, No. 7, pp. 2656-2661 (Feb. 18, 2014).

Botten, et al.; "Identification of Protective Lassa Virus Epitopes That Are Restricted by HLA-A2"; Journal of Virology; vol. 80, No. 17, pp. 8351-8361 (Sep. 1, 2006).

Chen, et al.; "Human papillomavirus type 16 nucleoprotein E7 is a tumor rejection antigen"; PNAS; vol. 88, No. 1, pp. 110-114 (Jan. 1, 1991).

Hedley, et al.; "The frequency and significance of WT-1 expression in serous endometrial carcinoma"; Human Pathology; vol. 45, No. 9, pp. 1879-1884 (Sep. 2014).

HLA Nomenclature; "HLA Alleles Numbers"; 2 pages (Mar. 2023).

Reche, et al.; "Definition of MHC Supertypes Through Clustering of MHC Peptide Binding Repertoires"; Nicosia, G., Cutello, V., Bentley, P.J., Timmis, J. (eds); Artificial Immune Systems, Third International Conference, ICARIS 2004, Catania, Sicily, Italy; vol. 3239, pp. 189-196 (Sep. 13-16, 2004).

Yao, et al.; "HPV-16 E6 and E7 protein T cell epitopes prediction analysis based on distributions of HLA-A loci across populations: An in silico approach"; Vaccine; vol. 31, No. 18, pp. 2289-2294 (Apr. 26, 2013).

Accession No. 1 IRL_A chain A Interleukin-2; 1 page (Aug. 25, 1995).

Ackerman, et al.; "Highly Avid Magnetic Bead Capture: An Efficient Selection Method for de novo Protein Engineering Utilizing yeast Surface Display"; Biotechnol. Prog.; vol. 25, No. 3, pp. 774-783 (2009).

Aina, et al.; "Identification of novel targeting peptides for human ovarian cancer cells using 'one-bead one-compount' combinatorial libraries"; Mol. Cancer Ther.; vol. 4, No. 5, 8 pages (May 2005).

Arduin, et al.; "Highly reduced binding to high and low affinity mouse Fc gamma receptors by L234A/L235A and N297A Fc mutations engineered into mouse IgG2a"; Molecular Immunology; vol. 63, pp. 456-463 (Feb. 2015).

Azuma, et al.; "B7-H1 is a ubiquitous antiapoptotic receptor on cancer cells"; Immunobiology; vol. 111, No. 7, pp. 3635-3643 (Apr. 1, 2008).

Baldi, et al.; "Recombinant protein production by large-scale transient gene expression in mammalian cells: state of the art and future perspectives"; Biotechnol. Lett.; vol. 29, pp. 677-684 (2007).

Bowers, et al.; "Coupling mammalian cell surface display with somatic hypermutation for the discovery and maturation of human antibodies"; PNAS; vol. 108, No. 51, pp. 20455-20460 (Dec. 20, 2011).

Brophy, et al.; "A yeast display system for engineering functional peptide-MHC complexes"; Journal of Immunological Methods; vol. 272, pp. 235-246 (2003).

Buonaguro, et al.; "Translating Tumor Antigens into Cancer Vaccines"; Clinical and Vaccine Immunology; vol. 18, No. 1, pp. 23-24 (Jan. 2011).

Buttner; "Cell-based assays for high-throughput screening"; Expert Opin. Drug Discov..; vol. 1, No. 4, pp. 301-306 (Sep. 2006).

Card, et al.; "A soluble single-chain T-cell receptor IL-2 fusion protein retains MHC-restricted peptide specificity and IL-2 bioactivity"; Cancer Immunol Immunother; vol. 53, pp. 345-357 (Nov. 11, 2003).

Cafri, et al.; "Development of novel genetic cancer vaccines based on membrane-attached β2 microglobulin"; Ann. N.Y. Acad. Sci.; vol. 1283, pp. 87-90 (2013).

Carey, et al.; "A soluble divalent class I MHC/IgG1 fusion protein activates CD8+ T cells in vivo"; Clinical Immunology; vol. 116, pp. 65-76 (2005).

(56) References Cited

OTHER PUBLICATIONS

Cebecauer, et al.; "Soluble MHC-Peptide Complexes Induce Rapid Death of CD8+ Ctl"; The Journal of Immunology; vol. 174, pp. 6809-6819 (2005).
Celis, et al.; "Identification of Potential CTL Epitopes of Tumor-Associated Antigen Mage-1 for Five Common HLA-A Alleles"; Molecular Immunology; vol. 31, No. 18, pp. 1423-1430 (1994).
Center for Disease Control and Prevention; "How Many Cancers Are Linked with HPV Each Year?"; 4 pages (2016).
Chames, et al.; "Bispecific antibodies for cancer therapy; The light at the end of the tunnel?" mAbs; vol. 1, No. 6, pp. 539-547 (Nov.-Dec. 2009).
Cheever, et al.; "The Prioritization of Cancer Antigens: A National Cancer Institute Pilot Project for the Acceleration of Translational Research"; Clinical Cancer Research; vol. 15, No. 17, pp. 5324-5337 (Sep. 1, 2009).
Crawford, et al.; "Use of baculovirus MHC/ peptide display libraries to characterize T-cell receptor ligands"; Immunological Reviews; vol. 210, pp. 156-170 (2006).
Crisci, et al.; "Virus-like particles: The new frontier of vaccines for animal viral infections"; Veterinary Immunology and Immunopathology; vol. 148, pp. 211-225 (2012).
Czajkowsky, et al.; "Fc-fusion proteins: new developments and future perspectives"; EMBO Mol. Med.; vol. 4, pp. 1015-1028 (2012).
Das, et al.; "Generation of murine tumor cell lines deficient in MHC molecule surface expression using the CRISPR/Cas9 system"; PLoS One; vol. 12, No. 3, 19 pages (Mar. 16, 2017).
De Charette, et al.; "Turning tumour cells into antigen presenting cells: The next step to improve cancer immunotherapy?"; European Journal of Cancer; vol. 68, pp. 134-147 (Oct. 2016).
Desmond, et al.; "A systematic review of T-cell epitopes in hepatitis B virus: identification, genotypic variation and relevance to antiviral therapeutics"; Antiviral Therapy; vol. 13, pp. 161-175 (2008).
Dimasi, et al.; "The design and characterization of oligospecific antibodies for simultaneous targeting of multiple disease mediators"; Journal of Molecular Biology; 393(3): p. 672-692 (2009).
Doussal, et al.; "Phage display of peptide /major histocompatibility complex"; Journal of Immunological Methods; vol. 241, pp. 147-158 (2000).
Dulberger, et al.; "Human leukocyte antigen F (HLA-F) presents peptides and regulates immunity through interactions with NK-cell receptors"; Immunity; vol. 46, No. 6, pp. 1018-1027 (Jun. 20, 2017).
Emboss Needle; 2 pages (Feb. 10, 2022).
Edwards, et al.; "The Remarkable Flexibility of the Human Antibody Repertoire; Isolation of Over One Thousand Different Antibodies to a Single Protein, BLyS"; J. Mol. Biol.; vol. 334, pp. 103-118 (2003).
Engelhard; "Structure of peptides associated with MHC class I molecules"; Current Opinion in Immunology; vol. 6, pp. 13-23 (1994).
Engler, et al.; "Peptide vaccines against hepatitis B virus: from animal model to human studies"; Molecular Immunology; vol. 38, pp. 457-465 (Dec. 2001).
GENBANK:AEV43323.1; "Fc IgG1 heavy chain constant region, partial [*Homo sapiens*]"; 2 pages (Jul. 25, 2016).
GENBANK:NP_068693.1; "programmed cell death 1 ligand 1 precursor [Mus musculus]"; 3 pages (Jun. 9, 2021).
GENBANK:NP_001009066.1; 2 pages (2003).
GENBANK:NP_001300958.1; "programmed cell death 1 ligand 1 isoform c precursor [*Homo sapiens*]"; 3 pages (Jun. 9, 2021).
GenCore AEE04235; 4 pages (2005).
Goel, et al.; "Plasticity within the Antigen-Combining Site May Manifest as Molecufar Mimicry in the Humoral Immune Response"; The Journal of Immunology; vol. 173, pp. 7358-7367 (2004).
Gough, et al.; "The HLA Region and Autoimmune Disease: Associations and Mechanisms of Action"; Current Genomics; vol. 8, pp. 453-465 (2007).
Greten, et al.; "Peptide-β2-microglobulin-MHC fusion molecules bind antigen-specific T cells and can be used for multivalent MHC-Ig complexes"; Journal of Immunological Methods; vol. 271, pp. 125-135 (2002).
Grupp, et al.; "Adoptive Cellular Therapy"; Curr Top Microbiol Immunol.; 344: p. 149-172 (2011).
Guo, et al.; "Different length peptides bind to HLA-Aw68 similarly at their ends but bulge out in the middle"; Nature; vol. 360, pp. 364-366 (Nov. 26, 1992).
Hansen, et al.; "Phage display of peptide/major histocompatibility class I complexes"; Eur. J. Immunol.; vol. 31, pp. 32-38 (2001).
HLA Nomenclature; "HLA Alleles Numbers"; 2 pages (Mar. 17, 2015).
Huang, et al.; "Bone regeneration in a rat cranial defect with delivery of PEI-condensed plasmid DNA encoding for bone morphogenetic protein-4 (BMP-4)"; Gene Therapy; vol. 12, No. 5, p. 418 (2005).
Huang, et al.; "Cancer immunotherapy using a DNA vaccine encoding a single-chain trimer of MHC class I linked to an HPV-16 E6 immunodominant CTL epitope"; Gene Ther.; vol. 12, No. 15, pp. 1180-1186 (Aug. 2005).
Hug, et al.; "T-cadherin is a receptor for hexameric and high-molecular-weight forms of Acrp30/adiponectin"; PNAS; vol. 101, No. 28, pp. 10308-10313 (Jul. 13, 2004).
Hugues, et al.; "Generation and use of alternative multimers of peptide/MHC complexes"; Journal of Immunological Methods; vol. 268, pp. 83-92 (2002).
Judkowski, et al.; "Identification of MHC Class II-Restricted Peptide Ligands, Including a Glutamic Acid Decarboxylase 65 Sequence, that Stimulate Diabetogenic T Cells from Transgenic BDC2.5 Nonobese Diabetic Mice"; The Journal of Immunology; vol. 166, pp. 908-917 (2001).
Karaki, et al.; "Is There Still Room for Cancer Vaccines at the Era of Checkpoint Inhibitors"; Vaccines; vol. 4, No. 37, 24 pages (2016).
Karin, et al.; "Reversal of Experimental Autoimmune Encephalomyelitis by a Soluble Peptide Variant of a Myelin Basic Protein Epitope: T Cell Receptor Antagonism and Reduction of Interferon γ and Tumor Necrosis Factor α Production"; J. Exp. Med.; vol. 180, pp. 2227-2237 (Dec. 1994).
Khan, et al.; "Adjustable Locks and Flexible Keys: Plasticity of Epitope-Paratope Interactions in Germline Antibodies"; The Journal of Immunology; vol. 192, pp. 5398-5405 (2014).
Kim, et al.; "Single chain MHC I trimer-based DNA vaccines for protection against *Listeria monocytogenes* infection"; Vaccine; vol. 30, pp. 2178-2186 (2012).
Krautwurst, et al.; "Identification of Ligands for Olfactory Receptors by Functional Expression of a Receptor Library"; Cell; vol. 95, pp. 917-926 (Dec. 23, 1998).
Kreiter, et al.; "Increased Antigen Presentation Efficiency by Coupling Antigens to MHC Class I Trafficking Signals"; The Journal of Immunology; vol. 180, No. 1, pp. 309-318 (Jan. 1, 2008).
Kushnir, et al.; "Virus-like particles as a highly efficient vaccine platform: Diversity of targets and production systems and advances in clinical development"; Vaccine; vol. 31, pp. 58-83 (2012).
Lazar-Molnar, et al.; "Crystal structure of the complex between programmed death-1 (PD-1) and its ligand PD-L2"; PNAS; vol. 105, No. 30, pp. 10483-10488 (Jul. 29, 2008).
Lazar-Molnar, et al.; "The PD-1/PD-L costimulatory pathway critically affects host resistance to the pathogenic fungus *Histoplasma capsulatum*"; PNAS; vol. 105, No. 7, pp. 2658-2663 (Feb. 19, 2008).
Lenormand, et al.; "HLA-DQA2 and HLA-DQB2 Genes Are Specifically Expressed in Human Langerhans Cells and Encode a New HLA Class II Molecule"; The Journal of Immunology; vol. 199, No. 8, pp. 3903-3911 (Apr. 15, 2012).
Liao, et al.; "Interleukin-2 at the Crossroads of Effector Responses, Tolerance, and Immunotherapy"; Immunity; vol. 38, No. 1, pp. 13-25 (Jan. 1, 2013).
Lin, et al.; "The PD-1/PD-L1 complex resembles the antigen-binding Fv domains of antibodies and T cell receptors"; PNAS; vol. 105, No. 8, pp. 3011-3016 (Feb. 26, 2008).

(56) References Cited

OTHER PUBLICATIONS

Liu, et al.; "Attaining High Transient Titers in CHO Cells"; Genetic Engineering & Biotechnology News; vol. 35, No. 17, 3 pages (Oct. 1, 2015).
Liu, et al.; "Major Histocompatibility Complex: Interaction with Peptides"; eLS; 12 pages (Aug. 15, 2011).
Lloyd, et al.; "Modelling the human immune response: performance of a 1011 human antibody repertoire against a broad panel of therapeutically relevant antigens"; Protein Engineering, Design & Selection; vol. 22, No. 3, pp. 159-168 (2009).
Mallone, et al.; "T Cell Recognition of Autoantigens in Human Type 1 Diabetes: Clinical Perspectives"; Clinical and Developmental Immunology; vol. 2011, 16 pages (2011).
Margalit, et al.; "Induction of Antitumor Immunity by CTL Epitopes Genetically Linked to Membrane-Anchored β2-Microglobulin"; The Journal of Immunology; vol. 176, pp. 217-224 (2006).
Martin-Orozco, et al.; "Melanoma Cells Express ICOS Ligand to Promote the Activation and Expansion of T-Regulatory Cells"; Cancer Research; vol. 70, No. 23, pp. 9581-9590 (2010).
Mcallister, et al.; "Adaptation of Recombinant HEK-293 Cells to Growth in Serum Free Suspension"; Animal Cell Technology: Products from Cells, Cells as Products; 3 pages (1999).
Mcnally, et al.; "CD4+CD25+ regulatory T cells control CD8+ T-cell effector differentiation by modulating IL-2 homeostasis"; PNAS; vol. 108, No. 18, pp. 7529-7534 (May 3, 2011).
Medina, et al.; "PD-1 Pathway Inhibitors: Immuno-Onology Agents for Restoring Anititumor Immune Responses"; Pharmacotherapy; vol. 36, No. 3, pp. 317-334 (Mar. 2016).
Miao, et al.; "Transient expression of fluorescent fusion proteins in protoplasts of suspension cultured cells"; Nature Protocols; vol. 2, No. 10, pp. 2348-2353 (2007).
Mizukoshi, et al.; "Identification of α-fetoprotein-derived peptides recognized by cytotoxic T lymphocytes in HLA-A24+ patients with hepatocellular carcinoma"; Int. J. Cancer; vol. 118, pp. 1194-1204 (2006).
Mott, et al.; "The Solution Structure of the F42A Mutant of Human Interleukin 2"; J. Mol. Biol.; vol. 247, pp. 979-994 (1995).
Mottez, et al.; "Cells Expressing a Major Histocompatibility Complex Class I Molecule with a Single Covalently Bound Peptide Are Highly Immunogenic"; J. Exp. Med.; vol. 181, pp. 493-502 (Feb. 1995).
Motz, et al.; "Tumor Endothelium FasL Establishes a Selective Immune Barrier Promoting Tolerance in Tumors"; Nat. Med.; vol. 20, No. 6, pp. 607-615 (Jun. 2014).
Muller, et al.; "Random peptide libraries displayed on adeno-associated virus to select for targeted gene therapy vectors"; Nature Biotechnology; vol. 21, No. 9, pp. 1040-1046 (Sep. 2003).
Naidoo, et al.; "Toxicities of the anti-PD-1 and anti-PD-L1 immune checkpoint antibodies"; Annals of Oncology; vol. 26, pp. 2375-2391 (Sep. 2015).
Nielsen, et al.; "MHC Class II epitope predictive algorithms"; Immunology; vol. 130, pp. 319-328 (2010).
Oates, et al.; "ImmTACs: Novel bi-specific agents for targeted cancer therapy"; OncoImmunology; vol. 2, No. 2, 3 pages (Feb. 2013).
Obermann, et al.; "Peptide-β2-microglobulin-major histocompatibility complex expressing cells are potent antigen-presenting cells that can generate specific T cells"; Immunology; vol. 122, pp. 90-97 (2007).
Ochoa-Garay, et al.; "The Ability of Peptides to Induce Cytotoxic T Cells In Vitro Does Not Strongly Correlate with Their Affinity for the H-2Ld Molecule: Implications for Vaccine Design and Immunotherapy"; Molecular Immunology; vol. 34, No. 3, pp. 273-281 (1997).
Oka, et al.; "Induction of WT1 (Wilms' tumor gene)-specific cytotoxic T lymphocytes by WT1 peptide vaccine and the resultant cancer regression"; PNAS; vol. 101, No. 38, pp. 13885-13890 (Sep. 21, 2004).
Oliveira, et al.; "Design, Immune Responses and Anti-Tumor Potential of an HPV16 E6E7 Multi-Epitope Vaccine"; PLoS One; vol. 10, No. 9, 13 pages (Sep. 21, 2015).
PDB:1I8L_A; "Chain A, T Lymphocyte Activation Antigen Cd80" 2 pages (Dec. 27, 2012).
Peach, et al.; "Both Extracellular Immunoglobin-like Domains of CD80 Contain Residues Critical for Binding T Cell Surface Receptors CTLA-4 and CD28*"; The Journal of Biological Chemistry; vol. 270, No. 36, pp. 21181-21187 (1995).
Ponstingl, et al.; "The Rule of Antibody Structure: The Primary Structure of a Monoclonal IgG1 Immunoglobulin (Myeloma Protein Nie)"; Hoppe Seylers Z Physiol Chem.; vol. 357, No. 11, pp. 1571-1604 (Nov. 1976). [English translation of Abstract Only].
Poosarla, et al.; "Computational De Novo Design of Antibodies Binding to a Peptide With High Affinity"; Biotechnology & Bioengineering; vol. 114, No. 6, pp. 1331-1342 (Jun. 2017).
Quayle, et al.; "CUE-101, a Novel HPV16 E7-pHLA-IL-2-Fc Fusion Protein, Enhances Tumor Antigen Specific T Cell Activation for the Treatment of HPV16-Driven Malignancies"; Clinical Cancer Research; vol. 26, No. 8, pp. 1953-1964 (Jan. 21, 2020).
Quayle, et al.; "Immuno-STAT(TM) (Selective Targeting and Alteration of T cells) Platform: Targeting Tumor Heterogeneity and Tumor Escape Mechanisms"; DOI:10.1158/1078-0432.CCR-19-3354; URL:https://www.cuebiopharma.com/our-appro ch/scien ific-presentations-publications/; 1 page (Jan. 21, 2020).
Rabu, et al.; "Production of recombinant human trimeric CD137L (4-1BBL). Cross-linking is essential to its T cell co-stimulation activity"; The Journal of Biological Chemistry; vol. 280, No. 50, pp. 41472-41481 (Dec. 16, 2005).
Ramani, et al.; "A secreted protein microarray platform for extracellular protein interaction discovery"; Analytical Biochemistry; vol. 420, pp. 127-138 (2012).
Reche, et al.; "Sequence Variability Analysis of Human Class I and Class II MHC Molecules: Functional and Structural Correlates of Amino Acid Polymorphisms"; Journal of Molecular Biology; vol. 331, No. 3, pp. 623-641 (Aug. 15, 2003).
Repana, et al.; "The Network of Cancer Genes (NCG): a comprehensive catalogue of known and candidate cancer genes from cancer sequencing screens"; Genome Biology; vol. 20, No. 1, 12 pages (2019).
Ressing, et al.; "Human CTL epitopes encoded by human papillomavirus type 16 E6 and E7 identified through in vivo and in vitro immunogenicity studies of HLA-A*0201-binding peptides"; The Journal of Immunology; vol. 154, pp. 5934-5943 (1995).
Rocha-Zavaleta, et al.; "Interleukin-2 (IL-2) receptor-βγ signalling is activated by c-Kit in the absence of IL-2, or by exogenous IL-2 via JAK3/STAT5 in human papillomavirus-associated cervical cancer"; Cellular Signalling; vol. 16, pp. 1239-1247 (2004).
Schmittnaegel, et al.; "A New Class of Bifunctional Major Histocompatibility Class I Antibody Fusion Molecules to Redirect Cds T Cells"; Molecular Cancer Therapeutics; vol. 15, No. 9, pp. 2130-2142 (Sep. 2016).
Schumacher, et al.; "Neoantigens in cancer immunotherapy"; Science; vol. 348, No. 6230, pp. 69-74 (Apr. 2, 2015).
Seidel, et al.; "Peptide-HLA-based immunotherapeutics platforms for direct modulation of antigen-specific T cells"; Scientific Reports; vol. 11, No. 19220, 8 pages (Sep. 2021).
Shah, et al.; "Bio-layer Interferometry for Measuring Kinetics of Protein-protein Interactions and Allosteric Ligand Effects; Journal of Visualized Experiments"; vol. 84, 11 pages (2014).
Sharma, et al.; "A synthetic chimeric peptide harboring human papillomavirus 16 cytotoxic T lymphocyte epitopes shows therapeutic potential in a murine model of cervical cancer"; Immunologic Research; 58(1): p. 132-138 (2014).
Solinas, et al.; "The rationale behind targeting the ICOS-ICOS ligand costimulatory pathway in cancer immunotherapy"; ESMO Open; vol. 5, 7 pages (Jan. 2020).
Spang, et al.; "Heterodimeric Barnase-Barstar Vaccine Molecules: Influence of One versus Two Targeting Units Specific for Antigen Presenting Cells"; PLoS One; vol. 7, No. 9, 11 pages (Sep. 2012).
Stadinski, et al.; "Diabetogenic T cells recognize insulin bound to IAg7 in an unexpected, weakly binding register"; PNAS; vol. 107, No. 24, pp. 10978-10983 (Jun. 15, 2010).

(56) References Cited

OTHER PUBLICATIONS

Stamper, et al.; "Crystal structure of the B7-1/CTLA-4 complex that inhibits human immune responses"; Nature; vol. 410, pp. 608-611 (Mar. 29, 2001).
Strohl; "Optimization of Fc-mediated effector functions of monoclonal antibodies"; Current Opinion in Biotechnology; vol. 20, pp. 685-691 (2009).
Tafuro, et al.; "Reconstitution of antigen presentation in HLA class I-negative cancer cells with peptide-β2m fusion molecules"; Eur. J. Immunol.; vol. 31, pp. 440-449 (2001).
Taube, et al.; "Lentivirus Display: Stable Expression of Human Antibodies on the Surface of Human Cells and Virus Particles"; PLoS One; vol. 3, No. 9, 12 pages (Sep. 2008).
Tham, et al.; "Activation of antigen-specific T cells by artificial cell constructs having immobilized multimeric peptide-class I complexes and recombinant B7-Fc proteins"; Journal of Immunological Methods; vol. 249, pp. 111-119 (2001).
Torres, et al.; "The immunoglobulin constant region contributes to affinity and specificity"; Trends in Immunology; vol. 29, No. 2, pp. 91-97 (Jan. 10, 2008).
Toukam, et al.; "Targeting Antibody Responses to the Membrane Proximal External Region of the Envelope Glycoprotein of Human Immunodeficiency Virus"; PLoS One; vol. 7, No. 5, 10 pages (May 2012).
Trolle, et al.; "The length distribution of class I restricted T cell epitopes is determined by both peptide supply and MHC allele specific binding preference"; J Immunol; vol. 196, No. 4, pp. 1480-1487 (Feb. 15, 2016).
Van Der Burg, et al.; "An HLA Class I Peptide-Binding Assay Based on Competition for Binding to Class I Molecules on Intact Human B Cells Identification of Conserved HIV-1 Polymerase Peptides Binding to HLA-A*0301"; Hum. Immunol.; vol. 44, No. 4, pp. 189-198 (Dec. 1995).
Venkatakrishnan, et al.; "The Structural Biology of Hepatitis B Virus: Form and Function"; Annu. Rev. Virol.; vol. 3, No. 1, pp. 429-451 (Sep. 29, 2016).
Vitello, et al.; "Neoantigen prediction and the need for validation"; Nature Biotechnology; vol. 35, No. 9, pp. 815-817 (Sep. 2017).
Wang, et al.; "Molecular Modeling and Functional Mapping of B7-H1 and B7-DC Uncouple Costimulatory Function from PD-1 Interaction"; J. Exp. Med.; vol. 197, No. 9, pp. 1083-1091 (May 5, 2003).
Wang, et al.; "Using a baculovirus display library to identify MHC class I mimotopes"; PNAS; vol. 102, No. 7, pp. 2476-2481 (Feb. 15, 2005).
Wen, et al.; "Construction and screening of an antigen-derived peptide library displayed on yeast cell surface for CD4+ T cell epitope identification"; Methods Mol. Biol.; vol. 1061, pp. 245-264 (2013).
White, et al.; "Soluble Class I MHC with $\beta_2$-MicroglobulinCovalently Linked Peptides: Specific Binding to a T Cell Hybridoma"; J Immunol; vol. 162, pp. 2671-2676 (1999).
Whitehead, et al.; "Optimization of affinity, specificity and function of designed influenza inhibitors using deep sequencing"; Nat. Biotechnol.; vol. 30, No. 6, pp. 543-548 (Apr. 29, 2013).
Wieczorek, et al.; "Major Histocompatibility Complex (MHC) Class I and MHC Class II Proteins: Conformational Plasticity in Antigen Presentation"; Frontiers in Immunology; vol. 8, No. 292, pp. 1-16 (Mar. 2017).
Won, et al.; "The structure of the trimer of human 4-1BB ligand is unique among members of the tumor necrosis factor superfamily"; J Biol Chem; vol. 285, No. 12, pp. 9202-9210 (Mar. 19, 2010).
Wu, et al.; "Simultaneous targeting of multiple disease mediators by a dual-variable-domain immunoglobulin"; Nature Biotechnology; 25: p. 1290-1297 (2007).
Xu, et al.; "Cytokine release syndrome in cancer immunotherapy with chimeric antigen receptor engineered T cells"; Cancer Letters; 343(2): p. 172-178 (2014).
Zheng, et al.; "B7-CTLA4 interaction enhances both production of antitumor cytotoxic T lymphocytes and resistance to tumor challenge"; PNAS; vol. 95, pp. 6284-6289 (May 1998).
Ziauddin, et al.; "Microarrays of cells expressing defined cDNAs"; Nature; vol. 411, pp. 107-110 (May 3, 2011).
Chung, et al.; "A phase 1 dose-escalation and expansion study of CUE-101, a novel HPV16 E7-pHLA-IL2-Fc fusion protein, given alone and in combination with pembrolizumab in patients with recurrent/metastatic HPV16+ head and neck cancer."; poster, ASCO 2022 (1 page).
Chung, et al.; "#674 A phase 1 dose-escalation and expansion study of CUE-101, given as monotherapy and in combination with pembrolizumab in recurrent/metastatic HPV16+ head and neck cancer patients"; Poster; Presented at the Society for Immunotherapy of Cancer (SITC) Annual Meeting; 1 page (Nov. 3-5, 2023).
Chung, et al.; "# 681 A phase 1 study of CUE-101, a novel HPV16 E7-pHLA-IL2-Fc fusion protein, as monotherapy and in combination with pembrolizumab in patients with recurrent/metastatic HPV16+ head and neck cancer"; poster, Presented at the Society for Immunotherapy of Cancer (SITC) Annual Meeting, 1 page (Nov. 8-12, 2022).
Chung, et al.; "A phase 1 dose-escalation and expansion study of CUE-101, a novel HPV16 E7-pHLA-IL2-Fc fusion protein, given as monotherapy and in combination with pembrolizumab in patients with recurrent/metastatic HPV16+ head and neck cancer."; poster, ASCO 2023 (1 page).
Kowalski, et al.; "Delivering the Messenger: Advances in Technologies for Therapeutic mRNA Delivery"; Molecular Therapy; vol. 27, No. 4, pp. 710-728 (Feb. 18, 2019).
Wu, et al.; "Remote control of therapeutic T cells through a small molecule-gated chimeric receptor"; Science; vol. 350, No. 6258, 12 pages (Oct. 16, 2015).
Carmenate, et al.; "Human IL-2 Mutein with Higher Antitumor Efficacy Than Wild Type IL-2"; The Journal of Immunology; vol. 190, No. 12, pp. 6230-6238 (Jun. 15, 2013).
Stauber et al.; "Crystal structure of the IL-2 signaling complex: Paradigm for a heterotrimeric cytokine receptor"; Proc. Natl. Acad. Sci.; vol. 103, No. 8, pp. 2788-2793 (Feb. 21, 2006).
Truscott et al., "Human major histocompatibility complex (MHC) class I molecules with disulfide traps secure disease-related antigenic peptides and exclude competitor peptides" Journal of Biological Chemistry, vol. 283, No. 12, pp. 7480-7490 (Mar. 21, 2008).
Fellner; "Ipilimumab (Yervoy) Prolongs Survival In Advanced Melanoma"; Drug Forecast; vol. 37, No. 9, pp. 503-530 (Sep. 2012).
Li, et al.; "Chain A, anti-connexin26 scFv,Ig heavy chain,Linker,anti-connexin26 scFv,Ig light chain"; Accession 5WYM_A, Front Mol Neurosci 10, 298, 3 pages (Jan. 13, 2017).
Zhou, et al.; "Epitopes of MUC1 Tandem Repeats in Cancer as Revealed by Antibody Crystallography: Toward Glycopeptide Signature-Guided Therapy"; Molecules; vol. 23, No. 1326, 27 pages (2018).
Favier, et al.; "Tolerogenic Function of Dimeric Forms of HLA-G Recombinant Proteins: A Comparative Study In Vivo"; PLoS One; vol. 6, No. 7, 26 pages (Jul. 2011).
Anonymous; "Rationally engineered biologics to harness nature's cues for selective and specific immune modulation", Powerpoint presentation; 24 pages (Feb. 1, 2021).
GENBANK:ALM96677.1; "MHC class I antigen, partial [*Homo sapiens*]"; 3 pages (Nov. 11, 2015).
Johannsen, et al.; "Definition of Key Variables for the Induction of Optimal NY-ESO-1-Specific T Cells in HLA Transgene Mice"; The Journal of Immunology; vol. 185, pp. 3445-3455 (2010).
Linard, et al.; "A ras-Mutated Peptide Targeted by CTL Infiltrating a Human Melanoma Lesion"; The Journal of Immunology; vol. 168, pp. 4802-4808 (2002).
Terashima, et al.; "P53, hTERT, WT-1, and VEGFR2 are the most suitable targets for cancer vaccine therapy in HLA-A24 positive pancreatic adenocarcinoma"; Cancer Immunol Immunother; vol. 63, pp. 479-489 (2014).
Balagopalan et al. (2009) "Endocytic events in TCR Signaling: Focus on Adapters in Microclusters" Immunological Reviews, 232:1 84-98.
Powderly et al (2022) "636 A phase 1, open-label, dose escalation and expansion study of CUE-102 monotherapy in HLA-A*0201

(56) References Cited

OTHER PUBLICATIONS positive patients with WT1-positive recurrent/metastatic cancers" Journal of Clinical Oncology, vol. 42, No. 16_suppl.
Burtness et al., "Pembrolizumab Alone or With Chemotherapy for Recurrent/Metastatic Head and Neck Squamous Cell Carcinoma in KEYNOTE-048: Subgroup Analysis by Programmed Death Ligand-1 Combined Positive Score", Journal of Clinical Oncology, vol. 40, No. 21, pp. 2321-2332 (Mar. 25, 2022).
Celik et al., "The diversity of the HLA-E-restricted peptide repertoire explains the immunological impact of the Arg107Gly mismatch" Immunogenetics, vol. 68, pp. 29-41 (2016).
Chen et al., "Fusion protein linkers: property, design and functionality", Advanced Drug Delivery Reviews, vol. 65, No. 10, pp. 1357-1369 (Oct. 15, 2013).
Hammer et al., "Peptide-specific recognition of human cytomegalovirus strains controls adaptive natural killer cells" Nature Immunology, vol. 19, No. 5, pp. 453-463 (May 2018).
Harrington et al., "Pembrolizumab With or Without Chemotherapy in Recurrent or Metastatic Head and Neck Squamous Cell Carcinoma: Updated Results of the Phase III KEYNOTE-048 Study", Journal of Clinical Oncology, vol. 41, No. 4, pp. 790-802 (Oct. 11, 2022).
Huisman et al., "An unbiased characterization of the HLA-E and CD94/NKG2x peptide repertoire reveals peptide ligands that skew NK cell activation", bioRxiv, Available Online at: https://doi.org/10.1101/2022.08.03.502719, 36 pages (2022).
Klein et al., "Design and characterization of structured protein linkers with differing flexibilities" Protein Engineering, Design and Selection, vol. 27, No. 10, pp. 325-330 (Oct. 2014).
Ling et al., "Effect of VH-VL Families in Pertuzumab and Trastuzumab Recombinant Production, Her2 and FcγIIA Binding", Frontiers in Immunology, vol. 9, No. 469, 11 pages (Mar. 2018).
Lu, et al.; "KRAS G12V neoantigen specific T cell receptor for adoptive T cell therapy against tumors"; Nature Communications; vol. 14, No. 6389, pp. 1-16 (2023).
Pan, et al.; "Potentiation of Kras peptide cancer vaccine by avasimibe, a cholesterol modulator"; EBioMedicine; vol. 49, pp. 72-81 (Nov. 2019).
Pardee et al., "Tumor-derived α-fetoprotein impairs the differentiation and T cell stimulatory activity of human dendritic cells", Journal of Immunology, vol. 193, No. 11, pp. 5723-5732 (Dec. 1, 2014).
Rölle et al., "Distinct HLA-E peptide complexes modify antibody-driven effector functions of adaptive NK cells" Cell Reports, vol. 24, No. 8, pp. 1967-1976 (Aug. 21, 2018).
Samanta, D. et al., 'Structural and functional characterization of a single-chain peptide-MHC molecule that modulates both naive and activated CD 8+ T cells', PNAS, (Aug. 8, 2011), vol. 108, No. 33, pp. 13682-13687, doi:10.1073/pnas.1110971108.
Shimasaki et al., "NK cells for cancer immunotherapy" Nature Reviews, Drug Discovery, vol. 19, pp. 200-218 (2020).
Terakura et al., "Generation of CD19-chimeric antigen receptor modified CD8+ T cells derived from virus-specific central memory T cells" Blood, vol. 119, No. 1, pp. 72-82 (Jan. 5, 2012).
Xu, et al.; "Neoantigen-targeted TCR-T cell therapy for solid tumors: How far from clinical application"; Cancer Letters; vol. 546, No. 215840, pp. 1-12 (Oct. 10, 2022).
Unverdorben, et al.; "Pharmacokinetic properties of IgG and various Fc fusion proteins in mice"; MABS; vol. 8, No. 1, pp. 120-128 (Oct. 29, 2015).
Fischer; "Targeted tumor cell elimination by redirecting vaccination-induced CD8+ T cells in vivo with novel bifunctional peptide-MHC class I-IgG antibody fusions"; Dissertation, University of Munich; pp. 1-161 (2017).
Schmittnaegel, et al.; "Committing Cytomegalovirus-Specific CD8 T Cells to Eliminate Tumor Cells by Bifunctional Major Histocompatibility Class I Antibody Fusion Molecules"; Cancer Immunology Research; vol. 3, No. 7, pp. 764-776 (Jul. 2015).
Doubrovina, et al.; "Mapping of novel peptides of WT-1 and presenting HLA alleles that induce epitope-specific HLA-restricted T cells with cytotoxic activity against WT-1+ leukemias"; Blood; vol. 120, No. 8, pp. 1633-1646 (2012).
Girgis, et al.; "1323 CUE-102 selectively activates and expands WT1-specific T cells for the treatment of patients with WT1+ malignancies"; Journal for Immuno Therapy of Cancer; vol. 10, No. Supplemental 2, pp. A1374-A1374 (Nov. 7, 2022).
Tsuboi, et al.; "A phase I clinical study of a cocktail vaccine of Wilms' tumor 1 (WT1) HLA class I and II peptides for recurrent malignant glioma"; Cancer Immunology, Immunotherapy; vol. 68, pp. 331-340 (2019).

FIG. 3A

WT-1 isoform A

1 MDFLLLQDPA STCVPEPASQ HTLRSGPGCL QQPEQQGVRD PGGIWAKLGA AEASAERLQG

61 RRSRGASGSE PQQMGSDVRD LNALLPAVPS LGGGGGCALP VSGAAQWAPV LDFAPPGASA

121 YGSLGGPAPP PAPPPPPPPP PHSFIKQEPS WGGAEPHEEQ CLSAFTVHFS GQFTGTAGAC

181 RYGPFGPPPP SQASSGQARM FPNAPYLPSC LESQPAIRNQ GYSTVTFDGT PSYGHTPSHH

241 AAQFPNHSFK HEDPMGQQGS LGEQQYSVPP PVYGCHTPTD SCTGSQALLL RTPYSSDNLY

301 QMTSQLECMT WNQMNLGATL KGHSTGYESD NHTTPILCGA QYRIHTHGVF RGIQDVRRVP

361 GVAPTLVRSA SETSEKRPFM CAYPGCNKRY FKLSHLQMHS RKHTGEKPYQ CDFKDCERRF

421 SRSDQLKRHQ RRHTGVKPFQ CKTCQRKFSR SDHLKTHTRT HTGEKPFSCR WPSCQKKFAR

481 SDELVRHHNM HQRNMTKLQL AL

FIG. 3B

WT-1 isoform B

1 MDFLLLQDPA STCVPEPASQ HTLRSGPGCL QQPEQQGVRD PGGIWAKLGA AEASAERLQG

61 RRSRGASGSE PQQMGSDVRD LNALLPAVPS LGGGGGCALP VSGAAQWAPV LDFAPPGASA

121 YGSLGGPAPP PAPPPPPPPP PHSFIKQEPS WGGAEPHEEQ CLSAFTVHFS GQFTGTAGAC

181 RYGPFGPPPP SQASSGQARM FPNAPYLPSC LESQPAIRNQ GYSTVTFDGT PSYGHTPSHH

241 AAQFPNHSFK HEDPMGQQGS LGEQQYSVPP PVYGCHTPTD SCTGSQALLL RTPYSSDNLY

301 QMTSQLECMT WNQMNLGATL KGVAAGSSSS VKWTEGQSNH STGYESDNHT TPILCGAQYR

361 IHTHGVFRGI QDVRRVPGVA PTLVRSASET SEKRPFMCAY PGCNKRYFKL SHLQMHSRKH

421 TGEKPYQCDF KDCERRFSRS DQLKRHQRRH TGVKPFQCKT CQRKFSRSDH LKTHTRTHTG

481 EKPFSCRWPS CQKKFARSDE LVRHHNMHQR NMTKLQLAL

FIG. 3C

WT-1 isoform D

```
  1 MDFLLLQDPA STCVPEPASQ HTLRSGPGCL QQPEQQGVRD PGGIWAKLGA AEASAERLQG
 61 RRSRGASGSE PQQMGSDVRD LNALLPAVPS LGGGGGCALP VSGAAQWAPV LDFAPPGASA
121 YGSLGGPAPP PAPPPPPPPP PHSFIKQEPS WGGAEPHEEQ CLSAFTVHFS GQFTGTAGAC
181 RYGPFGPPPP SQASSGQARM FPNAPYLPSC LESQPAIRNQ GYSTVTFDGT PSYGHTPSHH
241 AAQFPNHSFK HEDPMGQQGS LGEQQYSVPP PVYGCHTPTD SCTGSQALLL RTPYSSDNLY
301 QMTSQLECMT WNQMNLGATL KGVAAGSSSS VKWTEGQSNH STGYESDNHT TPILCGAQYR
361 IHTHGVFRGI QDVRRVPGVA PTLVRSASET SEKRPFMCAY PGCNKRYFKL SHLQMHSRKH
421 TGEKPYQCDF KDCERRFSRS DQLKRHQRRH TGVKPFQCKT CQRKFSRSDH LKTHTRTHTG
481 KTSEKPFSCR WPSCQKKFAR SDELVRHHNM HQRNMTKLQL AL
```

FIG. 3D

WT-1 isoform E

```
  1 MEKGYSTVTF DGTPSYGHTP SHHAAQFPNH SFKHEDPMGQ QGSLGEQQYS VPPPVYGCHT
 61 PTDSCTGSQA LLLRTPYSSD NLYQMTSQLE CMTWNQMNLG ATLKGVAAGS SSSVKWTEGQ
121 SNHSTGYESD NHTTPILCGA QYRIHTHGVF RGIQDVRRVP GVAPTLVRSA SETSEKRPFM
181 CAYPGCNKRY FKLSHLQMHS RKHTGEKPYQ CDFKDCERRF SRSDQLKRHQ RRHTGVKPFQ
241 CKTCQRKFSR SDHLKTHTRT HTGEKPFSCR WPSCQKKFAR SDELVRHHNM HQRNMTKLQL
301 AL
```

FIG. 3E

WT-1 isoform F

```
  1 MEKGYSTVTF DGTPSYGHTP SHHAAQFPNH SFKHEDPMGQ QGSLGEQQYS VPPPVYGCHT
 61 PTDSCTGSQA LLLRTPYSSD NLYQMTSQLE CMTWNQMNLG ATLKGHSTGY ESDNHTTPIL
121 CGAQYRIHTH GVFRGIQDVR RVPGVAPTLV RSASETSEKR PFMCAYPGCN KRYFKLSHLQ
181 MHSRKHTGEK PYQCDFKDCE RRFSRSDQLK RHQRRHTGVK PFQCKTCQRK FSRSDHLKTH
241 TRTHTGKTSE KPFSCRWPSC QKKFARSDEL VRHHNMHQRN MTKLQLAL
```

FIG. 4A

Construct 3158

GSHSMRYFSTSVSRPGRGEPRFIAVGYVDDTQFVRFDSDAASQRMEPRAPWIEQE
GPEYWDEETGKVKAHSQTDRENLRIALRAYNQSEAGSHTLQMMFGCDVGSDGR
FLRGYHQYAYDGKDYIALKEDLRSWTAADMAAQITKRKWEAAHVAEQQRAYL
EGTCVDGLRRYLENGKETLQRTDPPKTHMTHHPISDHEATLRCWALGFYPAEITL
TWQRDGEDQTQDTELVETRPCGDGTFQKWAAVVVPSGEEQRYTCHVQHEGLP
KPLTLRWEGGGGSGGGGSGGGGS**APTSSSTKKTQLQLEALLLDLQMILNGIN
NYKNPKLTRMLTAKFYMPKKATELKHLQCLEEELKPLEEVLNLAQSKNFH
LRPRDLISNINVIVLELKGSETTFMCEYADETATIVEFLNRWITFCQSIISTLT**G
GGGSGGGGSGGGGSGGGGS**APTSSSTKKTQLQLEALLLDLQMILNGINNYKN
PKLTRMLTAKFYMPKKATELKHLQCLEEELKPLEEVLNLAQSKNFHLRPR
DLISNINVIVLELKGSETTFMCEYADETATIVEFLNRWITFCQSIISTLT**GGGGS
GGGGSGGGGS*DKTHTCPPCPAPEAAGGPSVFLFPPKPKDTLMISRTPEVTCVVVDVS
HEDPEVKFNWYVDGVEVHNAKTKPREEQYNSTYRVVSVLTVLHQDWLNGKEYKCKV
SNKALPAPIEKTISKAKGQPREPQVYTLPPSREEMTKNQVSLTCLVKGFYPSDIAVEWE
SNGQPENNYKTTPPVLDSDGSFFLYSKLTVDKSRWQQGNVFSCSVMHEALHNHYTQK
SLSLSPG* (SEQ ID NO:405)

HLA-A*24:02 – double underlined
(G4S)3 and (G4S)4 – underlined (SEQ ID NOs:379-380)
IL-2 (H16A; F42A) – bold
Human IgG1 Fc (LALA) – italicized

FIG. 4B

Construct 2750

APTSSSTKKTQLQLEALLLDLQMILNGINNYKNPKLTRMLTAKFYMPKKATELKHLQCLEEELKPLEEVLNLAQSKNFHLRPRDLISNINVIVLELKGSETTFMCEYADETATIVEFLNRWITFCQSIISTLT*GGGGSGGGGSGGGGSGGGGS*APTSSSTKKTQLQLEALLLDLQMILNGINNYKNPKLTRMLTAKFYMPKKATELKHLQCLEEELKPLEEVLNLAQSKNFHLRPRDLISNINVIVLELKGSETTFMCEYADETATIVEFLNRWITFCQSIISTLT***GGGGSGGGGSGGGGSGGGGS*GSHSMRYFSTSVSRPGRGEPRFIAVGYVDDTQFVRFDSDAASQRMEPRAPWIEQEGPEYWDEETGKVKAHSQTDRENLRIALRAYNQSEAGSHTLQMMFGCDVGSDGRFLRGYHQYAYDGKDYIALKEDLRSWTAADMAAQITKRKWEAAHVAEQQRAYLEGTCVDGLRRYLENGKETLQRTDPPKTHMTHHPISDHEATLRCWALGFYPAEITLTWQRDGEDQTQDTELVETRPCGDGTFQKWAAVVVPSGEEQRYTCHVQHEGLPKPLTLRWE***AAAGG*DKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK**** (SEQ ID NO:406)

IL2(H16A; F42A) – bold
(G4S)4 linker – italicized (SEQ ID NO:380)
HLA-A*2402 (Y84A; A236C) – double underlined
AAAGG linker – bold and italicized (SEQ ID NO:283)
hIgG1 Fc (L234A; L235A) – bold and underlined

FIG. 4C

Construct 3159

GSHSMRYFSTSVSRPGRGEPRFIAVGYVDDTQFVRFDSDAASQRMEPRAPWIEQE
GPEYWDEETGKVKAHSQTDRENLRIALRAYNQSEAGSHTLQMMFGCDVGSDGR
FLRGYHQYAYDGKDYIALKEDLRSWTAADMAAQITKRKWEAAHVAEQQRAYL
EGTCVDGLRRYLENGKETLQRTDPPKTHMTHHPISDHEATLRCWALGFYPAEITL
TWQRDGEDQTQDTELVETRPCGDGTFQKWAAVVVPSGEEQRYTCHVQHEGLP
KPLTLRWEAAAGG*DKTHTCPPCPAPEAAGGPSVFLFPPKPKDTLMISRTPEVTCVV*
*VDVSHEDPEVKFNWYVDGVEVHNAKTKPREEQYNSTYRVVSVLTVLHQDWLNGKEY*
*KCKVSNKALPAPIEKTISKAKGQPREPQVYTLPPSREEMTKNQVSLTCLVKGFYPSDIA*
*VEWESNGQPENNYKTTPPVLDSDGSFFLYSKLTVDKSRWQQGNVFSCSVMHEALHN*
*HYTQKSLSLSPG*GGGGSGGGGSGGGGSAPTSSSTKKTQLQLEALLLDLQMILN
GINNYKNPKLTRMLTAKFYMPKKATELKHLQCLEEELKPLEEVLNLAQSK
NFHLRPRDLISNINVIVLELKGSETTFMCEYADETATIVEFLNRWITFCQSIIS
TLTGGGGSGGGGSGGGGSGGGGSAPTSSSTKKTQLQLEALLLDLQMILNGIN
NYKNPKLTRMLTAKFYMPKKATELKHLQCLEEELKPLEEVLNLAQSKNFH
LRPRDLISNINVIVLELKGSETTFMCEYADETATIVEFLNRWITFCQSIISTLT
(SEQ ID NO:407)

HLA-A*24:02 – double underlined
Human IgG1 Fc (LALA) – italicized
$(G4S)_3$ and $(G4S)_4$ – underlined (SEQ ID NOs:379-380)
IL-2 (H16A; F42A) – bold

FIG. 4D

Construct 2752

CMTWNQMNLGGGGSGGGGSGGGGS*IQRTPKIQVYSCHPAENGKSNFLNCYVSGFHPSDI*
*EVDLLKNGERIEKVEHSDLSFSKDWSFYLLYYTEFTPTEKDEYACRVNHVTLSQPKIVK*
*WDRDM* (SEQ ID NO:408)

epitope: CMTWNQMNL – WT1 (235-243) (SEQ ID NO:266)
(G4S)3 – underlined (SEQ ID NO:379)
β2M (R12C) – italicized

FIG. 4E

Construct 2753

CYTWNQMNLGGGGSGGGGSGGGGS*IQRTPKIQVYSCHPAENGKSNFLNCYVSGFHPSDIE*
*VDLLKNGERIEKVEHSDLSFSKDWSFYLLYYTEFTPTEKDEYACRVNHVTLSQPKIVKW*
*DRDM* (SEQ ID NO:409)

epitope: CYTWNQMNL – WT1 (235-243) (SEQ ID NO:267)
(G4S)3 – underlined (SEQ ID NO:379)
β2M (R12C) – italicized

FIG. 5A

GenBank 3S7G_A
*Homo sapiens* IgG1 Fc
227 aa

```
  1 dkthtcppcp apellggpsv flfppkpkdt lmisrtpevt cvvvdvshed pevkfnwyvd
 61 gvevhnaktk preeqynsty rvvsvltvlh qdwlngkeyk ckvsnkalpa piektiskak
121 gqprepqvyt lppsrdeltk nqvsltclvk gfypsdiave wesngqpenn ykttppvlds
181 dgsfflyskl tvdksrwqqg nvfscsvmhe alhnhytqks lslspgk
```

GenBank AAN76044
*Homo sapiens* IgG2 Fc (amino acids 99-325)
227 aa

```
  1 stkgpsvfpl apcsrstses taalgclvkd yfpepvtvsw nsgaltsgvh tfpavlqssg
 61 lyslssvvtv pssnfgtqty tcnvdhkpsn tkvdktverk ccvecppcpa ppvagpsvfl
121 fppkpkdtlm isrtpevtcv vvdvshedpe vqfnwyvdgv evhnaktkpr eeqfnstfrv
181 vsvltvvhqd wlngkeykck vsnkglpapi ektisktkgq prepqvytlp psreemtknq
241 vsltclvkgf ypsdiavewe sngqpennyk ttppmldsdg sfflyskltv dksrwqqgnv
301 fscsvmheal hnhytqksls lspgk
```

GenBank AAW65947
*Homo sapiens* IgG3 Fc (amino acids 19-246)
238 aa

```
  1 hkpsntkvdk rvelktplgd tthtcppcpa pellggpsvf lfppkpkdtl misrtpevtc
 61 vvvdvshedp evkfnwyvdg vevhnaktkp reeqynstyr vvsvltvlhq dwlngkeykc
121 kvsnkalpap iektiskakg qprepqvytl ppsrdeltkn qvsltclvkg fypsdiavew
181 esngqpenny kttppvldsd gsfflysklt vdksrwqqgn vfscsvmhea lhnhytqksl
241 slspgk
```

FIG. 5B

GenBank AAA52770
*Homo sapiens* IgD Fc (amino acids 162-383)
222 aa

```
  1 ptkapdvfpi isgcrhpkdn spvvlaclit gyhptsvtvt wymgtqsqpq rtfpeiqrrd
 61 syymtssqls tplqqwrqge ykcvvqhtas kskkeifrwp espkaqassv ptaqpqaegs
121 lakattapat trntgrggee kkkekekeeq eeretktpec pshtqplgvy lltpavqdlw
181 lrdkatftcf vvgsdlkdah ltwevagkvp tggveeglle rhsngsqsqh srltlprslw
241 nagtsvtctl nhpslppqrl malrepaaqa pvklslnlla ssdppeaasw llcevsgfsp
301 pnillmwled qrevntsgfa parpppqprs ttfwawsvlr vpappspqpa tytcvvshed
361 srtllnasrs levsyvtdhg pmk
```

GenBank 0308221A
*Homo sapiens* IgM Fc
276 aa

```
  1 vtstltikzs dwlgesmftc rvdhrgltfq qnassmcvpd qdtairvfai ppsfasiflt
 61 kstkltclvt dlttybsvti swtreengav kthtnisesh pnatfsavge asicedbdws
121 gerftctvth tdlpsplkqt isrpkgvalh rpbvyllppa rzzlnlresa titclvtgfs
181 padvfvewmq rgeplspqky vtsapmpepq apgryfahsi ltvseeewnt ggtytcvvah
241 ealpnrvter tvdkstgkpt lynvslvmsd tagtcy
```

FIG. 5C

GenBank P01876
*Homo sapiens* IgA Fc (amino acids 120-353)
234 aa

```
  1 asptspkvfp lslcstqpdg nvviaclvqg ffpqeplsvt wsesgqgvta rnfppsqdas
 61 gdlyttssql tlpatqclag ksvtchvkhy tnpsqdvtvp cpvpstpptp spstpptpsp
121 scchprlslh rpaledlllg seanltctlt glrdasgvtf twtpssgksa vqgpperdlc
181 gcysvssvlp gcaepwnhgk tftctaaype sktpltatls ksgntfrpev hllpppseel
241 alnelvtltc largfspkdv lvrwlqgsqe lprekyltwa srqepsqgtt tfavtsilrv
301 aaedwkkgdt fscmvgheal plaftqktid rlagkpthvn vsvvmaevdg tcy
```

GenBank 1F6A_B
*Homo sapiens* IgE Fc (amino acids 6-222)
212 aa

```
  1 adpcdsnprg vsaylsrpsp fdlfirkspt itclvvdlap skgtvnltws rasgkpvnhs
 61 trkeekqrng tltvtstlpv gtrdwieget yqcrvthphl pralmrsttk tsgpraapev
121 yafatpewpg srdkrtlacl iqnfmpedis vqwlhnevql pdarhsttqp rktkgsgffv
181 fsrlevtrae weqkdeficr avheaaspsq tvqravsvnp gk
```

GenBank P01861
*Homo sapiens* IgG4 Fc (amino acids 100-327)
228 aa

```
  1 astkgpsvfp lapcsrstse staalgclvk dyfpepvtvs wnsgaltsgv htfpavlqss
 61 glyslssvvt vpssslgtkt ytcnvdhkps ntkvdkrves kygppcpscp apeflggpsv
121 flfppkpkdt lmisrtpevt cvvvdvsqed pevqfnwyvd gvevhnaktk preeqfnsty
181 rvvsvltvlh qdwlngkeyk ckvsnkglps siektiskak gqprepqvyt lppsqeemtk
241 nqvsltclvk gfypsdiave wesngqpenn ykttppvlds dgsfflysrl tvdksrwqeg
301 nvfscsvmhe alhnhytqks lslslgk
```

FIG. 5D

WT Human IgG1 Fc Sequence:
DKTHTCPPCPAPELLGGPSVFLFPPKPKDTLMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYTLPPSREEMTKNQVSLTCLVKGFYPSDIAVEW
ESNGQPENNYKTTPPVLDSDGSFFLYSKLTVDKSRWQQGNVFSCSVMHEALHNHYTQKSLSLSPGK

FIG. 5E

Human IgG1 Fc Mutant: L234F/L235E/P331S (Triple Mutant "TM")
DKTHTCPPCPAPEFEGGPSVFLFPPKPKDTLMISRTPEVTCVVVDVSHEDPEVKFNWYVDGVEVHNAKTKPREEQYNSTY
RVVSVLTVLHQDWLNGKEYKCKVSNKALPASIEKTISKAKGQPREPQVYTLPPSREEMTKNQVSLTCLVKGFYPSDIAVEW
ESNGQPENNYKTTPPVLDSDGSFFLYSKLTVDKSRWQQGNVFSCSVMHEALHNHYTQKSLSLSPGK

FIG. 5F

Human IgG1 Fc Mutant: N297A
DKTHTCPPCPAPELLGGPSVFLFPPKPKDTLMISRTPEVTCVVVDVSHEDPEVKFNWYVDGVEVHNAKTKPREEQYASTY
RVVSVLTVLHQDWLNGKEYKCKVSNKALPAPIEKTISKAKGQPREPQVYTLPPSREEMTKNQVSLTCLVKGFYPSDIAVEW
ESNGQPENNYKTTPPVLDSDGSFFLYSKLTVDKSRWQQGNVFSCSVMHEALHNHYTQKSLSLSPGK

FIG. 5G

Human IgG1 Fc Mutant: L234A/L235A ("LALA")
DKTHTCPPCPAPEAAGGPSVFLFPPKPKDTLMISRTPEVTCVVVDVSHEDPEVKFNWYVDGVEVHNAKTKPREEQYNST
YRVVSVLTVLHQDWLNGKEYKCKVSNKALPAPIEKTISKAKGQPREPQVYTLPPSREEMTKNQVSLTCLVKGFYPSDIAVE
WESNGQPENNYKTTPPVLDSDGSFFLYSKLTVDKSRWQQGNVFSCSVMHEALHNHYTQKSLSLSPGK Residue numbered according to EU index (Kabat Numbering)

FIG. 5H

<u>Human IgG1 Fc Mutant: L234A/L235A ("LALA") without C-terminal Lys</u>

DKTHTCPPCPAPE<u>AA</u>GGPSVFLFPPKPKDTLMISRTPEVTCVVVDVSHEDPEV
KFNWYVDGVEVHNAKTKPREEQYNSTYRVVSVLTVLHQDWLNGKEYKCKVSN
KALPAPIEKTISKAKGQPREPQVYTLPPSREEMTKNQVSLTCLVKGFYPSDIAVE
WESNGQPENNYKTTPPVLDSDGSFFLYSKLTVDKSRWQQGNVFSCSVMHEAL
HNHYTQKSLSLSPG

FIG. 6

```
NP_004039.1    msrsvalavlallslsgleaiqrtpkiqvysrhpaengksnflncyvsgfhpsdievdll 60
NP_001009066.1 msrsvalavlallslsgleaiqrtpkiqvysrhpaengksnflncyvsgfhpsdievdll 60
NP_001040602.1 msrsvalavlallslsgleaiqrtpkiqvysrhppengkpnflncyvsgfhpsdievdll 60
NP_776318.1    marfvalvllgllslsgldaiqrppkiqvysrhppedgkpnylncyvygfhppqieidll 60
NP_033865.2    marsvtlvflvlvsltglyaiqktpqiqvysrhppengkpnilncyvtqfhpphieiqml 60
               *:* *:*..* *:**:** ***: *:******** *:** * *****  *** .**:::*

NP_004039.1    kngeriekvehsdlsfskdwsfyllyyteftptekdeyacrvnhvtlsqpkivkwdrdm 119
NP_001009066.1 kngeriekvehsdlsfskdwsfyllyyteftptekdeyacrvnhvtlsqpkivkwdrdm 119
NP_001040602.1 kngekmgkvehsdlsfskdwsfyllyyteftpnekdeyacrvnhvtlsgprtvkwdrdm 119
NP_776318.1    kngekik-seqsdlsfskdwsfyllshaeftpnskdqyscrvkhvtleqprivkwdrdl 118
NP033865       kngkkipkvemsdmsfskdwsfyilahteftptetdtyacrvkhasmaepktvywdrdm 119
               ***:::   * **:*********:* ::****...* *:***:*.::  *: * ****:
```

FIG. 7A

*Homo sapiens* HLA-A

**5A.1 HLA-A*01:01:01:01 NCBI (National Center for Biotechnology Information) Accession NP_001229687.1**

(SEQ ID NO://)

1 MAVMAPRTLL LLLSGALALT QTWAGSHSMR YFFTSVSRPG RGEPRFIAVG YVDDTQFVRF
61 DSDAASQKME PRAPWIEQEG PEYWDQETRN MKAHSQTDRA NLGTLRGYYN QSEDGSHTIQ
121 IMYGCDVGPD GRFLRGYRQD AYDGKDYIAL NEDLRSWTAA DMAAQITKRK WEAVHAAEQR
181 RVYLEGRCVD GLRRYLENGK ETLQRTDPPK THMTHHPISD HEATLRCWAL GFYPAEITLT
241 WQRDGEDQTQ DTELVETRPA GDGTFQKWAA VVVPSGEEQR YTCHVQHEGL PKPLTLRWEL
301 SSQPTIPIVG IIAGLVLLGA VITGAVVAAV MWRRKSSDRK GGSYTQAASS DSAQGSDVSL
361 TACKV (SEQ ID NO: 23)

**5A.2 HLA-A*1101 NCBI Accession P13746.1**

1 MAVMAPRTLL LLLSGALALT QTWAGSHSMR YFYTSVSRPG RGEPRFIAVG YVDDTQFVRF
61 DSDAASQRME PRAPWIEQEG PEYWDQETRN VKAQSQTDRV DLGTLRGYYN QSEDGSHTIQ
121 IMYGCDVGPD GRFLRGYRQD AYDGKDYIAL NEDLRSWTAA DMAAQITKRK WEAAHAAEQQ
181 RAYLEGRCVE WLRRYLENGK ETLQRTDPPK THMTHHPISD HEATLRCWAL GFYPAEITLT
241 WQRDGEDQTQ DTELVETRPA GDGTFQKWAA VVVPSGEEQR YTCHVQHEGL PKPLTLRWEL
301 SSQPTIPIVG IIAGLVLLGA VITGAVVAAV MWRRKSSDRK GGSYTQAASS DSAQGSDVSL
361 TACKV (SEQ ID NO: 24)

**5A.3 HLA-A*2402 NCBI Accession P05534.2**

1 MAVMAPRTLV LLLSGALALT QTWAGSHSMR YFSTSVSRPG RGEPRFIAVG YVDDTQFVRF
61 DSDAASQRME PRAPWIEQEG PEYWDEETGK VKAHSQTDRE NLRIALRYYN QSEAGSHTLQ
121 MMFGCDVGSD GRFLRGYHQY AYDGKDYIAL KEDLRSWTAA DMAAQITKRK WEAAHVAEQQ
181 RAYLEGTCVD GLRRYLENGK ETLQRTDPPK THMTHHPISD HEATLRCWAL GFYPAEITLT
241 WQRDGEDQTQ DTELVETRPA GDGTFQKWAA VVVPSGEEQR YTCHVQHEGL PKPLTLRWEP
301 SSQPTVPIVG IIAGLVLLGA VITGAVVAAV MWRRNSSDRK GGSYSQAASS DSAQGSDVSL
361 TACKV (SEQ ID NO: 25)

**5A.4 HLA-A*3303 NCBI Accession AAA79865.1**

1 MAVMAPRTLL LLLLGALALT QTWAGSHSMR YFTTSVSRPG RGEPRFIAVG YVDDTQFVRF
61 DSDAASQRME PRAPWIEQEG PEYWDRNTRN VKAHSQIDRV DLGTLRGYYN QSEAGSHTIQ
121 MMYGCDVGSD GRFLRGYQQD AYDGKDYIAL NEDLRSWTAA DMAAQITQRK WEAARVAEQL
181 RAYLEGTCVE WLRRYLENGK ETLQRTDPPK THMTHHAVSD HEATLRCWAL SFYPAEITLT
241 WQRDGEDQTQ DTELVETRPA GDGTFQKWAS VVVPSGQEQR YTCHVQHEGL PKPLTLRWEP
301 SSQPTIPIVG IIAGLVLFGA VFAGAVVAAV RWRRKSSDRK GGSYSQAASS DSAQGSDMSL
361 TACKV (SEQ ID NO: 26)

FIG. 7B

*Homo sapiens* HLA-B*07:02:01 HLA-B GenBank Accession NP_005505.2

```
  1 mlvmaprtvl lllsaalalt etwagshsmr yfytsvsrpg rgeprfisvg yvddtqfvrf
 61 dsdaaspree prapwieqeg peywdrntqi ykaqaqtdre slrnlrgyyn qseagshtlq
121 smygcdvgpd grllrghdqy aydgkdyial nedlrswtaa dtaaqitqrk weaareaeqr
181 raylegecve wlrrylengk dkleradppk thvthhpisd heatlrcwal gfypaeitlt
241 wqrdgedqtq dtelvetrpa gdrtfqkwaa vvvpsgeeqr ytchvqhegl pkpltlrwep
301 ssqstvpivg ivaglavlav vvigavvaav mcrrkssggk ggsysqaacs dsaqgsdvsl
361 ta  (SEQ ID NO: 27)
```

FIG. 7C

*Homo sapiens* HLA-C
HLA-C GenBank Accession NP_001229971.1,

```
  1 mrvmaprall lllsgglalt etwacshsmr yfdtavsrpg rgeprfisvg yvddtqfvrf
 61 dsdaasprge prapwveqeg peywdretqn ykrqaqadrv slrnlrgyyn qsedgshtlq
121 rmygcdlgpd grllrgydqs aydgkdyial nedlrswtaa dtaaqitqrk leaaraaeql
181 raylegtcve wlrrylengk etlqraeppk thvthhplsd heatlrcwal gfypaeitlt
241 wqrdgedqtq dtelvetrpa gdgtfqkwaa vvvpsgqeqr ytchmqhegl qepltlswep
301 ssqptipimg ivaglavlvv lavlgavvta mmcrrkssgg kggscsqaac snsaqgsdes
361 litck  (SEQ ID NO: 28)
```

FIG. 8

```
HLA-A            GSHSMRYFFTSVSRPGRGEPRFIAVGYVDDTQFVRFDSDAASQKMEPRAPWIEQEGPEYW
HLA-B            GSHSMRYFYTSVSRPGRGEPRFISVGYVDDTQFVRFDSDAASPREEPRAPWIEQEGPEYW
HLA-C            CSHSMRYFDTAVSRPGRGEPRFISVGYVDDTQFVRFDSDAASPRGEPRAPWVEQEGPEYW
HLA-A*0201       GSHSMRYFFTSVSRPGRGEPRFIAVGYVDDTQFVRFDSDAASQRMEPRAPWIEQEGPEYW
Mouse H2K        GPHSLRYFVTAVSRPGLGEPRFIAVGYVDDTQFVRFDSDADNPRFEPRAPWMEQEGPEYW
HLA_A(var. 2)    GSHSMRYFFTSVSRPGRGEPRFIAVGYVDDTQFVRFDSDAASQRMEPRAPWIEQEGPEYW
HLA_A(var. 2C)   GSHSMRYFFTSVSRPGRGEPRFIAVGYVDDTQFVRFDSDAASQRMEPRAPWIEQEGPEYW
HLA-A(var.2CP)   GSHSMRYFFTSVSRPGRGEPRFIAVGYVDDTQFVRFDSDAASQRMEPRAPWIEQEGPEYW
HLA-A*1101       GSHSMRYFYTSVSRPGRGEPRFIAVGYVDDTQFVRFDSDAASQRMEPRAPWIEQEGPEYW
HLA-A*2402       GSHSMRYFSTSVSRPGRGEPRFIAVGYVDDTQFVRFDSDAASQRMEPRAPWIEQEGPEYW
HLA-A*3303       GSHSMRYFTTSVSRPGRGEPRFIAVGYVDDTQFVRFDSDAASQRMEPRAPWIEQEGPEYW
                  **:*** *:***** ******:***************  . : ******:********

                                        84
                                        ↓
HLA-A            DQETRNMKAHSQTDRANLGTLRGYYNQSEDGSHTIQIMYGCDVGPDGRFLRGYRQDAYDG
HLA-B            DRNTQIYKAQAQTDRESLRNLRGYYNQSEAGSHTLQSMYGCDVGPDGRLLRGHDQYAYDG
HLA-C            DRETQNYKRQAQADRVSLRNLRGYYNQSEDGSHTLQRMYGCDLGPDGRLLRGYDQSAYDG
HLA-A*0201       DGETRKVKAHSQTHRVDLGTLRGYYNQSEAGSHTVQRMYGCDVGSDWRFLRGYHQYAYDG
MOUSE H2K        EEQTQRAKSDEQWFRVSLRTAQRYYNQSKGGSHTFQRMFGCDVGSDWRLLRGYQQFAYDG
HLA_A(var. 2)    DGETRKVKAHSQTHRVDLGTLRGAYNQSEAGSHTVQRMYGCDVGSDWRFLRGYHQYAYDG
HLA_A(var. 2C)   DGETRKVKAHSQTHRVDLGTLRGCYNQSEAGSHTVQRMYGCDVGSDWRFLRGYHQYAYDG
HLA-A(var.2CP)   DGETRKVKAHSQTHRVDLGTLRGAYNQSEAGSHTVQRMYGCDVGSDWRFLRGYHQYAYDG
HLA-A*1101       DQETRNVKAQSQTDRVDLGTLRGYYNQSEDGSHTIQIMYGCDVGPDGRFLRGYRQDAYDG
HLA-A*2402       DEETGKVKAHSQTDRENLRIALRYYNQSEAGSHTLQMMFGCDVGSDGRFLRGYHQYAYDG
HLA-A*3303       DRNTRNVKAHSQIDRVDLGTLRGYYNQSEAGSHTIQMMYGCDVGSDGRFLRGYQQDAYDG
                 : :*   *  .  *  *  .*      ****:  ****.* *:***:* * *:***: * ****
                                   aac1    aac2

                               139
                                ↓
HLA-A            KDYIALNEDLRSWTAADMAAQITKRKWEAVHAAEQRRVYLEGRCVDGLRRYLENGKETLQ
HLA-B            KDYIALNEDLRSWTAADTAAQITQRKWEAAREAEQRRAYLEGECVEWLRRYLENGKDKLE
HLA-C            KDYIALNEDLRSWTAADTAAQITQRKLEAARAAEQLRAYLEGTCVEWLRRYLENGKETLQ
HLA-A*0201       KDYIALKEDLRSWTAADMAAQTTKHKWEAAHVAEQLRAYLEGTCVEWLRRYLENGKETLQ
MOUSE H2K        RDYIALNEDLKTWTAADTAALITRRKWEQAGDAEYYRAYLEGECVEWLRRYLELGNETLL
HLA_A(var. 2)    KDYIALKEDLRSWTAADMAAQTTKHKWEAAHVAEQLRAYLEGTCVEWLRRYLENGKETLQ
HLA_A(var. 2C)   KDYIALKEDLRSWTAADMCAQTTKHKWEAAHVAEQLRAYLEGTCVEWLRRYLENGKETLQ
HLA-A(var.2CP)   KDYIALKEDLRSWTAADMAAQTTKHKWEAAHVAEQLRAYLEGTCVEWLRRYLENGKETLQ
HLA-A*1101       KDYIALNEDLRSWTAADMAAQITKRKWEAAHAAEQQRAYLEGRCVEWLRRYLENGKETLQ
HLA-A*2402       KDYIALKEDLRSWTAADMAAQITKRKWEAAHVAEQQRAYLEGTCVDGLRRYLENGKETLQ
HLA-A*3303       KDYIALNEDLRSWTAADMAAQITQRKWEAARVAEQLRAYLEGTCVEWLRRYLENGKETLQ
                 :*****:***::*****  *  *::* *  .  **  *.**** **: ****** *:.:*
                             aac3   aac4
```

FIG. 8 (Cont.)

```
                                                                        236
HLA-A            RTDPPKTHMTHHPISDHEATLRCWALGFYPAEITLTWQRDGEDQTQDTELVETRPAGDGTF
HLA-B            RADPPKTHVTHHPISDHEATLRCWALGFYPAEITLTWQRDGEDQTQDTELVETRPAGDRTF
HLA-C            RAEPPKTHVTHHPLSDHEATLRCWALGFYPAEITLTWQRDGEDQTQDTELVETRPAGDGTF
HLA-A*0201       RTDAPKTHMTHHAVSDHEATLRCWALSFYPAEITLTWQRDGEDQTQDTELVETRPAGDGTF
MOUSE H2K        RTDSPKAHVTYHPRSQVDVTLRCWALGFYPADITLTWQLNGEDLTQDMELVETRPAGDGTF
HLA_A(var. 2)    RTDAPKTHMTHHAVSDHEATLRCWALSFYPAEITLTWQRDGEDQTQDTELVETRPCGDGTF
HLA_A(var. 2C)   RTDAPKTHMTHHAVSDHEATLRCWALSFYPAEITLTWQRDGEDQTQDTELVETRPCGDGTF
HLA-A(var.2CP)   RTDAPKTHMTHHAVSDHEATLRCWALSFYPAEITLTWQRDGEDQTQDTELVETRPCGDGTF
HLA-A*1101       RTDPPKTHMTHHPISDHEATLRCWALGFYPAEITLTWQRDGEDQTQDTELVETRPAGDGTF
HLA-A*2402       RTDPPKTHMTHHPISDHEATLRCWALGFYPAEITLTWQRDGEDQTQDTELVETRPAGDGTF
HLA-A*3303       RTDPPKTHMTHHAVSDHEATLRCWALSFYPAEITLTWQRDGEDQTQDTELVETRPAGDGTF
                 *:: **:*:*:*  *: :.*******.****:****** :*** *** ********.** **
                                                                  aac5   aac6

HLA-A            QKWAAVVVPSGEEQRYTCHVQHEGLPKPLTLRWE (SEQ ID NO://)
HLA-B            QKWAAVVVPSGEEQRYTCHVQHEGLPKPLTLRWE (SEQ ID NO://)
HLA-C            QKWAAVVVPSGQEQRYTCHMQHEGLQEPLTLSWE (SEQ ID NO://)
HLA-A*0201       QKWAAVVVPSGQEQRYTCHVQHEGLPKPLTLRWEP (SEQ ID NO://)
MOUSE H2K        QKWAAVVVPLGKEQNYTCHVHHKGLPEPLTLRW (SEQ ID NO://)
HLA_A(var. 2)    QKWAAVVVPSGQEQRYTCHVQHEGLPKPLTLRWE (SEQ ID NO://)
HLA_A(var. 2C)   QKWAAVVVPSGQEQRYTCHVQHEGLPKPLTLRWE (SEQ ID NO://)
HLA-A(var.2CP)   QKWAAVVVPSGQEQRYTCHVQHEGLPKPLTLRWEP (SEQ ID NO://)
HLA-A*1101       QKWAAVVVPSGEEQRYTCHVQHEGLPKPLTLRWEL (SEQ ID NO://)
HLA-A*2402       QKWAAVVVPSGEEQRYTCHVQHEGLPKPLTLRWEP (SEQ ID NO://)
HLA-A*3303       QKWASVVVPSGQEQRYTCHVQHEGLPKPLTLRWEP (SEQ ID NO://)
                 ****:**** *:**.****::*:** :**** *
```

FIG. 9A

```
A*0101   GSHSMRYFFTSVSRPGRGEPRFIAVGYVDDTQFVRFDSDAASQKMEPRAPWIEQEGPEYW   60
A*0201   GSHSMRYFFTSVSRPGRGEPRFIAVGYVDDTQFVRFDSDAASQRMEPRAPWIEQEGPEYW   60
A*0301   GSHSMRYFFTSVSRPGRGEPRFIAVGYVDDTQFVRFDSDAASQRMEPRAPWIEQEGPEYW   60
A*1101   GSHSMRYFYTSVSRPGRGEPRFIAVGYVDDTQFVRFDSDAASQRMEPRAPWIEQEGPEYW   60
A*2301   GSHSMRYFSTSVSRPGRGEPRFIAVGYVDDTQFVRFDSDAASQRMEPRAPWIEQEGPEYW   60
A*2402   GSHSMRYFSTSVSRPGRGEPRFIAVGYVDDTQFVRFDSDAASQRMEPRAPWIEQEGPEYW   60
A*2407   GSHSMRYFSTSVSRPGRGEPRFIAVGYVDDTQFVRFDSDAASQRMEPRAPWIEQEGPEYW   60
A*3303   GSHSMRYFTTSVSRPGRGEPRFIAVGYVDDTQFVRFDSDAASQRMEPRAPWIEQEGPEYW   60
A*3401   GSHSMRYFYTSVSRPGRGEPRFIAVGYVDDTQFVRFDSDAASQRMEPRAPWIEQEGPEYW   60
         ******** **********************************:****************

                                  84
A*0101   DQETRNMKAHSQTDRANLGTLRGYYNQSEDGSHTIQIMYGCDVGPDGRFLRGYRQDAYDG   120
A*0201   DGETRKVKAHSQTHRVDLGTLRGYYNQSEAGSHTVQRMYGCDVGSDWRFLRGYHQYAYDG   120
A*0301   DQETRNVKAQSQTDRVDLGTLRGYYNQSEAGSHTIQIMYGCDVGSDGRFLRGYRQDAYDG   120
A*1101   DQETRNVKAQSQTDRVDLGTLRGYYNQSEDGSHTIQIMYGCDVGPDGRFLRGYRQDAYDG   120
A*2301   DEETGKVKAHSQTDRENLRIALRYYNQSEAGSHTLQMMFGCDVGSDGRFLRGYHQYAYDG   120
A*2402   DEETGKVKAHSQTDRENLRIALRYYNQSEAGSHTLQMMFGCDVGSDGRFLRGYHQYAYDG   120
A*2407   DEETGKVKAQSQTDRENLRIALRYYNQSEAGSHTLQMMFGCDVGSDGRFLRGYHQYAYDG   120
A*3303   DRNTRNVKAHSQIDRVDLGTLRGYYNQSEAGSHTIQMMYGCDVGSDGRFLRGYQQDAYDG   120
A*3401   DRNTRKVKAQSQTDRVDLGTLRGYYNQSEDGSHTIQRMYGCDVGPDGRFLRGYQQDAYDG   120
         * :* ::**:** .* :*     ****** ****:* *:***** * ******:* ****
                             aac1  aac2

                        139
A*0101   KDYIALNEDLRSWTAADMAAQITKRKWEAVHAAEQRRVYLEGRCVDGLRRYLENGKETLQ   180
A*0201   KDYIALKEDLRSWTAADMAAQTTKHKWEAAHVAEQLRAYLEGTCVEWLRRYLENGKETLQ   180
A*0301   KDYIALNEDLRSWTAADMAAQITKRKWEAAHEAEQLRAYLDGTCVEWLRRYLENGKETLQ   180
A*1101   KDYIALNEDLRSWTAADMAAQITKRKWEAAHAAEQQRAYLEGRCVEWLRRYLENGKETLQ   180
A*2301   KDYIALKEDLRSWTAADMAAQITQRKWEAARVAEQLRAYLEGTCVDGLRRYLENGKETLQ   180
A*2402   KDYIALKEDLRSWTAADMAAQITKRKWEAAHVAEQQRAYLEGTCVDGLRRYLENGKETLQ   180
A*2407   KDYIALKEDLRSWTAADMAAQITKRKWEAAHVAEQQRAYLEGTCVDGLRRYLENGKETLQ   180
A*3303   KDYIALNEDLRSWTAADMAAQITQRKWEAARVAEQLRAYLEGTCVEWLRRYLENGKETLQ   180
A*301    KDYIALNEDLRSWTAADMAAQITQRKWETAHEAEQWRAYLEGTCVEWLRRYLENGKETLQ   180
         ******.********** *** *:.***.  .*** ..**:* **: *************
                      aac3  aac4
```

FIG. 9A (Cont.)

```
                                                                        236
A*0101   RTDPPKTHMTHHPISDHEATLRCWALGFYPAEITLTWQRDGEDQTQDTEIVETRPAGDGTF   241
A*0201   RTDAPKTHMTHHAVSDHEATLRCWALSFYPAEITLTWQRDGEDQTQDTEIVETRPAGDGTF   241
A*0301   RTDPPKTHMTHHPISDHEATLRCWALGFYPAEITLTWQRDGEDQTQDTEIVETRPAGDGTF   241
A*1101   RTDPPKTHMTHHPISDHEATLRCWALGFYPAEITLTWQRDGEDQTQDTEIVETRPAGDGTF   241
A*2301   RTDPPKTHMTHHPISDHEATLRCWALGFYPAEITLTWQRDGEDQTQDTEIVETRPAGDGTF   241
A*2402   RTDPPKTHMTHHPISDHEATLRCWALGFYPAEITLTWQRDGEDQTQDTEIVETRPAGDGTF   241
A*2407   RTDPPKTHMTHHPISDHEATLRCWALGFYPAEITLTWQRDGEDQTQDTEIVETRPAGDGTF   241
A*3303   RTDPPKTHMTHHAVSDHEATLRCWALSFYPAEITLTWQRDGEDQTQDTEIVETRPAGDGTF   241
A*3401   RTDAPKTHMTHHAVSDHEATLRCWALSFYPAEITLTWQRDGEDQTQDTEIVETRPAGDGTF   241
         *** ******** :************.**********************************
                                                            aac5  aac6

A*0101   QKWAAVVVPSGEEQRYTCHVQHEGLPKPLTLRWEL   276   (SEQ ID NO: 198)
A*0201   QKWAAVVVPSGQEQRYTCHVQHEGLPKPLTLRWEP   276   (SEQ ID NO: 44)
A*0301   QKWAAVVVPSGEEQRYTCHVQHEGLPKPLTLRWEL   276   (SEQ ID NO: 200)
A*1101   QKWAAVVPPSGEEQRYTCHVQHEGLPKPLTLRWEL   276   (SEQ ID NO: 49)
A*2301   QKWAAVVVPSGEEQRYTCHVQHEGLPKPLTLRWEP   276   (SEQ ID NO: 202)
A*2402   QKWAAVVVPSGEEQRYTCHVQHEGLPKPLTLRWEP   276   (SEQ ID NO: 50)
A*2407   QKWAAVVVPSGEEQRYTCHVQHEGLPKPLTLRWEP   276   (SEQ ID NO: 204)
A*3303   QKWASVVVPSGQEQRYTCHVQHEGLPKPLTLRWEP   276   (SEQ ID NO: 51)
A*3401   QKWASVVVPSGQEQRYTCHVQHEGLPKPLTLRWEP   276   (SEQ ID NO: 206)
         ****.******.***********************
```

FIG. 9B

GSHSMRYFX1TSVSRPGRGEPRFIAVGYVDDTQFVRFDSDAASQX2MEPRAPWIEQEGPEYWDX
3X4TX5X6X7KAX8SQX9X10RX11X12LX13X14X15X16X17YYNQSEX18GSHTX19QX20
MX21GCDVGX22DX23RFLRGYX24QX25AYDGKDYIALX26EDLRSWTAADMAAQX27TX287
X29KWEX30X31X32EAEQX33RX34YLX35GX36CVX37X38LRRYLENGKETLQRTDX39PK
THMTHHX40X41SDHEATLRCWALX42FYPAEITLTWQRDGEDQTQDTELVETRPAGDGTFQKW
AX43VVVPSGX44EQRYTCHVQHEGLPKPLTLRWEX45

X1 is F, Y, S, or T; X2 is K or R; X3 is Q, G, E, or R; X4 is N or E; X5 is R or G; X6 is N or K; X7 is M or V; X8 is H or Q; X9 is T or I; X10 is D or H; X11 is A, V, or E; X12 is N or D; X13 is G or R; X14 is T or I; X15 is L or A; X16 is R or L; X17 is G or R; X18 is A or D; X19 is I, L, or V; X20 is I, R or M; X21 is F or Y; X22 is S or P; X23 is W or G; X24 is R, H, or Q; X25 is D or Y; X26 is N or K; X27 is T or I; X28 is K or Q; X29 is R or H; X30 is A or T; X31 is A or V; X32 is H or R; X33 is R, L, Q, or W; X34 is V or A; X35 is D or E; X36 is R or T; X37 is D or E; X38 is W or G; X39 is P or A; X40 is P or A; X41is V or I; X42 is S or G; X43 is A or S; X44 is Q or E; and X45 is P or L.

FIG. 10A

```
B*0702   GSHSMRYFYTSVSRPGRGEPRFISVGYVDDTQFVRFDSDAASPREEPRAPWIEQEGPEYW   60
B*0801   GSHSMRYFDTAMSRPGRGEPRFISVGYVDDTQFVRFDSDAASPREEPRAPWIEQEGPEYW   60
B*1502   GSHSMRYFYTAMSRPGRGEPRFIAVGYVDDTQFVRFDSDAASPRMAPRAPWIEQEGPEYW   60
B*3802   GSHSMRYFYTSVSRPGRGEPRFISVGYVDDTQFVRFDSDAASPREEPRAPWIEQEGPEYW   60
B*4001   GSHSMRYFHTAMSRPGRGEPRFITVGYVDDTLFVRFDSDATSPRKEPRAPWIEQEGPEYW   60
B*4601   GSHSMRYFYTAMSRPGRGEPRFIAVGYVDDTQFVRFDSDAASPRMAPRAPWIEQEGPEYW   60
B*5301   GSHSMRYFYTAMSRPGRGEPRFIAVGYVDDTQFVRFDSDAASPRTEPRAPWIEQEGPEYW   60
         ******** *::***********:******* ********:***  **************

                                     89
B*0702   DRNTQIYKAQAQTDRESLRNLRGYYNQSEAGSHTLQSMYGCDVGPDGRLLRGHDQYAYDG   120
B*0801   DRNTQIFKTNTQTDRESLRNLRGYYNQSEAGSHTLQSMYGCDVGPDGRLLRGHNQYAYDG   120
B*1502   DRNTQISKTNTQTYRESLRNLRGYYNQSEAGSHIIQRMYGCDVGPDGRLLRGYDQSAYDG   120
B*3802   DRNTQICKTNTQTYRENLRTALRYYNQSEAGSHTLQRMYGCDVGPDGRLLRGHNQFAYDG   120
B*4001   DRETQISKTNTQTYRESLRNLRGYYNQSEAGSHTLQRMYGCDVGPDGRLLRGHNQYAYDG   120
B*4601   DRETQKYKRQAQTDRVSLRNLRGYYNQSEAGSHTLQRMYGCDVGPDGRLLRGHDQSAYDG   120
B*5301   DRNTQIFKTNTQTYRENLRIALRYYNQSEAGSHIIQRMYGCDLGPDGRLLRGHDQSAYDG   120
         **:**  * ::** * .**    ********** :* *****:*********::* ****
                            aac1  aac2

                                  139
B*0702   KDYIALNEDLRSWTAADTAAQITQRKWEAAREAEQRRAYLEGECVEWLRRYLENGKDKLE   180
B*0801   KKYIALNEDLRSWTAADTAAQITQRKWEAARVAEQDRAYLEGTCVEWLRRYLENGKDTLE   180
B*1502   KDYIALNEDLSSWTAADTAAQITQRKWEAAREAEQLRAYLEGLCVEWLRRYLENGKETLQ   180
B*3802   KKYIALNEDLSSWTAADTAAQITQRKWEAARVAEQLRTYLEGTCVEWLRRYLENGKETLQ   180
B*4001   KDYIALNEDLRSWTAADTAAQISQRKLEAARVAEQLRAYLEGECVEWLRRYLENGKDKLE   180
B*4601   KDYIALNEDLSSWTAADTAAQITQRKWEAAREAEQWRAYLEGLCVEWLRRYLENGKETLQ   180
B*5301   KDYIALNEDLSSWTAADTAAQITQRKWEAARVAEQLRAYLEGLCVEWLRRYLENGKETLQ   180
         ********** ***********:*** **** *** *:**** *************:.*:
                      aac3  aac4
```

FIG. 10A (Cont.)

236

B*0702 RADPPKTHVTHHPISDHEATLRCWALGFYPAEITLTWQRDGEDQTQDTELVETRPAGDRTF 241
B*0801 RADPPKTHVTHHPISDHEATLRCWALGFYPAEITLTWQRDGEDQTQDTELVETRPAGDRTF 241
B*1502 RADPPKTHVTHHPISDHEATLRCWALGFYPAEITLTWQRDGEDQTQDTELVETRPAGDRTF 241
B*3802 RADPPKTHVTHHPISDHEATLRCWALGFYPAEITLTWQRDGEDQTQDTELVETRPAGDRTF 241
B*4001 RADPPKTHVTHHPISDHEATLRCWALGFYPAEITLTWQRDGEDQTQDTELVETRPAGDRTF 241
B*4601 RADPPKTHVTHHPISDHEATLRCWALGFYPAEITLTWQRDGEDQTQDTELVETRPAGDRTF 241
B*5301 RADPPKTHVTHHPVSDHEATLRCWALGFYPAEITLTWQRDGEDQTQDTELVETRPAGDRTF 241
***********:******************************************** aac5 aac6

B*0702 QKWAAVVVPSGEEQRYTCHVQHEGLPKPLTLRWEP 276
B*0801 QKWAAVVVPSGEEQRYTCHVQHEGLPKPLTLRWEP 276
B*1502 QKWAAVVVPSGEEQRYTCHVQHEGLPKPLTLRWEP 276
B*3802 QKWAAVVVPSGEEQRYTCHVQHEGLPKPLTLRWEP 276
B*4001 QKWAAVVVPSGEEQRYTCHVQHEGLPKPLTLRWEP 276
B*4601 QKWAAVVVPSGEEQRYTCHVQHEGLPKPLTLRWEP 276
B*5301 QKWAAVVVPSGEEQRYTCHVQHEGLPKPLTLRWEP 276
***********************************

FIG. 10B

GSHSMRYFX1TX2X3SRPGRGEPRFIX4VGYVDDTX5FVRFDSDAX6SPRX7X8PRAPWIEQEGPEYWDRX9TQX10X11KTX12X13TQX14YX15X16NLX17X18X19X20YYNQSEAGSHX21X22Q X23MYGCDLGPDGRLLRGHDQSAYDGKDYIALNEDLX24SWTAADTAAQIX25QRKX26EAARX27AEQX28RX29YLEGX30CVEWLRRYLENGKX31X32LX33RADPPKTHVTHHPX34SDHEATLRCWALGFYPAEITLTWQRDGEDQTQDTELVETRPAGDRTFQKWAAVVVPSGEEQRYTCHVQHEGLPKPLTLRWEP

X1 is H, Y, or D; X2 is A or S; X3 is M or V; X4 is A, S, or T; X5 is Q or L; X6 is A or T; X7 is E, M K, or T; X8 is A or T; X9 is E or N; X10 is I or K; X11 is Y, F, S, or C; X12 is N or Q; X13 is A or T; X14 is D or Y; X15 is E or V; X16 is S or N; X17 is T, N, or I; X18 is A or L; X19 is L, or R; X20 is R or G; X21 is T or I; X22 is L or I; X23 is R or S; X24 is R or S; X25 is S or T; X26 is L or W; X27 is E OR V; X28 is R, D, L or W; X29 is A or T; X30 is L, E or T; X31 is E or D; X32 is K or T; X33 is E or Q; and X34 is I or V.

FIG. 11A

```
C*0102   CSHSMKYFFTSVSRPGRGEPRFISVGYVDDTQFVRFDSDAASPRGEPRAPWVEQEGPEYW   60
C*0303   GSHSMRYFYTAVSRPGRGEPHFIAVGYVDDTQFVRFDSDAASPRGEPRAPWVEQEGPEYW   60
C*0304   GSHSMRYFYTAVSRPGRGEPHFIAVGYVDDTQFVRFDSDAASPRGEPRAPWVEQEGPEYW   60
C*0401   GSHSMRYFSTSVSWPGRGEPRFIAVGYVDDTQFVRFDSDAASPRGEPREPWVEQEGPEYW   60
C*0602   CSHSMRYFDTAVSRPGRGEPRFISVGYVDDTQFVRFDSDAASPRGEPRAPWVEQEGPEYW   60
C*0701   CSHSMRYFDTAVSRPGRGEPRFISVGYVDDTQFVRFDSDAASPRGEPRAPWVEQEGPEYW   60
C*0702   CSHSMRYFDTAVSRPGRGEPRFISVGYVDDTQFVRFDSDAASPRGEPRAPWVEQEGPEYW   60
C*0801   CSHSMRYFYTAVSRPGRGEPRFIAVGYVDDTQFVQFDSDAASPRGEPRAPWVEQEGPEYW   60
C*1502   CSHSMRYFYTAVSRPGRGEPHFIAVGYVDDTQFVRFDSDAASPRGEPRAPWVEQEGPEYW   60
          ****:** *:** ******:**:**********:************* ***********

                                 84
C*0102   DRETQKYKRQAQTDRVSLRNLRGYYNQSEAGSHTLQWMCGCDLGPDGRLLRGYDQYAYDG   120
C*0303   DRETQKYKRQAQTDRVSLRNLRGYYNQSEARSHIIQRMYGCDVGPDGRLLRGYDQYAYDG   120
C*0304   DRETQKYKRQAQTDRVSLRNLRGYYNQSEAGSHIIQRMYGCDVGPDGRLLRGYDQYAYDG   120
C*0401   DRETQKYKRQAQADRVNLRKLRGYYNQSEDGSHTLQRMFGCDLGPDGRLLRGYNQFAYDG   120
C*0602   DRETQKYKRQAQADRVNLRKLRGYYNQSEDGSHTLQWMYGCDLGPDGRLLRGYDQSAYDG   120
C*0701   DRETQNYKRQAQADRVSLRNLRGYYNQSEDGSHTLQRMYGCDLGPDGRLLRGYDQSAYDG   120
C*0702   DRETQKYKRQAQADRVSLRNLRGYYNQSEDGSHTLQRMSGCDLGPDGRLLRGYDQSAYDG   120
C*0801   DRETQKYKRQAQTDRVSLRNLRGYYNQSEAGSHTLQRMYGCDLGPDGRLLRGYNQFAYDG   120
C*1502   DRETQNYKRQAQTDRVNLRKLRGYYNQSEAGSHIIQRMYGCDLGPDGRLLRGHDQLAYDG   120
         *****:******:***.*.*:****** ** :* * ***:*********..* ****
                           aac1   aac2

                         139
C*0102   KDYIALNEDLRSWTAADTAAQITQRKWEAAREAEQRRAYLEGTCVEWLRRYLENGKETLQ   180
C*0303   KDYIALNEDLRSWTAADTAAQITQRKWEAAREAEQLRAYLEGLCVEWLRRYLKNGKETLQ   180
C*0304   KDYIALNEDLRSWTAADTAAQITQRKWEAAREAEQLRAYLEGLCVEWLRRYLKNGKETLQ   180
C*0401   KDYIALNEDLRSWTAADTAAQITQRKWEAAREAEQRRAYLEGTCVEWLRRYLENGKETLQ   180
C*0602   KDYIALNEDLRSWTAADTAAQITQRKWEAAREAEQWRAYLEGTCVEWLRRYLENGKETLQ   180
C*0701   KDYIALNEDLRSWTAADTAAQITQRKLEAARAAEQLRAYLEGTCVEWLRRYLENGKETLQ   180
C*0702   KDYIALNEDLRSWTAADTAAQITQRKLEAARAAEQLRAYLEGTCVEWLRRYLENGKETLQ   180
C*0801   KDYIALNEDLRSWTAADTAAQITQRKWEAARTAEQLRAYLEGTCVEWLRRYLENGKKTLQ   180
C*1502   KDYIALNEDLRSWTAADTAAQITQRKWEAAREAEQLRAYLEGTCVEWLRRYLENGKETLQ   180
         ************************** **** *** ****** *********:***:***
                      aac3  aac4
```

FIG. 11A (Cont.)

```
                                                                      236
C*0102   RAEHPKTHVTHHPVSDHEATLRCWALGFYPAEITLTWQWDGEDQTQDTELVETRPAGDGTF   241
C*0303   RAEHPKTHVTHHPVSDHEATLRCWALGFYPAEITLTWQWDGEDQTQDTELVETRPAGDGTF   241
C*0304   RAEHPKTHVTHHPVSDHEATLRCWALGFYPAEITLTWQWDGEDQTQDTELVETRPAGDGTF   241
C*0401   RAEHPKTHVTHHPVSDHEATLRCWALGFYPAEITLTWQWDGEDQTQDTELVETRPAGDGTF   241
C*0602   RAEHPKTHVTHHPVSDHEATLRCWALGFYPAEITLTWQRDGEDQTQDTELVETRPAGDGTF   241
C*0701   RAEPPKTHVTHHPLSDHEATLRCWALGFYPAEITLTWQRDGEDQTQDTELVETRPAGDGTF   241
C*0702   RAEPPKTHVTHHPLSDHEATLRCWALGFYPAEITLTWQRDGEDQTQDTELVETRPAGDGTF   241
C*0801   RAEHPKTHVTHHPVSDHEATLRCWALGFYPAEITLTWQRDGEDQTQDTELVETRPAGDGTF   241
C*1502   RAEHPKTHVTHHPVSDHEATLRCWALGFYPAEITLTWQRDGEDQTQDTELVETRPAGDGTF   241
         *** *********:*********************** ***************** ******
                                                        aac5   aac6

C*0102   QKWAAVMVPSGEEQRYTCHVQHEGLPEPLTLRWEP 276
C*0303   QKWAAVVVPSGEEQRYTCHVQHEGLPEPLTLRWEP 276
C*0304   QKWAAVVVPSGEEQRYTCHVQHEGLPEPLTLRWEP 276
C*0401   QKWAAVVVPSGEEQRYTCHVQHEGLPEPLTLRWKP 276
C*0602   QKWAAVVVPSGEEQRYTCHVQHEGLPEPLTLRWEP 276
C*0701   QKWAAVVVPSGQEQRYTCHMQHEGLQEPLTLSWEP 276
C*0702   QKWAAVVVPSGQEQRYTCHMQHEGLQEPLTLSWEP 276
C*0801   QKWAAVVVPSGEEQRYTCHVQHEGLPEPLTLRWGP 276
C*1502   QKWAAVVVPSGEEQRYTCHVQHEGLPEPLTLRWEP 276
         ******:****:*******:***** ***** * *
```

FIG. 11B

X1SHSMX2YFX3TAVSX4PGRGEPX5FIX6VGYVDDTQFVX7FDSDAASPRGEPRX8PWVEQEG
PEYWDRETQX9YKRQAQX10DRVX11LRX12LRGYYNQSEX13X14SHX15X16QX17MX18GC
DX19GPDGRLLRGX20X21QX22AYDGKDYIALNEDLRSWTAADTAAQITQRKX23EAARX24A
EQX25RAYLEGX26CVEWLRRYLX27NGKX28TLQRAEX29PKTHVTHHPX30SDHEATLRCWA
LGFYPAEITLTWQX31DGEDQTQDTELVETRPAGDGTFQKWAAVX32VPSGX33EQRYTCHX34
QHEGLX35EPLTLX36WX37P

X1 is C or G; X2 is R or K; X3 is F, Y, S, or D; X4 is R or W; X5 is H or R; X6 is A or S; X7 is Q or R; X8 is A or E; X9 is N or K;X10 is T or A; X11 is S or N; X12 is N or K; X13 is A or D; X14 is G or R; X15 is T or I; X16 is L or I; X17 is W or R; X18 is C, Y, F, or S; X19 is L, or V; X20 is Y or H; X21 is D or N; X22 is Y, F, S, or L; X23 is L or W; X24 is E, A, Or T; X25 is R, L, or W; X26 is L or T; X27 is E OR K; X28 is E or K; X29 is H or P; X30 is R or V; X31 is W or R; X32 is V or M; X33 is E or Q; X34 is M or V; X35 is P or Q; X36 is R or S; and X37 is P or G.

FIG. 12

| |
|---|
| HLA-E<br>GSHSLKYFHT SVSRPGRGEP RFISVGYVDD TQFVRFDNDA ASPRMVPRAP<br>WMEQEGSEYW DRETRSARDT AQIFRVNLRT LRGYYNQS**X1**A GSHTLQWMHG<br>CELGPD**X2**RFL RGYEQFAYDG KDYLTLNEDL RSWTAVDT**A**A QISEQKSNDA<br>SEAEHQ**X3X4**YL EDTCVEWLHK YLEKGKETLL HLEPPKTHVT HHPISDHEAT<br>LRCWALGFYP AEITLTWQQD GEGHTQDTEL VETRP**A**GDGT FQKWAAVVVP<br>SGEE**X5**RYTCH VQHEGL**X6**EPV TLRWKPASQP TIPI<br><br>X1= K or E; X2= R or G; X3= R or G; X4= A or V; X5= Q or P; and X6= P or S |
| Encompasses: HLA-E*0101 (HLA-E*01:01:01:01); HLA-E*01:03(HLA-E*01:03:01:01); HLA-E*01:04; HLA-E*01:05; HLA-E*01:06; HLA-E*01:07; HLA-E*01:09; HLA-E*01:10 |
| HLA-F<br>GSHSLR**X1**FST AVSRPGRGEP RYIAVEYVDD TQFLRFDSDA AIPRMEPRE**X2**<br>WVEQEGPQYW EWTTGYAKAN AQTDRVALRN LLR**R**YNQSEA GSHTLQGMNG<br>CDMGPDGRLL RGYHQHAYDG KDYISLNEDL RSWTAADT**V**A QITQRFYEAE<br>EYAEEFRTYL EGECLELLRR YLENGKETLQ RADPPKAHVA HHPISDHEAT<br>LRCWALGFYP AEITLTWQRD GEEQTQDTEL VETRP**A**GDGT FQKWAAVVVP<br>**X3**GEEQRYTCH VQHEGLPQPL ILRWEQS**X4**QP TIPI<br><br>X1= Y or F; X2= P or Q; X3= S or P; and X4= P or L |
| Encompasses: HLA-F*0101 (HLA-F*01:01:01:01); HLA-F*01:02; HLA-F*01:03(HLA-F*01:03:01:01); HLA-F*01:04; HLA-F*01:05; HLA-F*01:06; |
| HLA-G<br>GSHSMRYFSA AV**X1**RPGRGEP RFIAMG**X2**VDD **X3**QF**X4**RFDSDS ACPRMEPRAP<br>WVE**X5**EGPEYW EEETRNTKAH AQTDRMNLQT **X6**RG**Y**YNQSEA SSHTLQWMI**X7**<br>CDL**X8X9**DGRL**X10** RGYEQYAYDG KDYLALNEDL RSWTAADT**A**A QISKRKCEAA<br>NVAEQRRA**X11**L EGTCVEWL**X12**R **X13**LENGKE**X14**LQ RADP**X15**KTHVT HHPVFDYEAT<br>LRCWALGFYP AEIILTWQ**X16**D GEDQTQDVEL VETRP**A**GDGT FQKWAAVVVP<br>SGEEQRY**X17**CH VQHEGLPEPL MLRW**X18**QSSLP TIPI<br><br>X1= S or F; X2= Y or H; X3= T, S, or M; X4= L or V; X5= Q or R; X6= P or L; X7= G or D; X8= G or V; X9= S or C; X10= L or I; X11= Y or H; X12= H or R; X13= Y or H; X14= M or T; X15= P or A; X16= R, W, or Q; X17= T or M; X18= K or E; |
| Encompasses: HLA-G*0101 (HLA-G*01:01:01:01); HLA-G*01:02; HLA-G*01:03(HLA-G*01:03:01:01); HLA-G*01:04 (HLA-G*01:04:01:01); HLA-G*01:06; HLA-G*01:07; HLA-G*01:08; HLA-G*01:09: HLA-G*01:10; HLA-G*01:10; HLA-G*01:11; HLA-G*01:12; HLA-G*01:14; HLA-G*01:15; HLA-G*01:16; HLA-G*01:17; HLA-G*01:18: HLA-G*01:19; HLA-G*01:20; HLA-G*01:22 |

FIG. 13

```
HLA-A    GSHSMRYFXTSVSRPGRGEPRFIAVGYVDDTQFVRFDSDAASQXMEPRAPWIEQEGPEYW  60
HLA-B    GSHSMRYFXTXXSRPGRGEPRFIXVGYVDDTXFVRFDSDAXSPRXXPRAPWIEQEGPEYW  60
HLA-C    XSHSMXYFXTAVSXPGRGEPXFIXVGYVDDTQFVXFDSDAASPRGEPRXPWVEQEGPEYW  60
HLA-E    GSHSLKYFHTSVSRPGRGEPRFISVGYVDDTQFVRFDNDAASPRMVPRAPWMEQEGSEYW  60
HLA-F    GSHSLRXFSTAVSRPGRGEPRYIAVEYVDDTQFLRFDSDAAIPRMEPREXWVEQEGPQYW  60
HLA-G    GSHSMRYFSAAVXRPGRGEPRFIAMGXVDDXQFXRFDSDSACPRMEPRAPWVEXEGPEYW  60
          ***:  * :     ****** :* :  ***  *  **.*:      **  *:* ** :**

                                 84
HLA-A    DXXTXXXKAXSQXXRXXLXXXXXYYNQSEKGSHTXQXMXGCDVGXDXRFLRGYXQXAYDG  120
HLA-B    DRXTQXXKTXXTQXYXXNLXXXXYYNQSEAGSHXXQXMYGCDLGPDGRLLRGHDQSAYDG  120
HLA-C    DRETQXYKRQAQXDRVXLRXLRGYYNQSEKXSHXXQXMXGCDXGPDGRLLRGXXQXAYDG  120
HLA-E    DRETRSARDTAQIFRVNLRTLRGYYNQSXAGSHTLQWMHGCELGPDXRFLRGYEQFAYDG  120
HLA-F    EWTTGYAKANAQTDRVALRNLLRRYNQSEAGSHTLQGMNGCDMGPDGRLLRGYHQHAYDG  120
HLA-G    EEETRNTKAHAQTDRMNLQTXRGYYNQSEASSHTLQWMIXCDLXXDGRLXRGYEQYAYDG  120
         :  *   :                 ****   **  * *  *:   * *: **  * ****
                          aac1    aac2

                            139
HLA-A    KDYIALXEDLRSWTAADMAAQXTXXKWEXXXEAEQXRXYLXGXCVXXLRRYLENGKETLQ  180
HLA-B    KDYIALNEDLXSWTAADTAAQIXQRKXEAARXAEQXRXYLEGXCVEWLRRYLENGKXXLX  180
HLA-C    KDYIALNEDLRSWTAADTAAQITQRKXEAARXAEQXRAYLEGXCVEWLRRYLXNGKXTLQ  180
HLA-E    KDYLTLNEDLRSWTAVDTAAQISEQKSNDASEAEHQXXYLEDTCVEWLHKYLEKGKETLL  180
HLA-F    KDYISLNEDLRSWTAADTVAQITQRFYEAEEYAEEFRTYLEGECLELLRRYLENGKETLQ  180
HLA-G    KDYLALNEDLRSWTAADTAAQISKRKCEAANVAEQRRAXLEGTCVEWLXRXLENGKEXLQ  180
         ***::* *** ****.*  .**       :     **.     * . *:  * : * :**  *
                     aac3    aac4

                                                              236
HLA-A    RTDXPKTHMTHHXXSDHEATLRCWALXFYPAEITLTWQRDGEDQTQDTELVETRPAGDGTF  241
HLA-B    RADPPKTHVTHHPXSDHEATLRCWALGFYPAEITLTWQRDGEDQTQDTELVETRPAGDRTF  241
HLA-C    RAEXPKTHVTHHPXSDHEATLRCWALGFYPAEITLTWQXDGEDQTQDTELVETRPAGDGTF  241
HLA-E    HLEPPKTHVTHHPISDHEATLRCWALGFYPAEITLTWQQDGEGHTQDTELVETRPAGDGTF  241
HLA-F    RADPPKAHVAHHPISDHEATLRCWALGFYPAEITLTWQRDGEEQTQDTELVETRPAGDGTF  241
HLA-G    RADPXKTHVTHHPVFDYEATLRCWALGFYPAEIILTWQXDGEDQTQDVELVETRPAGDGTF  241
         : :  *:*::**   *:********* ****** **** *** :***.*********** **
                                                          ac5   aac6

HLA-A     QKWAXVVVPSGXEQRYTCHVQHEGLPKPLTLRWEX---------      276
HLA-B     QKWAAVVVPSGEEQRYTCHVQHEGLPKPLTLRWEP---------      276
HLA-C     QKWAAVXVPSGXEQRYTCHXQHEGLXEPLTLXWXP---------      276
HLA-E     QKWAAVVVPSGEEXRYTCHVQHEGLXEPVTLRWKPASQPTIPI      284
HLA-F     QKWAAVVVPXGEEQRYTCHVQHEGLPQPLILRWEQSXQPTIPI      284
HLA-G     QKWAAVVVPSGEEQRYXCHVQHEGLPEPLMLRWXQSSLPTIPI      284
          **** * ** * * ** ** ***** :*: * *
```

FIG. 14A

1715

APTSSSTKKTQLQLEALLLDLQMILNGINNYKNPKLTRMLTAKFYMPKKATELKHLQCLEEELKP
LEEVLNLAQSKNFHLRPRDLISNINVIVLELKGSETTFMCEYADETATIVEFLNRWITFCQSIIS
TLTGGGGSGGGGSGGGGSGGGGSAPTSSSTKKTQLQLEALLLDLQMILNGINNYKNPKLTRMLTA
KFYMPKKATELKHLQCLEEELKPLEEVLNLAQSKNFHLRPRDLISNINVIVLELKGSETTFMCEY
ADETATIVEFLNRWITFCQSIISTLTGGGGSGGGGSGGGGSGGGGSGSHSMRYFFTSVSRPGRGE
PRFIAVGYVDDTQFVRFDSDAASQRMEPRAPWIEQEGPEYWDGETRKVKAHSQTHRVDLGTLRGC
YNQSEAGSHTVQRMYGCDVGSDWRFLRGYHQYAYDGKDYIALKEDLRSWTAADMAAQTTKHKWEA
AHVAEQLRAYLEGTCVEWLRRYLENGKETLQRTDAPKTHMTHHAVSDHEATLRCWALSFYPAEIT
LTWQRDGEDQTQDTELVETRPCGDGTFQKWAAVVVPSGQEQRYTCHVQHEGLPKPLTLRWEAAAG
G*DKTHTCPPCPAPEAAGGPSVFLFPPKPKDTLMISRTPEVTCVVVDVSHEDPEVKFNWYVDGVEV*
*HNAKTKPREEQYNSTYRVVSVLTVLHQDWLNGKEYKCKVSNKALPAPIEKTISKAKGQPREPQVY*
*TLPPSREEMTKNQVSLTCLVKGFYPSDIAVEWESNGQPENNYKTTPPVLDSDGSFFLYSKLTVDK*
*SRWQQGNVFSCSVMHEALHNHYTQKSLSLSPGK* (SEQ ID NO:422)

hIL2 (H16A; F42A) -- underlined
(G4S)n – bold (SEQ ID NO:380)
HLA A0202 (Y84C; A236C) – double underlined
AAAGG – bold (SEQ ID NO:283)
IgG1 Fc (LALA) -- italicized

FIG. 14B

2380

VLDFAPPGAGCGGSGGGGSGGGGSIQRTPKIQVYSCHPAENGKSNFLNCYVSG
FHPSDIEVDLLKNGERIEKVEHSDLSFSKDWSFYLLYYTEFTPTEKDEYACRVNH
VTLSQPKIVKWDRDM (SEQ ID NO:423)

WT1(37-45) epitope: VLDFAPPGA (SEQ ID NO:259)
G2C linker – bold
β2M (R12C) – underlined

FIG. 14C

2381

RMFPNAPYLGCGGSGGGGSGGGGSIQRTPKIQVYSCHPAENGKSNFLNCYVSG
FHPSDIEVDLLKNGERIEKVEHSDLSFSKDWSFYLLYYTEFTPTEKDEYACRVNH
VTLSQPKIVKWDRDM (SEQ ID NO:424)

WT1(126-134) epitope: RMFPNAPYL (SEQ ID NO:260)
G2C linker -- bold
β2M (R12C) – underlined

FIG. 14D

2405

APTSSSTKKTQLQLEALLLDLQMILNGINNYKNPKLTRMLTAKFYMPKKATELKHLQCLEEELKP
LEEVLNLAQSKNFHLRPRDLISNINVIVLELKGSETTFMCEYADETATIVEFLNRWITFCQSIIS
TLTGGGGSGGGGSGGGGSGGGGSAPTSSSTKKTQLQLEALLLDLQMILNGINNYKNPKLTRMLTA
KFYMPKKATELKHLQCLEEELKPLEEVLNLAQSKNFHLRPRDLISNINVIVLELKGSETTFMCEY
ADETATIVEFLNRWITFCQSIISTLTGGGGSGGGGSGGGGSGGGGSGSHSMRYFFTSVSRPGRGE
PRFIAVGYVDDTQFVRFDSDAASQRMEPRAPWIEQEGPEYWDGETRKVKAHSQTHRVDLGTLRGC
YNQSEAGSHTVQRMYGCDVGSDWRFLRGYHQYAYDGKDYIALKEDLRSWTAADMAAQTTKHKWEA
AHVAEQLRAYLEGTCVEWLRRYLENGKETLQRTDAPKTHMTHHAVSDHEATLRCWALSFYPAEIT
LTWQRDGEDQTQDTELVETRPAGDGTFQKWAAVVVPSGQEQRYTCHVQHEGLPKPLTLRWEAAAG
G*DKTHTCPPCPAPEAAGGPSVFLFPPKPKDTLMISRTPEVTCVVVDVSHEDPEVKFNWYVDGVEV*
*HNAKTKPREEQYNSTYRVVSVLTVLHQDWLNGKEYKCKVSNKALPAPIEKTISKAKGQPREPQVY*
*TLPPSREEMTKNQVSLTCLVKGFYPSDIAVEWESNGQPENNYKTTPPVLDSDGSFFLYSKLTVDK*
*SRWQQGNVFSCSVMHEALHNHYTQKSLSLSPG* (SEQ ID NO:425)

hIL2 (H16A; F42A) -- underlined
(G4S)n – bold (SEQ ID NO:380)
HLA A0202 (Y84C) – double underlined
AAAGG – bold (SEQ ID NO:283)
IgG1 Fc (LALA) -- italicized

FIG. 14E

1380

APTSSSTKKTQLQLEALLLDLQMILNGINNYKNPKLTRMLTAKFYMPKKATELKHLQCLEEELKP
LEEVLNLAQSKNFHLRPRDLISNINVIVLELKGSETTFMCEYADETATIVEFLNRWITFCQSIIS
TLTGGGGSGGGGSGGGGSGGGGSAPTSSSTKKTQLQLEALLLDLQMILNGINNYKNPKLTRMLTA
KFYMPKKATELKHLQCLEEELKPLEEVLNLAQSKNFHLRPRDLISNINVIVLELKGSETTFMCEY
ADETATIVEFLNRWITFCQSIISTLTGGGGSGGGGSGGGGSGGGGSGSHSMRYFFTSVSRPGRGE
PRFIAVGYVDDTQFVRFDSDAASQRMEPRAPWIEQEGPEYWDGETRKVKAHSQTHRVDLGTLRGA
YNQSEAGSHTVQRMYGCDVGSDWRFLRGYHQYAYDGKDYIALKEDLRSWTAADMAAQTTKHKWEA
AHVAEQLRAYLEGTCVEWLRRYLENGKETLQRTDAPKTHMTHHAVSDHEATLRCWALSFYPAEIT
LTWQRDGEDQTQDTELVETRPCGDGTFQKWAAVVVPSGQEQRYTCHVQHEGLPKPLTLRWEAAAG
G_DKTHTCPPCPAPEAAGGPSVFLFPPKPKDTLMISRTPEVTCVVVDVSHEDPEVKFNWYVDGVEV_
_HNAKTKPREEQYNSTYRVVSVLTVLHQDWLNGKEYKCKVSNKALPAPIEKTISKAKGQPREPQVY_
_TLPPSREEMTKNQVSLTCLVKGFYPSDIAVEWESNGQPENNYKTTPPVLDSDGSFFLYSKLTVDK_
_SRWQQGNVFSCSVMHEALHNHYTQKSLSLSPGK_ (SEQ ID NO:426)

hIL2 (H16A; F42A) -- underlined
(G4S)n – bold (SEQ ID NO:380)
HLA A0202 (A236C) – double underlined
AAAGG – bold (SEQ ID NO:283)
IgG1 Fc (LALA) -- italicized

FIG. 14F

2762

VLDFAPPGAGCGGSGGGGSGGGGSIQRTPKIQVYSRHPAENGKSNFLNCYVSG
FHPSDIEVDLLKNGERIEKVEHSDLSFSKDWSFYLLYYTEFTPTEKDEYACRVNH
VTLSQPKIVKWDRDM (SEQ ID NO:427)

WT1(37-45) epitope: VLDFAPPGA (SEQ ID NO:259)
G2C linker – bold
β2M – underlined

FIG. 14G

2763

RMFPNAPYLGCGGSGGGGSGGGGSIQRTPKIQVYSRHPAENGKSNFLNCYVSG
FHPSDIEVDLLKNGERIEKVEHSDLSFSKDWSFYLLYYTEFTPTEKDEYACRVNH
VTLSQPKIVKWDRDM (SEQ ID NO:428)

WT1 (126-134) epitope: RMFPNAPYL (SEQ ID NO:260)
G2C linker – bold
β2M – underlined

FIG. 14H

3625

YMFPNAPYLGCGGSGGGGSGGGGSIQRTPKIQVYSCHPAENGKSNFLNCYVSG
FHPSDIEVDLLKNGERIEKVEHSDLSFSKDWSFYLLYYTEFTPTEKDEYACRVNH
VTLSQPKIVKWDRDM (SEQ ID NO:429)

WT1 (126-134; R126Y) epitope: YMFPNAPYL (SEQ ID NO:264)
G2C linker – bold
β2M (R12C) – underlined

FIG. 14I

3626

YMFPNAPYLGCGGSGGGGSGGGGSIQRTPKIQVYSRHPAENGKSNFLNCYVSG
FHPSDIEVDLLKNGERIEKVEHSDLSFSKDWSFYLLYYTEFTPTEKDEYACRVNH
VTLSQPKIVKWDRDM (SEQ ID NO:430)

WT1 (126-134; R126Y) epitope: YMFPNAPYL (SEQ ID NO:264)
G2C linker – bold
β2M – underlined

FIG. 14J

1715 without C-terminal Lys

APTSSSTKKTQLQLEALLLDLQMILNGINNYKNPKLTRMLTAKFYMPKKATELKHLQCLEEELKP
LEEVLNLAQSKNFHLRPRDLISNINVIVLELKGSETTFMCEYADETATIVEFLNRWITFCQSIIS
TLTGGGGSGGGGSGGGGSGGGGSAPTSSSTKKTQLQLEALLLDLQMILNGINNYKNPKLTRMLTA
KFYMPKKATELKHLQCLEEELKPLEEVLNLAQSKNFHLRPRDLISNINVIVLELKGSETTFMCEY
ADETATIVEFLNRWITFCQSIISTLTGGGGSGGGGSGGGGSGGGGSGSHSMRYFFTSVSRPGRGE
PRFIAVGYVDDTQFVRFDSDAASQRMEPRAPWIEQEGPEYWDGETRKVKAHSQTHRVDLGTLRGC
YNQSEAGSHTVQRMYGCDVGSDWRFLRGYHQYAYDGKDYIALKEDLRSWTAADMAAQTTKHKWEA
AHVAEQLRAYLEGTCVEWLRRYLENGKETLQRTDAPKTHMTHHAVSDHEATLRCWALSFYPAEIT
LTWQRDGEDQTQDTELVETRPCGDGTFQKWAAVVVPSGQEQRYTCHVQHEGLPKPLTLRWEAAAG
G*DKTHTCPPCPAPEAAGGPSVFLFPPKPKDTLMISRTPEVTCVVVDVSHEDPEVKFNWYVDGVEV*
*HNAKTKPREEQYNSTYRVVSVLTVLHQDWLNGKEYKCKVSNKALPAPIEKTISKAKGQPREPQVY*
*TLPPSREEMTKNQVSLTCLVKGFYPSDIAVEWESNGQPENNYKTTPPVLDSDGSFFLYSKLTVDK*
*SRWQQGNVFSCSVMHEALHNHYTQKSLSLSPG* (SEQ ID NO:486)

hIL2 (H16A; F42A) -- underlined
(G4S)n – bold (SEQ ID NO:380)
HLA A0202 (Y84C; A236C) – double underlined
AAAGG – bold (SEQ ID NO:283)
IgG1 Fc (LALA) -- italicized

FIG. 15

| | 1715-2380 |
|---|---|
| **Serotype** | A02:01 |
| **Peptide** | WT1 (37-45) |
| **MOD** | 2 x IL-2 (H16A, F42A) |
| **Engineered Disulfide** | R12C-A236C, G2C-Y84C |
| **Titer (mg/L)** | 309 |
| **% monomer (post ProtA)** | 80 |
| **% monomer (post SEC)** | 98 |
| **Stability** (28d @ 37°C / 42°C)* | 51/2 |
| **Freeze-thaw (3x)** | Stable, No Change |
| **Tm** (°C)** | 52 (pHLA) |
| | 67 (IL2) |
| | 82 (Fc) |
| **$T_{agg}$** (°C)** | 47 |
| **Intact mass (LC-MS)** | Confirmed |

* %monomer after one month incubation at 37°C or 42°C, respectively
** buffer = unformulated, PBS + 365 mM NaCl, pH 7.4

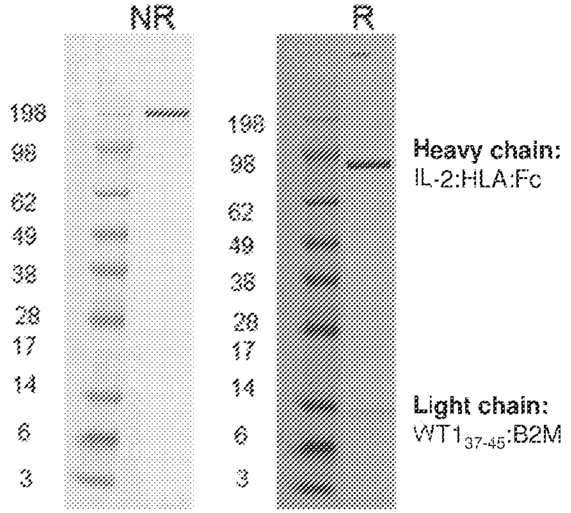

Non-reduced (NR) and Reduced (R)
Coomassie-stained SDS-PAGE
2.0 µg/lane

FIG. 16

| | 1715-2381 |
|---|---|
| Serotype | A02:01 |
| Peptide | WT1 (126-134) |
| MOD | 2 x IL-2 (H16A, F42A) |
| Engineered Disulfide | R12C-A236C; G2C-Y84C |
| Titer (mg/L) | 680 |
| % monomer (post ProtA) | 79 |
| % monomer (post SEC) | 97 |
| Stability (28d @ 37°C / 42°C)* | 37/3 |
| Freeze-thaw (3x) | Stable, No Change |
| Tm (°C) | 51 (pHLA) |
| | 68 (IL2) |
| | 82 (Fc) |
| $T_{agg}$ (°C) | 47 |
| Intact mass (LC-MS) | Confirmed |

* %monomer after one month incubation at 37°C or 42°C, respectively
** buffer = unformulated, PBS + 365 mM NaCl, pH 7.4

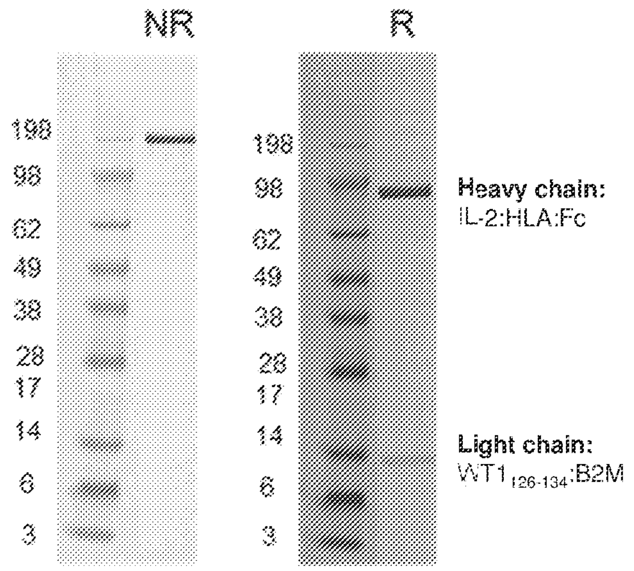

Non-reduced (NR) and Reduced (R) Coomassie-stained SDS-PAGE 2.0 µg/lane

FIG. 20A

3592

APTSSSTKKTQLQLEALLLDLQMILNGINNYKNPKLTRMLTAKFYMPKKAT
ELKHLQCLEEELKPLEEVLNLAQSKNFHLRPRDLISNINVIVLELKGSETTFM
CEYADETATIVEFLNRWITFCQSIISTLTGGGGSGGGGSGGGGSGGGGSAPTSS
STKKTQLQLEALLLDLQMILNGINNYKNPKLTRMLTAKFYMPKKATELKH
LQCLEEELKPLEEVLNLAQSKNFHLRPRDLISNINVIVLELKGSETTFMCEYA
DETATIVEFLNRWITFCQSIISTLTGGGGSGGGGSGGGGSGGGGSGSHSMRYFS
TSVSRPGRGEPRFIAVGYVDDTQFVRFDSDAASQRMEPRAPWIEQEGPEYWDEE
TGKVKAHSQTDRENLRIALRCYNQSEAGSHTLQMMFGCDVGSDGRFLRGYHQY
AYDGKDYIALKEDLRSWTAADMAAQITKRKWEAAHVAEQQRAYLEGTCVDGL
RRYLENGKETLQRTDPPKTHMTHHPISDHEATLRCWALGFYPAEITLTWQRDGE
DQTQDTELVETRPCGDGTFQKWAAVVVPSGEEQRYTCHVQHEGLPKPLTLRWE
AAAGGDKTHTCPPCPAPEAAGGPSVFLFPPKPKDTLMISRTPEVTCVVVDVS
HEDPEVKFNWYVDGVEVHNAKTKPREEQYNSTYRVVSVLTVLHQDWLNG
KEYKCKVSNKALPAPIEKTISKAKGQPREPQVYTLPPSREEMTKNQVSLTCL
VKGFYPSDIAVEWESNGQPENNYKTTPPVLDSDGSFFLYSKLTVDKSRWQQ
GNVFSCSVMHEALHNHYTQKSLSLSPG (SEQ ID NO:431)

IL-2 (H16A; F42A) – bold
(G4S)$_4$ – underlined (SEQ ID NO:380)
HLA-A*24:02 (Y84C; A236C) – double underlined
AAAGG linker – bold and italicized (SEQ ID NO:283)
hIgG1 Fc (L234A; L235A) – bold and underlined

FIG. 20B

3425

GSHSMRYFSTSVSRPGRGEPRFIAVGYVDDTQFVRFDSDAASQRMEPRAPWIEQE
GPEYWDEETGKVKAHSQTDRENLRIALRCYNQSEAGSHTLQMMFGCDVGSDGR
FLRGYHQYAYDGKDYIALKEDLRSWTAADMAAQITKRKWEAAHVAEQQRAYL
EGTCVDGLRRYLENGKETLQRTDPPKTHMTHHPISDHEATLRCWALGFYPAEITL
TWQRDGEDQTQDTELVETRPCGDGTFQKWAAVVVPSGEEQRYTCHVQHEGLP
KPLTLRWE*AAAGG***DKTHTCPPCPAPEAAGGPSVFLFPPKPKDTLMISRTPEVT
CVVVDVSHEDPEVKFNWYVDGVEVHNAKTKPREEQYNSTYRVVSVLTVLH
QDWLNGKEYKCKVSNKALPAPIEKTISKAKGQPREPQVYTLPPSREEMTKN
QVSLTCLVKGFYPSDIAVEWESNGQPENNYKTTPPVLDSDGSFFLYSKLTVD
KSRWQQGNVFSCSVMHEALHNHYTQKSLSLSPGGGGGSGGGGSGGGGSAPT
SSSTKKTQLQLEALLLDLQMILNGINNYKNPKLTRMLTAKFYMPKKATELK
HLQCLEEELKPLEEVLNLAQSKNFHLRPRDLISNINVIVLELKGSETTFMCEY
ADETATIVEFLNRWITFCQSIISTLTGGGGSGGGGSGGGGSGGGGSAPTSSSTK
KTQLQLEALLLDLQMILNGINNYKNPKLTRMLTAKFYMPKKATELKHLQC
LEEELKPLEEVLNLAQSKNFHLRPRDLISNINVIVLELKGSETTFMCEYADET
ATIVEFLNRWITFCQSIISTLT** (SEQ ID NO:432)

HLA-A*24:02 (Y84C; A236C) – double underlined
AAAGG linker – bold and italicized (SEQ ID NO:283)
hIgG1 Fc (L234A; L235A) – bold and underlined
(G4S)$_3$ and (G4S)$_4$ – underlined (SEQ ID NOs:379-380)
IL-2 (H16A; F42A) – bold

FIG. 20C

3196

GSHSMRYFSTSVSRPGRGEPRFIAVGYVDDTQFVRFDSDAASQRMEPRAPWIEQE
GPEYWDEETGKVKAHSQTDRENLRIALRCYNQSEAGSHTLQMMFGCDVGSDGR
FLRGYHQYAYDGKDYIALKEDLRSWTAADMAAQITKRKWEAAHVAEQQRAYL
EGTCVDGLRRYLENGKETLQRTDPPKTHMTHHPISDHEATLRCWALGFYPAEITL
TWQRDGEDQTQDTELVETRPCGDGTFQKWAAVVVPSGEEQRYTCHVQHEGLP
KPLTLRWE*AAAGG*DKTHTCPPCPAPEAAGGPSVFLFPPKPKDTLMISRTPEVT
CVVVDVSHEDPEVKFNWYVDGVEVHNAKTKPREEQYNSTYRVVSVLTVLH
QDWLNGKEYKCKVSNKALPAPIEKTISKAKGQPREPQVYTLPPSREEMTKN
QVSLTCLVKGFYPSDIAVEWESNGQPENNYKTTPPVLDSDGSFFLYSKLTVD
KSRWQQGNVFSCSVMHEALHNHYTQKSLSLSPG (SEQ ID NO:433)

HLA-A*24:02 (Y84C; A236C) – double underlined
AAAGG linker – bold and italicized (SEQ ID NO:283)
hIgG1 Fc (L234A; L235A) – bold and underlined

FIG. 20D

2764

GSHSMRYFSTSVSRPGRGEPRFIAVGYVDDTQFVRFDSDAASQRMEPRAPWIEQE
GPEYWDEETGKVKAHSQTDRENLRIALRAYNQSEAGSHTLQMMFGCDVGSDGR
FLRGYHQYAYDGKDYIALKEDLRSWTAADMAAQITKRKWEAAHVAEQQRAYL
EGTCVDGLRRYLENGKETLQRTDPPKTHMTHHPISDHEATLRCWALGFYPAEITL
TWQRDGEDQTQDTELVETRPCGDGTFQKWAAVVVPSGEEQRYTCHVQHEGLP
KPLTLRWE*AAAGG*DKTHTCPPCPAPEAAGGPSVFLFPPKPKDTLMISRTPEVT
CVVVDVSHEDPEVKFNWYVDGVEVHNAKTKPREEQYNSTYRVVSVLTVLH
QDWLNGKEYKCKVSNKALPAPIEKTISKAKGQPREPQVYTLPPSREEMTKN
QVSLTCLVKGFYPSDIAVEWESNGQPENNYKTTPPVLDSDGSFFLYSKLTVD
KSRWQQGNVFSCSVMHEALHNHYTQKSLSLSPGK (SEQ ID NO:434)

HLA-A*24:02 (Y84A; A236C) – double underlined
AAAGG linker – bold and italicized (SEQ ID NO:283)
hIgG1 Fc (L234A; L235A) – bold and underlined

FIG. 20E

3593

**APTSSSTKKTQLQLEALLLDLQMILNGINNYKNPKLTRMLTAKFYMPKKAT
ELKHLQCLEEELKPLEEVLNLAQSKNFHLRPRDLISNINVIVLELKGSETTFM
CEYADETATIVEFLNRWITFCQSIISTLTGGGGSGGGGSGGGGSGGGGSAPTSS
STKKTQLQLEALLLDLQMILNGINNYKNPKLTRMLTAKFYMPKKATELKH
LQCLEEELKPLEEVLNLAQSKNFHLRPRDLISNINVIVLELKGSETTFMCEYA
DETATIVEFLNRWITFCQSIISTLT**GGGGSGGGGSGGGGSGGGGSGSHSMRYFS
TSVSRPGRGEPRFIAVGYVDDTQFVRFDSDAASQRMEPRAPWIEQEGPEYWDEE
TGKVKAHSQTDRENLRIALRCYNQSEAGSHTLQMMFGCDVGSDGRFLRGYHQY
AYDGKDYIALKEDLRSWTAADMAAQITKRKWEAAHVAEQQRAYLEGTCVDGL
RRYLENGKETLQRTDPPKTHMTHHPISDHEATLRCWALGFYPAEITLTWQRDGE
DQTQDTELVETRPAGDGTFQKWAAVVVPSGEEQRYTCHVQHEGLPKPLTLRWE
*AAAGG***DKTHTCPPCPAPEAAGGPSVFLFPPKPKDTLMISRTPEVTCVVVDVS
HEDPEVKFNWYVDGVEVHNAKTKPREEQYNSTYRVVSVLTVLHQDWLNG
KEYKCKVSNKALPAPIEKTISKAKGQPREPQVYTLPPSREEMTKNQVSLTCL
VKGFYPSDIAVEWESNGQPENNYKTTPPVLDSDGSFFLYSKLTVDKSRWQQ
GNVFSCSVMHEALHNHYTQKSLSLSPG** (SEQ ID NO:435)

IL-2 (H16A; F42A) – bold
(G4S)4 – underlined (SEQ ID NO:380)
HLA-A*24:02 (Y84C; A236) – double underlined
AAAGG linker – bold and italicized (SEQ ID NO:283)
hIgG1 Fc (L234A; L235A) – bold and underlined

FIG. 20F

3426

GSHSMRYFSTSVSRPGRGEPRFIAVGYVDDTQFVRFDSDAASQRMEPRAPWIEQE
GPEYWDEETGKVKAHSQTDRENLRIALRCYNQSEAGSHTLQMMFGCDVGSDGR
FLRGYHQYAYDGKDYIALKEDLRSWTAADMAAQITKRKWEAAHVAEQQRAYL
EGTCVDGLRRYLENGKETLQRTDPPKTHMTHHPISDHEATLRCWALGFYPAEITL
TWQRDGEDQTQDTELVETRPAGDGTFQKWAAVVVPSGEEQRYTCHVQHEGLP
KPLTLRWE*AAAGG*DKTHTCPPCPAPEAAGGPSVFLFPPKPKDTLMISRTPEVT
CVVVDVSHEDPEVKFNWYVDGVEVHNAKTKPREEQYNSTYRVVSVLTVLH
QDWLNGKEYKCKVSNKALPAPIEKTISKAKGQPREPQVYTLPPSREEMTKN
QVSLTCLVKGFYPSDIAVEWESNGQPENNYKTTPPVLDSDGSFFLYSKLTVD
KSRWQQGNVFSCSVMHEALHNHYTQKSLSLSPGGGGSGGGGSGGGGSAPT
SSSTKKTQLQLEALLLDLQMILNGINNYKNPKLTRMLTAKFYMPKKATELK
HLQCLEEELKPLEEVLNLAQSKNFHLRPRDLISNINVIVLELKGSETTFMCEY
ADETATIVEFLNRWITFCQSIISTLTGGGGSGGGGSGGGGSGGGGSAPTSSSTK
KTQLQLEALLLDLQMILNGINNYKNPKLTRMLTAKFYMPKKATELKHLQC
LEEELKPLEEVLNLAQSKNFHLRPRDLISNINVIVLELKGSETTFMCEYADET
ATIVEFLNRWITFCQSIISTLT (SEQ ID NO:436)

HLA-A*24:02 (Y84C; A236) – double underlined
AAAGG linker – bold and italicized (SEQ ID NO:283)
hIgG1 Fc (L234A; L235A) – bold and underlined
(G4S)$_3$ and (G4S)$_4$ – underlined (SEQ ID NOs:379-380)
IL-2 (H16A; F42A) – bold

FIG. 20G

3197

GSHSMRYFSTSVSRPGRGEPRFIAVGYVDDTQFVRFDSDAASQRMEPRAPWIEQE
GPEYWDEETGKVKAHSQTDRENLRIALRCYNQSEAGSHTLQMMFGCDVGSDGR
FLRGYHQYAYDGKDYIALKEDLRSWTAADMAAQITKRKWEAAHVAEQQRAYL
EGTCVDGLRRYLENGKETLQRTDPPKTHMTHHPISDHEATLRCWALGFYPAEITL
TWQRDGEDQTQDTELVETRPAGDGTFQKWAAVVVPSGEEQRYTCHVQHEGLP
KPLTLRWE*AAAGG*DKTHTCPPCPAPEAAGGPSVFLFPPKPKDTLMISRTPEVT
CVVVDVSHEDPEVKFNWYVDGVEVHNAKTKPREEQYNSTYRVVSVLTVLH
QDWLNGKEYKCKVSNKALPAPIEKTISKAKGQPREPQVYTLPPSREEMTKN
QVSLTCLVKGFYPSDIAVEWESNGQPENNYKTTPPVLDSDGSFFLYSKLTVD
KSRWQQGNVFSCSVMHEALHNHYTQKSLSLSPG (SEQ ID NO:437)

HLA-A*24:02 (Y84C; A236) – double underlined
AAAGG linker – bold and italicized (SEQ ID NO:283)
hIgG1 Fc (L234A; L235A) – bold and underlined

FIG. 20H

3188

CYTWNQMNLGCGGSGGGGSGGGGS*IQRTPKIQVYSCHPAENGKSNFLNCYVSGFH*
*PSDIEVDLLKNGERIEKVEHSDLSFSKDWSFYLLYYTEFTPTEKDEYACRVNHVTLSQP*
*KIVKWDRDM* (SEQ ID NO:438)

epitope: CYTWNQMNL – WT1 (235-243; M236Y) (SEQ ID NO:262)
(GCGGS)(G4S)$_2$ – underlined (SEQ ID NO:317)
β2M (R12C) – italicized

FIG. 20I

3604

CYTWNQMNLGCGGSGGGGSGGGGS*IQRTPKIQVYSCHPAENGKSNFLNCYVSGFH*
*PSDIEVDLLKNGERIEKVEHSDLSFSKDWSFYLLYYTEFTPTEKDEYACRVNHVTLSQP*
*KIVKWDRDM*GGGGSGGGGSGGGGSAPTSSSTKKTQLQLEALLLDLQMILNGIN
NYKNPKLTRMLTAKFYMPKKATELKHLQCLEEELKPLEEVLNLAQSKNFH
LRPRDLISNINVIVLELKGSETTFMCEYADETATIVEFLNRWITFCQSIISTLTG
GGGSGGGGSGGGGSGGGGSAPTSSSTKKTQLQLEALLLDLQMILNGINNYKN
PKLTRMLTAKFYMPKKATELKHLQCLEEELKPLEEVLNLAQSKNFHLRPR
DLISNINVIVLELKGSETTFMCEYADETATIVEFLNRWITFCQSIISTLT

(SEQ ID NO:439)

epitope: CYTWNQMNL – WT1 (235-243; M236Y) (SEQ ID NO:262)
(GCGGS)(G4S)$_2$, (G4S)$_3$, and (G4S)$_4$ – underlined (SEQ ID NOs:317, 379 and 380)
β2M (R12C) – italicized
IL-2 (H16A; F42A) – bold

FIG. 20J

3603

CYTWNQMNLGGGGSGGGGSGGGGS*IQRTPKIQVYSCHPAENGKSNFLNCYVSGFH PSDIEVDLLKNGERIEKVEHSDLSFSKDWSFYLLYYTEFTPTEKDEYACRVNHVTLSQP KIVKWDRDM*GGGGSGGGGSGGGGSAPTSSSTKKTQLQLEALLLDLQMILNGIN NYKNPKLTRMLTAKFYMPKKATELKHLQCLEEELKPLEEVLNLAQSKNFH LRPRDLISNINVIVLELKGSETTFMCEYADETATIVEFLNRWITFCQSIISTLTGGGGSGGGGSGGGGSGGGGSAPTSSSTKKTQLQLEALLLDLQMILNGINNYKN PKLTRMLTAKFYMPKKATELKHLQCLEEELKPLEEVLNLAQSKNFHLRPR DLISNINVIVLELKGSETTFMCEYADETATIVEFLNRWITFCQSIISTLT

(SEQ ID NO:440)

epitope: CYTWNQMNL – WT1 (235-243; M236Y) (SEQ ID NO:262)
$(G4S)_3$ and $(G4S)_4$ – underlined (SEQ ID NOs:379-380)
β2M (R12C) – italicized
IL-2 (H16A; F42A) – bold

FIG. 20K

3192

CYTWNQMNLGCGGSGGGGSGGGGS*IQRTPKIQVYSRHPAENGKSNFLNCYVSGFH PSDIEVDLLKNGERIEKVEHSDLSFSKDWSFYLLYYTEFTPTEKDEYACRVNHVTLSQP KIVKWDRDM* (SEQ ID NO:441)

epitope: CYTWNQMNL – WT1 (235-243; M236Y) (SEQ ID NO:262)
$(GCGGS)(G4S)_2$ – underlined (SEQ ID NO:317)
β2M (R12) – italicized

FIG. 20L

3605

CYTWNQMNLGCGGSGGGGSGGGGS*IQRTPKIQVYSRHPAENGKSNFLNCYVSGFH*
*PSDIEVDLLKNGERIEKVEHSDLSFSKDWSFYLLYYTEFTPTEKDEYACRVNHVTLSQP*
*KIVKWDRDM*GGGGSGGGGSGGGGSAPTSSSTKKTQLQLEALLLDLQMILNGIN
NYKNPKLTRMLTAKFYMPKKATELKHLQCLEEELKPLEEVLNLAQSKNFH
LRPRDLISNINVIVLELKGSETTFMCEYADETATIVEFLNRWITFCQSIISTLT
GGGGSGGGGSGGGGSGGGGSAPTSSSTKKTQLQLEALLLDLQMILNGINNYK
NPKLTRMLTAKFYMPKKATELKHLQCLEEELKPLEEVLNLAQSKNFHLRP
RDLISNINVIVLELKGSETTFMCEYADETATIVEFLNRWITFCQSIISTLT
(SEQ ID NO:442)

epitope: CYTWNQMNL – WT1 (235-243; M236Y) (SEQ ID NO:262)
(GCGGS)$(G4S)_2$, $(G4S)_3$, and $(G4S)_4$ – underlined (SEQ ID NOs:317, 379 and 380)
β2M (R12) – italicized
IL-2 (H16A; F42A) – bold

FIG. 20M

3529

NYMNLGATLGCGGSGGGGSGGGGS*IQRTPKIQVYSCHPAENGKSNFLNCYVSGFH*
*PSDIEVDLLKNGERIEKVEHSDLSFSKDWSFYLLYYTEFTPTEKDEYACRVNHVTLSQP*
*KIVKWDRDM* (SEQ ID NO:443)

epitope: NYMNLGATL – WT1 (239-247; Q240Y) (SEQ ID NO:263)
(GCGGS)$(G4S)_2$ – underlined (SEQ ID NO:317)
β2M (R12C) – italicized

FIG. 20N

3709

NYMNLGATLGCGGSGGGGSGGGGS*IQRTPKIQVYSCHPAENGKSNFLNCYVSGFH*
*PSDIEVDLLKNGERIEKVEHSDLSFSKDWSFYLLYYTEFTPTEKDEYACRVNHVTLSQP*
*KIVKWDRDM*GGGGSGGGGSGGGGSAPTSSSTKKTQLQLEALLLDLQMILNGIN
NYKNPKLTRMLTAKFYMPKKATELKHLQCLEEELKPLEEVLNLAQSKNFH
LRPRDLISNINVIVLELKGSETTFMCEYADETATIVEFLNRWITFCQSIISTLTG
GGGSGGGGSGGGGSGGGGSAPTSSSTKKTQLQLEALLLDLQMILNGINNYKN
PKLTRMLTAKFYMPKKATELKHLQCLEEELKPLEEVLNLAQSKNFHLRPR
DLISNINVIVLELKGSETTFMCEYADETATIVEFLNRWITFCQSIISTLT
(SEQ ID NO:444)

epitope: NYMNLGATL – WT1 (239-247; Q240Y) (SEQ ID NO:263)
(GCGGS)(G4S)2, (G4S)3, and (G4S)4 – underlined (SEQ ID NOs:317, 379 and 380)
β2M (R12C) – italicized
IL-2 (H16A; F42A) – bold

FIG. 20O

3528

NYMNLGATLGGGGSGGGGSGGGGS*IQRTPKIQVYSCHPAENGKSNFLNCYVSGFH*
*PSDIEVDLLKNGERIEKVEHSDLSFSKDWSFYLLYYTEFTPTEKDEYACRVNHVTLSQP*
*KIVKWDRDM* (SEQ ID NO:445)

epitope: NYMNLGATL – WT1 (239-247; Q240Y) (SEQ ID NO:263)
(G4S)3 – underlined (SEQ ID NO:379)
β2M (R12C) – italicized

FIG. 20P

3708

NYMNLGATLGGGGSGGGGSGGGGS*IQRTPKIQVYSCHPAENGKSNFLNCYVSGFH*
*PSDIEVDLLKNGERIEKVEHSDLSFSKDWSFYLLYYTEFTPTEKDEYACRVNHVTLSQP*
*KIVKWDRDM*GGGGSGGGGSGGGGSAPTSSSTKKTQLQLEALLLDLQMILNGIN
NYKNPKLTRMLTAKFYMPKKATELKHLQCLEEELKPLEEVLNLAQSKNFH
LRPRDLISNINVIVLELKGSETTFMCEYADETATIVEFLNRWITFCQSIISTLTG
GGGSGGGGSGGGGSGGGGSAPTSSSTKKTQLQLEALLLDLQMILNGINNYKNPK
LTRMLTAKFYMPKKATELKHLQCLEEELKPLEEVLNLAQSKNFHLRPRDLISNIN
VIVLELKGSETTFMCEYADETATIVEFLNRWITFCQSIISTLT (SEQ ID NO:446)

epitope: NYMNLGATL (SEQ ID NO:263) – WT1 (239-247; Q240Y)
$(G4S)_3$ and $(G4S)_4$ – underlined (SEQ ID NOs:379-380)
β2M (R12C) – italicized
IL-2 (H16A; F42A) – bold

FIG. 20Q

3530

NYMNLGATLGCGGSGGGGSGGGGS*IQRTPKIQVYSRHPAENGKSNFLNCYVSGFH*
*PSDIEVDLLKNGERIEKVEHSDLSFSKDWSFYLLYYTEFTPTEKDEYACRVNHVTLSQP*
*KIVKWDRDM* (SEQ ID NO:447)

epitope: NYMNLGATL – WT1 (239-247; Q240Y) (SEQ ID NO:263)
$(GCGGS)(G4S)_2$ – underlined (SEQ ID NO:317)
β2M (R12) – italicized

FIG. 20R

3710

NYMNLGATLGCGGSGGGGSGGGGS*IQRTPKIQVYSRHPAENGKSNFLNCYVSGFHPSDIEVDLLKNGERIEKVEHSDLSFSKDWSFYLLYYTEFTPTEKDEYACRVNHVTLSQPKIVKWDRDM*GGGGSGGGGSGGGGSAPTSSSTKKTQLQLEALLLDLQMILNGINNYKNPKLTRMLTAKFYMPKKATELKHLQCLEEELKPLEEVLNLAQSKNFHLRPRDLISNINVIVLELKGSETTFMCEYADETATIVEFLNRWITFCQSIISTLTGGGGSGGGGSGGGGSGGGGSAPTSSSTKKTQLQLEALLLDLQMILNGINNYKNPKLTRMLTAKFYMPKKATELKHLQCLEEELKPLEEVLNLAQSKNFHLRPRDLISNINVIVLELKGSETTFMCEYADETATIVEFLNRWITFCQSIISTLT

(SEQ ID NO:448)

epitope: NYMNLGATL – WT1 (239-247; Q240Y) (SEQ ID NO:263)
(GCGGS)(G4S)$_2$, (G4S)$_3$, and (G4S)$_4$ – underlined (SEQ ID NOs:317, 379 and 380)
β2M (R12) – italicized
IL-2 (H16A; F42A) – bold

| Specificity | IST # | Mod position | Framework | Prism color legend |
|---|---|---|---|---|
| CMV | IST-1380-839-016 | 1 | R12C | ☆ |
| MART-1 | IST-1380-1571-011 | 1 | R12C | ☆ |
| WT-1 A02 constructs | IST-1715-2380-005 | 37-45 | R12C/G2C | ○ |
| | IST-2045-2762-004 | 37-45 | G2C | ○ |
| | IST-1715-2381-003 | 126-134 | R12C/G2C | ○ |
| | IST-1715-3625-004 | 126-134 R126Y | R12C/G2C | ○ |
| Proleuikin | | | | ● |
| rhIL-2 | | | | ● |

FIG. 27
37-45 double disulfide
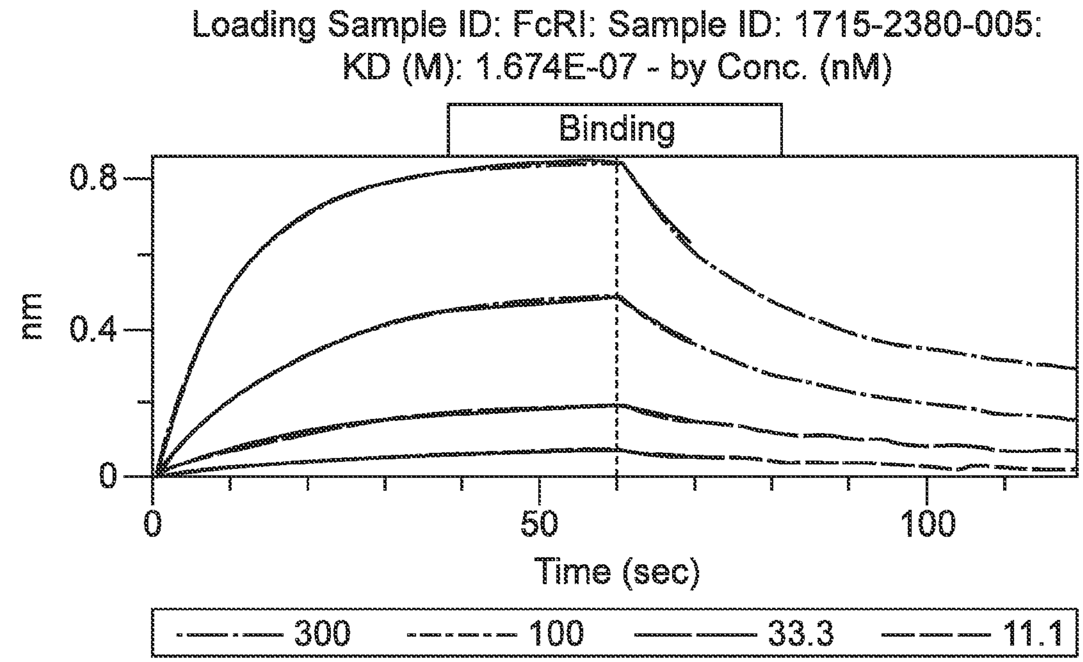
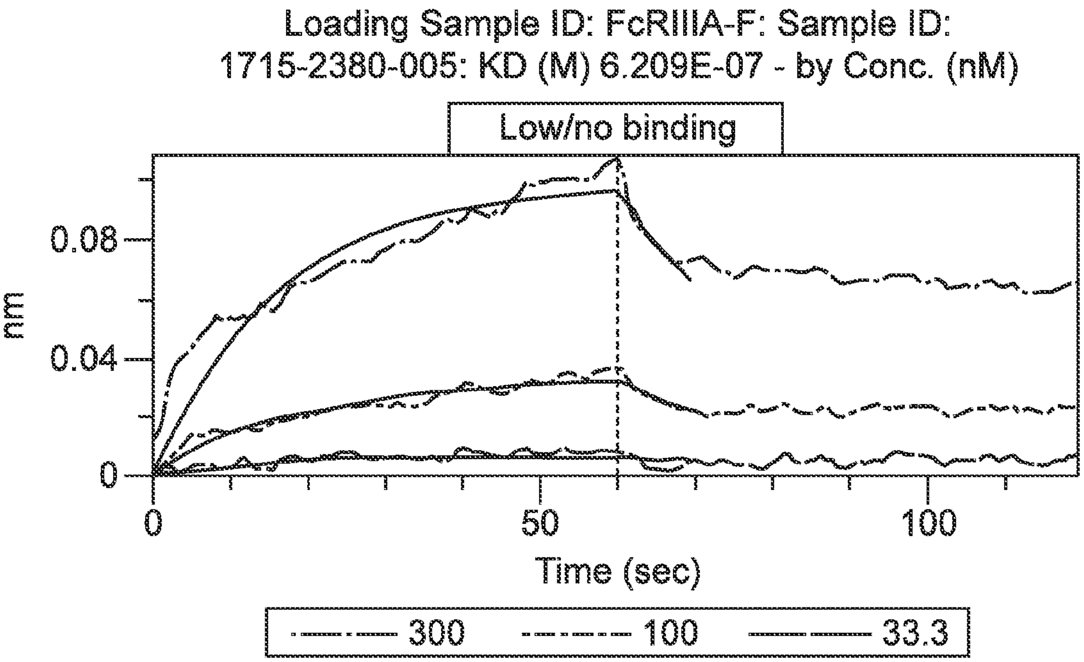

FIG. 27 (Cont.)
37-45 double disulfide
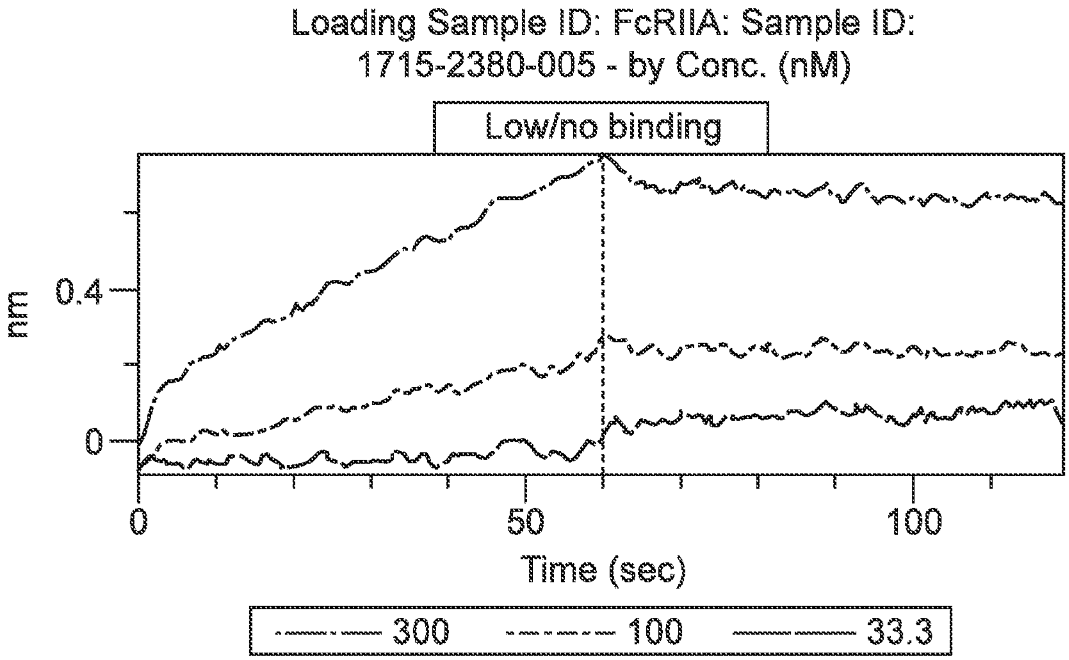
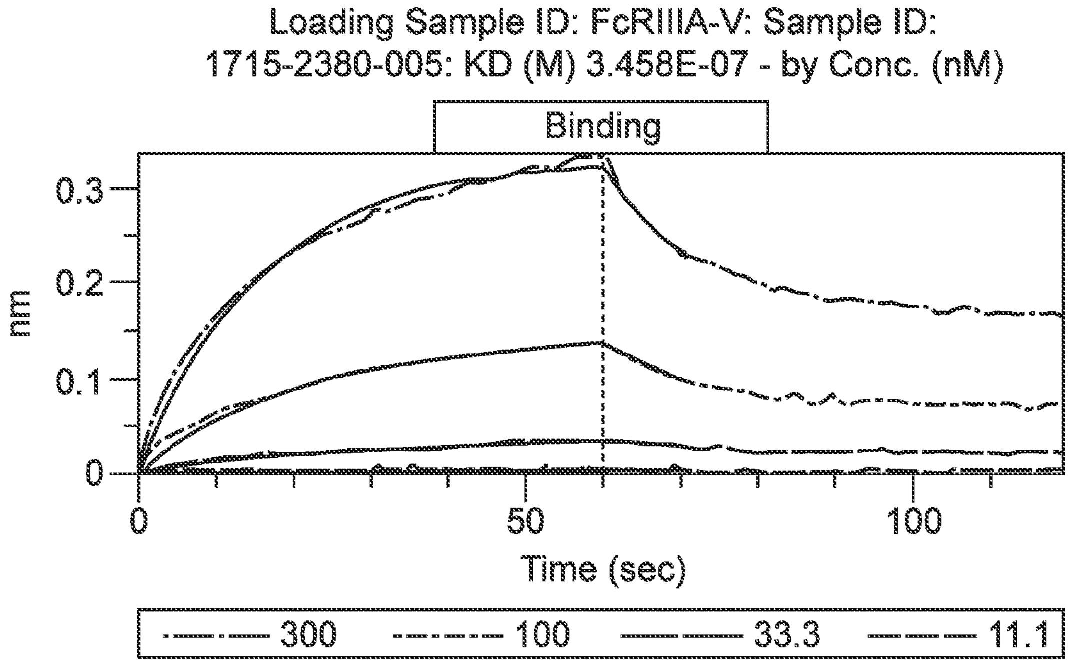

FIG. 27 (Cont.)
37-45 double disulfide
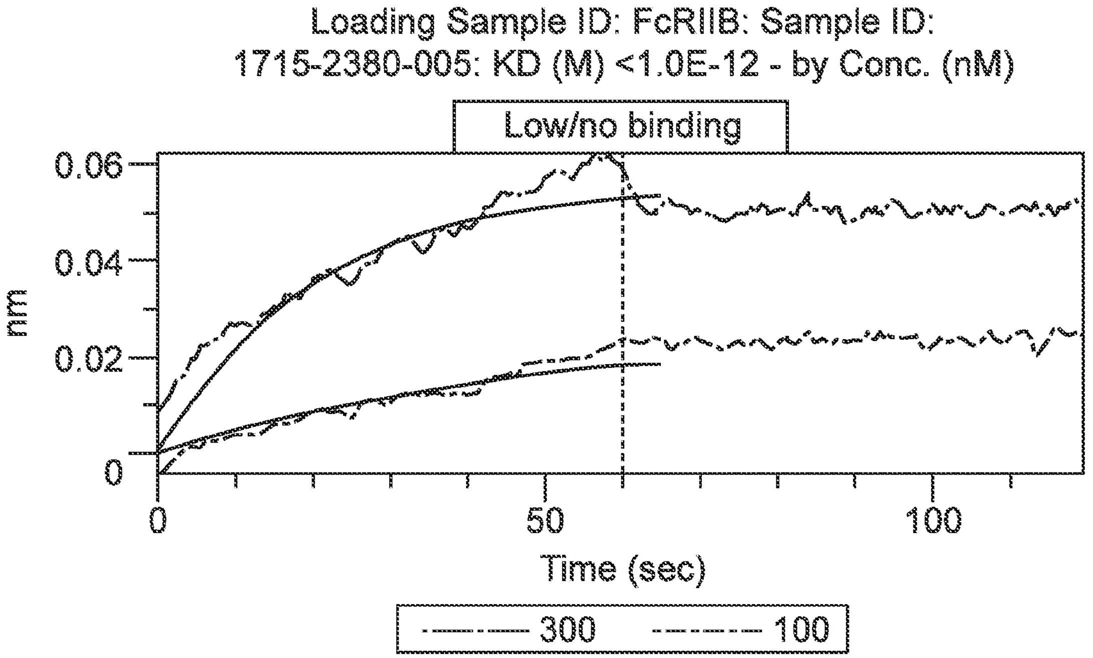
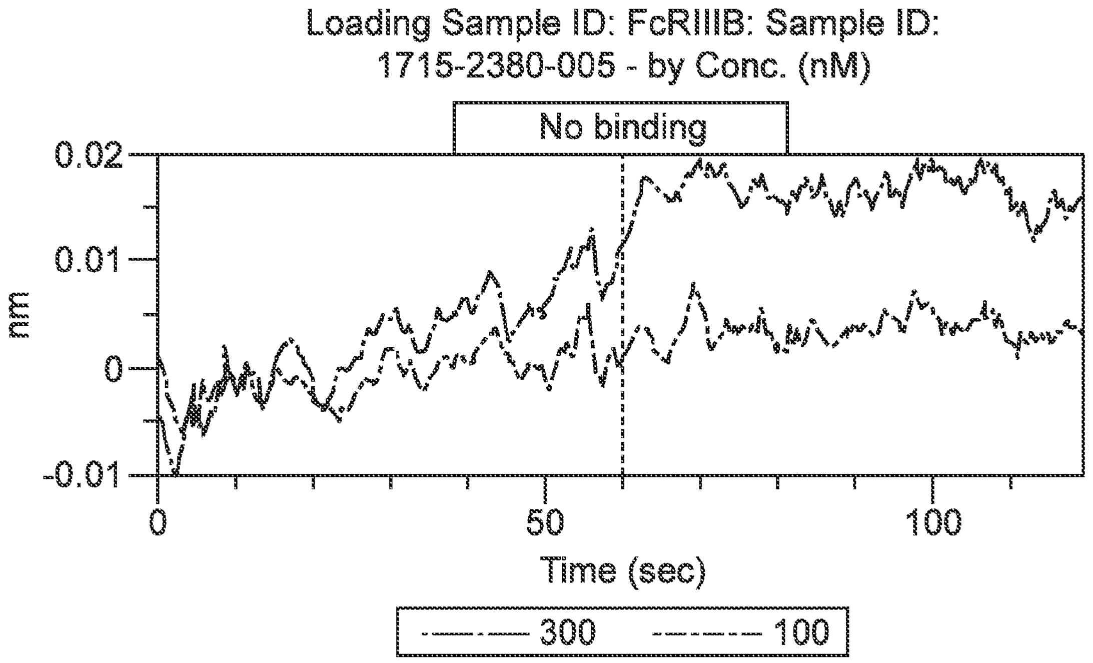

37-45 double disulfide

| Loading Sample ID | Sample ID | KD (M) | kon(1/Ms) | kdis(1/s) | Full X^2 | Full R^2 |
|---|---|---|---|---|---|---|
| FcRI | 1715-2380-005 | 1.67E-07 | 1.92E+05 | 0.03209 | 0.0063 | 0.9997 |
| FcRIIA | 1715-2380-005 | No binding | -- | -- | -- | -- |
| FcRIIB | 1715-2380-005 | <1.0E-12* | 1.61E+05 | <1.0E+05 | 0.0018 | 0.9608 |
| FcRIIIA-F | 1715-2380-005 | 6.21E-07 | 6.61E+04 | 4.11E-02 | 0.0046 | 0.9793 |
| FcRIIIA-V | 1715-2380-005 | 3.46E-07 | 9.83E+04 | 3.40E-02 | 0.0089 | 0.9973 |
| FcRIIIB | 1715-2380-005 | No Binding | -- | -- | -- | -- |
| FcRn (pH 6.0) | 1715-2380-005 | 1.05E-07 | 2.83E+05 | 2.98E-02 | 0.0139 | 0.9963 |

FIG. 28
WT1 235-243 M236Y ISTs
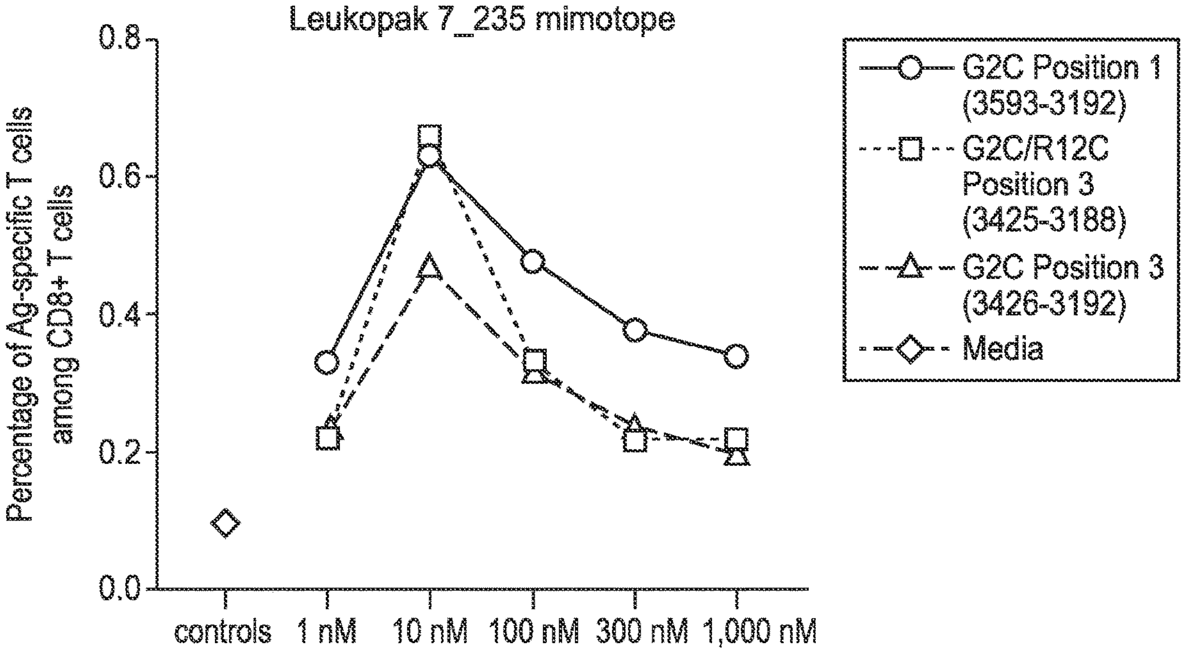
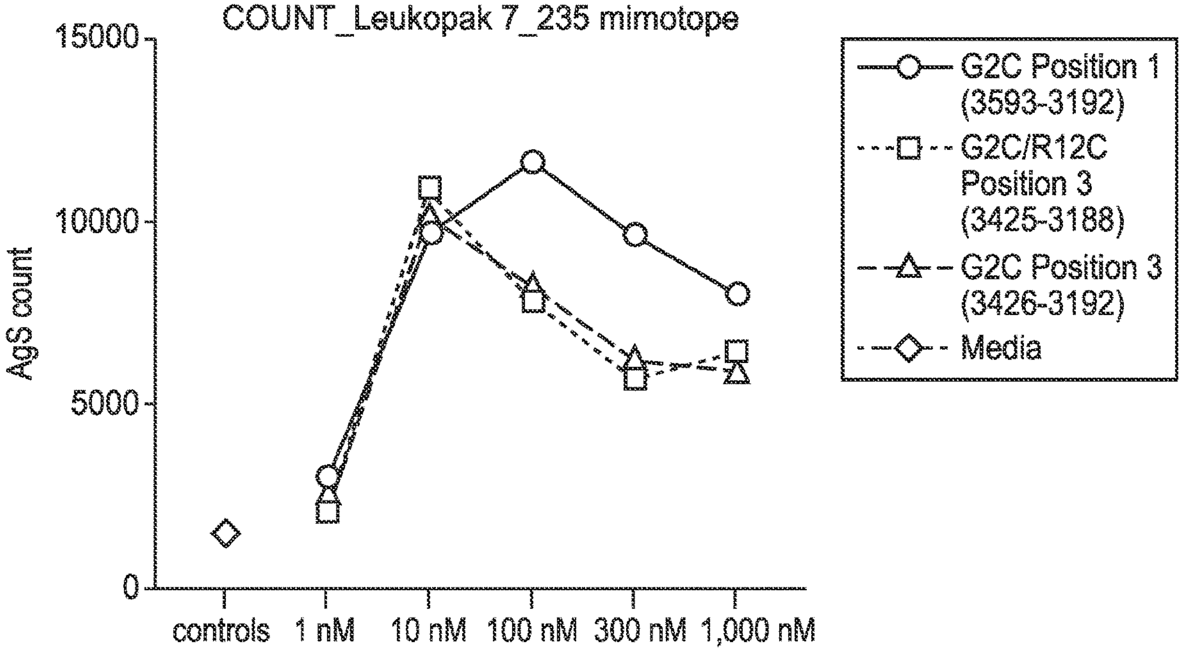

WT1 239-247 Q240Y ISTs

| Specificity | IST # | Mod position | Framework | Prism color legend |
|---|---|---|---|---|
| CMV | IST-1380-839-016 | 1 | R12C | ☆ |
| MART-1 | IST-1380-1571-011 | 1 | R12C | ☆ |
| WT-1 A02 (235-243; M236Y) | IST-3593-3192-002 | 1 | G2C | ○ |
| | IST-3425-3188-003 | 3 | R12C/G2C | □ |
| | IST-3426-3192-002 | 3 | G2C | □ |
| Proleuikin | | | | ● |
| rhIL-2 | | | | ● |

FIG. 31
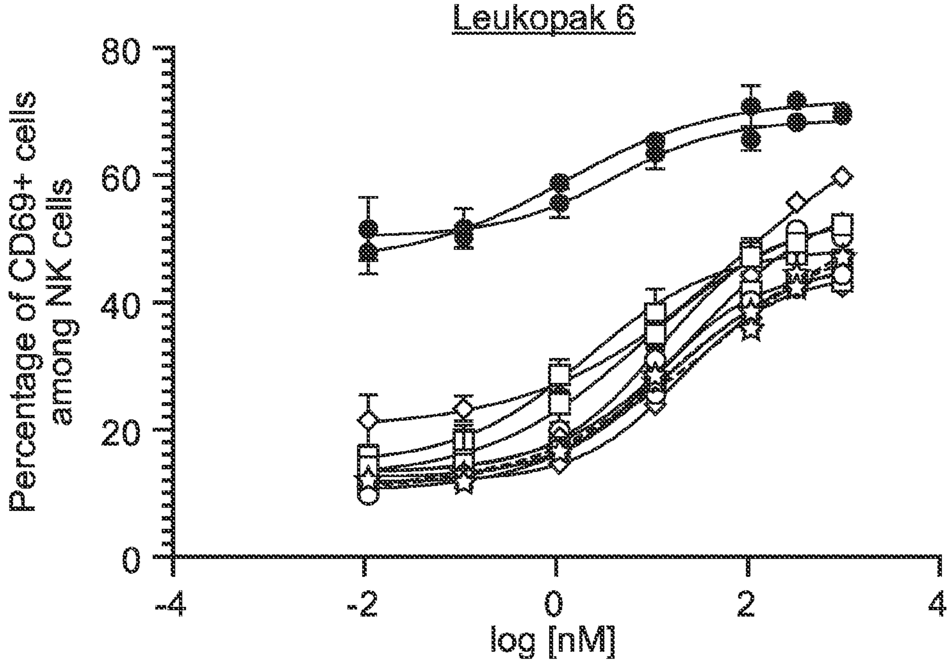
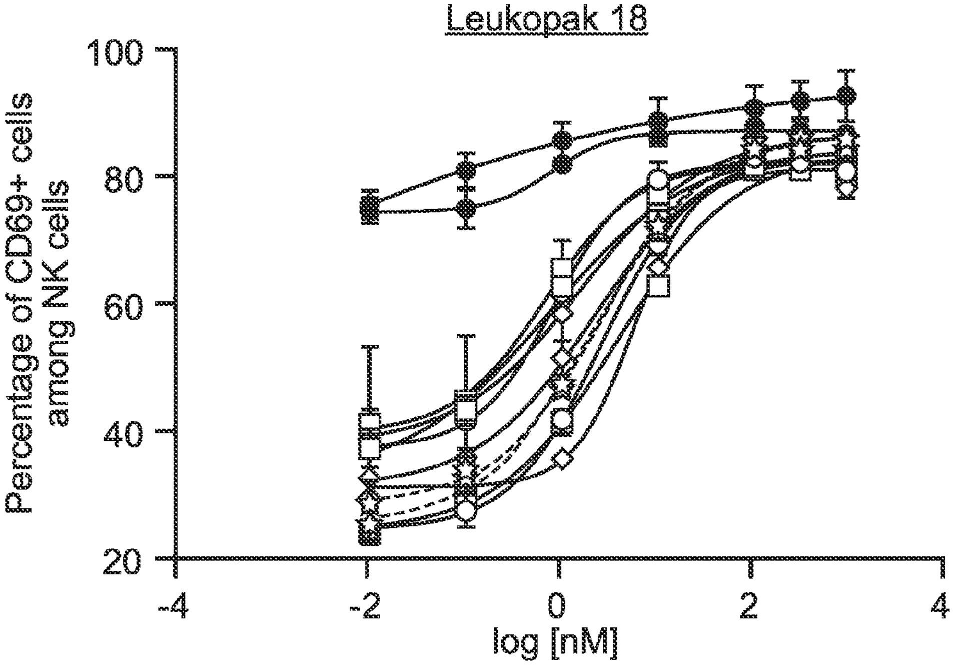

FIG. 31 (Cont.)

| Specificity | IST # | Mod position | Framework | Prism color legend |
|---|---|---|---|---|
| CMV | IST-1380-839-016 | 1 | R12C | ☆ |
| MART-1 | IST-1380-1571-011 | 1 | R12C | ☆ |
| WT-1 A24 (239-247; Q240Y) | IST-3592-3529-002 | 1 | R12C/G2C | ○ |
| | IST-3425-3529-001 | 3 | R12C/G2C | □ |
| | IST-3196-3709-001 | 5 | R12C/G2C | ◇ |
| | IST-3159-3528-001 | 3 | R12C | □ |
| | IST-2764-3708-002 | 5 | R12C | ◇ |
| | IST-3593-3530-001 | 1 | G2C | ○ |
| | IST-3426-3530-001 | 3 | G2C | □ |
| | IST-3197-3710-002 | 5 | G2C | ◇ |
| Proleukin | | | | ● |
| rhIL-2 | | | | ● |

FIG. 34
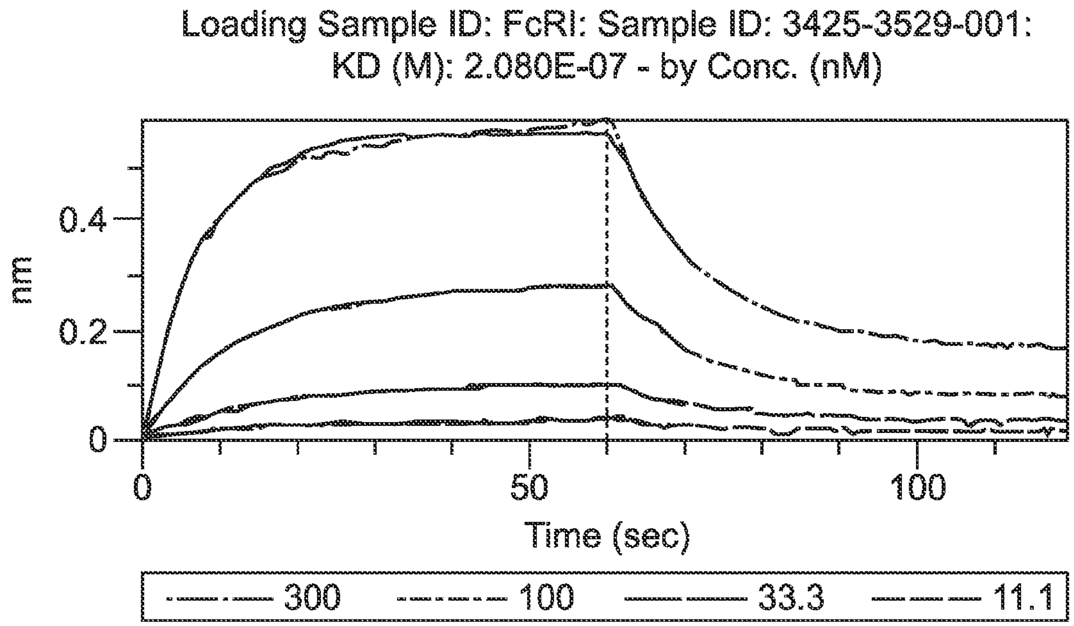
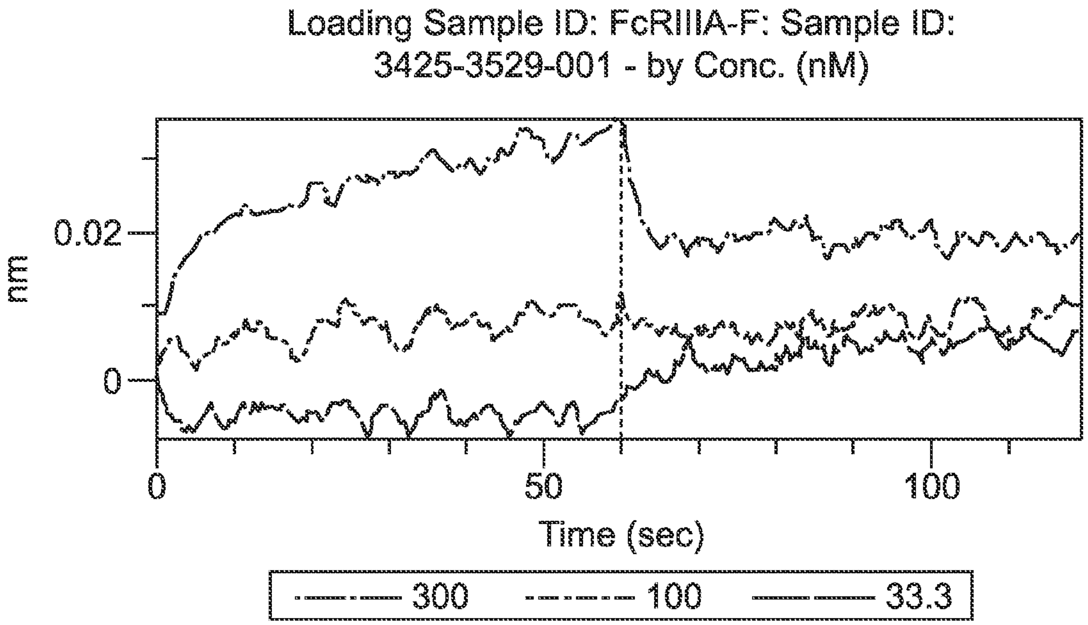

FIG. 34 (Cont.)
Loading Sample ID: FcRIIA: Sample ID: 3425-3529-001: KD (M): 1.560E-07 - by Conc. (nM)
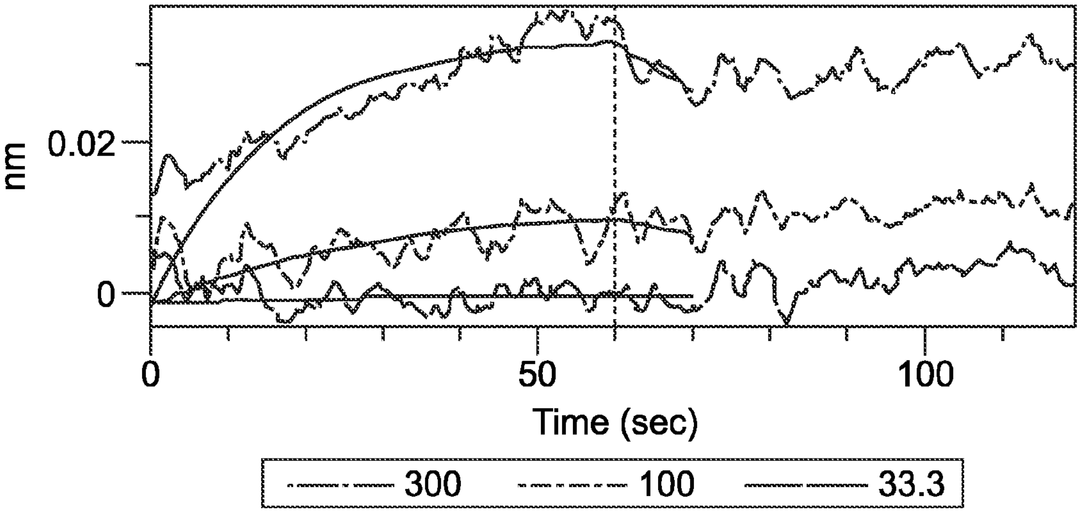
Loading Sample ID: FcRIIIA-V: Sample ID: 3425-3529-001: KD (M) 5.917E-07 - by Conc. (nM)
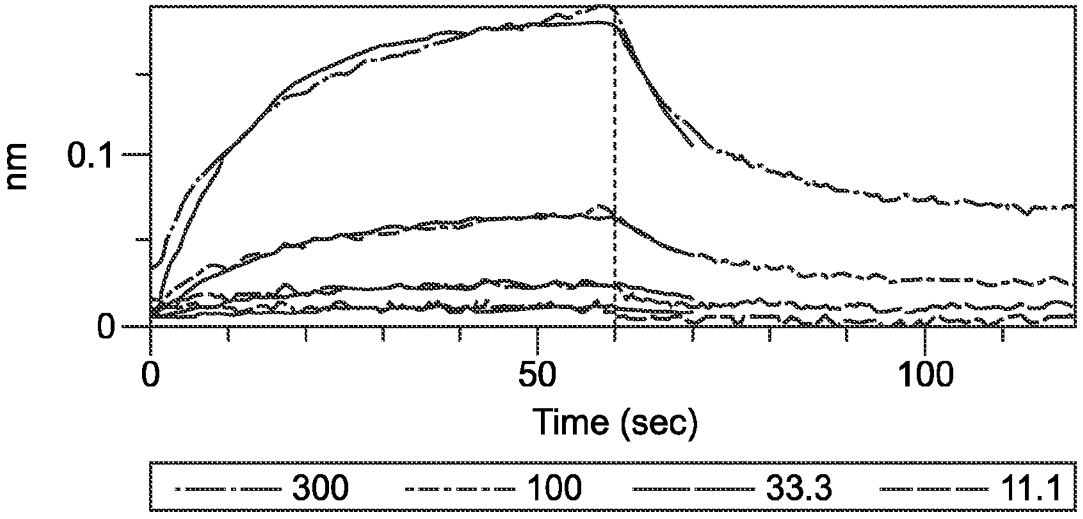

FIG. 34 (Cont.)
Loading Sample ID: FcRIIB: Sample ID:
3425-3529-001: KD (M): 5.716E-06 - by Conc. (nM)
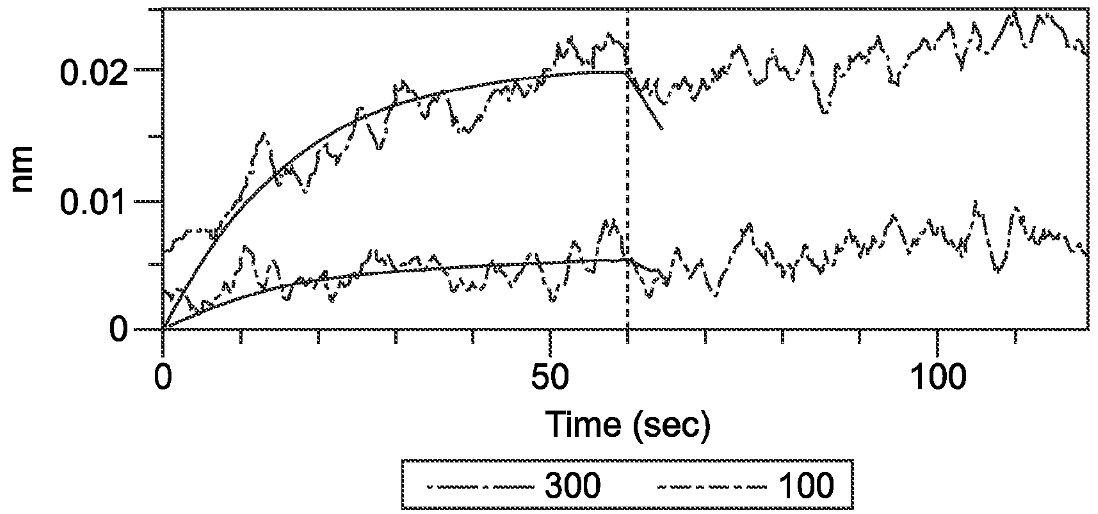
Loading Sample ID: FcRIIIB: Sample ID:
3425-3529-001 - by Conc. (nM)
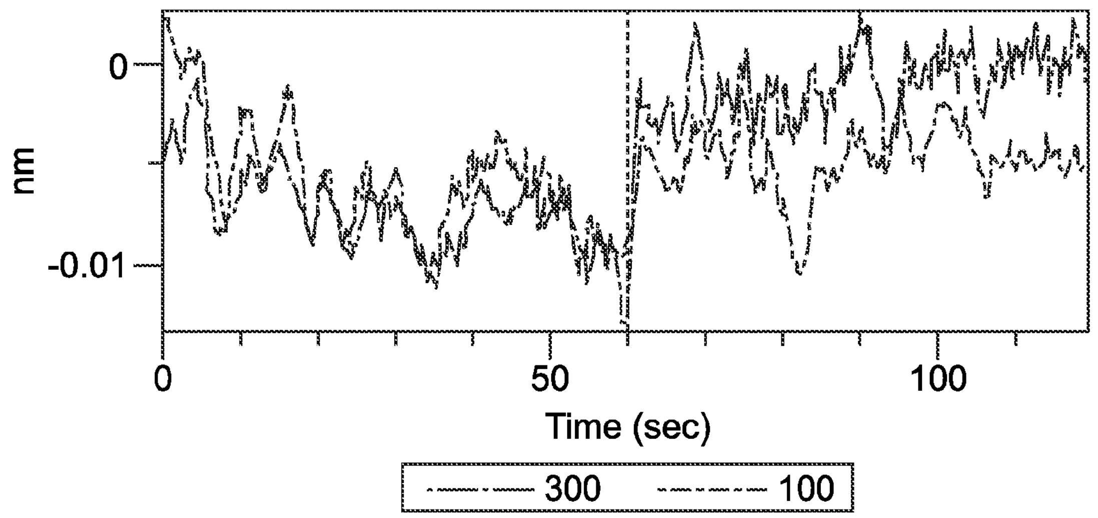

| Loading Sample ID | Sample ID | KD (M) | kon(1/Ms) | kdis(1/s) | Full X^2 | Full R^2 |
|---|---|---|---|---|---|---|
| FcRI | 3425-3529-001 | 2.08E-07 | 2.50E+05 | 5.20E-02 | 0.00687 | 0.9991 |
| FcRIIA | 3425-3529-001 | 1.56E-07* | 1.36E+05 | 2.12E-02 | 0.002 | 0.9269 |
| FcRIIB | 3425-3529-001 | 5.72E-06* | 1.00E+04 | 5.74E-02 | 0.0004 | 0.9277 |
| FcRIIIA-F | 3425-3529-001 | No binding | -- | -- | -- | -- |
| FcRIIIA-V | 3425-3529-001 | 5.92E-07 | 9.10E+04 | 5.39E-02 | 0.0078 | 0.9924 |
| FcRIIIB | 13425-3529-001 | No Binding | -- | -- | -- | -- |
| FcRn (pH 6.0) | 3425-3529-001 | 9.79E-08 | 2.31E+05 | 2.26E-02 | 0.0177 | 0.9922 |

FIG. 35A

SMTWNQMNL<u>GGGGSGGGGSGGGGS</u>*IQRTPKIQVYS<u>C</u>HPAENGKSNFLNCYVSGFHPSDIE VDLLKNGERIEKVEHSDLSFSKDWSFYLLYYTEFTPTEKDEYACRVNHVTLSQPKIVKWDRDM*
(SEQ ID NO:462)

epitope: SMTWNQMNL – WT1 (235-243; C235S) (SEQ ID NO:451)
(G4S)3 – underlined (SEQ ID NO:379)
β2M (R12C) – italicized (R12C in bold and underlined)

FIG. 35B

SMTWNQMNL<u>GCGGSGGGGSGGGGS</u>*IQRTPKIQVYS<u>C</u>HPAENGKSNFLNCYVSGFHPSDIEV DLLKNGERIEKVEHSDLSFSKDWSFYLLYYTEFTPTEKDEYACRVNHVTLSQPKIVKWDRDM*
(SEQ ID NO:463)

epitope: SMTWNQMNL – WT1 (235-243; C235S) (SEQ ID NO:451)
GCGGS(G4S)2 – underlined (SEQ ID NO:317)
β2M (R12C) – italicized (R12C in bold and underlined)

FIG. 35C

SMTWNQMNL<u>GCGGSGGGGSGGGGS</u>*IQRTPKIQVYS<u>R</u>HPAENGKSNFLNCYVSGFHPSDIEV DLLKNGERIEKVEHSDLSFSKDWSFYLLYYTEFTPTEKDEYACRVNHVTLSQPKIVKWDRDM*
(SEQ ID NO:464)

epitope: SMTWNQMNL – WT1 (235-243; C235S) (SEQ ID NO:451)
GCGGS(G4S)2 – underlined (SEQ ID NO:317)
β2M (R12) – italicized (R12 in bold and underlined)

FIG. 35D

SMTWNQMNLGCGGSGGGGSGGGGS*IQRTPKIQVYSRHPAENGKSNFLNCYVSGFHPSDIEV*

*DLLKNGERIEKVEHSDLSFSKDWSFYLLYYTEFTPTEKDEYACRVNHVTLSQPKIVKWDRDM*G

GGGSGGGGSGGGGSAPTSSSTKKTQLQLEALLLDLQMILNGINNYKNPKLTRMLTA

KFYMPKKATELKHLQCLEEELKPLEEVLNLAQSKNFHLRPRDLISNINVIVLELKGS

ETTFMCEYADETATIVEFLNRWITFCQSIISTLTGGGGSGGGGSGGGGSGGGGSAPTS

SSTKKTQLQLEALLLDLQMILNGINNYKNPKLTRMLTAKFYMPKKATELKHLQCL

EEELKPLEEVLNLAQSKNFHLRPRDLISNINVIVLELKGSETTFMCEYADETATIVEF

LNRWITFCQSIISTLT (SEQ ID NO:465)

epitope: SMTWNQMNL – WT1 (235-243; C235S) (SEQ ID NO:451)
(GCGGS)(G4S)$_2$, (G4S)$_3$, and (G4S)$_4$ – underlined (SEQ ID NOs:317, 379 and 380)
β2M (R12) – italicized
IL-2 (H16A; F42A) – bold

FIG. 35E

SMTWNQMNLGCGGSGGGGSGGGGS*IQRTPKIQVYSCHPAENGKSNFLNCYVSGFHPSDIEV*

*DLLKNGERIEKVEHSDLSFSKDWSFYLLYYTEFTPTEKDEYACRVNHVTLSQPKIVKWDRDM*G

GGGSGGGGSGGGGSAPTSSSTKKTQLQLEALLLDLQMILNGINNYKNPKLTRMLTA

KFYMPKKATELKHLQCLEEELKPLEEVLNLAQSKNFHLRPRDLISNINVIVLELKGS

ETTFMCEYADETATIVEFLNRWITFCQSIISTLTGGGGSGGGGSGGGGSGGGGSAPTS

SSTKKTQLQLEALLLDLQMILNGINNYKNPKLTRMLTAKFYMPKKATELKHLQCL

EEELKPLEEVLNLAQSKNFHLRPRDLISNINVIVLELKGSETTFMCEYADETATIVEF

LNRWITFCQSIISTLT (SEQ ID NO:466)

epitope: SMTWNQMNL – WT1 (235-243; C235S) (SEQ ID NO:451)
(GCGGS)(G4S)$_2$, (G4S)$_3$, and (G4S)$_4$ – underlined (SEQ ID NOs:317, 379 and 380)
β2M (R12C) – italicized
IL-2 (H16A; F42A) – bold

FIG. 35F

SMTWNQMNLGGGGSGGGGSGGGGS*IQRTPKIQVYSCHPAENGKSNFLNCYVSGFHPSDIE*
*VDLLKNGERIEKVEHSDLSFSKDWSFYLLYYTEFTPTEKDEYACRVNHVTLSQPKIVKWDRDM*
GGGGSGGGGSGGGGSAPTSSSTKKTQLQLEALLLDLQMILNGINNYKNPKLTRMLT
AKFYMPKKATELKHLQCLEEELKPLEEVLNLAQSKNFHLRPRDLISNINVIVLELKG
SETTFMCEYADETATIVEFLNRWITFCQSIISTLTGGGGSGGGGSGGGGSGGGGSAPT
SSSTKKTQLQLEALLLDLQMILNGINNYKNPKLTRMLTAKFYMPKKATELKHLQC
LEEELKPLEEVLNLAQSKNFHLRPRDLISNINVIVLELKGSETTFMCEYADETATIVE
FLNRWITFCQSIISTLT (SEQ ID NO:467)

epitope: SMTWNQMNL – WT1 (235-243; C235S) (SEQ ID NO:451)
$(G4S)_3$ and $(G4S)_4$ – underlined (SEQ ID NOs:379-380)
β2M (R12C) – italicized
IL-2 (H16A; F42A) – bold

FIG. 36A

GCMTWNQMNLGGGGSGGGGSGGGGS*IQRTPKIQVYSCHPAENGKSNFLNCYVSGFHPSDI*

*EVDLLKNGERIEKVEHSDLSFSKDWSFYLLYYTEFTPTEKDEYACRVNHVTLSQPKIVKWDRD*

*M* (SEQ ID NO:468)

epitope: GCMTWNQMNL – WT1 (235-243; G-1) (SEQ ID NO:452)
(G4S)3 – underlined (SEQ ID NO:379)
β2M (R12C) – italicized (R12C in bold and underlined)

FIG. 36B

GCMTWNQMNLGCGGSGGGGSGGGGS*IQRTPKIQVYSCHPAENGKSNFLNCYVSGFHPSDI*

*EVDLLKNGERIEKVEHSDLSFSKDWSFYLLYYTEFTPTEKDEYACRVNHVTLSQPKIVKWDRD*

*M* (SEQ ID NO:469)

epitope: GCMTWNQMNL – WT1 (235-243; G-1) (SEQ ID NO:452)
GCGGS(G4S)2 – underlined (SEQ ID NO:317)
β2M (R12C) – italicized (R12C in bold and underlined)

FIG. 36C

GCMTWNQMNLGCGGSGGGGSGGGGS*IQRTPKIQVYSRHPAENGKSNFLNCYVSGFHPSDI*

*EVDLLKNGERIEKVEHSDLSFSKDWSFYLLYYTEFTPTEKDEYACRVNHVTLSQPKIVKWDRD*

*M* (SEQ ID NO:470)

epitope: GCMTWNQMNL – WT1 (235-243; G-1) (SEQ ID NO:452)
GCGGS(G4S)2 – underlined (SEQ ID NO:317)
β2M (R12) – italicized (R12 in bold and underlined)

FIG. 36D

GCMTWNQMNLGCGGSGGGGSGGGGSIQRTPKIQVYSRHPAENGKSNFLNCYVSGFHPSDI
EVDLLKNGERIEKVEHSDLSFSKDWSFYLLYYTEFTPTEKDEYACRVNHVTLSQPKIVKWDRD
MGGGGSGGGGSGGGGSAPTSSSTKKTQLQLEALLLDLQMILNGINNYKNPKLTRML
TAKFYMPKKATELKHLQCLEEELKPLEEVLNLAQSKNFHLRPRDLISNINVIVLELK
GSETTFMCEYADETATIVEFLNRWITFCQSIISTLTGGGGSGGGGSGGGGSGGGGSAP
TSSSTKKTQLQLEALLLDLQMILNGINNYKNPKLTRMLTAKFYMPKKATELKHLQ
CLEEELKPLEEVLNLAQSKNFHLRPRDLISNINVIVLELKGSETTFMCEYADETATIV
EFLNRWITFCQSIISTLT (SEQ ID NO:471)

epitope: GCMTWNQMNL – WT1 (235-243; G-1) (SEQ ID NO:452)
(GCGGS)$(G4S)_2$, $(G4S)_3$, and $(G4S)_4$ – underlined (SEQ ID NOs:317, 379 and 380)
β2M (R12) – italicized
IL-2 (H16A; F42A) – bold

FIG. 36E

GCMTWNQMNLGCGGSGGGGSGGGGSIQRTPKIQVYSCHPAENGKSNFLNCYVSGFHPSDI
EVDLLKNGERIEKVEHSDLSFSKDWSFYLLYYTEFTPTEKDEYACRVNHVTLSQPKIVKWDRD
MGGGGSGGGGSGGGGSAPTSSSTKKTQLQLEALLLDLQMILNGINNYKNPKLTRML
TAKFYMPKKATELKHLQCLEEELKPLEEVLNLAQSKNFHLRPRDLISNINVIVLELK
GSETTFMCEYADETATIVEFLNRWITFCQSIISTLTGGGGSGGGGSGGGGSGGGGSAP
TSSSTKKTQLQLEALLLDLQMILNGINNYKNPKLTRMLTAKFYMPKKATELKHLQ
CLEEELKPLEEVLNLAQSKNFHLRPRDLISNINVIVLELKGSETTFMCEYADETATIV
EFLNRWITFCQSIISTLT (SEQ ID NO:472)

epitope: GCMTWNQMNL – WT1 (235-243; G-1) (SEQ ID NO:452)
(GCGGS)$(G4S)_2$, $(G4S)_3$, and $(G4S)_4$ – underlined (SEQ ID NOs:317, 379 and 380)
β2M (R12C) – italicized
IL-2 (H16A; F42A) – bold

FIG. 36F

GCMTWNQMNLGGGGSGGGGSGGGGS*IQRTPKIQVYSCHPAENGKSNFLNCYVSGFHPSDI EVDLLKNGERIEKVEHSDLSFSKDWSFYLLYYTEFTPTEKDEYACRVNHVTLSQPKIVKWDRD M*GGGGSGGGGSGGGGSAPTSSSTKKTQLQLEALLLDLQMILNGINNYKNPKLTRML TAKFYMPKKATELKHLQCLEEELKPLEEVLNLAQSKNFHLRPRDLISNINVIVLELK GSETTFMCEYADETATIVEFLNRWITFCQSIISTLTGGGGSGGGGSGGGGSGGGGSAP TSSSTKKTQLQLEALLLDLQMILNGINNYKNPKLTRMLTAKFYMPKKATELKHLQ CLEEELKPLEEVLNLAQSKNFHLRPRDLISNINVIVLELKGSETTFMCEYADETATIV EFLNRWITFCQSIISTLT (SEQ ID NO:473)

epitope: GCMTWNQMNL – WT1 (235-243; G-1) (SEQ ID NO:452)
$(G4S)_3$ and $(G4S)_4$ – underlined (SEQ ID NOs:379-380)
β2M (R12C) – italicized
IL-2 (H16A; F42A) – bold

FIG. 37A

SYTWNQMNL<u>GGGGSGGGGSGGGGS</u>*IQRTPKIQVYS<u>C</u>HPAENGKSNFLNCYVSGFHPSDIEV*

*DLLKNGERIEKVEHSDLSFSKDWSFYLLYYTEFTPTEKDEYACRVNHVTLSQPKIVKWDRDM*

(SEQ ID NO:474)

epitope: SYTWNQMNL – WT1 (235-243; C235S; M236Y) (SEQ ID NO:453)
(G4S)3 – underlined (SEQ ID NO:379)
β2M (R12C) – italicized (R12C in bold and underlined)

FIG. 37B

<u>3973</u>

SYTWNQMNL<u>GCGGSGGGGSGGGGS</u>*IQRTPKIQVYS<u>C</u>HPAENGKSNFLNCYVSGFHPSDIEV*

*DLLKNGERIEKVEHSDLSFSKDWSFYLLYYTEFTPTEKDEYACRVNHVTLSQPKIVKWDRDM*

(SEQ ID NO:475)

epitope: SYTWNQMNL – WT1 (235-243; C235S; M236Y) (SEQ ID NO:453)
GCGGS(G4S)2 – underlined (SEQ ID NO:317)
β2M (R12C) – italicized (R12C in bold and underlined)

FIG. 37C

SYTWNQMNL<u>GCGGSGGGGSGGGGS</u>*IQRTPKIQVYS<u>R</u>HPAENGKSNFLNCYVSGFHPSDIEV*

*DLLKNGERIEKVEHSDLSFSKDWSFYLLYYTEFTPTEKDEYACRVNHVTLSQPKIVKWDRDM*

(SEQ ID NO:476)

epitope: SYTWNQMNL – WT1 (235-243; C235S; M236Y) (SEQ ID NO:453)
GCGGS(G4S)2 – underlined (SEQ ID NO:317)
β2M (R12) – italicized (R12 in bold and underlined)

FIG. 37D

SYTWNQMNLGCGGSGGGGSGGGGSIQRTPKIQVYSRHPAENGKSNFLNCYVSGFHPSDIEV
DLLKNGERIEKVEHSDLSFSKDWSFYLLYYTEFTPTEKDEYACRVNHVTLSQPKIVKWDRDMG
GGGSGGGGSGGGGSAPTSSSTKKTQLQLEALLLDLQMILNGINNYKNPKLTRMLTA
KFYMPKKATELKHLQCLEEELKPLEEVLNLAQSKNFHLRPRDLISNINVIVLELKGS
ETTFMCEYADETATIVEFLNRWITFCQSIISTLTGGGGSGGGGSGGGGSGGGGSAPTS
SSTKKTQLQLEALLLDLQMILNGINNYKNPKLTRMLTAKFYMPKKATELKHLQCL
EEELKPLEEVLNLAQSKNFHLRPRDLISNINVIVLELKGSETTFMCEYADETATIVEF
LNRWITFCQSIISTLT (SEQ ID NO:477)

epitope: SYTWNQMNL – WT1 (235-243; C235S; M236Y) (SEQ ID NO:453)
(GCGGS)(G4S)2, (G4S)3, and (G4S)4 – underlined (SEQ ID NOs:317, 379 and 380)
β2M (R12) – italicized
IL-2 (H16A; F42A) – bold

FIG. 37E

SYTWNQMNLGCGGSGGGGSGGGGSIQRTPKIQVYSCHPAENGKSNFLNCYVSGFHPSDIEV
DLLKNGERIEKVEHSDLSFSKDWSFYLLYYTEFTPTEKDEYACRVNHVTLSQPKIVKWDRDMG
GGGSGGGGSGGGGSAPTSSSTKKTQLQLEALLLDLQMILNGINNYKNPKLTRMLTA
KFYMPKKATELKHLQCLEEELKPLEEVLNLAQSKNFHLRPRDLISNINVIVLELKGS
ETTFMCEYADETATIVEFLNRWITFCQSIISTLTGGGGSGGGGSGGGGSGGGGSAPTS
SSTKKTQLQLEALLLDLQMILNGINNYKNPKLTRMLTAKFYMPKKATELKHLQCL
EEELKPLEEVLNLAQSKNFHLRPRDLISNINVIVLELKGSETTFMCEYADETATIVEF
LNRWITFCQSIISTLT (SEQ ID NO:478)

epitope: SYTWNQMNL – WT1 (235-243; C235S; M236Y) (SEQ ID NO:453)
GCGGS)(G4S)2, (G4S)3, and (G4S)4 – underlined (SEQ ID NOs:317, 379 and 380)
β2M (R12C) – italicized
IL-2 (H16A; F42A) – bold

FIG. 37F

SYTWNQMNLGGGGSGGGGSGGGGS*IQRTPKIQVYSCHPAENGKSNFLNCYVSGFHPSDIEV DLLKNGERIEKVEHSDLSFSKDWSFYLLYYTEFTPTEKDEYACRVNHVTLSQPKIVKWDRDM*G GGGSGGGGSGGGGSAPTSSSTKKTQLQLEALLLDLQMILNGINNYKNPKLTRMLTA KFYMPKKATELKHLQCLEEELKPLEEVLNLAQSKNFHLRPRDLISNINVIVLELKGS ETTFMCEYADETATIVEFLNRWITFCQSIISTLTGGGGSGGGGSGGGGSGGGGSAPTS SSTKKTQLQLEALLLDLQMILNGINNYKNPKLTRMLTAKFYMPKKATELKHLQCL EEELKPLEEVLNLAQSKNFHLRPRDLISNINVIVLELKGSETTFMCEYADETATIVEF LNRWITFCQSIISTLT (SEQ ID NO:479)

epitope: SYTWNQMNL – WT1 (235-243; C235S; M236Y) (SEQ ID NO:453)
$(G4S)_3$ and $(G4S)_4$ – underlined (SEQ ID NOs:379-380)
β2M (R12C) – italicized
IL-2 (H16A; F42A) – bold

FIG. 38A

GCYTWNQMNL<u>GGGGSGGGGSGGGGS</u>*IQRTPKIQVYS<u>C</u>HPAENGKSNFLNCYVSGFHPSDI EVDLLKNGERIEKVEHSDLSFSKDWSFYLLYYTEFTPTEKDEYACRVNHVTLSQPKIVKWDRD M* (SEQ ID NO:480)

epitope: GCYTWNQMNL– WT1 (235-243; G-1; M236Y) (SEQ ID NO:454)
(G4S)3 – underlined (SEQ ID NO:379)
β2M (R12C) – italicized (R12C in bold and underlined)

FIG. 38B

GCYTWNQMNL<u>GCGGSGGGGSGGGGS</u>*IQRTPKIQVYS<u>C</u>HPAENGKSNFLNCYVSGFHPSDI EVDLLKNGERIEKVEHSDLSFSKDWSFYLLYYTEFTPTEKDEYACRVNHVTLSQPKIVKWDRD M* (SEQ ID NO:481)

epitope: GCYTWNQMNL– WT1 (235-243; G-1; M236Y) (SEQ ID NO:454)
GCGGS(G4S)2 – underlined (SEQ ID NO:317)
β2M (R12C) – italicized (R12C in bold and underlined)

FIG. 38C

GCYTWNQMNL<u>GCGGSGGGGSGGGGS</u>*IQRTPKIQVYS<u>R</u>HPAENGKSNFLNCYVSGFHPSDI EVDLLKNGERIEKVEHSDLSFSKDWSFYLLYYTEFTPTEKDEYACRVNHVTLSQPKIVKWDRD M* (SEQ ID NO:482)

epitope: GCYTWNQMNL– WT1 (235-243; G-1; M236Y) (SEQ ID NO:454)
GCGGS(G4S)2 – underlined (SEQ ID NO:317)
β2M (R12) – italicized (R12 in bold and underlined)

FIG. 38D

GCYTWNQMNLGCGGSGGGGSGGGGS*IQRTPKIQVYSRHPAENGKSNFLNCYVSGFHPSDIE*

*VDLLKNGERIEKVEHSDLSFSKDWSFYLLYYTEFTPTEKDEYACRVNHVTLSQPKIVKWDRDM*

GGGGSGGGGSGGGGSAPTSSSTKKTQLQLEALLLDLQMILNGINNYKNPKLTRMLT

AKFYMPKKATELKHLQCLEEELKPLEEVLNLAQSKNFHLRPRDLISNINVIVLELKG

SETTFMCEYADETATIVEFLNRWITFCQSIISTLTGGGGSGGGGSGGGGSGGGGSAPT

SSSTKKTQLQLEALLLDLQMILNGINNYKNPKLTRMLTAKFYMPKKATELKHLQC

LEEELKPLEEVLNLAQSKNFHLRPRDLISNINVIVLELKGSETTFMCEYADETATIVE

FLNRWITFCQSIISTLT (SEQ ID NO:483)

epitope: GCYTWNQMNL– WT1 (235-243; G-1; M236Y) (SEQ ID NO:454)
(GCGGS)(G4S)$_2$, (G4S)$_3$, and (G4S)$_4$ – underlined (SEQ ID NOs:317, 379 and 380)
β2M (R12) – italicized
IL-2 (H16A; F42A) – bold

FIG. 38E

GCYTWNQMNLGCGGSGGGGSGGGGS*IQRTPKIQVYSCHPAENGKSNFLNCYVSGFHPSDI*

*EVDLLKNGERIEKVEHSDLSFSKDWSFYLLYYTEFTPTEKDEYACRVNHVTLSQPKIVKWDRD*

*M*GGGGSGGGGSGGGGSAPTSSSTKKTQLQLEALLLDLQMILNGINNYKNPKLTRML

TAKFYMPKKATELKHLQCLEEELKPLEEVLNLAQSKNFHLRPRDLISNINVIVLELK

GSETTFMCEYADETATIVEFLNRWITFCQSIISTLTGGGGSGGGGSGGGGSGGGGSAP

TSSSTKKTQLQLEALLLDLQMILNGINNYKNPKLTRMLTAKFYMPKKATELKHLQ

CLEEELKPLEEVLNLAQSKNFHLRPRDLISNINVIVLELKGSETTFMCEYADETATIV

EFLNRWITFCQSIISTLT (SEQ ID NO:484)

epitope: GCYTWNQMNL– WT1 (235-243; G-1; M236Y) (SEQ ID NO:454)
(GCGGS)(G4S)$_2$, (G4S)$_3$, and (G4S)$_4$ – underlined (SEQ ID NOs:317, 379 and 380)
β2M (R12C) – italicized
IL-2 (H16A; F42A) – bold

FIG. 38F

GCYTWNQMNLGGGGSGGGGSGGGGS*IQRTPKIQVYSCHPAENGKSNFLNCYVSGFHPSDI EVDLLKNGERIEKVEHSDLSFSKDWSFYLLYYTEFTPTEKDEYACRVNHVTLSQPKIVKWDRD M*GGGGSGGGGSGGGGSAPTSSSTKKTQLQLEALLLDLQMILNGINNYKNPKLTRML TAKFYMPKKATELKHLQCLEEELKPLEEVLNLAQSKNFHLRPRDLISNINVIVLELK GSETTFMCEYADETATIVEFLNRWITFCQSIISTLTGGGGSGGGGSGGGGSGGGGSAP TSSSTKKTQLQLEALLLDLQMILNGINNYKNPKLTRMLTAKFYMPKKATELKHLQ CLEEELKPLEEVLNLAQSKNFHLRPRDLISNINVIVLELKGSETTFMCEYADETATIV EFLNRWITFCQSIISTLT (SEQ ID NO:485)

epitope: GCYTWNQMNL– WT1 (235-243; G-1; M236Y) (SEQ ID NO:454)
$(G4S)_3$ and $(G4S)_4$ – underlined (SEQ ID NOs:379-380)
β2M (R12C) – italicized
IL-2 (H16A; F42A) – bold Healthy donor PBMCs expanded 10 days with CUE-102/A02 $WT_{137\text{-}45}$ Immuno-STAT Healthy donor PBMCs expanded 10 days with $WT1_{37-45}$ peptide + rhIL-2

CD8+ T cells enriched by magnetic beads are 'diluted' with mitomycin C-treated autologous PBMCS and restimulated for 8 days with CUE-102/A02 $WT1_{37-45}$ IST

FIG. 46A

HLA-E*01:01 (Y84; A236) (R107 in bold) (wild-type)

GSHSLKYFHTSVSRPGRGEPRFISVGYVDDTQFVRFDNDAASPRMVPRAPWMEQEGSEYWDRE
TRSARDTAQIFRVNLRTLRGYYNQSEAGSHTLQWMHGCELGPDRRFLRGYEQFAYDGKDYLTL
NEDLRSWTAVDTAAQISEQKSNDASEAEHQRAYLEDTCVEWLHKYLEKGKETLLHLEPPKTHV
THHPISDHEATLRCWALGFYPAEITLTWQQDGEGHTQDTELVETRPAGDGTFQKWAAVVVPSG
EEQRYTCHVQHEGLPEPVTLRWK (SEQ ID NO:492)

FIG. 46B

HLA-E*01:01 (Y84C; A236C) (R107 in bold)

GSHSLKYFHTSVSRPGRGEPRFISVGYVDDTQFVRFDNDAASPRMVPRAPWMEQEGSEYWDRE
TRSARDTAQIFRVNLRTLRGCYNQSEAGSHTLQWMHGCELGPDRRFLRGYEQFAYDGKDYLTL
NEDLRSWTAVDTAAQISEQKSNDASEAEHQRAYLEDTCVEWLHKYLEKGKETLLHLEPPKTHV
THHPISDHEATLRCWALGFYPAEITLTWQQDGEGHTQDTELVETRPCGDGTFQKWAAVVVPSG
EEQRYTCHVQHEGLPEPVTLRWK (SEQ ID NO:493)

FIG. 46C

HLA-E*01:03 (Y84; A236) (G107 in bold) (wild-type)

GSHSLKYFHTSVSRPGRGEPRFISVGYVDDTQFVRFDNDAASPRMVPRAPWMEQEGSEYWDRE
TRSARDTAQIFRVNLRTLRGYYNQSEAGSHTLQWMHGCELGPDGRFLRGYEQFAYDGKDYLTL
NEDLRSWTAVDTAAQISEQKSNDASEAEHQRAYLEDTCVEWLHKYLEKGKETLLHLEPPKTHV
THHPISDHEATLRCWALGFYPAEITLTWQQDGEGHTQDTELVETRPAGDGTFQKWAAVVVPSG
EEQRYTCHVQHEGLPEPVTLRWK (SEQ ID NO:494)

FIG. 46D

HLA-E*01:03 (Y84C; A236C) (G107 in bold)

GSHSLKYFHTSVSRPGRGEPRFISVGYVDDTQFVRFDNDAASPRMVPRAPWMEQEGSEYWDRE
TRSARDTAQIFRVNLRTLRGCYNQSEAGSHTLQWMHGCELGPDGRFLRGYEQFAYDGKDYLTL
NEDLRSWTAVDTAAQISEQKSNDASEAEHQRAYLEDTCVEWLHKYLEKGKETLLHLEPPKTHV
THHPISDHEATLRCWALGFYPAEITLTWQQDGEGHTQDTELVETRPCGDGTFQKWAAVVVPSG
EEQRYTCHVQHEGLPEPVTLRWK (SEQ ID NO:495)

FIG. 47A

HLA-G*01:01 (Y84; A236) (L110 in bold) (wild-type)

GSHSMRYFSAAVSRPGRGEPRFIAMGYVDDTQFVRFDSDSACPRMEPRAPWVEQEGPEYWEEE
TRNTKAHAQTDRMNLQTLRGYYNQSEASSHTLQWMIGCDLGSDGRLLRGYEQYAYDGKDYLA
LNEDLRSWTAADTAAQISKRKCEAANVAEQRRAYLEGTCVEWLHRYLENGKEMLQRADPPKT
HVTHHPVFDYEATLRCWALGFYPAEIILTWQRDGEDQTQDVELVETRPAGDGTFQKWAAVVVP
SGEEQRYTCHVQHEGLPEPLMLRWK (SEQ ID NO:496)

FIG. 47B

HLA-G*01:01 (Y84C; A236C) (L110 in bold)

GSHSMRYFSAAVSRPGRGEPRFIAMGYVDDTQFVRFDSDSACPRMEPRAPWVEQEGPEYWEEE
TRNTKAHAQTDRMNLQTLRGCYNQSEASSHTLQWMIGCDLGSDGRLLRGYEQYAYDGKDYLA
LNEDLRSWTAADTAAQISKRKCEAANVAEQRRAYLEGTCVEWLHRYLENGKEMLQRADPPKT
HVTHHPVFDYEATLRCWALGFYPAEIILTWQRDGEDQTQDVELVETRPCGDGTFQKWAAVVVP
SGEEQRYTCHVQHEGLPEPLMLRWK (SEQ ID NO:497)

FIG. 47C

HLA-G*01:04 (Y84; A236) (I110 in bold) (wild-type)

GSHSMRYFSAAVSRPGRGEPRFIAMGYVDDTQFVRFDSDSACPRMEPRAPWVEQEGPEYWEEE
TRNTKAHAQTDRMNLQTLRGYYNQSEASSHTLQWMIGCDLGSDGRLIRGYEQYAYDGKDYLA
LNEDLRSWTAADTAAQISKRKCEAANVAEQRRAYLEGTCVEWLHRYLENGKEMLQRADPPKT
HVTHHPVFDYEATLRCWALGFYPAEIILTWQRDGEDQTQDVELVETRPAGDGTFQKWAAVVVP
SGEEQRYTCHVQHEGLPEPLMLRWK (SEQ ID NO:498)

FIG. 47D

HLA-G*01:04 (Y84C; A236C) (I110 in bold) (wild-type)

GSHSMRYFSAAVSRPGRGEPRFIAMGYVDDTQFVRFDSDSACPRMEPRAPWVEQEGPEYWEEE
TRNTKAHAQTDRMNLQTLRGCYNQSEASSHTLQWMIGCDLGSDGRLIRGYEQYAYDGKDYLA
LNEDLRSWTAADTAAQISKRKCEAANVAEQRRAYLEGTCVEWLHRYLENGKEMLQRADPPKT
HVTHHPVFDYEATLRCWALGFYPAEIILTWQRDGEDQTQDVELVETRPCGDGTFQKWAAVVVP
SGEEQRYTCHVQHEGLPEPLMLRWK (SEQ ID NO:499)

MULTIMERIC T-CELL MODULATORY POLYPEPTIDES AND METHODS OF USE THEREOF

CROSS-REFERENCE

This application claims the benefit of U.S. Provisional Patent Application No. 63/023,834, filed May 12, 2020, and U.S. Provisional Patent Application No. 63/041,451, filed Jun. 19, 2020, which applications are incorporated herein by reference in their entirety.

INCORPORATION BY REFERENCE OF MATERIAL ELECTRONICALLY SUBMITTED

A Sequence Listing is provided herewith as a Sequence Listing XML, "CUEB-133CON_SEQ_LIST" created on Nov. 29, 2022 and having a size of 615 KB. The contents of the Sequence Listing XML are incorporated by reference herein in their entirety.

INTRODUCTION

An adaptive immune response involves the engagement of the T cell receptor (TCR), present on the surface of a T cell, with a small peptide antigen non-covalently presented on the surface of an antigen presenting cell (APC) by a major histocompatibility complex (MHC; also referred to in humans as a human leukocyte antigen (HLA) complex). This engagement represents the immune system's targeting mechanism and is a requisite molecular interaction for T cell modulation (activation or inhibition) and effector function. Following epitope-specific cell targeting, the targeted T cells are activated through engagement of costimulatory proteins found on the APC with counterpart costimulatory proteins the T cells. Both signals—epitope/TCR binding and engagement of APC costimulatory proteins with T cell costimulatory proteins—are required to drive T cell specificity and activation or inhibition. The TCR is specific for a given epitope; however, the costimulatory protein not epitope specific and instead is generally expressed on all T cells or on large T cell subsets.

SUMMARY

The present disclosure provides T-cell modulatory multimeric polypeptides (TMMPs) that comprise an immunomodulatory polypeptide and that comprise an epitope-presenting Wilms tumor peptide. A T-cell modulatory multimeric polypeptide is useful for modulating the activity of a T cell, and for modulating an immune response in an individual.

BRIEF DESCRIPTION OF THE DRAWINGS

FIG. 3A-3E provides an amino acid sequence of WT-1 polypeptides. The sequences of FIGS. 3A-3E are set forth in SEQ ID NOs: 399-403, respectively.

FIG. 4A-4E provide amino acid sequences of exemplary polypeptide chains of TMMPs of the present disclosure. The sequences of the exemplary polypeptide chains of FIGS. 4A-4E are set forth in SEQ ID NOs: 405-409, respectively. The epitope sequences are set forth as follows: FIG. 4D:

CMTWNQMNL (SEQ ID NO:266); FIG. 4E: CYTWNQMNL (SEQ ID NO:267).

FIG. 5A-5H provide amino acid sequences of immunoglobulin Fc polypeptides. The sequences of FIGS. 5A-5G are set forth in SEQ ID NOs: 410-421, respectively. The sequence depicted in FIG. 5H is set forth in SEQ ID NO:487.

FIG. 6 provides a multiple amino acid sequence alignment of beta-2 microglobulin (β2M) precursors (i.e., including the leader sequence) from *Homo sapiens* (NP_004039.1; SEQ ID NO: 19), Pan troglodytes (NP_001009066.1; SEQ ID NO: 19), *Macaca* mulatta (NP_001040602.1; SEQ ID NO: 20), *Bos taurus* (NP_776318.1; SEQ ID NO: 21) and *Mus musculus* (NP_033865.2; SEQ ID NO: 22). Amino acids 1-20 are a signal peptide.

FIG. 7A-7C provide amino acid sequences of full-length human HLA heavy chains of alleles A*0101 (SEQ ID NO: 23), A*1101 (SEQ ID NO: 24), A*2402 (SEQ ID NO: 25), and A*3303 (SEQ ID NO: 26) (FIG. 7A); full-length human HLA heavy chain of allele B*0702 (SEQ ID NO: 27) (FIG. 7B); and a full-length human HLA-C heavy chain (SEQ ID NO: 28) (FIG. 7C).

FIG. 8 provides an alignment of eleven mature MHC class I heavy chain amino acid sequences without their leader sequences, transmembrane domains, and intracellular domains. Top to bottom: SEQ ID NOs: 41-51.

FIGS. 9A-9B provide an alignment of HLA-A heavy chain amino acid sequences (FIG. 9A) and a consensus sequence (FIG. 9B; SEQ ID NO: 29).

FIGS. 10A-10B provide an alignment of HLA-B heavy chain amino acid sequences (FIG. 10A; SEQ ID NOs: 207-213, respectively) and a consensus sequence (FIG. 10B; SEQ ID NO: 30).

FIGS. 11A-11B provide an alignment of HLA-C heavy chain amino acid sequences (FIG. 11A; SEQ ID NOs: 214-222, respectively) and a consensus sequence (FIG. 11B; SEQ ID NO: 31).

FIG. 12 provides a consensus amino acid sequence for each of HLA-E, -F, and -G heavy chains (SEQ ID NOs: 32-34, respectively). Variable amino acid (aa) positions are indicated as "X" residues sequentially numbered; the locations of amino acids 84, 139, and 236 are double underlined.

FIG. 13 provides an alignment of consensus amino acid sequences for HLA-A (SEQ ID NO: 29), -B (SEQ ID NO: 30), -C(SEQ ID NO: 31), -E (SEQ ID NO: 32), -F (SEQ ID NO: 33), and -G (SEQ ID NO: 34).

FIG. 14A-14J provide amino acid sequences of polypeptide chains of double disulfide-linked TMMP of the present disclosure. The sequences of the polypeptide chains of FIGS. 14A-14I are set forth in SEQ ID NOs: 422-430, respectively. The epitope sequences are set forth as follows: FIG. 14B: VLDFAPPGA (SEQ ID NO: 259); FIG. 14C: RMFPNAPYL (SEQ ID NO: 260); FIG. 14F: VLDFAPPGA (SEQ ID NO: 259); FIG. 14G: RMFPNAPYL (SEQ ID NO: 260); FIG. 14H: YMFPNAPYL (SEQ ID NO: 264); FIG. 14I, YMFPNAPYL (SEQ ID NO: 264) and 14J (SEQ ID NO: 486).

FIG. 15 depicts expression and stability data for a WT1 (37-45) epitope-containing TMMP of the present disclosure.

FIG. 16 depicts expression and stability data for a WT1 (126-134) epitope-containing TMMP of the present disclosure.

FIG. 20A-20R provide amino acid sequences of exemplary polypeptide chains of TMMPs of the present disclosure. The sequences of the exemplary polypeptide chains of FIGS. 20A-20R are set forth in SEQ ID NOs: 431-448, respectively. The epitope sequences are set forth as follows: FIG. 20H: CYTWNQMNL (SEQ ID NO: 262); FIG. 20L CYTWNQMNL (SEQ ID NO: 262); FIG. 20J: CYTWNQMNL (SEQ ID NO: 262); FIG. 20K: CYTWNQMNL (SEQ ID NO: 262); FIG. 20L: CYTWNQMNL (SEQ ID NO: 262); FIG. 20M: NYMNLGATL (SEQ ID NO: 263); FIG. 20N: NYMNLGATL (SEQ ID NO: 263); FIG. 20O: NYMNLGATL (SEQ ID NO: 263); FIG. 20P: NYMNLGATL (SEQ ID NO: 263); FIG. 20Q: NYMNLGATL (SEQ ID NO: 263); FIG. 20R: NYMNLGATL (SEQ ID NO: 263).

FIG. 28 depicts the effect of TMMPs, containing the WT1 peptide epitope 235-243 (M236Y) and HLA-A*24 heavy chains, on antigen-specific CD8+ T cell expansion.

FIG. 31 depicts the effect of TMMPs (with IL-2 polypeptide engineered at position 1 or 3, peptide epitope WT1 239-247 (Q240Y), HLA-A24 heavy chains, and G2C or R12C/G2C disulfide frameworks) on CD69 expression, compared to proleukine and recombinant human IL-2 (rhIL-2).

FIG. 35A-35F provide amino acid sequences of exemplary polypeptide chains of TMMPs of the present disclosure, in which the polypeptide chains comprise the WT-1 peptide SMTWNQMNL (SEQ ID NO:451).

FIG. 36A-36F provide amino acid sequences of exemplary polypeptide chains of TMMPs of the present disclosure, in which the polypeptide chains comprise the WT-1 peptide GCMTWNQMNL (SEQ ID NO:452).

FIG. 37A-37F provide amino acid sequences of exemplary polypeptide chains of TMMPs of the present disclosure, in which the polypeptide chains comprise the WT-1 peptide SYTWNQMNL (SEQ ID NO:453).

FIG. 38A-38F provide amino acid sequences of exemplary polypeptide chains of TMMPs of the present disclosure, in which the polypeptide chains comprise the WT-1 peptide GCYTWNQMNL (SEQ ID NO:454).

FIG. 46A-46D provide amino acid sequences of HLA-E heavy chains.

FIG. 47A-47D provide amino acid sequences of HLA-G heavy chains.

DEFINITIONS

Figure 1A:
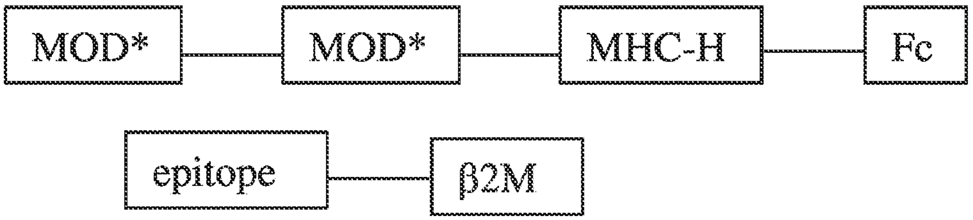
FIG. 1A-1F are schematic depictions of various TMMPs of the present disclosure.
Figure 1B:
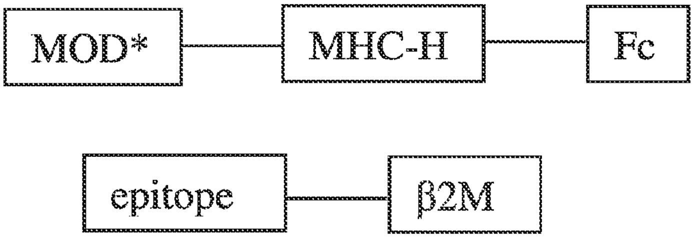
Figure 1C:
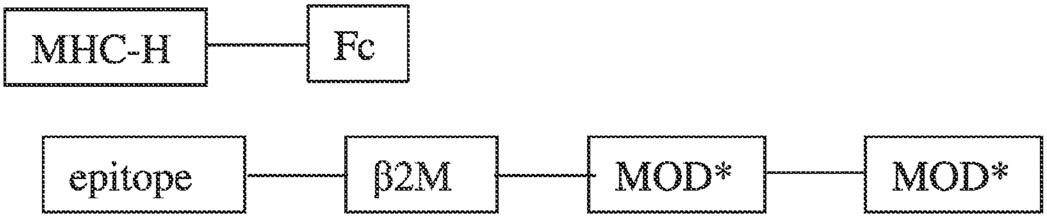
Figure 1D:
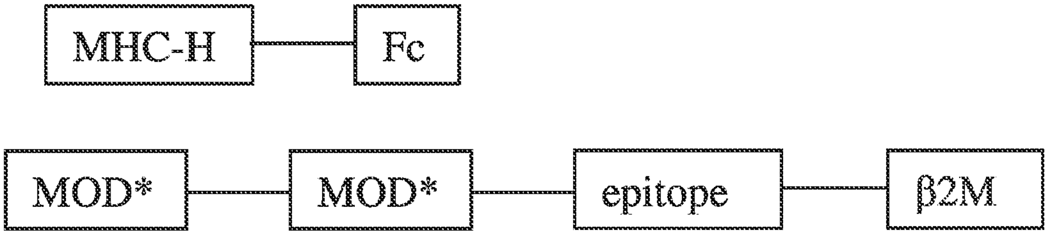
Figure 1E:
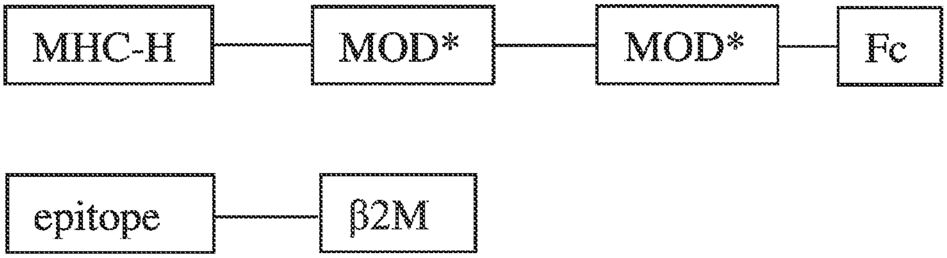
Figure 1F:
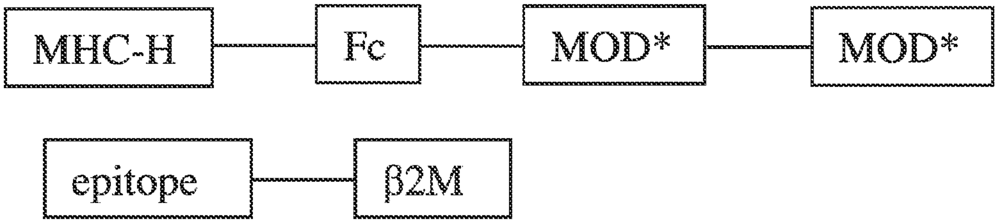
Figure 2A:
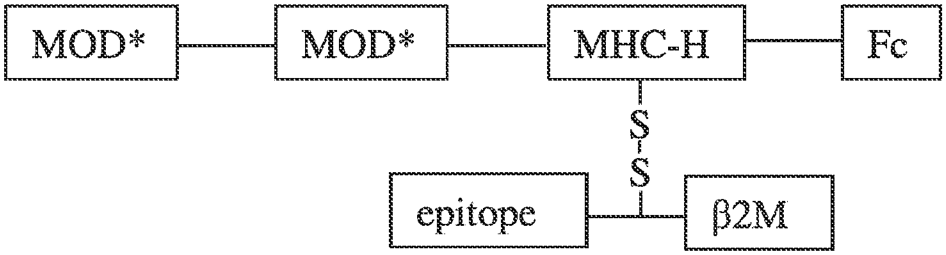
FIG. 2A-2F are schematic depictions of various disulfide-linked TMMPs of the present disclosure.
Figure 2B:
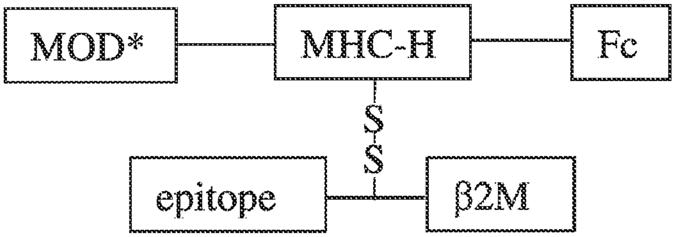
Figure 2C:
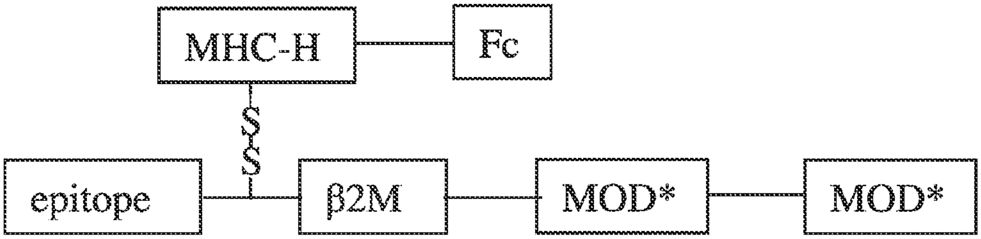
Figure 2D:
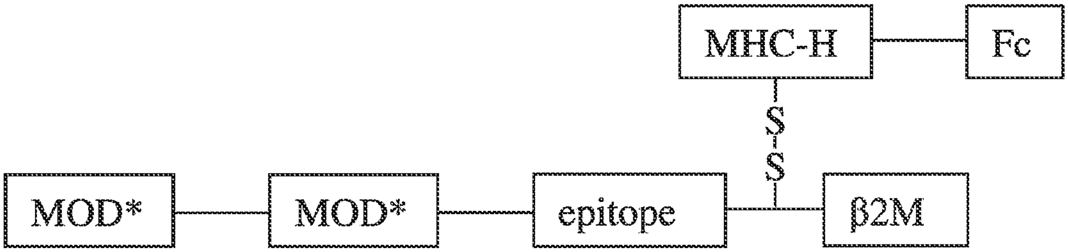
Figure 2E:
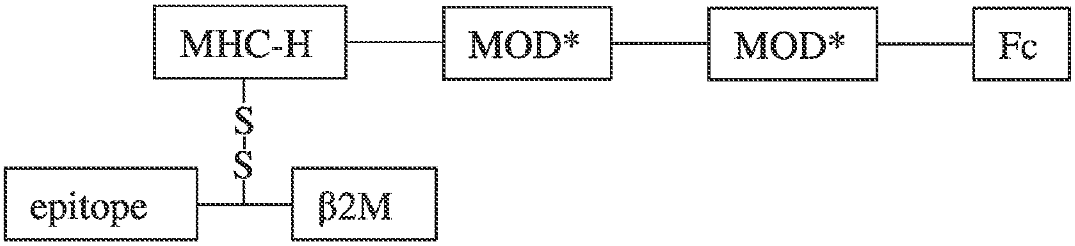
Figure 2F:
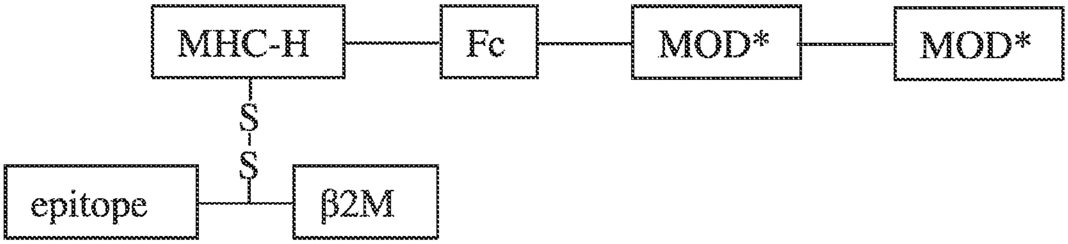

The terms "polynucleotide" and "nucleic acid," used interchangeably herein, refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones. Furthermore, as used herein, a "polypeptide" refers to a protein that includes modifications, such as deletions, additions, and substitutions (generally conservative in nature as would be known to a person in the art) to the native sequence, as long as the protein maintains the desired activity. These modifications can be deliberate, as through site-directed mutagenesis, or can be accidental, such as through mutations of hosts that produce the proteins, or errors due to polymerase chain reaction (PCR) amplification or other recombinant DNA methods. References herein to a specific residue or residue number in a known polypeptide are understood to refer to the amino acid at that position in the wild-type polypeptide. To the extent that the sequence of the wild-type polypeptide is altered, either by addition or deletion of one or more amino acids, one of ordinary skill will understand that a reference to the specific residue or residue number will be correspondingly altered so as to refer to the same specific amino acid in the altered polypeptide, which would be understood to reside at an altered position number. For example, if an MHC class I polypeptide is altered by the addition of one amino acid at the N-terminus, then a reference to position 84 or a specific residue at position 84, will be understood to indicate the amino acids that are at position 85 on the altered polypeptide. Likewise, a reference herein to substitution of a specific amino acid at a specific position, e.g., Y84, is understood to refer to a substitution of an amino acid for the amino acid at position 84 in the wild-type polypeptide. A Y84C substitution is thus understood to be a substitution of Cys residue for the Tyr residue that is present in the wild-type sequence. If, e.g., the wild-type polypeptide is altered to change the amino acid at position 84 from its wild-type amino acid to an alternate amino acid, then the substitution for the amino acid at position 84 will be understood to refer to the substitution for the alternate amino acid. If in such case the polypeptide is also altered by the addition or deletion of one or more amino acids, then the reference to the substitution will be understood to refer to the substitution for the alternate amino acid at the altered position number. A reference to a "non-naturally occurring Cys residue" in a polypeptide, e.g., an MHC class I polypeptide, means that the polypeptide comprises a Cys residue in a location where there is no Cys in the corresponding wild-type polypeptide. This can be accomplished through routine protein engineering in which a cysteine is substituted for the amino acid that occurs in the wild-type sequence.

A polynucleotide or polypeptide has a certain percent "sequence identity" to another polynucleotide or polypeptide, meaning that, when aligned, that percentage of bases or amino acids are the same, and in the same relative position, when comparing the two sequences. Sequence identity can be determined in a number of different ways. To determine sequence identity, sequences can be aligned using various convenient methods and computer programs (e.g., BLAST, T-COFFEE, MUSCLE, MAFFT, etc.), available over the world wide web at sites including ncbi.nlm.nili.gov/BLAST, ebi.ac.uk/Tools/msa/tcoffee/, ebi.ac.uk/Tools/msa/muscle/, mafft.cbrc.jp/alignment/software/. See, e.g., Altschul et al. (1990), J. Mol. Bioi. 215:403-10. Unless otherwise stated, sequence identity is determined using the BLAST computer program.

The term "conservative amino acid substitution" refers to the interchangeability in proteins of amino acid residues having similar side chains. For example, a group of amino acids having aliphatic side chains consists of glycine, alanine, valine, leucine, and isoleucine; a group of amino acids having aliphatic-hydroxyl side chains consists of serine and threonine; a group of amino acids having amide containing side chains consisting of asparagine and glutamine; a group of amino acids having aromatic side chains consists of phenylalanine, tyrosine, and tryptophan; a group of amino acids having basic side chains consists of lysine, arginine, and histidine; a group of amino acids having acidic side chains consists of glutamate and aspartate; and a group of amino acids having sulfur containing side chains consists of cysteine and methionine. Exemplary conservative amino acid substitution groups are: valine-leucine-isoleucine, phenylalanine-tyrosine, lysine-arginine, alanine-valine-glycine, and asparagine-glutamine.

The term "immunological synapse" or "immune synapse" as used herein generally refers to the natural interface between two interacting immune cells of an adaptive immune response including, e.g., the interface between an antigen-presenting cell (APC) or target cell and an effector cell, e.g., a lymphocyte, an effector T cell, a natural killer cell, and the like. An immunological synapse between an APC and a T cell is generally initiated by the interaction of a T cell antigen receptor and major histocompatibility complex molecules, e.g., as described in Bromley et al., Annu Rev Immunol. 2001; 19:375-96; the disclosure of which is incorporated herein by reference in its entirety.

"T cell" includes all types of immune cells expressing CD3, including T-helper cells ($CD4^+$ cells), cytotoxic T-cells ($CD8^+$ cells), T-regulatory cells (Treg), and NK-T cells.

The term "immunomodulatory polypeptide" (also referred to as a "co-stimulatory polypeptide"), as used herein, includes a polypeptide on an antigen presenting cell (APC) (e.g., a dendritic cell, a B cell, and the like) that specifically binds a cognate co-immunomodulatory polypeptide on a T cell, thereby providing a signal which, in addition to the primary signal provided by, for instance, binding of a TCR/CD3 complex with a major histocompatibility complex (MHC) polypeptide loaded with peptide, mediates a T cell response, including, but not limited to, proliferation, activation, differentiation, and the like. An immunomodulatory polypeptide can include, but is not limited to, CD7, B7-1 (CD80), B7-2 (CD86), PD-L1, PD-L2, 4-1BBL, OX40L, Fas ligand (FasL), inducible costimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, an agonist or antibody that binds Toll ligand receptor and a ligand that specifically binds with B7-H3.

As noted above, an "immunomodulatory polypeptide" (also referred to herein as a "MOD") specifically binds a cognate co-immunomodulatory polypeptide on a T cell.

An "immunomodulatory domain" ("MOD") of a TMMP of the present disclosure binds a cognate co-immunomodulatory polypeptide, which may be present on a target T cell.

As used herein the term "in vivo" refers to any process or procedure occurring inside of the body.

As used herein, "in vitro" refers to any process or procedure occurring outside of the body.

"Heterologous," as used herein, means a nucleotide or polypeptide that is not found in the native nucleic acid or protein, respectively.

"Recombinant," as used herein, means that a particular nucleic acid (DNA or RNA) is the product of various combinations of cloning, restriction, polymerase chain reaction (PCR) and/or ligation steps resulting in a construct having a structural coding or non-coding sequence distinguishable from endogenous nucleic acids found in natural systems. DNA sequences encoding polypeptides can be assembled from cDNA fragments or from a series of synthetic oligonucleotides, to provide a synthetic nucleic acid which is capable of being expressed from a recombinant transcriptional unit contained in a cell or in a cell-free transcription and translation system.

The terms "recombinant expression vector," or "DNA construct" are used interchangeably herein to refer to a DNA molecule comprising a vector and at least one insert. Recombinant expression vectors are usually generated for the purpose of expressing and/or propagating the insert(s), or for the construction of other recombinant nucleotide sequences. The insert(s) may or may not be operably linked to a promoter sequence and may or may not be operably linked to DNA regulatory sequences.

As used herein, the term "affinity" refers to the equilibrium constant for the reversible binding of two agents (e.g., an antibody and an antigen) and is expressed as a dissociation constant ($K_D$). As used herein, the term "avidity" refers to the resistance of a complex of two or more agents to dissociation after dilution. The terms "immunoreactive" and "preferentially binds" are used interchangeably herein with respect to antibodies and/or antigen-binding fragments.

The term "binding," as used herein (e.g. with reference to binding of a TMMP to a polypeptide (e.g., a T-cell receptor) on a T cell), refers to a non-covalent interaction between two molecules. Non-covalent binding refers to a direct association between two molecules, due to, for example, electrostatic, hydrophobic, ionic, and/or hydrogen-bond interactions, including interactions such as salt bridges and water bridges. "Affinity" refers to the strength of non-covalent binding, increased binding affinity being correlated with a lower $K_D$. "Specific binding" generally refers to binding of a ligand to a moiety that is its designated binding site or receptor. "Non-specific binding" generally refers to binding of a ligand to a moiety other than its designated binding site or receptor. Covalent binding" or "covalent bond," as used herein, refers to the formation of one or more covalent chemical binds between two different molecules.

The terms "treatment", "treating" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease or symptom in a mammal, and includes: (a) preventing the disease or symptom from occurring in a subject which may be predisposed to acquiring the disease or symptom but has not yet been diagnosed as having it; (b) inhibiting the disease or symptom, i.e., arresting its development; and/or (c) relieving the disease, i.e., causing regression of the disease. The therapeutic agent may be administered before, during or after the onset of disease or injury. The treatment of ongoing disease, where the treatment stabilizes or reduces the undesirable clinical symptoms of the patient, is of particular interest. Such treatment is desirably performed prior to complete loss of function in the affected tissues. The subject therapy will desirably be administered during the symptomatic stage of the disease, and in some cases after the symptomatic stage of the disease.

The terms "individual," "subject," "host," and "patient," are used interchangeably herein and refer to any mammalian subject for whom diagnosis, treatment, or therapy is desired. Mammals include, e.g., humans, non-human primates, rodents (e.g., rats; mice), lagomorphs (e.g., rabbits), ungulates (e.g., cows, sheep, pigs, horses, goats, and the like), etc.

Unless indicated otherwise, the term "substantially" is intended to encompass both "wholly" and "largely but not wholly". For example, an Ig Fc that "substantially does not induce cell lysis" means an Ig Fc that induces no cell lysis at all or that largely does not induce cell lysis.

As used herein, the term "about" used in connection with an amount indicates that the amount can vary by 10% of the stated amount. For example, "about 100" means an amount of from 90-110. Where about is used in the context of a range, the "about" used in reference to the lower amount of the range means that the lower amount includes an amount that is 10% lower than the lower amount of the range, and "about" used in reference to the higher amount of the range means that the higher amount includes an amount 10% higher than the higher amount of the range. For example, from about 100 to about 1000 means that the range extends from 90 to 1100.

Before the present disclosure is further described, it is to be understood that this invention is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present disclosure, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to a "T-cell modulatory multimeric polypeptide" includes a plurality of such polypeptides and reference to "the immunomodulatory polypeptide" includes reference to one or more immunomodulatory polypeptides and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the disclosure, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present disclosure and are disclosed herein just as if each and every such sub-combination was individually and explicitly disclosed herein.

The publications discussed herein are provided solely for their disclosure prior to the filing date of the present application. Nothing herein is to be construed as an admission that the present disclosure is not entitled to antedate such publication. Further, the dates of publication provided may be different from the actual publication dates which may need to be independently confirmed.

DETAILED DESCRIPTION

The present disclosure provides T-cell modulatory multimeric polypeptides that comprise an immunomodulatory polypeptide ("MOD") and that comprise an epitope-presenting Wilms tumor-1 (WT-1) peptide. A TMMP is useful for modulating the activity of a T cell, and for modulating an immune response in an individual.

T-Cell Modulatory Multimeric Polypeptides

The present disclosure provides a T-cell modulatory multimeric polypeptide (TMMP) comprising: a) a first polypeptide; and b) a second polypeptide, wherein the TMMP comprises an epitope; a first major histocompatibility complex (MHC) polypeptide; a second MHC polypeptide; one or more MODs; and optionally an immunoglobulin (Ig) Fc polypeptide or a non-Ig scaffold. The present disclosure provides a TMMP, wherein the TMMP is a heterodimer comprising: a) a first polypeptide comprising a first MHC polypeptide; and b) a second polypeptide comprising a second MHC polypeptide, wherein the first polypeptide or the second polypeptide comprises an epitope (e.g., a peptide that presents an epitope); wherein the first polypeptide and/or the second polypeptide comprises one or more MODs that can be the same or different; and optionally an Ig F c polypeptide or a non-Ig scaffold. A TMMP of the present disclosure is also referred to herein as a "multimeric polypeptide of the present disclosure" or a "synTac." In some cases, the peptide epitope present in a TMMP of the present disclosure is a WT-1 peptide.

The present disclosure provides a TMMP comprising a heterodimeric polypeptide comprising: a) a first polypeptide comprising: i) a peptide epitope; and ii) a first MHC polypeptide; b) a second polypeptide comprising a second MHC polypeptide; and c) at least one MOD, where the first and/or the second polypeptide comprises the at least one (i.e., one or more) MODs. Optionally, the first or the second polypeptide comprises an Ig Fc polypeptide or a non-Ig scaffold. At least one of the one or more MODs is a variant MOD that exhibits reduced affinity to a cognate co-immunomodulatory polypeptide ("co-MOD") compared to the affinity of a corresponding wild-type MOD for the co-MOD. The epitope present in a TMMP binds to a T-cell receptor (TCR) on a T cell with an affinity of at least 100 μM (e.g., at least 10 μM, at least 1 μM, at least 100 nM, at least 10 nM, or at least 1 nM). A TMMP binds to a first T cell with an affinity that is at least 25% higher than the affinity with which the TMMP binds a second T cell, where the first T cell expresses on its surface the cognate co-MOD and a TCR that binds the epitope with an affinity of at least 100 μM, and where the second T cell expresses on its surface the cognate co-MOD but does not express on its surface a TCR that binds the epitope with an affinity of at least 100 μM (e.g., at least 10 μM, at least 1 μM, at least 100 nM, at least 10 nM, or at least 1 nM). In some cases, the peptide epitope present in a TMMP is a WT-1 peptide.

The present disclosure provides a TMMP, wherein the TMMP is:

A) a heterodimer comprising: a) a first polypeptide comprising a first MHC polypeptide; and b) a second polypeptide comprising a second MHC polypeptide, wherein the first polypeptide or the second polypeptide comprises an epitope (e.g., a peptide that presents an epitope to a T cell); wherein the first polypeptide and/or the second polypeptide comprises one or more MODs that can be the same or different, and wherein at least one of the one or more MODs may be a wild-type MOD or a variant of a wild-type MOD, wherein the variant MOD comprises 1, 2, 3, 4, 5, 6, 7, 8, 9, 10, 11, 12, 13, 14, 15, 16, 17, 18, 19, or 20 amino acid substitutions compared to the amino acid sequence of the corresponding wild-type MOD; and wherein the first polypeptide or the second polypeptide optionally comprises an Ig Fc polypeptide or a non-Ig scaffold; or B) a heterodimer comprising: a) a first polypeptide comprising a first MHC polypeptide; and b) a second polypeptide comprising a second MHC polypeptide, wherein the first polypeptide or the second polypeptide comprises an epitope; wherein the first polypeptide and/or the second polypeptide comprises one or more MODs that can be the same or different, wherein at least one of the one or more MODs is a variant of a wild-type MOD, wherein the variant MOD comprises 1, 2, 3, 4, 5, 6, 7, 8, 9, 10, 11, 12, 13, 14, 15, 16, 17, 18, 19, or 20 amino acid substitutions compared to the amino acid sequence of the corresponding wild-type MOD, wherein at least one of the one or more MODs is a variant MOD that exhibits reduced affinity to a cognate co-MOD compared to the affinity of a corresponding wild-type MOD for the cognate co-MOD, and wherein the epitope binds to a TCR on a T cell with an affinity of at least $10^{-7}$ M, such that: i) the TMMP polypeptide binds to a first T cell with an affinity that is at least 25% higher than the affinity with which the TMMP binds a second T cell, wherein the first T cell expresses on its surface the cognate co-MOD and a TCR that binds the epitope with an affinity of at least $10^{-7}$ M, and wherein the second T cell expresses on its surface the cognate co-MOD but does not express on its surface a TCR that binds the epitope with an affinity of at least $10^{-7}$ M; and/or ii) the ratio of the binding affinity of a control TMMP, wherein the control comprises a wild-type MOD, to a cognate co-MOD to the binding affinity of the TMMP comprising a variant of the wild-type MOD to the cognate co-MOD, when measured by bio-layer interferometry, is in a range of from 1.5:1 to $10^6$:1; and wherein the variant MOD comprises 1, 2, 3, 4, 5, 6, 7, 8, 9, 10, 11, 12, 13, 14, 15, 16, 17, 18, 19, or 20 amino acid substitutions compared to the amino acid sequence of the corresponding wild-type MOD; and wherein the first polypeptide or the second polypeptide optionally comprises an Ig Fc polypeptide or a non-Ig scaffold; or C) a heterodimer comprising: a) a first polypeptide comprising, in order from N-terminus to C-terminus: i) an epitope; ii) a first MHC polypeptide; and b) a second polypeptide comprising, in order from N-terminus to C-terminus: i) a second MHC polypeptide; and ii) optionally an Ig Fc polypeptide or a non-Ig scaffold, wherein the TMMP comprises one or more MODs that can be the same or different, wherein at least one of the one or more MOD is: A) at the C-terminus of the first polypeptide; B) at the N-terminus of the second polypeptide; C) at the C-terminus of the second polypeptide; or D) at the C-terminus of the first polypeptide and at the N-terminus of the second polypeptide, and wherein at least one of the one or more MODs may be a wild-type MOD or a variant of a wild-type MOD, wherein the variant MOD comprises 1, 2, 3, 4, 5, 6, 7, 8, 9, 10, 11, 12, 13, 14, 15, 16, 17, 18, 19, or 20 amino acid substitutions compared to the amino acid sequence of the corresponding wild-type MOD; and optionally wherein at least one of the one or more MODs is a variant MOD that exhibits reduced affinity to a cognate co-MOD compared to the affinity of a corresponding wild-type MOD for the cognate co-MOD, and wherein the epitope binds to a TCR on a T cell with an affinity of at least $10^{-7}$ M, such that: i) the TMMP binds to a first T cell with an affinity that is at least 25% higher than the affinity with which the TMMP binds a second T cell, wherein the first T cell expresses on its surface the cognate co-MOD and a TCR that binds the epitope with an affinity of at least $10^{-7}$ M, and wherein the second T cell expresses on its surface the cognate co-MOD but does not express on its surface a TCR that binds the epitope with an affinity of at least $10^{-7}$ M; and/or ii) the ratio of the binding affinity of a control TMMP, wherein the control comprises a wild-type MOD, to a cognate co-MOD to the binding affinity of the TMMP comprising a variant of the wild-type MOD to the cognate co-MOD, when measured by bio-layer interferometry, is in a range of from 1.5:1 to $10^6$:1; and wherein the variant MOD comprises 1, 2, 3, 4, 5, 6, 7, 8, 9, 10, 11, 12, 13, 14, 15, 16, 17, 18, 19, or 20 amino acid substitutions compared to the amino acid sequence of the corresponding wild-type MOD. In some cases, the peptide epitope present in a TMMP is a WT-1 peptide.

The present disclosure provides a TMMP comprising: a) a first polypeptide comprising, in order from N-terminus to C-terminus: i) an epitope; ii) a first MHC polypeptide; and b) a second polypeptide comprising, in order from N-terminus to C-terminus: i) a second MHC polypeptide; and ii) optionally an Ig Fc polypeptide or a non-Ig scaffold. A TMMP comprises one or more MODs, wherein at least one of the one or more MODs is: A) at the C-terminus of the first polypeptide; B) at the N-terminus of the second polypeptide; C) at the C-terminus of the second polypeptide; or D) at the C-terminus of the first polypeptide and at the N-terminus of the second polypeptide. At least one of the one or more MODs is a variant MOD that exhibits reduced affinity to a cognate co-MOD compared to the affinity of a corresponding wild-type MOD for the cognate co-MOD. The epitope present in a TMMP binds to a T-cell receptor (TCR) on a T cell with an affinity of at least 100 μM (e.g., at least 10 μM, at least 1 μM, at least 100 nM, at least 10 nM, or at least 1 nM). A TMMP binds to a first T cell with an affinity that is at least 25% higher than the affinity with which the TMMP binds a second T cell, where the first T cell expresses on its surface the cognate co-MOD and a TCR that binds the epitope with an affinity of at least 100 μM, and where the second T cell expresses on its surface the cognate co-MOD but does not express on its surface a TCR that binds the epitope with an affinity of at least 100 μM (e.g., at least 10 μM, at least 1 μM, at least 100 nM, at least 10 nM, or at least 1 nM).

A MOD present in a TMMP binds to its cognate co-MOD with an affinity that it at least 10% less, at least 15% less, at least 20% less, at least 25% less, at least 30% less, at least 35% less, at least 40% less, at least 45% less, at least 50% less, at least 55% less, at least 60% less, at least 65% less, at least 70% less, at least 75% less, at least 80% less, at least 85% less, at least 90% less, at least 95% less, or more than 95% less, than the affinity of a corresponding wild-type MOD for the cognate co-MOD.

The combination of the reduced affinity of the MOD for its cognate co-MOD, and the affinity of the epitope for a TCR, provides for enhanced selectivity of a TMMP. For example, a TMMP of the present disclosure binds selectively to a first T cell that displays both: i) a TCR specific for the epitope present in the TMMP; and ii) a co-MOD that binds to the MOD present in the TMMP, compared to binding to a second T cell that displays: i) a TCR specific for an epitope other than the epitope present in the TMMP; and ii) a co-MOD that binds to the MOD present in the TMMP. For example, a TMMP of the present disclosure binds to the first T cell with an affinity that is at least 10%, at least 15%, at least 20%, at least 25%, at least 30%, at least 40%, at least 50%, at least 60%, at least 70%, at least 80%, at least 90%, at least 2-fold, at least 2.5-fold, at least 5-fold, at least 10-fold, at least 15-fold, at least 20-fold, at least 25-fold, at least 50-fold, at least 100-fold, or more than 100-fold, higher than the affinity to which it binds the second T cell.

In some cases, a TMMP, when administered to an individual in need thereof, induces both an epitope-specific T cell response and an epitope non-specific T cell response. In other words, in some cases, a TMMP, when administered to an individual in need thereof, induces an epitope-specific T cell response by modulating the activity of a first T cell that displays both: i) a TCR specific for the epitope present in the TMMP; ii) a co-MOD that binds to the MOD present in the TMMP; and induces an epitope non-specific T cell response by modulating the activity of a second T cell that displays: i) a TCR specific for an epitope other than the epitope present in the TMMP; and ii) a co-MOD that binds to the MOD present in the TMMP. The ratio of the epitope-specific T cell response to the epitope-non-specific T cell response is at least 2:1, at least 5:1, at least 10:1, at least 15:1, at least 20:1, at least 25:1, at least 50:1, or at least 100:1. The ratio of the epitope-specific T cell response to the epitope-non-specific T cell response is from about 2:1 to about 5:1, from about 5:1 to about 10:1, from about 10:1 to about 15:1, from about 15:1 to about 20:1, from about 20:1 to about 25:1, from about 25:1 to about 50:1, or from about 50:1 to about 100:1, or more than 100:1. "Modulating the activity" of a T cell can include one or more of: i) activating a cytotoxic (e.g., $CD8^+$) T cell; ii) inducing cytotoxic activity of a cytotoxic (e.g., $CD8^+$) T cell; iii) inducing production and release of a cytotoxin (e.g., a perforin; a granzyme; a granulysin) by a cytotoxic (e.g., $CD8^+$) T cell; iv) inhibiting activity of an autoreactive T cell; and the like.

The combination of the reduced affinity of the MOD for its cognate co-MOD, and the affinity of the epitope for a TCR, provides for enhanced selectivity of a TMMP. Thus, for example, a TMMP binds with higher avidity to a first T cell that displays both: i) a TCR specific for the epitope present in the TMMP; and ii) a co-MOD that binds to the MOD present in the TMMP, compared to the avidity to which it binds to a second T cell that displays: i) a TCR specific for an epitope other than the epitope present in the TMMP; and ii) a co-MOD that binds to the MOD present in the TMMP.

Binding affinity between a MOC and its cognate co-MOD can be determined by bio-layer interferometry (BLI) using purified MOD and purified cognate co-MOD. Binding affinity between a TMMP and its cognate co-MOD can be determined by BLI using purified TMMP and the cognate co-MOD. BLI methods are well known to those skilled in the art. See, e.g., Lad et al. (2015) *J. Biomol. Screen.* 20(4):498-507; and Shah and Duncan (2014) *J. Vis. Exp.* 18:e51383.

A BLI assay can be carried out using an Octet RED 96 (Pal FortéBio) instrument, or a similar instrument, as follows. A TMMP (e.g., a TMMP of the present disclosure; a control TMMP (where a control TMMP comprises a wild-type immunomodulatory polypeptide)) is immobilized onto an insoluble support (a "biosensor"). The immobilized TMMP is the "target" Immobilization can be effected by immobilizing a capture antibody onto the insoluble support, where the capture antibody immobilizes the TMMP. For example, immobilization can be effected by immobilizing anti-Fc (e.g., anti-human IgG Fc) antibodies onto the insoluble support, where the immobilized anti-Fc antibodies bind to and immobilize the TMMP (where the TMMP comprises an IgFc polypeptide). A co-immunomodulatory polypeptide is applied, at several different concentrations, to the immobilized TMMP, and the instrument's response recorded. Assays are conducted in a liquid medium comprising 25 mM HEPES pH 6.8, 5% poly(ethylene glycol) 6000, 50 mM KCl, 0.1% bovine serum albumin, and 0.02% Tween 20 nonionic detergent. Binding of the co-immunomodulatory polypeptide to the immobilized TMMP is conducted at 30° C. As a positive control for binding affinity, an anti-MHC Class I monoclonal antibody can be used. For example, anti-HLA Class I monoclonal antibody W6/32 (American Type Culture Collection No. HB-95; Parham et al. (1979) *J. Immunol.* 123:342), which has a $K_D$ of 7 nM, can be used. A standard curve can be generated using serial dilutions of the anti-MHC Class I monoclonal antibody. The co-immunomodulatory polypeptide, or the anti-MHC Class I mAb, is the "analyte." BLI analyzes the interference pattern of white light reflected from two surfaces: i) from the immobilized polypeptide ("target"); and ii) an internal reference layer. A change in the number of molecules ("analyte"; e.g., co-immunomodulatory polypeptide; anti-HLA antibody) bound to the biosensor tip causes a shift in the interference pattern; this shift in interference pattern can be measured in real time. The two kinetic terms that describe the affinity of the target/analyte interaction are the association constant ($k_a$) and dissociation constant ($k_d$) The ratio of these two terms ($k_{d/a}$) gives rise to the affinity constant $K_D$.

The BLI assay is carried out in a multi-well plate. To run the assay, the plate layout is defined, the assay steps are defined, and biosensors are assigned in Octet Data Acquisition software. The biosensor assembly is hydrated. The hydrated biosensor assembly and the assay plate are equilibrated for 10 minutes on the Octet instrument. Once the data are acquired, the acquired data are loaded into the Octet Data Analysis software. The data are processed in the Processing window by specifying method for reference subtraction, y-axis alignment, inter-step correction, and Savitzky-Golay filtering. Data are analyzed in the Analysis window by specifying steps to analyze (Association and Dissociation), selecting curve fit model (1:1), fitting method (global), and window of interest (in seconds). The quality of fit is evaluated. $K_D$ values for each data trace (analyte concentration) can be averaged if within a 3-fold range. $K_D$ error values should be within one order of magnitude of the affinity constant values; $R^2$ values should be above 0.95. See, e.g., Abdiche et al. (2008) *J. Anal. Biochem.* 377:209.

Unless otherwise stated herein, the affinity of a TMMP of the present disclosure for a cognate co-immunomodulatory polypeptide, or the affinity of a control TMMP (where a control TMMP comprises a wild-type immunomodulatory polypeptide) for a cognate co-immunomodulatory polypeptide, is determined using BLI, as described above.

In some cases, the ratio of: i) the binding affinity of a control TMMP (where the control comprises a wild-type immunomodulatory polypeptide) to a cognate co-immunomodulatory polypeptide to ii) the binding affinity of a TMMP of the present disclosure comprising a variant of the wild-type immunomodulatory polypeptide to the cognate co-immunomodulatory polypeptide, when measured by BLI (as described above), is at least 1.5:1, at least 2:1, at least 5:1, at least 10:1, at least 15:1, at least 20:1, at least 25:1, at least 50:1, at least 100:1, at least 500:1, at least $10^2$:1, at least $5\times10^2$:1, at least $10^3$:1, at least $5\times10^3$:1, at least $10^4$:1, at least $10^5$:1, or at least $10^6$:1. In some cases, the ratio of: i) the binding affinity of a control TMMP (where the control comprises a wild-type immunomodulatory polypeptide) to a cognate co-immunomodulatory polypeptide to ii) the binding affinity of a TMMP of the present disclosure comprising a variant of the wild-type immunomodulatory polypeptide to the cognate co-immunomodulatory polypeptide, when measured by BLI, is in a range of from 1.5:1 to $10^6$:1, e.g., from 1.5:1 to 10:1, from 10:1 to 50:1, from 50:1 to $10^2$:1, from $10^2$:1 to $10^3$:1, from $10^3$:1 to $10^4$:1, from $10^4$:1 to $10^5$:1, or from $10^5$:1 to $10^6$:1.

As an example, where a control TMMP comprises a wild-type IL-2 polypeptide, and where a TMMP of the present disclosure comprises a variant IL-2 polypeptide (comprising from 1 to 10 amino acid substitutions relative to the amino acid sequence of the wild-type IL-2 polypeptide) as the immunomodulatory polypeptide, the ratio of: i) the binding affinity of the control TMMP to an IL-2 receptor (i.e., the cognate co-immunomodulatory polypeptide) to ii) the binding affinity of the TMMP of the present disclosure to the IL-2 receptor, when measured by BLI, is at least 1.5:1, at least 2:1, at least 5:1, at least 10:1, at least 15:1, at least 20:1, at least 25:1, at least 50:1, at least 100:1, at least 500:1, at least $10^2$:1, at least $5\times10^2$:1, at least $10^3$:1, at least $5\times10^3$:1, at least $10^4$:1, at least $10^5$:1, or at least $10^6$:1. In some cases, where a control TMMP comprises a wild-type IL-2 polypeptide, and where a TMMP of the present disclosure comprises a variant IL-2 polypeptide (comprising from 1 to 10 amino acid substitutions relative to the amino acid sequence of the wild-type IL-2 polypeptide) as the immunomodulatory polypeptide, the ratio of: i) the binding affinity of the control TMMP to an IL-2 receptor (i.e., the cognate co-immunomodulatory polypeptide) to ii) the binding affinity of the TMMP of the present disclosure to the IL-2 receptor, when measured by BLI, is in a range of from 1.5:1 to $10^6$:1, e.g., from 1.5:1 to 10:1, from 10:1 to 50:1, from 50:1 to $10^2$:1, from $10^2$:1 to $10^3$:1, from $10^3$:1 to $10^4$:1, from $10^4$:1 to $10^5$:1, or from $10^5$:1 to $10^6$:1.

Binding affinity of a TMMP of the present disclosure to a target T cell can be measured according to the procedure describes in published PCT application WO 2019/051091, published Mar. 14, 2019. See [0063].

In some cases, when measured as described in the preceding paragraph, a TMMP of the present disclosure exhibits its selective binding to target T-cell, compared to binding of the TMMP library member to a control T cell that comprises: i) the cognate co-immunomodulatory polypeptide that binds the parental wild-type immunomodulatory polypeptide; and ii) a T-cell receptor that binds to an epitope other than the epitope present in the TMMP library member.

Dimerized TMMPs

A TMMP of the present disclosure can be dimerized; i.e., the present disclosure provides a multimeric polypeptide comprising a dimer of a TMMP of the present disclosure. Thus, the present disclosure provides a TMMP comprising: A) a first heterodimer comprising: a) a first polypeptide comprising: i) a peptide epitope; and ii) a first MHC polypeptide; and b) a second polypeptide comprising: i) a second MHC polypeptide, wherein the first heterodimer comprises one or more MODs; and B) a second heterodimer comprising: a) a first polypeptide comprising: i) a peptide epitope; and ii) a first MHC polypeptide; and b) a second polypeptide comprising: i) a second MHC polypeptide, wherein the second heterodimer comprises one or more MODs, and wherein the first heterodimer and the second heterodimer are covalently linked to one another. In some cases, the two TMMPs are identical to one another in amino acid sequence. In some cases, the first heterodimer and the second heterodimer are covalently linked to one another via a C-terminal region of the second polypeptide of the first heterodimer and a C-terminal region of the second polypeptide of the second heterodimer. In some cases, first heterodimer and the second heterodimer are covalently linked to one another via the C-terminal amino acid of the second polypeptide of the first heterodimer and the C-terminal region of the second polypeptide of the second heterodimer; for example, in some cases, the C-terminal amino acid of the second polypeptide of the first heterodimer and the C-terminal region of the second polypeptide of the second heterodimer are linked to one another, either directly or via a linker. The linker can be a peptide linker. The peptide linker can have a length of from 1 amino acid to 200 amino acids (e.g., from 1 amino acid (aa) to 5 aa, from 5 aa to 10 aa, from 10 aa to 25 aa, from 25 aa to 50 aa, from 50 aa to 100 aa, from 100 aa to 150 aa, or from 150 aa to 200 aa). In some cases, the peptide epitope of the first heterodimer and the peptide epitope of the second heterodimer comprise the same amino acid sequence. In some cases, the first MHC polypeptide of the first and the second heterodimer is an MHC Class I β2-microglobulin, and wherein the second MHC polypeptide of the first and the second heterodimer is an MHC Class I heavy chain. In some cases, the MODs of the first heterodimer and the MODs of the second heterodimer comprise the same amino acid sequence. In some cases, the MOD(s) of the first heterodimer and the MOD(s) of the second heterodimer are variant MODs that comprise from 1 to 10 amino acid substitutions compared to a corresponding parental wild-type MOD, and wherein the from 1 to 10 amino acid substitutions result in reduced affinity binding of the variant immunomodulatory polypeptide to a cognate co-immunomodulatory polypeptide. In some cases, the immunomodulatory polypeptide of the first heterodimer and the immunomodulatory polypeptide of the second heterodimer are each independently selected from the group consisting of IL-2, 4-1BBL, PD-L1, CD80, CD86, ICOS-L, OX-40L, FasL, JAG1 (CD339), TGFβ, CD70, and ICAM. Examples, of suitable MHC polypeptides, MODs, and peptide epitopes are described below.

MHC Polypeptides

As noted above, a TMMP of the present disclosure includes MHC polypeptides. For the purposes of the instant disclosure, the term "major histocompatibility complex (MHC) polypeptides" is meant to include MHC polypeptides of various species, including human MHC (also referred to as human leukocyte antigen (HLA)) polypeptides, rodent (e.g., mouse, rat, etc.) MHC polypeptides, and MHC polypeptides of other mammalian species (e.g., lagomorphs, non-human primates, canines, felines, ungulates (e.g., equines, bovines, ovines, caprines, etc.), and the like. The term "MHC polypeptide" is meant to include Class I MHC polypeptides (e.g., β-2 microglobulin and MHC class I heavy chain).

In some cases, the first MHC polypeptide is an MHC Class I β2M (β2M) polypeptide, and the second MHC polypeptide is an MHC Class I heavy chain (H chain) ("MHC-H")). In other instances, the first MHC polypeptide is an MHC Class I heavy chain polypeptide; and the second MHC polypeptide is a β2M polypeptide. In some cases, both the β2M and MHC-H chain are of human origin; i.e., the MHC-H chain is an HLA heavy chain, or a variant thereof. Unless expressly stated otherwise, a TMMP of the present disclosure does not include membrane anchoring domains (transmembrane regions) of an MHC Class I heavy chain, or a part of MHC Class I heavy chain sufficient to anchor the resulting TMMP to a cell (e.g., eukaryotic cell such as a mammalian cell) in which it is expressed. In some cases, the MHC Class I heavy chain present in a TMMP of the present disclosure does not include a signal peptide, a transmembrane domain, or an intracellular domain (cytoplasmic tail) associated with a native MHC Class I heavy chain. Thus, e.g., in some cases, the MHC Class I heavy chain present in a TMMP of the present disclosure includes only the α1, α2, and α3 domains of an MHC Class I heavy chain. In some cases, the MHC Class I heavy chain present in a TMMP has a length of from about 270 amino acids (aa) to about 290 aa. In some cases, the MHC Class I heavy chain present in a TMMP has a length of 270 aa, 271 aa, 272 aa, 273 aa, 274 aa, 275 aa, 276 aa, 277 aa, 278 aa, 279 aa, 280 aa, 281 aa, 282 aa, 283 aa, 284 aa, 285 aa, 286 aa, 287 aa, 288 aa, 289 aa, or 290 aa.

In some cases, an MHC polypeptide of a TMMP is a human MHC polypeptide, where human MHC polypeptides are also referred to as "human leukocyte antigen" ("HLA") polypeptides. In some cases, an MHC polypeptide of a TMMP is a Class I HLA polypeptide, e.g., a β2-microglobulin polypeptide, or a Class I HLA heavy chain polypeptide. Class I HLA heavy chain polypeptides include HLA-A heavy chain polypeptides, HLA-B heavy chain polypeptides, HLA-C heavy chain polypeptides, HLA-E heavy chain polypeptides, HLA-F heavy chain polypeptides, and HLA-G heavy chain polypeptides.

MHC Class I Heavy Chains

In some cases, an MHC Class I heavy chain polypeptide present in a TMMP comprises an amino acid sequence having at least 75%, at least 80%, at least 85%, at least 90%, at least 95%, at least 98%, at least 99%, or 100%, amino acid sequence identity to all or part (e.g., 50, 75, 100, 150, 200, or 250 contiguous amino acids) of the amino acid sequence of any of the human HLA heavy chain polypeptides depicted in FIGS. 7-13. In some cases, the MHC Class I heavy chain has a length of 270 aa, 271 aa, 272 aa, 273 aa, 274 aa, 275 aa, 276 aa, 277 aa, 278 aa, 279 aa, 280 aa, 281 aa, 282 aa, 283 aa, 284 aa, 285 aa, 286 aa, 287 aa, 288 aa, 289 aa, or 290 aa. In some cases, an MHC Class I heavy chain polypeptide present in a TMMP comprises 1-30, 1-5, 5-10, 10-15, 15-20, 20-25 or 25-30 amino acid insertions, deletions, and/or substitutions (in addition to those locations indicated as being variable in the heavy chain consensus sequences) of any one of the amino acid sequences depicted in FIGS. 7-13. In some cases, the MHC Class I heavy chain does not include transmembrane or cytoplasmic domains. As an example, a MHC Class I heavy chain polypeptide of a TMMP can comprise an amino acid sequence having at least 75%, at least 80%, at least 85%, at least 90%, at least 95%, at least 98%, at least 99%, or 100%, amino acid sequence identity to amino acids 25-300 (lacking all, or substantially all, of the leader, transmembrane and cytoplasmic sequence) or amino acids 25-365 (lacking the leader) of a human HLA-A heavy chain polypeptides depicted in any one of FIGS. 7A, 7B, and 7C.

FIGS. 7A, 7B and 7C provide amino acid sequences of human leukocyte antigen (HLA) Class I heavy chain polypeptides. Signal sequences, amino acids 1-24, are bolded and underlined. FIG. 7A entry: 3A.1 is the HLA-A heavy chain (HLA-A*01:01:01:01 or A*0101) (NCBI accession NP_001229687.1), SEQ ID NO:23; entry 3A.2 is from HLA-A*1101 SEQ ID NO:24; entry 3A.3 is from HLA-A*2402 SEQ ID NO:25 and entry 3A.4 is from HLA-A*3303 SEQ ID NO:26. FIG. 7B provides the sequence HLA-B*07:02:01 (HLA-B*0702) NCBI GenBank Accession NP_005505.2 (see also GenBank Accession AUV50118.1.). FIG. 7C provides the sequence HLA-C*0701 (GenBank Accession NP_001229971.1) (HLA-C*07:01:01:01 or HLA-Cw*070101, HLA-Cw*07 see GenBank Accession CAO78194.1).

FIG. 8 provides an alignment of eleven mature MHC class I heavy chain amino acid sequences without their leader sequences or transmembrane domains or intracellular domains. The aligned sequences are human HLA-A, HLA-B, and HLA-C, a mouse H2K protein sequence, three variants of HLA-A (var.1, var. 2C, and var.2CP), and 3 human HLA-A variants (HLA-A*1101; HLA-A*2402; and HLA-A*3303). Indicated in the alignment are the locations (84 and 139 of the mature proteins) where cysteine residues may be introduced (e.g., by substitution) for the formation of a disulfide bond to stabilize the MHC H chain-β2M complex. Also shown in the alignment is position 236 (of the mature polypeptide), which may be substituted by a cysteine residue that can form an inter-chain disulfide bond with β2M (e.g., at aa 12). An arrow appears above each of those locations and the residues are bolded. The seventh HLA-A sequence shown in the alignment (var. 2c), shows the sequence of variant 2 substituted with C residues at positions 84, 139 and 236. The boxes flanking residues 84, 139 and 236 show the groups of five amino acids on either sides of those six sets of five residues, denoted aac1 (for “amino acid cluster 1”), aac2 (for “amino acid cluster 2”), aac3 (for “amino acid cluster 3”), aac4 (for “amino acid cluster 4”), aac5 (for “amino acid cluster 5”), and aac6 (for “amino acid cluster 6”), that may be replaced by 1 to 5 amino acids selected independently from (i) any naturally occurring amino acid or (ii) any naturally occurring amino acid except proline or glycine.

With regard to FIG. 8, in some cases: i) aac1 (amino acid cluster 1) may be the amino acid sequence GTLRG (SEQ ID NO:287) or that sequence with one or two amino acids deleted or substituted with other naturally occurring amino acids (e.g., L replaced by I, V, A or F); ii) aac2 (amino acid cluster 2) may be the amino acid sequence YNQSE (SEQ ID NO:288) or that sequence with one or two amino acids deleted or substituted with other naturally occurring amino acids (e.g., N replaced by Q, Q replaced by N, and/or E replaced by D); iii) aac3 (amino acid cluster 3) may be the amino acid sequence TAADM (SEQ ID NO:289) or that sequence with one or two amino acids deleted or substituted with other naturally occurring amino acids (e.g., T replaced by S, A replaced by G, D replaced by E, and/or M replaced by L, V, or I); iv) aac4 (amino acid cluster 4) may be the amino acid sequence AQTTK (SEQ ID NO:290) or that sequence with one or two amino acids deleted or substituted with other naturally occurring amino acids (e.g., A replaced by G, Q replaced by N, or T replaced by S, and/or K replaced by R or Q); v) aac5 (amino acid cluster 5) may be the amino acid sequence VETRP (SEQ ID NO:291) or that sequence with one or two amino acids deleted or substituted with other naturally occurring amino acids (e.g., V replaced by I or L, E replaced by D, T replaced by S, and/or R replaced by K); and/or vi) aac6 (amino acid cluster 6) may be the amino acid sequence GDGTF (SEQ ID NO:292) or that sequence with one or two amino acids deleted or substituted with other naturally occurring amino acids (e.g., D replaced by E, T replaced by S, or F replaced by L, W, or Y).

FIGS. 9-11 provide alignments of mature HLA class I heavy chain amino acid sequences (without leader sequences or transmembrane domains or intracellular domains). The aligned amino acid sequences in FIG. 9A are HLA-A class I heavy chains of the following alleles: A*0101, A*0201, A*0301, A*1101, A*2301, A*2402, A*2407, A*3303, and A*3401. The aligned amino acid sequences in FIG. 10A are HLA-B class I heavy chains of the following alleles: B*0702, B*0801, B*1502, B*3802, B*4001, B*4601, and B*5301. The aligned amino acid sequences in FIG. 11A are HLA-C class I heavy chains of the following alleles: C*0102, C*0303, C*0304, C*0401, C*0602, C*0701, C*0801, and C*1502. Indicated in the alignments are the locations (84 and 139 of the mature proteins) where cysteine residues may be introduced (e.g., by substitution) for the formation of a disulfide bond to stabilize the HLA H chain-β2M complex. Also shown in the alignment is position 236 (of the mature polypeptide), which may be substituted by a cysteine residue that can form an inter-chain disulfide bond with β2M (e.g., at aa 12). The boxes flanking residues 84, 139 and 236 show the groups of five amino acids on either sides of those six sets of five residues, denoted aac1 (for “amino acid cluster 1”), aac2 (for “amino acid cluster 2”), aac3 (for “amino acid cluster 3”), aac4 (for “amino acid cluster 4”), aac5 (for “amino acid cluster 5”), and aac6 (for “amino acid cluster 6”), that may be replaced by 1 to 5 amino acids selected independently from (i) any naturally occurring amino acid or (ii) any naturally occurring amino acid except proline or glycine.

FIGS. 9A, 10A, and 11A provide alignments of the amino acid sequences of mature HLA-A, -B, and -C class I heavy chains, respectively. The sequences are provided for the extracellular portion of the mature protein (without leader sequences or transmembrane domains or intracellular domains). As described in FIG. 8, the positions of aa residues 84, 139, and 236 and their flanking residues (aac1 to aac6) that may be replaced by 1 to 5 amino acids selected independently from (i) any naturally occurring amino acid or (ii) any naturally occurring amino acid except proline or glycine ae also shown. FIGS. 9B, 10B, and 11B provide consensus amino acid sequences for the HLA-A, -B, and -C sequences, respectively, provide in FIGS. 9A, 10A, and 11A. The consensus sequences show the variable amino acid positions as “X” residues sequentially numbered and the locations of amino acids 84, 139 and 236 double underlined.

With regard to FIG. 9A, in some cases: i) aac1 (amino acid cluster 1) may be the amino acid sequence GTLRG (SEQ ID NO:287) or that sequence with one or two amino acids deleted or substituted with other naturally occurring amino acids (e.g., L replaced by I, V, A or F); ii) aac2 (amino acid cluster 2) may be the amino acid sequence YNQSE (SEQ ID NO:288) or that sequence with one or two amino acids deleted or substituted with other naturally occurring amino acids (e.g., N replaced by Q, Q replaced by N, and/or E replaced by D); iii) aac3 (amino acid cluster 3) may be the amino acid sequence TAADM (SEQ ID NO:289) or that sequence with one or two amino acids deleted or substituted with other naturally occurring amino acids (e.g., T replaced by S, A replaced by G, D replaced by E, and/or M replaced by L, V, or I); iv) aac4 (amino acid cluster 4) may be the amino acid sequence AQTTK (SEQ ID NO:290) or that sequence with one or two amino acids deleted or substituted with other naturally occurring amino acids (e.g., A replaced by G, Q replaced by N, or T replaced by S, and or K replaced by R or Q); v) aac5 (amino acid cluster 5) may be the amino acid sequence VETRP (SEQ ID NO:291) or that sequence with one or two amino acids deleted or substituted with other naturally occurring amino acids (e.g., V replaced by I or L, E replaced by D, T replaced by S, and/or R replaced by K); and/or vi) aac6 (amino acid cluster 6) may be the amino acid sequence GDGTF (SEQ ID NO:292) or that sequence with one or two amino acids deleted or substituted with other naturally occurring amino acids (e.g., D replaced by E, T replaced by S, or F replaced by L, W, or Y).

With regard to FIG. 10A, in some cases: i) aac1 (amino acid cluster 1) may be the amino acid sequence RNLRG (SEQ ID NO:293) or that sequence with one or two amino acids deleted or substituted with other naturally occurring amino acids (e.g., N replaced by T or I; and/or L replaced by A; and/or the second R replaced by L; and/or the G replaced by R); ii) aac2 (amino acid cluster 2) may be the amino acid sequence YNQSE (SEQ ID NO:288) or that sequence with one or two amino acids deleted or substituted with other naturally occurring amino acids (e.g., N replaced by Q, Q replaced by N, and/or E replaced by D); iii) aac3 (amino acid cluster 3) may be the amino acid sequence TAADT (SEQ ID NO:294) or that sequence with one or two amino acids deleted or substituted with other naturally occurring amino acids (e.g., the first T replaced by S; and/or A replaced by G; and/or D replaced by E; and/or the second T replaced by S); iv) aac4 (amino acid cluster 4) may be the amino acid sequence AQITQ (SEQ ID NO:295) or that sequence with one or two amino acids deleted or substituted with other naturally occurring amino acids (e.g., A replaced by G; and/or the first Q replaced by N; and/or I replaced by L or V; and/or the T replaced by S; and/or the second Q replaced by N); v) aac5 (amino acid cluster 5) may be the amino acid sequence VETRP (SEQ ID NO:291) or that sequence with one or two amino acids deleted or substituted with other naturally occurring amino acids (e.g., V replaced by I or L, E replaced by D, T replaced by S, and/or R replaced by K); and/or vi) aac6 (amino acid cluster 6) may be the amino acid sequence GDRTF (SEQ ID NO:296) or that sequence with one or two amino acids deleted or substituted with other naturally occurring amino acids (e.g., D replaced by E; and/or T replaced by S; and/or R replaced by K or H; and/or F replaced by L, W, or Y).

With regard to FIG. 11A, in some cases: i) aac1 (amino acid cluster 1) may be the amino acid sequence RNLRG (SEQ ID NO:293) or that sequence with one or two amino acids deleted or substituted with other naturally occurring amino acids (e.g., N replaced by K; and/or L replaced by A or I; and/or the second R replaced by H; and/or the G replaced by T or S); ii) aac2 (amino acid cluster 2) may be the amino acid sequence YNQSE (SEQ ID NO:288) or that sequence with one or two amino acids deleted or substituted with other naturally occurring amino acids (e.g., N replaced by Q, Q replaced by N, and/or E replaced by D); iii) aac3 (amino acid cluster 3) may be the amino acid sequence TAADT (SEQ ID NO:294) or that sequence with one or two amino acids deleted or substituted with other naturally occurring amino acids (e.g., the first T replaced by S; and/or A replaced by G; and/or D replaced by E; and/or the second T replaced by S); iv) aac4 (amino acid cluster 4) may be the amino acid sequence AQITQ (SEQ ID NO:295) or that sequence with one or two amino acids deleted or substituted with other naturally occurring amino acids (e.g., A replaced by G; and/or the first Q replaced by N; and/or I replaced by L; and/or the second Q replaced by N or K); v) aac5 (amino acid cluster 5) may be the amino acid sequence VETRP (SEQ ID NO:291) or that sequence with one or two amino acids deleted or substituted with other naturally occurring amino acids (e.g., V replaced by I or L, E replaced by D, T replaced by S, and/or R replaced by K or H); and/or vi) aac6 (amino acid cluster 6) may be the amino acid sequence GDGTF (SEQ ID NO:292) or that sequence with one or two amino acids deleted or substituted with other naturally occurring amino acids (e.g., D replaced by E; and/or T replaced by S; and/or F replaced by L, W, or Y).

HLA-A

In some cases, a TMMP comprises an HLA-A heavy chain polypeptide. The HLA-A heavy chain peptide sequences, or portions thereof, that may be that may be incorporated into a TMMP of the present disclosure include, but are not limited to, the alleles: A*0101, A*0201, A*0301, A*1101, A*2301, A*2402, A*2407, A*3303, and A*3401, which are aligned without all, or substantially all, of the leader, transmembrane and cytoplasmic sequences in FIG. 9A. Any of those alleles may comprise a mutation at one or more of positions 84, 139 and/or 236 (as shown in FIG. 9A) selected from: a tyrosine to alanine at position 84 (Y84A); a tyrosine to cysteine at position 84 (Y84C); an alanine to cysteine at position 139 (A139C); and an alanine to cysteine substitution at position 236 (A236C). In addition, HLA-A sequence having at least 75% (e.g., at least 80%, at least 85%, at least 90%, at least 95%, at least 98%, at least 99%) or 100% amino acid sequence identity to all or part (e.g., 50, 75, 100, 150, 200, or 250 contiguous amino acids) of the sequence of those HLA-A alleles may also be employed (e.g., it may comprise 1-25, 1-5, 5-10, 10-15, 15-20, 20-25, or 25-30 amino acid insertions, deletions, and/or substitutions).

In some cases, a TMMP comprises an HLA-A heavy chain polypeptide comprising the following HLA-A consensus amino acid sequence:

GSHSMRYFX1TSVSRPGRGEPRFIAVGYVDDTQFV
RFDSDAASQX2MEPRAPWIE
QEGPEYWDX3X4TX5X6X7KAX8SQX9X10RX11X12
LX13X14X15X16X17YLYNQSEX18GSHTX1
9QX20MX21GCDVGX22DX23RFLRGYX24QX25AYD
GKDYIALX26EDLRSWTAADMAAQX27T
X287X29KWEX30X31X32EAEQX33RX34YLX35GX36
CVX37X38LRRYLENGKETLQRTDX39PK
THMTHHX40X41SDHEATLRCWALX42FYPAEITLTW
QRDGEDQTQDTELVETRPAGDGTFQK
WAX43VVVPSGX44EQRYTCHVQHEGLPKPLTLR
WEX45 (SEQ ID NO:29), wherein X1 is F, Y, S, or T; X2 is K or R; X3 is Q, G, E, or R; X4 is N or E; X5 is R or G; X6 is N or K; X7 is M or V; X8 is H or Q; X9 is T or 1; X10 is D or H; X11 is A, V, or E; X12 is N or D; X13 is G or R; X14 is T or 1; X15 is L or A; X16 is R or L; X17 is G or R; X18 is A or D; X19 is 1, L, or V; X20 is I, R or M; X21 is F or Y; X22 is S or P; X23 is W or G; X24 is R, H, or Q; X25 is D or Y; X26 is N or K; X27 is T or I; X28 is K or Q; X29 is R or H; X30 is A or I; X31 is A or V; X32 is H or R; X33 is R, L, Q, or W; X34 is V or A; X35 is D or E; X36 is R or T; X37 is D or E; X38 is W or G; X39 is P or A; X40 is P or A; X41 is V or I; X42 is S or G; X43 is A or S; X44 is Q or E; and X45 is P or L.

As one example, an MHC Class I heavy chain polypeptide of a TMMP can comprise an amino acid sequence having at least 75%, at least 80%, at least 85%, at least 90%, at least 95%, at least 98%, at least 99%, or 100%, amino acid sequence identity to the following human HLA-A heavy chain amino acid sequence:

(SEQ ID NO: 44)
GSHSMRYFFTSVSRPGRGEPRFIAVGYVDDTQFVRFDSDAASQRMEPRAP
WIEQEGPEYWDGETRKVKAHSQTHRVDLGTLRGYYNQSEAGSHTVQRMYG
CDVGSDWRFLRGYHQYAYDGKDYIALKEDLRSWTAADMAAQTTKHKWEAA
HVAEQLRAYLEGTCVEWLRRYLENGKETLQRTDAPKTHMTHHAVSDHEAT
LRCWALSFYPAEITLTWQRDGEDQTQDTELVETRPAGDGTFQKWAAVVVP
SGQEQRYTCHVQHEGLPKPLTLRWEP.

In some cases, an HLA-A heavy chain polypeptide suitable for inclusion in a TMMP comprises the following amino acid sequence: GSHSMRYFFTSVSRPGRGEPRFIAVGYVDDTQFVRFDSDAASQRMEPRAPWIEQEGPEYWDGET RKVKAHSQTHRVDLGTLRGYYNQSEAGSHTVQRMYGCDVGSDWRFLRGYHQYAYDGKDYIA LKEDLRSWTAADMAAQTTKHKWEAAHVAEQLRAYLEGTCVEWLRRYLENGKETLQRTDAPK THMTHHAVSDHEATLRCWALSFYPAEITLTWQRDGEDQTQDTELVETRPAGDGTFQKWAAVV VPSGQEQRYTCHVQHEGLPKPLTLRWEP (SEQ ID NO:44). This HLA-A heavy chain polypeptide is also referred to as "HLA-A*0201" or simply "HLA-A02." In some cases, the C-terminal Pro is not included in a TMMP. For example, in some cases, an HLA-A02 polypeptide suitable for inclusion in a TMMP comprises the following amino acid sequence:

(SEQ ID NO: 449)
GSHSMRYFFTSVSRPGRGEPRFIAVGYVDDTQFVRFDSDAASQRMEPRAP
WIEQEGPEYWDGETRKVKAHSQTHRVDLGTLRGYYNQSEAGSHTVQRMYG
CDVGSDWRFLRGYHQYAYDGKDYIALKEDLRSWTAADMAAQTTKHKWEAA
HVAEQLRAYLEGTCVEWLRRYLENGKETLQRTDAPKTHMTHHAVSDHEAT
LRCWALSFYPAEITLTWQRDGEDQTQDTELVETRPAGDGTFQKWAAVVVP
SGQEQRYTCHVQHEGLPKPLTLRWE.

HLA-A (Y84C; A236C)

In some cases, an HLA-A heavy chain polypeptide suitable for inclusion in a TMMP comprises an amino acid sequence having at least 75%, at least 80%, at least 85%, at least 90%, at least 95%, at least 98%, at least 99%, or 100%, amino acid sequence identity to the following human HLA-A heavy chain (Y84C; A236C) amino acid sequence: GSHSMRYFFTSVSRPGRGEPRFIAVGYVDDTQFVRFDSDAASQRMEPRAPWIEQEGPEYWDGET RKVKAHSQTHRVDLGTLRGCYNQSEAGSHTVQRMYGCDVGSDWRFLRGYHQYAYDGKDYIA LKEDLRSWTAADMAAQTTKHKWEAAHVAEQLRAYLEGTCVEWLRRYLENGKETLQRTDAPK THMTHHAVSDHEATLRCWALSFYPAEITLTWQRDGEDQTQDTELVETRPCGDGTFQKWAAVV VPSGQEQRYTCHVQHEGLPKPLTLRWE (SEQ ID NO:488), where amino acid 84 is a Cys and where amino acid 236 is a Cys.

HLA-A (Y84A; A236C)

In some cases, the MHC Class I heavy chain polypeptide comprises Y84A and A236C substitutions. For example, in some cases, the MHC Class I heavy chain polypeptide comprises an amino acid sequence having at least 75%, at least 80%, at least 85%, at least 90%, at least 95%, at least 98%, at least 99%, or 100%, amino acid sequence identity to the following human HLA-A heavy chain (Y84A; A236C) amino acid sequence: GSHSMRYFFTSVSRPGRGEPRFIAVGYVDDTQFVRFDSDAASQRMEPRAPWIEQEGPEYWDGET RKVKAHSQTHRVDLGTLRGAYNQSEAGSHTVQRMYGCDVGSDWRFLRGYHQYAYDGKDYIA LKEDLRSWTAADMAAQTTKHKWEAAHVAEQLRAYLEGTCVEWLRRYLENGKETLQRTDAPK THMTHHAVSDHEATLRCWALSFYPAEITLTWQRDGEDQTQDTELVETRPCGDGTFQKWAAVV VPSGQEQRYTCHVQHEGLPKPLTLRWEP (SEQ ID NO:48), where amino acid 84 is Ala and amino acid 236 is Cys. In some cases, the Cys-236 forms an interchain disulfide bond with Cys-12 of a variant β2M polypeptide that comprises an R12C substitution.

In some cases, an HLA-A heavy chain polypeptide suitable for inclusion in a TMMP is an HLA-A02 (Y84A; A236C) polypeptide comprising the following amino acid sequence:

(SEQ ID NO: 48)
GSHSMRYFFTSVSRPGRGEPRFIAVGYVDDTQFVRFDSDAASQRMEPRAP
WIEQEGPEYWDGETRKVKAHSQTHRVDLGTLRGAYNQSEAGSHTVQRMYG
CDVGSDWRFLRGYHQYAYDGKDYIALKEDLRSWTAADMAAQTTKHKWEAA
HVAEQLRAYLEGTCVEWLRRYLENGKETLQRTDAPKTHMTHHAVSDHEAT
LRCWALSFYPAEITLTWQRDGEDQTQDTELVETRPCGDGTFQKWAAVVVP
SGQEQRYTCHVQHEGLPKPLTLRWEP.

In some cases, an HLA-A heavy chain polypeptide suitable for inclusion in a TMMP is an HLA-A02 (Y84A; A236C) polypeptide comprising the following amino acid sequence:

(SEQ ID NO: 46)
GSHSMRYFFTSVSRPGRGEPRFIAVGYVDDTQFVRFDSDAASQRMEPRAP
WIEQEGPEYWDGETRKVKAHSQTHRVDLGTLRGAYNQSEAGSHTVQRMYG
CDVGSDWRFLRGYHQYAYDGKDYIALKEDLRSWTAADMAAQTTKHKWEAA
HVAEQLRAYLEGTCVEWLRRYLENGKETLQRTDAPKTHMTHHAVSDHEAT
LRCWALSFYPAEITLTWQRDGEDQTQDTELVETRPCGDGTFQKWAAVVVP
SGQEQRYTCHVQHEGLPKPLTLRWE.

HLA-A (Y84C; A139C)

In some cases, the MHC Class I heavy chain polypeptide comprises Y84C and A139C substitutions. For example, in some cases, the MHC Class I heavy chain polypeptide comprises an amino acid sequence having at least 75%, at least 80%, at least 85%, at least 90%, at least 95%, at least 98%, at least 99%, or 100%, amino acid sequence identity to the following human HLA-A heavy chain (Y84C; A139C) amino acid sequence: GSHSMRYFFTSVSRPGRGEPRFIAVGYVDDTQFVRFDSDAASQRMEPRAPWIEQEGPEYWDGET RKVKAHSQTHRVDLGTLRGCYNQSEAGSHTVQRMYGCDVGSDWRFLRGYHQYAYDGKDYIA LKEDLRSWTAADMCAQTTKHKWEAAHVAEQLRAYLEGTCVEWLRRYLENGKETLQRTDAPK THMTHHAVSDHEATLRCWALSFYPAEITLTWQRDGEDQTQDTELVETRPAGDGTFQK- WAAVV VPSGQEQRYTCHVQHEGLPKPLTLRWEP (SEQ ID NO:299), where amino acid 84 is Cys and amino acid 139 is Cys. In some cases, Cys-84 forms an intrachain disulfide bond with Cys-139.

HLA-A11 (HLA-A*1101)

As one non-limiting example, an MHC Class I heavy chain polypeptide of a TMMP can comprise an amino acid sequence having at least 75%, at least 80%, at least 85%, at least 90%, at least 95%, at least 98%, at least 99%, or 100%, amino acid sequence identity to the following human HLA-A11 heavy chain amino acid sequence: GSHSMRYFYTSVSRPGRGEPRFIAVGYVDDTQFVRFDSDAASQRMEPRAPWIEQEGPEYWDQE TRNVKAQSQTDRVDLGTLRGYYNQSEDGSHTIQIMYGCDVGPDGRFLRGYRQDAYDGKDYIA LNEDLRSWTADMAAQITKRKWEAAHAAEQQRAYLEGTCVEWLRRYLENGKETLQR TDPPKT HMTHHPISDHEATLRCWALGFYPAEITLTWQRDGEDQTQDTELVETRPAGDGTFQKWAAVVV PSGEEQRYTCHVQHEGLPKPLTLRWE (SEQ ID NO:300). Such an MHC Class I heavy chain may be prominent in Asian populations, including populations of individuals of Asian descent.

HLA-A11 (Y84A; A236C)

As one non-limiting example, in some cases, the MHC Class I heavy chain polypeptide is an HLA-A11 allele that comprises Y84A and A236C substitutions. For example, in some cases, the MHC Class I heavy chain polypeptide comprises an amino acid sequence having at least 75%, at least 80%, at least 85%, at least 90%, at least 95%, at least 98%, at least 99%, or 100%, amino acid sequence identity to the following human HLA-A All heavy chain (Y84A; A236C) amino acid sequence: GSHSMRYFYTSVSRPGRGEPRFIAVGYVDDTQFVRFDSDAASQRMEPRAPWIEQEGPEYWDQE TRNVKAQSQTDRVDLGTLRGAYNQSEDGSHTIQIMYGCDVGPDGRFLRGYRQDAYDGKDYIA LNEDLRSWTADMAAQITKRKWEAAHAAEQQRAYLEGTCVEWLRRYLENGKETLQR TDPPKT HMTHHPISDHEATLRCWALGFYPAEITLTWQRDGEDQTQDTELVETRPCGDGTFQKWAAVVV PSGEEQRYTCHVQHEGLPKPLTLRWE (SEQ ID NO:301), where amino acid 84 is Ala and amino acid 236 is Cys. In some cases, the Cys-236 forms an interchain disulfide bond with Cys-12 of a variant β2M polypeptide that comprises an R12C substitution.

HLA-A11 (Y84C; A236C)

In some cases, the MHC Class I heavy chain polypeptide present in a TMMP comprises an amino acid sequence having at least 75%, at least 80%, at least 85%, at least 90%, at least 95%, at least 98%, at least 99%, or 100%, amino acid sequence identity to the following human HLA-A All heavy chain (Y84C; A236C) amino acid sequence: GSHSMRYFYTSVSRPGRGEPRFIAVGYVDDTQFVRFDSDAASQRMEPRAPWIEQEGPEYWDQE TRNVKAQSQTDRVDLGTLRGCYNQSEDGSHTIQIMYGCDVGPDGRFLRGYRQDAYDGKDYIA LNEDLRSWTADMAAQITKRKWEAAHAAEQQRAYLEGTCVEWLRRYLENGKETLQR TDPPKT HMTHHPISDHEATLRCWALGFYPAEITLTWQRDGEDQTQDTELVETRPCGDGTFQKWAAVVV PSGEEQRYTCHVQHEGLPKPLTLRWE (SEQ ID NO:301), where amino acid 84 is Cys and amino acid 236 is Cys.

HLA-A24 (HLA-A*2402)

As one non-limiting example, an MHC Class I heavy chain polypeptide of a TMMP can comprise an amino acid sequence having at least 75%, at least 80%, at least 85%, at least 90%, at least 95%, at least 98%, at least 99%, or 100%, amino acid sequence identity to the following human HLA-A24 (also referred to as HLA-A*2402) heavy chain amino acid sequence: GSHSMRYFSTSVSRPGRGEPRFIAVGYVDDTQFVRFDSDAASQRMEPRAPWIEQEGPEYWDEET GKVKAHSQTDRENLRIALRYYNQSEAGSHTLQMMFGCDVGSDGRFLRGYHQYAYDGKDYIAL KEDLRSWTAADMAAQITKRKWEAAHVAEQQRAYLEGTCVDGLRRYLENGKETLQRTDPPKT HMTHHPISDHEATLRCWALGFYPAEITLTWQRDGEDQTQDTELVETRPAGDGTFQKWAAVVV PSGEEQRYTCHVQHEGLPKPLTLRWEPSSQPTVPIVGIIAGLVLLGAVITGAVVAAVMWR RNSS DRKGGSYSQAASSDSAQGSDVSLTACKV (SEQ ID NO:302). Such an MHC Class I heavy chain may be prominent in Asian populations, including populations of individuals of Asian descent. In some cases, amino acid 84 is an Ala. In some cases, amino acid 84 is a Cys. In some cases, amino acid 236 is a Cys. In some cases, amino acid 84 is an Ala and amino acid 236 is a Cys. In some cases, amino acid 84 is an Cys and amino acid 236 is a Cys.

In some cases, an MHC Class I heavy chain polypeptide of a TMMP can comprise an amino acid sequence having at least 75%, at least 80%, at least 85%, at least 90%, at least 95%, at least 98%, at least 99%, or 100%, amino acid sequence identity to the following human HLA-A24 (also referred to as HLA-A*2402) heavy chain amino acid sequence: GSHSMRYFSTSVSRPGRGEPRFIAVGYVDDTQFVRFDSDAASQRMEPRAPWIEQEGPEYWDEET GKVKAHSQTDRENLRIALR YYNQSEAGSHTLQMMFGCDVGSDGRFLRGYHQYAYDGKDYIAL KEDLRSWTAADMAAQITKRKWEAAHVAEQQRAYLEGTCVDGLRRYLENGKETLQRTDPPKT HMTHHPISDHEATLRCWALGFYPAEITLTWQRDGEDQTQDTELVETRPAGDGTFQKWAAVVV PSGEEQRYTCHVQHEGLPKPLTLRWE (SEQ ID NO:455), where amino acid 84 is Tyr and amino acid 236 is Ala (amino acids 84 and 236 are bold and underlined); and where the MHC Class I heavy chain has a length of about 275 amino acids.

In some cases, an MHC Class I heavy chain polypeptide of a TMMP can comprise an amino acid sequence having at least 75%, at least 80%, at least 85%, at least 90%, at least 95%, at least 98%, at least 99%, or 100%, amino acid sequence identity to the following human HLA-A24 (also referred to as HLA-A*2402) heavy chain amino acid sequence: GSHSMRYFSTSVSRPGRGEPRFIAVGYVDDTQFVRFDSDAASQRMEPRAPWIEQEGPEYWDEET GKVKAHSQTDRENLRIALRAYNQSEAGSHTLQMMFGCDVGSDGRFLRGYHQYAYDGKDYIAL KEDLRSWTAADMAAQITKRKWEAAHVAEQQRAYLEGTCVDGLRRYLENGKETLQRTDPPKT HMTHHPISDHEATLRCWALGFYPAEITLTWQRDGEDQTQDTELVETRPAGDGTFQKWAAVVV PSGEEQRYTCHVQHEGLPKPLTLRWE (SEQ ID NO:456), where amino acid 84 is Ala and amino acid 236 is Ala (amino acids 84 and 236 are bold and underlined); and where the MHC Class I heavy chain has a length of about 275 amino acids.

In some cases, an MHC Class I heavy chain polypeptide of a TMMP can comprise an amino acid sequence having at least 75%, at least 80%, at least 85%, at least 90%, at least 95%, at least 98%, at least 99%, or 100%, amino acid sequence identity to the following human HLA-A24 (also referred to as HLA-A*2402) heavy chain amino acid sequence: GSHSMRYFSTSVSRPGRGEPRFIAVGYVDDTQFVRFDSDAASQRMEPRAPWIEQEGPEYWDEET GKVKAHSQTDRENLRIALRYYNQSEAGSHTLQMMFGCDVGSDGRFLRGYHQYAYDGKDYI AL KEDLRSWTAADMAAQITKRKWEAAHVAEQQRAYLEGTCVDGLRRYLENGKETLQRTDPPKT HMTHHPISDHEATLRCWALGFYPAEITLTWQRDGEDQTQDTELVETRPCGDGTFQKWAAVVV PSGEEQRYTCHVQHEGLPKPLTLRWE (SEQ ID NO:457), where amino acid 84 is Tyr and amino acid 236 is Cys (amino acids 84 and 236 are bold and underlined); and where the MHC Class I heavy chain has a length of about 275 amino acids.

In some cases, an MHC Class I heavy chain polypeptide of a TMMP can comprise an amino acid sequence having at least 75%, at least 80%, at least 85%, at least 90%, at least 95%, at least 98%, at least 99%, or 100%, amino acid sequence identity to the following human HLA-A24 (also referred to as HLA-A*2402) heavy chain amino acid sequence: GSHSMRYFSTSVSRPGRGEPRFIAVGYVDDTQFVRFDSDAASQRMEPRAPWIEQEGPEYWDEET GKVKAHSQTDRENLRIALRAYNQSEAGSHTLQMMFGCDVGSDGRFLRGYHQYAYDGKDYI AL KEDLRSWTAADMAAQITKRKWEAAHVAEQQRAYLEGTCVDGLRRYLENGKETLQRTDPPKT HMTHHPISDHEATLRCWALGFYPAEITLTWQRDGEDQTQDTELVETRPCGDGTFQKWAAVVV PSGEEQRYTCHVQHEGLPKPLTLRWE (SEQ ID NO:458), where amino acid 84 is Ala and amino acid 236 is Cys (amino acids 84 and 236 are bold and underlined); and where the MHC Class I heavy chain has a length of about 275 amino acids.

In some cases, an MHC Class I heavy chain polypeptide of a can comprise an amino acid sequence having at least 75%, at least 80%, at least 85%, at least 90%, at least 95%, at least 98%, at least 99%, or 100%, amino acid sequence identity to the following human HLA-A24 (also referred to as HLA-A*2402) heavy chain amino acid sequence: GSHSMRYFSTSVSRPGRGEPRFIAVGYVDDTQFVRFDSDAASQRMEPRAPWIEQEGPEYWDEET GKVKAHSQTDRENLRIALRCYNQSEAGSHTLQMMFGCDVGSDGRFLRGYHQYAYDGKDYI AL KEDLRSWTAADMAAQITKRKWEAAHVAEQQRAYLEGTCVDGLRRYLENGKETLQRTDPPKT HMTHHPISDHEATLRCWALGFYPAEITLTWQRDGEDQTQDTELVETRP AGDGTFQKWAAVVV PSGEEQRYTCHVQHEGLPKPLTLRWE (SEQ ID NO:459), where amino acid 84 is Cys and amino acid 236 is Ala (amino acids 84 and 236 are bold and underlined); and where the MHC Class I heavy chain has a length of about 275 amino acids.

In some cases, an MHC Class I heavy chain polypeptide of a TMMP can comprise an amino acid sequence having at least 75%, at least 80%, at least 85%, at least 90%, at least 95%, at least 98%, at least 99%, or 100%, amino acid sequence identity to the following human HLA-A24 (also referred to as HLA-A*2402) heavy chain amino acid sequence: GSHSMRYFSTSVSRPGRGEPRFIAVGYVDDTQFVRFDSDAASQRMEPRAPWIEQEGPEYWDEET GKVKAHSQTDRENLRIALRCYNQSEAGSHTLQMMFGCDVGSDGRFLRGYHQYAYDGKDYI AL KEDLRSWTAADMAAQITKRKWEAAHVAEQQRAYLEGTCVDGLRRYLENGKETLQRTDPPKT HMTHHPISDHEATLRCWALGFYPAEITLTWQRDGEDQTQDTELVETRPCGDGTFQKWAAVVV PSGEEQRYTCHVQHEGLPKPLTLRWE (SEQ ID NO:346), where amino acid 84 is Cys and amino acid 236 is Cys (amino acids 84 and 236 are bold and underlined); and where the MHC Class I heavy chain has a length of about 275 amino acids.

HLA-A33 (HLA-A*3303)

As one non-limiting example, an MHC Class I heavy chain polypeptide of a TMMP can comprise an amino acid sequence having at least 75%, at least 80%, at least 85%, at least 90%, at least 95%, at least 98%, at least 99%, or 100%, amino acid sequence identity to the following human HLA-A33 heavy chain amino acid sequence: GSHSMRYFTTSVSRPGRGEPRFIAVGYVDDTQFVRFDSDAASQRMEPRAPWIEQEGPEYWDRN TRNVKAHSQIDRVDLGTLRGYYNQSEAGSHTIQMMYGCDVGSDGRFLRGYQQDAYDGKDYIA LNEDLRSWTAADMAAQITQRKWEAARVAEQLRAYLEGTCVEWLRRYLENGKETLQRTDPPKT HMTHHAVSDHEATLRCWALSFYPAEITLTWQRDGEDQTQDTELVETRPAGDGTFQKWASVVV PSGQEQRYTCHVQHEGLPKPLTLRWEPSSQPTIPIVGIIAGLVLFGAVFAGAVVAAVRWRRK SSD RKGGSYSQAASSDSAQGSDMSLTACKV (SEQ ID NO:303). Such an MHC Class I heavy chain may be prominent in Asian populations, including populations of individuals of Asian descent. In some cases, amino acid 84 is an Ala. In some cases, amino acid 84 is a Cys. In some cases, amino acid 236 is a Cys. In some cases, amino acid 84 is an Ala and amino acid 236 is a Cys. In some cases, amino acid 84 is an Cys and amino acid 236 is a Cys.

HLA-B

In some cases, a TMMP comprises an HLA-B heavy chain polypeptide. The HLA-B heavy chain peptide sequences, or portions thereof, that may be that may be incorporated into a TMMP include, but are not limited to, the alleles: B*0702, B*0801, B*1502, B*3802, B*4001, B*4601, and B*5301, which are aligned without all, or substantially all, of the leader, transmembrane and cytoplasmic sequences in FIG. 10A. Any of those alleles may comprise a mutation at one or more of positions 84, 139 and/or 236 (as shown in FIG. 10A) selected from: a tyrosine to alanine at position 84 (Y84A); a tyrosine to cysteine at position 84 (Y84C); an alanine to cysteine at position 139 (A139C); and an alanine to cysteine substitution at position 236 (A236C). In addition, a HLA-B polypeptide comprising an amino acid sequence having at least 75% (e.g., at least 80%, at least 85%, at least 90%, at least 95%, at least 98%, at least 99%) or 100% amino acid sequence identity to all or part (e.g., 50, 75, 100, 150, 200, or 250 contiguous amino acids) of the sequence of those HLA-B alleles may also be employed (e.g., it may comprise 1-25, 1-5, 5-10, 10-15, 15-20, 20-25, or 25-30 amino acid insertions, deletions, and/or substitutions).

In some cases, a TMMP comprises an HLA-B heavy chain polypeptide comprising the following HLA-B consensus amino acid sequence:

GSHSMRYFX1TX2X3SRPGRGEPRFIX4VGYVDDT X5FVRFDSDAX6SPRX7X8PR APWIEQEGPEYWDRX9TQX10X11KTX12X13TQX14 YX15X16NLX17X18X19X20YYNQSEAGS HX21X22QX23MYGCDLGPDGRLLRGHDQSAYDGK DYIALNEDLX24SWTAADTAAQIX25QRK X26EAARX27AEQX28RX29YLEGX30CVEWLRRYLE NGKX31X32LX33RADPPKTHVTHHPX34 SDHEATLRCWALGFYPAEITLTWQRDGEDQTQDTEL-VETRPAGDRTFQKWAAVVVPSGEEQR YTCHVQHEGLPKPLTLRWEP (SEQ ID NO:30), wherein X1 is H, Y, or D; X2 is A or S; X3 is M or V; X4 is A, S, or T; X5 is Q or L; X6 is A or T; X7 is E, M K, or T; X8 is A or T; X9 is E or N; X10 is I or K; X11 is Y, F, S, or C; X12 is N or Q; X13 is A or T; X14 is D or Y; X15 is E or V; X16 is S or N; X17 is T, N, or I; X18 is A or L; X19 is L, or R; X20 is R or G; X21 is T or I; X22 is L or I; X23 is R or S; X24 is R or S; X25 is S or T; X26 is L or W; X27 is E OR V; X28 is R, D, L or W; X29 is A or T; X30 is L, E or T; X31 is E or D; X32 is K or T; X33 is E or Q; and X34 is I or V.

As an example, an MHC Class I heavy chain polypeptide of a TMMP can comprise an amino acid sequence having at least 75%, at least 80%, at least 85%, at least 90%, at least 95%, at least 98%, at least 99%, or 100%, amino acid sequence identity to the following human HLA-B heavy chain amino acid sequence:

(SEQ ID NO: 207)

```
GSHSMRYFYTSVSRPGRGEPRFISVGYVDDTQFVRFDSDAASPREEPRAP
WIEQEGPEYWDRNTQIYKAQAQTDRESLRNLRGYYNQSEAGSHTLQSMYG
CDVGPDGRLLRGHDQYAYDGKDYIALNEDLRSWTAADTAAQITQRKWEAA
REAEQRRAYLEGECVEWLRRYLENGKDKLERADPPKTHVTHHPISDHEAT
LRCWALGFYPAEITLTWQRDGEDQTQDTELVETRPAGDRTFQKWAAVVVP
SGEEQRYTCHVQHEGLPKPLTLRWEP.
```

HLA-B (Y84A; A236C)

As one non-limiting example, in some cases, the MHC Class I heavy chain polypeptide is an HLA-B polypeptide that comprises Y84A and A236C substitutions. For example, in some cases, the MHC Class I heavy chain polypeptide comprises an amino acid sequence having at least 75%, at least 80%, at least 85%, at least 90%, at least 95%, at least 98%, at least 99%, or 100%, amino acid sequence identity to the following human HLA-B heavy chain (Y84A; A236C) amino acid sequence: GSHSMRYFYTSVSRPGRGEPRFISVGYVDDTQFVRFDSDAASPREEPRAPWIEQEGPEYWDRNT QIYKAQAQTDRESLRNLRGAYNQSEAGSHTLQSMYGCDVGPDGR LLRGHDQYAYDGKDYIAL NEDLRSWTAADTAAQITQRKWEAAREAEQRRAYLEGECVEWLRRYLENGKDKLERADPPKTH VTHHPISDHEATLRCWALGFYPAEITLTWQRDGEDQTQDTELVETRPCGDRTFQ KWAAVVVPS GEEQRYTCHVQHEGLPKPLTLRWEP (SEQ ID NO:305), where amino acid 84 is Ala and amino acid 236 is Cys. In some cases, the Cys-236 forms an interchain disulfide bond with Cys-12 of a variant β2M polypeptide that comprises an R12C substitution.

HLA-B (Y84C; A139C)

In some cases, the MHC Class I heavy chain polypeptide comprises Y84C and A139C substitutions. For example, in some cases, the MHC Class I heavy chain polypeptide comprises an amino acid sequence having at least 75%, at least 80%, at least 85%, at least 90%, at least 95%, at least 98%, at least 99%, or 100%, amino acid sequence identity to the following human HLA-B heavy chain (Y84C; A139C) amino acid sequence: GSHSMRYFYTSVSRPGRGEPRFISVGYVDDTQFVRFDSDAASPREEPRAPWIEQEGPEYWDRNT QIYKAQAQTDRESLRNLRGCYNQSEAGSHTLQSMYGCDVGPDGR LLRGHDQYAYDGKDYIAL NEDLRSWTAADTCAQITQRKWEAAREAEQRRAYLEGECVEWLRRYLENGKDKLERADPPKTH VTHHPISDHEATLRCWALGFYPAEITLTWQRDGEDQTQDTELVETRPAGDRTFQKWAAVVVPS GEEQRYTCHVQHEGLPKPLTLRWEP (SEQ ID NO:306), where amino acid 84 is Cys and amino acid 139 is Cys. In some cases, Cys-84 forms an intrachain disulfide bond with Cys-139.

HLA-B*0702

As an example, in some cases, a MHC Class I heavy chain polypeptide present in a TMMP comprises an amino acid sequence of HLA-B*0702 (SEQ ID NO:207) in FIG. 10A, or a sequence having at least 75% (e.g., at least 80%, at least 85%, at least 90%, at least 95%, at least 98%, at least 99%) or 100%, amino acid sequence identity to all or part (e.g., 50, 75, 100, 150, 200, or 250 contiguous amino acids) of that sequence (e.g., it may comprise 1-25, 1-5, 5-10, 10-15, 15-20, 20-25, or 25-30 amino acid insertions, deletions, and/or substitutions). In some cases, where the HLA-B heavy chain polypeptide of TMMP of the present disclosure has less than 100% identity to the sequence labeled HLA-B in FIG. 8, or labeled "B*0702 in FIG. 10A, it may comprise a mutation at one or more of positions 84, 139 and/or 236 selected from: a tyrosine to alanine substitution at position 84 (Y84A); a tyrosine to cysteine substitution at position 84 (Y84C); an alanine to cysteine at position 139 (A139C); and an alanine to cysteine substitution at position 236 (A236C). In some cases, the HLA-B heavy chain polypeptide of TMMP of the present disclosure comprises Y84A and A236C substitutions. In some cases, the HLA-B*0702 heavy chain polypeptide of TMMP of the present disclosure comprises Y84C and A139C substitutions. In some cases, the HLA-B heavy chain polypeptide of TMMP of the present disclosure comprises Y84C, A139C, and A236C substitutions.

HLA-C

In some cases, a TMMP comprises an HLA-C heavy chain polypeptide. The HLA-C heavy chain polypeptide, or portions thereof, that may be that may be incorporated into a TMMP of the present disclosure include, but are not limited to, the alleles: C*0102, C*0303, C*0304, C*0401, C*0602, C*0701, C*0801, and C*1502, which are aligned without all, or substantially all, of the leader, transmembrane and cytoplasmic sequences in FIG. 11A. Any of those alleles may comprise a mutation at one or more of positions 84, 139 and/or 236 (as shown in FIG. 11A) selected from: a tyrosine to alanine substitution at position 84 (Y84A); a tyrosine to cysteine substitution at position 84 (Y84C); an alanine to cysteine substitution at position 139 (A139C); and an alanine to cysteine substitution at position 236 (A236C). In addition, an HLA-C polypeptide comprising an amino acid sequence having at least 75% (e.g., at least 80%, at least 85%, at least 90%, at least 95%, at least 98%, at least 99%) or 100% amino acid sequence identity to all or part (e.g., 50, 75, 100, 150, 200, or 250 contiguous amino acids) of the sequence of those HLA-C alleles may also be employed (e.g., it may comprise 1-25, 1-5, 5-10, 10-15, 15-20, 20-25, or 25-30 amino acid insertions, deletions, and/or substitutions).

In some cases, a TMMP comprises an HLA-C heavy chain polypeptide comprising the following HLA-C consensus amino acid sequence:

X1SHSMX2YFX3TAVSX4PGRGEPX5FIX6VGYVDDTQFVX7FDSDAASPRGEPRX8PWVEQEGPEYWDRETQX9YKRQAQX10DRVX11LRX12LRGYYNQSEX13X14SHX15X16QX17MX18GCDX19GPDGRLLRGX20X21QX22AYDGKDYIALNEDLRSWTAADTAAQITQRKX23EA ARX24AEQX25RAYLEGX26CVEWLRRYLX27NGKX28TLQRAEX29PKTHVTHHPX30SDHEAT LRCWALGFYPAEITLTWQX31DGEDQTQDTELVETRP AGDGTFQKWAAVX32VPSGX33EQRY

TCHX34QHEGLX35EPLTLX36WX37P (SEQ ID NO:31), wherein X1 is C or G; X2 is R or K; X3 is F, Y, S, or D; X4 is R or W; X5 is H or R; X6 is A or S; X7 is Q or R; X8 is A or E; X9 is N or K; X10 is T or A; X11 is S or N; X12 is N or K; X13 is A or D; X14 is G or R; X15 is T or I; X16 is L or I; X17 is W or R; X18 is C, Y, F, or S; X19 is L, or V; X20 is Y or H; X21 is D or N; X22 is Y, F, S, or L; X23 is L or W; X24 is E, A, Or T; X25 is R, L, or W; X26 is L or T; X27 is E OR K; X28 is E or K; X29 is H or P; X30 is R or V; X31 is W or R; X32 is V or M; X33 is E or Q; X34 is M or V; X35 is P or Q; X36 is R or S; and X37 is P or G.

As an example, an MHC Class I heavy chain polypeptide of a TMMP can comprise an amino acid sequence having at least 75%, at least 80%, at least 85%, at least 90%, at least 95%, at least 98%, at least 99%, or 100%, amino acid sequence identity to the following human HLA-C heavy chain amino acid sequence:

```
                                    (SEQ ID NO: 219)
CSHSMRYFDTAVSRPGRGEPRFISVGYVDDTQFVRFDSDAASPRGEPRAP

WVEQEGPEYWDRETQNYKRQAQADRVSLRNLRGYYNQSEDGSHTLQRMYG

CDLGPDGRLLRGYDQSAYDGKDYIALNEDLRSWTAADTAAQITQRKLEAA

RAAEQLRAYLEGTCVEWLRRYLENGKETLQRAEPPKTHVTHHPLSDHEAT

LRCWALGFYPAEITLTWQRDGEDQTQDTELVETRPAGDGTFQKWAAVVVP

SGQEQRYTCHMQHEGLQEPLTLSWEP.
```

HLA-C(Y84A; A236C)

As one non-limiting example, in some cases, the MHC Class I heavy chain polypeptide is an HLA-C polypeptide that comprises Y84A and A236C substitutions. For example, in some cases, the MHC Class I heavy chain polypeptide comprises an amino acid sequence having at least 75%, at least 80%, at least 85%, at least 90%, at least 95%, at least 98%, at least 99%, or 100%, amino acid sequence identity to the following human HLA-C heavy chain (Y84A; A236C) amino acid sequence: CSHSMRYFD-TAVSRPGRGEPRFISVGYVDDTQFVRFDS-DAASPRGEPRAPWVEQEGPEYWDRE TQNYKRQAQADRVSLRNLR-GAYNQSEDGSHTLQRMYGCDLGPDGRLLR-GYDQSAYDGKDYI ALNEDLRSWTAAD-TAAQITQRKLEAARAAEQLRAYLEGTCVEWLRRYLE NGKETLQRAEPPKT HVTHHPLSDHEATLRCWAL-GFYPAEITLTWQRDGEDQTQDTELVE-TRPCGDGTFQKWAAVVV PSGQEQRYTCHMQHEGLQEPLTLSWEP (SEQ ID NO:308), where amino acid 84 is Ala and amino acid 236 is Cys. In some cases, the Cys-236 forms an interchain disulfide bond with Cys-12 of a variant β2M polypeptide that comprises an R12C substitution.

HLA-C(Y84C; A139C)

In some cases, the MHC Class I heavy chain polypeptide comprises Y84C and A139C substitutions. For example, in some cases, the MHC Class I heavy chain polypeptide comprises an amino acid sequence having at least 75%, at least 80%, at least 85%, at least 90%, at least 95%, at least 98%, at least 99%, or 100%, amino acid sequence identity to the following human HLA-C heavy chain (Y84C; A139C) amino acid sequence: CSHSMRYFD-TAVSRPGRGEPRFISVGYVDDTQFVRFDS-DAASPRGEPRAPWVEQEGPEYWDRE TQNYKRQAQADRVSLRNLRGCYN-QSEDGSHTLQRMYGCDLGPDGRLLR-GYDQSAYDGKDYI ALNEDLRSWTAADT-CAQITQRKLEAARAAEQLRAYLEGTCVEWLRRYLEN GKETLQRAEPPKT HVTHHPLSDHEATLRCWALGFY-PAEITLTWQRDGEDQTQDTELVETRPAGDGTFQK-WAAVVV PSGQEQRYTCHMQHEGLQEPLTLSWEP (SEQ ID NO:397), where amino acid 84 is Cys and amino acid 139 is Cys. In some cases, Cys-84 forms an intrachain disulfide bond with Cys-139.

HLA-C*0701

In some cases, a MHC Class I heavy chain polypeptide of a TMMP comprises an amino acid sequence of HLA-C*0701 of FIG. 11A (labeled HLA-C in FIG. 8), or an amino acid sequence having at least 75% (e.g., at least 80%, at least 85%, at least 90%, at least 95%, at least 98%, at least 99%) or 100% amino acid sequence identity to all or part (e.g., 50, 75, 100, 150, 200, or 250 contiguous amino acids) of that sequence (e.g., it may comprise 1-25, 1-5, 5-10, 10-15, 15-20, 20-25, or 25-30 amino acid insertions, deletions, and/or substitutions). In some cases, where the HLA-C heavy chain polypeptide of a TMMP has less than 100% identity to the sequence labeled HLA-C*0701 in FIG. 11A, it may comprise a mutation at one or more of positions 84, 139 and/or 236 selected from: a tyrosine to alanine substitution at position 84 (Y84A); a tyrosine to cysteine substitution at position 84 (Y84C); an alanine to cysteine at position 139 (A139C); and an alanine to cysteine substitution at position 236 (A236C). In some cases, the HLA-C heavy chain polypeptide of a TMMP comprises Y84A and A236C substitutions. In some cases, the HLA-C*0701 heavy chain polypeptide of a T-Cell-MMP or its epitope conjugate comprises Y84C and A139C substitutions. In some cases, the HLA-C heavy chain polypeptide of a TMMP of the present disclosure comprises Y84C, A139C, and A236C substitutions.

Non-Classical HLA-E, -F, and -G MHC Class I Heavy Chains

In some cases, a TMMP comprises a non-classical MHC Class I heavy chain polypeptide. Among the non-classical HLA heavy chain polypeptides, or portions thereof, that may be that may be incorporated into a TMMP of the present disclosure include, but are not limited to, those of HLA-E, -F, and -G alleles Amino acid sequences for HLA-E, -F, and -G heavy chain polypeptides, (and the HLA-A, B and C alleles) may be found on the world wide web hla.alleles.org/nomenclature/index.html, the European Bioinformatics Institute (www(dot)ebi(dot)ac(dot)uk), which is part of the European Molecular Biology Laboratory(EMBL), and at the National Center for Biotechnology Information (www(dot)ncbi(dot)nlm(dot)nih(dot)gov).

Non-limiting examples of suitable HLA-E alleles include, but are not limited to, HLA-E*0101 (HLA-E*01:01:01:01), HLA-E*01:03(HLA-E*01:03:01:01), HLA-E*01:04, HLA-E*01:05, HLA-E*01:06, HLA-E*01:07, HLA-E*01:09, and HLA-E*01:10. Non-limiting examples of suitable HLA-F alleles include, but are not limited to, HLA-F*0101 (HLA-F*01:01:01:01), HLA-F*01:02, HLA-F*01:03(HLA-F*01:03:01:01), HLA-F*01:04, HLA-F*01:05, and HLA-F*01:06. Non-limiting examples of suitable HLA-G alleles include, but are not limited to, HLA-G*0101 (HLA-G*01:01:01:01), HLA-G*01:02, HLA-G*01:03(HLA-G*01:03:01:01), HLA-G*01:04 (HLA-G*01:04:01:01), HLA-G*01:06, HLA-G*01:07, HLA-G*01:08, HLA-G*01:09: HLA-G*01:10, HLA-G*01:10, HLA-G*01:11, HLA-G*01:12, HLA-G*01:14, HLA-G*01:15, HLA-G*01:16, HLA-G*01:17, HLA-G*01:18: HLA-G*01:19, HLA-G*01:20, and HLA-G*01:22. Consensus sequences for those HLA E, —F and -G alleles without all, or substantially all, of the leader, transmembrane and cytoplasmic sequences are provided in FIG. 12, and aligned with consensus sequences of the above-mentioned HLA-A, -B and -C alleles in FIG. 13.

Amino acid sequences of suitable HLA-E heavy chain polypeptides are provided in FIG. 46A-46D, where FIG. 46A provides the amino acid sequence of HLA-E*01:01 (wild-type); FIG. 46B provides the amino acid sequence of HLA-E*01:01 with Y84C and A2346C substitutions; FIG. 46C provides the amino acid sequence of HLA-E*01:03 (wild-type); and FIG. 46D provides the amino acid sequence of HLA-E*01:03 with Y84C and A2346C substitutions.

Amino acid sequences of suitable HLA-G heavy chain polypeptides are provided in FIG. 47A-7D, where FIG. 47A provides the amino acid sequence of HLA-G*01:01 (wild-type); FIG. 47B provides the amino acid sequence of HLA-G*01:01 with Y84C and A2346C substitutions; FIG. 47C provides the amino acid sequence of HLA-G*01:04 (wild-type); and FIG. 47D provides the amino acid sequence of HLA-G*01:04 with Y84C and A2346C substitutions.

FIG. 12 provides a consensus sequence for each of HLA-E, -F, and -G with the variable aa positions indicated as "X" residues sequentially numbered and the locations of aas 84, 139 and 236 double underlined.

FIG. 13 provides an alignment of the consensus amino acid sequences for HLA-A, -B, -C, -E, -F, and -G, which are given in FIGS. 9-13. Variable residues in each sequence are listed as "X" with the sequential numbering removed. As indicated in FIG. 8, the locations of aas 84, 139 and 236 are indicated with their flanking five-amino acid clusters that may be replaced by 1 to 5 amino acids selected independently from (i) any naturally occurring amino acid or (ii) any naturally occurring amino acid except proline or glycine are also shown.

Any of the above-mentioned HLA-E, -F, and/or -G alleles may comprise a substitution at one or more of positions 84, 139 and/or 236 as shown in FIG. 13 for the consensus sequences. In some cases, the substitutions may be selected from a: position 84 tyrosine to alanine (Y84A) or cysteine (Y84C), or, in the case of HLA-F, an R84A or R84C substitution; a position 139 alanine to cysteine (A139C), or, in the case of HLA-F, a V139C; and an alanine to cysteine substitution at position 236 (A236C). In addition, an HLA-E, -F and/or -G sequence having at least 75% (e.g., at least 80%, at least 85%, at least 90%, at least 95%, at least 98%, at least 99%) or 100% amino acid sequence identity to all or part (e.g., 50, 75, 100, 150, 200, or 250 contiguous amino acids) of any of the consensus sequences of set forth in FIG. 13 may also be employed (e.g., the sequences may comprise 1-25, 1-5, 5-10, 10-15, 15-20, 20-25, or 25-30 amino acid insertions, deletions, and/or substitutions in addition to changes at variable residues listed therein).

Mouse H2K

In some cases, a MHC Class I heavy chain polypeptide present in a TMMP comprises an amino acid sequence of mouse H2K (SEQ ID NO:45) (Mouse H2K in FIG. 8), or a sequence having at least 75%, at least 80%, at least 85%, at least 90%, at least 95%, at least 98%, at least 99%, or 100% amino acid sequence identity to all or part (e.g., 50, 75, 100, 150, 200, or 250 contiguous amino acids) of that sequence (e.g., it may comprise 1-25, 1-5, 5-10, 10-15, 15-20, 20-25, or 25-30 amino acid insertions, deletions, and/or substitutions). In some cases, where the Mouse H2K heavy chain polypeptide of a TMMP has less than 100% identity to the sequence labeled Mouse H2K in FIG. 8, it may comprise a mutation at one or more of positions 84, 139 and/or 236 selected from: a tyrosine to alanine at position 84 (Y84A); a tyrosine to cysteine at position 84 (Y84C); an alanine to cysteine at position 139 (A139C); and an alanine to cysteine substitution at position 236 (A236C). In some cases, the MOUSE H2K heavy chain polypeptide of a TMMP comprises Y84A and A236C substitutions. In some cases, the Mouse H2K heavy chain polypeptide of a TMMP of the present disclosure comprises Y84C and A139C substitutions. In some cases, the MOUSE H2K heavy chain polypeptide of a TMMP of the present disclosure comprises Y84C, A139C and A236C substitutions.

Exemplary Combinations

Table 1, below, presents various combinations of MHC Class I heavy chain sequence modifications that can be incorporated in a TMMP of the present disclosure.

TABLE 1

| Entry | HLA Heavy Chain Sequence | Sequence Identity Range‡ | Specific Substitutions at aa positions 84, 139 and/or 236 |
|---|---|---|---|
| 1 | HLA-A Consensus (FIG. 9B) | 75%-99.8%, 80%-99.8%, 85%-99.8%, 90%-99.8%, 95%-99.8%, 98%-99.8%, or 99%-99.8%; or 1-25, 1-5, 5-10, 10-15, 15-20, or 20-25 aa insertions, deletions, and/or substitutions (not counting variable residues) | None; Y84C; Y84A; A139C; A236C; (Y84A & A236C); (Y84C & A139C); or (Y84C, A139C & A236C) |
| 2 | A*0101, A*0201, A*0301, A*1101, A*2402, A*2301, A*2402, A*2407, A*3303, or A*3401 (FIG. 9A) | 75%-99.8%, 80%-99.8%, 85%-99.8%, 90%-99.8%, 95%-99.8%, 98%-99.8%, or 99%-99.8%; or 1-25, 1-5, 5-10, 10-15, 15-20, or 20-25 aa insertions, deletions, and/or substitutions | None; Y84C; Y84A; A139C; A236C; (Y84A & A236C); (Y84C& A139C); or (Y84C, A139C & A236C) |
| 3 | HLA-B Consensus (FIG. 10B) | 75%-99.8%, 80%-99.8%, 85%-99.8%, 90%-99.8%, 95%-99.8%, 98%-99.8%, or 99%-99.8%; or 1-25, 1-5, 5-10, 10-15, 15-20, or 20-25 aa insertions, deletions, and/or substitutions (not counting variable residues) | None; Y84C; Y84A; A139C; A236C; (Y84A & A236C); (Y84C & A139C); or (Y84C, A139C & A236C) |
| 4 | B*0702, B*0801, B*1502, B*3802, B*4001, B*4601, | 75%-99.8%, 80%-99.8%, 85%-99.8%, 90%-99.8%, 95%-99.8%, 98%-99.8%, or 99%-99.8%; or 1-25, 1-5, 5-10, 10-15, | None; Y84C; Y84A; A139C; A236C; (Y84A & A236C); |

TABLE 1-continued

| Entry | HLA Heavy Chain Sequence | Sequence Identity Range‡ | Specific Substitutions at aa positions 84, 139 and/or 236 |
|---|---|---|---|
| | or B*5301 (FIG. 10A) | 15-20, or 20-25 aa insertions, deletions, and/or substitutions | (Y84C & A139C); or (Y84C, A139C & A236C) |
| 5 | HLA-C Consensus (FIG. 11B) | 75%-99.8%, 80%-99.8%, 85%-99.8%, 90%-99.8%, 95%-99.8%, 98%-99.8%, or 99%-99.8%; or 1-25, 1-5, 5-10, 10-15, 15-20, or 20-25 aa insertions, deletions, and/or substitutions (not counting variable residues) | None; Y84C; Y84A; A139C; A236C; (Y84A & A236C); (Y84C & A139C); or (Y84C, A139C & A236C) |
| 6 | C*0102, C*0303, C*0304, C*0401, C*0602, C*0701, C*0801, or C*1502 (FIG. 11A) | 75%-99.8%, 80%-99.8%, 85%-99.8%, 90%-99.8%, 95%-99.8%, 98%-99.8%, or 99%-99.8%; or 1-25, 1-5, 5-10, 10-15, 15-20, or 20-25 aa insertions, deletions, and/or substitutions | None; Y84C; Y84A; A139C; A236C; (Y84A & A236C); (Y84C & A139C); or (Y84C, A139C & A236C) |
| 7 | HLA-E, F, or G Consensus (FIG. 12) | 75%-99.8%, 80%-99.8%, 85%-99.8%, 90%-99.8%, 95%-99.8%, 98%-99.8%, or 99%-99.8%; or 1-25, 1-5, 5-10, 10-15, 15-20, or 20-25 aa insertions, deletions, and/or substitutions (not counting variable residues) | None; Y84C; Y84A; A139C; A236C; (Y84A & A236C); (Y84C & A139C); or (Y84C, A139C & A236C) |
| 8 | MOUSE H2K (FIG. 8) | 75%-99.8%, 80%-99.8%, 85%-99.8%, 90%-99.8%, 95%-99.8%, 98%-99.8%, or 99%-99.8%; or 1-25, 1-5, 5-10, 10-15, 15-20, or 20-25 aa insertions, deletions, and/or substitutions | None; Y84C; Y84A; A139C; A236C; (Y84A & A236C); (Y84C & A139C); or (Y84C, A139C & A236C) |

‡ The Sequence Identity Range is the permissible range in sequence identity of a MHC-H polypeptide sequence incorporated into a TMMP relative to the corresponding portion of the sequences listed in FIG. 8-13 not counting the variable residues in the consensus sequences.

Beta-2 Microglobulin

A β2-microglobulin (β2M) polypeptide of a TMMP of the present disclosure can be a human β2M polypeptide, a non-human primate β2M polypeptide, a murine β2M polypeptide, and the like. In some instances, a β2M polypeptide comprises an amino acid sequence having at least 75%, at least 80%, at least 85%, at least 90%, at least 95%, at least 98%, at least 99%, or 100%, amino acid sequence identity to a β2M amino acid sequence depicted in FIG. 6. In some instances, a β2M polypeptide comprises an amino acid sequence having at least 75%, at least 80%, at least 85%, at least 90%, at least 95%, at least 98%, at least 99%, or 100%, amino acid sequence identity to amino acids 21 to 119 of a β2M amino acid sequence depicted in FIG. 6.

In some cases, a suitable β2M polypeptide comprises the following amino acid sequence:

```
                                        (SEQ ID NO: 311)
IQRTPKIQVYSCHPAENGKSNFLNCYVSGFHPSDIEVDLLKNGERIEKVE

HSDLSFSKDWSFYLLYYTEFTPTEKDEYACRVNHVTLSQPKIVKWDRDM;
```

and the HLA Class I heavy chain polypeptide comprises the following amino acid sequence:

GSHSMRYFFTSVSRPGRGEPRFIAVGYVDDTQFVRFDSDAASQRMEPRAPWIEQEGPEYWDGETRKVKAHSQTHRVDL(aa1) {C}(aa2) AGSHTVQRMYGCDVGSDWRFLRGYHQYAYDGKDYIALKEDLRSW(aa3){C}(aa4))HKWEAAHVAEQLRAYLEGTCVEWLRRYLENGKETLQRTDAPKTHMTHHAVSDHEATLRCWALSFYPAEITLTWQRDGEDQTQDTEL(aa5)(C)(aa6)QKWAAVVVPSGQEQRYTCHVQHEGLPKPLTLRWEP (SEQ ID NO:309), where the cysteine residues indicated as {C} form an disulfide bond between the α1 and α2-1 helices and the (C) residue forms a disulfide bond with the β2M polypeptide cysteine at position 12. In the sequence above, "aa1" is "amino acid cluster 1"; "aa2" is "amino acid cluster 2"; "aa3" is "amino acid cluster 3"; "aa4" is "amino acid cluster 4"; "aa5" is "amino acid cluster 5"; and "aa6" is "amino acid cluster 6"; see, e.g., FIG. 10. Each occurrence of aa1, aa2, aa3, aa4, aa5, and aa6 is and independently selected to be 1-5 amino acid residues, wherein the amino acid residues are i) selected independently from any naturally occurring (e.g., encoded) amino acid or ii) any naturally occurring amino acid except proline or glycine.

In some cases, an MHC polypeptide comprises a single amino acid substitution relative to a reference MHC polypeptide (where a reference MHC polypeptide can be a wild-type MHC polypeptide), where the single amino acid substitution substitutes an amino acid with a cysteine (Cys) residue. Such cysteine residues, when present in an MHC polypeptide of a first polypeptide of a TMMP of the present disclosure, can form a disulfide bond with a cysteine residue present in a second polypeptide chain of a TMMP.

In some cases, a first MHC polypeptide in a first polypeptide of a TMMP, and/or the second MHC polypeptide in the second polypeptide of a TMMP, includes an amino acid substitution to substitute an amino acid with a cysteine, where the substituted cysteine in the first MHC polypeptide forms a disulfide bond with a cysteine in the second MHC polypeptide, where a cysteine in the first MHC polypeptide forms a disulfide bond with the substituted cysteine in the second MHC polypeptide, or where the substituted cysteine in the first MHC polypeptide forms a disulfide bond with the substituted cysteine in the second MHC polypeptide.

For example, in some cases, one of following pairs of residues in an HLA β2-microglobulin and an HLA Class I heavy chain is substituted with cysteines (where residue numbers are those of the mature polypeptide): 1) β2M residue 12, HLA Class I heavy chain residue 236; 2) β2M residue 12, HLA Class I heavy chain residue 237; 3) β2M residue 8, HLA Class I heavy chain residue 234; 4) β2M residue 10, HLA Class I heavy chain residue 235; 5) β2M residue 24, HLA Class I heavy chain residue 236; 6) β2M residue 28, HLA Class I heavy chain residue 232; 7) β2M residue 98, HLA Class I heavy chain residue 192; 8) β2M residue 99, HLA Class I heavy chain residue 234; 9) β2M residue 3, HLA Class I heavy chain residue 120; 10) β2M residue 31, HLA Class I heavy chain residue 96; 11) β2M residue 53, HLA Class I heavy chain residue 35; 12) β2M residue 60, HLA Class I heavy chain residue 96; 13) β2M residue 60, HLA Class I heavy chain residue 122; 14) β2M residue 63, HLA Class I heavy chain residue 27; 15) β2M residue Arg3, HLA Class I heavy chain residue Gly120; 16) β2M residue His31, HLA Class I heavy chain residue Gln96; 17) β2M residue Asp53, HLA Class I heavy chain residue Arg35; 18) β2M residue Trp60, HLA Class I heavy chain residue Gln96; 19) β2M residue Trp60, HLA Class I heavy chain residue Asp122; 20) β2M residue Tyr63, HLA Class I heavy chain residue Tyr27; 21) β2M residue Lys6, HLA Class I heavy chain residue Glu232; 22) β2M residue Gln8, HLA Class I heavy chain residue Arg234; 23) β2M residue Tyr10, HLA Class I heavy chain residue Pro235; 24) β2M residue Ser11, HLA Class I heavy chain residue Gln242; 25) β2M residue Asn24, HLA Class I heavy chain residue Ala236; 26) β2M residue Ser28, HLA Class I heavy chain residue Glu232; 27) β2M residue Asp98, HLA Class I heavy chain residue His192; and 28) β2M residue Met99, HLA Class I heavy chain residue Arg234. The amino acid numbering of the MHC/HLA Class I heavy chain is in reference to the mature MHC/HLA Class I heavy chain, without a signal peptide. For example, in some cases, residue 236 of the mature HLA-A amino acid sequence is substituted with a Cys. In some cases, residue 236 of the mature HLA-B amino acid sequence is substituted with a Cys. In some cases, residue 236 of the mature HLA-C amino acid sequence is substituted with a Cys. In some cases, residue 32 (corresponding to Arg-12 of mature β2M) of an amino acid sequence depicted in FIG. 6 is substituted with a Cys.

In some cases, a β2M polypeptide comprises the amino acid sequence: IQRTPKIQVY SRHPAENGKS NFLNCYVSGF HPSDIEVDLLKNGERIEKVE HSDLSFSKDW SFYLLYYTEF TPTEKDEYAC RVNHVTLSQP KIVKWDRDM (SEQ ID NO:310). In some cases, a β2M polypeptide comprises the amino acid sequence: IQRTPKIQVY SCHPAENGKS NFLNCYVSGF HPSDIEVDLLKNGERIEKVE HSDLSFSKDW SFYLLYYTEF TPTEKDEYAC RVNHVTLSQP KIVKWDRDM (SEQ ID NO:311).

In some cases, an HLA Class I heavy chain polypeptide comprises the HLA-A*2402 amino acid sequence:

(SEQ ID NO: 455)
GSHSMRYFSTSVSRPGRGEPRFIAVGYVDDTQFVRFDSDAASQRMEPRAP
WIEQEGPEYWDEETGKVKAHSQTDRENLRIALRYYNQSEAGSHTLQMMFG
CDVGSDGRFLRGYHQYAYDGKDYIALKEDLRSWTAADMAAQITKRKWEAA
HVAEQQRAYLEGTCVDGLRRYLENGKETLQRTDPPKTHMTHHPISDHEAT
LRCWALGFYPAEITLTWQRDGEDQTQDTELVETRPAGDGTFQKWAAVVVP
SGEEQRYTCHVQHEGLPKPLTLRWE.

In some cases, an HLA Class I heavy chain polypeptide comprises the HLA-A*2402 amino acid sequence:

(SEQ ID NO: 456)
GSHSMRYFSTSVSRPGRGEPRFIAVGYVDDTQFVRFDSDAASQRMEPRAP
WIEQEGPEYWDEETGKVKAHSQTDRENLRIALRAYNQSEAGSHTLQMMFG
CDVGSDGRFLRGYHQYAYDGKDYIALKEDLRSWTAADMAAQITKRKWEAA
HVAEQQRAYLEGTCVDGLRRYLENGKETLQRTDPPKTHMTHHPISDHEAT
LRCWALGFYPAEITLTWQRDGEDQTQDTELVETRPAGDGTFQKWAAVVVP
SGEEQRYTCHVQHEGLPKPLTLRWE.

In some cases, an HLA Class I heavy chain polypeptide comprises the amino acid sequence:

(SEQ ID NO: 459)
GSHSMRYFSTSVSRPGRGEPRFIAVGYVDDTQFVRFDSDAASQRMEPRAP
WIEQEGPEYWDEETGKVKAHSQTDRENLRIALRCYNQSEAGSHTLQMMFG
CDVGSDGRFLRGYHQYAYDGKDYIALKEDLRSWTAADMAAQITKRKWEAA
HVAEQQRAYLEGTCVDGLRRYLENGKETLQRTDPPKTHMTHHPISDHEAT
LRCWALGFYPAEITLTWQRDGEDQTQDTELVETRPAGDGTFQKWAAVVVP
SGEEQRYTCHVQHEGLPKPLTLRWE.

In some cases, an HLA Class I heavy chain polypeptide comprises the amino acid sequence:

(SEQ ID NO: 457)
GSHSMRYFSTSVSRPGRGEPRFIAVGYVDDTQFVRFDSDAASQRMEPRAP
WIEQEGPEYWDEETGKVKAHSQTDRENLRIALRYYNQSEAGSHTLQMMFG
CDVGSDGRFLRGYHQYAYDGKDYIALKEDLRSWTAADMAAQITKRKWEAA
HVAEQQRAYLEGTCVDGLRRYLENGKETLQRTDPPKTHMTHHPISDHEAT
LRCWALGFYPAEITLTWQRDGEDQTQDTELVETRPCGDGTFQKWAAVVVP
SGEEQRYTCHVQHEGLPKPLTLRWE.

In some cases, an HLA Class I heavy chain polypeptide comprises the amino acid sequence:

(SEQ ID NO: 458)
GSHSMRYFSTSVSRPGRGEPRFIAVGYVDDTQFVRFDSDAASQRMEPRAP
WIEQEGPEYWDEETGKVKAHSQTDRENLRIALRAYNQSEAGSHTLQMMFG
CDVGSDGRFLRGYHQYAYDGKDYIALKEDLRSWTAADMAAQITKRKWEAA
HVAEQQRAYLEGTCVDGLRRYLENGKETLQRTDPPKTHMTHHPISDHEAT
LRCWALGFYPAEITLTWQRDGEDQTQDTELVETRPCGDGTFQKWAAVVVP
SGEEQRYTCHVQHEGLPKPLTLRWE.

In some cases, an HLA Class I heavy chain polypeptide comprises the amino acid sequence:

(SEQ ID NO: 346)
GSHSMRYFSTSVSRPGRGEPRFIAVGYVDDTQFVRFDSDAASQRMEPRAP
WIEQEGPEYWDEETGKVKAHSQTDRENLRIALRCYNQSEAGSHTLQMMFG
CDVGSDGRFLRGYHQYAYDGKDYIALKEDLRSWTAADMAAQITKRKWEAA

-continued

```
HVAEQQRAYLEGTCVDGLRRYLENGKETLQRTDPPKTHMTHHPISDHEAT

LRCWALGFYPAEITLTWQRDGEDQTQDTELVETRPCGDGTFQKWAAVVVP

SGEEQRYTCHVQHEGLPKPLTLRWE.
```

In some cases, an HLA Class I heavy chain polypeptide comprises the amino acid sequence:

```
                                           (SEQ ID NO: 44)
GSHSMRYFFTSVSRPGRGEPRFIAVGYVDDTQFVRFDSDAASQRMEPRAP

WIEQEGPEYWDGETRKVKAHSQTHRVDLGTLRGYYNQSEAGSHTVQRMYG

CDVGSDWRFLRGYHQYAYDGKDYIALKEDLRSWTAADMAAQTTKHKWEAA

HVAEQLRAYLEGTCVEWLRRYLENGKETLQRTDAPKTHMTHHAVSDHEAT

LRCWALSFYPAEITLTWQRDGEDQTQDTELVETRPAGDGTFQKWAAVVVP

SGQEQRYTCHVQHEGLPKPLTLRWEP.
```

In some cases, an HLA Class I heavy chain polypeptide comprises the amino acid sequence:

```
                                          (SEQ ID NO: 312)
GSHSMRYFFTSVSRPGRGEPRFIAVGYVDDTQFVRFDSDAASQRMEPRAP

WIEQEGPEYWDGETRKVKAHSQTHRVDLGTLRGYYNQSEAGSHTVQRMYG

CDVGSDWRFLRGYHQYAYDGKDYIALKEDLRSWTAADMAAQTTKHKWEAA

HVAEQLRAYLEGTCVEWLRRYLENGKETLQRTDAPKTHMTHHAVSDHEAT

LRCWALSFYPAEITLTWQRDGEDQTQDTELVETRPCGDGTFQKWAAVVVP

SGQEQRYTCHVQHEGLPKPLTLRWEP.
```

In some cases, an HLA Class I heavy chain polypeptide comprises the amino acid sequence:

```
                                           (SEQ ID NO: 46)
GSHSMRYFFTSVSRPGRGEPRFIAVGYVDDTQFVRFDSDAASQRMEPRAP

WIEQEGPEYWDGETRKVKAHSQTHRVDLGTLRGAYNQSEAGSHTVQRMYG

CDVGSDWRFLRGYHQYAYDGKDYIALKEDLRSWTAADMAAQTTKHKWEAA

HVAEQLRAYLEGTCVEWLRRYLENGKETLQRTDAPKTHMTHHAVSDHEAT

LRCWALSFYPAEITLTWQRDGEDQTQDTELVETRPCGDGTFQKWAAVVVP

SGQEQRYTCHVQHEGLPKPLTLRWE.
```

In some cases, the β2M polypeptide comprises the following amino acid sequence:

IQRTPKIQVY SCHPAENGKS NFLNCYVSGF HPSDIEVDLLKNGERIEKVE HSDLSFSKDW SFYLLYYTEF TPTEKDEYAC RVNHVTLSQP KIVKWDRDM (SEQ ID NO:311); and the HLA Class I heavy chain polypeptide of a TMMP comprises the following amino acid sequence:

GSHSMRYFFTSVSRPGRGEPRFIAVGYVDDTQFVRFDSDAASQRMEPRAPWIEQE GPEYWDGETRKVKAHSQTHRVDLGTLRGYYNQSEAGSHTVQRMYGCDVGSDWRFLRGYHQY AYDGKDYIALKEDLRSWTAADMAAQTTKHKWEAAHVAEQLRAYLEGTCVEWLRRYLENGKE TLQRTDAPKTHMTHHAVSDHEATLRCWALSFYPAEITLTWQRDGEDQTQDTELVETRPCGDGT FQKWAAVVVPSGQEQRYTCHVQHEGLPKPLTLRWEP (SEQ ID NO:312), where the Cys residues that are underlined and in bold form a disulfide bond with one another in the TMMP.

In some cases, the β2M polypeptide comprises the following amino acid sequence:

IQRTPKIQVY SCHPAENGKS NFLNCYVSGF HPSDIEVDLLKNGERIEKVE HSDLSFSKDW SFYLLYYTEF TPTEKDEYAC RVNHVTLSQP KIVKWDRDM (SEQ ID NO:311); and the HLA Class I heavy chain polypeptide of a TMMP comprises the following amino acid sequence:

GSHSMRYFSTSVSRPGRGEPRFIAVGYVDDTQFVRFDSDAASQRMEPRAPWIEQE GPEYWDEETGKVKAHSQTDRENLRIALRYYNQSEAGSHTLQMMFGCDVGSDGRFLRGYHQYA YDGKDYIALKEDLRSWTAADMAAQITKRKWEAAHVAEQQRAYLEGTCVDGLRRYLENGKET LQRTDPPKTHMTHHPISDHEATLRCWALGFYPAEITLTWQRDGEDQTQDTELVETRPCGDGTF QKWAAVVVPSGEEQRYTCHVQHEGLPKPLTLRWE (SEQ ID NO:457), where the Cys residue at amino acid 236 in the HLA Cass I heavy chain polypeptide and the Cys at residue 12 of the β2M polypeptide form a disulfide bond with one another in the TMMP.

In some cases, the β2M polypeptide comprises the amino acid sequence:

```
                                          (SEQ ID NO: 311)
IQRTPKIQVYSCHPAENGKSNFLNCYVSGFHPSDIEVDLLKNGERIEKVE

HSDLSFSKDWSFYLLYYTEFTPTEKDEYACRVNHVTLSQPKIVKWDRDM.
```

In some cases, the first polypeptide and the second polypeptide of a TMMP are disulfide linked to one another through: i) a Cys residue present in a linker connecting the peptide epitope and a β2M polypeptide in the first polypeptide chain; and ii) a Cys residue present in an MHC Class I heavy chain in the second polypeptide chain. In some cases, the Cys residue present in the MHC Class I heavy chain is a Cys introduce as a Y84C substitution. In some cases, the linker connecting the peptide epitope and the β2M polypeptide in the first polypeptide chain is GCGGS(G4S)n (SEQ ID NO:315), where n is 1, 2, 3, 4, 5, 6, 7, 8, or 9. For example, in some cases, the linker comprises the amino acid sequence GCGGSGGGGSGGGGSGGGGS (SEQ ID NO:316). As another example, the linker comprises the amino acid sequence GCGGSGGGGSGGGGS (SEQ ID NO:317). Examples of disulfide-linked first and second polypeptides of a TMMP are depicted schematically in FIG. 2A-2F.

Multiple Disulfide Bonded TMMPs

Figure 17A:
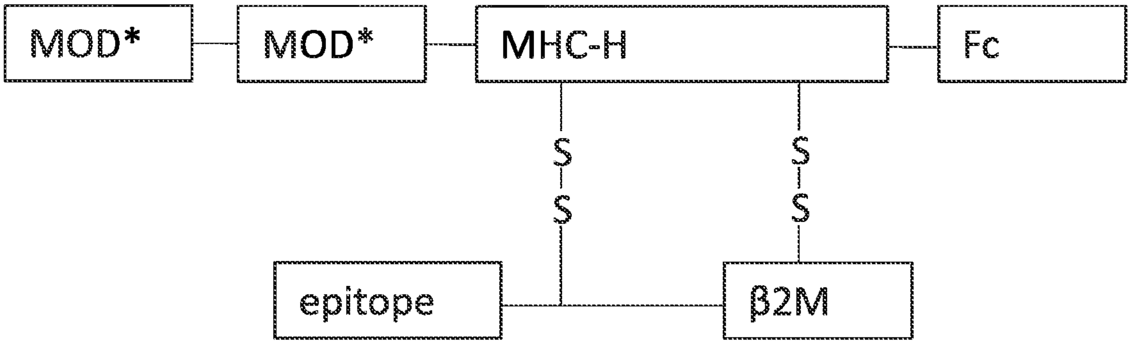
FIG. 17A-17D provide schematic depictions of double disulfide-linked TMMP of the present disclosure.
Figure 17B:
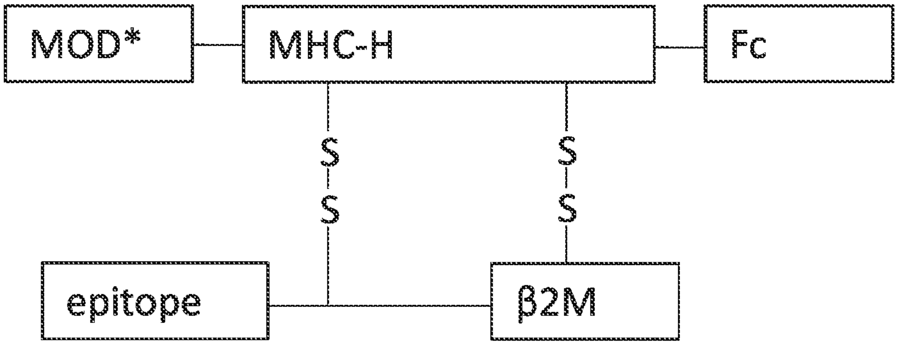
Figure 17C:
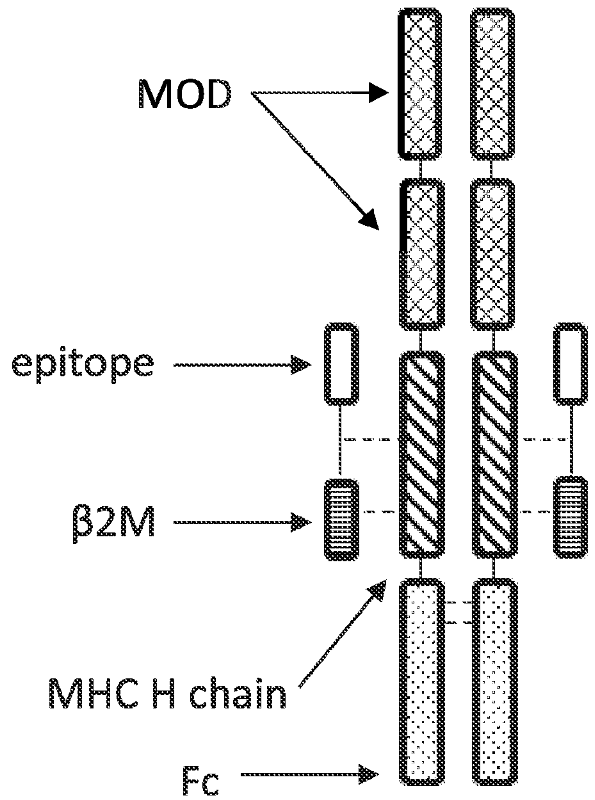
Figure 17D:
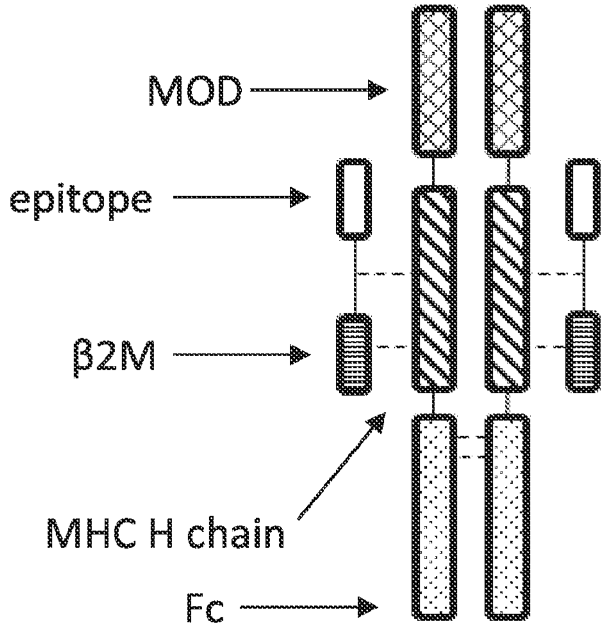
Figure 18A:
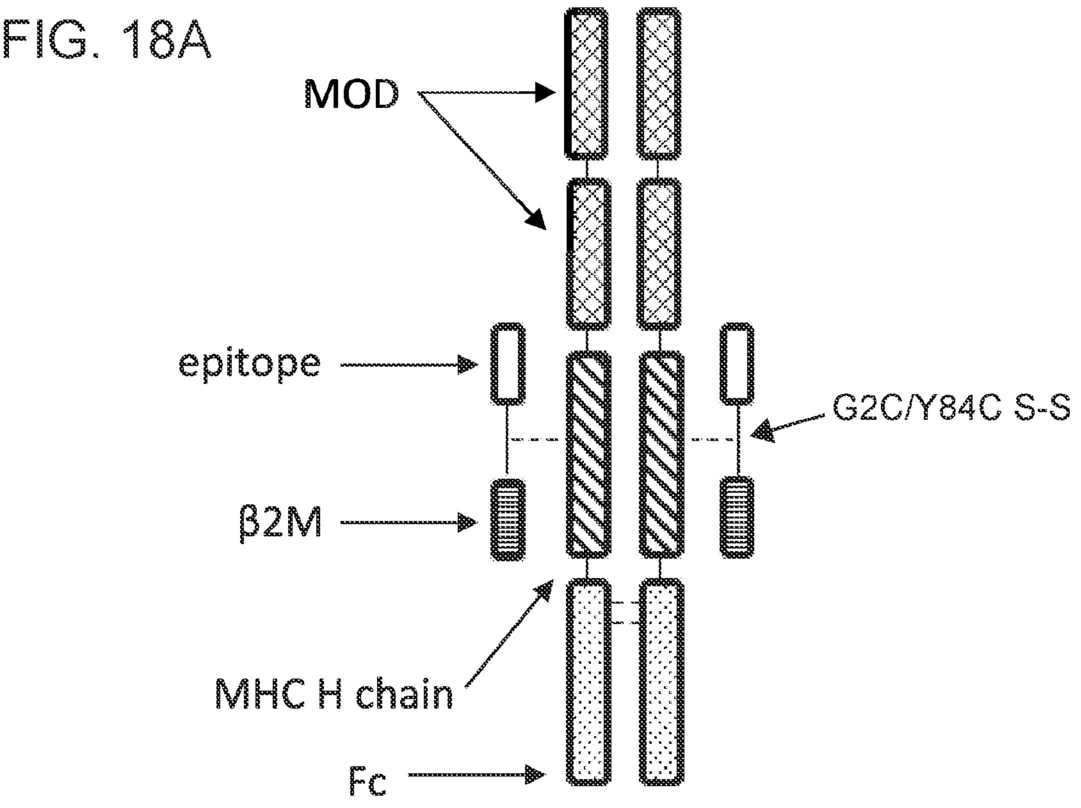
FIG. 18A-18C provide schematic depictions of examples of configurations of disulfide-linked TMMPs of the present disclosure.
Figure 18B:
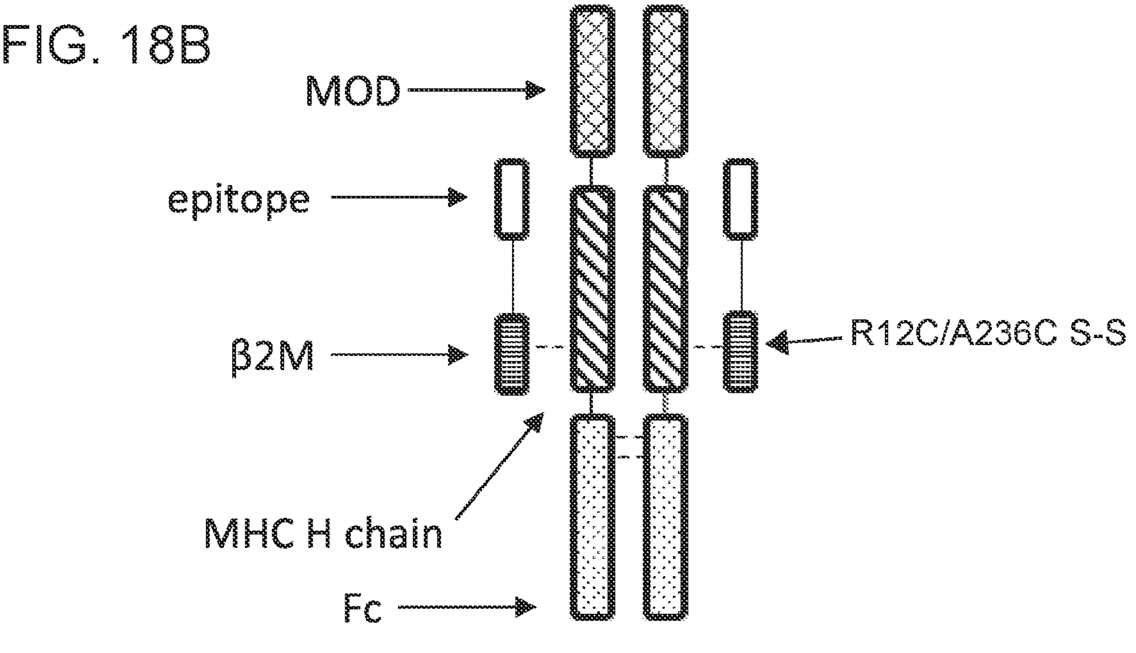
Figure 18C:
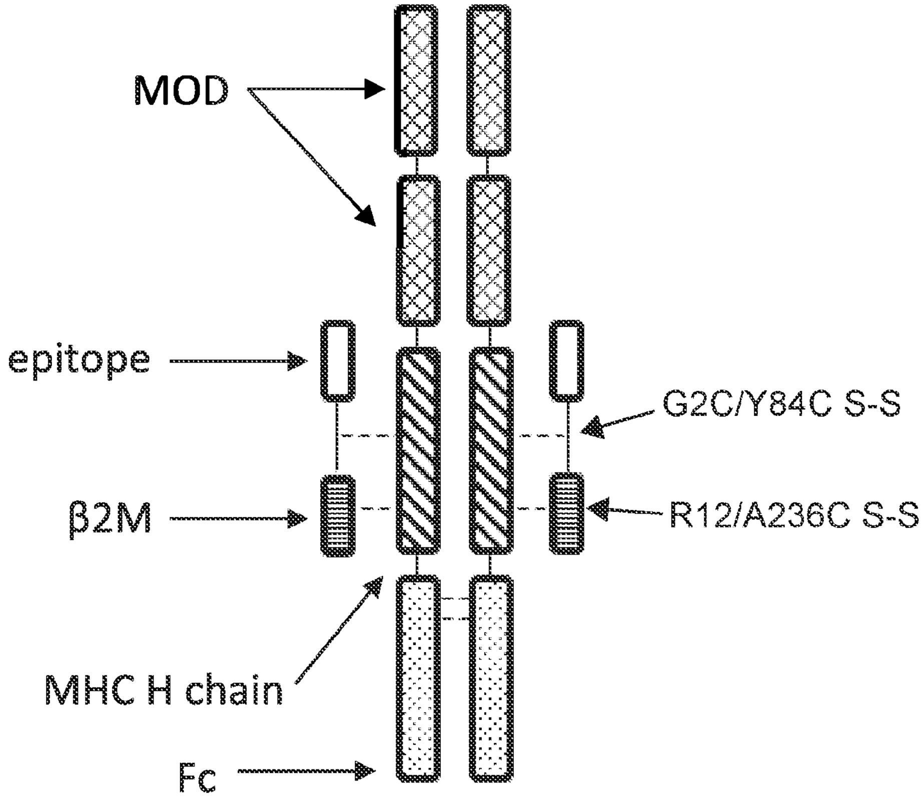

In some cases, the first polypeptide and the second polypeptide of a TMMP of the present disclosure are linked to one another by at least two disulfide bonds (i.e., two interchain disulfide bonds). Examples of such multiple disulfide-linked TMMP are depicted schematically in FIGS. 17A and 17B and FIG. 18A-18C. In addition, where a TMMP comprises an IgFc polypeptide, a heterodimeric TMMP can be dimerized, such that disulfide bonds link the IgFc polypeptides in the two heterodimeric TMMPs. Such an arrangement is depicted schematically in FIGS. 17C and 17D, where disulfide bonds are represented by dashed lines. Unless otherwise stated, the at least two disulfide bonds described in the multiple disulfide-linked TMMPPs in this section are not referring to disulfide bonds linking IgFc polypeptides in dimerized TMMPs.

As noted above, in some cases, the first polypeptide and the second polypeptide of a TMMP are linked to one another by at least two disulfide bonds (i.e., two interchain disulfide bonds). For example, in some instances, the first polypeptide and the second polypeptide of a TMMP are linked to one another by 2 interchain disulfide bonds. As another example, in some instances, the first polypeptide and the second polypeptide of a TMMP are linked to one another by 3 interchain disulfide bonds. As another example, in some instances, the first polypeptide and the second polypeptide of a TMMP of the present disclosure are linked to one another by 4 interchain disulfide bonds.

In some cases where a peptide epitope in a first polypeptide of a TMMP is linked to a β2M polypeptide by a linker comprising a Cys, at least one of the at least two disulfide bonds links a Cys in the linker to a Cys in an MHC Class I heavy chain in the second polypeptide. In some cases, where a peptide epitope in a first polypeptide of a TMMP is linked to an MHC Class I heavy chain polypeptide by a linker, at least one of the at least two disulfide bonds links a Cys in the linker to a Cys in a β2M polypeptide present in the second polypeptide.

In some cases, a multiple disulfide-linked TMMP (e.g., a double disulfide-linked TMMP) exhibits increased stability, compared to a control TMMP that includes only one of the at least two disulfide bonds. In some cases, a multiple disulfide-linked TMMP (e.g., a double disulfide-linked TMMP) exhibits increased in vitro stability, compared to a control TMMP that includes only one of the at least two disulfide bonds. For example, in some cases, a multiple disulfide-linked TMMP (e.g., a double disulfide-linked TMMP) exhibits at least 5%, at least 10%, at least 15%, at least 20%, at least 25%, at least 50%, at least 2-fold, at least 5-fold, or at least 10-fold, greater in vitro stability, compared to a control TMMP that includes only one of the at least two disulfide bonds.

Whether a multiple disulfide-linked TMMP (e.g., a double disulfide-linked TMMP) exhibits increased in vitro stability, compared to a control TMMP that includes only one of the at least two disulfide bonds, can be determined by measuring the amount disulfide-linked heterodimeric TMMP present in a sample over time and/or under a specified condition and/or during purification of the TMMP, For example, in some cases, a multiple disulfide-linked TMMP (e.g., a double disulfide-linked TMMP) exhibits at least 5%, at least 10%, at least 15%, at least 20%, at least 25%, at least 50%, at least 2-fold, at least 5-fold, or at least 10-fold, greater in vitro stability, compared to a control TMMP that includes only one of the at least two disulfide bonds, when the TMMP is stored at 37° C. for a period of time (e.g., for a period of time of from about 1 week to about 2 weeks, from about 2 weeks to about 4 weeks, or from about 4 weeks to about 2 months). For example, in some cases, the amount of disulfide-linked heterodimeric TMMP remaining after storing a multiple disulfide-linked TMMP (e.g., a double disulfide-linked TMMP) in vitro at 37° C. for 28 days is at least at least 5%, at least 10%, at least 15%, at least 20%, at least 25%, at least 50%, at least 2-fold, at least 5-fold, or at least 10-fold, greater than the amount of disulfide-linked heterodimeric TMMP remaining after storing a control TMMP (a TMMP that includes only one of the at least two disulfide bonds present in the multiple disulfide-linked TMMP) in vitro at 37° C. for 28 days.

As an example, a double disulfide-linked TMMP comprising polypeptides 1715 and 2380, as depicted in FIGS. 14A and 14B, exhibits greater in vitro stability, compared to a TMMP comprising polypeptides 2405 and 2380, where polypeptide 2405 is depicted in FIG. 14D, where such TMMP comprises only one disulfide linkage, where the single disulfide linkage is formed between: i) the Cys of the G2C linker between the epitope and the β2M; and ii) the Cys provided by a Y84C substitution in the MHC Class I heavy chain. As another example, a double disulfide-linked TMMP comprising polypeptides 1715 and 2380, as depicted in FIGS. 14A and 14B, exhibits greater in vitro stability, compared to a TMMP comprising polypeptides 1380 and 2380, where polypeptide 1380 is depicted in FIG. 14E, where such TMMP comprises only one disulfide linkage, where the single disulfide linkage is formed between: i) the Cys provided by an R12C substitution in the β2M polypeptide; and ii) the Cys provided by the A236C substitution in the MHC Class I heavy chain.

In some cases, a multiple disulfide-linked TMMP exhibits increased in vivo stability, compared to a control TMMP that includes only one of the at least two disulfide bonds. For example, in some cases, a multiple disulfide-linked TMMP exhibits at least 5%, at least 10%, at least 15%, at least 20%, at least 25%, at least 50%, at least 2-fold, at least 5-fold, or at least 10-fold, greater in vivo stability, compared to a control TMMP that includes only one of the at least two disulfide bonds.

In some cases, the presence of two disulfide bonds in a multiple disulfide-linked TMMP (e.g., a double disulfide-linked TMMP) provides for increased production of disulfide-linked heterodimeric TMMP, compared to the amount of disulfide-linked heterodimeric TMMP produced when the TMMP is a control TMMP that includes only one of the at least two disulfide bonds. For example, a multiple disulfide-linked TMMP (e.g., a double disulfide-linked TMMP) can be produced in a mammalian cell in in vitro cell culture, where the mammalian cell is cultured in a liquid cell culture medium. The TMMP can be secreted into the cell culture medium. The cells can be lysed, generating a cell lysate, and the TMMP can be present in the cell lysate. The TMMP can be purified from the cell culture medium and/or the cell lysate. For example, where the TMMP comprises an IgG1 Fc polypeptide, the cell culture medium and/or the cell lysate can be contacted with immobilized protein A (e.g., the cell culture medium and/or the cell lysate can be applied to a protein A column, where protein A is immobilized onto beads). TMMP present in the cell culture medium and/or the cell lysate becomes bound to the immobilized protein A. After washing the column to remove unbound materials, the bound TMMP is eluted, generating a protein A eluate. The amount of disulfide-linked heterodimeric TMMP present in the protein A eluate is a least 0.5%, at least 1%, at least 2%, at least 3%, at least 4%, at least 5%, at least 6%, at least 7%, at least 8%, at least 9%, or at least 10%, higher than the amount of disulfide-linked heterodimeric TMMP present in the protein A eluate when the TMMP is a control TMMP that includes only one of the at least two disulfide bonds present in the multiple disulfide-linked TMMP (e.g., a double disulfide-linked TMMP). In some cases, the percent of the total TMMP protein in the eluate that is non-aggregated disulfide-linked heterodimeric TMMP is at least 70%, at least 75%, at least 80%, at least 85%, at least 90%, at least 95%, or at least 99%. The protein A eluate can be subjected to size exclusion chromatography (SEC) and/or one or more other additional purification steps.

In some cases, a TMMP comprises at least one heterodimer comprising: a) a first polypeptide comprising: i) a WT1 peptide epitope, where the WT1 peptide has a length of at least 4 amino acids (e.g., from 4 amino acids to 25 amino acids; e.g., the WT1 peptide has a length of 4, 5, 6, 7, 8, 9, 10-15, 15-20, or 20-25 amino acids); and ii) first MHC polypeptide; b) a second polypeptide comprising a second MHC polypeptide, and c) at least one MOD, where the first and/or the second polypeptide comprises the MOD, and where the heterodimer comprises 2 disulfide bonds between the first polypeptide and the second polypeptide (i.e., the heterodimer comprises: i) a first disulfide bond linking the first polypeptide and the second polypeptide; and ii) a second disulfide bond linking the first polypeptide and the second polypeptide). Expressed another way, the first polypeptide comprises a first Cys residue that forms a disulfide bond (a first disulfide bond) with a first Cys residue in the second polypeptide; and the first polypeptide comprises a second Cys residue that forms a disulfide bond (a second disulfide bond) with a second Cys residue in the second polypeptide.

In some cases, a TMMP comprises: a) a first polypeptide comprising, in order from N-terminus to C-terminus: i) a peptide epitope; ii) a peptide linker; and iii) a β2M polypeptide; and b) a second polypeptide comprising an MHC Class I heavy chain polypeptide, where one or both of the first and the second polypeptides comprises at least one MOD, where the TMMP comprises: a) a first disulfide linkage between: i) a Cys present in the linker between the peptide epitope and the β2M polypeptide; and ii) a first Cys introduced into the MHC Class I heavy chain polypeptide; and b) at least a second disulfide linkage between the first polypeptide and the second polypeptide, where the at least a second disulfide linkage is between: i) a Cys in the first polypeptide that is C-terminal to the Cys present in the linker; and ii) a Cys in the second polypeptide that is C-terminal to the first Cys introduced into the MHC Class I heavy chain polypeptide.

In some cases, a first and a second disulfide bond-forming Cys residues in a first or a second polypeptide of a TMMP are from about 10 amino acids to about 200 amino acids apart from one another. For example, in some cases, a first and a second disulfide bond-forming Cys residues in a first or a second polypeptide of a TMMP are from about 10 amino acids (aa) to about 15 aa, from about 15 aa to about 20 aa, from about 20 aa to about 25 aa, from about 25 aa to about 30 aa, from about 30 aa to about 40 aa, from about 40 aa to about 50 aa, from about 50 aa to about 60 aa, from about 60 aa to about 70 aa, from about 70 aa to about 80 aa, from about 80 aa to about 90 aa, from about 90 aa to about 100 aa, from about 100 aa to about 110 aa, from about 110 aa to about 120 aa, from about 120 aa to about 130 aa, from about 130 aa to about 140 aa, from about 140 aa to about 150 aa, from about 150 aa to about 160 aa, from about 160 aa to about 170 aa, from about 170 aa to about 180 aa, from about 180 aa to about 190 aa, or from about 190 aa to about 200 aa.

As an example, in some cases, the first and second disulfide bond-forming Cys residues in the first polypeptide of a TMMP are from about 10 amino acids to about 80 amino acid residues apart from one another. For example, in some cases, the second disulfide bond-forming Cys residue in the first polypeptide is from about 10 amino acids to about 80 amino acids (e.g., from about 10 amino acids (aa) to about 15 aa, from about 15 aa to about 20 aa, from about 20 aa to about 25 aa, from about 25 aa to about 30 aa, from about 30 aa to about 40 aa, from about 40 aa to about 50 aa, from about 50 aa to about 60 aa, from about 60 aa to about 70 aa, or from about 70 aa to about 80 aa) C-terminal to the first disulfide bond-forming Cys residue in the first polypeptide. In some cases, the second disulfide bond-forming Cys residue in the first polypeptide is 10 aa, 11 aa, 12 aa, 13 aa, 14 aa, 15 aa, 16 aa, 17 aa, 18 aa, 19 aa, 20 aa, 21 aa, 22 aa, 23 aa, 24 aa, or 25 aa, C-terminal to the first disulfide bond-forming Cys residue in the first polypeptide. In some cases, the second disulfide bond-forming Cys residue in the first polypeptide is 15 aa C-terminal to the first disulfide bond-forming Cys residue in the first polypeptide. In some cases, the second disulfide bond-forming Cys residue in the first polypeptide is 20 aa C-terminal to the first disulfide bond-forming Cys residue in the first polypeptide. In some cases, the second disulfide bond-forming Cys residue in the first polypeptide is 25 aa C-terminal to the first disulfide bond-forming Cys residue in the first polypeptide.

In some cases, the first and second disulfide bond-forming Cys residues in the second polypeptide of a TMMP of the present disclosure are from about 140 amino acids to about 160 amino acids apart from one another. For example, in some cases, the second disulfide bond-forming Cys residue in the second polypeptide is from about 140 amino acids to about 160 amino acids C-terminal to the first disulfide bond-forming Cys residue in the second polypeptide. In some cases, the second disulfide bond-forming Cys residue in the second polypeptide is 140 amino acids (aa), 141 aa, 142 aa, 143 aa, 144 aa, 145 aa, 146 aa, 147 aa, 148 aa, 149 aa, 150 aa, 151 aa, 152 aa, 153 aa, 154 aa, 155 aa, 156 aa, 157 aa, 158 aa, 159 aa, or 160 aa, C-terminal to the first disulfide bond-forming Cys residue in the second polypeptide.

A multiple disulfide-linked TMMP (e.g., a double disulfide-linked TMMP) can comprise: a) a first polypeptide comprising: i) a WT1 peptide (e.g., a WT1 peptide of from 4 amino acids to about 25 amino acids); and ii) a first MHC polypeptide, where the first polypeptide comprises a peptide linker between the WT1 peptide and the first MHC polypeptide, where the peptide linker comprises a Cys residue, and where the first MHC polypeptide is a β2M polypeptide that comprises an amino acid substitution that introduces a Cys residue; b) and a second polypeptide comprising a second MHC polypeptide, where the second MHC polypeptide is a Class I heavy chain comprising a Y84C substitution and an A236C substitution, based on the amino acid numbering of HLA-A*0201 (depicted in FIG. 9A), or at corresponding positions in another Class I heavy chain allele, where the TMMP comprises a disulfide bond between the Cys residue in the peptide linker and the Cys residue at amino acid position 84 of the Class I heavy chain or corresponding position of another Class I heavy chain allele, and where the TMMP comprises a disulfide bond between the introduced Cys residue in the β2M polypeptide and the Cys at amino acid position 236 of the Class I heavy chain or corresponding position of another Class I heavy chain allele; and c) at least one MOD, where the first and/or the second polypeptide comprises the at least one MOD. Examples are depicted schematically in FIG. 17A and FIG. 17B.

In some cases, the peptide linker comprises the amino acid sequence GCGGS (SEQ ID NO:318). In some cases, the peptide linker comprises the amino acid sequence GCGGS(GGGGS)n (SEQ ID NO:319), where n is an integer from 1 to 10. In some cases, the peptide linker comprises the amino acid sequence GCGGS(GGGGS)n (SEQ ID NO:398), where n is 1. In some cases, the peptide linker comprises the amino acid sequence GCGGS(GGGGS)n (SEQ ID NO:320), where n is 2. In some cases, the peptide linker comprises the amino acid sequence GCGGS (GGGGS)n (SEQ ID NO:321), where n is 3. In some cases, the peptide linker comprises the amino acid sequence GCGGS(GGGGS)n (SEQ ID NO:322), where n is 4. In some cases, the peptide linker comprises the amino acid sequence GCGGS(GGGGS)n (SEQ ID NO:323), where n is 5. In some cases, the peptide linker comprises the amino acid sequence GCGGS(GGGGS)n (SEQ ID NO:324), where n is 6. In some cases, the peptide linker comprises the amino acid sequence GCGGS(GGGGS)n (SEQ ID NO:325), where n is 7. In some cases, the peptide linker comprises the amino acid sequence GCGGS(GGGGS)n (SEQ ID NO:326), where n is 8. In some cases, the peptide linker comprises the amino acid sequence GCGGS(GGGGS)n (SEQ ID NO: 327), where n is 9. In some cases, the peptide linker comprises the amino acid sequence GCGGS(GGGGS)n (SEQ ID NO:328), where n is 10.

In some cases, the peptide linker comprises the amino acid sequence CGGGS (SEQ ID NO:329). In some cases, the peptide linker comprises the amino acid sequence CGGGS(GGGGS)n (SEQ ID NO: 330), where n is an integer from 1 to 10. In some cases, the peptide linker comprises the amino acid sequence CGGGS(GGGGS)n (SEQ ID NO:331), where n is 1. In some cases, the peptide linker comprises the amino acid sequence CGGGS (GGGGS)n (SEQ ID NO:332), where n is 2. In some cases, the peptide linker comprises the amino acid sequence CGGGS(GGGGS)n (SEQ ID NO:333), where n is 3. In some cases, the peptide linker comprises the amino acid sequence CGGGS(GGGGS)n (SEQ ID NO:334), where n is 4. In some cases, the peptide linker comprises the amino acid sequence CGGGS(GGGGS)n (SEQ ID NO:335), where n is 5. In some cases, the peptide linker comprises the amino acid sequence CGGGS(GGGGS)n (SEQ ID NO:336), where n is 6. In some cases, the peptide linker comprises the amino acid sequence CGGGS(GGGGS)n (SEQ ID NO:337), where n is 7. In some cases, the peptide linker comprises the amino acid sequence CGGGS(GGGGS)n (SEQ ID NO:338), where n is 8. In some cases, the peptide linker comprises the amino acid sequence CGGGS(GGGGS)n (SEQ ID NO:339), where n is 9. In some cases, the peptide linker comprises the amino acid sequence CGGGS(GGGGS)n (SEQ ID NO:340), where n is 10.

The following are non-limiting examples of MHC Class I heavy chain comprising a Y84C substitution and an A236C substitution, based on the amino acid numbering of HLA-A*0201 (depicted in FIG. 9A), or at corresponding positions in another Class I heavy chain allele.

HLA-A

In some cases, a multiple disulfide-linked TMMP a double disulfide-linked TMMP) comprises: a) a first polypeptide comprising: i) a WT1 peptide (e.g., a WT1 peptide of from 4 amino acids to about 25 amino acids); and ii) a first MHC polypeptide, where the first polypeptide comprises a peptide linker between the WT1 peptide and the first MHC polypeptide, where the peptide linker comprises a Cys residue, and where the first MHC polypeptide is a β2M polypeptide that comprises an amino acid substitution that introduces a Cys residue; and b) a second polypeptide comprising an HLA-A MHC Class I heavy chain comprising an amino acid sequence having at least 60%, at least 70%, at least 80%, at least 90%, at least 95%, at least 98%, at least 99%, or 100%, amino acid sequence identity to the following amino acid sequence: GSHSM-RYFFTSVSRPGRGEPRFIAVGYVDDTQFVRFDS-DAASQRMEPRAPWIEQEGPEYWDGET RKVKAHSQTHRVDLGTLRGCYNQSEA-GSHTVQRMYGCDVGSDWRFLR-GYHQYAYDGKDYIA LKEDLRSWTAAD-MAAQTTKHKWEAAHVAEQLRAYLEGTCVEWLRRY LENGKETLQRTDAPK THMTHHAVSDHEATLRCW-ALSFYPAEITLTWQRDGEDQTQDTELVE-TRPCGDGTFQKWAAVV VPSGQEQRYTCHVQHEGLPKPLTLRWEP (SEQ ID NO:342), where amino acid 84 is a Cys and amino acid 236 is a Cys; and c) at least one MOD, where the first and/or the second polypeptide comprises the at least one MOD. In some cases, the peptide linker comprises the amino acid sequence GCGGS (SEQ ID NO:318). In some cases, the peptide linker comprises the amino acid sequence GCGGS (GGGGS)n (SEQ ID NO:319), where n is an integer from 1 to 10. In some cases, the β2M polypeptide comprises an R12C substitution. For example, the β2M polypeptide can comprises an amino acid sequence having at least 90%, at least 95%, at least 98%, at least 99%, or 100%, amino acid sequence identity to the following amino acid sequence: IQRTPKIQVYSCHPAENGKSNFLNCYVSGFHPSDI-EVDLLKNGERIEKVEHSDLSFSKDWSFYLL YYTEFTPTEKDEYACRVNHVTLSQPKIVKWDRDM (SEQ ID NO:311), where amino acid 12 is a Cys. The at least one MOD can be a polypeptide that exerts an activating/stimulating effect on the target T cell or a suppressing/inhibitory effect on the target T cell. For example, the at least one MOD can be a cytokine (e.g., an IL2 polypeptide, an IL7 polypeptide, an IL12 polypeptide, an IL15 polypeptide, an IL17 polypeptide, an IL21 polypeptide, an IL27 polypeptide, an IL-23 polypeptide, a TGFβ polypeptide, and the like; and including all family members, e.g., IL17A, IL-17B, IL-17C, IL-17D, IL-17E, IL-17F, IL-17E), a 4-1BBL polypeptide, an ICOS-L polypeptide, an OX-40L polypeptide, a CD80 polypeptide, a CD86 polypeptide, (CD80 and CD86 are also known as B7-1 and B7-2, respectively), a CD40 polypeptide, a CD70 polypeptide, a JAG1 (CD339) polypeptide, an ICAM (CD540 polypeptide, a PD-L1 polypeptide, a FasL polypeptide, a PD-L2 polypeptide, a PD-1H (VISTA) polypeptide, an ICOS-L (CD275) polypeptide, a GITRL polypeptide, an HVEM polypeptide, a CXCL10 polypeptide, a CXCL9 polypeptide, a CXCL11 polypeptide, a CXCL13 polypeptide, and a CX3CL1 polypeptide, a Galectin-9 polypeptide, a CD83 polypeptide, a CD30L polypeptide, a HLA-G polypeptide, a MICA polypeptide, a MICB polypeptide, a HVEM (CD270) polypeptide, a lymphotoxin beta receptor polypeptide, a 3/TR6 polypeptide, an ILT3 polypeptide, an ILT4 polypeptide, a CXCL10 polypeptide, a CXCL9 polypeptide, a CXCL11 polypeptide, a CXCL13 polypeptide, or a CX3CL1 polypeptide. These MODs may be the wild type polypeptide or a variant of a wild type polypeptide. In some cases, the MOD is an activating ("stimulatory") immunomodulatory polypeptide; e.g., the MOD may produce an activating/stimulating effect on a T cell. Examples of activating MODs include, e.g., CD80, CD86, 4-1BBL, OX40L, CD70, ICOS-L, CD40, ICAM (CD54), IL2, IL7, IL12, IL15, IL17, IL21, IL27, IL23, GITRL, TGFβ, and lymphotoxin beta receptor. In some cases, the MOD is an inhibitory ("suppressing") MOD; e.g., the MOD may produce a suppressing/inhibitory effect on a T cell. Examples of inhibitory MOD include, e.g., PD-1H, PD-L1, PD-L2, TGFβ, FasL, HVEM, Galectin-9, ILT3, and ILT4. TGFβ polypeptides may produce either an activating/stimulating effect or a suppressing/inhibitory effect, depending on the context.

In some cases, a multiple disulfide-linked TMMP a double disulfide-linked TMMP) comprises: a) a first polypeptide comprising: i) a WT1 peptide (e.g., a WT1 peptide of from 4 amino acids to about 25 amino acids); and ii) a first MHC polypeptide, where the first polypeptide comprises a peptide linker between the WT1 peptide and the first MHC polypeptide, where the peptide linker comprises a Cys residue, and where the first MHC polypeptide is a β2M polypeptide that comprises an amino acid substitution that introduces a Cys residue; and b) a second polypeptide comprising an HLA-A MHC Class I heavy chain comprising an amino acid sequence having at least 60%, at least 70%, at least 80%, at least 90%, at least 95%, at least 98%, at least 99%, or 100%, amino acid sequence identity to the following amino acid sequence: GSHSMRYFSTSVSRPGRGEPRFIAVGYVDDTQFVRFDSDAASQRMEPRAPWIEQEGPEYWDEET GKVKAHSQTDRENLRIALRCYNQSEAGSHTLQMMFGCDVGSDGRFLRGYHQYAYDGKDYIAL KEDLRSWTAADMAAQITKRKWEAAHVAEQQRAYLEGTCVDGLRRYL ENGKETLQRTDPPKT HMTHHPISDHEATLRCWALGFYPAEITLTWQRDGEDQTQDTELVETRPCGDGTFQKWAAVVV PSGEEQRYTCHVQHEGLPKPLTLRWE (SEQ ID NO:346), where amino acid 84 is a Cys and amino acid 236 is a Cys; and c) at least one MOD, where the first and/or the second polypeptide comprises the at least one immunomodulatory polypeptide. In some cases, the peptide linker comprises the amino acid sequence GCGGS (SEQ ID NO:318). In some cases, the peptide linker comprises the amino acid sequence GCGGS(GGGGS)n (SEQ ID NO:319), where n is an integer from 1 to 10. In some cases, the β2M polypeptide comprises an R12C substitution. For example, the β2M polypeptide can comprises an amino acid sequence having at least 90%, at least 95%, at least 98%, at least 99%, or 100%, amino acid sequence identity to the following amino acid sequence: IQRTPKIQVYSCHPAENGKSNFLNCYVSGFHPSDIEVDLLKNGERIEKVEHSDLSFSKDWSFYLL YYTEFTPTEKDEYACRVNHVTLSQPKIVKWDRDM (SEQ ID NO:311), where amino acid 12 is a Cys. The at least one MOD can be a polypeptide that exerts an activating/stimulating effect on the target T cell or a suppressing/inhibitory effect on the target T cell. For example, the at least one MOD can be a cytokine (e.g., an IL2 polypeptide, an IL7 polypeptide, an IL12 polypeptide, an IL15 polypeptide, an IL17 polypeptide, an IL21 polypeptide, an IL27 polypeptide, an IL-23 polypeptide, a TGFβ polypeptide, and the like; and including all family members, e.g., IL17A, IL-17B, IL-17C, IL-17D, IL-17E, IL-17F, IL-17E), a 4-1BBL polypeptide, an ICOS-L polypeptide, an OX-40L polypeptide, a CD80 polypeptide, a CD86 polypeptide, (CD80 and CD86 are also known as B7-1 and B7-2, respectively), a CD40 polypeptide, a CD70 polypeptide, a JAG1 (CD339) polypeptide, an ICAM (CD540 polypeptide, a PD-L1 polypeptide, a FasL polypeptide, a PD-L2 polypeptide, a PD-1H (VISTA) polypeptide, an ICOS-L (CD275) polypeptide, a GITRL polypeptide, an HVEM polypeptide, a CXCL10 polypeptide, a CXCL9 polypeptide, a CXCL11 polypeptide, a CXCL13 polypeptide, and a CX3CL1 polypeptide, a Galectin-9 polypeptide, a CD83 polypeptide, a CD30L polypeptide, a HLA-G polypeptide, a MICA polypeptide, a MICB polypeptide, a HVEM (CD270) polypeptide, a lymphotoxin beta receptor polypeptide, a 3/TR6 polypeptide, an ILT3 polypeptide, an ILT4 polypeptide, a CXCL10 polypeptide, a CXCL9 polypeptide, a CXCL11 polypeptide, a CXCL13 polypeptide, and a CX3CL1 polypeptide. These MODs may be the wild type polypeptide or a variant of wild type polypeptide. Of these, the following MODs may produce an activating/stimulating effect: CD80, CD86, 4-1BBL, OX40L, CD70, ICOS-L, CD40, ICAM (CD54), IL2, IL7, IL12, IL15, IL17, IL21, IL27, IL23, GITRL, TGFβ, lymphotoxin beta receptor, 3/TR6, ILT3, ILT4, CXCL10, CXCL9, CXCL11, CXCL13 and CX3CL1. Of these, the following MODs may produce a suppressing/inhibitory effect: PD-1H, PD-L1, PD-L2, TGFβ, FasL, HVEM, Galectin-9, ILT3, ILT4. TGFβ polypeptides may produce either an activating/stimulating effect or a suppressing/inhibitory effect, depending on the context. In some cases, the at least one MOD is a reduced affinity variant, as described elsewhere herein. In some cases, the first or the second polypeptide comprises an Ig Fc polypeptide.

In some cases, the at least one MOD is a reduced affinity variant, as described elsewhere herein. In some cases, the first or the second polypeptide comprises an Ig Fc polypeptide.

In some cases, a multiple disulfide-linked TMMP a double disulfide-linked TMMP) comprises an HLA-A Class I heavy chain polypeptide. In some cases, the HLA-A heavy chain polypeptide present in a multiple disulfide-linked TMMP of the present disclosure (e.g., a double disulfide-linked TMMP) comprises an amino acid sequence having at least 95%, at least 98%, or at least 99%, amino acid sequence identity to the HLA-A*0101, HLA-A*0201, HLA-A*0202, HLA-A*1101, HLA-A*2301, HLA-A*2402, HLA-A*2407, HLA-A*3303, or HLA-A*3401 amino acid sequence depicted in FIG. 9A, where the HLA-A heavy chain polypeptide comprises Y84C and A236C substitutions.

HLA-A*0101 (Y84C; A236C)

In some cases, the HLA-A heavy chain polypeptide present in a multiple disulfide-linked TMMP (e.g., a double disulfide-linked TMMP) comprises an amino acid sequence having at least 95%, at least 98%, at least 99%, or 100%, amino acid sequence identity to the following HLA-A*0101 (Y84C; A236C) amino acid sequence:

GSHSMRYFFTSVSRPGRGEPRFIAVGYVDDTQFVRFDSDAASQKMEPRAPWIEQEGPEYWDQETRNMKAHSQTDRANLGTLRGCYNQSEDGSHTIQIMYGCDVGPDGRFLRGYRQDAYDGKDYIALNEDLRSWTAADMAAQITKRKWEAVHAAEQRRVYLEGRCVDGLRRYLENGKETLQRTDPPKTHMTHHPISDHEATLRCWALGFYPAEITLTWQRDGEDQTQDTELVETRPCGDGTFQKWAAVVVPSGEEQRYTCHVQHEGLPKPLTLRWE (SEQ ID NO:343), where amino acid 84 is a Cys and amino acid 236 is a Cys.

HLA-A*0201 (Y84C; A236C)

In some cases, the HLA-A heavy chain polypeptide present in a multiple disulfide-linked TMMP (e.g., a double disulfide-linked TMMP) comprises an amino acid sequence having at least 95%, at least 98%, at least 99%, or 100%, amino acid sequence identity to the following HLA-A*0201 (Y84C; A236C) amino acid sequence: GSHSMRYFFTSVSRPGRGEPRFIAVGYVDDTQFVRFDSDAASQRMEPRAPWIEQEGPEYWDGET RKVKAHSQTHRVDLGTLRGCYNQSEAGSHTVQRMYGCDVGSDWRFLRGYHQYAYDGKDYIA LKEDLRSWTAADMAAQTTKHKWEAAHVAEQLRAYLEGTCVEWLRRYLENGKETLQRTDAPK THMTHHAVSDHEATLRCWALSFYPAEITLTWQRDGEDQTQDTELVETRPCGDGTFQKWAAVV VPSGQEQRYTCHVQHEGLPKPLTLRWEP (SEQ ID NO:342), where amino acid 84 is a Cys and amino acid 236 is a Cys.

HLA-A*0202 (Y84C; A236C)

In some cases, the HLA-A heavy chain polypeptide present in a multiple disulfide-linked TMMP (e.g., a double disulfide-linked TMMP) comprises an amino acid sequence having at least 95%, at least 98%, at least 99%, or 100%, amino acid sequence identity to the following HLA-A*0202 (Y84C; A236C) amino acid sequence: GSHSMRYFFTSVSRPGRGEPRFIAVGYVDDTQFVRFDSDAASQRMEPRAPWIEQEGPEYWDGET RKVKAHSQTHRVDLGTLRGCYNQSEAGSHTVQRMYGCDVGSDWRFLRGYHQYAYDGKDYIA LKEDLRSWTAADMAAQTTKHKWEAAHVAEQLRAYLEGTCVEWLRRY- LENGKETLQRTDAPK THMTHHAVSDHEATLRCW-ALSFYPAEITLTWQRDGEDQTQDTELVETRPCGDGTF QKWAAVV VPSGQEQRYTCHVQHEGLPKPLTLRWE (SEQ ID NO:341), where amino acid 84 is a Cys and amino acid 236 is a Cys.

HLA-A*1101 (Y84C; A236C)

In some cases, the HLA-A heavy chain polypeptide present in a multiple disulfide-linked TMMP (e.g., a double disulfide-linked TMMP) comprises an amino acid sequence having at least 95%, at least 98%, at least 99%, or 100%, amino acid sequence identity to the following HLA-A*1101 (Y84C; A236C) amino acid sequence: GSHSM-RYFYTSVSRPGRGEPRFIAVGYVDDTQFVRFDS-DAASQRMEPRAPWIEQEGPEYWDQE TRNVKAQSQTDRVDLGTLRGCYN-QSEDGSHTIQIMYGCDVGPDGRFLRGYRQ-DAYDGKDYIA LNEDLRSWTAADMAAQITKRK-WEAAHAAEQQRAYLEGRCVEWLRRYLENGKETLQ RTDPPK THMTHHPISDHEATLRCWALGFY-PAEITLTWQRDGEDQTQDTELVETRPCGDGTFQK-WAAVV VPSGEEQRYTCHVQHEGLPKPLTLRWE (SEQ ID NO:344), where amino acid 84 is a Cys and amino acid 236 is a Cys.

HLA-A*2301 (Y84C; A236C)

In some cases, the HLA-A heavy chain polypeptide present in a multiple disulfide-linked TMMP (e.g., a double disulfide-linked TMMP) comprises an amino acid sequence having at least 95%, at least 98%, at least 99%, or 100%, amino acid sequence identity to the following HLA-A*2301 (Y84C; A236C) amino acid sequence: GSHSMRYF-STSVSRPGRGEPRFIAVGYVDDTQFVRFDS-DAASQRMEPRAPWIEQEGPEYWDEET GKVKAHSQTDRENLRIALRCYNQSEA-GSHTLQMMFGCDVGSDGRFLR-GYHQYAYDGKDYIAL KEDLRSWTAAD-MAAQITQRKWEAARVAEQLRAYLEGTCVDGLRRYL ENGKETLQRTDPPKTH MTHHPISDHEATLRCWAL-GFYPAEITLTWQRDGEDQTQDTELVE-TRPCGDGTFQKWAAVVVPS GEEQRYTCHVQHEGLPKPLTLRWE (SEQ ID NO:345), where amino acid 84 is a Cys and amino acid 236 is a Cys.

HLA-A*2402 (Y84C; A236C)

In some cases, the HLA-A heavy chain polypeptide present in a multiple disulfide-linked TMMP (e.g., a double disulfide-linked TMMP) comprises an amino acid sequence having at least 95%, at least 98%, at least 99%, or 100%, amino acid sequence identity to the following HLA-A*2402 (Y84C; A236C) amino acid sequence: GSHSMRYF-STSVSRPGRGEPRFIAVGYVDDTQFVRFDS-DAASQRMEPRAPWIEQEGPEYWDEET GKVKAHSQTDRENLRIALRCYNQSEA-GSHTLQMMFGCDVGSDGRFLR-GYHQYAYDGKDYIAL KEDLRSWTAAD-MAAQITKRKWEAAHVAEQQRAYLEGTCVDGLRRYL ENGKETLQRTDPPKT HMTHHPISDHEATLRCWAL-GFYPAEITLTWQRDGEDQTQDTELVE-TRPCGDGTFQKWAAVVV PSGE-EQRYTCHVQHEGLPKPLTLRWE (SEQ ID NO:346), where amino acid 84 is a Cys and amino acid 236 is a Cys.

HLA-A*2407 (Y84C; A236C)

In some cases, the HLA-A heavy chain polypeptide present in a multiple disulfide-linked TMMP (e.g., a double disulfide-linked TMMP) comprises an amino acid sequence having at least 95%, at least 98%, at least 99%, or 100%, amino acid sequence identity to the following HLA-A*2407 (Y84C; A236C) amino acid sequence: GSHSMRYF-STSVSRPGRGEPRFIAVGYVDDTQFVRFDS-DAASQRMEPRAPWIEQEGPEYWDEET GKVKAQSQTDRENLRIALRCYNQSEA-GSHTLQMMFGCDVGSDGRFLR-GYHQYAYDGKDYIAL KEDLRSWTAAD-MAAQITKRKWEAAHVAEQQRAYLEGTCVDGLRRYL ENGKETLQRTDPPKT HMTHHPISDHEATLRCWAL-GFYPAEITLTWQRDGEDQTQDTELVE-TRPCGDGTFQKWAAVVV PSGE-EQRYTCHVQHEGLPKPLTLRWE (SEQ ID NO:347), where amino acid 84 is a Cys and amino acid 236 is a Cys.

HLA-A*3303 (Y84C; A236C)

In some cases, the HLA-A heavy chain polypeptide present in a multiple disulfide-linked TMMP (e.g., a double disulfide-linked TMMP) comprises an amino acid sequence having at least 95%, at least 98%, at least 99%, or 100%, amino acid sequence identity to the following HLA-A*3303 (Y84C; A236C) amino acid sequence:

GSHSMRYFTTSVSRPGRGEPRFIA-VGYVDDTQFVRFDSDAASQRMEPRAPWIEQE GPEYWDRNTRNVKAHSQIDRVDLGTLRGCYNQSEA-GSHTIQMMYGCDVGSDGRFLRGYQQD AYDGKDYIALNEDLRSWTAADMAAQITQRK-WEAARVAEQLRAYLEGTCVEWLRRYLENGKE TLQRTDPPKTHMTHHAVSDHEATLRCWALSFY-PAEITLTWQRDGEDQTQDTELVETRPCGDGT FQK-WASVVVPSGQEQRYTCHVQHEGLPKPLTLRWE (SEQ ID NO:348), where amino acid 84 is a Cys and amino acid 236 is a Cys.

HLA-A*3401 (Y84C; A236C)

In some cases, the HLA-A heavy chain polypeptide present in a multiple disulfide-linked TMMP (e.g., a double disulfide-linked TMMP) comprises an amino acid sequence having at least 95%, at least 98%, at least 99%, or 100%, amino acid sequence identity to the following HLA-A*3401 (Y84C; A236C) amino acid sequence: GSHSM-RYFYTSVSRPGRGEPRFIAVGYVDDTQFVRFDS-DAASQRMEPRAPWIEQEGPEYWDRN TRKVKAQSQTDRVDLGTLRGCYN-QSEDGSHTIQRMYGCDVGPDGRFLRGYQQ-DAYDGKDYIA LNEDLRSWTAADMAAQITQRKWE-TAHEAEQWRAYLEGTCVEWLRRYLENGKETLQRTD APK THMTHHAVSDHEATLRCWALSFY-PAEITLTWQRDGEDQTQDTELVETRPCGDGTFQK-WASVV VPSGQEQRYTCHVQHEGLPKPLTLRWE (SEQ ID NO:349), where amino acid 84 is a Cys and amino acid 236 is a Cys.

HLA-B

In some cases, a multiple disulfide-linked TMMP a double disulfide-linked TMMP) comprises: a) a first polypeptide comprising: i) a WT1 peptide (e.g., a WT1 peptide of from 4 amino acids to about 25 amino acids); and ii) a first MHC polypeptide, where the first polypeptide comprises a peptide linker between the WT1 peptide and the first MHC polypeptide, where the peptide linker comprises a Cys residue, and where the first MHC polypeptide is a β2M polypeptide that comprises an amino acid substitution that introduces a Cys residue; and b) a second polypeptide comprising an HLA-B MHC Class I heavy chain comprising an amino acid sequence having at least 60%, at least 70%, at least 80%, at least 90%, at least 95%, at least 98%, at least 99%, or 100%, amino acid sequence identity to the following amino acid sequence: GSHSM-RYFYTSVSRPGRGEPRFISVGYVDDTQFVRFDS-DAASPREEPRAPWIEQEGPEYWDRNT QIYKAQAQTDRESLRNLRGCYNQSEA-GSHTLQSMYGCDVGPDGRLLRGHDQYAYDGKDYI AL NEDLRSWTAADTAAQITQRKWEAAREAEQRRAY- LEGECVEWLRRYLENGKDKLERADPPKTH VTHHPISDHEATLRCWALGFYPAEITLTWQRDGEDQTQDTELVETRPCGDRTFQKWA AVVVPS GEEQRYTCHVQHEGLPKPLTLRWEP (SEQ ID NO:350), where amino acid 84 is a Cys and amino acid 236 is a Cys; and c) at least one MOD, where the first and/or the second polypeptide comprises the at least one MOD. In some cases, the peptide linker comprises the amino acid sequence GCGGS (SEQ ID NO:318). In some cases, the peptide linker comprises the amino acid sequence GCGGS (GGGGS)n (SEQ ID NO:319), where n is an integer from 1 to 10. In some cases, the β2M polypeptide comprises an R12C substitution. For example, the β2M polypeptide can comprises an amino acid sequence having at least 90%, at least 95%, at least 98%, at least 99%, or 100%, amino acid sequence identity to the following amino acid sequence: IQRTPKIQVYSCHPAENGKSNFLNCYVSGFHPSDIEVDLLKNGERIEKVEHSDLSFSKDWSFYLL YYTEFTPTEKDEYACRVNHVTLSQPKIVKWDRDM (SEQ ID NO:311), where amino acid 12 is a Cys. The at least one MOD can be a polypeptide that exerts an activating/stimulating effect on the target T cell or a suppressing/inhibitory effect on the target T cell. For example, the at least one MOD can be a cytokine (e.g., an IL2 polypeptide, an IL7 polypeptide, an IL12 polypeptide, an IL15 polypeptide, an IL17 polypeptide, an IL21 polypeptide, an IL27 polypeptide, an IL-23 polypeptide, a TGFβ polypeptide, and the like; and including all family members, e.g., IL17A, IL-17B, IL-17C, IL-17D, IL-17E, IL-17F, IL-17E), a 4-1BBL polypeptide, an ICOS-L polypeptide, an OX-40L polypeptide, a CD80 polypeptide, a CD86 polypeptide, (CD80 and CD86 are also known as B7-1 and B7-2, respectively), a CD40 polypeptide, a CD70 polypeptide, a JAG1 (CD339) polypeptide, an ICAM (CD540 polypeptide, a PD-L1 polypeptide, a FasL polypeptide, a PD-L2 polypeptide, a PD-1H (VISTA) polypeptide, an ICOS-L (CD275) polypeptide, a GITRL polypeptide, an HVEM polypeptide, a CXCL10 polypeptide, a CXCL9 polypeptide, a CXCL11 polypeptide, a CXCL13 polypeptide, and a CX3CL1 polypeptide, a Galectin-9 polypeptide, a CD83 polypeptide, a CD30L polypeptide, a HLA-G polypeptide, a MICA polypeptide, a MICB polypeptide, a HVEM (CD270) polypeptide, a lymphotoxin beta receptor polypeptide, a 3/TR6 polypeptide, an ILT3 polypeptide, an ILT4 polypeptide, a CXCL10 polypeptide, a CXCL9 polypeptide, a CXCL11 polypeptide, a CXCL13 polypeptide, or a CX3CL1 polypeptide. These MODs may be the wild type polypeptide or a variant of a wild type polypeptide. In some cases, the MOD is an activating ("stimulatory") immunomodulatory polypeptide; e.g., the MOD may produce an activating/stimulating effect on a T cell. Examples of activating MODs include, e.g., CD80, CD86, 4-1BBL, OX40L, CD70, ICOS-L, CD40, ICAM (CD54), IL2, IL7, IL12, IL15, IL17, IL21, IL27, IL23, GITRL, TGFβ, and lymphotoxin beta receptor. In some cases, the immunomodulatory polypeptide is an inhibitory ("suppressing") MOD; e.g., MOD may produce a suppressing/inhibitory effect on a T cell. Examples of inhibitory MODs include, e.g., PD-1H, PD-L1, PD-L2, TGFβ, FasL, HVEM, Galectin-9, ILT3, and ILT4. TGFβ polypeptides may produce either an activating/stimulating effect or a suppressing/inhibitory effect, depending on the context.

In some cases, the at least one MOD is a reduced affinity variant, as described elsewhere herein. In some cases, the first or the second polypeptide comprises an Ig Fc polypeptide.

In some cases, a multiple disulfide-linked TMMP (e.g., a double disulfide-linked TMMP) comprises an HLA-B Class I heavy chain polypeptide. In some cases, the HLA-B heavy chain polypeptide present in a multiple disulfide-linked TMMP (e.g., a double disulfide-linked TMMP) comprises an amino acid sequence having at least 95%, at least 98%, or at least 99%, amino acid sequence identity to the HLA-B*0702, HLA-B*0801, HLA-B*1502, HLA-B*3802, HLA-B*4001, HLA-B*4601, or HLA-B*5301 amino acid sequence depicted in FIG. 10A, where the HLA-B heavy chain polypeptide comprises Y84C and A236C substitutions.

HLA-B*0702 (Y84C; A236C)

In some cases, the HLA-B heavy chain polypeptide present in a multiple disulfide-linked TMMP (e.g., a double disulfide-linked TMMP) comprises an amino acid sequence having at least 95%, at least 98%, at least 99%, or 100%, amino acid sequence identity to the following HLA-B*0702 (Y84C; A236C) amino acid sequence:

GSHSMRYFYTSVSRPGRGEPRFISVGYVDDTQFVRFDSDAASPREEPRAPWIEQE GPEYWDRNTQIYKAQAQTDRESLRNLRGCYNQSEAGSHTLQSMYGCDVGPDGR LLRGHDQYA YDGKDYIALNEDLRSWTAADTAAQITQRKWEAAREAEQRRAYLEGECVEWLRRYLENGKDKL ERADPPKTHVTHHPISDHEATLRCWALGFYPAEITLTWQRDGEDQTQDTELVETRPCGDRTFQK WAAVVVPSGEEQRYTCHVQHEGLPKPLTLRWE (SEQ ID NO:350), where amino acid 84 is a Cys and amino acid 236 is a Cys.

HLA-B*0801 (Y84C; A236C)

In some cases, the HLA-B heavy chain polypeptide present in a multiple disulfide-linked TMMP (e.g., a double disulfide-linked TMMP) comprises an amino acid sequence having at least 95%, at least 98%, at least 99%, or 100%, amino acid sequence identity to the following HLA-B*0801 (Y84C; A236C) amino acid sequence:

GSHSMRYFDTAMSRPGRGEPRFISVGYVDDTQFVRFDSDAASPREEPRAPWIEQE GPEYWDRNTQIFKTNTQTDRESLRNLRGCYNQSEAGSHTLQSMYGCDVGPDGR LLRGHNQYA YDGKDYIALNEDLRSWTAADTAAQITQRKWEAARVAEQDRAYLEGTCVEWLRRYLENGKDTL ERADPPKTHVTHHPISDHEATLRCWALGFYPAEITLTWQRDGEDQTQDTELVETRPCGDRTFQK WAAVVVPSGEEQRYTCHVQHEGLPKPLTLRWE (SEQ ID NO:351), where amino acid 84 is a Cys and amino acid 236 is a Cys.

HLA-B*1502 (Y84C; A236C)

In some cases, the HLA-B heavy chain polypeptide present in a multiple disulfide-linked TMMP (e.g., a double disulfide-linked TMMP) comprises an amino acid sequence having at least 95%, at least 98%, at least 99%, or 100%, amino acid sequence identity to the following HLA-B*1502 (Y84C; A236C) amino acid sequence:

GSHSMRYFYTAMSRPGRGEPRFIAVGYVDDTQFVRFDSDAASPRMAPRAPWIEQ EGPEYWDRNTQISKTNTQTYRESLRNLRGCYNQSEAGSHIIQRMYGCDVGPDGRLLRGYDQSA YDGKDYIALNEDLSSWTAADTAAQITQRKWEAAREAEQLRAYLEGLCVEWLRRYLENGKETL QRADPPKTHVTHHPISDHEATLRCWALGFYPAEITLTWQRDGEDQTQDTELVETRPCGDRTFQ KWAAVVVPSGEEQRYTCHVQHEGLPKPLTLRWE (SEQ ID NO:352), where amino acid 84 is a Cys and amino acid 236 is a Cys.

HLA-B*3802 (Y84C; A236C)

In some cases, the HLA-B heavy chain polypeptide present in a multiple disulfide-linked TMMP (e.g., a double disulfide-linked TMMP) comprises an amino acid sequence having at least 95%, at least 98%, at least 99%, or 100%, amino acid sequence identity to the following HLA-B*3802 (Y84C; A236C) amino acid sequence:

GSHSM-RYFYTSVSRPGRGEPRFISVGYVDDTQFVRFDS-DAASPREEPRAPWIEQE GPEYWDRNTQICKTNTQ-TYRENLRTALRCYNQSEAGSHTLQRMYGCDVGPDG RLLRGHNQFA YDGKDYIALNEDLSSWTAAD-TAAQITQRKWEAARVAEQLRTYLEGTCVEWLRRY-LENGKETL QRADPPKTHVTHHPISDHEATLRCWAL-GFYPAEITLTWQRDGEDQTQDTELVETRPCGDRTFQ KWAAVVVPSGEEQRYTCHVQHEGLPKPLTLRWE (SEQ ID NO:353), where amino acid 84 is a Cys and amino acid 236 is a Cys.

HLA-B*4001 (Y84C; A2346C)

In some cases, the HLA-B heavy chain polypeptide present in a multiple disulfide-linked TMMP (e.g., a double disulfide-linked TMMP) comprises an amino acid sequence having at least 95%, at least 98%, at least 99%, or 100%, amino acid sequence identity to the following HLA-B*4001 (Y84C; A236C) amino acid sequence:

GSHSMRYFHTAM-SRPGRGEPRFITVGYVDDTLFVRFDSDATSPRKE-PRAPWIEQE GPEYWDRETQISKTNTQ-TYRESLRNLRGCYNQSEAGSHTLQRMYGCDVGPDG RLLRGHNQYA YDGKDYIALNEDLRSWTAADTAAQ-ISQRKLEAARVAEQLRAYLEGECVEWLRRY-LENGKDKL ERADPPKTHVTHHPISDHEATLRCWAL-GFYPAEITLTWQRDGEDQTQDTELVETRPCGDRTFQK WAAVVVPSGEEQRYTCHVQHEGLPKPLTLRWE (SEQ ID NO:354) where amino acid 84 is a Cys and amino acid 236 is a Cys.

HLA-B*4601 (Y84C; A236C)

In some cases, the HLA-B heavy chain polypeptide present in a multiple disulfide-linked TMMP a double disulfide-linked TMMP) comprises an amino acid sequence having at least 95%, at least 98%, at least 99%, or 100%, amino acid sequence identity to the following HLA-B*4601 (Y84C; A236C) amino acid sequence:

GSHSMRYFYTAMSRPGRGEPRFIA-VGYVDDTQFVRFDSDAASPRMAPRAPWIEQ EGPEYWDRETQKYKRQAQTDRVSLRNLRGCYN-QSEAGSHTLQRMYGCDVGPDGRLLRGHDQ SAYDGKDYIALNEDLSSWTAADTAAQITQRK-WEAAREAEQWRAYLEGLCVEWLRRYLENGKE TLQRADPPKTHVTHHPISDHEATLRCWALGFY-PAEITLTWQRDGEDQTQDTELVETRPCGDRTF QKWAAVVVPSGEEQRYTCHVQHEGLPKPLTLRWE (SEQ ID NO:355) where amino acid 84 is a Cys and amino acid 236 is a Cys.

HLA-B*5301 (Y84C; A236C)

In some cases, the HLA-B heavy chain polypeptide present in a multiple disulfide-linked TMMP (e.g., a double disulfide-linked TMMP) comprises an amino acid sequence having at least 95%, at least 98%, at least 99%, or 100%, amino acid sequence identity to the following HLA-B*5301 (Y84C; A236C) amino acid sequence:

GSHSMRYFYTAMSRPGRGEPRFIA-VGYVDDTQFVRFDSDAASPRTEPRAPWIEQE GPEYWDRNTQIFKTNTQTYRENLRIALRCYNQSEA-GSHIIQRMYGCDLGPDGRLLRGHDQSAY DGKDYIALNEDLSSWTAADTAAQITQRKWEAAR-VAEQLRAYLEGLCVEWLRRYLENGKETLQ RADPPKTHVTHHPVSDHEATLRCWALGFY-PAEITLTWQRDGEDQTQDTELVETRPCGDRTFQK WAAVVVPSGEEQRYTCHVQHEGLPKPLTLRWE (SEQ ID NO:356) where amino acid 84 is a Cys and amino acid 236 is a Cys.

HLA-C

In some cases, a multiple disulfide-linked TMMP (e.g., a double disulfide-linked TMMP) comprises: a) a first polypeptide comprising: i) a WT-1 peptide (e.g., 1 WT-1 peptide of from 4 amino acids to about 25 amino acids); and ii) a first MHC polypeptide, where the first polypeptide comprises a peptide linker between the WT-1 peptide and the first MHC polypeptide, where the peptide linker comprises a Cys residue, and where the first MHC polypeptide is a β2M polypeptide that comprises an amino acid substitution that introduces a Cys residue; and b) a second polypeptide comprising an HLA-C MHC Class I heavy chain comprising an amino acid sequence having at least 60%, at least 70%, at least 80%, at least 90%, at least 95%, at least 98%, at least 99%, or 100%, amino acid sequence identity to the following amino acid sequence: CSHSMRYFD-TAVSRPGRGEPRFISVGYVDDTQFVRFDS-DAASPRGEPRAPWVEQEGPEYWDRE TQNYKRQAQADRVSLRNLRGCYN-QSEDGSHTLQRMYGCDLGPDGRLLR-GYDQSAYDGKDYI ALNEDLRSWTAAD-TAAQITQRKLEAARAAEQLRAYLEGTCVEWLRRYLE NGKETLQRAEPPKT HVTHHPLSDHEATLRCWAL-GFYPAEITLTWQRDGEDQTQDTELVE-TRPCGDGTFQKWAAVVV PSGQEQRYTCHMQHEGLQEPLTLSWEP (SEQ ID NO:357), where amino acid 84 is a Cys and amino acid 236 is a Cys; and c) at least one MOD, where the first and/or the second polypeptide comprises the at least one MOD. In some cases, the peptide linker comprises the amino acid sequence GCGGS (SEQ ID NO:318). In some cases, the peptide linker comprises the amino acid sequence GCGGS (GGGGS)n (SEQ ID NO:319), where n is an integer from 1 to 10. In some cases, the β2M polypeptide comprises an R12C substitution. For example, the β2M polypeptide can comprises an amino acid sequence having at least 90%, at least 95%, at least 98%, at least 99%, or 100%, amino acid sequence identity to the following amino acid sequence: IQRTPKIQVYSCHPAENGKSNFLNCYVSGFHPSDI-EVDLLKNGERIEKVEHSDLSFSKDWSFYLL YYTEFTPTEKDEYACRVNHVTLSQPKIVKWDRDM (SEQ ID NO:311), where amino acid 12 is a Cys. The at least one MOD can be a polypeptide that exerts an activating/stimulating effect on the target T cell or a suppressing/inhibitory effect on the target T cell. For example, the at least one MOD can be a cytokine (e.g., an IL2 polypeptide, an IL7 polypeptide, an IL12 polypeptide, an IL15 polypeptide, an IL17 polypeptide, an IL21 polypeptide, an IL27 polypeptide, an IL-23 polypeptide, a TGFβ polypeptide, and the like; and including all family members, e.g., IL17A, IL-17B, IL-17C, IL-17D, IL-17E, IL-17F, IL-17E), a 4-1BBL polypeptide, an ICOS-L polypeptide, an OX-40L polypeptide, a CD80 polypeptide, a CD86 polypeptide, (CD80 and CD86 are also known as B7-1 and B7-2, respectively), a CD40 polypeptide, a CD70 polypeptide, a JAG1 (CD339) polypeptide, an ICAM (CD540 polypeptide, a PD-L1 polypeptide, a FasL polypeptide, a PD-L2 polypeptide, a PD-1H (VISTA) polypeptide, an ICOS-L (CD275) polypeptide, a GITRL polypeptide, an HVEM polypeptide, a CXCL10 polypeptide, a CXCL9 polypeptide, a CXCL11 polypeptide, a CXCL13 polypeptide, and a CX3CL1 polypeptide, a Galectin-9 polypeptide, a CD83 polypeptide, a CD30L polypeptide, a HLA-G polypeptide, a MICA polypeptide, a MICB polypeptide, a HVEM (CD270) polypeptide, a lymphotoxin beta receptor polypeptide, a 3/TR6 polypeptide, an ILT3 polypeptide, an ILT4 polypeptide, a CXCL10 polypeptide, a CXCL9 polypeptide, a CXCL11 polypeptide, a CXCL13 polypeptide, or a CX3CL1 polypeptide. These MODs may be the wild type polypeptide or a variant of a wild type polypeptide. In some cases, the immunomodulatory polypeptide is an activating ("stimulatory") MOD; e.g., the MOD may produce an activating/stimulating effect on a T cell. Examples of activating immunomodulatory polypeptides include, e.g., CD80, CD86, 4-1BBL, OX40L, CD70, ICOS-L, CD40, ICAM (CD54), IL2, IL7, IL12, IL15, IL17, IL21, IL27, IL23, GITRL, TGFβ, and lymphotoxin beta receptor. In some cases, the MOD is an inhibitory ("suppressing") MOD; e.g., the MOD may produce a suppressing/inhibitory effect on a T cell. Examples of inhibitory MODs include, e.g., PD-1H, PD-L1, PD-L2, TGFβ, FasL, HVEM, Galectin-9, ILT3, and ILT4. TGFβ polypeptides may produce either an activating/stimulating effect or a suppressing/inhibitory effect, depending on the context.

In some cases, the at least one MOD is a reduced affinity variant, as described elsewhere herein. In some cases, the first or the second polypeptide comprises an Ig Fc polypeptide.

In some cases, a multiple disulfide-linked TMMP a double disulfide-linked TMMP) comprises an HLA-C Class I heavy chain polypeptide. In some cases, the HLA-C heavy chain polypeptide present in a multiple disulfide-linked TMMP (e.g., a double disulfide-linked TMMP) comprises an amino acid sequence having at least 95%, at least 98%, or at least 99%, amino acid sequence identity to the HLA-C*0102, HLA-C*0303, HLA-C*0304, HLA-C*0401, HLA-C*0602, HLA-C*0701, HLA-C*0702, HLA-C*0801, or HLA-C*1502 amino acid sequence depicted in FIG. 11A, where the HLA-C heavy chain polypeptide comprises Y84C and A236C substitutions.

HLA-C*01:02 (Y84C; A236C)

In some cases, the HLA-C heavy chain polypeptide present in a multiple disulfide-linked TMMP a double disulfide-linked TMMP) comprises an amino acid sequence having at least 95%, at least 98%, at least 99%, or 100%, amino acid sequence identity to the following HLA-C*01:02 (Y84C; A236C) amino acid sequence:

CSHSMKYFFTSVSRPGRGEPRFISVGYVDDTQFVR FDSDAASPRGEPRAPWVEQE GPEYW-DRETQKYKRQAQTDRVSLRNLRGCYNQSEA-GSHTLQWMCGCDLGPDGRLLRGYDQY AYDGKDYIALNEDLRSWTAADTAAQITQRK-WEAAREAEQRRAYLEGTCVEWLRRYLENGKET LQRAEHPKTHVTHHPVSDHEATLRCWALGFY-PAEITLTWQWDGEDQTQDTELVETRPCGDGTF QKWAAVMVPSGEEQRYTCHVQHEGLPEPLTLRWEP (SEQ ID NO:358), where amino acid 84 is a Cys and amino acid 236 is a Cys.

HLA-C*0303 (Y84C; A236C)

In some cases, the HLA-C heavy chain polypeptide present in a multiple disulfide-linked TMMP (e.g., a double disulfide-linked TMMP) comprises an amino acid sequence having at least 95%, at least 98%, at least 99%, or 100%, amino acid sequence identity to the following HLA-C*03:03 (Y84C; A236C) amino acid sequence:

GSHSMRYFYTAVSRPGRGEPHFIA-VGYVDDTQFVRFDSDAASPRGEPRAPWVEQ EGPEYWDRETQKYKRQAQTDRVSLRNLRGCYN-QSEARSHIIQRMYGCDVGPDGRLLRGYDQY AYDGKDYIALNEDLRSWTAADTAAQITQRK-WEAAREAEQLRAYLEGLCVEWLRRYLKNGKET LQRAEHPKTHVTHHPVSDHEATLRCWALGFY-PAEITLTWQWDGEDQTQDTELVETRPCGDGTF QKWAAVVVPSGEEQRYTCHVQHEGLPEPLTLRWEP (SEQ ID NO:359), where amino acid 84 is a Cys and amino acid 236 is a Cys.

HLA-C*0304 (Y84C; A236C)

In some cases, the HLA-C heavy chain polypeptide present in a multiple disulfide-linked TMMP (e.g., a double disulfide-linked TMMP) comprises an amino acid sequence having at least 95%, at least 98%, at least 99%, or 100%, amino acid sequence identity to the following HLA-C*03:04 (Y84C; A236C) amino acid sequence:

GSHSMRYFYTAVSRPGRGEPHFIA-VGYVDDTQFVRFDSDAASPRGEPRAPWVEQ EGPEYWDRETQKYKRQAQTDRVSLRNLRGCYN-QSEAGSHIIQRMYGCDVGPDGRLLRGYDQY AYDGKDYIALNEDLRSWTAADTAAQITQRK-WEAAREAEQLRAYLEGLCVEWLRRYLKNGKET LQRAEHPKTHVTHHPVSDHEATLRCWALGFY-PAEITLTWQWDGEDQTQDTELVETRPCGDGTF QKWAAVVVPSGEEQRYTCHVQHEGLPEPLTLRWEP (SEQ ID NO:360), where amino acid 84 is a Cys and amino acid 236 is a Cys.

HLA-C*0401 (Y84C; A236C)

In some cases, the HLA-C heavy chain polypeptide present in a multiple disulfide-linked TMMP a double disulfide-linked TMMP) comprises an amino acid sequence having at least 95%, at least 98%, at least 99%, or 100%, amino acid sequence identity to the following HLA-C*04:01 (Y84C; A236C) amino acid sequence:

GSHSMRYFSTSVSWPGRGEPRFIA-VGYVDDTQFVRFDSDAASPRGEPREPWVEQ EGPEYWDRETQKYKRQAQADRVNLRKLRGCYN-QSEDGSHTLQRMFGCDLGPDGRLLRGYNQ FAYDGKDYIALNEDLRSWTAADTAAQITQRK-WEAAREAEQRRAYLEGTCVEWLRRYLENGKE TLQRAEHPKTHVTHHPVSDHEATLRCWALGFY-PAEITLTWQWDGEDQTQDTELVETRPCGDGT FQK-WAAVVVPSGEEQRYTCHVQHEGLPEPLTLRWKP (SEQ ID NO:361), where amino acid 84 is a Cys and amino acid 236 is a Cys.

HLA-C*0602 (Y84C; A236C)

In some cases, the HLA-C heavy chain polypeptide present in a multiple disulfide-linked TMMP (e.g., a double disulfide-linked TMMP) comprises an amino acid sequence having at least 95%, at least 98%, at least 99%, or 100%, amino acid sequence identity to the following HLA-C*06:02 (Y84C; A236C) amino acid sequence:

CSHSMRYFD-TAVSRPGRGEPRFISVGYVDDTQFVRFDS-DAASPRGEPRAPWVEQ EGPEYW-DRETQKYKRQAQADRVNLRKLRGCYNQSEDGSHTL QWMYGCDLGPDGRLLRGYD QSAYDGKDYIAL-NEDLRSWTAADTAAQITQRKWEAAREAEQWRAY-LEGTCVEWLRRYLENG KETLQRAEHPKTHVTHHPVSDHEATLRCWALGFY-PAEITLTWQRDGEDQTQDTELVETRPCGD GTFQK-WAAVVVPSGEEQRYTCHVQHEGLPEPLTLRWEP (SEQ ID NO:362), where amino acid 84 is a Cys and amino acid 236 is a Cys.

HLA-C*0701 (Y84C; A236C)

In some cases, the HLA-C heavy chain polypeptide present in a multiple disulfide-linked TMMP (e.g., a double disulfide-linked TMMP) comprises an amino acid sequence having at least 95%, at least 98%, at least 99%, or 100%, amino acid sequence identity to the following HLA-C*07:01 (Y84C; A236C) amino acid sequence:

CSHSMRYFD-TAVSRPGRGEPRFISVGYVDDTQFVRFDS-DAASPRGEPRAPWVEQ EGPEYW-DRETQNYKRQAQADRVSLRNLRGCYNQSEDGSHTL QRMYGCDLGPDGRLLRGYDQ SAYDGKDYIAL-NEDLRSWTAADTAAQITQRKLEAARAAEQLRAY-LEGTCVEWLRRYLENGKE TLQRAE-PPKTHVTHHPLSDHEATLRCWALGFYPAEITLTWQRD GEDQTQDTELVETRPCGDGT FQK-WAAVVVPSGQEQRYTCHMQHEGLQEPLTLSWEP (SEQ ID NO:357), where amino acid 84 is a Cys and amino acid 236 is a Cys.

HLA-C*0702 (Y84C; A236C)

In some cases, the HLA-C heavy chain polypeptide present in a multiple disulfide-linked TMMP a double disulfide-linked TMMP) comprises an amino acid sequence having at least 95%, at least 98%, at least 99%, or 100%, amino acid sequence identity to the following HLA-C*07:02 (Y84C; A236C) amino acid sequence:

CSHSMRYFD-TAVSRPGRGEPRFISVGYVDDTQFVRFDS-DAASPRGEPRAPWVEQ EGPEYW-DRETQKYKRQAQADRVSLRNLRGCYNQSEDGSHTL QRMSGCDLGPDGRLLRGYDQS AYDGKDYIAL-NEDLRSWTAADTAAQITQRKLEAARAAEQLRAY-LEGTCVEWLRRYLENGKET LQRAE-PPKTHVTHHPLSDHEATLRCWALGFYPAEITLTWQR DGEDQTQDTELVETRPCGDGTF QKWAAVVVPSGQEQRYTCHMQHEGLQEPLTLSWEP (SEQ ID NO:404), where amino acid 84 is a Cys and amino acid 236 is a Cys.

HLA-C*0801 (Y84C; A236C)

In some cases, the HLA-C heavy chain polypeptide present in a multiple disulfide-linked TMMP (e.g., a double disulfide-linked TMMP) comprises an amino acid sequence having at least 95%, at least 98%, at least 99%, or 100%, amino acid sequence identity to the following HLA-C*08:01 (Y84C; A236C) amino acid sequence:

CSHSMRYFYTAVSRPGRGEPRFIA-VGYVDDTQFVQFDSDAASPRGEPRAPWVEQ EGPEYWDRETQKYKRQAQTDRVSLRNLRGCYN-QSEAGSHTLQRMYGCDLGPDGRLLRGYNQ FAYDGKDYIALNEDLRSWTAADTAAQITQRK-WEAARTAEQLRAYLEGTCVEWLRRYLENGKK TLQRAEHPKTHVTHHPVSDHEATLRCWALGFY-PAEITLTWQRDGEDQTQDTELVETRPCGDGT FQK-WAAVVVPSGEEQRYTCHVQHEGLPEPLTLRWGP (SEQ ID NO:363), where amino acid 84 is a Cys and amino acid 236 is a Cys.

HLA-C*1502 (Y84C; A236C)

In some cases, the HLA-C heavy chain polypeptide present in a multiple disulfide-linked TMMP (e.g., a double disulfide-linked TMMP) comprises an amino acid sequence having at least 95%, at least 98%, at least 99%, or 100%, amino acid sequence identity to the following HLA-C*15:02 (Y84C; A236C) amino acid sequence:

CSHSMRYFYTAVSRPGRGEPHFIA-VGYVDDTQFVRFDSDAASPRGEPRAPWVEQ EGPEYWDRETQNYKRQAQTDRVNLRKLRGCYN-QSEAGSHIIQRMYGCDLGPDGRLLRGHDQL AYDGKDYIALNEDLRSWTAADTAAQITQRK-WEAAREAEQLRAYLEGTCVEWLRRYLENGKET LQRAEHPKTHVTHHPVSDHEATLRCWALGFY-PAEITLTWQRDGEDQTQDTELVETRPCGDGTF QKWAAVVVPSGEEQRYTCHVQHEGLPEPLTLRWEP (SEQ ID NO:364), where amino acid 84 is a Cys and amino acid 236 is a Cys.

Scaffold Polypeptides

A TMMP can comprise an Fc polypeptide, or can comprise another suitable scaffold polypeptide.

Suitable scaffold polypeptides include antibody-based scaffold polypeptides and non-antibody-based scaffolds. Non-antibody-based scaffolds include, e.g., albumin, an XTEN (extended recombinant) polypeptide, transferrin, an Fc receptor polypeptide, an elastin-like polypeptide (see, e.g., Hassouneh et al. (2012) *Methods Enzymol.* 502:215; e.g., a polypeptide comprising a pentapeptide repeat unit of (Val-Pro-Gly-X-Gly; SEQ ID NO:59), where X is any amino acid other than proline), an albumin-binding polypeptide, a silk-like polypeptide (see, e.g., Valluzzi et al. (2002) *Philos Trans R Soc Lond B Biol Sci.* 357:165), a silk-elastin-like polypeptide (SELP; see, e.g., Megeed et al. (2002) *Adv Drug Deliv Rev.* 54:1075), and the like. Suitable XTEN polypeptides include, e.g., those disclosed in WO 2009/023270, WO 2010/091122, WO 2007/103515, US 2010/0189682, and US 2009/0092582; see also Schellenberger et al. (2009) *Nat Biotechnol.* 27:1186). Suitable albumin polypeptides include, e.g., human serum albumin.

Suitable scaffold polypeptides will in some cases be a half-life extending polypeptides. Thus, in some cases, a suitable scaffold polypeptide increases the in vivo half-life (e.g., the serum half-life) of the TMMP, compared to a control TMMP lacking the scaffold polypeptide. For example, in some cases, a scaffold polypeptide increases the in vivo half-life (e.g., the serum half-life) of the TMMP, compared to a control TMMP lacking the scaffold polypeptide, by at least about 10%, at least about 15%, at least about 20%, at least about 25%, at least about 50%, at least about 2-fold, at least about 2.5-fold, at least about 5-fold, at least about 10-fold, at least about 25-fold, at least about 50-fold, at least about 100-fold, or more than 100-fold. As an example, in some cases, an Fc polypeptide increases the in vivo half-life (e.g., the serum half-life) of the TMMP, compared to a control TMMP lacking the Fc polypeptide, by at least about 10%, at least about 15%, at least about 20%, at least about 25%, at least about 50%, at least about 2-fold, at least about 2.5-fold, at least about 5-fold, at least about 10-fold, at least about 25-fold, at least about 50-fold, at least about 100-fold, or more than 100-fold.

Fc Polypeptides

In some cases, the first and/or the second polypeptide chain of a TMMP of the present disclosure comprises an Fc polypeptide. The Fc polypeptide of a TMMP can be a human IgG1 Fc, a human IgG2 Fc, a human IgG3 Fc, a human IgG4 Fc, etc. In some cases, the Fc polypeptide comprises an amino acid sequence having at least about 70%, at least about 75%, at least about 80%, at least about 85%, at least about 90%, at least about 95%, at least about 98%, at least about 99%, or 100%, amino acid sequence identity to an amino acid sequence of an Fc region depicted in FIG. 5A-5G or 5H. In some cases, the Fc region comprises an amino acid sequence having at least about 70%, at least about 75%, at least about 80%, at least about 85%, at least about 90%, at least about 95%, at least about 98%, at least about 99%, or 100%, amino acid sequence identity to the human IgG1 Fc polypeptide depicted in FIG. 5A. In some cases, the Fc region comprises an amino acid sequence having at least about 70%, at least about 75%, at least about 80%, at least about 85%, at least about 90%, at least about 95%, at least about 98%, at least about 99%, or 100%, amino acid sequence identity to the human IgG1 Fc polypeptide depicted in FIG. 5A; and comprises a substitution of N77; e.g., the Fc polypeptide comprises an N77A substitution. In some cases, the Fc polypeptide comprises an amino acid sequence having at least about 70%, at least about 75%, at least about 80%, at least about 85%, at least about 90%, at least about 95%, at least about 98%, at least about 99%, or 100%, amino acid sequence identity to the human IgG2 Fc polypeptide depicted in FIG. 5A; e.g., the Fc polypeptide comprises an amino acid sequence having at least about 70%, at least about 75%, at least about 80%, at least about 85%, at least about 90%, at least about 95%, at least about 98%, at least about 99%, or 100%, amino acid sequence identity to amino acids 99-325 of the human IgG2 Fc polypeptide depicted in FIG. 5A. In some cases, the Fc polypeptide comprises an amino acid sequence having at least about 70%, at least about 75%, at least about 80%, at least about 85%, at least about 90%, at least about 95%, at least about 98%, at least about 99%, or 100%, amino acid sequence identity to the human IgG3 Fc polypeptide depicted in FIG. 5A; e.g., the Fc polypeptide comprises an amino acid sequence having at least about 70%, at least about 75%, at least about 80%, at least about 85%, at least about 90%, at least about 95%, at least about 98%, at least about 99%, or 100%, amino acid sequence identity to amino acids 19-246 of the human IgG3 Fc polypeptide depicted in FIG. 5A. In some cases, the Fc polypeptide comprises an amino acid sequence having at least about 70%, at least about 75%, at least about 80%, at least about 85%, at least about 90%, at least about 95%, at least about 98%, at least about 99%, or 100%, amino acid sequence identity to the human IgM Fc polypeptide depicted in FIG. 5B; e.g., the Fc polypeptide comprises an amino acid sequence having at least about 70%, at least about 75%, at least about 80%, at least about 85%, at least about 90%, at least about 95%, at least about 98%, at least about 99%, or 100%, amino acid sequence identity to amino acids 1-276 to the human IgM Fc polypeptide depicted in FIG. 5B. In some cases, the Fc polypeptide comprises an amino acid sequence having at least about 70%, at least about 75%, at least about 80%, at least about 85%, at least about 90%, at least about 95%, at least about 98%, at least about 99%, or 100%, amino acid sequence identity to the human IgA Fc polypeptide depicted in FIG. 5C; e.g., the Fc polypeptide comprises an amino acid sequence having at least about 70%, at least about 75%, at least about 80%, at least about 85%, at least about 90%, at least about 95%, at least about 98%, at least about 99%, or 100%, amino acid sequence identity to amino acids 1-234 to the human IgA Fc polypeptide depicted in FIG. 5C.

In some cases, the Fc polypeptide comprises an amino acid sequence having at least about 70%, at least about 75%, at least about 80%, at least about 85%, at least about 90%, at least about 95%, at least about 98%, at least about 99%, or 100%, amino acid sequence identity to the human IgG4 Fc polypeptide depicted in FIG. 5C. In some cases, the Fc polypeptide comprises an amino acid sequence having at least about 70%, at least about 75%, at least about 80%, at least about 85%, at least about 90%, at least about 95%, at least about 98%, at least about 99%, or 100%, amino acid sequence identity to amino acids 100 to 327 of the human IgG4 Fc polypeptide depicted in FIG. 5C.

In some cases, the IgG4 Fc polypeptide comprises the following amino acid sequence:

```
                                          (SEQ ID NO: 365)
PPCPSCPAPEFLGGPSVFLFPPKPKDTLMISRTPEVTCVVVDVSQEDPEV

QFNWYVDGVEVHNAKTKPREEQFNSTYRVVSVLTVLHQDWLNGKEYKCKV

SNKGLPSSIEKTISKAKGQPREPQVYTLPPSQEEMTKNQVSLTCLVKGFY
```

-continued

```
PSDIAVEWESNGQPENNYKTTPPVLDSDGSFFLYSRLTVDKSRWQEGNVF

SCSVMHEALHNHYTQKSLSLSPG.
```

In some cases, the Fc polypeptide present in a TMMP comprises the amino acid sequence depicted in FIG. 5A (human IgG1 Fc). In some cases, the Fc polypeptide present in a TMMP comprises the amino acid sequence depicted in FIG. 5A (human IgG1 Fc), except for a substitution of N297 (N77 of the amino acid sequence depicted in FIG. 5A) with an amino acid other than asparagine. In some cases, the Fc polypeptide present in a TMMP comprises the amino acid sequence depicted in FIG. 5C (human IgG1 Fc comprising an N297A substitution, which is N77 of the amino acid sequence depicted in FIG. 5A). In some cases, the Fc polypeptide present in a TMMP comprises the amino acid sequence depicted in FIG. 5A (human IgG1 Fc), except for a substitution of L234 (L14 of the amino acid sequence depicted in FIG. 5A) with an amino acid other than leucine. In some cases, the Fc polypeptide present in a TMMP comprises the amino acid sequence depicted in FIG. 5A (human IgG1 Fc), except for a substitution of L235 (L15 of the amino acid sequence depicted in FIG. 5A) with an amino acid other than leucine. In some cases, the IgG1 Fc polypeptide comprises the C-terminal Lys depicted in FIG. 5A. In other cases, the IgG1 Fc polypeptide does not include the C-terminal Lys depicted in FIG. 5A.

In some cases, the Fc polypeptide present in a TMMP comprises the amino acid sequence depicted in FIG. 5E. In some cases, the Fc polypeptide comprises the amino acid sequence depicted in FIG. 5E, but without the C-terminal Lys. In some cases, the Fc polypeptide present in a TMMP comprises the amino acid sequence depicted in FIG. 5F. In some cases, the Fc polypeptide comprises the amino acid sequence depicted in FIG. 5F, but without the C-terminal Lys. In some cases, the Fc polypeptide present in a TMMP comprises the amino acid sequence depicted in FIG. 5G (human IgG1 Fc comprising an L234A substitution and an L235A substitution, corresponding to positions 14 and 15 of the amino acid sequence depicted in FIG. 5G). In some cases, the Fc polypeptide comprises the amino acid sequence depicted in FIG. 5G, but without the C-terminal Lys. In some cases, the Fc polypeptide present in a TMMP comprises the amino acid sequence depicted in FIG. 5A (human IgG1 Fc), except for a substitution of P331 (P111 of the amino acid sequence depicted in FIG. 5A) with an amino acid other than proline; in some cases, the substitution is a P331S substitution. In some cases, the Fc polypeptide present in a TMMP comprises the amino acid sequence depicted in FIG. 5A (human IgG1 Fc), except for substitutions at L234 and L235 (L14 and L15 of the amino acid sequence depicted in FIG. 5A) with amino acids other than leucine. In some cases, the Fc polypeptide present in a TMMP comprises the amino acid sequence depicted in FIG. 5A (human IgG1 Fc), except for substitutions at L234 and L235 (L14 and L15 of the amino acid sequence depicted in FIG. 5A) with amino acids other than leucine, and a substitution of P331 (P111 of the amino acid sequence depicted in FIG. 5A) with an amino acid other than proline. In some cases, the Fc polypeptide present in a TMMP comprises the amino acid sequence depicted in FIG. 5E (human IgG1 Fc comprising L234F, L235E, and P331S substitutions (corresponding to amino acid positions 14, 15, and 111 of the amino acid sequence depicted in FIG. 5E). In some cases, the Fc polypeptide present in a TMMP is an IgG1 Fc polypeptide that comprises L234A and L235A substitutions (substitutions of L14 and L15 of the amino acid sequence depicted in FIG. 5A with Ala), as depicted in FIG. 5G.

In some cases, the Fc polypeptide present in a TMMP has the following amino acid sequence: DKTHTCPPCPA-PEAAGGPSVFLFPPKPKDTLMISRTPE-VTCVVVDVSHEDPEVKFNWYVDGVEV HNAKTKPREEQYN-STYRVVSVLTVLHQDWLNGKEYKCKVSNKALPA-PIEKTISKAKGQPREPQ VYTLPPSREEMTKNQVSLT-CLVKGFYPSDIAVEWESNGQPENNYKTTPPVLDSDGS FFLYSKLT VDKSRWQQGNVFSCSVMHEALHN-HYTQKSLSLSPG (SEQ ID NO:489); and has a length of 226 amino acids.

Linkers

A TMMP of the present disclosure can include one or more linkers, where the one or more linkers are between one or more of: i) an MHC Class I polypeptide and an Ig Fc polypeptide, where such a linker is referred to herein as "L1"; ii) a MOD and an MHC Class I polypeptide, where such a linker is referred to herein as "L2"; iii) a first MOD and a second MOD, where such a linker is referred to herein as "L3"; iv) a peptide antigen ("epitope") and an MHC Class I polypeptide; v) an MHC Class I polypeptide and a dimerization polypeptide (e.g., a first or a second member of a dimerizing pair); and vi) a dimerization polypeptide (e.g., a first or a second member of a dimerizing pair) and an Ig Fc polypeptide.

As used herein, the phrase "a peptide linker between any two of the components of a TMMP" refers to a peptide linker between any two adjacent polypeptides within the TMMP. For example, as used herein, the phrase "a peptide linker between any two of the components of a TMMP" refers to a peptide linker between one or more of: i) a peptide and a β2M polypeptide; ii) a β2M polypeptide and an MHC class I heavy chain polypeptide; iii) an MHC class I heavy chain polypeptide and an Ig Fc polypeptide; iv) an MHC class I heavy chain polypeptide and a MOD; v) an Ig Fc polypeptide and a MOD; and vi) a first MOD and a second MOD.

Suitable linkers (also referred to as "spacers") can be readily selected and can be of any of a number of suitable lengths, such as from 1 amino acid to 25 amino acids, from 3 amino acids to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids. A suitable linker can be 1, 2, 3, 4, 5, 6, 7, 8, 9, 10, 11, 12, 13, 14, 15, 16, 17, 18, 19, 20, 21, 22, 23, 24, or 25 amino acids in length. In some cases, a linker has a length of from 25 amino acids to 50 amino acids, e.g., from 25 to 30, from 30 to 35, from 35 to 40, from 40 to 45, or from 45 to 50 amino acids in length.

Exemplary linkers include glycine polymers $(G)_n$, glycine-serine polymers (including, for example, $(GS)_n$, $(GSGGS)_n$ (SEQ ID NO:366) and $(GGGS)_n$ (SEQ ID NO:367), where n is an integer of at least one), glycine-alanine polymers, alanine-serine polymers, and other flexible linkers known in the art. Glycine and glycine-serine polymers can be used; both Gly and Ser are relatively unstructured, and therefore can serve as a neutral tether between components. Glycine polymers can be used; glycine accesses significantly more phi-psi space than even alanine, and is much less restricted than residues with longer side chains (see Scheraga, *Rev. Computational Chem.* 11173-142 (1992)). Exemplary linkers can comprise amino acid sequences including, but not limited to, GGSG (SEQ ID NO:368), GGSGG (SEQ ID NO:369), GSGSG (SEQ ID NO:370), GSGGG (SEQ ID NO:371), GGGSG (SEQ ID NO:372), GSSSG (SEQ ID NO:373), and the like. Exemplary linkers can include, e.g., Gly(Ser$_4$)n (SEQ ID NO:374), where n is 1, 2, 3, 4, 5, 6, 7, 8, 9, or 10. In some cases, a linker comprises the amino acid sequence (GSSSS)n (SEQ ID NO:375), where n is 4. In some cases, a linker comprises the amino acid sequence (GSSSS)n (SEQ ID NO:376), where n is 5. In some cases, a linker comprises the amino acid sequence (GGGGS)n (SEQ ID NO:377), where n is 1. In some cases, a linker comprises the amino acid sequence (GGGGS)n (SEQ ID NO:378), where n is 2. In some cases, a linker comprises the amino acid sequence (GGGGS)n (SEQ ID NO:379), where n is 3. In some cases, a linker comprises the amino acid sequence (GGGGS)n (SEQ ID NO:380), where n is 4. In some cases, a linker comprises the amino acid sequence (GGGGS)n (SEQ ID NO:381), where n is 5. In some cases, a linker comprises the amino acid sequence (GGGGS)n (SEQ ID NO:382), where n is 6. In some cases, a linker comprises the amino acid sequence (GGGGS)n (SEQ ID NO:383), where n is 7, In some cases, a linker comprises the amino acid sequence (GGGGS)n (SEQ ID NO:384), where n is 8, In some cases, a linker comprises the amino acid sequence (GGGGS)n (SEQ ID NO:385), where n is 9, In some cases, a linker comprises the amino acid sequence (GGGGS)n (SEQ ID NO:386), where n is 10. In some cases, a linker comprises the amino acid sequence AAAGG (SEQ ID NO:283).

In some cases, a linker polypeptide, present in a first polypeptide of a TMMP, includes a cysteine residue that can form a disulfide bond with a cysteine residue present in a second polypeptide of a TMMP. In some cases, for example, a suitable linker comprises the amino acid sequence GCGGSGGGGSGGGGS (SEQ ID NO:317). As another example, a suitable linker can comprise the amino acid sequence GCGGS(G4S)n (SEQ ID NO:315), where n is 1, 2, 3, 4, 5, 6, 7, 8, or 9. For example, in some cases, the linker comprises the amino acid sequence GCGGSGGGGSGGGGSGGGGS (SEQ ID NO:316). As another example, the linker comprises the amino acid sequence GCGGSGGGGSGGGGS (SEQ ID NO:317).

Epitopes

In some cases, an epitope (a peptide presenting one or more epitopes) present in a TMMP is a WT-1 peptide, e.g., a WT-1 peptide that, together with MHC, presents an epitope to a TCR Amino acid sequences of WT-1 isoforms are presented in FIG. 3A-3E. A WT-1 peptide that presents one or more epitopes is referred to herein as a "WT-1 peptide" or a "WT-1 epitope." In some cases, a WT-1 epitope present in a TMMP of the present disclosure can be a peptide of from 4 to 25 contiguous amino acids (e.g., 4 amino acids (aa), 5 aa, 6 aa, 7 aa, 8 aa, 9 aa, 10-15 aa, 15-20 aa, or 20-25 aa) of an amino acid sequence having at least 90%, at least 95%, at least 98%, at least 99%, or 100%, amino acid sequence identity to the WT-1 amino acid sequence depicted in any one of FIG. 3A-3E. In some cases, a WT-1 epitope present in a TMMP of the present disclosure can be a peptide of from 4 to 25 contiguous amino acids (e.g., 4 amino acids (aa), 5 aa, 6 aa, 7 aa, 8 aa, 9 aa, 10-15 aa, 15-20 aa, or 20-25 aa) of an amino acid sequence having at least 90%, at least 95%, at least 98%, at least 99%, or 100%, amino acid sequence identity to the WT-1 amino acid sequence depicted in FIG. 3A. In some cases, a WT-1 epitope present in a TMMP can be a peptide of from 4 to 25 contiguous amino acids (e.g., 4 amino acids (aa), 5 aa, 6 aa, 7 aa, 8 aa, 9 aa, 10-15 aa, 15-20 aa, or 20-25 aa) of an amino acid sequence having at least 90%, at least 95%, at least 98%, at least 99%, or 100%, amino acid sequence identity to the WT-1 amino acid sequence depicted in FIG. 3B. In some cases, a WT-1 epitope present in a TMMP of the present disclosure can be a peptide of from 4 to 25 contiguous amino acids (e.g., 4 amino acids (aa), 5 aa, 6 aa, 7 aa, 8 aa, 9 aa, 10-15 aa, 15-20 aa, or 20-25 aa) of an amino acid sequence having at least 90%, at least 95%, at least 98%, at least 99%, or 100%, amino acid sequence identity to the WT-1 amino acid sequence depicted in FIG. 3C. In some cases, a WT-1 epitope present in a TMMP can be a peptide of from 4 to 25 contiguous amino acids (e.g., 4 amino acids (aa), 5 aa, 6 aa, 7 aa, 8 aa, 9 aa, 10-15 aa, 15-20 aa, or 20-25 aa) of an amino acid sequence having at least 90%, at least 95%, at least 98%, at least 99%, or 100%, amino acid sequence identity to the WT-1 amino acid sequence depicted in FIG. 3D. In some cases, a WT-1 epitope present in a TMMP of the present disclosure can be a peptide of from 4 to 25 contiguous amino acids (e.g., 4 amino acids (aa), 5 aa, 6 aa, 7 aa, 8 aa, 9 aa, 10-15 aa, 15-20 aa, or 20-25 aa) of an amino acid sequence having at least 90%, at least 95%, at least 98%, at least 99%, or 100%, amino acid sequence identity to the WT-1 amino acid sequence depicted in FIG. 3E. In some cases, a WT-1 epitope present in a TMMP is 6 amino acids in length. In some cases, a WT-1 epitope present in a TMMP is 7 amino acids in length. In some cases, a WT-1 epitope present in a TMMP is 8 amino acids in length. In some cases, a WT-1 epitope present in a TMMP is 9 amino acids in length. In some cases, a WT-1 epitope present in a TMMP is 10 amino acids in length. In some cases, a WT-1 epitope present in a TMMP is 11 amino acids in length. In some cases, a WT-1 epitope present in a TMMP is from 6 amino acids to 25 amino acids in length. In some cases, a WT-1 epitope present in a TMMP is from 6 amino acids to 20 amino acids in length. In some cases, a WT-1 epitope present in a TMMP is from 7 amino acids to 25 amino acids in length. In some cases, a WT-1 epitope present in a TMMP is from 7 amino acids to 20 amino acids in length. In some cases, a WT-1 epitope present in a TMMP is at least 4 amino acids in length, at least 6 amino acids in length, or at least 7 amino acids in length.

An epitope present in a TMMP can have a length of from about 4 amino acids to about 25 amino acids, e.g., the epitope can have a length of from 4 amino acids (aa) to 10 aa, from 10 aa to 15 aa, from 15 aa to 20 aa, or from 20 aa to 25 aa. For example, an epitope present in a TMMP can have a length of 4 amino acids (aa), 5 aa, 6 aa, 7, aa, 8 aa, 9 aa, 10 aa, 11 aa, 12 aa, 13 aa, 14 aa, 15 aa, 16 aa, 17 aa, 18 aa, 19 aa, 20 aa, 21 aa, 22 aa, 23 aa, 24 aa, or 25 aa. In some cases, an epitope present in a TMMP has a length of from 5 amino acids to 10 amino acids, e.g., 5 aa, 6 aa, 7 aa, 8 aa, 9 aa, or 10 aa.

A WT-1 epitope present in a TMMP is a peptide specifically bound by a T-cell, i.e., the epitope is specifically bound by a WT-1 epitope-specific T cell. An epitope-specific T cell binds an epitope having a reference amino acid sequence, but does not substantially bind an epitope that differs from the reference amino acid sequence. For example, an epitope-specific T cell binds an epitope having a reference amino acid sequence, and binds an epitope that differs from the reference amino acid sequence, if at all, with an affinity that is less than $10^{-6}$ M, less than $10^{-5}$ M, or less than $10^{-4}$ M. An epitope-specific T cell can bind an epitope for which it is specific with an affinity of at least $10^{-7}$ M, at least $10^{-8}$ M, at least $10^{-9}$ M, or at least $10^{-10}$ M.

Examples of WT-1 peptides suitable for inclusion in a TMMP include, but are not limited to, CMTWNQMNLGATLKG (SEQ ID NO:223), WNQMNLGATLKGVAA (SEQ ID NO:224), CMTWNYMNLGATLKG (SEQ ID NO:225), WNYMNLGATLKGVAA (SEQ ID NO:226), MTWNQMNLGATLKGV (SEQ ID NO:227), TWNQMNLGATLKGVA (SEQ ID NO:228), CMTWNLMNLGATLKG (SEQ ID NO:229), MTWNLMNLGATLKGV (SEQ ID NO:230), TWNLMNLGATLKGVA (SEQ ID NO:231), WNLMNLGATLKGVAA (SEQ ID NO:232), MNLGATLK (SEQ ID NO:233), MTWNYMNLGATLKGV (SEQ ID NO:234), TWNYMNLGATLKGVA (SEQ ID NO:235), CMTWNQMNLGATLKGVA (SEQ ID NO:236), CMTWNLMNLGATLKGVA (SEQ ID NO:237), CMTWNYMNLGATLKGVA (SEQ ID NO:238), GYLRNPTAC (SEQ ID NO:239), GALRNPTAL (SEQ ID NO:240), YALRNPTAC (SEQ ID NO:241), GLLRNPTAC (SEQ ID NO:242), RYRPHPGAL (SEQ ID NO:243), YQRPHPGAL (SEQ ID NO:244), RLRPHPGAL (SEQ ID NO:245), RIRPHPGAL (SEQ ID NO:246), QFPNHSFKHEDPMGQ (SEQ ID NO:247), HSFKHEDPY (SEQ ID NO:248), QFPNHSFKHEDPM (SEQ ID NO:249), QFPNHSFKHEDPY (SEQ ID NO:250), KRPFMCAYPGCNK (SEQ ID NO:251), KRPFMCAYPGCYK (SEQ ID NO:252), FMCAYPGCY (SEQ ID NO:253), FMCAYPGCK (SEQ ID NO:254), KRPFMCAYPGCNKRY (SEQ ID NO:255), SEKRPFMCAYPGCNK (SEQ ID NO:256), KRPFMCAYPGCYKRY (SEQ ID NO:257), NLMNLGATL (SEQ ID NO:258), VLDFAPPGA (SEQ ID NO:259); RMFPNAPYL (SEQ ID NO:260); CMTWNQMN (SEQ ID NO:261); CYTWNQMNL (SEQ ID NO:262); NYMNLGATL (SEQ ID NO:263); YMFPNAPYL (SEQ ID NO:264); SLGEQQYSV (SEQ ID NO:265); CMTWNQMNL (SEQ ID NO:266); and NQMNLGATL (SEQ ID NO:267). In some cases, the WT-1 peptide present in a TMMP is CMTWNQMN (SEQ ID NO:261). In some cases, the WT-1 peptide present in a TMMP is CYTWNQMNL (SEQ ID NO:262).

In some cases, the WT-1 peptide present in a TMMP presents an HLA-A*2402-restricted epitope. WT-1 peptides that present an HLA-A*2402-restricted epitope include, e.g., CMTWNQMN (SEQ ID NO:261); NYMNLGATL (SEQ ID NO:263) (WT-1 239-247; Q240Y); CYTWNQMNL (SEQ ID NO:262) (WT-1 235-243); CMTWNQMNL (SEQ ID NO:266) (WT-1 235-243); NQMNLGATL (SEQ ID NO:267) (WT-1 239-247); and NLMNLGATL (SEQ ID NO:258) (WT-1 239-247; Q240L).

In some cases, the WT-1 peptide present in a TMMP presents an HLA-A*0201-restricted epitope. WT-1 peptides that present an HLA-A*0201-restricted epitope include, e.g., VLDFAPPGA (SEQ ID NO:259) (WT-1 37-45); RMFPNAPYL (SEQ ID NO:260) (WT-1 126-134); YMFPNAPYL (SEQ ID NO:264) (WT-1 126-134; R126Y); SLGEQQYSV (SEQ ID NO:265) (WT-1 187-195); and NLMNLGATL (SEQ ID NO:258) (WT-1 239-247; Q240L).

In some cases, a WT-1 peptide present in a TMMP presents an HLA-A*2402-restricted epitope and does not have an N-terminal Cys. For example, where a WT-1 peptide comprises an N-terminal Cys, the N-terminal Cys can be replaced by a Ser. As another example, where a WT-1 peptide comprises an N-terminal Cys, a Gly can be added to the N-terminus. For example, a WT-1 peptide present in a TMMP can comprise the amino acid sequence $X_1X_2X_3$TWNQMNL (SEQ ID NO:460) or $X_2X_3$TWNQMNL (SEQ ID NO:461), where each of $X_1$, $X_2$, and $X_3$ is independently any amino acid, with the proviso that the N-terminal amino acid is not a Cys, and where the WT-1 peptide epitope has a length from 9 to 25 amino acids. In some of these embodiments, the WT-1 peptide has a length of 9 amino acids or 10 amino acids. Examples of WT-1 peptides suitable for inclusion in a TMMP include, but are not limited to, SMTWNQMNL (SEQ ID NO:451), GCMTWNQMNL (SEQ ID NO:452), SYTWNQMNL (SEQ ID NO:453), or GCYTWNQMNL (SEQ ID NO:454). In some cases, a WT-1 peptide present in a TMMP of the present disclosure has the amino acid sequence SMTWNQMNL (SEQ ID NO:451); and has a length of 9 amino acids. In some cases, a WT-1 peptide present in a TMMP has the amino acid sequence GCMTWNQMNL (SEQ ID NO:452); and has a length of 10 amino acids. In some cases, a WT-1 peptide present in a TMMP has the amino acid sequence SYTWNQMNL (SEQ ID NO:453); and has a length of 9 amino acids. In some cases, a WT-1 peptide present in a TMMP has the amino acid sequence GCYTWNQMNL (SEQ ID NO:454); and has a length of 10 amino acids.

HLA/Peptide Binding Assays

Whether a given peptide (e.g., WT-1 peptide) binds a class I HLA (comprising an HLA heavy chain and a β2M polypeptide), and, when bound to the HLA complex, can effectively present an epitope to a TCR, can be determined using any of a number of well-known methods. Assays include binding assays and T-cell activation assays.

Cell-Based Binding Assay

As one example, a cell-based peptide-induced stabilization assay can be used to determine peptide-HLA class I binding. In this assay, a peptide of interest is allowed to bind to a TAP-deficient cell, i.e., a cell that has defective transporter associated with antigen processing (TAP) machinery, and consequently, few surface class I molecules. Such cells include, e.g., the human T2 cell line (T2 (174×CEM.T2; American Type Culture Collection (ATCC) No. CRL-1992). Henderson et al. (1992) *Science* 255:1264. Without efficient TAP-mediated transport of cytosolic peptides into the endoplasmic reticulum, assembled class I complexes are structurally unstable, and retained only transiently at the cell surface. However, when T2 cells are incubated with an exogenous peptide capable of binding class I, surface peptide-HLA class I complexes are stabilized and can be detected by flow cytometry with, e.g., a pan anti-class I monoclonal antibody. The stabilization and resultant increased life-span of peptide-HLA complexes on the cell surface by the addition of a peptide validates their identity. Analysis can be carried out using flow cytometry, e.g., where the pan-HLA class I antibody comprises a fluorescent label. Binding of the peptide to various allelic forms of HLA H chains can be tested by genetically modifying the T2 cells to express an allelic HLA H chain of interest.

The following is a non-limiting example of use of a T2 assay to assess peptide binding to HLA A*0201. T2 cells are washed in cell culture medium, and concentrated to $10^6$ cells/ml. Peptides of interest are prepared in cell culture medium and serially diluted providing concentrations of 200 μM, 100 μM, 20 μM and 2 μM. The cells are mixed 1:1 with each peptide dilution to give a final volume of 200 μL and final peptide concentrations of 100 μM, 50 μM, 10 μM and 1 μM. A HLA A*0201 binding peptide, GILGFVFTL (SEQ ID NO: 395), and a non-HLA A*0201-restricted peptide, HPVGEADYF (SEQ ID NO: 396) (HLA-B*3501), are included as positive and negative controls, respectively. The cell/peptide mixtures are kept at 37° C. 5% $CO_2$ for ten minutes; then incubated at room temperature overnight. Cells are then incubated for 2 hours at 37° C. and stained with a fluorescently-labeled anti-human HLA antibody. The cells are washed twice with phosphate-buffered saline and analyzed using flow cytometry. The average mean fluorescence intensity (MFI) of the anti-HLA antibody staining is used to measure the strength of binding.

Biochemical Binding Assay

HLA polypeptides (HLA heavy chain polypeptide complexed with β2M polypeptide) can be tested for binding to a peptide of interest in a cell-free in vitro assay system. For example, a labeled reference peptide (e.g., fluorescently labeled) is allowed to bind to HLA polypeptides (HLA heavy chain polypeptide complexed with β2M polypeptide), to form an HLA-reference peptide complex. The ability of a test peptide of interest to displace the labeled reference peptide from the HLA-reference peptide complex is tested. The relative binding affinity is calculated as the amount of test peptide needed to displace the bound reference peptide. See, e.g., van der Burg et al. (1995) *Human Immunol.* 44:189.

As another example, a peptide of interest can be incubated with an HLA molecule (HLA heavy chain complexed with a β2M polypeptide), and the stabilization of the HLA/peptide complex can be measured in an immunoassay format. The ability of a peptide of interest to stabilize an HLA molecule is compared to that of a control peptide presenting a known T-cell epitope. Detection of stabilization is based on the presence or absence of the native conformation of the HLA/peptide complex, detected using an anti-HLA antibody. See, e.g., Westrop et al. (2009) *J. Immunol. Methods* 341:76; Steinitz et al. (2012) *Blood* 119:4073; and U.S. Pat. No. 9,205,144.

T-Cell Activation Assays

Whether a given peptide binds a class I HLA (comprising an HLA heavy chain and a β2M polypeptide), and, when bound to the HLA complex, can effectively present an epitope to a TCR, can be determined by assessing T-cell response to the peptide-HLA complex. T-cell responses that can be measured include, e.g., interferon-gamma (IFNγ) production, cytotoxic activity, and the like.

ELISPOT Assay

Suitable assays include, e.g., an enzyme linked immunospot (ELISPOT) assay. In this assay, production of IFNγ by $CD8^+$ T cells is measured following with an antigen-presenting cell (APC) that presents a peptide of interest complexed with HLA class I. Antibody to IFNγ is immobilized on wells of a multi-well plate. APCs are added to the wells, and incubated for a period of time with a peptide of interest, such that the peptide binds HLA class I on the surface of the APCs. $CD8^+$ T cells specific for the peptide are added to the wells, and the plate is incubated for about 24 hours. The wells are then washed, and any IFNγ bound to the immobilized anti-IFNγ antibody is detected using a detectably labeled anti-IFNγ antibody. A colorimetric assay can be used. For example, the detectably labeled anti-IFNγ antibody can be a biotin-labeled anti-IFNγ antibody, which can be detected using, e.g., streptavidin conjugated to alkaline phosphatase. A BCIP/NBT (5-bromo-4-chloro-3-indolyl phosphate/nitro blue tetrazolium) solution is added, to develop the assay. The presence of IFNγ-secreting T cells is identified by colored spots. Negative controls include APCs not contacted with the peptide. APCs expressing various HLA H chain alleles can be used to determine whether a peptide of interest effectively binds to a HLA class I molecule comprising a particular HLA H chain.

Cytotoxicity Assays

Whether a given peptide binds to a particular HLA class I H chain and, when bound to a HLA class I complex comprising the H chain, can effectively present an epitope to a TCR, can also be determined using a cytotoxicity assay. A cytotoxicity assay involves incubation of a target cell with a cytotoxic $CD8^+$ T cell. The target cell displays on its surface a peptide/HLA class I complex comprising a peptide of interest and an HLA class I molecule comprising an HLA H chain to be tested. The target cells can be radioactively labeled, e.g., with $^{51}Cr$. Whether the target cell effectively presents an epitope to a TCR on the cytotoxic $CD8^{+}$ T cell, thereby inducing cytotoxic activity by the $CD8^{+}$ T cell toward the target cell, is determined by measuring release of $^{51}Cr$ from the lysed target cell. Specific cytotoxicity can be calculated as the amount of cytotoxic activity in the presence of the peptide minus the amount of cytotoxic activity in the absence of the peptide.

Detection of Antigen-Specific T Cells with Peptide-HLA Tetramers

As another example, multimers (e.g., tetramers) of peptide-HLA complexes are generated with fluorescent or heavy metal tags. The multimers can then be used to identify and quantify specific T cells via flow cytometry (FACS) or mass cytometry (CyTOF). Detection of epitope-specific T cells provides direct evidence that the peptide-bound HLA molecule is capable of binding to a specific TCR on a subset of antigen-specific T cells. See, e.g., Klenerman et al. (2002) *Nature Reviews Immunol.* 2:263.

Immunomodulatory Polypeptides ("MODs")

In some cases, a MOD present in a TMMP is a wild-type ("wt") MOD. As discussed above, in other cases, a MOD present in a TMMP is a variant of a wt MOD that has reduced affinity for a co-MOD compared to the affinity of a corresponding wild-type MOD for the co-MOD. Suitable MODs that exhibit reduced affinity for a co-MOD can have from 1 amino acid (aa) to 20 aa differences from a wild-type MOD. For example, in some cases, a variant MOD present in a TMMP differs in amino acid sequence by 1 aa, 2 aa, 3 aa, 4 aa, 5 aa, 6 aa, 7 aa, 8 aa, 9 aa, or 10 aa, from a corresponding wild-type MOD. As another example, in some cases, a variant MOD present in a TMMP differs in amino acid sequence by 11 aa, 12 aa, 13 aa, 14 aa, 15 aa, 16 aa, 17 aa, 18 aa, 19 aa, or 20 aa, from a corresponding wild-type MOD.

As discussed above, a MOD may comprise a variant of a wt immunomodulatory polypeptide that may exhibit reduced binding to its co-MOD, including e.g., reduced binding to one or more chains or domains of the co-MOD. For example, a variant MOD present in a TMMP may bind its co-MOD with an affinity that it at least 10% less, at least 15% less, at least 20% less, at least 25% less, at least 30% less, at least 35% less, at least 40% less, at least 45% less, at least 50% less, at least 55% less, at least 60% less, at least 65% less, at least 70% less, at least 75% less, at least 80% less, at least 85% less, at least 90% less, at least 95% less, or more than 95% less, than the affinity of a corresponding wild-type MOD for the co-MOD. Exemplary pairs of immunomodulatory polypeptide and cognate co-immunomodulatory polypeptide include, but are not limited to:

a) 4-1BBL (immunomodulatory polypeptide) and 4-1BB (cognate co-immunomodulatory polypeptide);
b) PD-L1 (immunomodulatory polypeptide) and PD1 (cognate co-immunomodulatory polypeptide);
c) IL-2 (immunomodulatory polypeptide) and IL-2 receptor (cognate co-immunomodulatory polypeptide);
d) CD80 (immunomodulatory polypeptide) and CD86 (cognate co-immunomodulatory polypeptide);
e) CD86 (immunomodulatory polypeptide) and CD28 (cognate co-immunomodulatory polypeptide);
f) OX40L (CD252) (immunomodulatory polypeptide) and OX40 (CD134) (cognate co-immunomodulatory polypeptide);
g) Fas ligand (immunomodulatory polypeptide) and Fas (cognate co-immunomodulatory polypeptide);
h) ICOS-L (immunomodulatory polypeptide) and ICOS (cognate co-immunomodulatory polypeptide);
i) ICAM (immunomodulatory polypeptide) and LFA-1 (cognate co-immunomodulatory polypeptide);
j) CD30L (immunomodulatory polypeptide) and CD30 (cognate co-immunomodulatory polypeptide);
k) CD40 (immunomodulatory polypeptide) and CD40L (cognate co-immunomodulatory polypeptide);
l) CD83 (immunomodulatory polypeptide) and CD83L (cognate co-immunomodulatory polypeptide);
m) HVEM (CD270) (immunomodulatory polypeptide) and CD160 (cognate co-immunomodulatory polypeptide);
n) JAG1 (CD339) (immunomodulatory polypeptide) and Notch (cognate co-immunomodulatory polypeptide);
o) JAG1 (immunomodulatory polypeptide) and CD46 (cognate co-immunomodulatory polypeptide);
p) CD80 (immunomodulatory polypeptide) and CTLA4 (cognate co-immunomodulatory polypeptide);
q) CD86 (immunomodulatory polypeptide) and CTLA4 (cognate co-immunomodulatory polypeptide); and
r) CD70 (immunomodulatory polypeptide) and CD27 (cognate co-immunomodulatory polypeptide).

Figure 19:
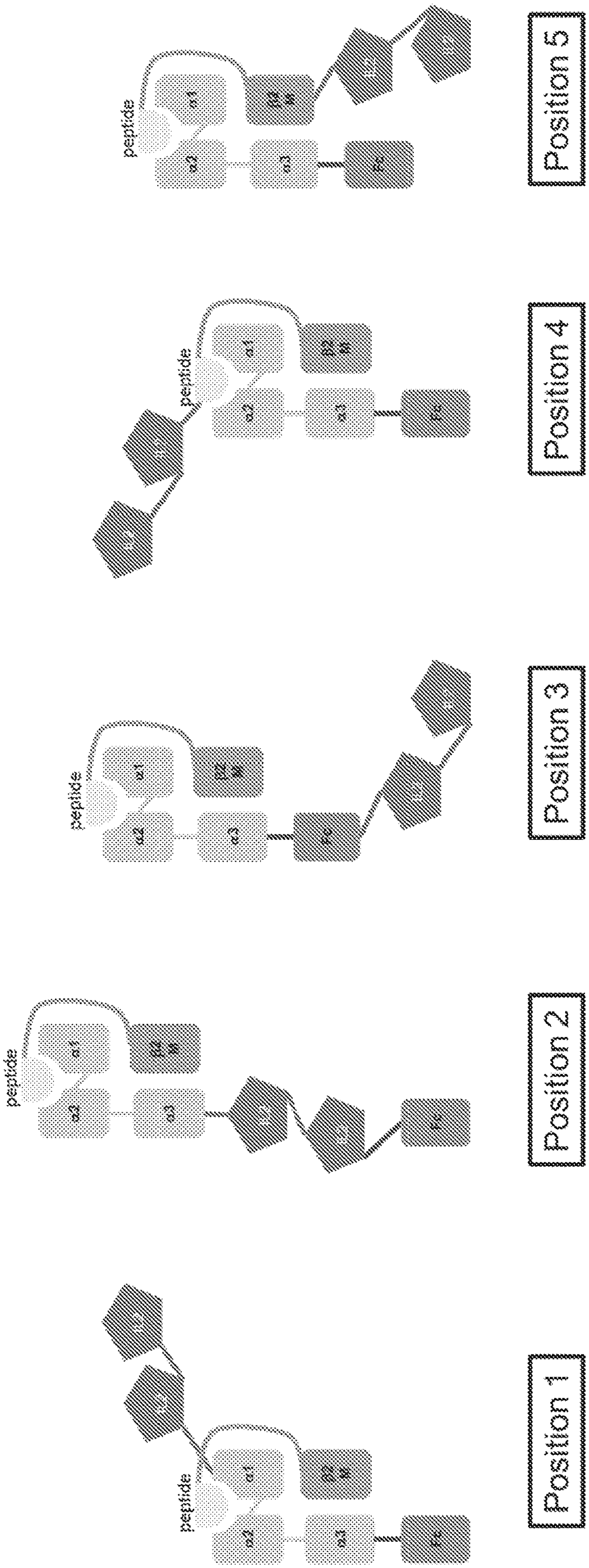
FIG. 19 provide schematic depictions of examples of positions of immunomodulatory polypeptides in TMMPs of the present disclosure.

As depicted schematically in FIG. 19, a MOD (i.e., one or more MODs) can be present in a TMMP at any of a variety of positions. FIG. 19 depicts the position of two copies of a variant IL-2 polypeptide; however, the MOD can be any of a variety of MODs, as described herein. As depicted in FIG. 19, a MOD can be: 1) N-terminal to the MHC class I heavy chain; 2) C-terminal to the MHC class I heavy chain and N-terminal to the Ig Fc polypeptide; in other words, between the MHC class I heavy chain and the Ig Fc polypeptide; 3) C-terminal to the Ig Fc polypeptide; 4) N-terminal to the peptide epitope; or 5) C-terminal to the β2M polypeptide.

PD-L1—Wild-Type and Variants

A MOD present in a TMMP can be a wild-type PD-L1 polypeptide or a variant PD-L1 polypeptide.

In some cases, a MOD present in a TMMP is a PD-L1 polypeptide. In some cases, a PD-L1 polypeptide of a TMP comprises an amino acid sequence having at least 75%, at least 80%, at least 85%, at least 90%, at least 95%, at least 98%, at least 99%, or 100%, amino acid sequence identity to a PD-L1 amino acid sequence set forth in SEQ ID NO:1, SEQ ID NO:2, or SEQ ID NO:3. PD-L1 variant MODs are described in published PCT application WO 2019/051091, published Mar. 14, 2019. See [00157]-[00169].

In some cases, a variant PD-L1 polypeptide exhibits reduced binding affinity to PD-1 (e.g., a PD-1 polypeptide comprising the amino acid sequence set forth in SEQ ID NO:3), compared to the binding affinity of a PD-L1 polypeptide comprising the amino acid sequence set forth in SEQ ID NO:1 or SEQ ID NO:2. For example, in some cases, a variant PD-L1 polypeptide of the present disclosure binds PD-1 (e.g., a PD-1 polypeptide comprising the amino acid sequence set forth in SEQ ID NO:3) with a binding affinity that is at least 10%, at least 15%, at least 20%, at least 25%, at least 30%, at least 35%, at least 40%, at least 45%, at least 50% less, at least 55% less, at least 60% less, at least 65% less, at least 70% less, at least 75% less, at least 80% less, at least 85% less, at least 90% less, at least 95% less, or more than 95% less, than the binding affinity of a PD-L1 polypeptide comprising the amino acid sequence set forth in SEQ ID NO:1, SEQ ID NO: 2 or SEQ ID NO:3.

CD80—Wild-Type and Variants

A MOD present in a TMMP can be a wild-type CD80 polypeptide or a variant CD80 polypeptide. CD80 variant MODs are described in published PCT application WO 2019/051091, published Mar. 14, 2019. See [00170]-[00196].

In some cases, a MOD present in a TMMP is a CD80 polypeptide. In some cases, a CD80 polypeptide of a TMMP comprises an amino acid sequence having at least 75%, at least 80%, at least 85%, at least 90%, at least 95%, at least 98%, at least 99%, or 100%, amino acid sequence identity to the amino acid sequence set forth in SEQ ID NO:4, SEQ ID NO:5, SEQ ID NO:6, and SEQ ID NO:7.

In some cases, a variant CD80 polypeptide exhibits reduced binding affinity to CD28, compared to the binding affinity of a CD80 polypeptide comprising the amino acid sequence set forth in SEQ ID NO:4 for CD28. For example, in some cases, a variant CD80 polypeptide binds CD28 with a binding affinity that is at least 10%, at least 15%, at least 20%, at least 25%, at least 30%, at least 35%, at least 40%, at least 45%, at least 50% less, at least 55% less, at least 60% less, at least 65% less, at least 70% less, at least 75% less, at least 80% less, at least 85% less, at least 90% less, at least 95% less, or more than 95% less, than the binding affinity of a CD80 polypeptide comprising the amino acid sequence set forth in SEQ ID NO:4 for CD28 (e.g., a CD28 polypeptide comprising the amino acid sequence set forth in one of SEQ ID NO:5, 6, or 7).

CD86—Wild-Type and Variants

A MOD present in a TMMP can be a wild-type CD86 polypeptide or a variant CD86 polypeptide. CD80 variant MODs are described in published PCT application WO 2019/051091, published Mar. 14, 2019. See [00197]-[00228].

In some cases, a MOD present in a TMMP is a CD86 polypeptide. In some cases, a CD86 polypeptide of a TMMP comprises an amino acid sequence having at least 75%, at least 80%, at least 85%, at least 90%, at least 95%, at least 98%, at least 99%, or 100%, amino acid sequence identity to a CD86 amino acid sequence set forth in SEQ ID NO:8 or SEQ ID NO:9.

4-1BBL—Wild-Type and Variants

A MOD present in a TMMP can be a wild-type 4-1BBL polypeptide or a variant 4-1BBL polypeptide. 4-1BBL variant MODs are described in published PCT application WO 2019/051091, published Mar. 14, 2019. See [00229]-[00324].

In some cases, a MOD present in a TMMP is a 4-1BBL polypeptide. In some cases, a 4-1BBL polypeptide of a TMMP comprises an amino acid sequence having at least 75%, at least 80%, at least 85%, at least 90%, at least 95%, at least 98%, at least 99%, or 100%, amino acid sequence identity to a 4-1BBL amino acid sequence set forth in SEQ ID NO:10, SEQ ID NO:11, SEQ ID NO:12, SEQ ID NO:13, or SEQ ID NO:14.

In some cases, a variant 4-1BBL polypeptide exhibits reduced binding affinity to 4-1BB, compared to the binding affinity of a 4-1BBL polypeptide comprising the amino acid sequence set forth in one of SEQ ID NOs:10-13. For example, in some cases, a variant 4-1BBL polypeptide of the present disclosure binds 4-1BB with a binding affinity that is at least 10% less, at least 15% less, at least 20% less, at least 25%, at least 30% less, at least 35% less, at least 40% less, at least 45% less, at least 50% less, at least 55% less, at least 60% less, at least 65% less, at least 70% less, at least 75% less, at least 80% less, at least 85% less, at least 90% less, at least 95% less, or more than 95% less, than the binding affinity of a 4-1BBL polypeptide comprising the amino acid sequence set forth in one of SEQ ID NOs:10-13 for a 4-1BB polypeptide (e.g., a 4-1BB polypeptide comprising the amino acid sequence set forth in SEQ ID NO:14), when assayed under the same conditions.

IL-2 Variants

In some cases, a variant MOD present in a TMMP of the present disclosure is a variant IL-2 polypeptide. Wild-type IL-2 binds to IL-2 receptor (IL-2R), i.e., a heterotrimeric polypeptide comprising IL-2Rα, IL-2Rβ, and IL-2Rγ.

A wild-type IL-2 amino acid sequence can be as follows: APTSSSTKKT QLQLEHLLLD LQMILNGINN YKNPKLTRML TFKFYMPKKA TELKHLQCLEEELKPLEEVL NLAQSKNFHL RPRDLISNIN VIVLELKGSE TTFMCEYADE TATIVE-FLNRWITFCQSIIS TLT (SEQ ID NO:15).

Wild-type IL2 binds to an IL2 receptor (IL2R) on the surface of a cell. An IL2 receptor is in some cases a heterotrimeric polypeptide comprising an alpha chain (IL-2Rα; also referred to as CD25), a beta chain (IL-2Rβ; also referred to as CD122: and a gamma chain (IL-2Rγ; also referred to as CD132). Amino acid sequences of human IL-2Rα, IL2Rβ, and IL-2Rγ can be as follows.

```
Human IL-2Rα:
                                         (SEQ ID NO: 16)
ELCDDDPPE IPHATFKAMA YKEGTMLNCE CKRGFRRIKS

GSLYMLCTGN SSHSSWDNQC QCTSSATRNT TKQVTPQPEE

QKERKTTEMQ SPMQPVDQAS LPGHCREPPP WENEATERIY

HFVVGQMVYY QCVQGYRALH RGPAESVCKM THGKTRWTQP

QLICTGEMET SQFPGEEKPQ ASPEGRPESE TSCLVTTTDF

QIQTEMAATM ETSIFTTEYQ VAVAGCVFLL ISVLLLSGLT

WQRRQRKSRR TI.

Human IL-2Rβ:
                                         (SEQ ID NO: 17)
VNG TSQFTCFYNS RANISCVWSQ DGALQDTSCQ

VHAWPDRRRW NQTCELLPVS QASWACNLIL GAPDSQKLTT

VDIVTLRVLC REGVRWRVMA IQDFKPFENL RLMAPISLQV

VHVETHRCNI SWEISQASHY FERHLEFEAR TLSPGHTWEE

APLLTLKQKQ EWICLETLTP DTQYEFQVRV KPLQGEFTTW

SPWSQPLAFR TKPAALGKDT IPWLGHLLVG LSGAFGFIIL

VYLLINCRNT GPWLKKVLKC NTPDPSKFFS QLSSEHGGDV

QKWLSSPFPS SSFSPGGLAP EISPLEVLER DKVTQLLLQQ

DKVPEPASLS SNHSLTSCFT NQGYFFFHLP DALEIEACQV

YFTYDPYSEE DPDEGVAGAP TGSSPQPLQP LSGEDDAYCT

FPSRDDLLLF SPSLLGGPSP PSTAPGGSGA GEERMPPSLQ

ERVPRDWDPQ PLGPPTPGVP DLVDFQPPPE LVLREAGEEV

PDAGPREGVS FPWSRPPGQG EFRALNARLP LNTDAYLSLQ

ELQGQDPTHL V.

Human IL-2Rγ:
                                         (SEQ ID NO: 18)
LNTTILTP NGNEDTTADF FLTTMPTDSL SVSTLPLPEV

QCFVFNVEYM NCTWNSSSEP QPTNLTLHYW YKNSDNDKVQ

KCSHYLFSEE ITSGCQLQKK EIHLYQTFVV QLQDPREPRR

QATQMLKLQN LVIPWAPENL TLHKLSESQL ELNWNNRFLN
```

-continued

```
HCLEHLVQYR TDWDHSWTEQ SVDYRHKFSL PSVDGQKRYT

FRVRSRFNPL CGSAQHWSEW SHPIHWGSNT SKENPFLFAL

EAVVISVGSM GLIISLLCVY FWLERTMPRI PTLKNLEDLV

TEYHGNFSAW SGVSKGLAES LQPDYSERLC LVSEIPPKGG

ALGEGPGASP CNQHSPYWAP PCYTLKPET.
```

In some cases, where a TMMP comprises a variant IL-2 polypeptide, a "cognate co-MOD" is an IL-2R comprising polypeptides comprising the amino acid sequences of SEQ ID NO:16, 17, and 18.

In some cases, a variant IL-2 polypeptide exhibits reduced binding affinity to IL-2R, compared to the binding affinity of a IL-2 polypeptide comprising the amino acid sequence set forth in SEQ ID NO:15. For example, in some cases, a variant IL-2 polypeptide binds IL-2R with a binding affinity that is at least 10% less, at least 15% less, at least 20% less, at least 25%, at least 30% less, at least 35% less, at least 40% less, at least 45% less, at least 50% less, at least 55% less, at least 60% less, at least 65% less, at least 70% less, at least 75% less, at least 80% less, at least 85% less, at least 90% less, at least 95% less, or more than 95% less, than the binding affinity of an IL-2 polypeptide comprising the amino acid sequence set forth in SEQ ID NO:15 for an IL-2R (e.g., an IL-2R comprising polypeptides comprising the amino acid sequence set forth in SEQ ID NOs:16-18), when assayed under the same conditions.

In some cases, a variant IL-2 polypeptide has a binding affinity to IL-2R that is from 100 nM to 100 μM. As another example, in some cases, a variant IL-2 polypeptide has a binding affinity for IL-2R (e.g., an IL-2R comprising polypeptides comprising the amino acid sequence set forth in SEQ ID NOs:16-18) that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, to about 1 μM to about 5 μM, from about 5 μM to about 10 μM, from about 10 μM to about 15 μM, from about 15 μM to about 20 μM, from about 20 μM to about 25 μM, from about 25 μM to about 50 μM, from about 50 μM to about 75 μM, or from about 75 μM to about 100 μM.

In some cases, a variant IL-2 polypeptide has a single amino acid substitution compared to the IL-2 amino acid sequence set forth in SEQ ID NO:15. In some cases, a variant IL-2 polypeptide has from 2 to 10 amino acid substitutions compared to the IL-2 amino acid sequence set forth in SEQ ID NO:15. In some cases, a variant IL-2 polypeptide has 2 amino acid substitutions compared to the IL-2 amino acid sequence set forth in SEQ ID NO:15. In some cases, a variant IL-2 polypeptide has 3 amino acid substitutions compared to the IL-2 amino acid sequence set forth in SEQ ID NO:15. In some cases, a variant IL-2 polypeptide has 4 amino acid substitutions compared to the IL-2 amino acid sequence set forth in SEQ ID NO:15. In some cases, a variant IL-2 polypeptide has 5 amino acid substitutions compared to the IL-2 amino acid sequence set forth in SEQ ID NO:15. In some cases, a variant IL-2 polypeptide has 6 amino acid substitutions compared to the IL-2 amino acid sequence set forth in SEQ ID NO:15. In some cases, a variant IL-2 polypeptide has 7 amino acid substitutions compared to the IL-2 amino acid sequence set forth in SEQ ID NO:15. In some cases, a variant IL-2 polypeptide has 8 amino acid substitutions compared to the IL-2 amino acid sequence set forth in SEQ ID NO:15. In some cases, a variant IL-2 polypeptide has 9 amino acid substitutions compared to the IL-2 amino acid sequence set forth in SEQ ID NO:15. In some cases, a variant IL-2 polypeptide has 10 amino acid substitutions compared to the IL-2 amino acid sequence set forth in SEQ ID NO:15.

Suitable IL-2 variants include a polypeptide that comprises an amino acid sequence having at least 90%, at least 95%, at least 98%, at least 99%, or 100%, amino acid sequence identity to any one of the following amino acid sequences:

APTSSSTKKT QLQLEHLLLD LQMILNGINN YKNPKLTRML TXKFYMPKKA TELKHLQCLE EELKPLEEVL NLAQSKNFHL RPRDLISNIN VIVLELKGSE TTFMCEYADE TATIVEFLNR WITFCQSIIS TLT (SEQ ID NO:181), where X is any amino acid other than Phe. In some cases, X is Ala. In some cases, X is Met. In some cases, X is Pro. In some cases, X is Ser. In some cases, X is Thr. In some cases, X is Trp. In some cases, X is Tyr. In some cases, X is Val. In some cases, X is His;

APTSSSTKKT QLQLEHLLLX LQMILNGINN YKNPKLTRML TFKFYMPKKA TELKHLQCLE EELKPLEEVL NLAQSKNFHL RPRDLISNIN VIVLELKGSE TTFMCEYADE TATIVEFLNR WITFCQSIIS TLT (SEQ ID NO:182), where X is any amino acid other than Asp. In some cases, X is Ala;

APTSSSTKKT QLQLXHLLLD LQMILNGINN YKNPKLTRML TFKFYMPKKA TELKHLQCLE EELKPLEEVL NLAQSKNFHL RPRDLISNIN VIVLELKGSE TTFMCEYADE TATIVEFLNR WITFCQSIIS TLT (SEQ ID NO:183), where X is any amino acid other than Glu. In some cases, X is Ala.

APTSSSTKKT QLQLEXLLLD LQMILNGINN YKNPKLTRML TFKFYMPKKA TELKHLQCLE EELKPLEEVL NLAQSKNFHL RPRDLISNIN VIVLELKGSE TTFMCEYADE TATIVEFLNR WITFCQSIIS TLT (SEQ ID NO:184), where X is any amino acid other than His. In some cases, X is Ala. In some cases, X is Thr. In some cases, X is Asn. In some cases, X is Cys. In some cases, X is Gln. In some cases, X is Met. In some cases, X is Val. In some cases, X is Trp;

APTSSSTKKT QLQLEXLLLD LQMILNGINN YKNPKLTRML TFKFYMPKKA TELKHLQCLE EELKPLEEVL NLAQSKNFHL RPRDLISNIN VIVLELKGSE TTFMCEYADE TATIVEFLNR WITFCQSIIS TLT (SEQ ID NO:185), where X is any amino acid other than His. In some cases, X is Ala. In some cases, X is Arg. In some cases, X is Asn. In some cases, X is Asp. In some cases, X is Cys. In some cases, X is Glu. In some cases, X is Gln. In some cases, X is Gly. In some cases, X is Ile. I n some cases, X is Lys. In some cases, X is Leu. In some cases, X is Met. In some cases, X is Phe. In some cases, X is Pro. In some cases, X is Ser. In some cases, X is Thr. In some cases, X is Tyr. In some cases, X is Trp. In some cases, X is Val;

APTSSSTKKT QLQLEHLLLD LQMILNGINN YKNPKLTRML TFKFXMPKKA TELKHLQCLE EELKPLEEVL NLAQSKNFHL RPRDLISNIN VIVLELKGSE TTFMCEYADE TATIVEFLNR WITFCQSIIS TLT (SEQ ID NO:186), where X is any amino acid other than Tyr. In some cases, X is Ala;

APTSSSTKKT QLQLEHLLLD LQMILNGINN YKNPKLTRML TFKFYMPKKA TELKHLQCLE

EELKPLEEVL NLAQSKNFHL RPRDLISNIN VIVLELKGSE TTFMCEYADE TATIVEFLNR WITFCXSIIS TLT (SEQ ID NO:187), where X is any amino acid other than Gln. In some cases, X is Ala;

APTSSSTKKT QLQLE$X_1$LLLD LQMILNGINN YKNPKLTRML T$X_2$KFYMPKKA TELKHLQCLE EELKPLEEVL NLAQSKNFHL RPRDLISNIN VIVLELKGSE TTFMCEYADE TATIVEFLNR WITFCQSIIS TLT (SEQ ID NO:188), where $X_1$ is any amino acid other than His, and where $X_2$ is any amino acid other than Phe. In some cases, $X_1$ is Ala. In some cases, $X_2$ is Ala. In some cases, $X_1$ is Ala; and $X_2$ is Ala. In some cases, $X_1$ is Thr; and $X_2$ is Ala;

APTSSSTKKT QLQLEHLLL$X_1$ LQMILNGINN YKNPKLTRML T$X_2$KFYMPKKA TELKHLQCLE EELKPLEEVL NLAQSKNFHL RPRDLISNIN VIVLELKGSE TTFMCEYADE TATIVEFLNR WITFCQSIIS TLT (SEQ ID NO:189), where $X_1$ is any amino acid other than Asp; and where $X_2$ is any amino acid other than Phe. In some cases, $X_1$ is Ala. In some cases, $X_2$ is Ala. In some cases, $X_1$ is Ala; and $X_2$ is Ala;

APTSSSTKKT QLQL$X_1$HLLL$X_2$ LQMILNGINN YKNPKLTRML T$X_3$KFYMPKKA TELKHLQCLE EELKPLEEVL NLAQSKNFHL RPRDLISNIN VIVLELKGSE TTFMCEYADE TATIVEFLNR WITFCQSIIS TLT (SEQ ID NO:190), where $X_1$ is any amino acid other than Glu; where $X_2$ is any amino acid other than Asp; and where $X_3$ is any amino acid other than Phe. In some cases, $X_1$ is Ala. In some cases, $X_2$ is Ala. In some cases, $X_3$ is Ala. In some cases, $X_1$ is Ala; $X_2$ is Ala; and $X_3$ is Ala;

APTSSSTKKT QLQLE$X_1$LLL$X_2$ LQMILNGINN YKNPKLTRML T$X_3$KFYMPKKA TELKHLQCLE EELKPLEEVL NLAQSKNFHL RPRDLISNIN VIVLELKGSE TTFMCEYADE TATIVEFLNR WITFCQSIIS TLT (SEQ ID NO:191), where $X_1$ is any amino acid other than His; where $X_2$ is any amino acid other than Asp; and where $X_3$ is any amino acid other than Phe. In some cases, $X_1$ is Ala. In some cases, $X_2$ is Ala. In some cases, $X_3$ is Ala. In some cases, $X_1$ is Ala; $X_2$ is Ala; and $X_3$ is Ala;

APTSSSTKKT QLQLEHLLL$X_1$ LQMILNGINN YKNPKLTRML T$X_2$KFYMPKKA TELKHLQCLE EELKPLEEVL NLAQSKNFHL RPRDLISNIN VIVLELKGSE TTFMCEYADE TATIVEFLNR WITFC$X_3$SIIS TLT (SEQ ID NO:192), where $X_1$ is any amino acid other than Asp; where $X_2$ is any amino acid other than Phe; and where $X_3$ is any amino acid other than Gln. In some cases, $X_1$ is Ala. In some cases, $X_2$ is Ala. In some cases, $X_3$ is Ala. In some cases, $X_1$ is Ala; $X_2$ is Ala; and $X_3$ is Ala;

APTSSSTKKT QLQLEHLLL$X_1$ LQMILNGINN YKNPKLTRML T$X_2$KF$X_3$MPKKA TELKHLQCLE EELKPLEEVL NLAQSKNFHL RPRDLISNIN VIVLELKGSE TTFMCEYADE TATIVEFLNR WITFCQSIIS TLT (SEQ ID NO:193), where $X_1$ is any amino acid other than Asp; where $X_2$ is any amino acid other than Phe; and where $X_3$ is any amino acid other than Tyr. In some cases, $X_1$ is Ala. In some cases, $X_2$ is Ala. In some cases, $X_3$ is Ala. In some cases, $X_1$ is Ala; $X_2$ is Ala; and $X_3$ is Ala;

APTSSSTKKT QLQLE$X_1$LLL$X_2$ LQMILNGINN YKNPKLTRML T$X_3$KF$X_4$MPKKA TELKHLQCLE EELKPLEEVL NLAQSKNFHL RPRDLISNIN VIVLELKGSE TTFMCEYADE TATIVEFLNR WITFCQSIIS TLT (SEQ ID NO:194), where $X_1$ is any amino acid other than His; where $X_2$ is any amino acid other than Asp; where $X_3$ is any amino acid other than Phe; and where $X_4$ is any amino acid other than Tyr. In some cases, $X_1$ is Ala. In some cases, $X_2$ is Ala. In some cases, $X_3$ is Ala. In some cases, $X_4$ is Ala. In some cases, $X_1$ is Ala; $X_2$ is Ala; $X_3$ is Ala; and $X_4$ is Ala;

APTSSSTKKT QLQLEHLLL$X_1$ LQMILNGINN YKNPKLTRML T$X_2$KF$X_3$MPKKA TELKHLQCLE EELKPLEEVL NLAQSKNFHL RPRDLISNIN VIVLELKGSE TTFMCEYADE TATIVEFLNR WITFC$X_4$SIIS TLT (SEQ ID NO:195), where $X_1$ is any amino acid other than Asp; where $X_2$ is any amino acid other than Phe; where $X_3$ is any amino acid other than Tyr; and where $X_4$ is any amino acid other than Gln. In some cases, $X_1$ is Ala. In some cases, $X_2$ is Ala. In some cases, $X_3$ is Ala. In some cases, $X_4$ is Ala. In some cases, $X_1$ is Ala; $X_2$ is Ala; $X_3$ is Ala; and $X_4$ is Ala;

APTSSSTKKT QLQLE$X_1$LLL$X_2$ LQMILNGINN YKNPKLTRML T$X_3$KF$X_4$MPKKA TELKHLQCLE EELKPLEEVL NLAQSKNFHL RPRDLISNIN VIVLELKGSE TTFMCEYADE TATIVEFLNR WITFC$X_5$SIIS TLT (SEQ ID NO:196), where $X_1$ is any amino acid other than His; where $X_2$ is any amino acid other than Asp; where $X_3$ is any amino acid other than Phe; where $X_4$ is any amino acid other than Tyr; and where $X_5$ is any amino acid other than Gln. In some cases, $X_1$ is Ala. In some cases, $X_2$ is Ala. In some cases, $X_3$ is Ala. In some cases, $X_4$ is Ala. In some cases, $X_5$ is Ala. In some cases, $X_1$ is Ala; $X_2$ is Ala; $X_3$ is Ala; $X_4$ is Ala; $X_5$ is Ala; and APTSSSTKKT QLQLE$X_1$LLLD LQMILNGINN YKNPKLTRML T$X_2$KFYMPKKA TELKHLQCLE EELKPLEEVL NLAQSKNFHL RPRDLISNIN VIVLELKGSE TTFMCEYADE TATIVEFLNR WITFC$X_3$SIIS TLT (SEQ ID NO:197), where $X_1$ is any amino acid other than His; where $X_2$ is any amino acid other than Phe; and where $X_3$ is any amino acid other than Gln. In some cases, $X_1$ is Ala. In some cases, $X_2$ is Ala. In some cases, $X_3$ is Ala. In some cases, $X_1$ is Ala; $X_2$ is Ala; and $X_3$ is Ala.

In some cases, a suitable variant IL-2 polypeptide comprises an amino acid sequence having at least 90%, at least 95%, at least 98%, at least 99%, or 100% amino acid sequence identity to the amino acid sequence: APTSSSTKKT QLQLEALLLD LQMILNGINN YKNPKLTRML TAKFYMPKKA TELKHLQCLEEELKPLEEVL NLAQSKNFHL RPRDLISNIN VIVLELKGSE TTFMCEYADE TATIVEFLNRWITFCQSIIS TLT (SEQ ID NO:490), i.e., the variant IL-2 polypeptide has the amino acid sequence of wild-type IL-2 but with H16A and F42A substitutions (shown in bold). Alternatively, the foregoing sequence, but with substitutions other than Ala at H16 and/or F42 may be employed, e.g., H16T may be employed instead of H16A. In some cases, a variant IL-2 polypeptide present in a TMP comprises the amino acid sequence: APTSSSTKKT QLQLEALLLD LQMILNGINN YKNPKLTRML TAKFYMPKKA TELKHLQCLEEELKPLEEVL NLAQSKNFHL RPRDLISNIN VIVLELKGSE TTFMCEYADE TATIVEFLNRWITFCQSIIS TLT (SEQ ID NO:490). In some cases, a variant IL-2 polypeptide present in a TMMP comprises the amino acid sequence: APTSSSTKKT QLQLETLLLD LQMILNGINN YKNPKLTRML TAKFYMPKKA TELKHLQCLEEELKPLEEVL NLAQSKNFHL RPRDLISNIN VIVLELKGSE TTFMCEYADE TATIVEFLNRWITFCQSIIS TLT (SEQ ID NO:491). In some cases, a M comprises two copies of such a variant IL-2 polypeptide.

Additional Polypeptides

A polypeptide chain of a TMMP of the present disclosure can include one or more polypeptides in addition to those described above. Suitable additional polypeptides include epitope tags and affinity domains. The one or more additional polypeptide can be included at the N-terminus of a polypeptide chain of a TMMP, at the C-terminus of a polypeptide chain of a TMMP, or internally within a polypeptide chain of a TMMP.

Epitope Tag

Suitable epitope tags include, but are not limited to, hemagglutinin (HA; e.g., YPYDVPDYA (SEQ ID NO:271); FLAG (e.g., DYKDDDDK (SEQ ID NO:272); c-myc (e.g., EQKLISEEDL; SEQ ID NO:273), and the like.

Affinity Domain

Affinity domains include peptide sequences that can interact with a binding partner, e.g., such as one immobilized on a solid support, useful for identification or purification. DNA sequences encoding multiple consecutive single amino acids, such as histidine, when fused to the expressed protein, may be used for one-step purification of the recombinant protein by high affinity binding to a resin column, such as nickel sepharose. Exemplary affinity domains are provided in published PCT application WO 2019/051091, published Mar. 14, 2019. See [00355].

Drug Conjugates

A polypeptide chain of a TMMP of the present disclosure can comprise a small molecule drug linked (e.g., covalently attached) to the polypeptide chain. For example, where a TMMP of the present disclosure comprises an Fc polypeptide, the Fc polypeptide can comprise a covalently linked small molecule drug. In some cases, the small molecule drug is a cancer chemotherapeutic agent, e.g., a cytotoxic agent. Disclosures of such drug conjugates and suitable chemotherapeutic agents are provided in published PCT application WO 2019/051091, published Mar. 14, 2019. See [00356]-[00363].

Exemplary TMMPs

A TMMP of the present disclosure comprises at least one heterodimer comprising: a) a first polypeptide comprising: i) a WT-1 peptide epitope; and ii) first MHC polypeptide; b) a second polypeptide comprising a second MHC polypeptide, and c) at least one MOD, where the first and/or the second polypeptide comprises the MOD. Thus, in some cases, a TMMP comprises at least one heterodimer comprising: a) a first polypeptide comprising: i) a WT-1 peptide epitope; ii) first MHC polypeptide; and iii) at least one MOD; and b) a second polypeptide comprising a second MHC polypeptide. In other instances, a TMMP comprises at least one heterodimer comprising: a) a first polypeptide comprising: i) a WT-1 peptide epitope; and ii) first MHC polypeptide; and b) a second polypeptide comprising: i) a second MHC polypeptide; and ii) at least one MOD. In some cases, a TMMP comprises at least one heterodimer comprising: a) a first polypeptide comprising: i) a WT-1 peptide epitope; ii) first MHC polypeptide; and iii) at least one MOD; and b) a second polypeptide comprising: i) a second MHC polypeptide; and ii) at least one MOD. In some cases, the at least one MOD is a wild-type immunomodulatory polypeptide. In other cases, the at least one MOD is a variant MOD that exhibits reduced affinity for a co-immunomodulatory polypeptide, compared to the affinity of a corresponding wild-type MOD for the co-immunomodulatory polypeptide. In some cases, a TMMP comprises two MODs, where the two MODs have the same amino acid sequence.

In some cases, a TMMP comprises: a) a first polypeptide comprising, in order from N-terminus to C-terminus: i) a WT-1 peptide epitope; ii) a first MHC polypeptide; and iii) at least one MOD; and b) a second polypeptide comprising, in order from N-terminus to C-terminus: i) a second MHC polypeptide; and ii) an Ig Fc polypeptide. In some cases, the first MHC polypeptide is a $\beta$2M polypeptide; and the second MHC polypeptide is an HLA heavy chain polypeptide. In some cases, the HLA heavy chain polypeptide is an HLA-A24 polypeptide. In some cases, the HLA heavy chain polypeptide is an HLA-A24 polypeptide with a Y84C substitution. In some cases, the HLA heavy chain polypeptide is an HLA-A24 polypeptide with a Y84C substitution and an Ala at position 236. In some cases, the HLA heavy chain polypeptide is an HLA-A24 polypeptide with a Y84A substitution. In some cases, the HLA heavy chain polypeptide is an HLA-A24 polypeptide with a Y84A substitution and an A236C substitution. In some cases, the HLA heavy chain polypeptide is an HLA-A24 polypeptide with a Y84C substitution and an A236C substitution. In some cases, the $\beta$2M polypeptide comprises an Arg at position 12 (R12). In some cases, the $\beta$2M polypeptide comprises an R12C substitution. In some cases, the HLA heavy chain polypeptide is an HLA-A24 polypeptide with an A236C substitution. In some cases, the first polypeptide comprises, in order from N-terminus to C-terminus: i) a WT-1 peptide epitope; ii) a first MHC polypeptide; and iii) two MODs, where the two MODs have the same amino acid sequence. In some cases, the Ig Fc polypeptide is a human IgG1 Fc polypeptide. In some cases, the Ig Fc polypeptide is an IgG1 Fc polypeptide comprising L234A and L235A substitutions. In some cases, the first and the second polypeptides are disulfide linked to one another. In some cases, the MOD is a variant IL-2 polypeptide comprising H16A and F42A substitutions. In some cases, the MOD is a variant IL-2 polypeptide comprising H16T and F42A substitutions. In some cases, a peptide linker is between one or more of: i) the second MHC polypeptide and the Ig Fc polypeptide; ii) the epitope and the first MHC polypeptide; iii) the first MHC polypeptide and the MOD; and (where the TMMP comprises two MODs on the first polypeptide chain) iv) between the two MODs. In some cases, the peptide linker comprises the amino acid sequence AAAGG (SEQ ID NO: 283). In some cases, the peptide linker comprises the amino acid sequence (GGGGS)n (SEQ ID NO: 284), where n is an integer from 1 to 10 (e.g., where n is 2, 3, or 4). In some cases, the peptide linker comprises the amino acid sequence GCGGS (GGGGS)n (SEQ ID NO:319), where n is an integer from 1 to 9 (e.g., where n is 2, 3, or 4). In some cases, the WT-1 peptide epitope is CMTWNQMN (SEQ ID NO: 261). In some cases, the WT-1 peptide epitope is CYTWNQMNL (SEQ ID NO: 262). In some cases, the WT-1 peptide epitope is SMTWNQMNL (SEQ ID NO:451). In some cases, the WT-1 peptide epitope is GCMTWNQMNL (SEQ ID NO:452). In some cases, the WT-1 peptide epitope is SYTWNQMNL (SEQ ID NO:453). In some cases, the WT-1 peptide epitope is GCYTWNQMNL (SEQ ID NO:454).

In some cases, a TMMP comprises: a) a first polypeptide comprising, in order from N-terminus to C-terminus: i) a WT-1 peptide epitope; and ii) a first MHC polypeptide; and b) a second polypeptide comprising, in order from N-terminus to C-terminus: i) at least one MOD; ii) a second MHC polypeptide; and iii) an Ig Fc polypeptide. In some cases, the first MHC polypeptide is a $\beta$2M polypeptide; and the second MHC polypeptide is an HLA heavy chain polypeptide. In some cases, the HLA heavy chain polypeptide is an HLA-A24 polypeptide. In some cases, the HLA heavy chain polypeptide is an HLA-A24 polypeptide with an A236C substitution. In some cases, the HLA heavy chain polypeptide is an HLA-A24 polypeptide with a Y84C substitution. In some cases, the HLA heavy chain polypeptide is an HLA-A24 polypeptide with a Y84C substitution and an Ala at position 236. In some cases, the HLA heavy chain polypeptide is an HLA-A24 polypeptide with a Y84A substitution. In some cases, the HLA heavy chain polypeptide is an HLA-A24 polypeptide with a Y84A substitution and an A236C substitution. In some cases, the HLA heavy chain polypeptide is an HLA-A24 polypeptide with a Y84C substitution and an A236C substitution. In some cases, the β2M polypeptide comprises an Arg at position 12 (R12). In some cases, the β2M polypeptide comprises an R12C substitution. In some cases, the second polypeptide comprises, in order from N-terminus to C-terminus: i) two MODs, where the two MODs have the same amino acid sequence; ii) a second MHC polypeptide; and iii) an Ig Fc polypeptide. In some cases, the Ig Fc polypeptide is a human IgG1 Fc polypeptide. In some cases, the Ig Fc polypeptide is an IgG1 Fc polypeptide comprising L234A and L235A substitutions. In some cases, the first and the second polypeptides are disulfide linked to one another. In some cases, the MOD is a variant IL-2 polypeptide comprising H16A and F42A substitutions. In some cases, the MOD is a variant IL-2 polypeptide comprising H16T and F42A substitutions. In some cases, a peptide linker is between one or more of: i) the second MHC polypeptide and the Ig Fc polypeptide; ii) the epitope and the first MHC polypeptide; iii) the first MHC polypeptide and the MOD; and (where the TMMP comprises two MODs on the second polypeptide chain) iv) between the two MODs. In some cases, the peptide linker comprises the amino acid sequence AAAGG (SEQ ID NO: 283). In some cases, the peptide linker comprises the amino acid sequence (GGGGS)n (SEQ ID NO: 284), where n is an integer from 1 to 10 (e.g., where n is 2, 3, or 4). In some cases, the peptide linker comprises the amino acid sequence GCGGS (GGGGS)n (SEQ ID NO:319), where n is an integer from 1 to 9 (e.g., where n is 2, 3, or 4). In some cases, the WT-1 peptide epitope is CMTWNQMN (SEQ ID NO: 261). In some cases, the WT-1 peptide epitope is CYTWNQMNL (SEQ ID NO: 262). In some cases, the WT-1 peptide epitope is SMTWNQMNL (SEQ ID NO:451). In some cases, the WT-1 peptide epitope is GCMTWNQMNL (SEQ ID NO:452). In some cases, the WT-1 peptide epitope is SYTWNQMNL (SEQ ID NO:453). In some cases, the WT-1 peptide epitope is GCYTWNQMNL (SEQ ID NO:454).

In some cases, a TMMP comprises: a) a first polypeptide comprising, in order from N-terminus to C-terminus: i) a WT-1 peptide epitope; and ii) a first MHC polypeptide; and b) a second polypeptide comprising, in order from N-terminus to C-terminus: i) a second MHC polypeptide; ii) an Ig Fc polypeptide; and iii) at least one MOD. In some cases, the first MHC polypeptide is a β2M polypeptide; and the second MHC polypeptide is an HLA heavy chain polypeptide. In some cases, the HLA heavy chain polypeptide is an HLA-A24 polypeptide. In some cases, the HLA heavy chain polypeptide is an HLA-A24 polypeptide with an A236C substitution. In some cases, the HLA heavy chain polypeptide is an HLA-A24 polypeptide with a Y84C substitution. In some cases, the HLA heavy chain polypeptide is an HLA-A24 polypeptide with a Y84C substitution and an Ala at position 236. In some cases, the HLA heavy chain polypeptide is an HLA-A24 polypeptide with a Y84A substitution. In some cases, the HLA heavy chain polypeptide is an HLA-A24 polypeptide with a Y84A substitution and an A236C substitution. In some cases, the HLA heavy chain polypeptide is an HLA-A24 polypeptide with a Y84C substitution and an A236C substitution. In some cases, the β2M polypeptide comprises an Arg at position 12 (R12). In some cases, the β2M polypeptide comprises an R12C substitution. In some cases, the second polypeptide comprises, in order from N-terminus to C-terminus: i) a second MHC polypeptide; ii) an Ig Fc polypeptide; and iii) two MODs, where the two MODs have the same amino acid sequence. In some cases, the Ig Fc polypeptide is a human IgG1 Fc polypeptide. In some cases, the Ig Fc polypeptide is an IgG1 Fc polypeptide comprising L234A and L235A substitutions. In some cases, the first and the second polypeptides are disulfide linked to one another. In some cases, the MOD is a variant IL-2 polypeptide comprising H16A and F42A substitutions. In some cases, the MOD is a variant IL-2 polypeptide comprising H16T and F42A substitutions. In some cases, a peptide linker is between one or more of: i) the second MHC polypeptide and the Ig Fc polypeptide; ii) the epitope and the first MHC polypeptide; iii) the Ig Fc polypeptide and the MOD; and (where the TMMP comprises two MODs on the second polypeptide chain) iv) between the two immunomodulatory polypeptides. In some cases, the peptide linker comprises the amino acid sequence AAAGG (SEQ ID NO: 283). In some cases, the peptide linker comprises the amino acid sequence (GGGGS)n (SEQ ID NO: 284), where n is an integer from 1 to 10 (e.g., where n is 2, 3, or 4). In some cases, the peptide linker comprises the amino acid sequence GCGGS(GGGGS)n (SEQ ID NO:319), where n is an integer from 1 to 9 (e.g., where n is 2, 3, or 4). In some cases, the WT-1 peptide epitope is CMTWNQMN (SEQ ID NO: 261). In some cases, the WT-1 peptide epitope is CYTWNQMNL (SEQ ID NO: 262). In some cases, the WT-1 peptide epitope is SMTWNQMNL (SEQ ID NO:451). In some cases, the WT-1 peptide epitope is GCMTWNQMNL (SEQ ID NO:452). In some cases, the WT-1 peptide epitope is SYTWNQMNL (SEQ ID NO:453). In some cases, the WT-1 peptide epitope is GCYTWNQMNL (SEQ ID NO:454).

In some cases, a TMMP comprises: a) a first polypeptide comprising, in order from N-terminus to C-terminus: i) a WT-1 peptide epitope; and ii) a first MHC polypeptide; and b) a second polypeptide comprising, in order from N-terminus to C-terminus: i) at least one MOD; ii) a second MHC polypeptide; and iii) an Ig Fc polypeptide. In some cases, the first MHC polypeptide is a β2M polypeptide; and the second MHC polypeptide is an HLA heavy chain polypeptide. In some cases, the HLA heavy chain polypeptide is an HLA-A24 polypeptide. In some cases, the HLA heavy chain polypeptide is an HLA-A24 polypeptide with an A236C substitution. In some cases, the Ig Fc polypeptide is a human IgG1 Fc polypeptide. In some cases, the Ig Fc polypeptide is an IgG1 Fc polypeptide comprising L234A and L235A substitutions. In some cases, the first and the second polypeptides are disulfide linked to one another. In some cases, the MOD is a variant IL-2 polypeptide comprising H16A and F42A substitutions. In some cases, the MOD is a variant IL-2 polypeptide comprising H16T and F42A substitutions. In some cases, the WT-1 peptide epitope is CMTWNQMN (SEQ ID NO: 261). In some cases, the WT-1 peptide epitope is CYTWNQMNL (SEQ ID NO: 262).

In some cases, a TMMP comprises: a) a first polypeptide comprising, in order from N-terminus to C-terminus: i) at least one MOD; ii) a WT-1 peptide epitope; and iii) a first MHC polypeptide; and b) a second polypeptide comprising, in order from N-terminus to C-terminus: i) a second MHC polypeptide; and ii) an Ig Fc polypeptide. In some cases, the first MHC polypeptide is a β2M polypeptide; and the second MHC polypeptide is an HLA heavy chain polypeptide. In some cases, the HLA heavy chain polypeptide is an HLA- A24 polypeptide. In some cases, the HLA heavy chain polypeptide is an HLA-A24 polypeptide with an A236C substitution. In some cases, the first polypeptide comprises, in order from N-terminus to C-terminus: i) two MODs, where the two MODs have the same amino acid sequence; ii) a WT-1 peptide epitope; and iii) a first MHC polypeptide. In some cases, the Ig Fc polypeptide is a human IgG1 Fc polypeptide. In some cases, the Ig Fc polypeptide is an IgG1 Fc polypeptide comprising L234A and L235A substitutions. In some cases, the first and the second polypeptides are disulfide linked to one another. In some cases, the MOD is a variant IL-2 polypeptide comprising H16A and F42A substitutions. In some cases, the MOD is a variant IL-2 polypeptide comprising H16T and F42A substitutions. In some cases, a peptide linker is between one or more of: i) the second MHC polypeptide and the Ig Fc polypeptide; ii) the epitope and the first MHC polypeptide; iii) the MOD and the epitope; and (where the TMMP comprises two MODs on the first polypeptide chain) iv) between the two MODs. In some cases, the peptide linker comprises the amino acid sequence AAAGG (SEQ ID NO: 283). In some cases, the peptide linker comprises the amino acid sequence (GGGGS)n (SEQ ID NO: 284), where n is an integer from 1 to 10 (e.g., where n is 2, 3, or 4). In some cases, the WT-1 peptide epitope is CMTWNQMN (SEQ ID NO: 261). In some cases, the WT-1 peptide epitope is CYTWNQMNL (SEQ ID NO: 262).

In some cases, a TMMP comprises: a) a first polypeptide comprising, in order from N-terminus to C-terminus: i) a WT-1 peptide epitope; and ii) a first MHC polypeptide; and b) a second polypeptide comprising, in order from N-terminus to C-terminus: i) a second MHC polypeptide; ii) at least one MOD; and iii) an Ig Fc polypeptide. In some cases, the first MHC polypeptide is a β2M polypeptide; and the second MHC polypeptide is an HLA heavy chain polypeptide. In some cases, the HLA heavy chain polypeptide is an HLA-A24 polypeptide. In some cases, the HLA heavy chain polypeptide is an HLA-A24 polypeptide with an A236C substitution. In some cases, the second polypeptide comprises, in order from N-terminus to C-terminus: i) a second MHC polypeptide; ii) two MODs, where the two MODs have the same amino acid sequence; and iii) an Ig Fc polypeptide. In some cases, the Ig Fc polypeptide is a human IgG1 Fc polypeptide. In some cases, the Ig Fc polypeptide is an IgG1 Fc polypeptide comprising L234A and L235A substitutions. In some cases, the first and the second polypeptides are disulfide linked to one another. In some cases, the MOD is a variant IL-2 polypeptide comprising H16A and F42A substitutions. In some cases, the MOD is a variant IL-2 polypeptide comprising H16T and F42A substitutions. In some cases, a peptide linker is between one or more of: i) the second MHC polypeptide and the MOD; ii) the MOD and the Ig Fc polypeptide; iii) the epitope and the first MHC polypeptide; iii) the first MHC polypeptide and the MOD; and (where the TMMP comprises two MODs on the second polypeptide chain) iv) between the two MODs. In some cases, the peptide linker comprises the amino acid sequence AAAGG (SEQ ID NO: 283). In some cases, the peptide linker comprises the amino acid sequence (GGGGS)n (SEQ ID NO: 284), where n is an integer from 1 to 10 (e.g., where n is 2, 3, or 4). In some cases, the WT-1 peptide epitope is CMTWNQMN (SEQ ID NO: 261). In some cases, the WT-1 peptide epitope is CYTWNQMNL (SEQ ID NO: 262).

In some cases, a TMMP comprises: a) a first polypeptide comprising, in order from N-terminus to C-terminus: i) at least one MOD; ii) a WT-1 peptide epitope; and iii) a first MHC polypeptide; and b) a second polypeptide comprising, in order from N-terminus to C-terminus: i) a second MHC polypeptide; and ii) an Ig Fc polypeptide. In some cases, the first MHC polypeptide is a β2M polypeptide; and the second MHC polypeptide is an HLA heavy chain polypeptide. In some cases, the HLA heavy chain polypeptide is an HLA-A24 polypeptide. In some cases, the HLA heavy chain polypeptide is an HLA-A24 polypeptide with an A236C substitution. In some cases, the HLA heavy chain polypeptide is an HLA-A24 polypeptide with a Y84C substitution. In some cases, the HLA heavy chain polypeptide is an HLA-A24 polypeptide with a Y84C substitution and an Ala at position 236. In some cases, the HLA heavy chain polypeptide is an HLA-A24 polypeptide with a Y84A substitution. In some cases, the HLA heavy chain polypeptide is an HLA-A24 polypeptide with a Y84A substitution and an A236C substitution. In some cases, the HLA heavy chain polypeptide is an HLA-A24 polypeptide with a Y84C substitution and an A236C substitution. In some cases, the β2M polypeptide comprises an Arg at position 12 (R12). In some cases, the β2M polypeptide comprises an R12C substitution. In some cases, the first polypeptide comprises, in order from N-terminus to C-terminus: i) two MODs, where the two MODs have the same amino acid sequence; ii) a WT-1 peptide epitope; and iii) a first MHC polypeptide. In some cases, the Ig Fc polypeptide is a human IgG1 Fc polypeptide. In some cases, the Ig Fc polypeptide is an IgG1 Fc polypeptide comprising L234A and L235A substitutions. In some cases, the first and the second polypeptides are disulfide linked to one another. In some cases, the MOD is a variant IL-2 polypeptide comprising H16A and F42A substitutions. In some cases, the MOD is a variant IL-2 polypeptide comprising H16T and F42A substitutions. In some cases, a peptide linker is between one or more of: i) the second MHC polypeptide and the Ig Fc polypeptide; ii) the epitope and the first MHC polypeptide; iii) the MOD and the epitope; and iv) (where the TMMP comprises two immunomodulatory polypeptides on the first polypeptide chain) the two MODs. In some cases, the peptide linker comprises the amino acid sequence AAAGG (SEQ ID NO:283). In some cases, the peptide linker comprises the amino acid sequence (GGGGS)n (SEQ ID NO: 284), where n is an integer from 1 to 10 (e.g., where n is 2, 3, or 4). In some cases, the peptide linker comprises the amino acid sequence GCGGS(GGGGS)n (SEQ ID NO:319), where n is an integer from 1 to 9 (e.g., where n is 2, 3, or 4). In some cases, the WT-1 peptide epitope is CMTWNQMN (SEQ ID NO: 261). In some cases, the WT-1 peptide epitope is CYTWNQMNL (SEQ ID NO: 262). In some cases, the WT-1 peptide epitope is SMTWNQMNL (SEQ ID NO:451). In some cases, the WT-1 peptide epitope is GCMTWNQMNL (SEQ ID NO:452). In some cases, the WT-1 peptide epitope is SYTWNQMNL (SEQ ID NO:453). In some cases, the WT-1 peptide epitope is GCYTWNQMNL (SEQ ID NO:454).

In some cases, a TMMP comprises: a) a first polypeptide comprising, in order from N-terminus to C-terminus: i) a WT-1 peptide epitope; and ii) a first MHC polypeptide; and b) a second polypeptide comprising, in order from N-terminus to C-terminus: i) a second MHC polypeptide; ii) at least one MOD; and iii) an Ig Fc polypeptide. In some cases, the first MHC polypeptide is a β2M polypeptide; and the second MHC polypeptide is an HLA heavy chain polypeptide. In some cases, the HLA heavy chain polypeptide is an HLA-A24 polypeptide. In some cases, the HLA heavy chain polypeptide is an HLA-A24 polypeptide with an A236C substitution. In some cases, the HLA heavy chain polypeptide is an HLA-A24 polypeptide with a Y84C substitution. In some cases, the HLA heavy chain polypeptide is an HLA-A24 polypeptide with a Y84C substitution and an Ala at position 236. In some cases, the HLA heavy chain polypeptide is an HLA-A24 polypeptide with a Y84A substitution. In some cases, the HLA heavy chain polypeptide is an HLA-A24 polypeptide with a Y84A substitution and an A236C substitution. In some cases, the HLA heavy chain polypeptide is an HLA-A24 polypeptide with a Y84C substitution and an A236C substitution. In some cases, the β2M polypeptide comprises an Arg at position 12 (R12). In some cases, the β2M polypeptide comprises an R12C substitution. In some cases, the second polypeptide comprises, in order from N-terminus to C-terminus: i) a second MHC polypeptide; ii) two MODs, where the two MODs have the same amino acid sequence; and iii) an Ig Fc polypeptide. In some cases, the Ig Fc polypeptide is a human IgG1 Fc polypeptide. In some cases, the Ig Fc polypeptide is an IgG1 Fc polypeptide comprising L234A and L235A substitutions. In some cases, the first and the second polypeptides are disulfide linked to one another. In some cases, the MOD is a variant IL-2 polypeptide comprising H16A and F42A substitutions. In some cases, the MOD is a variant IL-2 polypeptide comprising H16T and F42A substitutions. In some cases, a peptide linker is between one or more of: i) the second MHC polypeptide and the MOD; ii) the MOD and the Ig Fc polypeptide; iii) the epitope and the first MHC polypeptide; iii) the first MHC polypeptide and the MOD; and iv) (where the TMMP comprises two MODs on the second polypeptide chain) the two MODs. In some cases, the peptide linker comprises the amino acid sequence AAAGG (SEQ ID NO:283). In some cases, the peptide linker comprises the amino acid sequence (GGGGS)n (SEQ ID NO:284), where n is an integer from 1 to 10 (e.g., where n is 2, 3, or 4). In some cases, the peptide linker comprises the amino acid sequence GCGGS(GGGGS)n (SEQ ID NO:319), where n is an integer from 1 to 9 (e.g., where n is 2, 3, or 4). In some cases, the WT-1 peptide epitope is CMTWNQMN (SEQ ID NO:261). In some cases, the WT-1 peptide epitope is CYTWNQMNL (SEQ ID NO:262). In some cases, the WT-1 peptide epitope is SMTWNQMNL (SEQ ID NO:451). In some cases, the WT-1 peptide epitope is GCMTWNQMNL (SEQ ID NO:452). In some cases, the WT-1 peptide epitope is SYTWNQMNL (SEQ ID NO:453). In some cases, the WT-1 peptide epitope is GCYTWNQMNL (SEQ ID NO:454).

As noted above, and as depicted schematically in FIG. 19, an MOD (i.e., one or more MODs) can be present in a TMMP of the present disclosure at any of a variety of positions. FIG. 19 depicts the position of two copies of a variant IL-2 polypeptide; however, the MOD can be any of a variety of MODs, as described herein. As depicted in FIG. 19, a MOD can be: 1) N-terminal to the MHC class I heavy chain (position 1); 2) C-terminal to the MHC class I heavy chain and N-terminal to the Ig Fc polypeptide; in other words, between the MHC class I heavy chain and the Ig Fc polypeptide (position 2); 3) C-terminal to the Ig Fc polypeptide (position 3); 4) N-terminal to the peptide epitope (position 4); or 5) C-terminal to the β2M polypeptide (position 5). “Position 1” refers to a position of the MOD on the same polypeptide chain as the class I MHC heavy chain and N-terminal to the class I MHC heavy chain; e.g., where the TMMP comprises: a) a first polypeptide comprising, in order from N-terminus to C-terminus: i) a peptide epitope (e.g., a WT-1 peptide); and ii) a β2M polypeptide; and b) a second polypeptide comprising, in order from N-terminus to C-terminus: i) one or more MODs; and ii) a class I MHC heavy chain polypeptide. “Position 2” refers to a position of the MOD on the same polypeptide chain as the class I MHC heavy chain and C-terminal to the class I MHC heavy chain, but not at the C-terminus of the polypeptide chain; e.g., where the TMMP comprises: a) a first polypeptide comprising, in order from N-terminus to C-terminus: i) a peptide epitope (e.g., WT-1 peptide); and ii) a β2M polypeptide; and b) a second polypeptide comprising, in order from N-terminus to C-terminus: i) a class I MHC heavy chain polypeptide; ii) one or more MODs; and iii) an Ig Fc polypeptide. “Position 3” refers to a position of the MOD on the same polypeptide chain as the class I MHC heavy chain and at the C-terminus of the polypeptide chain; e.g., where the TMMP comprises: a) a first polypeptide comprising, in order from N-terminus to C-terminus: i) a peptide epitope (e.g., a WT-1 peptide); and ii) a β2M polypeptide; and b) a second polypeptide comprising, in order from N-terminus to C-terminus: i) a class I MHC heavy chain polypeptide; ii) an Ig Fc polypeptide; and iii) one or more MODs. “Position 4” refers to a position of the MOD on the same polypeptide chain as the β2M polypeptide and N-terminal to the peptide epitope and the β2M polypeptide; e.g., where the TMMP comprises: a) a first polypeptide comprising, in order from N-terminus to C-terminus: i) one or more MODs; ii) a peptide epitope (e.g., a WT-1 peptide); and iii) a β2M polypeptide; and b) a second polypeptide comprising a class I MHC heavy chain polypeptide (e.g., a second polypeptide comprising, in order from N-terminus to C-terminus: i) a class I MHC heavy chain polypeptide; and ii) an Ig Fc polypeptide. “Position 5” refers to a position of the MOD on the same polypeptide chain as the β2M polypeptide and C-terminal to the β2M polypeptide (e.g., at the C-terminus of the polypeptide chain); e.g., where the TMMP comprises: a) a first polypeptide comprising, in order from N-terminus to C-terminus: i) a peptide epitope (e.g., a WT-1 peptide); ii) a β2M polypeptide; and iii) one or more MODs; and b) a second polypeptide comprising a class I MHC heavy chain polypeptide (e.g., a second polypeptide comprising, in order from N-terminus to C-terminus: i) a class I MHC heavy chain polypeptide; and ii) an Ig Fc polypeptide.

Furthermore, as discussed above and as depicted schematically in FIG. 18A-18C, the first polypeptide chain and the second polypeptide chain of a TMMP can be linked by one or more disulfide bonds. For example, a TMMP can comprise: a) a first polypeptide chain comprising an β2M polypeptide having an R12C substitution; and b) a second polypeptide chain comprising a class I MHC heavy chain polypeptide having an A236C substitution; such that a disulfide bond forms between the Cys at position 12 of the β2M polypeptide in the first polypeptide chain and the Cys at position 236 of the class I MHC heavy chain polypeptide in the second polypeptide chain. As another example, a TMMP can comprise: a) a first polypeptide comprising, in order from N-terminus to C-terminus: i) a peptide epitope; ii) a peptide linker comprising a GCGGS(G4S)$_n$ (SEQ ID NO:315) sequence, where n is 1, 2, or 3; and iii) a β2M polypeptide; and b) a second polypeptide comprising a class I MHC heavy chain polypeptide having a Y84C substitution, such that a disulfide bond forms between the Cys in the peptide linker in the first polypeptide chain and the Cys at position 84 of the class I MHC heavy chain polypeptide in the second polypeptide chain. In other examples, a TMMP can comprise: a) a first polypeptide comprising, in order from N-terminus to C-terminus: i) a peptide epitope; ii) a peptide linker comprising a GCGGS(G4S)$_n$ (SEQ ID NO:315) sequence, where n is 1, 2, or 3; and iii) a β2M polypeptide having an R12C substitution; and b) a second polypeptide comprising a class I MHC heavy chain polypeptide having a Y84C substitution and an A236C substitution; such that: i) a first disulfide bond forms between the Cys in the peptide linker in the first polypeptide chain and the Cys at position 84 of the class I MHC heavy chain polypeptide in the second polypeptide chain; and ii) a second disulfide bond forms between the Cys at position 12 of the β2M polypeptide in the first polypeptide chain and the Cys at position 236 of the class I MHC heavy chain polypeptide in the second polypeptide chain. For simplicity, the first disulfide bond is referred to as "G2C/Y84C"; and the second disulfide bond is referred to as "R12C/A236C." A TMMP can include: a) a G2C/Y84C disulfide bond and not an R12C/A236C disulfide bond; b) an R12C/A236C disulfide bond and not a G2C/Y84C disulfide bond; or c) a G2C/Y84C disulfide bond and an R12C/A236C disulfide bond.

A TMMP can include: a) a G2C/Y84C disulfide bond and not an R12C/A236C disulfide bond; and b) at least one immunomodulatory polypeptide at position 1. A TMMP can include: a) a G2C/Y84C disulfide bond and not an R12C/A236C disulfide bond; and b) at least one MOD at position 2. A TMMP of the present disclosure can include: a) a G2C/Y84C disulfide bond and not an R12C/A236C disulfide bond; and b) at least one MOD at position 3. A TMMP can include: a) a G2C/Y84C disulfide bond and not an R12C/A236C disulfide bond; and b) at least one MOD at position 4. A TMMP can include: a) a G2C/Y84C disulfide bond and not an R12C/A236C disulfide bond; and b) at least one MOD at position 5.

A TMMP can include: a) an R12C/A236C disulfide bond and not a G2C/Y84C disulfide bond; and at least one MOD at position 1. A TMMP can include: a) an R12C/A236C disulfide bond and not a G2C/Y84C disulfide bond; and at least one MOD at position 2. A TMMP can include: a) an R12C/A236C disulfide bond and not a G2C/Y84C disulfide bond; and at least one MOD at position 3. A TMMP of the present disclosure can include: a) an R12C/A236C disulfide bond and not a G2C/Y84C disulfide bond; and at least one immunomodulatory polypeptide at position 4. A TMMP can include: a) an R12C/A236C disulfide bond and not a G2C/Y84C disulfide bond; and at least one MOD at position 5.

A TMMP can include: a) a G2C/Y84C disulfide bond and an R12C/A236C disulfide bond; and b) and at least one MOD at position 1. A TMMP can include: a) a G2C/Y84C disulfide bond and an R12C/A236C disulfide bond; and b) and at least one MOD at position 2. A TMMP can include: a) a G2C/Y84C disulfide bond and an R12C/A236C disulfide bond; and b) and at least one MOD at position 3. A TMMP of the present disclosure can include: a) a G2C/Y84C disulfide bond and an R12C/A236C disulfide bond; and b) and at least one MOD at position 4. A TMMP can include: a) a G2C/Y84C disulfide bond and an R12C/A236C disulfide bond; and b) and at least one MOD at position 5.

Non-limiting examples of amino acid sequences of first and second polypeptide chains of a TMMP of the present disclosure are provided in FIGS. 4A-4K and FIGS. 20A-20R.

In some cases, a TMMP comprises: a) a first polypeptide chain comprising the amino acid sequence designated "2752" as depicted in FIG. 4D; and b) a second polypeptide chain comprising the amino acid sequence designated "3159" as depicted in FIG. 4C.

In some cases, a TMMP comprises: a) a first polypeptide chain comprising the amino acid sequence designated "2753" as depicted in FIG. 4E; and b) a second polypeptide chain comprising the amino acid sequence designated "3159" as depicted in FIG. 4C. Such a TMMP comprises: a) a MOD at position 3 as depicted in FIG. 19; and b) an R12C/A236C disulfide bond (but not a G2C/Y84C disulfide bond).

In some cases, a TMMP comprises: a) a first polypeptide chain comprising the amino acid sequence designated "2752" as depicted in FIG. 4D; and b) a second polypeptide chain comprising the amino acid sequence designated "2750" as depicted in FIG. 4B.

In some cases, a TMMP comprises: a) a first polypeptide chain comprising the amino acid sequence designated "2753" as depicted in FIG. 4E; and b) a second polypeptide chain comprising the amino acid sequence designated "2750" as depicted in FIG. 4B. Such a TMMP comprises: a) a MOD at position 1 as depicted in FIG. 19; and b) an R12C/A236C disulfide bond (but not a G2C/Y84C disulfide bond).

In some cases, a TMMP comprises: a) a first polypeptide chain comprising the amino acid sequence designated "2752" as depicted in FIG. 4D; and b) a second polypeptide chain comprising the amino acid sequence designated "3158" as depicted in FIG. 4A.

In some cases, a TMMP comprises: a) a first polypeptide chain comprising the amino acid sequence designated "2753" as depicted in FIG. 4E; and b) a second polypeptide chain comprising the amino acid sequence designated "3158" as depicted in FIG. 4A.

In some cases, a TMMP comprises: a) a first polypeptide chain comprising the amino acid sequence designated "2380" as depicted in FIG. 14B; and b) a second polypeptide chain comprising the amino acid sequence designated "1715" as depicted in FIG. 14A.

In some cases, a TMMP comprises: a) a first polypeptide chain comprising, in order from N-terminus to C-terminus: i) a WT-1 peptide of the sequence VLDFAPPGA (SEQ ID NO:259); ii) a linker having the amino acid sequence GCGGSGGGGSGGGGS (SEQ ID NO:317); and iii) a β2M polypeptide comprising a Cys at position 12 (e.g., a β2M having the amino acid sequence set forth in SEQ ID NO:311); and b) a second polypeptide chain comprising, in order from N-terminus to C-terminus: i) a variant IL-2 polypeptide comprising H16A and F42A substitutions (i.e., comprising Ala at positions 16 and 42, e.g., the amino acid sequence set forth in SEQ ID NO:188, where $X_1$ is Ala and where $X_2$ is Ala); ii) a (GGGGS)4 linker; iii) a variant IL-2 polypeptide comprising H16A and F42A substitutions (i.e., comprising Ala at positions 16 and 42, e.g., the amino acid sequence set forth in SEQ ID NO:188, where $X_1$ is Ala and where $X_2$ is Ala); iv) a (GGGGS)4 linker; v) an HLA A0202 heavy chain comprising Cys at positions 84 and 236 (e.g., an HLA heavy chain polypeptide comprising the amino acid sequence set forth in SEQ ID NO:341); vi) an AAAGG linker; and vii) an Ig Fc polypeptide. In some cases, the Ig Fc polypeptide comprises an amino acid sequence having at least at least about 95%, at least about 98%, at least about 99%, or 100%, amino acid sequence identity to an amino acid sequence of an Fc region depicted in FIG. 5A-5G or 5H. In some cases, the Ig Fc polypeptide is a variant Ig Fc polypeptide comprising one or more sequence variations relative to the wild-type polypeptide, where the ability of the Ig Fc polypeptide to induce cell lysis through complement-dependent cytotoxicity (CDC) and/or antibody-dependent cellular cytotoxicity (ADCC) is reduced or substantially eliminated. In some cases, the Ig Fc polypeptide is a variant human IgG1 Fc polypeptide comprising comprises an L234A and/or L235A substitutions (L14 and L15 in the amino acid sequence depicted in FIG. 5H. In some cases, the Ig Fc polypeptide comprises the amino acid sequence depicted in FIG. 5H and set forth in SEQ ID NO:487.

In some cases, a TMMP comprises: a) a first polypeptide chain comprising, in order from N-terminus to C-terminus: i) a WT-1 peptide of the sequence VLDFAPPGA (SEQ ID NO:259); ii) a linker having the amino acid sequence GCGGSGGGGSGGGGS (SEQ ID NO:317); and iii) a β2M polypeptide comprising a Cys at position 12 (e.g., a β2M having the amino acid sequence set forth in SEQ ID NO:311); and b) a second polypeptide chain comprising, in order from N-terminus to C-terminus: i) a variant IL-2 polypeptide comprising H16A and F42A substitutions (i.e., comprising Ala at positions 16 and 42, e.g., the amino acid sequence set forth in SEQ ID NO:188, where $X_1$ is Ala and where $X_2$ is Ala); ii) a (GGGGS)4 linker; iii) a variant IL-2 polypeptide comprising H16A and F42A substitutions (i.e., comprising Ala at positions 16 and 42, e.g., the amino acid sequence set forth in SEQ ID NO:188, where $X_1$ is Ala and where $X_2$ is Ala); iv) a (GGGGS)4 linker; v) an HLA A0202 heavy chain comprising Cys at positions 84 and 236 (e.g., an HLA heavy chain polypeptide comprising the amino acid sequence set forth in SEQ ID NO:341); vi) an AAAGG linker; and vii) an Ig Fc polypeptide comprising Ala at positions 14 and 15, and lacking a C-terminal Lys (e.g., an Ig Fc polypeptide comprising the amino acid sequence depicted in FIG. 5H and set forth in SEQ ID NO:487). For example, in some cases, a TMMP comprises: a) a first polypeptide chain comprising the amino acid sequence designated "2380" as depicted in FIG. 14B; and b) a second polypeptide chain comprising the amino acid sequence designated "1715 without C-terminal Lys" as depicted in FIG. 14J. The construct depicted in FIG. 14J ("1715 without C-terminal Lys") is also referred to herein as "1715Δ".

In some cases, a TMMP comprises: a) a first polypeptide chain comprising the amino acid sequence designated "2381" as depicted in FIG. 14B; and b) a second polypeptide chain comprising the amino acid sequence designated "1715" as depicted in FIG. 14A or 1715Δ as depicted in FIG. 14J and as set forth in SEQ ID NO:486.

In some cases, a TMMP comprises: a) a first polypeptide chain comprising the amino acid sequence designated "2380" as depicted in FIG. 14B; and b) a second polypeptide chain comprising the amino acid sequence designated "2405" as depicted in FIG. 14D.

In some cases, a TMMP comprises: a) a first polypeptide chain comprising the amino acid sequence designated "2381" as depicted in FIG. 14B; and b) a second polypeptide chain comprising the amino acid sequence designated "2405" as depicted in FIG. 14D. In some cases, a TMMP comprises: a) a first polypeptide chain comprising the amino acid sequence designated "2762" as depicted in FIG. 14F; and b) a second polypeptide chain comprising the amino acid sequence designated "2405" as depicted in FIG. 14D.

In some cases, a TMMP comprises: a) a first polypeptide chain comprising the amino acid sequence designated "2380" as depicted in FIG. 14B; and b) a second polypeptide chain comprising the amino acid sequence designated "1380" as depicted in FIG. 14E.

In some cases, a TMMP comprises: a) a first polypeptide chain comprising the amino acid sequence designated "2381" as depicted in FIG. 14B; and b) a second polypeptide chain comprising the amino acid sequence designated "1380" as depicted in FIG. 14E.

In some cases, a TMMP comprises: a) a first polypeptide chain comprising the amino acid sequence designated "3592" as depicted in FIG. 20A; and b) a second polypeptide chain comprising the amino acid sequence designated "3188" as depicted in FIG. 20H. Such a TMMP comprises: a) a MOD at position 1 as depicted in FIG. 19; and b) both a G2C/Y84C disulfide bond and an R12C/A236C disulfide bond.

In some cases, a TMMP comprises: a) a first polypeptide chain comprising the amino acid sequence designated "3425" as depicted in FIG. 20B; and b) a second polypeptide chain comprising the amino acid sequence designated "3188" as depicted in FIG. 20H. Such a TMMP comprises: a) a MOD at position 3 as depicted in FIG. 19; and b) both a G2C/Y84C disulfide bond and an R12C/A236C disulfide bond.

In some cases, a TMMP comprises: a) a first polypeptide chain comprising the amino acid sequence designated "3196" as depicted in FIG. 20C; and b) a second polypeptide chain comprising the amino acid sequence designated "3604" as depicted in FIG. 20I. Such a TMMP comprises: a) a MOD at position 5 as depicted in FIG. 19; and b) both a G2C/Y84C disulfide bond and an R12C/A236C disulfide bond.

In some cases, a TMMP comprises: a) a first polypeptide chain comprising the amino acid sequence designated "2764" as depicted in FIG. 20D; and b) a second polypeptide chain comprising the amino acid sequence designated "3603" as depicted in FIG. 20J. Such a TMMP comprises: a) a MOD at position 5 as depicted in FIG. 19; and b) an R12C/A236C disulfide bond (but not a G2C/Y84C disulfide bond).

In some cases, a TMMP comprises: a) a first polypeptide chain comprising the amino acid sequence designated "3593" as depicted in FIG. 20E; and b) a second polypeptide chain comprising the amino acid sequence designated "3192" as depicted in FIG. 20K. Such a TMMP comprises: a) a MOD at position 1 as depicted in FIG. 19; and b) a G2C/Y84C disulfide bond (but not an R12C/A236C disulfide bond).

In some cases, a TMMP comprises: a) a first polypeptide chain comprising the amino acid sequence designated "3426" as depicted in FIG. 20F; and b) a second polypeptide chain comprising the amino acid sequence designated "3192" as depicted in FIG. 20K. Such a TMMP comprises: a) a MOD at position 3 as depicted in FIG. 19; and b) a G2C/Y84C disulfide bond (but not an R12C/A236C disulfide bond).

In some cases, a TMMP comprises: a) a first polypeptide chain comprising the amino acid sequence designated "3197" as depicted in FIG. 20G; and b) a second polypeptide chain comprising the amino acid sequence designated "3605" as depicted in FIG. 20L. Such a TMMP comprises: a) a MOD at position 5 as depicted in FIG. 19; and b) a G2C/Y84C disulfide bond (but not an R12C/A236C disulfide bond).

In some cases, a TMMP comprises: a) a first polypeptide chain comprising the amino acid sequence designated "3592" as depicted in FIG. 20A; and b) a second polypeptide chain comprising the amino acid sequence designated "3529" as depicted in FIG. 20M. Such a TMMP comprises: a) a MOD at position 1 as depicted in FIG. 19; and b) both a G2C/Y84C disulfide bond and an R12C/A236C disulfide bond.

In some cases, a TMMP comprises: a) a first polypeptide chain comprising the amino acid sequence designated "3425" as depicted in FIG. 20B; and b) a second polypeptide chain comprising the amino acid sequence designated "3529" as depicted in FIG. 20M. Such a TMMP comprises: a) a MOD at position 3 as depicted in FIG. 19; and b) both a G2C/Y84C disulfide bond and an R12C/A236C disulfide bond; and also comprises a WT1 239-247 (Q240Y) epitope.

In some cases, a TMMP comprises: a) a first polypeptide chain comprising the amino acid sequence designated "3196" as depicted in FIG. 20C; and b) a second polypeptide chain comprising the amino acid sequence designated "3709" as depicted in FIG. 20N. Such a TMMP comprises: a) a MOD at position 3 as depicted in FIG. 19; and b) both a G2C/Y84C disulfide bond and an R12C/A236C disulfide bond.

In some cases, a TMMP comprises: a) a first polypeptide chain comprising the amino acid sequence designated "2750" as depicted in FIG. 4B; and b) a second polypeptide chain comprising the amino acid sequence designated "3528" as depicted in FIG. 20O. Such a TMMP comprises: a) a MOD at position 1 as depicted in FIG. 19; and b) an R12C/A236C disulfide bond (but not a G2C/Y84C disulfide bond).

In some cases, a TMMP comprises: a) a first polypeptide chain comprising the amino acid sequence designated "3159" as depicted in FIG. 4C; and b) a second polypeptide chain comprising the amino acid sequence designated "3528" as depicted in FIG. 20O. Such a TMMP comprises: a) a MOD at position 3 as depicted in FIG. 19; and b) an R12C/A236C disulfide bond (but not a G2C/Y84C disulfide bond).

In some cases, a TMMP comprises: a) a first polypeptide chain comprising the amino acid sequence designated "2764" as depicted in FIG. 20D; and b) a second polypeptide chain comprising the amino acid sequence designated "3708" as depicted in FIG. 20P. Such a TMMP comprises: a) a MOD at position 5 as depicted in FIG. 19; and b) an R12C/A236C disulfide bond (but not a G2C/Y84C disulfide bond).

In some cases, a TMMP comprises: a) a first polypeptide chain comprising the amino acid sequence designated "3593" as depicted in FIG. 20E; and b) a second polypeptide chain comprising the amino acid sequence designated "3530" as depicted in FIG. 20Q. Such a TMMP comprises: a) a MOD at position 1 as depicted in FIG. 19; and b) a G2C/Y84C disulfide bond (but not an R12C/A236C disulfide bond).

In some cases, a TMMP comprises: a) a first polypeptide chain comprising the amino acid sequence designated "3426" as depicted in FIG. 20F; and b) a second polypeptide chain comprising the amino acid sequence designated "3530" as depicted in FIG. 20Q. Such a TMMP comprises: a) a MOD at position 3 as depicted in FIG. 19; and b) a G2C/Y84C disulfide bond (but not an R12C/A236C disulfide bond).

In some cases, a TMMP comprises: a) a first polypeptide chain comprising the amino acid sequence designated "3197" as depicted in FIG. 20G; and b) a second polypeptide chain comprising the amino acid sequence designated "3710" as depicted in FIG. 20R. Such a TMMP comprises: a) a MOD at position 5 as depicted in FIG. 19; and b) a G2C/Y84C disulfide bond (but not an R12C/A236C disulfide bond).

In some cases, a TMMP comprises: a) a first polypeptide chain comprising the amino acid sequence designated "3426" as depicted in FIG. 20F; and b) a second polypeptide chain comprising the amino acid sequence designated "3529" as depicted in FIG. 20M. Such a TMMP comprises: a) a MOD at position 3 as depicted in FIG. 19; and b) a G2C/Y84C disulfide bond (but not an R12C/A236C disulfide bond), and also includes a WT1 239-247 (Q240Y) epitope.

In some cases, a TMMP comprises: a) a first polypeptide chain comprising the amino acid sequence designated "3425" as depicted in FIG. 20B; and b) a second polypeptide chain comprising the amino acid sequence designated "3528" as depicted in FIG. 20O. Such a TMMP comprises: a) a MOD at position 3 as depicted in FIG. 19; and b) an R12C/A236C disulfide bond (but not a G2C/Y84C disulfide bond) and also includes a WT1 239-247 (Q240Y) epitope.

In some cases, a TMMP comprises: a) a first polypeptide chain comprising the amino acid sequence designated "3425" as depicted in FIG. 20B; and b) a second polypeptide chain comprising the amino acid sequence designated "3530" as depicted in FIG. 20Q. Such a TMMP comprises: a) a MOD at position 3 as depicted in FIG. 19; and b) a G2C/Y84C disulfide bond (but not an R12C/A236C disulfide bond), and also includes a WT1 239-247 (Q240Y) epitope.

In some cases, a TMMP comprises: a) a first polypeptide chain comprising the amino acid sequence designated "3159" as depicted in FIG. 4C; and b) a second polypeptide chain comprising the amino acid sequence designated "3188" as depicted in FIG. 20H. Such a TMMP comprises: a) a MOD at position 3 as depicted in FIG. 19; and b) an R12C/A236C disulfide bond (but not a G2C/Y84C disulfide bond), and also includes a WT1 235-243 (M236Y) epitope.

Exemplary TMMPs with Epitope SMTWNQMNL (WT1 (235-243; C235S))

In some cases, a TMMP comprises: a) a first polypeptide chain comprising the amino acid sequence depicted in FIG. 35A; and b) a second polypeptide chain comprising the amino acid sequence depicted in FIG. 4B. Such a TMMP comprises: a) a MOD at position 1 as depicted in FIG. 19; and b) an R12C/A236C disulfide bond (but not a G2C/Y84C disulfide bond).

In some cases, a TMMP comprises: a) a first polypeptide chain comprising the amino acid sequence depicted in FIG. 35A; and b) a second polypeptide chain comprising the amino acid sequence depicted in FIG. 4C. Such a TMMP comprises: a) a MOD at position 3 as depicted in FIG. 19; and b) an R12C/A236C disulfide bond (but not a G2C/Y84C disulfide bond).

In some cases, a TMMP comprises: a) a first polypeptide chain comprising the amino acid sequence depicted in FIG. 35B; and b) a second polypeptide chain comprising the amino acid sequence depicted in FIG. 20A. Such a TMMP comprises: a) a MOD at position 1 as depicted in FIG. 19; and b) both a G2C/Y84C disulfide bond and an R12C/A236C disulfide bond.

In some cases, a TMMP comprises: a) a first polypeptide chain comprising the amino acid sequence depicted in FIG. 35B; and b) a second polypeptide chain comprising the amino acid sequence depicted in FIG. 20B. Such a TMMP comprises: a) a MOD at position 3 as depicted in FIG. 19; and b) both a G2C/Y84C disulfide bond and an R12C/A236C disulfide bond.

In some cases, a TMMP comprises: a) a first polypeptide chain comprising the amino acid sequence depicted in FIG. 35C; and b) a second polypeptide chain comprising the amino acid sequence depicted in FIG. 20E. Such a TMMP comprises: a) a MOD at position 1 as depicted in FIG. 19; and b) a G2C/Y84C disulfide bond (but not an R12C/A236C disulfide bond).

In some cases, a TMMP comprises: a) a first polypeptide chain comprising the amino acid sequence depicted in FIG. 35C; and b) a second polypeptide chain comprising the amino acid sequence depicted in FIG. 20F. Such a TMMP comprises: a) a MOD at position 3 as depicted in FIG. 19; and b) a G2C/Y84C disulfide bond (but not an R12C/A236C disulfide bond).

In some cases, a TMMP comprises: a) a first polypeptide chain comprising the amino acid sequence depicted in FIG. 35D; and b) a second polypeptide chain comprising the amino acid sequence depicted in FIG. 20G. Such a TMMP comprises: a) a MOD at position 5 as depicted in FIG. 19; and b) a G2C/Y84C disulfide bond (but not an R12C/A236C disulfide bond).

In some cases, a TMMP comprises: a) a first polypeptide chain comprising the amino acid sequence depicted in FIG. 35E; and b) a second polypeptide chain comprising the amino acid sequence depicted in FIG. 20C. Such a TMMP comprises: a) a MOD at position 5 as depicted in FIG. 19; and b) both a G2C/Y84C disulfide bond and an R12C/A236C disulfide bond.

In some cases, a TMMP comprises: a) a first polypeptide chain comprising the amino acid sequence depicted in FIG. 35F; and b) a second polypeptide chain comprising the amino acid sequence depicted in FIG. 20D. Such a TMMP comprises: a) a MOD at position 5 as depicted in FIG. 19; and b) an R12C/A236C disulfide bond (but not a G2C/Y84C disulfide bond).

Exemplary TMMPs with Epitope GCMTWNQMNL (WT1 (235-243; G-1))

In some cases, a TMMP comprises: a) a first polypeptide chain comprising the amino acid sequence depicted in FIG. 36A; and b) a second polypeptide chain comprising the amino acid sequence depicted in FIG. 4B. Such a TMMP comprises: a) a MOD at position 1 as depicted in FIG. 19; and b) an R12C/A236C disulfide bond (but not a G2C/Y84C disulfide bond).

In some cases, a TMMP comprises: a) a first polypeptide chain comprising the amino acid sequence depicted in FIG. 36A; and b) a second polypeptide chain comprising the amino acid sequence depicted in FIG. 4C. Such a TMMP comprises: a) a MOD at position 3 as depicted in FIG. 19; and b) an R12C/A236C disulfide bond (but not a G2C/Y84C disulfide bond).

In some cases, a TMMP comprises: a) a first polypeptide chain comprising the amino acid sequence depicted in FIG. 36B; and b) a second polypeptide chain comprising the amino acid sequence depicted in FIG. 20A. Such a TMMP comprises: a) a MOD at position 1 as depicted in FIG. 19; and b) both a G2C/Y84C disulfide bond and an R12C/A236C disulfide bond.

In some cases, a TMMP comprises: a) a first polypeptide chain comprising the amino acid sequence depicted in FIG. 36B; and b) a second polypeptide chain comprising the amino acid sequence depicted in FIG. 20B. Such a TMMP comprises: a) a MOD at position 3 as depicted in FIG. 19; and b) both a G2C/Y84C disulfide bond and an R12C/A236C disulfide bond.

In some cases, a TMMP comprises: a) a first polypeptide chain comprising the amino acid sequence depicted in FIG. 36C; and b) a second polypeptide chain comprising the amino acid sequence depicted in FIG. 20E. Such a TMMP comprises: a) a MOD at position 1 as depicted in FIG. 19; and b) a G2C/Y84C disulfide bond (but not an R12C/A236C disulfide bond).

In some cases, a TMMP comprises: a) a first polypeptide chain comprising the amino acid sequence depicted in FIG. 36C; and b) a second polypeptide chain comprising the amino acid sequence depicted in FIG. 20F. Such a TMMP comprises: a) a MOD at position 3 as depicted in FIG. 19; and b) a G2C/Y84C disulfide bond (but not an R12C/A236C disulfide bond).

In some cases, a TMMP comprises: a) a first polypeptide chain comprising the amino acid sequence depicted in FIG. 36D; and b) a second polypeptide chain comprising the amino acid sequence depicted in FIG. 20G. Such a TMMP comprises: a) an immunomodulatory polypeptide at position 5 as depicted in FIG. 19; and b) a G2C/Y84C disulfide bond (but not an R12C/A236C disulfide bond).

In some cases, a TMMP comprises: a) a first polypeptide chain comprising the amino acid sequence depicted in FIG. 36E; and b) a second polypeptide chain comprising the amino acid sequence depicted in FIG. 20C. Such a TMMP comprises: a) a MOD at position 5 as depicted in FIG. 19; and b) both a G2C/Y84C disulfide bond and an R12C/A236C disulfide bond.

In some cases, a TMMP comprises: a) a first polypeptide chain comprising the amino acid sequence depicted in FIG. 36F; and b) a second polypeptide chain comprising the amino acid sequence depicted in FIG. 20D. Such a TMMP comprises: a) a MOD at position 5 as depicted in FIG. 19; and b) an R12C/A236C disulfide bond (but not a G2C/Y84C disulfide bond).

Exemplary TMMPs with Epitope SYTWNQMNL (WT1 (235-243; C235S; M236Y))

In some cases, a TMMP comprises: a) a first polypeptide chain comprising the amino acid sequence depicted in FIG. 37A; and b) a second polypeptide chain comprising the amino acid sequence depicted in FIG. 4B. Such a TMMP comprises: a) a MOD at position 1 as depicted in FIG. 19; and b) an R12C/A236C disulfide bond (but not a G2C/Y84C disulfide bond).

In some cases, a TMMP comprises: a) a first polypeptide chain comprising the amino acid sequence depicted in FIG. 37A; and b) a second polypeptide chain comprising the amino acid sequence depicted in FIG. 4C. Such a TMMP comprises: a) a MOD at position 3 as depicted in FIG. 19; and b) an R12C/A236C disulfide bond (but not a G2C/Y84C disulfide bond).

In some cases, a TMMP comprises: a) a first polypeptide chain comprising the amino acid sequence depicted in FIG. 37B; and b) a second polypeptide chain comprising the amino acid sequence depicted in FIG. 20A. Such a TMMP comprises: a) a MOD at position 1 as depicted in FIG. 19; and b) both a G2C/Y84C disulfide bond and an R12C/A236C disulfide bond.

In some cases, a TMMP comprises: a) a first polypeptide chain comprising the amino acid sequence depicted in FIG. 37B; and b) a second polypeptide chain comprising the amino acid sequence depicted in FIG. 20B. Such a TMMP comprises: a) a MOD at position 3 as depicted in FIG. 19; and b) both a G2C/Y84C disulfide bond and an R12C/A236C disulfide bond.

In some cases, a TMMP comprises: a) a first polypeptide chain comprising the amino acid sequence depicted in FIG. 37C; and b) a second polypeptide chain comprising the amino acid sequence depicted in FIG. 20E. Such a TMMP comprises: a) a MOD at position 1 as depicted in FIG. 19; and b) a G2C/Y84C disulfide bond (but not an R12C/A236C disulfide bond).

In some cases, a TMMP comprises: a) a first polypeptide chain comprising the amino acid sequence depicted in FIG. 37C; and b) a second polypeptide chain comprising the amino acid sequence depicted in FIG. 20F. Such a TMMP comprises: a) a MOD at position 3 as depicted in FIG. 19; and b) a G2C/Y84C disulfide bond (but not an R12C/A236C disulfide bond).

In some cases, a TMMP comprises: a) a first polypeptide chain comprising the amino acid sequence depicted in FIG. 37D; and b) a second polypeptide chain comprising the amino acid sequence depicted in FIG. 20G. Such a TMMP comprises: a) a MOD at position 5 as depicted in FIG. 19; and b) a G2C/Y84C disulfide bond (but not an R12C/A236C disulfide bond).

In some cases, a TMMP comprises: a) a first polypeptide chain comprising the amino acid sequence depicted in FIG. 37E; and b) a second polypeptide chain comprising the amino acid sequence depicted in FIG. 20C. Such a TMMP comprises: a) a MOD at position 5 as depicted in FIG. 19; and b) both a G2C/Y84C disulfide bond and an R12C/A236C disulfide bond.

In some cases, a TMMP comprises: a) a first polypeptide chain comprising the amino acid sequence depicted in FIG. 37F; and b) a second polypeptide chain comprising the amino acid sequence depicted in FIG. 20D. Such a TMMP comprises: a) a MOD at position 5 as depicted in FIG. 19; and b) an R12C/A236C disulfide bond (but not a G2C/Y84C disulfide bond).

Exemplary TMMPs with Epitope GCYTWNQMNL (WT1 (235-243; G-1; M236Y))

In some cases, a TMMP comprises: a) a first polypeptide chain comprising the amino acid sequence depicted in FIG. 38A; and b) a second polypeptide chain comprising the amino acid sequence depicted in FIG. 4B. Such a TMMP comprises: a) a MOD at position 1 as depicted in FIG. 19; and b) an R12C/A236C disulfide bond (but not a G2C/Y84C disulfide bond).

In some cases, a TMMP comprises: a) a first polypeptide chain comprising the amino acid sequence depicted in FIG. 38A; and b) a second polypeptide chain comprising the amino acid sequence depicted in FIG. 4C. Such a TMMP comprises: a) a MOD at position 3 as depicted in FIG. 19; and b) an R12C/A236C disulfide bond (but not a G2C/Y84C disulfide bond).

In some cases, a TMMP comprises: a) a first polypeptide chain comprising the amino acid sequence depicted in FIG. 38B; and b) a second polypeptide chain comprising the amino acid sequence depicted in FIG. 20A. Such a TMMP comprises: a) a MOD at position 1 as depicted in FIG. 19; and b) both a G2C/Y84C disulfide bond and an R12C/A236C disulfide bond.

In some cases, a TMMP comprises: a) a first polypeptide chain comprising the amino acid sequence depicted in FIG. 38B; and b) a second polypeptide chain comprising the amino acid sequence depicted in FIG. 20B. Such a TMMP comprises: a) a MOD at position 3 as depicted in FIG. 19; and b) both a G2C/Y84C disulfide bond and an R12C/A236C disulfide bond.

In some cases, a TMMP comprises: a) a first polypeptide chain comprising the amino acid sequence depicted in FIG. 38C; and b) a second polypeptide chain comprising the amino acid sequence depicted in FIG. 20E. Such a TMMP comprises: a) a MOD at position 1 as depicted in FIG. 19; and b) a G2C/Y84C disulfide bond (but not an R12C/A236C disulfide bond).

In some cases, a TMMP comprises: a) a first polypeptide chain comprising the amino acid sequence depicted in FIG. 38C; and b) a second polypeptide chain comprising the amino acid sequence depicted in FIG. 20F. Such a TMMP comprises: a) a MOD at position 3 as depicted in FIG. 19; and b) a G2C/Y84C disulfide bond (but not an R12C/A236C disulfide bond).

In some cases, a TMMP comprises: a) a first polypeptide chain comprising the amino acid sequence depicted in FIG. 38D; and b) a second polypeptide chain comprising the amino acid sequence depicted in FIG. 20G. Such a TMMP comprises: a) a MOD at position 5 as depicted in FIG. 19; and b) a G2C/Y84C disulfide bond (but not an R12C/A236C disulfide bond).

In some cases, a TMMP comprises: a) a first polypeptide chain comprising the amino acid sequence depicted in FIG. 38E; and b) a second polypeptide chain comprising the amino acid sequence depicted in FIG. 20C. Such a TMMP comprises: a) a MOD at position 5 as depicted in FIG. 19; and b) both a G2C/Y84C disulfide bond and an R12C/A236C disulfide bond.

In some cases, a TMMP comprises: a) a first polypeptide chain comprising the amino acid sequence depicted in FIG. 38F; and b) a second polypeptide chain comprising the amino acid sequence depicted in FIG. 20D. Such a TMMP comprises: a) a MOD at position 5 as depicted in FIG. 19; and b) an R12C/A236C disulfide bond (but not a G2C/Y84C disulfide bond).

Methods of Generating a Multimeric T-Cell Modulatory Polypeptide

Methods of obtaining a TMMP comprising one or more variant MODs that exhibit lower affinity for a cognate co-MOD compared to the affinity of the corresponding parental wild-type immunomodulatory polypeptide for the co-immunomodulatory polypeptide are provided in according to published PCT application WO 2019/051091, published Mar. 14, 2019. See [00364]-[00387].

Nucleic Acids

The present disclosure provides a nucleic acid comprising a nucleotide sequence encoding a TMMP of the present disclosure.

In some cases, the individual polypeptide chains of a TMMP are encoded in separate nucleic acids. In some cases, all polypeptide chains of a TMMP are encoded in a single nucleic acid. In some cases, a first nucleic acid comprises a nucleotide sequence encoding a first polypeptide of a TMMP; and a second nucleic acid comprises a nucleotide sequence encoding a second polypeptide of a TMMP. In some cases, single nucleic acid comprises a nucleotide sequence encoding a first polypeptide of a TMMP and a second polypeptide of a TMMP.

Separate Nucleic Acids Encoding Individual Polypeptide Chains of a Multimeric Polypeptide The present disclosure provides nucleic acids comprising nucleotide sequences encoding a TMMP. As noted above, in some cases, the individual polypeptide chains of a TMMP are encoded in separate nucleic acids. In some cases, nucleotide sequences encoding the separate polypeptide chains of a TMMP are operably linked to transcriptional control elements, e.g., promoters, such as promoters that are functional in a eukaryotic cell, where the promoter can be a constitutive promoter or an inducible promoter.

The present disclosure provides a first nucleic acid and a second nucleic acid, where the first nucleic acid comprises a nucleotide sequence encoding a first polypeptide of a TMMP, where the first polypeptide comprises, in order from N-terminus to C-terminus: a) an epitope (e.g., a T-cell epitope); b) a first MHC polypeptide; and c) a MOD (e.g., a wild-type MOD or a reduced-affinity variant MOD, as described above); and where the second nucleic acid comprises a nucleotide sequence encoding a second polypeptide of a TMMP, where the second polypeptide comprises, in order from N-terminus to C-terminus: a) a second MHC polypeptide; and b) an Ig Fc polypeptide. Suitable T-cell epitopes, MHC polypeptides, MODs, and Ig Fc polypeptides, are described above. In some cases, the nucleotide sequences encoding the first and the second polypeptides are operably linked to transcriptional control elements. In some cases, the transcriptional control element is a promoter that is functional in a eukaryotic cell. In some cases, the nucleic acids are present in separate expression vectors.

The present disclosure provides a first nucleic acid and a second nucleic acid, where the first nucleic acid comprises a nucleotide sequence encoding a first polypeptide of a TMMP, where the first polypeptide comprises, in order from N-terminus to C-terminus: a) an epitope (e.g., a T-cell epitope); and b) a first MHC polypeptide; and where the second nucleic acid comprises a nucleotide sequence encoding a second polypeptide of a TMMP, where the second polypeptide comprises, in order from N-terminus to C-terminus: a) a MOD (e.g., a wild-type MOD or a reduced-affinity variant MOD, as described above); b) a second MHC polypeptide; and c) an Ig Fc polypeptide. Suitable T-cell epitopes, MHC polypeptides, MODs, and Ig Fc polypeptides, are described above. In some cases, the nucleotide sequences encoding the first and the second polypeptides are operably linked to transcriptional control elements. In some cases, the transcriptional control element is a promoter that is functional in a eukaryotic cell. In some cases, the nucleic acids are present in separate expression vectors.

Nucleic Acid Encoding Two or More Polypeptides Present in a Multimeric Polypeptide The present disclosure provides a nucleic acid comprising nucleotide sequences encoding at least the first polypeptide and the second polypeptide of a TMMP. In some cases, where a TMMP of the present disclosure includes a first, second, and third polypeptide, the nucleic acid includes a nucleotide sequence encoding the first, second, and third polypeptides. In some cases, the nucleotide sequences encoding the first polypeptide and the second polypeptide of a TMMP includes a proteolytically cleavable linker interposed between the nucleotide sequence encoding the first polypeptide and the nucleotide sequence encoding the second polypeptide. In some cases, the nucleotide sequences encoding the first polypeptide and the second polypeptide of a TMMP includes an internal ribosome entry site (IRES) interposed between the nucleotide sequence encoding the first polypeptide and the nucleotide sequence encoding the second polypeptide. In some cases, the nucleotide sequences encoding the first polypeptide and the second polypeptide of a TMMP includes a ribosome skipping signal (or cis-acting hydrolase element, CHYSEL (SEQ ID NO: 394)) interposed between the nucleotide sequence encoding the first polypeptide and the nucleotide sequence encoding the second polypeptide. Examples of nucleic acids are described below, where a proteolytically cleavable linker is provided between nucleotide sequences encoding the first polypeptide and the second polypeptide of a TMMP; in any of these embodiments, an IRES or a ribosome skipping signal can be used in place of the nucleotide sequence encoding the proteolytically cleavable linker.

In some cases, a first nucleic acid (e.g., a recombinant expression vector, an mRNA, a viral RNA, etc.) comprises a nucleotide sequence encoding a first polypeptide chain of a TMMP of the present disclosure; and a second nucleic acid (e.g., a recombinant expression vector, an mRNA, a viral RNA, etc.) comprises a nucleotide sequence encoding a second polypeptide chain of a TMMP of the present disclosure. In some cases, the nucleotide sequence encoding the first polypeptide, and the second nucleotide sequence encoding the second polypeptide, are each operably linked to transcriptional control elements, e.g., promoters, such as promoters that are functional in a eukaryotic cell, where the promoter can be a constitutive promoter or an inducible promoter.

The present disclosure provides a nucleic acid comprising a nucleotide sequence encoding a recombinant polypeptide, where the recombinant polypeptide comprises, in order from N-terminus to C-terminus: a) an epitope (e.g., a T-cell epitope); b) a first MHC polypeptide; c) a MOD (e.g., a wild-type MOD or a reduced-affinity variant MOD, as described above); d) a proteolytically cleavable linker; e) a second MHC polypeptide; and f) Ig Fc polypeptide. The present disclosure provides a nucleic acid comprising a nucleotide sequence encoding a recombinant polypeptide, where the recombinant polypeptide comprises, in order from N-terminus to C-terminus: a) a first leader peptide; b) the epitope; c) the first MHC polypeptide; d) the MOD (e.g., a reduced-affinity variant as described above); e) the proteolytically cleavable linker; f) a second leader peptide; g) the second MHC polypeptide; and h) the Ig Fc polypeptide. The present disclosure provides a nucleic acid comprising a nucleotide sequence encoding a recombinant polypeptide, where the recombinant polypeptide comprises, in order from N-terminus to C-terminus: a) an epitope; b) a first MHC polypeptide; c) a proteolytically cleavable linker; d) a MOD (e.g., a reduced-affinity variant as described above); e) a second MHC polypeptide; and f) an Ig Fc polypeptide. In some cases, the first leader peptide and the second leader peptide are a β2-M leader peptide. In some cases, the nucleotide sequence is operably linked to a transcriptional control element. In some cases, the transcriptional control element is a promoter that is functional in a eukaryotic cell.

Suitable MHC polypeptides are described above. In some cases, the first MHC polypeptide is a β2-microglobulin polypeptide; and wherein the second MHC polypeptide is an MHC class I heavy chain polypeptide. In some cases, the β2-microglobulin polypeptide comprises an amino acid sequence having at least 85% amino acid sequence identity to a β2M amino acid sequence depicted in FIG. 6. In some cases, the MHC class I heavy chain polypeptide is an HLA-A, HLA-B, HLA-C, HLA-E, HLA-F, HLA-G, HLA-K, or HLA-L heavy chain. In some cases, the MHC class I heavy chain polypeptide comprises an amino acid sequence having at least 85% amino acid sequence identity to the amino acid sequence depicted in any one of FIG. 3A-3C.

Suitable Fc polypeptides are described above. In some cases, the Ig Fc polypeptide is an IgG1 Fc polypeptide, an IgG2 Fc polypeptide, an IgG3 Fc polypeptide, an IgG4 Fc polypeptide, an IgA Fc polypeptide, or an IgM Fc polypeptide. In some cases, the Ig Fc polypeptide comprises an amino acid sequence having at least 85% amino acid sequence identity to an amino acid sequence depicted in FIGS. 5A-5H.

Suitable MODs are described above.

Suitable proteolytically cleavable linkers are described above. In some cases, the proteolytically cleavable linker comprises an amino acid sequence selected from: a) LEVLFQGP (SEQ ID NO:388); b) ENLYTQS (SEQ ID NO:389); c) DDDDK (SEQ ID NO:390); d) LVPR (SEQ ID NO:391); and e) GSGATNFSLLKQAGDVEENPGP (SEQ ID NO:392).

In some cases, a linker between the epitope and the first MHC polypeptide comprises a first Cys residue, and the second MHC polypeptide comprises an amino acid substitution to provide a second Cys residue, such that the first and the second Cys residues provide for a disulfide linkage between the linker and the second MHC polypeptide. In some cases, first MHC polypeptide comprises an amino acid substitution to provide a first Cys residue, and the second MHC polypeptide comprises an amino acid substitution to provide a second Cys residue, such that the first Cys residue and the second Cys residue provide for a disulfide linkage between the first MHC polypeptide and the second MHC polypeptide.

The present disclosure provides a nucleic acid comprising a nucleotide sequence encoding a TMMP, where the TMMP comprises: a) a first polypeptide chain comprising, in order from N-terminus to C-terminus: i) a WT-1 peptide of the sequence VLDFAPPGA (SEQ ID NO:259); ii) a linker having the amino acid sequence GCGGSGGGGSGGGGS (SEQ ID NO:317); and iii) a β2M polypeptide comprising a Cys at position 12 (e.g., a β2M having the amino acid sequence set forth in SEQ ID NO:311); and b) a second polypeptide chain comprising, in order from N-terminus to C-terminus: i) a variant IL-2 polypeptide comprising H16A and F42A substitutions (i.e., comprising Ala at positions 16 and 42, e.g., the amino acid sequence set forth in SEQ ID NO:188, where $X_1$ is Ala and where $X_2$ is Ala); ii) a (GGGGS)4 linker; iii) a variant IL-2 polypeptide comprising H16A and F42A substitutions (i.e., comprising Ala at positions 16 and 42, e.g., the amino acid sequence set forth in SEQ ID NO:188, where $X_1$ is Ala and where $X_2$ is Ala); iv) a (GGGGS)4 linker; v) an HLA A0202 heavy chain comprising Cys at positions 84 and 236 (e.g., an HLA heavy chain polypeptide comprising the amino acid sequence set forth in SEQ ID NO:341); vi) an AAAGG linker; and vii) an Ig Fc polypeptide. In some cases, the Ig Fc polypeptide is a variant Ig Fc polypeptide comprising one or more sequence variations relative to the wild type polypeptide, where the ability of the Ig Fc polypeptide to induce cell lysis through complement-dependent cytotoxicity (CDC) and/or antibody-dependent cellular cytotoxicity (ADCC) is reduced or substantially eliminated. In some cases, the Ig Fc polypeptide is a variant human IgG1 Fc polypeptide comprising comprises an L234A and/or L235A substitutions (L14 and L15 in the amino acid sequence depicted in FIG. 5H). In some cases, the Ig Fc polypeptide comprises the amino acid sequence depicted in FIG. 5H. In some cases, the first polypeptide and the second polypeptide are encoded on separate nucleic acids; e.g., the present disclosure provides a first nucleic acid comprising a nucleotide sequence encoding the first polypeptide and a second nucleic acid comprising a nucleotide sequence encoding the second polypeptide. In other cases, a single nucleic acid comprises nucleotide sequences encoding the first polypeptide and the second polypeptide; e.g., the present disclosure provides a nucleic acid comprising a first nucleotide sequence encoding the first polypeptide and a second nucleotide sequence encoding the second polypeptide. In some cases, the nucleic acid(s) is/are in expression vector(s).

The present disclosure provides a nucleic acid comprising a nucleotide sequence encoding a TMMP, where the TMMP comprises: a) a first polypeptide chain comprising, in order from N-terminus to C-terminus: i) a WT-1 peptide of the sequence VLDFAPPGA (SEQ ID NO:259); ii) a linker having the amino acid sequence GCGGSGGGGSGGGGS (SEQ ID NO:317); and iii) a β2M polypeptide comprising a Cys at position 12 (e.g., a β2M having the amino acid sequence set forth in SEQ ID NO:311); and b) a second polypeptide chain comprising, in order from N-terminus to C-terminus: i) a variant IL-2 polypeptide comprising H16A and F42A substitutions (i.e., comprising Ala at positions 16 and 42, e.g., the amino acid sequence set forth in SEQ ID NO:188, where $X_1$ is Ala and where $X_2$ is Ala); ii) a (GGGGS)4 linker; iii) a variant IL-2 polypeptide comprising H16A and F42A substitutions (i.e., comprising Ala at positions 16 and 42, e.g., the amino acid sequence set forth in SEQ ID NO:188, where $X_1$ is Ala and where $X_2$ is Ala); iv) a (GGGGS)4 linker; v) an HLA A0202 heavy chain comprising Cys at positions 84 and 236 (e.g., an HLA heavy chain polypeptide comprising the amino acid sequence set forth in SEQ ID NO:341); vi) an AAAGG linker; and vii) an Ig Fc polypeptide comprising Ala at positions 14 and 15, and lacking a C-terminal Lys (e.g., an Ig Fc polypeptide comprising the amino acid sequence depicted in FIG. 5H and set forth in SEQ ID NO:487). In some cases, the first polypeptide and the second polypeptide are encoded on separate nucleic acids; e.g., the present disclosure provides a first nucleic acid comprising a nucleotide sequence encoding the first polypeptide and a second nucleic acid comprising a nucleotide sequence encoding the second polypeptide. In other cases, a single nucleic acid comprises nucleotide sequences encoding the first polypeptide and the second polypeptide; e.g., the present disclosure provides a nucleic acid comprising a first nucleotide sequence encoding the first polypeptide and a second nucleotide sequence encoding the second polypeptide. In some cases, the nucleic acid(s) is/are in expression vector(s).

The present disclosure provides a nucleic acid comprising a nucleotide sequence encoding a TMMP, where the TMMP comprises: a) a first polypeptide chain comprising the amino acid sequence designated "2380" as depicted in FIG. 14B and as set forth in SEQ ID NO:423; and b) a second polypeptide chain comprising the amino acid sequence 1715Δ as depicted in FIG. 14J and as set forth in SEQ ID NO:486. In some cases, the present disclosure provides: i) a first nucleic acid comprising a nucleotide sequence encoding the 2380 polypeptide as depicted in FIG. 14B and as set forth in SEQ ID NO:423; and ii) a second nucleic acid comprising a nucleotide sequence encoding the 1715Δ polypeptide as depicted in FIG. 14J and as set forth in SEQ ID NO:486. In some cases, the first nucleic acid is in a first expression vector and the second nucleic acid is in a second expression vector. In some cases, the present disclosure provides a nucleic acid comprising: i) a first nucleotide sequence encoding the 2380 polypeptide as depicted in FIG. 14B and as set forth in SEQ ID NO:423; and ii) a second nucleotide sequence encoding the 1715Δ polypeptide as depicted in FIG. 14J and as set forth in SEQ ID NO:486. In some cases, the nucleic acid is in an expression vector. Suitable expression vectors are described below.

Recombinant Expression Vectors

The present disclosure provides recombinant expression vectors comprising nucleic acids of the present disclosure. In some cases, the recombinant expression vector is a non-viral vector. In some cases, the recombinant expression vector is a viral construct, e.g., a recombinant adeno-associated virus construct (see, e.g., U.S. Pat. No. 7,078,387), a recombinant adenoviral construct, a recombinant lentiviral construct, a recombinant retroviral construct, a non-integrating viral vector, etc.

Suitable expression vectors include, but are not limited to, viral vectors (e.g. viral vectors based on vaccinia virus; poliovirus; adenovirus (see, e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769; WO 93/19191; WO 94/28938;

WO 95/11984 and WO 95/00655); adeno-associated virus (see, e.g., Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al., Virol. (1988) 166:154-165; and Flotte et al., PNAS (1993) 90:10613-10617); SV40; herpes simplex virus; human immunodeficiency virus (see, e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus); and the like.

Numerous suitable expression vectors are known to those of skill in the art, and many are commercially available. The following vectors are provided by way of example; for eukaryotic host cells: pXT1, pSG5 (Stratagene), pSVK3, pBPV, pMSG, and pSVLSV40 (Pharmacia). However, any other vector may be used so long as it is compatible with the host cell.

Depending on the host/vector system utilized, any of a number of suitable transcription and translation control elements, including constitutive and inducible promoters, transcription enhancer elements, transcription terminators, etc. may be used in the expression vector (see e.g., Bitter et al. (1987) *Methods in Enzymology,* 153:516-544).

In some cases, a nucleotide sequence encoding a DNA-targeting RNA and/or a site-directed modifying polypeptide is operably linked to a control element, e.g., a transcriptional control element, such as a promoter. The transcriptional control element may be functional in either a eukaryotic cell, e.g., a mammalian cell; or a prokaryotic cell (e.g., bacterial or archaeal cell). In some cases, a nucleotide sequence encoding a DNA-targeting RNA and/or a site-directed modifying polypeptide is operably linked to multiple control elements that allow expression of the nucleotide sequence encoding a DNA-targeting RNA and/or a site-directed modifying polypeptide in both prokaryotic and eukaryotic cells.

Non-limiting examples of suitable eukaryotic promoters (promoters functional in a eukaryotic cell) include those from cytomegalovirus (CMV) immediate early, herpes simplex virus (HSV) thymidine kinase, early and late SV40, long terminal repeats (LTRs) from retrovirus, and mouse metallothionein-I. Selection of the appropriate vector and promoter is well within the level of ordinary skill in the art. The expression vector may also contain a ribosome binding site for translation initiation and a transcription terminator. The expression vector may also include appropriate sequences for amplifying expression.

Genetically Modified Host Cells

The present disclosure provides a genetically modified host cell, where the host cell is genetically modified with a nucleic acid of the present disclosure.

Suitable host cells include eukaryotic cells, such as yeast cells, insect cells, and mammalian cells. In some cases, the host cell is a cell of a mammalian cell line. Suitable mammalian cell lines include human cell lines, non-human primate cell lines, rodent (e.g., mouse, rat) cell lines, and the like. Suitable mammalian cell lines include, but are not limited to, HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), HLHepG2 cells, and the like.

In some cases, the host cell is a mammalian cell that has been genetically modified such that it does not synthesize endogenous MHC β2-M.

In some cases, the host cell is a mammalian cell that has been genetically modified such that it does not synthesize endogenous MHC Class I heavy chain. In some cases, the host cell is a mammalian cell that has been genetically modified such that it does not synthesize endogenous MHC β2-M and such that it does not synthesize endogenous MHC Class I heavy chain.

Compositions

The present disclosure provides compositions, including pharmaceutical compositions, comprising a TMMP (synTac) of the present disclosure. The present disclosure provides compositions, including pharmaceutical compositions, comprising a TMMP. The present disclosure provides compositions, including pharmaceutical compositions, comprising a nucleic acid or a recombinant expression vector of the present disclosure.

Compositions Comprising a Multimeric Polypeptide

A composition of the present disclosure can comprise, in addition to a TMMP of the present disclosure, one or more of: a salt, e.g., NaCl, $MgCl_2$, KCl, $MgSO_4$, etc.; a buffering agent, e.g., a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), N-tris[Hydroxymethyl]methyl-3-aminopropanesulfonic acid (TAPS), etc.; a solubilizing agent; a detergent, e.g., a non-ionic detergent such as Tween-20, etc.; a protease inhibitor; glycerol; and the like.

The composition may comprise a pharmaceutically acceptable excipient, a variety of which are known in the art and need not be discussed in detail herein. Pharmaceutically acceptable excipients have been amply described in a variety of publications, including, for example, "Remington: The Science and Practice of Pharmacy", $19^{th}$ Ed. (1995), or latest edition, Mack Publishing Co; A. Gennaro (2000) "Remington: The Science and Practice of Pharmacy", 20th edition, Lippincott, Williams, & Wilkins; Pharmaceutical Dosage Forms and Drug Delivery Systems (1999) H. C. Ansel et al., eds 7th ed., Lippincott, Williams, & Wilkins; and Handbook of Pharmaceutical Excipients (2000) A. H. Kibbe et al., eds., $3^{rd}$ ed. Amer. Pharmaceutical Assoc.

A pharmaceutical composition can comprise a TMMP, and a pharmaceutically acceptable excipient. In some cases, a subject pharmaceutical composition will be suitable for administration to a subject, e.g., will be sterile. For example, in some cases, a subject pharmaceutical composition will be suitable for administration to a human subject, e.g., where the composition is sterile and is free of detectable pyrogens and/or other toxins.

The protein compositions may comprise other components, such as pharmaceutical grades of mannitol, lactose, starch, magnesium stearate, sodium saccharin, talcum, cellulose, glucose, sucrose, magnesium, carbonate, and the like. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate, hydrochloride, sulfate salts, solvates (e.g., mixed ionic salts, water, organics), hydrates (e.g., water), and the like.

For example, compositions may include aqueous solution, powder form, granules, tablets, pills, suppositories, capsules, suspensions, sprays, and the like. The composition may be formulated according to the various routes of administration described below.

Where a TMMP is administered as an injectable (e.g. subcutaneously, intraperitoneally, intramuscularly, and/or intravenously) directly into a tissue, a formulation can be provided as a ready-to-use dosage form, or as non-aqueous form (e.g. a reconstitutable storage-stable powder) or aqueous form, such as liquid composed of pharmaceutically acceptable carriers and excipients. The protein-containing formulations may also be provided so as to enhance serum half-life of the TMMP following administration. For example, the TMMP may be provided in a liposome formulation, prepared as a colloid, or other conventional techniques for extending serum half-life. A variety of methods are available for preparing liposomes, as described in, e.g., Szoka et al. 1980 *Ann. Rev. Biophys. Bioeng.* 9:467, U.S. Pat. Nos. 4,235,871, 4,501,728 and 4,837,028. The preparations may also be provided in controlled release or slow-release forms.

Other examples of formulations suitable for parenteral administration include isotonic sterile injection solutions, anti-oxidants, bacteriostats, and solutes that render the formulation isotonic with the blood of the intended recipient, suspending agents, solubilizers, thickening agents, stabilizers, and preservatives. For example, a subject pharmaceutical composition can be present in a container, e.g., a sterile container, such as a syringe. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets.

The concentration of a TMMP in a formulation can vary widely (e.g., from less than about 0.1%, usually at or at least about 2% to as much as 20% to 50% or more by weight) and will usually be selected primarily based on fluid volumes, viscosities, and patient-based factors in accordance with the particular mode of administration selected and the patient's needs.

The present disclosure provides a container comprising a composition of the present disclosure, e.g., a liquid composition. The container can be, e.g., a syringe, an ampoule, and the like. In some cases, the container is sterile. In some cases, both the container and the composition are sterile.

The present disclosure provides compositions, including pharmaceutical compositions, comprising a TMMP. A composition can comprise: a) a TMMP of the present disclosure; and b) an excipient, as described above. In some cases, the excipient is a pharmaceutically acceptable excipient.

In some cases, a TMMP is present in a liquid composition. Thus, the present disclosure provides compositions (e.g., liquid compositions, including pharmaceutical compositions) comprising a TMMP. In some cases, a composition of the present disclosure comprises: a) a TMMP of the present disclosure; and b) saline (e.g., 0.9% NaCl). In some cases, the composition is sterile. In some cases, the composition is suitable for administration to a human subject, e.g., where the composition is sterile and is free of detectable pyrogens and/or other toxins. Thus, the present disclosure provides a composition comprising: a) a TMMP of the present disclosure; and b) saline (e.g., 0.9% NaCl), where the composition is sterile and is free of detectable pyrogens and/or other toxins.

Compositions Comprising a Nucleic Acid or a Recombinant Expression Vector

The present disclosure provides compositions, e.g., pharmaceutical compositions, comprising a nucleic acid or a recombinant expression vector of the present disclosure. A wide variety of pharmaceutically acceptable excipients is known in the art and need not be discussed in detail herein. Pharmaceutically acceptable excipients have been amply described in a variety of publications, including, for example, A. Gennaro (2000) "Remington: The Science and Practice of Pharmacy", 20th edition, Lippincott, Williams, & Wilkins; Pharmaceutical Dosage Forms and Drug Delivery Systems (1999) H. C. Ansel et al., eds $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc.

A composition of the present disclosure can include: a) one or more nucleic acids or one or more recombinant expression vectors comprising nucleotide sequences encoding a TMMP; and b) one or more of: a buffer, a surfactant, an antioxidant, a hydrophilic polymer, a dextrin, a chelating agent, a suspending agent, a solubilizer, a thickening agent, a stabilizer, a bacteriostatic agent, a wetting agent, and a preservative. Suitable buffers include, but are not limited to, (such as N,N-bis(2-hydroxyethyl) aminoethanesulfonic acid (BES), bis(2-hydroxyethyl)amino-tris(hydroxymethyl) methane (BIS-Tris), N-(2-hydroxyethyl)piperazine-N'3-propanesulfonic acid (EPPS or HEPPS), glycylglycine, N hydroxyehtylpiperazine-N'-2-ethanesulfonic acid (HEPES), 3-(N-morpholino)propane sulfonic acid (MOPS), piperazine-N,N'-bis(2-ethane-sulfonic acid) (PIPES), sodium bicarbonate, 3-(N-tris(hydroxymethyl)-methyl-amino)-2-hydroxy-propanesulfonic acid) TAPSO, (N-tris(hydroxymethyl)methyl-2-aminoethanesulfonic acid (TES), N-tris(hydroxymethyl)methyl-glycine (Tricine), tris (hydroxymethyl)-aminomethane (Tris), etc.). Suitable salts include, e.g., NaCl, $MgCl_2$, KCl, $MgSO_4$, etc.

A pharmaceutical formulation of the present disclosure can include a nucleic acid or recombinant expression vector of the present disclosure in an amount of from about 0.001% to about 90% (w/w). In the description of formulations, below, "subject nucleic acid or recombinant expression vector" will be understood to include a nucleic acid or recombinant expression vector of the present disclosure. For example, in some cases, a subject formulation comprises a nucleic acid or recombinant expression vector of the present disclosure.

A subject nucleic acid or recombinant expression vector can be admixed, encapsulated, conjugated or otherwise associated with other compounds or mixtures of compounds; such compounds can include, e.g., liposomes or receptor-targeted molecules. A subject nucleic acid or recombinant expression vector can be combined in a formulation with one or more components that assist in uptake, distribution and/or absorption.

A subject nucleic acid or recombinant expression vector composition can be formulated into any of many possible dosage forms such as, but not limited to, tablets, capsules, gel capsules, liquid syrups, soft gels, suppositories, and enemas. A subject nucleic acid or recombinant expression vector composition can also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

A formulation comprising a subject nucleic acid or recombinant expression vector can be a liposomal formulation. As used herein, the term "liposome" means a vesicle composed of amphiphilic lipids arranged in a spherical bilayer or bilayers. Liposomes are unilamellar or multilamellar vesicles which have a membrane formed from a lipophilic material and an aqueous interior that contains the composition to be delivered. Cationic liposomes are positively charged liposomes that can interact with negatively charged DNA molecules to form a stable complex. Liposomes that are pH sensitive or negatively charged are believed to entrap DNA rather than complex with it. Both cationic and non-cationic liposomes can be used to deliver a subject nucleic acid or recombinant expression vector.

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860, which is incorporated herein by reference in its entirety.

The formulations and compositions may also include surfactants. The use of surfactants in drug products, formulations and in emulsions is well known in the art. Surfactants and their uses are further described in U.S. Pat. No. 6,287,860.

In one embodiment, various penetration enhancers are included, to effect the efficient delivery of nucleic acids. In addition to aiding the diffusion of non-lipophilic drugs across cell membranes, penetration enhancers also enhance the permeability of lipophilic drugs. Penetration enhancers may be classified as belonging to one of five broad categories, i.e., surfactants, fatty acids, bile salts, chelating agents, and non-chelating non-surfactants. Penetration enhancers and their uses are further described in U.S. Pat. No. 6,287,860, which is incorporated herein by reference in its entirety.

Compositions and formulations for oral administration include powders or granules, microparticulates, nanoparticulates, suspensions or solutions in water or non-aqueous media, capsules, gel capsules, sachets, tablets, or minitablets. Thickeners, flavoring agents, diluents, emulsifiers, dispersing aids or binders may be desirable. Suitable oral formulations include those in which a subject antisense nucleic acid is administered in conjunction with one or more penetration enhancers surfactants and chelators. Suitable surfactants include, but are not limited to, fatty acids and/or esters or salts thereof, bile acids and/or salts thereof. Suitable bile acids/salts and fatty acids and their uses are further described in U.S. Pat. No. 6,287,860. Also suitable are combinations of penetration enhancers, for example, fatty acids/salts in combination with bile acids/salts. An exemplary suitable combination is the sodium salt of lauric acid, capric acid, and UDCA. Further penetration enhancers include, but are not limited to, polyoxyethylene-9-lauryl ether, and polyoxyethylene-20-cetyl ether. Suitable penetration enhancers also include propylene glycol, dimethylsulfoxide, triethanoiamine, N,N-dimethylacetamide, N,N-dimethylformamide, 2-pyrrolidone and derivatives thereof, tetrahydrofurfuryl alcohol, and AZONE™

Methods of Modulating T Cell Activity

The present disclosure provides a method of selectively modulating the activity of an epitope-specific T cell, the method comprising contacting the T cell with a TMMP of the present disclosure, where contacting the T cell with a TMMP selectively modulates the activity of the epitope-specific T cell. In some cases, the contacting occurs in vitro. In some cases, the contacting occurs in vivo. In some cases, the contacting occurs ex vivo.

In some cases, e.g., where the target T cell is a $CD8^+$ T cell, the TMMP comprises Class I MHC polypeptides (e.g., β2-microglobulin and Class I MHC heavy chain).

Where a TMMP includes an immunomodulatory polypeptide that is an activating polypeptide, contacting the T cell with the TMMP activates the epitope-specific T cell. In some instances, the epitope-specific T cell is a T cell that is specific for an epitope present on a cancer cell, and contacting the epitope-specific T cell with the TMMP increases cytotoxic activity of the T cell toward the cancer cell. In some instances, the epitope-specific T cell is a T cell that is specific for an epitope present on a cancer cell, and contacting the epitope-specific T cell with the TMMP increases the number of the epitope-specific T cells.

In some instances, the epitope-specific T cell is a T cell that is specific for an epitope present on a virus-infected cell, and contacting the epitope-specific T cell with the TMMP increases cytotoxic activity of the T cell toward the virus-infected cell. In some instances, the epitope-specific T cell is a T cell that is specific for an epitope present on a virus-infected cell, and contacting the epitope-specific T cell with the TMMP increases the number of the epitope-specific T cells.

Where a TMMP includes an immunomodulatory polypeptide that is an inhibiting polypeptide, contacting the T cell with the TMMP inhibits the epitope-specific T cell. In some instances, the epitope-specific T cell is a self-reactive T cell that is specific for an epitope present in a self antigen, and the contacting reduces the number of the self-reactive T cells.

The present disclosure provides a method of modulating an immune response in an individual, the method comprising administering to the individual an effective amount of a TMMP. Administering the TMMP induces an epitope-specific T cell response (e.g., a WT-1 epitope-specific T-cell response) and an epitope-non-specific T cell response, where the ratio of the epitope-specific T cell response to the epitope-non-specific T cell response is at least 2:1. In some cases, the ratio of the epitope-specific T cell response to the epitope-non-specific T cell response is at least 5:1. In some cases, the ratio of the epitope-specific T cell response to the epitope-non-specific T cell response is at least 10:1. In some cases, the ratio of the epitope-specific T cell response to the epitope-non-specific T cell response is at least 25:1. In some cases, the ratio of the epitope-specific T cell response to the epitope-non-specific T cell response is at least 50:1. In some cases, the ratio of the epitope-specific T cell response to the epitope-non-specific T cell response is at least 100:1. In some cases, the individual is a human. In some cases, the modulating increases a cytotoxic T-cell response to a cancer cell, e.g., a WT-1-expressing cancer cell. In some cases, the administering is intravenous, subcutaneous, intramuscular, systemic, intralymphatic, distal to a treatment site, local, or at or near a treatment site.

The present disclosure provides a method of delivering a costimulatory (i.e., immunomodulatory) polypeptide selectively to target T cell, the method comprising contacting a mixed population of T cells with a TMMP of the present disclosure, where the mixed population of T cells comprises the target T cell and non-target T cells, where the target T cell is specific for the epitope present within the TMMP (e.g., where the target T cell is specific for the WT-1 epitope present within the TMMP), and where the contacting step delivers the one or more costimulatory polypeptides (immunomodulatory polypeptides) present within the TMMP to the target T cell. In some cases, the population of T cells is in vitro. In some cases, the population of T cells is in vivo in an individual. In some cases, the method comprises administering the TMMP to the individual. In some case, the T cell is a cytotoxic T cell. In some cases, the mixed population of T cells is an in vitro population of mixed T cells obtained from an individual, and the contacting step results in activation and/or proliferation of the target T cell, generating a population of activated and/or proliferated target T cells; in some of these instances, the method further comprises administering the population of activated and/or proliferated target T cells to the individual.

The present disclosure provides a method of detecting, in a mixed population of T cells obtained from an individual, the presence of a target T cell that binds an epitope of interest (e.g., a WT-1 epitope), the method comprising: a) contacting in vitro the mixed population of T cells with a TMMP, wherein the TMMP comprises the epitope of interest (e.g., the WT-1 epitope); and b) detecting activation and/or proliferation of T cells in response to said contacting, wherein activated and/or proliferated T cells indicates the presence of the target T cell.

Treatment Methods

The present disclosure provides a method of treatment of an individual, the method comprising administering to the individual an amount of a TMMP of the present disclosure, or one or more nucleic acids encoding the TMMP, effective to treat the individual. Also provided is a TMMP for use in a method of treatment of the human or animal body. In some cases, a treatment method of the present disclosure comprises administering to an individual in need thereof one or more recombinant expression vectors comprising nucleotide sequences encoding a TMMP. In some cases, a treatment method of the present disclosure comprises administering to an individual in need thereof one or more mRNA molecules comprising nucleotide sequences encoding a TMMP. In some cases, a treatment method of the present disclosure comprises administering to an individual in need thereof a TMMP of the present disclosure. Conditions that can be treated include, e.g., cancer and autoimmune disorders, as described below.

In some cases, a TMMP, when administered to an individual in need thereof, induces both an epitope-specific T cell response and an epitope non-specific T cell response. In other words, in some cases, a TMMP, when administered to an individual in need thereof, induces an epitope-specific T cell response by modulating the activity of a first T cell that displays both: i) a TCR specific for the epitope present in the TMMP; ii) a co-immunomodulatory polypeptide that binds to the immunomodulatory polypeptide present in the TMMP; and induces an epitope non-specific T cell response by modulating the activity of a second T cell that displays: i) a TCR specific for an epitope other than the epitope present in the TMMP; and ii) a co-immunomodulatory polypeptide that binds to the immunomodulatory polypeptide present in the TMMP. The ratio of the epitope-specific T cell response to the epitope-non-specific T cell response is at least 2:1, at least 5:1, at least 10:1, at least 15:1, at least 20:1, at least 25:1, at least 50:1, or at least 100:1. The ratio of the epitope-specific T cell response to the epitope-non-specific T cell response is from about 2:1 to about 5:1, from about 5:1 to about 10:1, from about 10:1 to about 15:1, from about 15:1 to about 20:1, from about 20:1 to about 25:1, from about 25:1 to about 50:1, or from about 50:1 to about 100:1, or more than 100:1. "Modulating the activity" of a T cell can include one or more of: i) activating a cytotoxic (e.g., $CD8^+$) T cell; ii) inducing cytotoxic activity of a cytotoxic (e.g., $CD8^+$) T cell; iii) inducing production and release of a cytotoxin (e.g., a perforin; a granzyme; a granulysin) by a cytotoxic (e.g., $CD8^+$) T cell; iv) inhibiting activity of an autoreactive T cell; and the like.

The combination of the reduced affinity of the MOD for its cognate co-MOD, and the affinity of the epitope for a TCR, provides for enhanced selectivity of a TMMP of the present disclosure. Thus, for example, a TMMP binds with higher avidity to a first T cell that displays both: i) a TCR specific for the epitope present in the TMMP; and ii) a co-immunomodulatory polypeptide that binds to the immunomodulatory polypeptide present in the TMMP, compared to the avidity to which it binds to a second T cell that displays: i) a TCR specific for an epitope other than the epitope present in the TMMP; and ii) a co-MOD that binds to the immunomodulatory polypeptide present in the TMMP.

The present disclosure provides a method of selectively modulating the activity of an epitope-specific T cell in an individual, the method comprising administering to the individual an effective amount of a TMMP, or one or more nucleic acids (e.g., expression vectors; mRNA; etc.) comprising nucleotide sequences encoding the TMMP, where the TMMP selectively modulates the activity of the epitope-specific T cell in the individual. Selectively modulating the activity of an epitope-specific T cell can treat a disease or disorder in the individual. Thus, the present disclosure provides a treatment method comprising administering to an individual in need thereof an effective amount of a TMMP.

In some cases, the MOD is an activating polypeptide, and the TMMP activates the epitope-specific T cell. In some cases, the epitope is a cancer-associated epitope, and the TMMP increases the activity of a T cell specific for the cancer-associate epitope. In some cases, the MOD is an activating polypeptide, and the TMMP activates a WT-1 epitope-specific T-cell. In some cases, the T cells are T-helper cells ($CD4^+$ cells), cytotoxic T-cells ($CD8^+$ cells), or NK-T-cells. In some cases, the epitope is a WT-1 epitope, and the TMMP increases the activity of a T-cell specific for a cancer cell expressing the WT-1 epitope (e.g., T-helper cells ($CD4^+$ cells), cytotoxic T-cells ($CD8^+$ cells), and/or NK-T-cells). Activation of $CD4^+$ T cells can include increasing proliferation of $CD4^+$ T cells and/or inducing or enhancing release cytokines by $CD4^+$ T cells. Activation of NK-T-cells and/or $CD8^+$ cells can include: increasing proliferation of NK-T-cells and/or $CD8^+$ cells; and/or inducing release of cytokines such as interferon $\gamma$ by NK-T-cells and/or $CD8^+$ cells. In some cases, a TMMP of the present disclosure reduces proliferation and/or activity of a regulatory T (Treg) cell. Tregs are $FoxP3^+$, $CD4^+$ T cells. In some cases, e.g., where a TMMP of the present disclosure comprises an inhibitory immunomodulatory polypeptide (e.g., PD-L1, FasL, and the like), the TMMP reduces the proliferation and/or activity of a Treg.

In some cases, the MOD is an activating polypeptide, and the TMMP activates the epitope-specific T cell. In some cases, the epitope is a cancer-associated epitope, and the TMMP increases the activity of a T cell specific for the cancer-associate epitope.

Where a TMMP comprises a WT-1 peptide epitope, the TMMP can be administered to an individual having a WT-1-expressing cancer. WT1-expressing cancers include a leukemia, a desmoplastic small round cell tumor, a gastric cancer, a colon cancer, a lung cancer, a breast cancer, a germ cell tumor, an ovarian cancer, a uterine cancer, a thyroid cancer, a liver cancer, a renal cancer, a Kaposi's sarcoma, a sarcoma, a hepatocellular carcinoma, a Wilms' tumor, an acute myelogenous leukemia (AML), a myelodysplastic syndrome (MDS), an a non-small cell lung cancer (NSCLC), a myeloma, pancreatic cancer, colorectal cancer, a mesothelioma, a soft tissue sarcoma, a neuroblastoma, and a nephroblastoma.

Where a TMMP comprises a WT-1 peptide epitope, the TMMP can be administered to an individual in need thereof to treat acute myeloid leukemia (AML) in the individual. Where a TMMP comprises a WT-1 peptide epitope, the TMMP can be administered to an individual in need thereof to treat a myeloma in the individual. Where a TMMP comprises a WT-1 peptide epitope, the TMMP can be administered to an individual in need thereof to treat ovarian cancer in the individual. Where a TMMP of the present disclosure comprises a WT-1 peptide epitope, the TMMP can be administered to an individual in need thereof to treat pancreatic cancer in the individual. Where a TMMP comprises a WT-1 peptide epitope, the TMMP can be administered to an individual in need thereof to treat non-small cell lung cancer (NSCLC) in the individual. Where a TMMP comprises a WT-1 peptide epitope, the TMMP can be administered to an individual in need thereof to treat colorectal cancer (CRC) in the individual. Where a TMMP comprises a WT-1 peptide epitope, the TMMP can be administered to an individual in need thereof to treat breast cancer in the individual. Where a TMMP comprises a WT-1 peptide epitope, the TMMP can be administered to an individual in need thereof to treat a Wilms tumor in the individual. Where a TMMP of the present disclosure comprises a WT-1 peptide epitope, the TMMP can be administered to an individual in need thereof to treat mesothelioma in the individual. Where a TMMP comprises a WT-1 peptide epitope, the TMMP can be administered to an individual in need thereof to treat soft tissue sarcoma in the individual. Where a TMMP comprises a WT-1 peptide epitope, the TMMP can be administered to an individual in need thereof to treat a neuroblastoma in the individual. Where a TMMP comprises a WT-1 peptide epitope, the TMMP can be administered to an individual in need thereof to treat a nephroblastoma in the individual.

The present disclosure provides a method of treating cancer in an individual, the method comprising administering to the individual an effective amount of a TMMP of the present disclosure, or one or more nucleic acids (e.g., expression vectors; mRNA; etc.) comprising nucleotide sequences encoding the TMMP, where the TMMP comprises a T-cell epitope that is a cancer epitope, and where the TMMP comprises a stimulatory MOD. In some cases, an "effective amount" of a TMMP is an amount that, when administered in one or more doses to an individual in need thereof, reduces the number of cancer cells in the individual. For example, in some cases, an "effective amount" of a TMMP of the present disclosure is an amount that, when administered in one or more doses to an individual in need thereof, reduces the number of cancer cells in the individual by at least 10%, at least 15%, at least 20%, at least 25%, at least 30%, at least 40%, at least 50%, at least 60%, at least 70%, at least 80%, at least 90%, or at least 95%, compared to the number of cancer cells in the individual before administration of the TMMP, or in the absence of administration with the TMMP. In some cases, an "effective amount" of a TMMP is an amount that, when administered in one or more doses to an individual in need thereof, reduces the number of cancer cells in the individual to undetectable levels.

In some cases, an "effective amount" of a TMMP is an amount that, when administered in one or more doses to an individual in need thereof, reduces the tumor mass in the individual. For example, in some cases, an "effective amount" of a TMMP is an amount that, when administered in one or more doses to an individual in need thereof (an individual having a tumor), reduces the tumor mass in the individual by at least 10%, at least 15%, at least 20%, at least 25%, at least 30%, at least 40%, at least 50%, at least 60%, at least 70%, at least 80%, at least 90%, or at least 95%, compared to the tumor mass in the individual before administration of the TMMP, or in the absence of administration with the TMMP. In some cases, an "effective amount" of a TMMP is an amount that, when administered in one or more doses to an individual in need thereof (an individual having a tumor), reduces the tumor volume in the individual. For example, in some cases, an "effective amount" of a TMMP is an amount that, when administered in one or more doses to an individual in need thereof (an individual having a tumor), reduces the tumor volume in the individual by at least 10%, at least 15%, at least 20%, at least 25%, at least 30%, at least 40%, at least 50%, at least 60%, at least 70%, at least 80%, at least 90%, or at least 95%, compared to the tumor volume in the individual before administration of the TMMP, or in the absence of administration with the TMMP. In some cases, an "effective amount" of a TMMP is an amount that, when administered in one or more doses to an individual in need thereof, increases survival time of the individual. For example, in some cases, an "effective amount" of a TMMP is an amount that, when administered in one or more doses to an individual in need thereof, increases survival time of the individual by at least 1 month, at least 2 months, at least 3 months, from 3 months to 6 months, from 6 months to 1 year, from 1 year to 2 years, from 2 years to 5 years, from 5 years to 10 years, or more than 10 years, compared to the expected survival time of the individual in the absence of administration with the TMMP.

In some cases, an "effective amount" of a TMMP is an amount that, when administered in one or more doses to an individual in need thereof, either as a monotherapy or as part of a combination therapy (e.g., as part of a combination therapy with an immune checkpoint inhibitor), as discussed below, reduces the overall tumor burden in the individual, i.e., the amount of cancer in the body, or alternatively, causes the total tumor burden in the patient to remain relatively stable for a sufficient period of time for the patient to have a confirmed "stable disease" as determined by standard RECIST criteria. See, e.g., Aykan and Özatli (2020) *World J. Clin. Oncol.* 11:53.

In some cases, an effective amount of a TMMP is an amount that, when administered in one or more doses to an individual in need thereof, either as a monotherapy or as part of a combination therapy, e.g., with an immune checkpoint inhibitor, as discussed below, causes the tumor size to be reduced by a sufficient amount, and for a sufficient period of time, for the patient to have a confirmed "partial response" as determined by standard RECIST criteria.

In some cases, an effective amount of a TMMP is an amount that, when administered in one or more doses to an individual in need thereof, either as a monotherapy or as part of a combination therapy, e.g., with an immune checkpoint inhibitor, causes the tumor size to be reduced by a sufficient amount, and for a sufficient period of time, for the patient to have a confirmed "complete response" as determined by standard RECIST criteria.

In some instances, the epitope-specific T cell is a T cell that is specific for an epitope present on a virus-infected cell, and contacting the epitope-specific T cell with the TMMP increases cytotoxic activity of the T cell toward the virus-infected cell. In some instances, the epitope-specific T cell is a T cell that is specific for an epitope present on a virus-infected cell, and contacting the epitope-specific T cell with the TMMP increases the number of the epitope-specific T cells.

Thus, the present disclosure provides a method of treating a virus infection in an individual, the method comprising administering to the individual an effective amount of a TMMP, or one or more nucleic acids comprising nucleotide sequences encoding the TMMP, where the TMMP comprises a T-cell epitope that is a viral epitope, and where the TMMP comprises a stimulatory MOD. In some cases, an "effective amount" of a TMMP is an amount that, when administered in one or more doses to an individual in need thereof, reduces the number of virus-infected cells in the individual. For example, in some cases, an "effective amount" of a TMMP is an amount that, when administered in one or more doses to an individual in need thereof, reduces the number of virus-infected cells in the individual by at least 10%, at least 15%, at least 20%, at least 25%, at least 30%, at least 40%, at least 50%, at least 60%, at least 70%, at least 80%, at least 90%, or at least 95%, compared to the number of virus-infected cells in the individual before administration of the TMMP, or in the absence of administration with the TMMP. In some cases, an "effective amount" of a TMMP is an amount that, when administered in one or more doses to an individual in need thereof, reduces the number of virus-infected cells in the individual to undetectable levels.

Thus, the present disclosure provides a method of treating an infection in an individual, the method comprising administering to the individual an effective amount of a TMMP, or one or more nucleic acids comprising nucleotide sequences encoding the TMMP, where the TMMP comprises a T-cell epitope that is a pathogen-associated epitope, and where the TMMP comprises a stimulatory immunomodulatory polypeptide. In some cases, an "effective amount" of a TMMP of the present disclosure is an amount that, when administered in one or more doses to an individual in need thereof, reduces the number of pathogens in the individual. For example, in some cases, an "effective amount" of a TMMP is an amount that, when administered in one or more doses to an individual in need thereof, reduces the number of pathogens in the individual by at least 10%, at least 15%, at least 20%, at least 25%, at least 30%, at least 40%, at least 50%, at least 60%, at least 70%, at least 80%, at least 90%, or at least 95%, compared to the number of pathogens in the individual before administration of the TMMP, or in the absence of administration with the TMMP. In some cases, an "effective amount" of a TMMP is an amount that, when administered in one or more doses to an individual in need thereof, reduces the number of pathogens in the individual to undetectable levels. Pathogens include viruses, bacteria, protozoans, and the like.

In some cases, the MOD is an inhibitory polypeptide, and the TMMP inhibits activity of the epitope-specific T cell. In some cases, the epitope is a self-epitope, and the TMMP selectively inhibits the activity of a T cell specific for the self-epitope.

The present disclosure provides a method of treating an autoimmune disorder in an individual, the method comprising administering to the individual an effective amount of a TMMP, or one or more nucleic acids comprising nucleotide sequences encoding the TMMP, where the TMMP comprises a T-cell epitope that is a self epitope, and where the TMMP comprises an inhibitory MOD. In some cases, an "effective amount" of a TMMP is an amount that, when administered in one or more doses to an individual in need thereof, reduces the number self-reactive T cells by at least 10%, at least 15%, at least 20%, at least 25%, at least 30%, at least 40%, at least 50%, at least 60%, at least 70%, at least 80%, at least 90%, or at least 95%, compared to number of self-reactive T cells in the individual before administration of the TMMP, or in the absence of administration with the TMMP. In some cases, an "effective amount" of a TMMP is an amount that, when administered in one or more doses to an individual in need thereof, reduces production of Th2 cytokines in the individual. In some cases, an "effective amount" of a TMMP is an amount that, when administered in one or more doses to an individual in need thereof, ameliorates one or more symptoms associated with an autoimmune disease in the individual.

As noted above, in some cases, in carrying out a subject treatment method, a TMMP is administered to an individual in need thereof, as the TMMP per se. In other instances, in carrying out a subject treatment method, one or more nucleic acids comprising nucleotide sequences encoding a TMMP is/are administering to an individual in need thereof. Thus, in other instances, one or more nucleic acids of the present disclosure, e.g., one or more recombinant expression vectors of the present disclosure, is/are administered to an individual in need thereof.

Formulations

Suitable formulations are described above, where suitable formulations include a pharmaceutically acceptable excipient. In some cases, a suitable formulation comprises: a) a TMMP of; and b) a pharmaceutically acceptable excipient. In some cases, a suitable formulation comprises: a) a nucleic acid comprising a nucleotide sequence encoding a TMMP; and b) a pharmaceutically acceptable excipient; in some instances, the nucleic acid is an mRNA. In some cases, a suitable formulation comprises: a) a first nucleic acid comprising a nucleotide sequence encoding the first polypeptide of a TMMP; b) a second nucleic acid comprising a nucleotide sequence encoding the second polypeptide of a TMMP; and c) a pharmaceutically acceptable excipient. In some cases, a suitable formulation comprises: a) a recombinant expression vector comprising a nucleotide sequence encoding a TMMP; and b) a pharmaceutically acceptable excipient. In some cases, a suitable formulation comprises: a) a first recombinant expression vector comprising a nucleotide sequence encoding the first polypeptide of a TMMP; b) a second recombinant expression vector comprising a nucleotide sequence encoding the second polypeptide of a TMMP; and c) a pharmaceutically acceptable excipient.

Suitable pharmaceutically acceptable excipients are described above.

Dosages

A suitable dosage can be determined by an attending physician or other qualified medical personnel, based on various clinical factors. As is well known in the medical arts, dosages for any one patient depend upon many factors, including the patient's size, body surface area, age, the particular polypeptide or nucleic acid to be administered, sex of the patient, time, and route of administration, general health, and other drugs being administered concurrently. A TMMP of the present disclosure may be administered in amounts between 1 ng/kg body weight and 20 mg/kg body weight per dose, e.g. between 0.1 mg/kg body weight to 10 mg/kg body weight, e.g. between 0.5 mg/kg body weight to 5 mg/kg body weight; however, doses below or above this exemplary range are envisioned, especially considering the aforementioned factors. If the regimen is a continuous infusion, it can also be in the range of 1 μg to 10 mg per kilogram of body weight per minute. A TMMP of the present disclosure can be administered in an amount of from about 1 mg/kg body weight to 50 mg/kg body weight, e.g., from about 1 mg/kg body weight to about 5 mg/kg body weight, from about 5 mg/kg body weight to about 10 mg/kg body weight, from about 10 mg/kg body weight to about 15 mg/kg body weight, from about 15 mg/kg body weight to about 20 mg/kg body weight, from about 20 mg/kg body weight to about 25 mg/kg body weight, from about 25 mg/kg body weight to about 30 mg/kg body weight, from about 30 mg/kg body weight to about 35 mg/kg body weight, from about 35 mg/kg body weight to about 40 mg/kg body weight, or from about 40 mg/kg body weight to about 50 mg/kg body weight.

In some cases, a suitable dose of a TMMP is from 0.01 μg to 100 g per kg of body weight, from 0.1 μg to 10 g per kg of body weight, from 1 μg to 1 g per kg of body weight, from 10 μg to 100 mg per kg of body weight, from 100 μg to 10 mg per kg of body weight, or from 100 μg to 1 mg per kg of body weight. Persons of ordinary skill in the art can easily estimate repetition rates for dosing based on measured residence times and concentrations of the administered agent in bodily fluids or tissues. Following successful treatment, it may be desirable to have the patient undergo maintenance therapy to prevent the recurrence of the disease state, wherein a TMMP is administered in maintenance doses, ranging from 0.01 μg to 100 g per kg of body weight, from 0.1 μg to 10 g per kg of body weight, from 1 μg to 1 g per kg of body weight, from 10 μg to 100 mg per kg of body weight, from 100 μg to 10 mg per kg of body weight, or from 100 μg to 1 mg per kg of body weight.

Those of skill will readily appreciate that dose levels can vary as a function of the specific TMMP, the severity of the symptoms and the susceptibility of the subject to side effects. Preferred dosages for a given compound are readily determinable by those of skill in the art by a variety of means.

In some cases, multiple doses of a TMMP, a nucleic acid of the present disclosure, or a recombinant expression vector of the present disclosure are administered. The frequency of administration of a TMMP, a nucleic acid of the present disclosure, or a recombinant expression vector of the present disclosure can vary depending on any of a variety of factors, e.g., severity of the symptoms, etc. For example, in some cases, a TMMP, a nucleic acid of the present disclosure, or a recombinant expression vector of the present disclosure is administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid).

The duration of administration of a TMMP, a nucleic acid of the present disclosure, or a recombinant expression vector of the present disclosure, e.g., the period of time over which a TMMP, a nucleic acid of the present disclosure, or a recombinant expression vector of the present disclosure is administered, can vary, depending on any of a variety of factors, e.g., patient response, etc. For example, a TMMP, a nucleic acid of the present disclosure, or a recombinant expression vector of the present disclosure can be administered over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more.

Routes of Administration

An active agent (a TMMP of the present disclosure, a nucleic acid of the present disclosure, or a recombinant expression vector of the present disclosure) is administered to an individual using any available method and route suitable for drug delivery, including in vivo and ex vivo methods, as well as systemic and localized routes of administration.

Conventional and pharmaceutically acceptable routes of administration include intratumoral, peritumoral, intramuscular, intralymphatic, intratracheal, intracranial, subcutaneous, intradermal, topical application, intravenous, intraarterial, rectal, nasal, oral, and other enteral and parenteral routes of administration. Routes of administration may be combined, if desired, or adjusted depending upon the TMMP and/or the desired effect. A TMMP, or a nucleic acid or recombinant expression vector of the present disclosure, can be administered in a single dose or in multiple doses.

In some cases, a TMMP, a nucleic acid, or a recombinant expression vector is administered intravenously. In some cases, a TMMP of the present disclosure, a nucleic acid of the present disclosure, or a recombinant expression vector of the present disclosure is administered intramuscularly. In some cases, a TMMP, a nucleic acid, or a recombinant expression vector is administered intralymphatically. In some cases, a TMMP, a nucleic acid, or a recombinant expression vector is administered locally. In some cases, a TMMP, a nucleic acid, or a recombinant expression vector is administered intratumorally. In some cases, a TMMP, a nucleic acid, or a recombinant expression vector is administered peritumorally. In some cases, a TMMP, a nucleic acid, or a recombinant expression vector is administered intracranially. In some cases, a TMMP, a nucleic acid, or a recombinant expression vector is administered subcutaneously.

In some cases, a TMMP is administered intravenously. In some cases, a TMMP is administered intramuscularly. In some cases, a TMMP is administered locally. In some cases, a TMMP is administered intratumorally. In some cases, a TMMP is administered peritumorally. In some cases, a TMMP is administered intracranially. In some cases, a TMMP is administered subcutaneously. In some cases, a TMMP is administered intralymphatically.

A TMMP, a nucleic acid, or a recombinant expression vector can be administered to a host using any available conventional methods and routes suitable for delivery of conventional drugs, including systemic or localized routes. In general, routes of administration contemplated for use in a method of the present disclosure include, but are not necessarily limited to, enteral, parenteral, and inhalational routes.

Parenteral routes of administration other than inhalation administration include, but are not necessarily limited to, topical, transdermal, subcutaneous, intramuscular, intraorbital, intracapsular, intraspinal, intrasternal, intratumoral, intralymphatic, peritumoral, and intravenous routes, i.e., any route of administration other than through the alimentary canal. Parenteral administration can be carried to effect systemic or local delivery of a TMMP of the present disclosure, a nucleic acid of the present disclosure, or a recombinant expression vector of the present disclosure. Where systemic delivery is desired, administration typically involves invasive or systemically absorbed topical or mucosal administration of pharmaceutical preparations.

Combination Therapies

In some cases, a method of the present disclosure for treating cancer in an individual comprises: a) administering a TMMP; and b) administering at least one additional therapeutic agent or therapeutic treatment. Suitable additional therapeutic agents include, but are not limited to, a small molecule cancer chemotherapeutic agent, and an immune checkpoint inhibitor. Suitable additional therapeutic treatments include, e.g., radiation, surgery (e.g., surgical resection of a tumor), and the like.

A treatment method of the present disclosure can comprise co-administration of a TMMP and at least one additional therapeutic agent. By "co-administration" is meant that both a TMMP and at least one additional therapeutic agent are administered to an individual, although not necessarily at the same time, in order to achieve a therapeutic effect that is the result of having administered both the TMMP and the at least one additional therapeutic agent. The administration of the TMMP and the at least one additional therapeutic agent can be substantially simultaneous, e.g., the TMMP can be administered to an individual within about 1 minute to about 24 hours (e.g., within about 1 minute, within about 5 minutes, within about 15 minutes, within about 30 minutes, within about 1 hour, within about 4 hours, within about 8 hours, within about 12 hours, or within about 24 hours) of administration of the at least one additional therapeutic agent. In some cases, a TMMP of the present disclosure is administered to an individual who is undergoing treatment with, or who has undergone treatment with, the at least one additional therapeutic agent. The administration of the TMMP can occur at different times and/or at different frequencies.

As an example, a treatment method of the present disclosure can comprise co-administration of a TMMP and an immune checkpoint inhibitor such as an antibody specific for an immune checkpoint. By "co-administration" is meant that both a TMMP and an immune checkpoint inhibitor (e.g., an antibody specific for an immune checkpoint polypeptide) are administered to an individual, although not necessarily at the same time, in order to achieve a therapeutic effect that is the result of having administered both the TMMP and the immune checkpoint inhibitor (e.g., an antibody specific for an immune checkpoint polypeptide). The administration of the TMMP and the immune checkpoint inhibitor (e.g., an antibody specific for an immune checkpoint polypeptide) can be substantially simultaneous, e.g., the TMMP can be administered to an individual within about 1 minute to about 24 hours (e.g., within about 1 minute, within about 5 minutes, within about 15 minutes, within about 30 minutes, within about 1 hour, within about 4 hours, within about 8 hours, within about 12 hours, or within about 24 hours) of administration of the immune checkpoint inhibitor (e.g., an antibody specific for an immune checkpoint polypeptide). In some cases, a TMMP of the present disclosure is administered to an individual who is undergoing treatment with, or who has undergone treatment with, an immune checkpoint inhibitor (e.g., an antibody specific for an immune checkpoint polypeptide). The administration of the TMMP and the immune checkpoint inhibitor (e.g., an antibody specific for an immune checkpoint polypeptide) can occur at different times and/or at different frequencies.

Exemplary immune checkpoint inhibitors include inhibitors that target an immune checkpoint polypeptide such as CD27, CD28, CD40, CD122, CD96, CD73, CD47, OX40, GITR, CSF1R, JAK, PI3K delta, PI3K gamma, TAM, arginase, CD137 (also known as 4-1BB), ICOS, A2AR, B7-H3, B7-H4, BTLA, CTLA-4, LAG3, TIM3, VISTA, CD96, TIGIT, CD122, PD-1, PD-L1 and PD-L2. In some cases, the immune checkpoint polypeptide is a stimulatory checkpoint molecule selected from CD27, CD28, CD40, ICOS, OX40, GITR, CD122 and CD137. In some cases, the immune checkpoint polypeptide is an inhibitory checkpoint molecule selected from A2AR, B7-H3, B7-H4, BTLA, CTLA-4, IDO, KIR, LAG3, PD-1, TIM3, CD96, TIGIT and VISTA.

In some cases, the immune checkpoint inhibitor is an antibody specific for an immune checkpoint polypeptide. In some cases, the anti-immune checkpoint antibody is a monoclonal antibody. In some cases, the anti-immune checkpoint antibody is humanized, or de-immunized such that the antibody does not substantially elicit an immune response in a human. In some cases, the anti-immune checkpoint antibody is a humanized monoclonal antibody. In some cases, the anti-immune checkpoint antibody is a de-immunized monoclonal antibody. In some cases, the anti-immune checkpoint antibody is a fully human monoclonal antibody. In some cases, the anti-immune checkpoint antibody inhibits binding of the immune checkpoint polypeptide to a ligand for the immune checkpoint polypeptide. In some cases, the anti-immune checkpoint antibody inhibits binding of the immune checkpoint polypeptide to a receptor for the immune checkpoint polypeptide.

Suitable anti-immune checkpoint antibodies include, but are not limited to, nivolumab (Bristol-Myers Squibb), pembrolizumab (Merck), pidilizumab (Curetech), AMP-224 (GlaxoSmithKline/Amplimmune), MPDL3280A (Roche), MDX-1105 (Medarex, Inc./Bristol Myer Squibb), MEDI-4736 (Medimmune/AstraZeneca), arelumab (Merck Serono), ipilimumab (YERVOY, (Bristol-Myers Squibb), tremelimumab (Pfizer), pidilizumab (CureTech, Ltd.), IMP321 (Immutep S.A.), MGA271 (Macrogenics), BMS-986016 (Bristol-Meyers Squibb), lirilumab (Bristol-Myers Squibb), urelumab (Bristol-Meyers Squibb), PF-05082566 (Pfizer), IPH2101 (Innate Pharma/Bristol-Myers Squibb), MEDI-6469 (MedImmune/AZ), CP-870,893 (Genentech), Mogamulizumab (Kyowa Hakko Kirin), Varlilumab (CellDex Therapeutics), Avelumab (EMD Serono), Galiximab (Biogen Idec), AMP-514 (Amplimmune/AZ), AUNP 12 (Aurigene and Pierre Fabre), Indoximod (NewLink Genetics), NLG-919 (NewLink Genetics), INCB024360 (Incyte); KN035; and combinations thereof. For example, in some cases, the immune checkpoint inhibitor is an anti-PD-1 antibody. Suitable anti-PD-1 antibodies include, e.g., nivolumab, pembrolizumab (also known as MK-3475), pidilizumab, SHR-1210, PDR001, and AMP-224. In some cases, the anti-PD-1 monoclonal antibody is nivolumab, pembrolizumab or PDR001. Suitable anti-PD1 antibodies are described in U.S. Patent Publication No. 2017/0044259. For pidilizumab, see, e.g., Rosenblatt et al. (2011) *J. Immunother.* 34:409-18. In some cases, the immune checkpoint inhibitor is an anti-CTLA-4 antibody. In some cases, the anti-CTLA-4 antibody is ipilimumab or tremelimumab. For tremelimumab, see, e.g., Ribas et al. (2013) *J. Clin. Oncol.* 31:616-22. In some cases, the immune checkpoint inhibitor is an anti-PD-L1 antibody. In some cases, the anti-PD-L1 monoclonal antibody is BMS-935559, MEDI4736, MPDL3280A (also known as RG7446), KN035, or MSB0010718C. In some embodiments, the anti-PD-L1 monoclonal antibody is MPDL3280A (atezolizumab) or MEDI4736 (durvalumab). For durvalumab, see, e.g., WO 2011/066389. For atezolizumab, see, e.g., U.S. Pat. No. 8,217,149.

Subjects Suitable for Treatment

Subjects suitable for treatment with a method of the present disclosure include individuals who have cancer, including individuals who have been diagnosed as having cancer, individuals who have been treated for cancer but who failed to respond to the treatment, and individuals who have been treated for cancer and who initially responded but subsequently became refractory to the treatment. Subjects suitable for treatment with a method of the present disclosure include individuals who have an infection (e.g., an infection with a pathogen such as a bacterium, a virus, a protozoan, etc.), including individuals who have been diagnosed as having an infection, and individuals who have been treated for an infection but who failed to respond to the treatment. Subjects suitable for treatment with a method of the present disclosure include individuals who have bacterial infection, including individuals who have been diagnosed as having a bacterial infection, and individuals who have been treated for a bacterial infection but who failed to respond to the treatment. Subjects suitable for treatment with a method of the present disclosure include individuals who have a viral infection, including individuals who have been diagnosed as having a viral infection, and individuals who have been treated for a viral infection but who failed to respond to the treatment. Subjects suitable for treatment with a method of the present disclosure include individuals who have an autoimmune disease, including individuals who have been diagnosed as having an autoimmune disease, and individuals who have been treated for an autoimmune disease but who failed to respond to the treatment.

Examples of Non-Limiting Aspects of the Disclosure

Aspects Set A

Aspects, including embodiments, of the present subject matter described above may be beneficial alone or in combination, with one or more other aspects or embodiments. Without limiting the foregoing description, certain non-limiting aspects of the disclosure numbered 1-95 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

Aspect 1. T-cell modulatory multimeric polypeptide comprising: at least one heterodimer comprising: a) a first polypeptide comprising: i) a Wilms tumor-1 (WT-1) peptide epitope; and ii) first major histocompatibility complex (MHC) polypeptide; b) a second polypeptide comprising a second MHC polypeptide, and c) at least one immunomodulatory polypeptide, wherein the first and/or the second polypeptide comprises the immunomodulatory polypeptide.

Aspect 2. A T-cell modulatory multimeric polypeptide of aspect 1, wherein at least one of the one or more immunomodulatory domains is a variant immunomodulatory polypeptide that exhibits reduced affinity to a cognate co-immunomodulatory polypeptide compared to the affinity of a corresponding wild-type immunomodulatory polypeptide for the cognate co-immunomodulatory polypeptide, and wherein the epitope binds to a T-cell receptor (TCR) on a T cell with an affinity of at least $10^{-7}$ M, such that: i) the T-cell modulatory multimeric polypeptide binds to a first T cell with an affinity that is at least 25% higher than the affinity with which the T-cell modulatory multimeric polypeptide binds a second T cell, wherein the first T cell expresses on its surface the cognate co-immunomodulatory polypeptide and a TCR that binds the epitope with an affinity of at least $10^{-7}$ M, and wherein the second T cell expresses on its surface the cognate co-immunomodulatory polypeptide but does not express on its surface a TCR that binds the epitope with an affinity of at least $10^{-7}$ M; and/or ii) the ratio of the binding affinity of a control T-cell modulatory multimeric polypeptide, wherein the control comprises a wild-type immunomodulatory polypeptide, to a cognate co-immunomodulatory polypeptide to the binding affinity of the T-cell modulatory multimeric polypeptide comprising a variant of the wild-type immunomodulatory polypeptide to the cognate co-immunomodulatory polypeptide, when measured by bio-layer interferometry, is in a range of from 1.5:1 to 106:1.

Aspect 3. A T-cell modulatory multimeric polypeptide of aspect 2, wherein: a) the T-cell modulatory multimeric polypeptide binds to the first T cell with an affinity that is at least 50%, at least 2-fold, at least 5-fold, or at least 10-fold higher than the affinity with which it binds the second T cell; and/or b) the variant immunomodulatory polypeptide binds the co-immunomodulatory polypeptide with an affinity of from about 10 M to about $10^{-7}$ M, from about 10 M to about $10^{-6}$M, from about $10^{-4}$ M to about $10^{-5}$ M; and/or c) wherein the ratio of the binding affinity of a control T-cell modulatory multimeric polypeptide, wherein the control comprises a wild-type immunomodulatory polypeptide, to a cognate co-immunomodulatory polypeptide to the binding affinity of the T-cell modulatory multimeric polypeptide comprising a variant of the wild-type immunomodulatory polypeptide to the cognate co-immunomodulatory polypeptide, when measured by bio-layer interferometry, is at least 10:1, at least 50:1, at least $10^2$:1, or at least $10^3$:1.

Aspect 4. A T-cell modulatory multimeric polypeptide of any one of aspects 1-3, wherein the first or the second polypeptide comprises an immunoglobulin (Ig) Fc polypeptide.

Aspect 5. A T-cell modulatory multimeric polypeptide of aspect 4, wherein the Ig Fc polypeptide is an IgG1 Fc polypeptide.

Aspect 6. A T-cell modulatory multimeric polypeptide of aspect 5, wherein IgG1 Fc polypeptide comprises one or more amino acid substitutions selected from N297A, L234A, L235A, L234F, L235E, and P331S.

Aspect 7. A T-cell modulatory multimeric polypeptide of any one of aspects 1-6, wherein: a1) the first polypeptide comprises, in order from N-terminus to C-terminus: i) the WT-1 peptide epitope; ii) the first MHC polypeptide; and iii) at least one immunomodulatory polypeptide; and b2) the second polypeptide comprises, in order from N-terminus to C-terminus: i) the second MHC polypeptide; and ii) an immunoglobulin (Ig) Fc polypeptide; or a2) the first polypeptide comprises, in order from N-terminus to C-terminus: i) the WT-1 peptide epitope; and ii) the first MHC polypeptide; and b2) the second polypeptide comprises, in order from N-terminus to C-terminus: i) at least one immunomodulatory polypeptide; ii) the second MHC polypeptide; and iii) an Ig Fc polypeptide; or a3) the first polypeptide comprises, in order from N-terminus to C-terminus: i) the WT-1 peptide epitope; and ii) the first MHC polypeptide; and b3) the second polypeptide comprises, in order from N-terminus to C-terminus: i) the second MHC polypeptide; and ii) an Ig Fc polypeptide; and iii) at least one immunomodulatory polypeptide; or a4) the first polypeptide comprises, in order from N-terminus to C-terminus: i) the WT-1 peptide epitope; and ii) the first MHC polypeptide; and b4) the second polypeptide comprises, in order from N-terminus to C-terminus: i) the second MHC polypeptide; and ii) at least one immunomodulatory polypeptide; or a5) the first polypeptide comprises, in order from N-terminus to C-terminus: i) the WT-1 peptide epitope; and ii) the first MHC polypeptide; and b5) a second polypeptide comprises, in order from N-terminus to C-terminus: i) at least one immunomodulatory polypeptide; and ii) the second MHC polypeptide; or a6) the first polypeptide comprises, in order from N-terminus to C-terminus: i) the WT-1 peptide epitope; ii) the first MHC polypeptide; and iii) at least one immunomodulatory polypeptide; and b6) the second polypeptide comprises: i) the second MHC polypeptide.

Aspect 8. A T-cell modulatory multimeric polypeptide of any one of aspects 1-7, wherein the first polypeptide comprises a peptide linker between the WT-1 epitope and the first MHC polypeptide and/or wherein the second polypeptide comprises a peptide linker between the immunomodulatory polypeptide and the second MHC polypeptide.

Aspect 9. A T-cell modulatory multimeric polypeptide of aspect 8, wherein the peptide linker comprises the amino acid sequence (GGGGS)n (SEQ ID NO:284), where n is an integer from 1 to 10.

Aspect 10. A T-cell modulatory multimeric polypeptide of any one of aspects 1-9, wherein the first MHC polypeptide is a β2-microglobulin polypeptide; and wherein the second MHC polypeptide is an MHC class I heavy chain polypeptide.

Aspect 11. A T-cell modulatory multimeric polypeptide of any one of aspects 1-10, wherein the at least one immunomodulatory polypeptide is selected from the group consisting of a cytokine (e.g., an IL2 polypeptide, an IL7 polypeptide, an IL12 polypeptide, an IL15 polypeptide, an IL17 polypeptide, an IL21 polypeptide, an IL27 polypeptide, an IL-23 polypeptide, a TGFβ polypeptide, and the like; and including all family members, e.g., IL17A, IL-17B, IL-17C, IL-17D, IL-17E, IL-17F, IL-17E), a 4-1BBL polypeptide, an ICOS-L polypeptide, an OX-40L polypeptide, a CD80 polypeptide, a CD86 polypeptide, (CD80 and CD86 are also known as B7-1 and B7-2, respectively), a CD40 polypeptide, a CD70 polypeptide, a JAG1 (CD339) polypeptide, an ICAM (CD540 polypeptide, a PD-L1 polypeptide, a FasL polypeptide, a PD-L2 polypeptide, a PD-1H (VISTA) polypeptide, an ICOS-L (CD275) polypeptide, a GITRL polypeptide, an HVEM polypeptide, a CXCL10 polypeptide, a CXCL9 polypeptide, a CXCL11 polypeptide, a CXCL13 polypeptide, and a CX3CL1 polypeptide, a Galectin-9 polypeptide, a CD83 polypeptide, a CD30L polypeptide, a HLA-G polypeptide, a MICA polypeptide, a MICB polypeptide, a HVEM (CD270) polypeptide, a lymphotoxin beta receptor polypeptide, a 3/TR6 polypeptide, an ILT3 polypeptide, an ILT4 polypeptide, a CXCL10 polypeptide, a CXCL9 polypeptide, a CXCL11 polypeptide, a CXCL13 polypeptide, and a CX3CL1 polypeptide, and combinations thereof.

Aspect 12. A T-cell modulatory multimeric polypeptide of any one of aspects 1-11, wherein the at least one immunomodulatory polypeptide is an IL-2 polypeptide.

Aspect 13. A T-cell modulatory multimeric polypeptide of any one of aspects 1-12, wherein the multimeric polypeptide comprises at least two immunomodulatory polypeptides, and wherein at least two of the immunomodulatory polypeptides are the same.

Aspect 14. A T-cell modulatory multimeric polypeptide of aspect 13, wherein the 2 or more immunomodulatory polypeptides are in tandem.

Aspect 15. A T-cell modulatory multimeric polypeptide of any one of aspects 1-14, wherein the first polypeptide and the second polypeptide are covalently linked to one another.

Aspect 16. A T-cell modulatory multimeric polypeptide of aspect 15, wherein the covalent linkage is via a disulfide bond.

Aspect 17. A T-cell modulatory multimeric polypeptide of any one of aspects 1-16, wherein the first MHC polypeptide or a linker between the epitope and the first MHC polypeptide comprises an amino acid substitution to provide a first Cys residue, wherein the second MHC polypeptide comprises an amino acid substitution to provide a second Cys residue, and wherein the disulfide linkage is between the first and the second Cys residues.

Aspect 18. A T-cell modulatory multimeric polypeptide of any one of aspects 1-17, wherein the WT-1 peptide epitope has a length of from about 4 amino acids to about 25 amino acids.

Aspect 19. A T-cell modulatory multimeric polypeptide of any one of aspects 1-18, wherein the WT-1 peptide epitope comprises an amino acid sequence selected from the group consisting of: NLMNLGATL (SEQ ID NO:258), NYMNLGATL (SEQ ID NO:263), CMTWNQMNLGATLKG (SEQ ID NO:223), WNQMNLGATLKGVAA (SEQ ID NO:224), CMTWNYMNLGATLKG (SEQ ID NO:225), WNYMNLGATLKGVAA (SEQ ID NO:226), MTWNQMNLGATLKGV (SEQ ID NO:227), TWNQMNLGATLKGVA (SEQ ID NO:228), CMTWNLMNLGATLKG (SEQ ID NO:229), MTWNLMNLGATLKGV (SEQ ID NO:230), TWNLMNLGATLKGVA (SEQ ID NO:231), WNLMNLGATLKGVAA (SEQ ID NO:232), MNLGATLK (SEQ ID NO:233), MTWNYMNLGATLKGV SEQ ID NO:234), TWNYMNLGATLKGVA (SEQ ID NO:235), CMTWNQMNLGATLKGVA (SEQ ID NO:236), CMTWNLMNLGATLKGVA (SEQ ID NO:237), CMTWNYMNLGATLKGVA (SEQ ID NO:238), GYLRNPTAC (SEQ ID NO:239), GALRNPTAL (SEQ ID NO:240), YALRNPTAC (SEQ ID NO:241), GLLRNPTAC (SEQ ID NO:242), RYRPHPGAL (SEQ ID NO:243), YQRPHPGAL (SEQ ID NO:244), RLRPHPGAL (SEQ ID NO:245), RIRPHPGAL (SEQ ID NO:246), QFPNHSFKHEDPMGQ (SEQ ID NO:247), HSFKHEDPY (SEQ ID NO:248), QFPNHSFKHEDPM (SEQ ID NO:249), QFPNHSFKHEDPY (SEQ ID NO:250), KRPFMCAYPGCNK (SEQ ID NO:251), KRPFMCAYPGCYK (SEQ ID NO:252), FMCAYPGCY (SEQ ID NO:253), FMCAYPGCK (SEQ ID NO:254), KRPFMCAYPGCNKRY (SEQ ID NO:255), SEKRPFMCAYPGCNK (SEQ ID NO:256), KRPFMCAYPGCYKRY (SEQ ID NO:257), NLMNLGATL (SEQ ID NO:258), VLDFAPPGA (SEQ ID NO:259), RMFPNAPYL (SEQ ID NO:260), CMTWNQMN (SEQ ID NO:261), CYTWNQMNL (SEQ ID NO:262), NYMNLGATL (SEQ ID NO:263), YMFPNAPYL (SEQ ID NO:264), SLGEQQYSV (SEQ ID NO:265), CMTWNQMNL (SEQ ID NO:266), and NQMNLGATL (SEQ ID NO:267).

Aspect 20. A T-cell modulatory multimeric polypeptide of any one of aspects 1-18, wherein the WT-1 peptide comprises the amino acid sequence CMTWNQMNL (SEQ ID NO:266) or CYTWNQMNL (SEQ ID NO:262).

Aspect 21. A T-cell modulatory multimeric polypeptide of any one of aspects 1-20, wherein the first or the second MHC polypeptide comprises: a) an amino acid sequence having at least 95% amino acid sequence identity to the HLA- A*0101, HLA-A*0201, HLA-A*0201, HLA-A*1101, HLA-A*2301, HLA-A*2402, HLA-A*2407, HLA-A*3303, or HLA-A*3401 amino acid sequence depicted in FIG. 9A; or b) an amino acid sequence having at least 95% amino acid sequence identity to the HLA-B*0702, HLA-B*0801, HLA-B*1502, HLA-B*3802, HLA-B*4001, HLA-B*4601, or HLA-B*5301 amino acid sequence depicted in FIG. 10A; or c) an amino acid sequence having at least 95% amino acid sequence identity to the HLA-C*0102, HLA-C*0303, HLA-C*0304, HLA-C*0401, HLA-C*0602, HLA-C*0701, HLA-C*0702, HLA-C*0801, or HLA-C*1502 depicted in FIG. 11A.

Aspect 22. A T-cell modulatory multimeric polypeptide of any one of aspects 1-20, wherein the first MHC polypeptide is a β2M polypeptide, and wherein the second MHC polypeptide comprises an amino acid sequence having at least 95% amino acid sequence identity to an HLA-A*2402 polypeptide.

Aspect 23. A T-cell modulatory multimeric polypeptide of any one of aspects 1-20, wherein the first MHC polypeptide is a β2M polypeptide, and wherein the second MHC polypeptide is an HLA-A*1101 polypeptide.

Aspect 24. A T-cell modulatory multimeric polypeptide of any one of aspects 1-20, wherein the first MHC polypeptide is a β2M polypeptide, and wherein the second MHC polypeptide comprises an amino acid sequence having at least 95% amino acid sequence identity to an HLA-A*3303 polypeptide.

Aspect 25. A T-cell modulatory multimeric polypeptide of any one of aspects 1-20, wherein the first MHC polypeptide is a β2M polypeptide, and wherein the second MHC polypeptide comprises an amino acid sequence having at least 95% amino acid sequence identity to an HLA-A*0201 polypeptide.

Aspect 26. A T-cell modulatory multimeric polypeptide of any one of aspects 21-25, wherein the MHC heavy chain polypeptide comprises a Cys at position 236.

Aspect 27. A T-cell modulatory multimeric polypeptide of any one of aspects 21-26, wherein the β2M polypeptide comprises a Cys at position 12.

Aspect 28. A T-cell modulatory multimeric polypeptide of any one of aspects 1-27, wherein the immunomodulatory polypeptide is a variant IL-2 polypeptide comprising: i) an H16A substitution and an F42A substation; or ii) an H16T substitution and an F42A substitution.

Aspect 29. A T-cell modulatory multimeric polypeptide of any one of aspects 4-28, wherein the multimeric polypeptide comprises a first and a second heterodimer, and wherein the first and second heterodimers are covalently bound by one or more disulfide bonds between the Ig Fc polypeptides of the first and second heterodimers.

Aspect 30. A nucleic acid comprising a nucleotide sequence encoding a first or second polypeptide according to any one of aspects 1-28, wherein the first or second polypeptide comprises at least one immunomodulatory domain Aspect 31. An expression vector comprising the nucleic acid of aspect 30.

Aspect 32. A method of selectively modulating the activity of T cell specific for a Wilms tumor-1 (WT-1) epitope, the method comprising contacting the T cell with a T-cell modulatory multimeric polypeptide according to any one of aspects 1-29, wherein said contacting selectively modulates the activity of the WT-1 epitope-specific T cell.

Aspect 33. A method of treating a patient having a cancer, the method comprising administering to the patient an effective amount of a pharmaceutical composition comprising T-cell modulatory multimeric polypeptide according to any one of aspects 1-29.

Aspect 34. The method of aspect 33, wherein the cancer is hepatocellular carcinoma, pancreatic cancer, stomach cancer, colorectal cancer, hepatoblastoma, or an ovarian yolk sac tumor.

Aspect 35. The method of aspect 33 or aspect 34, wherein said administering is intramuscular.

Aspect 36. The method of aspect 33 or aspect 34, wherein said administering is intravenous.

Aspect 37. A method of modulating an immune response in an individual, the method comprising administering to the individual an effective amount of the T-cell modulatory multimeric polypeptide (TMMP) of any one of aspects 1-29, wherein said administering induces an epitope-specific T cell response (e.g., a T cell response specific for the WT-1 epitope present in the TMMP) and an epitope-non-specific T cell response, wherein the ratio of the epitope-specific T cell response to the epitope-non-specific T cell response is at least 2:1.

Aspect 38 The method of aspect 37, wherein the ratio of the epitope-specific T cell response to the epitope-non-specific T cell response is at least 5:1.

Aspect 39. The method of aspect 37, wherein the ratio of the epitope-specific T cell response to the epitope-non-specific T cell response is at least 10:1.

Aspect 40. The method of aspect 37, wherein the ratio of the epitope-specific T cell response to the epitope-non-specific T cell response is at least 25:1.

Aspect 41. The method of aspect 37, wherein the ratio of the epitope-specific T cell response to the epitope-non-specific T cell response is at least 50:1.

Aspect 42. The method of aspect 37, wherein the ratio of the epitope-specific T cell response to the epitope-non-specific T cell response is at least 100:1.

Aspect 43. The method of any one of aspects 37-42, wherein the individual is a human.

Aspect 44. The method of any one of aspects 37-43, wherein said modulating comprises increasing a cytotoxic T-cell response to a cancer cell (e.g., a WT-1-expressing cancer cell).

Aspect 45. The method of any one of aspects 37-44, wherein said administering is intravenous, subcutaneous, intramuscular, systemic, intralymphatic, distal to a treatment site, local, or at or near a treatment site.

Aspect 46. The method of any one of aspects 37-45, wherein the epitope non-specific T-cell response is less than the epitope non-specific T-cell response that would be induced by a control T-cell modulatory multimeric polypeptide comprising a corresponding wild-type immunomodulatory polypeptide.

Aspect 47. A method of delivering a costimulatory (i.e., immunomodulatory) polypeptide selectively to target T cell, the method comprising contacting a mixed population of T cells with a T-cell modulatory multimeric polypeptide (TMMP) of any one of aspects 1-29, wherein the mixed population of T cells comprises the target T cell and non-target T cells, wherein the target T cell is specific for the epitope present within the TMMP (e.g., wherein the target T cell is specific for the WT-1 epitope present within the TMMP), and wherein said contacting delivers the one or more costimulatory polypeptides present within the TMMP to the target T cell.

Aspect 48. The method of aspect 47, wherein the population of T cells is in vitro.

Aspect 49. The method of aspect 47, wherein the population of T cells is in vivo in an individual.

Aspect 50. The method of aspect 49, comprising administering the multimeric polypeptide to the individual.

Aspect 51. The method of any one of aspects 47-50, wherein the target T cell is a cytotoxic T cell.

Aspect 52. The method of aspect 47, wherein the mixed population of T cells is an in vitro population of mixed T cells obtained from an individual, and wherein said contacting results in activation and/or proliferation of the target T cell, generating a population of activated and/or proliferated target T cells.

Aspect 53. The method of aspect 52, further comprising administering the population of activated and/or proliferated target T cells to the individual.

Aspect 54. A method of detecting, in a mixed population of T cells obtained from an individual, the presence of a target T cell that binds a WT-1 epitope of interest, the method comprising: a) contacting in vitro the mixed population of T cells with T-cell modulatory multimeric polypeptide (TMMP) of any one of aspects 1-29, wherein the TMMP comprises the WT-1 epitope of interest; and b) detecting activation and/or proliferation of T cells in response to said contacting, wherein activated and/or proliferated T cells indicates the presence of the target T cell.

Aspect 55. A T-cell modulatory multimeric polypeptide comprising: at least one heterodimer comprising: a) a first polypeptide comprising: i) a Wilms tumor-1 (WT-1) peptide epitope, wherein the WT-1 peptide has a length of from about 4 amino acids to about 25 amino acids; and ii) first major histocompatibility complex (MHC) class I polypeptide; b) a second polypeptide comprising a second MHC class I polypeptide, and c) at least one immunomodulatory polypeptide, wherein the first and/or the second polypeptide comprises the immunomodulatory polypeptide, and wherein the first and the second polypeptides are covalently linked to one another via at least 2 disulfide bonds.

Aspect 56. A T-cell modulatory multimeric polypeptide of aspect 55, wherein at least one of the at least one immunomodulatory polypeptides is a variant immunomodulatory polypeptide that exhibits reduced affinity to a cognate co-immunomodulatory polypeptide compared to the affinity of a corresponding wild-type immunomodulatory polypeptide for the cognate co-immunomodulatory polypeptide, and wherein the epitope binds to a T-cell receptor (TCR) on a T cell with an affinity of at least $10^{-7}$ M, such that: i) the T-cell modulatory multimeric polypeptide binds to a first T cell with an affinity that is at least 25% higher than the affinity with which the T-cell modulatory multimeric polypeptide binds a second T cell, wherein the first T cell expresses on its surface the cognate co-immunomodulatory polypeptide and a TCR that binds the epitope with an affinity of at least $10^{-7}$M, and wherein the second T cell expresses on its surface the cognate co-immunomodulatory polypeptide but does not express on its surface a TCR that binds the epitope with an affinity of at least $10^{-7}$ M; and/or ii) the ratio of the binding affinity of a control T-cell modulatory multimeric polypeptide, wherein the control comprises a wild-type immunomodulatory polypeptide, to a cognate co-immunomodulatory polypeptide to the binding affinity of the T-cell modulatory multimeric polypeptide comprising a variant of the wild-type immunomodulatory polypeptide to the cognate co-immunomodulatory polypeptide, when measured by bio-layer interferometry, is in a range of from 1.5:1 to 106:1.

Aspect 57. A T-cell modulatory multimeric polypeptide of aspect 56, wherein: a) the T-cell modulatory multimeric polypeptide binds to the first T cell with an affinity that is at least 50%, at least 2-fold, at least 5-fold, or at least 10-fold higher than the affinity with which it binds the second T cell; and/or b) the variant immunomodulatory polypeptide binds the co-immunomodulatory polypeptide with an affinity of from about $10^{-4}$M to about $10^{-7}$ M, from about $10^{-4}$ M to about $10^{-6}$ M, from about $10^{-4}$ M to about $10^{-5}$ M; and/or c) wherein the ratio of the binding affinity of a control T-cell modulatory multimeric polypeptide, wherein the control comprises a wild-type immunomodulatory polypeptide, to a cognate co-immunomodulatory polypeptide to the binding affinity of the T-cell modulatory multimeric polypeptide comprising a variant of the wild-type immunomodulatory polypeptide to the cognate co-immunomodulatory polypeptide, when measured by bio-layer interferometry, is at least 10:1, at least 50:1, at least $10^2$:1, or at least $10^3$:1.

Aspect 58. A T-cell modulatory multimeric polypeptide of any one of aspects 55-57, wherein the first or the second polypeptide comprises an immunoglobulin (Ig) Fc polypeptide.

Aspect 59. A T-cell modulatory multimeric polypeptide of aspect 58, wherein the Ig Fc polypeptide is an IgG1 Fc polypeptide.

Aspect 60. A T-cell modulatory multimeric polypeptide of aspect 58, wherein the Ig Fc polypeptide is an IgG4 Fc polypeptide.

Aspect 61. T-cell modulatory multimeric polypeptide of aspect 59, wherein IgG1 Fc polypeptide comprises one or more amino acid substitutions selected from N297A, L234A, L235A, L234F, L235E, and P331S.

Aspect 62. A T-cell modulatory multimeric polypeptide of any one of aspects 55-61, wherein a1) the first polypeptide comprises, in order from N-terminus to C-terminus:
  i) the WT-1 peptide epitope;
  ii) the first class I MHC polypeptide; and
  iii) at least one immunomodulatory polypeptide; and b1) the second polypeptide comprises, in order from N-terminus to C-terminus:
  i) the second class I MHC polypeptide; and
  ii) an immunoglobulin (Ig) Fc polypeptide; or a2) the first polypeptide comprises, in order from N-terminus to C-terminus:
  i) the WT-1 peptide epitope; and
  ii) the first class I MHC polypeptide; and b2) the second polypeptide comprises, in order from N-terminus to C-terminus:
  i) at least one immunomodulatory polypeptide;
  ii) the second class I MHC polypeptide; and
  iii) an Ig Fc polypeptide; or a3) the first polypeptide comprises, in order from N-terminus to C-terminus:
  i) the WT-1 peptide epitope; and
  ii) the first class I MHC polypeptide; and b3) the second polypeptide comprises, in order from N-terminus to C-terminus:
  i) the second class I MHC polypeptide; and
  ii) an Ig Fc polypeptide; and
  iii) at least one immunomodulatory polypeptide; or a4) the first polypeptide comprises, in order from N-terminus to C-terminus:
  i) the WT-1 peptide epitope; and
  ii) the first class I MHC polypeptide; and b4) the second polypeptide comprises, in order from N-terminus to C-terminus:
  i) the second class I MHC polypeptide; and
  ii) at least one immunomodulatory polypeptide; or a5) the first polypeptide comprises, in order from N-terminus to C-terminus:
i) the WT-1 peptide epitope; and
ii) the first class I MHC polypeptide; and
b5) a second polypeptide comprises, in order from N-terminus to C-terminus:
i) at least one immunomodulatory polypeptide; and
ii) the second class I MHC polypeptide; or
a6) the first polypeptide comprises, in order from N-terminus to C-terminus:
i) the WT-1 peptide epitope;
ii) the first class I MHC polypeptide; and
iii) at least one immunomodulatory polypeptide; and
b6) the second polypeptide comprises:
i) the second class I MHC polypeptide.

Aspect 63. A T-cell modulatory multimeric polypeptide of any one of aspects 55-62, wherein the first MHC polypeptide is a β2-microglobulin polypeptide; and wherein the second MHC polypeptide is an MHC class I heavy chain polypeptide.

Aspect 64. A T-cell modulatory multimeric polypeptide of any one of aspects 55-63, wherein the at least one immunomodulatory polypeptide is selected from the group consisting of a cytokine (e.g., an IL2 polypeptide, an IL7 polypeptide, an IL12 polypeptide, an IL15 polypeptide, an IL17 polypeptide, an IL21 polypeptide, an IL27 polypeptide, an IL-23 polypeptide, a TGFβ polypeptide, and the like; and including all family members, e.g., IL17A, IL-17B, IL-17C, IL-17D, IL-17E, IL-17F, IL-17E), a 4-1BBL polypeptide, an ICOS-L polypeptide, an OX-40L polypeptide, a CD80 polypeptide, a CD86 polypeptide, (CD80 and CD86 are also known as B7-1 and B7-2, respectively), a CD40 polypeptide, a CD70 polypeptide, a JAG1 (CD339) polypeptide, an ICAM (CD540 polypeptide, a PD-L1 polypeptide, a FasL polypeptide, a PD-L2 polypeptide, a PD-1H (VISTA) polypeptide, an ICOS-L (CD275) polypeptide, a GITRL polypeptide, an HVEM polypeptide, a CXCL10 polypeptide, a CXCL9 polypeptide, a CXCL11 polypeptide, a CXCL13 polypeptide, and a CX3CL1 polypeptide, a Galectin-9 polypeptide, a CD83 polypeptide, a CD30L polypeptide, a HLA-G polypeptide, a MICA polypeptide, a MICB polypeptide, a HVEM (CD270) polypeptide, a lymphotoxin beta receptor polypeptide, a 3/TR6 polypeptide, an ILT3 polypeptide, an ILT4 polypeptide, a CXCL10 polypeptide, a CXCL9 polypeptide, a CXCL11 polypeptide, a CXCL13 polypeptide, and a CX3CL1 polypeptide, and combinations thereof.

Aspect 65. A T-cell modulatory multimeric polypeptide of any one of aspects 55-63, wherein the at least one immunomodulatory polypeptide is an IL-2 polypeptide.

Aspect 66. A T-cell modulatory multimeric polypeptide of any one of aspects 55-65, wherein the multimeric polypeptide comprises at least two immunomodulatory polypeptides, and wherein at least two of the immunomodulatory polypeptides are the same.

Aspect 67. A T-cell modulatory multimeric polypeptide of aspect 66, wherein the 2 or more immunomodulatory polypeptides are in tandem.

Aspect 68. The T-cell modulatory multimeric polypeptide of any one of aspects 55-67, wherein: a) a first disulfide bond is between: i) a Cys present in a linker between the WT-1 peptide epitope and the first MHC class I polypeptide, wherein the first MHC class I polypeptide is a β2M polypeptide; and ii) a Cys residue introduced via a Y84C substitution in the second MHC class I polypeptide, wherein the second MHC class I polypeptide is a MHC Class I heavy chain polypeptide; and b) a second disulfide bond is between: i) a Cys residue introduced into the β2M polypeptide via an R12C substitution; and ii) a Cys residue introduced into the MHC Class I heavy chain polypeptide via an A236C substitution.

Aspect 69. A T-cell modulatory multimeric polypeptide of aspect 68, wherein the linker comprises the amino acid sequence GCGGS (SEQ ID NO:318).

Aspect 70. A T-cell modulatory multimeric polypeptide of aspect 69, wherein the linker comprises the amino acid sequence GCGGS(GGGGS)n (SEQ ID NO:319), where n is an integer from 1 to 10.

Aspect 71. A T-cell modulatory multimeric polypeptide of any one of aspects 55-70, wherein the WT-1 peptide epitope has a length of from about 4 amino acids to about 15 amino acids.

Aspect 72. A T-cell modulatory multimeric polypeptide of any one of aspects 55-71, wherein the WT-1 peptide epitope comprises an amino acid sequence selected from the group consisting of: NLMNLGATL (SEQ ID NO:258), NYMNLGATL (SEQ ID NO:263), CMTWNQMNLGATLKG (SEQ ID NO:223), WNQMNLGATLKGVAA (SEQ ID NO:224), CMTWNYMNLGATLKG (SEQ ID NO:225), WNYMNLGATLKGVAA (SEQ ID NO:226), MTWNQMNLGATLKGV (SEQ ID NO:227), TWNQMNLGATLKGVA (SEQ ID NO:228), CMTWNLMNLGATLKG (SEQ ID NO:229), MTWNLMNLGATLKGV (SEQ ID NO:230), TWNLMNLGATLKGVA (SEQ ID NO:231), WNLMNLGATLKGVAA (SEQ ID NO:232), MNLGATLK (SEQ ID NO:233), MTWNYMNLGATLKGV SEQ ID NO:234), TWNYMNLGATLKGVA (SEQ ID NO:235), CMTWNQMNLGATLKGVA (SEQ ID NO:236), CMTWNLMNLGATLKGVA (SEQ ID NO:237), CMTWNYMNLGATLKGVA (SEQ ID NO:238), GYLRNPTAC (SEQ ID NO:239), GALRNPTAL (SEQ ID NO:240), YALRNPTAC (SEQ ID NO:241), GLLRNPTAC (SEQ ID NO:242), RYRPHPGAL (SEQ ID NO:243), YQRPHPGAL (SEQ ID NO:244), RLRPHPGAL (SEQ ID NO:245), RIRPHPGAL (SEQ ID NO:246), QFPNHSFKHEDPMGQ (SEQ ID NO:247), HSFKHEDPY (SEQ ID NO:248), QFPNHSFKHEDPM (SEQ ID NO:249), QFPNHSFKHEDPY (SEQ ID NO:250), KRPFMCAYPGCNK (SEQ ID NO:251), KRPFMCAYPGCYK (SEQ ID NO:252), FMCAYPGCY (SEQ ID NO:253), FMCAYPGCK (SEQ ID NO:254), KRPFMCAYPGCNKRY (SEQ ID NO:255), SEKRPFMCAYPGCNK (SEQ ID NO:256), KRPFMCAYPGCYKRY (SEQ ID NO:257), NLMNLGATL (SEQ ID NO:258), VLDFAPPGA (SEQ ID NO:259), RMFPNAPYL (SEQ ID NO:260), CMTWNQMN (SEQ ID NO:261), CYTWNQMNL (SEQ ID NO:262), NYMNLGATL (SEQ ID NO:263), YMFPNAPYL (SEQ ID NO:264), SLGEQQYSV (SEQ ID NO:265), CMTWNQMNL (SEQ ID NO:266), and NQMNLGATL (SEQ ID NO:267).

Aspect 73. A T-cell modulatory multimeric polypeptide of any one of aspects 55-71, wherein the WT-1 peptide comprises the amino acid sequence VLDFAPPGA (SEQ ID NO:259) or RMFPNAPYL (SEQ ID NO:260).

Aspect 74. A T-cell modulatory multimeric polypeptide of any one of aspects 55-73, wherein the first or the second MHC class I polypeptide comprises: a) an amino acid sequence having at least 95% amino acid sequence identity to the HLA-A*0101, HLA-A*0201, HLA-A*0201, HLA-A*1101, HLA-A*2301, HLA-A*2402, HLA-A*2407, HLA-A*3303, or HLA-A*3401 amino acid sequence depicted in FIG. 9A; or b) an amino acid sequence having at least 95% amino acid sequence identity to the HLA-B*0702, HLA-B*0801, HLA-B*1502, HLA-B*3802, HLA-B*4001, HLA-B*4601, or HLA-B*5301 amino acid sequence depicted in FIG. 10A; or c) an amino acid sequence having at least 95% amino acid sequence identity to the HLA-C*0102, HLA-C*0303, HLA-C*0304, HLA-C*0401, HLA-C*0602, HLA-C*0701, HLA-C*0702, HLA-C*0801, or HLA-C*1502 depicted in FIG. 11A.

Aspect 75. A T-cell modulatory multimeric polypeptide of any one of aspects 55-74, wherein the first MHC polypeptide is a β2M polypeptide, and wherein the second MHC polypeptide comprises an amino acid sequence having at least 95% amino acid sequence identity to an HLA-A*2402 polypeptide.

Aspect 76. A T-cell modulatory multimeric polypeptide of any one of aspects 55-74, wherein the first MHC polypeptide is a β2M polypeptide, and wherein the second MHC polypeptide is an HLA-A*1101 polypeptide.

Aspect 77. A T-cell modulatory multimeric polypeptide of any one of aspects 55-74, wherein the first MHC polypeptide is a β2M polypeptide, and wherein the second MHC polypeptide comprises an amino acid sequence having at least 95% amino acid sequence identity to an HLA-A*3303 polypeptide.

Aspect 78. A T-cell modulatory multimeric polypeptide of any one of aspects 55-74, wherein the first MHC polypeptide is a β2M polypeptide, and wherein the second MHC polypeptide comprises an amino acid sequence having at least 95% amino acid sequence identity to an HLA-A*0201 polypeptide.

Aspect 79. A T-cell modulatory multimeric polypeptide of any one of aspects 55-78, wherein the at least one immunomodulatory polypeptide is a variant IL-2 polypeptide comprising: i) an H16A substitution and an F42A substation; or ii) an H16T substitution and an F42A substitution.

Aspect 80. A T-cell modulatory multimeric polypeptide of any one of aspects 55-79, wherein the multimeric polypeptide comprises a first and a second heterodimer.

Aspect 81. A nucleic acid comprising a nucleotide sequence encoding a first or second polypeptide according to any one of aspects 55-80, wherein the first or second polypeptide comprises at least one immunomodulatory domain Aspect 82. An expression vector comprising the nucleic acid of aspect 81.

Aspect 83. A method of selectively modulating the activity of T cell specific for a Wilms tumor-1 (WT-1) epitope, the method comprising contacting the T cell with a T-cell modulatory multimeric polypeptide according to any one of aspects 55-80, wherein said contacting selectively modulates the activity of the WT-1 epitope-specific T cell.

Aspect 84. A method of treating a patient having a cancer, the method comprising administering to the patient an effective amount of a pharmaceutical composition comprising T-cell modulatory multimeric polypeptide according to any one of aspects 55-80.

Aspect 85. The method of aspect 84, wherein the cancer expresses a WT-1 protein.

Aspect 86. The method of aspect 84 or aspect 85, wherein the cancer is acute myeloid leukemia, myeloma, ovarian cancer, pancreatic cancer, non-small cell lung cancer, colorectal cancer, breast cancer, Wilms tumor, mesothelioma, soft tissue sarcoma, neuroblastoma, or nephroblastoma.

Aspect 87. The method of any one of aspects 84-86, wherein said administering is intramuscular.

Aspect 88. The method of any one of aspects 84-86, wherein said administering is intravenous.

Aspect 89. A method of any one of aspects 84-88, further comprising administering one or more checkpoint inhibitors to the individual.

Aspect 90. A method according to aspect 89, wherein the checkpoint inhibitor is an antibody that binds to a polypeptide selected from the group consisting of CD27, CD28, CD40, CD122, CD96, CD73, CD47, OX40, GITR, CSF1R, JAK, PI3K delta, PI3K gamma, TAM, arginase, CD137, ICOS, A2AR, B7-H3, B7-H4, BTLA, CTLA-4, LAG3, TIM3, VISTA, CD96, TIGIT, CD122, PD-1, PD-L1, and PD-L2.

Aspect 91. A method according to aspect 90, wherein the checkpoint inhibitor is an antibody specific for PD-1, PD-L1, or CTLA4.

Aspect 92. A method according to aspect 89, wherein the one or more checkpoint inhibitors is selected from the group consisting of nivolumab, pembrolizumab, pidilizumab, AMP-224, MPDL3280A, MDX-1105, MEDI-4736, arelumab, ipilimumab, tremelimumab, pidilizumab, IMP321, MGA271, BMS-986016, lirilumab, urelumab, PF-05082566, IPH2101, MEDI-6469, CP-870,893, Mogamulizumab, Varlilumab, Avelumab, Galiximab, AMP-514, AUNP 12, Indoximod, NLG-919, INCB024360, KN035, and combinations thereof.

Aspect 93. A method of modulating an immune response in an individual, the method comprising administering to the individual an effective amount of the T-cell modulatory multimeric polypeptide of any one of aspects 55-80, wherein said administering induces an epitope-specific T cell response and an epitope-non-specific T cell response, wherein the ratio of the epitope-specific T cell response to the epitope-non-specific T cell response is at least 2:1.

Aspect 94. A method of delivering an immunomodulatory polypeptide selectively to a target T cell, the method comprising contacting a mixed population of T cells with a T-cell modulatory multimeric polypeptide of any one of aspects 55-80, wherein the mixed population of T cells comprises the target T cell and non-target T cells, wherein the target T cell is specific for the WT-1 epitope present within the T-cell modulatory multimeric polypeptide, and wherein said contacting delivers the one or more immunomodulatory polypeptides present within the T-cell modulatory multimeric polypeptide to the target T cell.

Aspect 95. A method of detecting, in a mixed population of T cells obtained from an individual, the presence of a target T cell that binds a Wilms tumor-1 (WT-1) epitope, the method comprising: a) contacting in vitro the mixed population of T cells with the T-cell modulatory multimeric polypeptide of any one of aspects 55-80, wherein the T-cell modulatory multimeric polypeptide comprises the WT-1 epitope; and b) detecting activation and/or proliferation of T cells in response to said contacting, wherein activated and/or proliferated T cells indicates the presence of the target T cell.

Aspects Set B

Aspects, including embodiments, of the present subject matter described above may be beneficial alone or in combination, with one or more other aspects or embodiments. Without limiting the foregoing description, certain non-limiting aspects of the disclosure numbered 1-36 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

Aspect 1. A T-cell modulatory multimeric polypeptide comprising: at least one heterodimer comprising: a) a first polypeptide comprising: i) a Wilms tumor-1 (WT-1) peptide epitope, wherein the WT-1 peptide has a length of at least 4 amino acids; and ii) first class I major histocompatibility complex (MHC) polypeptide; b) a second polypeptide comprising a second class I MHC polypeptide, and c) at least one activating immunomodulatory, wherein the first and/or the second polypeptide comprises the immunomodulatory polypeptide, and wherein the WT-1 peptide epitope comprises an amino acid sequence selected from the group consisting of: NLMNLGATL (SEQ ID NO:258), NYMNLGATL (SEQ ID NO:263), CMTWNQMNLGATLKG (SEQ ID NO:223), WNQMNLGATLKGVAA (SEQ ID NO:224), CMTWNYMNLGATLKG (SEQ ID NO:225), WNYMNLGATLKGVAA (SEQ ID NO:226), MTWNQMNLGATLKGV (SEQ ID NO:227), TWNQMNLGATLKGVA (SEQ ID NO:228), CMTWNLMNLGATLKG (SEQ ID NO:229), MTWNLMNLGATLKGV (SEQ ID NO:230), TWNLMNLGATLKGVA (SEQ ID NO:231), WNLMNLGATLKGVAA (SEQ ID NO:232), MNLGATLK (SEQ ID NO:233), MTWNYMNLGATLKGV SEQ ID NO:234), TWNYMNLGATLKGVA (SEQ ID NO:235), CMTWNQMNLGATLKGVA (SEQ ID NO:236), CMTWNLMNLGATLKGVA (SEQ ID NO:237), CMTWNYMNLGATLKGVA (SEQ ID NO:238), GYLRNPTAC (SEQ ID NO:239), GALRNPTAL (SEQ ID NO:240), YALRNPTAC (SEQ ID NO:241), GLLRNPTAC (SEQ ID NO:242), RYRPHPGAL (SEQ ID NO:243), YQRPHPGAL (SEQ ID NO:244), RLRPHPGAL (SEQ ID NO:245), RIRPHPGAL (SEQ ID NO:246), QFPNHSFKHEDPMGQ (SEQ ID NO:247), HSFKHEDPY (SEQ ID NO:248), QFPNHSFKHEDPM (SEQ ID NO:249), QFPNHSFKHEDPY (SEQ ID NO:250), KRPFMCAYPGCNK (SEQ ID NO:251), KRPFMCAYPGCYK (SEQ ID NO:252), FMCAYPGCY (SEQ ID NO:253), FMCAYPGCK (SEQ ID NO:254), KRPFMCAYPGCNKRY (SEQ ID NO:255), SEKRPFMCAYPGCNK (SEQ ID NO:256), KRPFMCAYPGCYKRY (SEQ ID NO:257), NLMNLGATL (SEQ ID NO:258), VLDFAPPGA (SEQ ID NO:259), RMFPNAPYL (SEQ ID NO:260), CMTWNQMN (SEQ ID NO:261), CYTWNQMNL (SEQ ID NO:262), NYMNLGATL (SEQ ID NO:263), YMFPNAPYL (SEQ ID NO:264), SLGEQQYSV (SEQ ID NO:265), CMTWNQMNL (SEQ ID NO:266), and NQMNLGATL (SEQ ID NO:267), optionally wherein the first or the second polypeptide comprises an immunoglobulin (Ig) Fc polypeptide.

Aspect 2. A T-cell modulatory multimeric polypeptide of aspect 1, wherein at least one of the one or more immunomodulatory domains is a variant immunomodulatory polypeptide that exhibits reduced affinity to a cognate co-immunomodulatory polypeptide compared to the affinity of a corresponding wild-type immunomodulatory polypeptide for the cognate co-immunomodulatory polypeptide, and wherein the epitope binds to a T-cell receptor (TCR) on a T cell with an affinity of at least $10^{-7}$ M, such that:

i) the T-cell modulatory multimeric polypeptide binds to a first T cell with an affinity that is at least 25% higher than the affinity with which the T-cell modulatory multimeric polypeptide binds a second T cell, wherein the first T cell expresses on its surface the cognate co-immunomodulatory polypeptide and a TCR that binds the epitope with an affinity of at least $10^{-7}$ M, and wherein the second T cell expresses on its surface the cognate co-immunomodulatory polypeptide but does not express on its surface a TCR that binds the epitope with an affinity of at least $10^{-7}$ M; and/or ii) the ratio of the binding affinity of a control T-cell modulatory multimeric polypeptide, wherein the control comprises a wild-type immunomodulatory polypeptide, to a cognate co-immunomodulatory polypeptide to the binding affinity of the T-cell modulatory multimeric polypeptide comprising a variant of the wild-type immunomodulatory polypeptide to the cognate co-immunomodulatory polypeptide, when measured by bio-layer interferometry, is in a range of from 1.5:1 to $10^6$:1.

Aspect 3. A T-cell modulatory multimeric polypeptide of aspect 2, wherein:

a) the T-cell modulatory multimeric polypeptide binds to the first T cell with an affinity that is at least 50%, at least 2-fold, at least 5-fold, or at least 10-fold higher than the affinity with which it binds the second T cell; and/or b) the variant immunomodulatory polypeptide binds the co-immunomodulatory polypeptide with an affinity of from about $10^{-4}$M to about $10^{-7}$ M, from about $10^{-4}$ M to about $10^{-6}$ M, from about $10^{-4}$ M to about $10^{-5}$ M; and/or c) wherein the ratio of the binding affinity of a control T-cell modulatory multimeric polypeptide, wherein the control comprises a wild-type immunomodulatory polypeptide, to a cognate co-immunomodulatory polypeptide to the binding affinity of the T-cell modulatory multimeric polypeptide comprising a variant of the wild-type immunomodulatory polypeptide to the cognate co-immunomodulatory polypeptide, when measured by bio-layer interferometry, is at least 10:1, at least 50:1, at least $10^2$:1, or at least $10^3$:1.

Aspect 4. A T-cell modulatory multimeric polypeptide of any one of aspects 1-3, wherein a1) the first polypeptide comprises, in order from N-terminus to C-terminus:
i) the WT-1 peptide epitope;
ii) the first MHC polypeptide; and
iii) at least one immunomodulatory polypeptide; and b1) the second polypeptide comprises, in order from N-terminus to C-terminus:
i) the second MHC polypeptide; and
ii) an immunoglobulin (Ig) Fc polypeptide; or a2) the first polypeptide comprises, in order from N-terminus to C-terminus:
i) the WT-1 peptide epitope; and
ii) the first MHC polypeptide; and b2) the second polypeptide comprises, in order from N-terminus to C-terminus:
i) at least one immunomodulatory polypeptide;
ii) the second MHC polypeptide; and
iii) an Ig Fc polypeptide; or a3) the first polypeptide comprises, in order from N-terminus to C-terminus:
i) the WT-1 peptide epitope; and
ii) the first MHC polypeptide; and b3) the second polypeptide comprises, in order from N-terminus to C-terminus:
i) the second MHC polypeptide; and
ii) an Ig Fc polypeptide; and
iii) at least one immunomodulatory polypeptide; or a4) the first polypeptide comprises, in order from N-terminus to C-terminus:
i) the WT-1 peptide epitope; and
ii) the first MHC polypeptide; and b4) the second polypeptide comprises, in order from N-terminus to C-terminus:
i) the second MHC polypeptide; and
ii) at least one immunomodulatory polypeptide; or
a5) the first polypeptide comprises, in order from N-terminus to C-terminus:
i) the WT-1 peptide epitope; and
ii) the first MHC polypeptide; and
b5) a second polypeptide comprises, in order from N-terminus to C-terminus:
i) at least one immunomodulatory polypeptide; and
ii) the second MHC polypeptide; or
a6) the first polypeptide comprises, in order from N-terminus to C-terminus:
i) the WT-1 peptide epitope;
ii) the first MHC polypeptide; and
iii) at least one immunomodulatory polypeptide; and
b6) the second polypeptide comprises:
i) the second MHC polypeptide.

Aspect 5. A T-cell modulatory multimeric polypeptide of any one of aspects 1-4, wherein:
a) the first MHC polypeptide is a β2-microglobulin polypeptide; and the second MHC polypeptide is an MHC class I heavy chain polypeptide; or
b) the first MHC polypeptide is an MHC class I heavy chain polypeptide; and the second MHC polypeptide is a β2-microglobulin polypeptide.

Aspect 6. A T-cell modulatory multimeric polypeptide of aspect 5, wherein:
a) the first polypeptide comprises, in order from N-terminus to C-terminus:
i) the WT-1 peptide epitope; and
ii) the β2-microglobulin polypeptide; and
b) the second polypeptide comprises, in order from N-terminus to C-terminus:
i) at least one immunomodulatory polypeptide;
ii) the MHC class I heavy chain polypeptide; and
iii) an Ig Fc polypeptide.

Aspect 7. A T-cell modulatory multimeric polypeptide of aspect 5, wherein:
a) the first polypeptide comprises, in order from N-terminus to C-terminus:
i) the WT-1 peptide epitope; and
ii) the β2-microglobulin polypeptide; and
b) the second polypeptide comprises, in order from N-terminus to C-terminus:
i) the MHC class I heavy chain polypeptide; and
ii) an Ig Fc polypeptide; and
iii) at least one immunomodulatory polypeptide Aspect 8. A T-cell modulatory multimeric polypeptide of any one of aspects 1-7, wherein the at least one immunomodulatory polypeptide is selected from the group consisting of a cytokine, a 4-1BBL polypeptide, an ICOS-L polypeptide, an OX-40L polypeptide, a CD80 polypeptide, a CD86 polypeptide, a CD40 polypeptide, a CD70 polypeptide, and combinations thereof.

Aspect 9. A T-cell modulatory multimeric polypeptide of any one of aspects 1-8, wherein the at least one immunomodulatory polypeptide is an IL-2 polypeptide.

Aspect 10. A T-cell modulatory multimeric polypeptide of any one of aspects 1-9, wherein the multimeric polypeptide comprises at least two immunomodulatory polypeptides, and wherein at least two of the immunomodulatory polypeptides are the same, optionally wherein the 2 or more immunomodulatory polypeptides are in tandem.

Aspect 11. A T-cell modulatory multimeric polypeptide of any one of aspects 1-10, wherein the immunomodulatory polypeptide is a variant IL-2 polypeptide that exhibits reduced affinity to an IL-2 receptor compared to the affinity of a wild-type IL-2 polypeptide for the IL-2 receptor.

Aspect 12. A T-cell modulatory multimeric polypeptide of aspect 11, wherein the variant IL-2 polypeptide comprises: i) an H16A substitution and an F42A substitution; or ii) an H16T substitution and an F42A substitution.

Aspect 13. A T-cell modulatory multimeric polypeptide of any one of aspects 1-12, wherein the first polypeptide and the second polypeptide are covalently linked to one another, optionally wherein the covalent linkage is via a disulfide bond.

Aspect 14. A T-cell modulatory multimeric polypeptide of any one of aspects 1-13, wherein the first MHC polypeptide or a linker between the epitope and the first MHC polypeptide comprises an amino acid substitution to provide a first Cys residue, wherein the second MHC polypeptide comprises an amino acid substitution to provide a second Cys residue, and wherein the disulfide linkage is between the first and the second Cys residues.

Aspect 15. The T-cell modulatory multimeric polypeptide of any one of aspects 1-14, wherein the polypeptide comprises a disulfide bond between: i) a Cys present in a linker between the WT-1 peptide epitope and the first MHC class I polypeptide, wherein the first MHC class I polypeptide is a β2M polypeptide; and ii) a Cys residue introduced via a Y84C substitution in the second MHC class I polypeptide, wherein the second MHC class I polypeptide is a MHC Class I heavy chain polypeptide.

Aspect 16. The T-cell modulatory multimeric polypeptide of any one of aspects 1-14, wherein the polypeptide comprises a disulfide bond between i) a Cys residue introduced into the first MHC class I polypeptide via an R12C substitution, wherein the first MHC class I polypeptide is a β2M polypeptide; and ii) a Cys residue introduced into the second MHC class I polypeptide, via an A236C substitution, wherein second MHC class I polypeptide is an MHC Class I heavy chain polypeptide.

Aspect 17. The T-cell modulatory multimeric polypeptide of any one of aspects 1-14, wherein the polypeptide comprises a first disulfide bond between: i) a Cys present in a linker between the WT-1 peptide epitope and the first MHC class I polypeptide, wherein the first MHC class I polypeptide is a β2M polypeptide; and ii) a Cys residue introduced via a Y84C substitution in the second MHC class I polypeptide, wherein the second MHC class I polypeptide is a MHC Class I heavy chain polypeptide, and a second disulfide bond between i) a Cys residue introduced into the β2M polypeptide via an R12C substitution; and ii) a Cys residue introduced into the MHC Class I heavy chain polypeptide via an A236C substitution.

Aspect 18. A T-cell modulatory multimeric polypeptide of aspect 15 or aspect 17, wherein the linker between the WT-1 peptide epitope and the first MHC is GCGGS(G4S)n (SEQ ID NO:315), where n is 1, 2, 3, 4, 5, 6, 7, 8, or 9.

Aspect 19. A T-cell modulatory multimeric polypeptide of any one of aspects 1-18, wherein the WT-1 peptide epitope has a length of from about 4 amino acids to about 25 amino acids.

Aspect 20. A T-cell modulatory multimeric polypeptide of any one of aspects 1-19, wherein the WT-1 peptide comprises the amino acid sequence CMTWNQMNL (SEQ ID NO: 266), CYTWNQMNL (SEQ ID NO:262), NYMNLGATL (SEQ ID NO:263), VLDFAPPGA (SEQ ID NO:259), YMFPNAPYL (SEQ ID NO:264), SLGEQQYSV (SEQ ID NO:265), RMFPNAPYL (SEQ ID NO:260), and NLMNLGATL (SEQ ID NO:258).

Aspect 21. A T-cell modulatory multimeric polypeptide of any one of aspects 1-20, wherein the first or the second MHC polypeptide comprises:

a) an amino acid sequence having at least 95% amino acid sequence identity to the HLA-A*0101, HLA-A*0201, HLA-A*0201, HLA-A*1101, HLA-A*2301, HLA-A*2402, HLA-A*2407, HLA-A*3303, or HLA-A*3401 amino acid sequence depicted in FIG. 9A; or b) an amino acid sequence having at least 95% amino acid sequence identity to the HLA-B*0702, HLA-B*0801, HLA-B*1502, HLA-B*3802, HLA-B*4001, HLA-B*4601, or HLA-B*5301 amino acid sequence depicted in FIG. 10A; or c) an amino acid sequence having at least 95% amino acid sequence identity to the HLA-C*0102, HLA-C*0303, HLA-C*0304, HLA-C*0401, HLA-C*0602, HLA-C*0701, HLA-C*0702, HLA-C*0801, or HLA-C*1502 depicted in FIG. 11A.

Aspect 22. A T-cell modulatory multimeric polypeptide of any one of aspects 1-21, wherein the first MHC polypeptide is a β2M polypeptide, and wherein the second MHC polypeptide comprises an amino acid sequence having at least 95% amino acid sequence identity to an HLA-A*2402 polypeptide, and wherein the epitope is selected from the group consisting of: RMFPNAPYL (SEQ ID NO:260), CYTWNQMNL (SEQ ID NO:262), and NYMNLGATL (SEQ ID NO:263).

Aspect 23. A T-cell modulatory multimeric polypeptide of any one of aspects 1-21, wherein the first MHC polypeptide is a β2M polypeptide, and wherein the second MHC polypeptide comprises an amino acid sequence having at least 95% amino acid sequence identity to an HLA-A*0201 polypeptide, and wherein the epitope is selected from the group consisting of: VLDFAPPGA (SEQ ID NO:259), RMFPNAPYL (SEQ ID NO:260), and YMFPNAPYL (SEQ ID NO:264).

Aspect 24. A T-cell modulatory multimeric polypeptide of any one of aspects 1-23, wherein the multimeric polypeptide comprises a first and a second heterodimer, and wherein the first and second heterodimers are covalently bound by one or more disulfide bonds between the Ig Fc polypeptides of the first and second heterodimers.

Aspect 25. A nucleic acid comprising a nucleotide sequence encoding a first or second polypeptide according to any one of aspects 1-24.

Aspect 26. An expression vector comprising the nucleic acid of aspect 25.

Aspect 27. A method of selectively modulating the activity of T cell specific for a Wilms tumor-1 (WT-1) epitope, the method comprising contacting the T cell with a T-cell modulatory multimeric polypeptide according to any one of aspects 1-24, wherein said contacting selectively modulates the activity of the WT-1 epitope-specific T cell.

Aspect 28. A method of treating a patient having a cancer, the method comprising administering to the patient an effective amount of a pharmaceutical composition comprising T-cell modulatory multimeric polypeptide according to any one of aspects 1-24.

Aspect 29. The method of aspect 28, wherein the cancer is acute myeloid leukemia, myeloma, ovarian cancer, pancreatic cancer, non-small cell lung cancer, colorectal cancer, breast cancer, Wilms tumor, mesothelioma, soft tissue sarcoma, neuroblastoma, or nephroblastoma.

Aspect 30. A method of aspect 28 or aspect 29, further comprising administering one or more checkpoint inhibitors to the individual.

Aspect 31. A method according to aspect 30, wherein the checkpoint inhibitor is an antibody that binds to a polypeptide selected from the group consisting of CD27, CD28, CD40, CD122, CD96, CD73, CD47, OX40, GITR, CSF1R, JAK, PI3K delta, PI3K gamma, TAM, arginase, CD137, ICOS, A2AR, B7-H3, B7-H4, BTLA, CTLA-4, LAG3, TIM3, VISTA, CD96, TIGIT, CD122, PD-1, PD-L1, and PD-L2.

Aspect 32. A method according to aspect 31, wherein the checkpoint inhibitor is an antibody specific for PD-1, PD-L1, or CTLA4.

Aspect 33. A method according to aspect 30, wherein the one or more checkpoint inhibitors is selected from the group consisting of nivolumab, pembrolizumab, pidilizumab, AMP-224, MPDL3280A, MDX-1105, MEDI-4736, arelumab, ipilimumab, tremelimumab, pidilizumab, IMP321, MGA271, BMS-986016, lirilumab, urelumab, PF-05082566, IPH2101, MEDI-6469, CP-870,893, Mogamulizumab, Varlilumab, Avelumab, Galiximab, AMP-514, AUNP 12, Indoximod, NLG-919, INCB024360, KN035, and combinations thereof.

Aspect 34. A method of modulating an immune response in an individual, the method comprising administering to the individual an effective amount of the T-cell modulatory multimeric polypeptide of any one of aspects 1-24, wherein said administering induces an epitope-specific T cell response and an epitope-non-specific T cell response, and wherein the ratio of the epitope-specific T cell response to the epitope-non-specific T cell response is at least 2:1.

Aspect 35. A method of delivering an immunomodulatory polypeptide selectively to a target T cell, the method comprising contacting a mixed population of T cells with a T-cell modulatory multimeric polypeptide of any one of aspects 1-24, wherein the mixed population of T cells comprises the target T cell and non-target T cells, wherein the target T cell is specific for the WT-1 epitope present within the T-cell modulatory multimeric polypeptide, and wherein said contacting delivers the one or more immunomodulatory polypeptides present within the T-cell modulatory multimeric polypeptide to the target T cell.

Aspect 36. A method of detecting, in a mixed population of T cells obtained from an individual, the presence of a target T cell that binds a WT-1 epitope, the method comprising: a) contacting in vitro the mixed population of T cells with the T-cell modulatory multimeric polypeptide of any one of aspects 1-24, wherein the T-cell modulatory multimeric polypeptide comprises the WT-1 epitope; and b) detecting activation and/or proliferation of T cells in response to said contacting, wherein activated and/or proliferated T cells indicates the presence of the target T cell.

Aspects Set C

Aspects, including embodiments, of the present subject matter described above may be beneficial alone or in combination, with one or more other aspects or embodiments. Without limiting the foregoing description, certain non-limiting aspects of the disclosure numbered 1-37 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

Aspect 1. A T-cell modulatory multimeric polypeptide comprising:

at least one heterodimer comprising:

a) a first polypeptide comprising:

i) a Wilms tumor-1 (WT-1) peptide epitope comprising the amino acid sequence $X_1X_2X_3$TWNQMNL (SEQ ID NO:460) or $X_2X_3$TWNQMNL (SEQ ID NO:461), wherein each of $X_1$, $X_2$, and $X_3$ is independently any amino acid, with the proviso that the N-terminal amino acid is not a Cys, and wherein the WT-1 peptide epitope has a length from 9 to 25 amino acids; and ii) a first Class I major histocompatibility complex (MHC) polypeptide;

b) a second polypeptide comprising a second class I MHC polypeptide, and c) at least one activating immunomodulatory polypeptide, wherein the first and/or the second polypeptide comprises the at least one immunomodulatory polypeptide, and optionally wherein the first or the second polypeptide comprises an immunoglobulin (Ig) Fc polypeptide.

Aspect 2. A T-cell modulatory multimeric polypeptide of aspect 1, wherein at least one of the one or more immunomodulatory polypeptides is a variant immunomodulatory polypeptide that exhibits reduced affinity to a cognate co-immunomodulatory polypeptide compared to the affinity of a corresponding wild-type immunomodulatory polypeptide for the cognate co-immunomodulatory polypeptide.

Aspect 3. A T-cell modulatory multimeric polypeptide of aspect 2, wherein the ratio of the binding affinity of the wild-type immunomodulatory polypeptide to a cognate co-immunomodulatory polypeptide to the binding affinity of the variant immunomodulatory polypeptide to the cognate co-immunomodulatory polypeptide, when measured by bio-layer interferometry, is at least 1.5:1.

Aspect 4. A T-cell modulatory multimeric polypeptide of aspect 2 or 3, wherein the variant immunomodulatory polypeptide binds the co-immunomodulatory polypeptide with an affinity selected from the group consisting of from about $10^{-4}$ M to about $10^{-7}$ M, from about $10^{-4}$ M to about $10^{-6}$ M, and from about $10^{-4}$ M to about $10^{-5}$ M.

Aspect 5. A T-cell modulatory multimeric polypeptide of any one of aspects 1-4, wherein:

a1) the first polypeptide comprises, in order from N-terminus to C-terminus:

i) the WT-1 peptide epitope; and ii) the first MHC polypeptide; and b1) the second polypeptide comprises, in order from N-terminus to C-terminus:

i) the at least one immunomodulatory polypeptide;

ii) the second MHC polypeptide; and iii) an Ig Fc polypeptide; or a2) the first polypeptide comprises, in order from N-terminus to C-terminus:

i) the WT-1 peptide epitope; and ii) the first MHC polypeptide; and b2) the second polypeptide comprises, in order from N-terminus to C-terminus:

i) the second MHC polypeptide;

ii) the at least one immunomodulatory polypeptide; and iii) an Ig Fc polypeptide; or a3) the first polypeptide comprises, in order from N-terminus to C-terminus:

i) the WT-1 peptide epitope; and ii) the first MHC polypeptide; and b3) the second polypeptide comprises, in order from N-terminus to C-terminus:

i) the second MHC polypeptide;

ii) an Ig Fc polypeptide; and iii) the at least one immunomodulatory polypeptide; or a4) the first polypeptide comprises, in order from N-terminus to C-terminus:

i) the at least one immunomodulatory polypeptide;

ii) the WT-1 peptide epitope;

ii) the first MHC polypeptide; and b4) the second polypeptide comprises, in order from N-terminus to C-terminus:

i) the second MHC polypeptide; and ii) the Ig Fc polypeptide; or a5) the first polypeptide comprises, in order from N-terminus to C-terminus:

i) the WT-1 peptide epitope;

ii) the first MHC polypeptide; and iii) the at least one immunomodulatory polypeptide; and b5) the second polypeptide comprises, in order from N-terminus to C-terminus:

i) the second MHC polypeptide; and ii) an immunoglobulin (Ig) Fc polypeptide.

Aspect 6. A T-cell modulatory multimeric polypeptide of any one of aspects 1-4, wherein:

a) the first MHC polypeptide is a β2-microglobulin polypeptide; and the second MHC polypeptide is an MHC class I heavy chain polypeptide; or b) the first MHC polypeptide is an MHC class I heavy chain polypeptide; and the second MHC polypeptide is a β2-microglobulin polypeptide.

Aspect 7. A T-cell modulatory multimeric polypeptide of aspect 6, wherein:

a) the first polypeptide comprises, in order from N-terminus to C-terminus:

i) the WT-1 peptide epitope; and ii) the β2-microglobulin polypeptide; and b) the second polypeptide comprises, in order from N-terminus to C-terminus:

i) the at least one immunomodulatory polypeptide;

ii) the MHC class I heavy chain polypeptide; and iii) an Ig Fc polypeptide.

Aspect 8. A T-cell modulatory multimeric polypeptide of aspect 6, wherein:

a) the first polypeptide comprises, in order from N-terminus to C-terminus:

i) the WT-1 peptide epitope; and ii) the β2-microglobulin polypeptide; and b) the second polypeptide comprises, in order from N-terminus to C-terminus:

i) the MHC class I heavy chain polypeptide; and ii) an Ig Fc polypeptide; and iii) at least one immunomodulatory polypeptide Aspect 9. A T-cell modulatory multimeric polypeptide of any one of aspects 1-8, wherein the at least one immunomodulatory polypeptide is selected from the group consisting of a cytokine, a 4-1BBL polypeptide, an ICOS-L polypeptide, an OX-40L polypeptide, a CD80 polypeptide, a CD86 polypeptide, a CD40 polypeptide, a CD70 polypeptide, and combinations thereof.

Aspect 10. A T-cell modulatory multimeric polypeptide of any one of aspects 1-9, wherein the at least one immunomodulatory polypeptide comprises an IL-2 polypeptide.

Aspect 11. A T-cell modulatory multimeric polypeptide of any one of aspects 1-10, wherein the multimeric polypeptide comprises at least two immunomodulatory polypeptides, and wherein at least two of the immunomodulatory polypeptides are the same, optionally wherein the 2 or more immunomodulatory polypeptides are in tandem.

Aspect 12. A T-cell modulatory multimeric polypeptide of any one of aspects 1-11, wherein one or more of the at least one immunomodulatory polypeptide is a variant IL-2 polypeptide that exhibits reduced affinity to an IL-2 receptor compared to the affinity of a wild-type IL-2 polypeptide for the IL-2 receptor.

Aspect 13. A T-cell modulatory multimeric polypeptide of aspect 12, wherein the one or more variant IL-2 polypeptides comprises: i) an H16A substitution and an F42A substitution; or ii) an H16T substitution and an F42A substitution.

Aspect 14. A T-cell modulatory multimeric polypeptide of any one of aspects 1-13, wherein the first polypeptide and the second polypeptide are covalently linked to one another, optionally wherein the covalent linkage is via a disulfide bond.

Aspect 15. A T-cell modulatory multimeric polypeptide of any one of aspects 1-14, wherein the first MHC polypeptide or a linker between the epitope and the first MHC polypeptide comprises an amino acid substitution to provide a first Cys residue, wherein the second MHC polypeptide comprises an amino acid substitution to provide a second Cys residue, and wherein the disulfide linkage is between the first and the second Cys residues.

Aspect 16. The T-cell modulatory multimeric polypeptide of any one of aspects 1-15, wherein the polypeptide comprises a disulfide bond between: i) a Cys present in a linker between the WT-1 peptide epitope and the first MHC class I polypeptide, wherein the first MHC class I polypeptide is a β2M polypeptide; and ii) a Cys residue introduced via a Y84C substitution in the second MHC class I polypeptide, wherein the second MHC class I polypeptide is a MHC Class I heavy chain polypeptide.

Aspect 17. The T-cell modulatory multimeric polypeptide of any one of aspects 1-15, wherein the polypeptide comprises a disulfide bond between i) a Cys residue introduced into the first MHC class I polypeptide via an R12C substitution, wherein the first MHC class I polypeptide is a β2M polypeptide; and ii) a Cys residue introduced into the second MHC class I polypeptide, via an A236C substitution, wherein second MHC class I polypeptide is an MHC Class I heavy chain polypeptide.

Aspect 18. The T-cell modulatory multimeric polypeptide of any one of aspects 1-15, wherein the polypeptide comprises a first disulfide bond between: i) a Cys present in a linker between the WT-1 peptide epitope and the first MHC class I polypeptide, wherein the first MHC class I polypeptide is a β2M polypeptide; and ii) a Cys residue introduced via a Y84C substitution in the second MHC class I polypeptide, wherein the second MHC class I polypeptide is a MHC Class I heavy chain polypeptide, and a second disulfide bond between i) a Cys residue introduced into the β2M polypeptide via an R12C substitution; and ii) a Cys residue introduced into the MHC Class I heavy chain polypeptide via an A236C substitution.

Aspect 19. A T-cell modulatory multimeric polypeptide of aspect 16 or aspect 18, wherein the linker between the WT-1 peptide epitope and the first MHC is GCGGS(GGGGS)n (SEQ ID NO:319), where n is 1, 2, 3, 4, 5, 6, 7, 8, or 9.

Aspect 20. A T-cell modulatory multimeric polypeptide of any one of aspects 1-19, wherein the WT-1 peptide epitope has a length of 9 or 10 amino acids.

Aspect 21. A T-cell modulatory multimeric polypeptide of any one of aspects 1-20, wherein the Ig Fc polypeptide comprises one of the amino acid sequences depicted in FIG. 5D, FIG. 5E, FIG. 5F, FIG. 4G, and FIG. 5H.

Aspect 22. A T-cell modulatory multimeric polypeptide of any one of aspects 1-21, wherein the WT-1 peptide comprises the amino acid sequence SMTWNQMNL (SEQ ID NO:451), GCMTWNQMNL (SEQ ID NO:452), SYTWNQMNL (SEQ ID NO:453), or GCYTWNQMNL (SEQ ID NO:454).

Aspect 23. A T-cell modulatory multimeric polypeptide of any one of aspects 1-21, wherein the first or the second MHC polypeptide comprises an amino acid sequence having at least 95% amino acid sequence identity to amino acids 25-299 of the HLA-A*2402 amino acid sequence depicted in FIG. 7A.3.

Aspect 24. A T-cell modulatory multimeric polypeptide of any one of aspects 1-23, wherein the first MHC polypeptide is a β2M polypeptide, and wherein the second MHC polypeptide comprises an amino acid sequence having at least 95% amino acid sequence identity to an HLA-A24 polypeptide, wherein the epitope is selected from the group consisting of: SMTWNQMNL (SEQ ID NO:451), GCMTWNQMNL (SEQ ID NO:452), SYTWNQMNL (SEQ ID NO:453), and GCYTWNQMNL (SEQ ID NO:454), and wherein the Ig Fc polypeptide comprises the amino acid sequence depicted in FIG. 5G or FIG. 5H.

Aspect 25. A T-cell modulatory multimeric polypeptide of aspect 1, wherein: a) the first polypeptide comprises the amino acid sequence depicted in FIG. 37B; and b) the second polypeptide comprises the amino acid sequence depicted in FIG. 20B.

Aspect 26. A T-cell modulatory multimeric polypeptide of any one of aspects 1-25, wherein the multimeric polypeptide comprises a first and a second heterodimer, and wherein the first and second heterodimers are covalently bound by one or more disulfide bonds between the Ig Fc polypeptides of the first and second heterodimers.

Aspect 27. A nucleic acid comprising a nucleotide sequence encoding a first or second polypeptide according to any one of aspects 1-26.

Aspect 28. An expression vector comprising the nucleic acid of aspect 27.

Aspect 29. A method of selectively modulating the activity of T cell specific for a Wilms tumor-1 (WT-1) epitope, the method comprising contacting the T cell with a T-cell modulatory multimeric polypeptide according to any one of aspects 1-26, wherein said contacting selectively modulates the activity of the WT-1 epitope-specific T cell.

Aspect 30. A method of treating a patient having a cancer, the method comprising administering to the patient an effective amount of a pharmaceutical composition comprising T-cell modulatory multimeric polypeptide according to any one of aspects 1-26.

Aspect 31. The method of aspect 30, wherein the cancer is acute myeloid leukemia, myeloma, ovarian cancer, pancreatic cancer, non-small cell lung cancer, colorectal cancer, breast cancer, Wilms tumor, mesothelioma, soft tissue sarcoma, neuroblastoma, or nephroblastoma.

Aspect 32. A method of aspect 30 or 31, further comprising administering one or more checkpoint inhibitors to the individual.

Aspect 33. A method according to aspect 32, wherein the checkpoint inhibitor is an antibody that binds to a polypeptide selected from the group consisting of CD27, CD28, CD40, CD122, CD96, CD73, CD47, OX40, GITR, CSF1R, JAK, PI3K delta, PI3K gamma, TAM, arginase, CD137, ICOS, A2AR, B7-H3, B7-H4, BTLA, CTLA-4, LAG3, TIM3, VISTA, CD96, TIGIT, CD122, PD-1, PD-L1, and PD-L2.

Aspect 34. A method according to aspect 33, wherein the checkpoint inhibitor is an antibody specific for PD-1, PD-L1, or CTLA4.

Aspect 35. A method according to aspect 33 or 34, wherein the one or more checkpoint inhibitors is selected from the group consisting of nivolumab, pembrolizumab, pidilizumab, AMP-224, MPDL3280A, MDX-1105, MEDI-4736, arelumab, ipilimumab, tremelimumab, pidilizumab, IMP321, MGA271, BMS-986016, lirilumab, urelumab, PF-05082566, IPH2101, MEDI-6469, CP-870,893, Mogamulizumab, Varlilumab, Avelumab, Galiximab, AMP-514, AUNP 12, Indoximod, NLG-919, INCB024360, KN035, and combinations thereof.

Aspect 36. A method of modulating an immune response in an individual, the method comprising administering to the individual an effective amount of the T-cell modulatory multimeric polypeptide of any one of aspects 1-26, wherein said administering induces an epitope-specific T cell response and an epitope-non-specific T cell response, and wherein the ratio of the epitope-specific T cell response to the epitope-non-specific T cell response is at least 2:1.

Aspect 37. A method of delivering an immunomodulatory polypeptide selectively to a target T cell, the method comprising contacting a mixed population of T cells with a T-cell modulatory multimeric polypeptide of any one of aspects 1-26, wherein the mixed population of T cells comprises the target T cell and non-target T cells, wherein the target T cell is specific for the WT-1 epitope present within the T-cell modulatory multimeric polypeptide, and wherein said contacting delivers the one or more immunomodulatory polypeptides present within the T-cell modulatory multimeric polypeptide to the target T cell.

Aspect 38. A method of detecting, in a mixed population of T cells obtained from an individual, the presence of a target T cell that binds a WT-1 epitope, the method comprising:

a) contacting in vitro the mixed population of T cells with the T-cell modulatory multimeric polypeptide of any one of aspects 1-26, wherein the T-cell modulatory multimeric polypeptide comprises the WT-1 epitope; and b) detecting activation and/or proliferation of T cells in response to said contacting, wherein activated and/or proliferated T cells indicates the presence of the target T cell.

Aspect 39. A T-cell modulatory multimeric polypeptide (TMMP) comprising: at least one heterodimer comprising: a) a first polypeptide comprising, in order from N-terminus to C-terminus: i) a Wilms tumor-1 (WT-1) peptide, wherein the WT-1 peptide has the amino acid sequence VLDFAPPGA (SEQ ID NO:259); ii) a linker having the amino acid sequence GCGGSGGGGSGGGGS (SEQ ID NO:317); and iii) a β2-microglobulin polypeptide comprising the amino acid sequence set forth in SEQ ID NO:311; and b) a second polypeptide comprising, in order from N-terminus to C-terminus: i) a variant IL-2 polypeptide comprising the amino acid sequence set forth in SEQ ID NO:188, where $X_1$ is Ala and where $X_2$ is Ala; ii) a (GGGGS)4 linker; iii) a variant IL-2 polypeptide comprising the amino acid sequence set forth in SEQ ID NO:188, where $X_1$ is Ala and where $X_2$ is Ala; iv) a major histocompatibility complex (MHC) heavy chain polypeptide comprising the amino acid sequence set forth in SEQ ID NO:341; v) a linker comprising the amino acid sequence AAAGG; and vi) an immunoglobulin (Ig) Fc polypeptide.

Aspect 40. A TMMP of aspect 39, wherein the Ig Fc polypeptide is a variant Ig Fc polypeptide comprising one or more sequence variations relative to the wild type polypeptide, wherein the ability of the Ig Fc polypeptide to induce cell lysis though complement-dependent cytotoxicity (CDC) and/or antibody-dependent cellular cytotoxicity (ADCC) is reduced or substantially eliminated, optionally wherein the Ig Fc polypeptide comprises an amino acid sequence having at least at least about 95%, at least about 98%, at least about 99%, or 100%, amino acid sequence identity to an amino acid sequence of an Fc region depicted in FIG. 5A-5G or 5H.

Aspect 41. A TMMP of aspect 40, wherein the Ig Fc polypeptide is a variant human IgG1 Fc polypeptide comprising comprises an L234A and/or L235A substitutions (L14 and L15 in the amino acid sequence depicted in FIG. 5H).

Aspect 42. A TMMP of any one of aspects 39-41, wherein the first polypeptide comprises construct 2380 having the amino acid sequence set forth in FIG. 14B and SEQ ID NO:423; and where the second polypeptide comprises construct 1715Δ having the amino acid sequence set forth in FIG. 14J and SEQ ID NO:486.

Aspect 43. A TMMP comprising a homodimer of the heterodimer of any one of aspects 39-42.

Aspect 44. A nucleic acid comprising a nucleotide sequence encoding the first and/or the second polypeptide of any one of aspects 39-42.

Aspect 45. An expression vector comprising the nucleic acid of aspect 44.

Aspect 46. A genetically modified host cell, wherein the host cell is genetically modified with a nucleic acid of aspect 44 or an expression vector of aspect 45.

Aspect 47. A method of making a T-cell modulatory multimeric polypeptide (TMMP), the method comprising culturing the genetically modified host cell of aspect 46 in vitro in a culture medium under conditions such that the host cell synthesizes the TMMP.

Aspect 48. A method of selectively modulating the activity of T cell specific for a Wilms tumor-1 (WT-1) epitope, the method comprising contacting the T cell with a T-cell modulatory multimeric polypeptide according to any one of aspects 39-43, wherein said contacting selectively modulates the activity of the WT-1 epitope-specific T cell.

Aspect 49. A method of treating a patient having a cancer associated with WT-1, the method comprising administering to the patient an effective amount of a pharmaceutical composition comprising T-cell modulatory multimeric polypeptide according to any one of aspects 39-43.

Aspect 50. A method of aspect 49, wherein the cancer is acute myeloid leukemia, myeloma, ovarian cancer, pancreatic cancer, non-small cell lung cancer, colorectal cancer, breast cancer, Wilms tumor, mesothelioma, soft tissue sarcoma, neuroblastoma, or nephroblastoma.

Aspect 51. A method of 49 or 50, further comprising administering one or more immune checkpoint inhibitors to the individual.

Aspect 52. A method according to aspect 51, wherein the immune checkpoint inhibitor is an antibody that binds to a polypeptide selected from the group consisting of CD27, CD28, CD40, CD122, CD96, CD73, CD47, OX40, GITR, CSF1R, JAK, PI3K delta, PI3K gamma, TAM, arginase, CD137, ICOS, A2AR, B7-H3, B7-H4, BTLA, CTLA-4, LAGS, TIM3, VISTA, CD96, TIGIT, CD122, PD-1, PD-L1, and PD-L2.

Aspect 53. A method according to aspect 52, wherein the immune checkpoint inhibitor is an antibody specific for PD-1, PD-L1, or CTLA4.

Aspect 54. A method according to aspect 52 or 53, wherein the one or more immune checkpoint inhibitors is selected from the group consisting of nivolumab, pembrolizumab, pidilizumab, AMP-224, MPDL3280A, MDX-1105, MEDI-4736, arelumab, ipilimumab, tremelimumab, pidilizumab, IMP321, MGA271, BMS-986016, lirilumab, urelumab, PF-05082566, IPH2101, MEDI-6469, CP-870,893, Mogamulizumab, Varlilumab, Avelumab, Galiximab, AMP-514, AUNP 12, Indoximod, NLG-919, INCB024360, KN035, and combinations thereof.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1

The effect of linking the two polypeptide chains of a TMMP heterodimer via two disulfide bonds on stability and production was tested.

The following TMMPs were generated: a) a TMMP comprising 1715+2380 polypeptides; and b) a TMMP comprising 1715 and 2381 polypeptides. The amino acid sequences of the polypeptide chains are provided in FIG. 14A-14C. As shown in FIG. 15 and FIG. 16, the TMMPs included: i) Class I HLA-A heavy chain polypeptides of the A02:01 allele; and ii) two copies of IL2 (H16A; F42A) immunomodulatory ("MOD") polypeptides. The 2380 polypeptide comprises the WT1 peptide WT1(37-45), while the 2381 polypeptide comprises the WT1 peptide WT1(126-134). The 1715-2380 TMMP is a homodimer of a heterodimer comprising the 1715 polypeptide and the 2380 polypeptide. Likewise, the 1715-2381 TMMP is a homodimer of a heterodimer comprising the 1715 polypeptide and the 2381 polypeptide. Thus, the TMMPs included: i) 2 copies of the 1715+2380 heterodimer, linked by 2 disulfide bonds between the IgFc polypeptide present in the 1715 polypeptides; or ii) 2 copies of the 1715+2381 heterodimer, linked by 2 disulfide bonds between the IgFc polypeptide present in the 1715 polypeptides. This arrangement is depicted schematically in FIG. 17C.

TMMP 1715+2380 is a double disulfide-linked heterodimer: a) a first disulfide linkage is between: i) the Cys present in the linker between the WT1 peptide and the β2M chain in the 2380 polypeptide; and ii) the Cys introduced by the Y84C substitution in the Class I heavy chain present in the 1715 polypeptide; and b) a second disulfide linkages is between: i) the Cys introduced by the R12C substitution in the β2M polypeptide present in the 2380 polypeptide; and ii) the Cys introduced by the A236C substitution in the Class I heavy chain present in the 1715 polypeptide.

TMMP 1715+2381 is a double disulfide-linked heterodimer: a) a first disulfide linkage is between: i) the Cys present in the linker between the WT1 peptide and the β2M chain in the 2381 polypeptide; and ii) the Cys introduced by the Y84C substitution in the Class I heavy chain present in the 1715 polypeptide; and b) a second disulfide linkages is between: i) the Cys introduced by the R12C substitution in the β2M polypeptide present in the 2381 polypeptide; and ii) the Cys introduced by the A236C substitution in the Class I heavy chain present in the 1715 polypeptide.

The TMMPs were produced in ExpiCHO cells (adapted from Chinese hamster ovary (CHO) cells; ThermoFisher; see, e.g., Jain et al. (2017) Protein Expr. Purif. 134:38) and were purified from the cell culture medium in which the cells were grown. Two purification steps were carried out. In a first step, the cell culture medium was clarified, and the clarified cell culture medium was subjected to Protein A column purification. In the second purification step, the eluate from the Protein A column was subjected to size exclusion chromatography.

The stability of the purified TMMPs was tested. The amount of heterodimeric TMMP present was determined after storage of the purified TMMPs in a liquid solution (phosphate-buffered saline (PBS) containing 365 mM NaCl, pH 7.4) for 28 days at 37° C. or for 28 days at 42° C.

In addition, the purified TMMPs were subjected to 3 freeze/thaw cycles.

The results are depicted in FIG. 15 and FIG. 16.

As shown in FIG. 15, a homodimer of the 1715-2380 heterodimer (referred to in FIG. 15 as "monomer") represented 80% of the eluate from the Protein A column. As shown in FIG. 16, a homodimer of the 1715-2381 heterodimer (referred to in FIG. 16 as "monomer") represented 79% of the eluate from the Protein A column.

Homodimers of heterodimers 1715-2380 and 1715-2381 were found to be stable to 3 freeze/thaw cycles.

Unfolding temperatures of the peptide/HLA, IL-2, and Fc domains of various TMMPs, expressed as $T_m$ (° C.), are provided in FIG. 15 and FIG. 16. In addition, the temperature at which aggregation occurs ($T_m$° C.) is provided in FIG. 15 and FIG. 16.

Stability assays (10-day in vitro stability at 4° C., 37° C., and 42° C.) were conducted, comparing the stability of double-disulfide-bonded TMMPs to that of single disulfide-bonded TMMPs. The data are shown in Tables 2-4, below.

Table 2 below illustrates the results obtained with TMMPs containing the WT-1 peptide VLDFAPPGA (SEQ ID NO:259):

TABLE 2

| Engineered disulfide | R12C-A236C | R12C-A236C; G2C-Y84C | G2C-Y84C |
|---|---|---|---|
| Titer (mg/L) | 157 | 281 | 243 |
| % Monomer (post ProtA) | <47 | 61 | NA |
| % Monomer (post SEC) | | 98 | 99 |
| Stability (10 d @ 4° C./37° C./42° C. Monomer recovery % | | 100/88/24 | 99/83/14 |

TABLE 2-continued

| Engineered disulfide | R12C-A236C | R12C-A236C; G2C-Y84C | G2C-Y84C |
|---|---|---|---|
| Freeze-thaw (0x/1x/3x) | | 98/98/98 | 99/94/90 |
| $T_m$ (° C.) | | 51 | 55 |
| | | 66 | 66 |
| | | 81 | 82 |
| Intact mass (LC-MS) | Confirmed | Confirmed | Confirmed |

NA = data not available

The middle data column of Table 2 presents in vitro stability data for a double-disulfide-bonded TMMP comprising the WT-1 peptide VLDFAPPGA (SEQ ID NO:259), compared to single-disulfide TMMPs that have only one of those two disulfide bonds (left-hand data column and right-hand data column).

The single-disulfide TMMP that has only the disulfide bond between the Cys at position 12 in the β2M polypeptide ("R12C") and the Cys at amino acid 236 of the MHC class I heavy chain ("A236C") was so unstable that it could not be purified in sufficient quantities to conduct stability assays. These data are presented in the left-hand data column in Table 2.

The single-disulfide TMMP that has only the disulfide bond between: i) the linker between the WT-1 epitope and the β2M polypeptide ("G2C"); and ii) the Cys at amino acid 84 of the MHC class I heavy chain ("Y84C") could be produced; however, it was less stable in vitro than the double-disulfide-bonded TMMP. For example, whereas the freeze/thaw values (representing the % monomer remaining after the indicated number of freeze/thaw cycles and thus the stability of the TMMP) for double-disulfide TMMP remained stable and unchanged over successive freeze/thaw cycles, the freeze/thaw values for this single-disulfide TMMP decreased over successive freeze/thaw cycles, indicating instability. Furthermore, the freeze/thaw value for the third freeze/thaw cycle was significantly lower than that of the double-disulfide-bonded TMMP. These data are presented in the right-hand data column in Table 2.

Similar results were obtained with TMMPs made with TMMPs containing the WT-1 peptide RMFPNAPYL (SEQ ID NO:260). The results are provided in Table 3, below.

TABLE 3

| Engineered disulfide | R12C-A236C | R12C-A236C; G2C-Y84C | G2C-Y84C |
|---|---|---|---|
| Titer (mg/L) | 228 | 280 | 236 |
| % Monomer (post ProtA) | 32 | 58 | 61 |
| % Monomer (post SEC) | 91 | 98 | 99 |
| Stability (10 d @ 4° C./37° C./ 42° C. Monomer recovery % | 100/11/7 | 100/85/11 | 100/80/7 |
| Freeze-thaw (0x/1x/3x) | 91/91/91 | 98/98/98 | 99/98/92 |
| $T_m$ (° C.) | 41 | 50 | 48 |
| | 66 | 67 | 66 |
| | 81 | 81 | 81 |
| Intact mass (LC-MS) | Confirmed | Confirmed | Confirmed |

The middle data column of Table 3 presents in vitro stability data for a double-disulfide-bonded TMMP comprising the WT-1 peptide RMFPNAPYL (SEQ ID NO:260), compared to single-disulfide TMMPs that have only one of those two disulfide bonds (left-hand data column and right-hand data columns). The data show that the double-disulfide-bonded TMMP is more stable in vitro than either of the single-disulfide TMMPs.

The data in the left-hand data column is for the single-disulfide TMMP that has only the disulfide bond between the Cys at position 12 in the β2M polypeptide ("R12C") and the Cys at amino acid 236 of the MHC class I heavy chain ("A236C"). This single-disulfide TMMP exhibited instability at 37° C., compared to the double-disulfide-bonded TMMP.

The data in the right-hand data column is for the single-disulfide TMMP that has only the disulfide bond between: i) the linker between the WT-1 epitope and the β2M polypeptide ("G2C"); and ii) the Cys at amino acid 84 of the MHC class I heavy chain ("Y84C"). Again, whereas the freeze/thaw values for double-disulfide TMMP remained stable and unchanged over successive freeze/thaw cycles, the freeze/thaw values for this single-disulfide TMMP decreased over successive freeze/thaw cycles, indicating instability. Furthermore, the freeze/thaw value for the third freeze/thaw cycle was significantly lower than that of the double-disulfide-bonded TMMP.

Similar results were obtained with TMMPs made with TMMPs containing the WT-1 peptide YMFPNAPYL (SEQ ID NO:264). The results are provided in Table 4, below.

TABLE 4

| Engineered disulfide | R12C-A236C | R12C-A236C; G2C-Y84C | G2C-Y84C |
|---|---|---|---|
| Titer (mg/L) | 280 | 300 | 290 |
| % Monomer (post ProtA) | 40 | 48 | 60 |
| % Monomer (post SEC) | 97 | 97 | 98 |
| Stability (10 d @ 4° C./37° C./ 42° C. Monomer recovery % | 100/41/0 | 100/87/27 | 100/86/29 |
| Freeze-thaw (0x/1x/3x) | 97/97/97 | 97/97/97 | 98/96/91 |
| $T_m$ (° C.) | 44 | 55 | 51 |
| | 67 | 66 | 66 |
| | 81 | 82 | 80 |
| Intact mass (LC-MS) | Confirmed | Confirmed | Confirmed |

The middle data column of Table 4 presents in vitro stability data for a double-disulfide-bonded TMMP comprising the WT-1 peptide YMFPNAPYL (SEQ ID NO:264), compared to single-disulfide TMMPs that have only one of those two disulfide bonds (left-hand data column and right-hand data columns). The data show that the double-disulfide-bonded TMMP is more stable in vitro than either of the single-disulfide TMMPs.

The data in the left-hand data column is for the single-disulfide TMMP that has only the disulfide bond between the Cys at position 12 in the β2M polypeptide ("R12C") and the Cys at amino acid 236 of the MHC class I heavy chain ("A236C"). This single-disulfide TMMP exhibited instability at 37° C., compared to the double-disulfide-bonded TMMP.

The data in the right-hand data column is for the single-disulfide TMMP that has only the disulfide bond between: i) the linker between the WT-1 epitope and the β2M polypeptide ("G2C"); and ii) the Cys at amino acid 84 of the MHC class I heavy chain ("Y84C"). Again, whereas the freeze/thaw values for double-disulfide TMMP remained stable and unchanged over successive freeze/thaw cycles, the freeze/thaw values for this single-disulfide TMMP decreased over successive freeze/thaw cycles, indicating instability. Furthermore, the freeze/thaw value for the third freeze/thaw cycle was significantly lower than that of the double-disulfide-bonded TMMP.

Example 2: Biochemical Characterization of TMMPs Comprising WT1 Epitopes, HLA-A*02 Heavy Chains, Either One or Two Disulfide Bonds Between the 2 Polypeptide Chains of the Heterodimer, and Variant IL-2 Immunomodulatory Polypeptides at Position 1

The constructs used in this study are summarized in Table 5.

TABLE 5

| Constructs | Epitope | S—S bond(s) | IL-2 position |
|---|---|---|---|
| 2405 + 2762 | WT-1 (37-45) | G2C | 1 |
| 1715 + 2380 | WT-1 (37-45) | G2C + R12C | 1 |
| 2405 + 2763 | WT-1 (126-134) | G2C | 1 |
| 1715 + 2381 | WT-1 (126-134) | G2C + R12C | 1 |
| 2405 + 3626 | WT-1 (126-134 (R126Y)) | G2C | 1 |
| 1715 + 3625 | WT-1 (126-134 (R126Y)) | G2C + R12C | 1 |

Amino acid sequences of the polypeptide chains of the constructs are provided in FIG. 14A-141.

"G2C" indicates that the TMMP includes a disulfide bond between: i) a Cys in the peptide linker between the peptide epitope and the β2M polypeptide; and ii) a Cys at position 84 of the MHC class I heavy chain, where the MHC class I heavy chain has a Y84C substitution.

"R12C" indicates that the TMMP includes a disulfide bond between: i) a Cys at position 12 in the β2M polypeptide, where the β2M polypeptide has an R12C substitution; and ii) a Cys at position 236 of the MHC class I heavy chain, where the MHC class I heavy chain has an A236C substitution.

"G2C+R12C" indicates that the TMMP includes both the "G2C" disulfide bond and the "R12C" disulfide bond.

WT-1 (37-45) is VLDFAPPGA (SEQ ID NO:259).

WT-1 (126-134) is RMFPNAPYL (SEQ ID NO:260).

WT-1 (126-134 (R126Y)) is YMFPNAPYL (SEQ ID NO:264) and is also referred to as "126-134 mimotope."

IL-2 "position 1" is depicted schematically in FIG. 19.

Results

The ability of TMMPs to stimulate antigen-specific proliferation of $CD8^+$ T cells was tested. The TMMPs included, as the epitope: i) WT1 37-45; ii) WT1 126-134; or iii) WT1 126-134 (R126Y). All TMMPs included A02 allele MHC class I heavy chains.

Peripheral blood mononuclear cells (PBMCs) obtained from human donors were incubated in vitro with the TMMPs at various concentrations (0 nM, 10 nM, 100 nM, 300 nM, or 1000 nM) for 10 days. After the 10-day incubation period, the number of cells specific for the epitope was determined. Data from PBMCs from two donors ("Leukopak 7 and Leukopak 12") are shown in FIG. 21.

Figure 21:
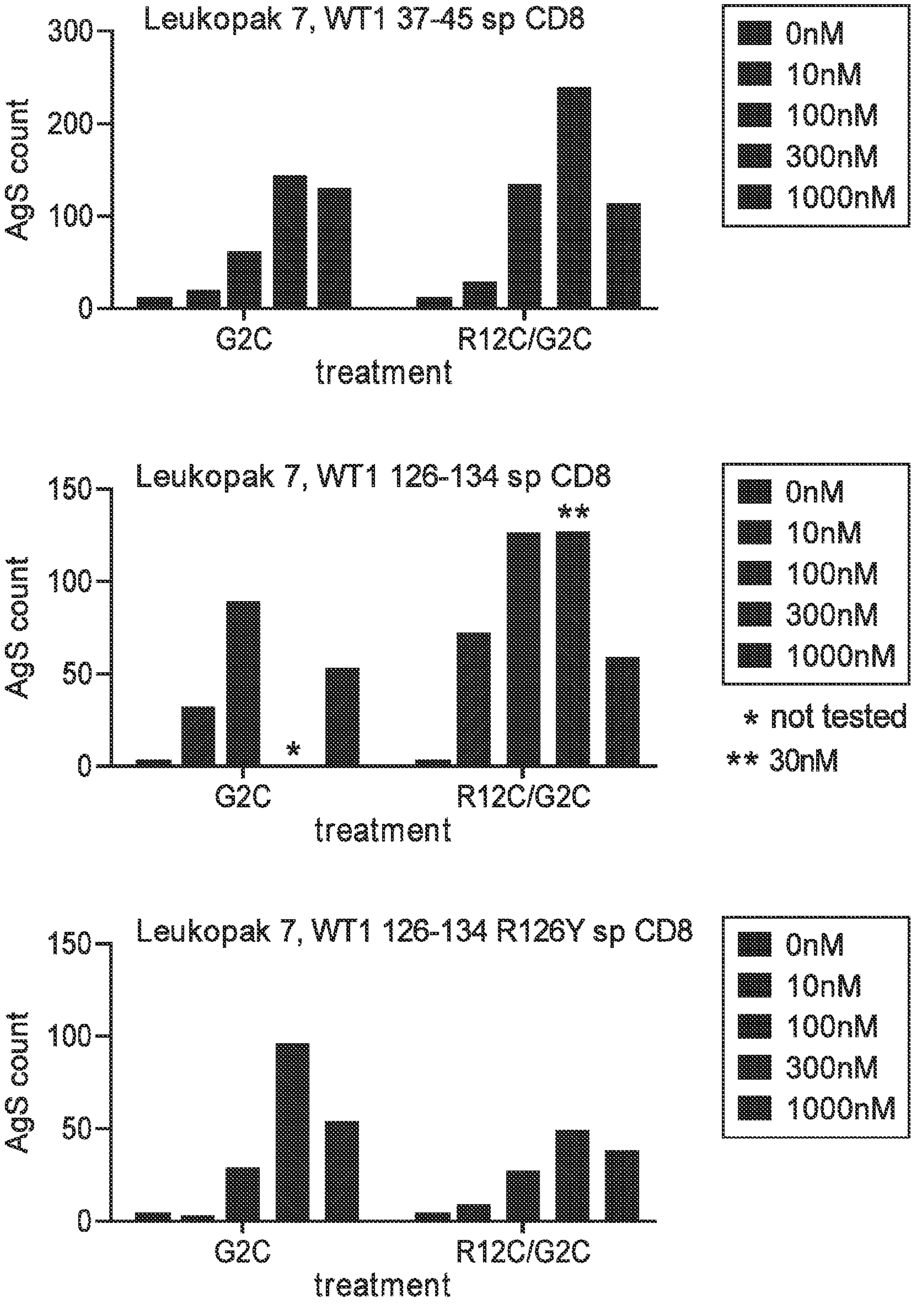
FIG. 21 depicts the effect of TMMPs, containing WT1 peptide epitopes and HLA-A*02 heavy chains, on antigen-specific CD8+ T cell expansion.
Figure 21:
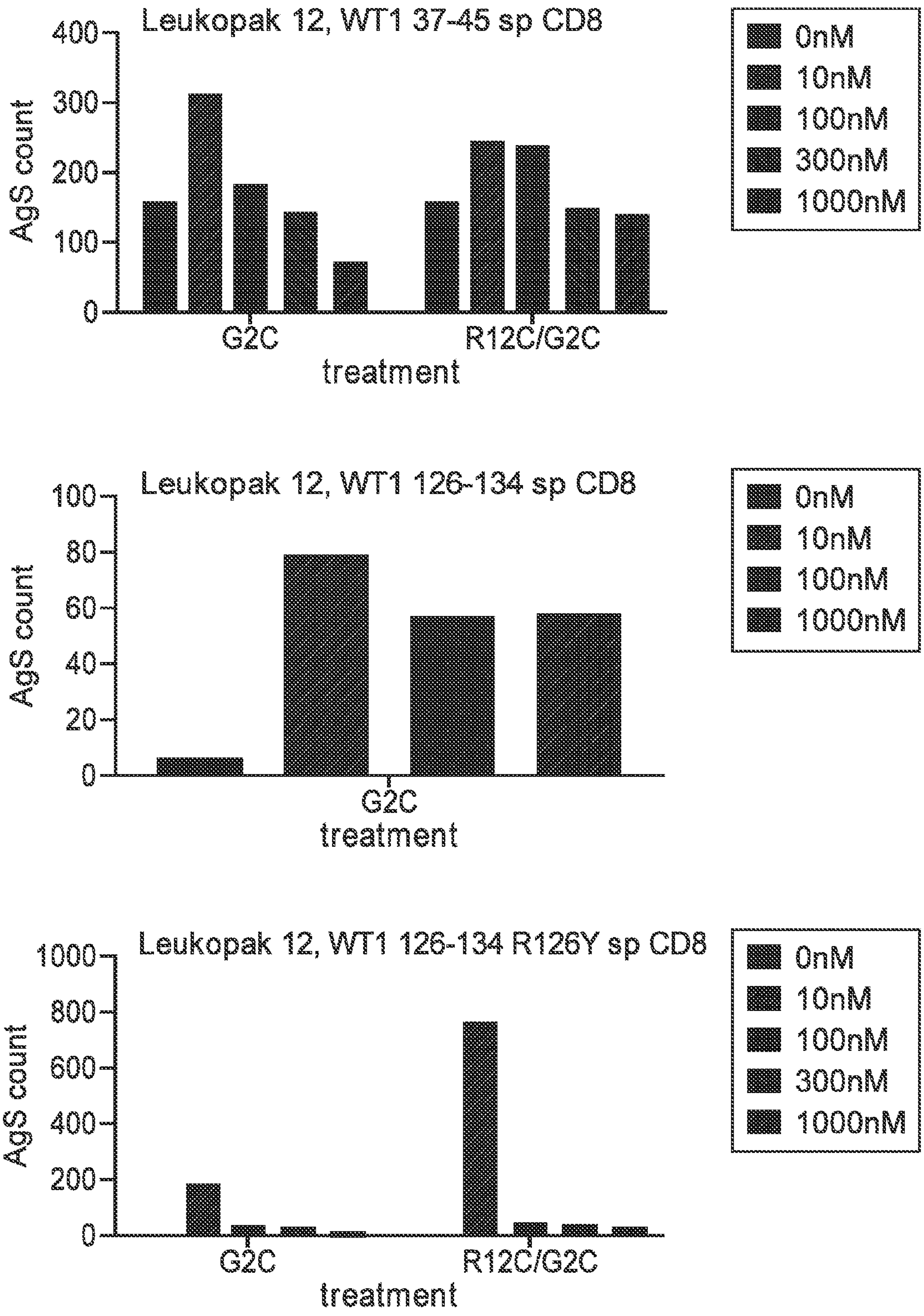

The data presented in FIG. 21 demonstrate, in two donors, that WT1-specific TMMPs can induce expansion of WT1-specific CD8+ T cells from total PBMCs over a course of a 10-day stimulation culture. This expansion was achieved in PBMCs that have low or no detectable WT1-specific T cell precursors, indicating that the TMMPs were able to induce antigen-specific responses in donors from an unprimed or naïve repertoire. The data demonstrate that TMMPs specific for any of the 3 selected WT1 peptides (37-45, 126-134, and 126-134 R126Y) and on either of the two tested disulfide frameworks (G2C and R12C/G2C) induce expansion of WT1-specific CD8+ T cells from total PBMCs.

PBMCs from different human donors (L7, L10, and L12) were stimulated for 10 days in vitro with the indicated WT1 peptides in the presence of recombinant human IL-2 and then re-stimulated for 8 days with TMMPs, containing the same peptides, and containing either the G2C disulfide bond or both the R12C and G2C disulfide bonds. The data are depicted in FIG. 22.

Figure 22:
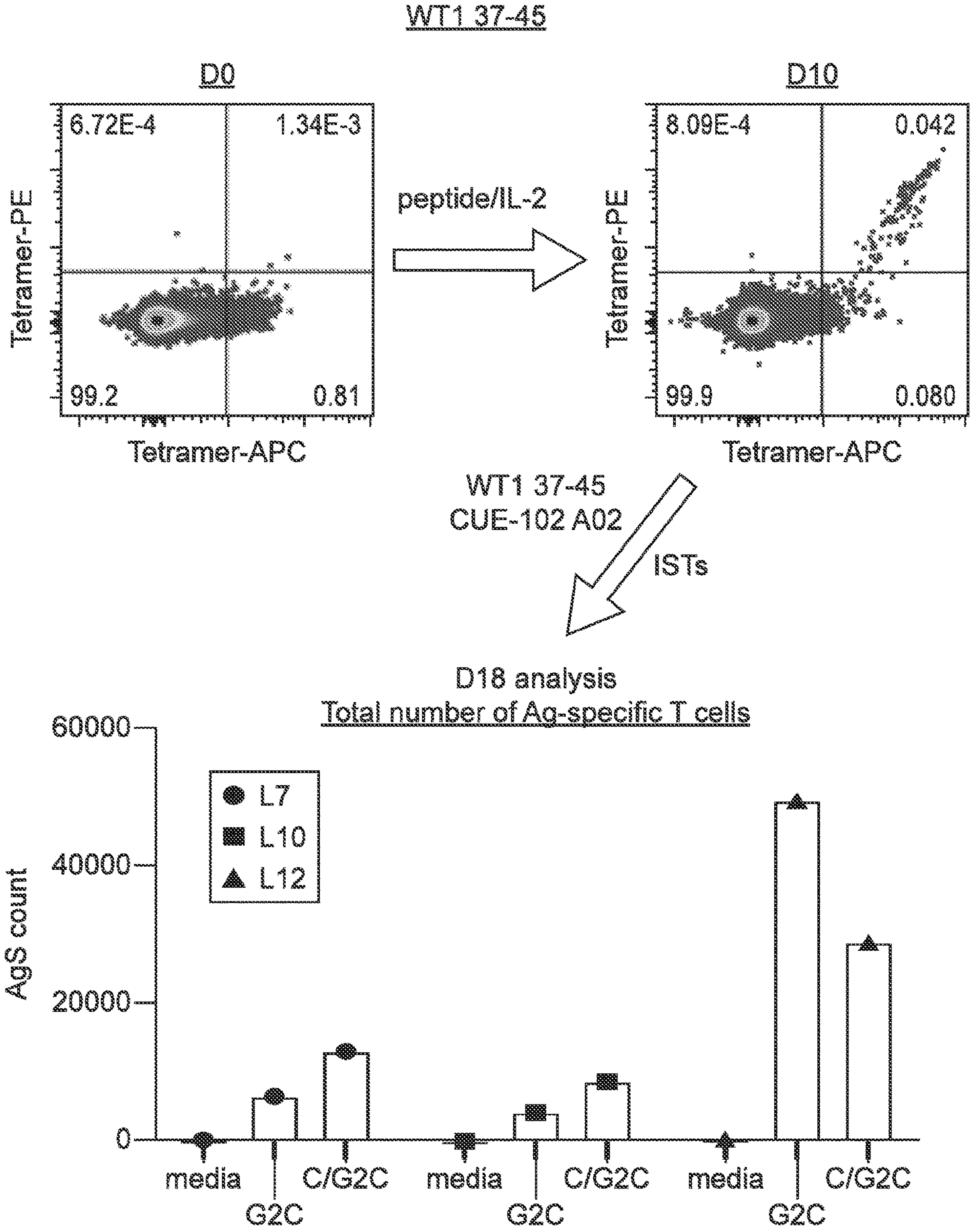
FIG. 22 depicts the effect of TMMPs containing WT1 peptide epitopes on expansion of WT1-specific CD8+ T cells from total PBMCs over a course of an 8-day re-stimulation culture following a 10-day priming culture.
Figure 22:
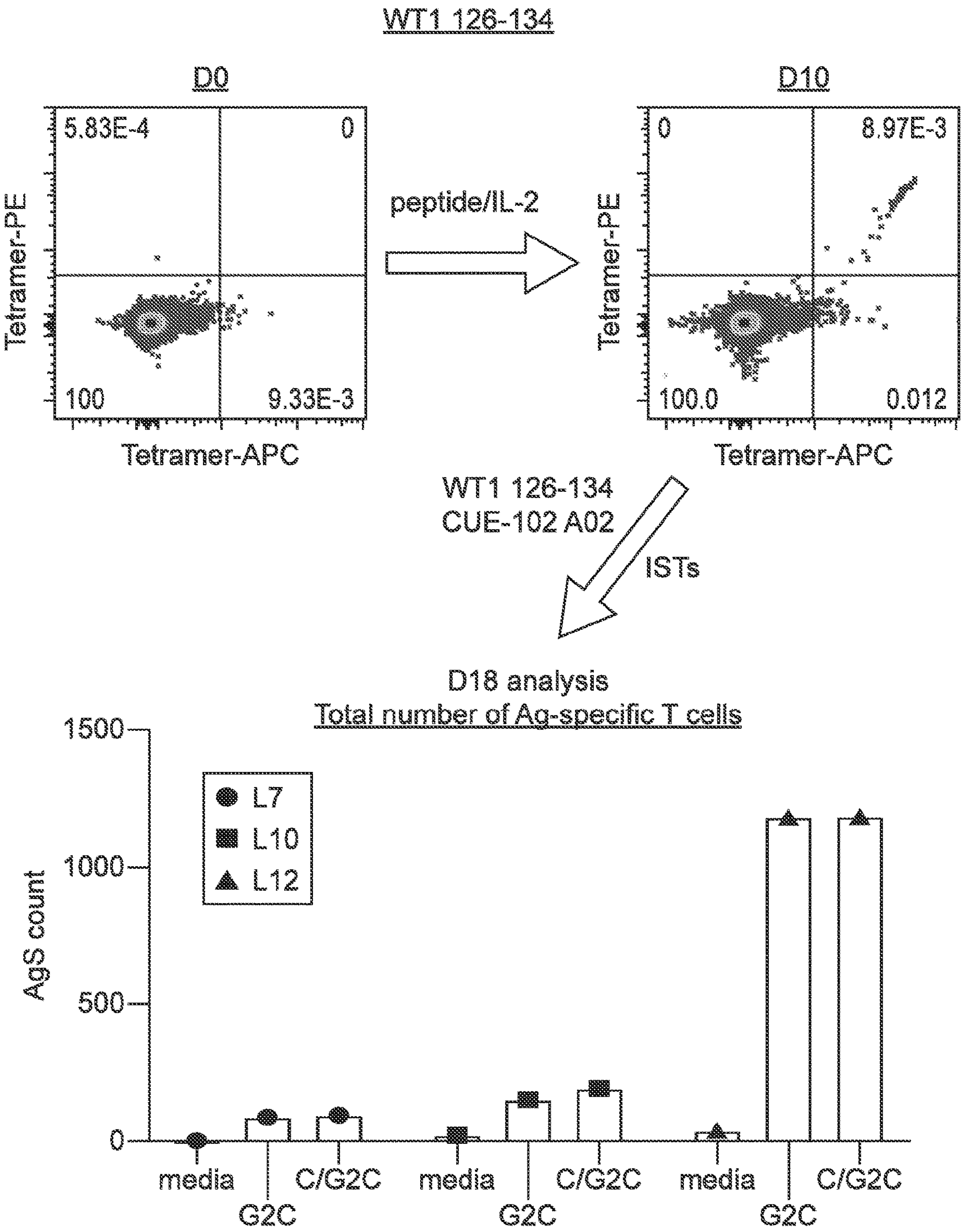
Figure 22:
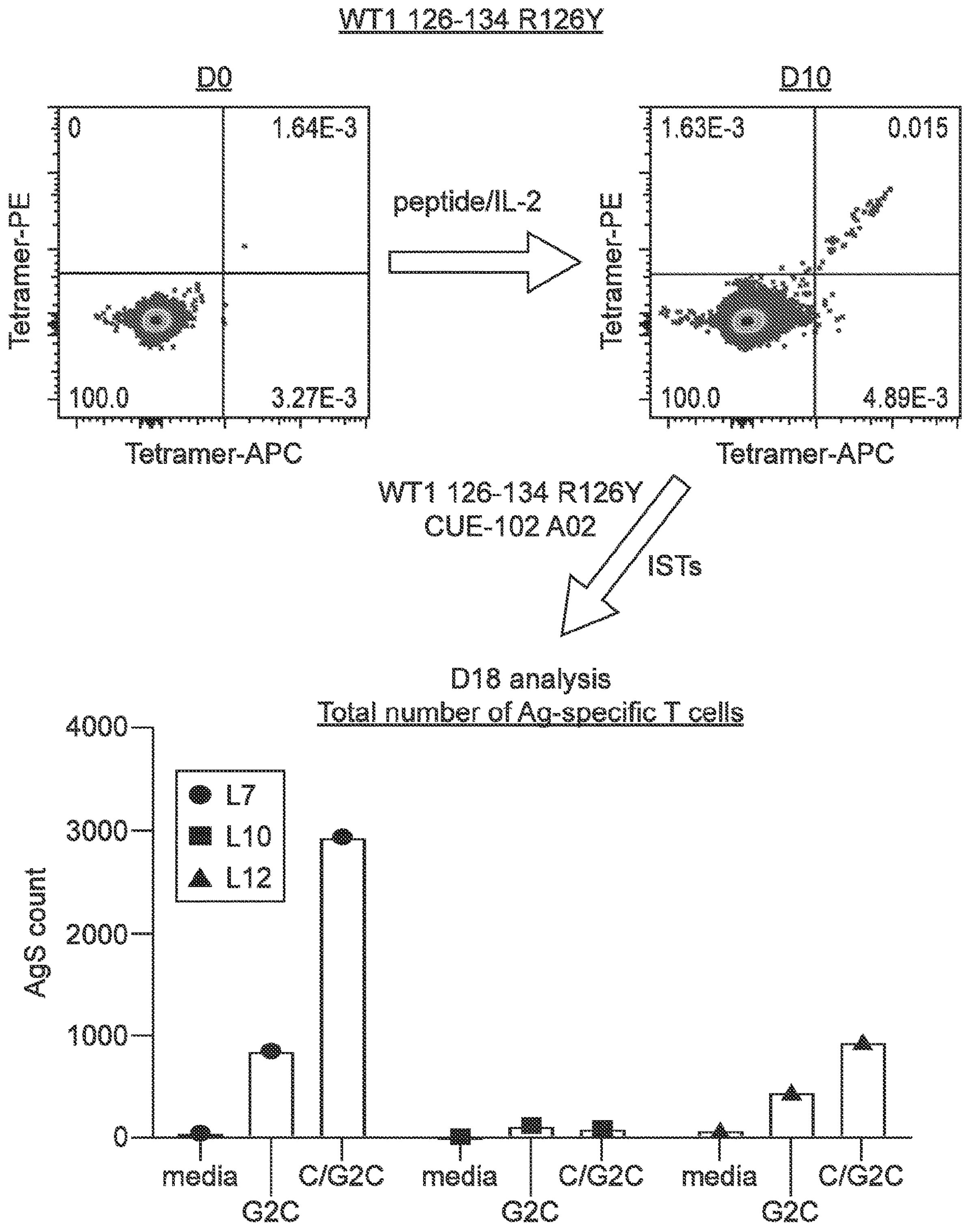

The data presented in FIG. 22 demonstrate, in PBMCs from three donors, that WT1-containing TMMPs can expand WT1-specific CD8+ T cells from total PBMCs over a course of an 8-day re-stimulation culture following a 10-day priming culture. This expansion occurred from cells that have a detectable number of WT1-specific T cell precursors, indicating that the TMMPs were able to expand antigen-specific T cells in donors with a primed/preexisting WT-1 specific T cell repertoire. The data demonstrate that TMMPs specific for any of the 3 WT1 peptides (37-45, 126-134, and 126-134 R126Y) and on either of the two tested disulfide frameworks (G2C and R12C/G2C) induce such expansions.

The ability of the $CD8^+$ T cells expanded by contacting with TMMPs containing the WT1 37-45 peptide and containing either the G2C disulfide bond or both the R12C and G2C disulfide bonds, to produce TNF-α and IFN-γ in response to target cells (T2 cells) presenting the WT1-37-45 peptide or an irrelevant peptide (SL9) was tested. Phorbol 12-myristate 13-acetate (PMA) and ionomycin ("iono") were used as a positive control. $CD8^+$ T cells treated with media were used as a negative control. $CD8^+$ T cells expanded by TMMPs were incubated with 'target cells' (T2 cells) that were loaded with either a WT1 peptide or with an irrelevant peptide (the SL9 peptide from HIV). The response, as indicated by production of IFN-γ and TNF-α, of the $CD8^+$ T cells to the T2 cells pulsed with WT 37-45 peptide was compared to the response to T2 cells pulsed with SL9 peptide. The data are shown in FIG. 23.

Figure 23:
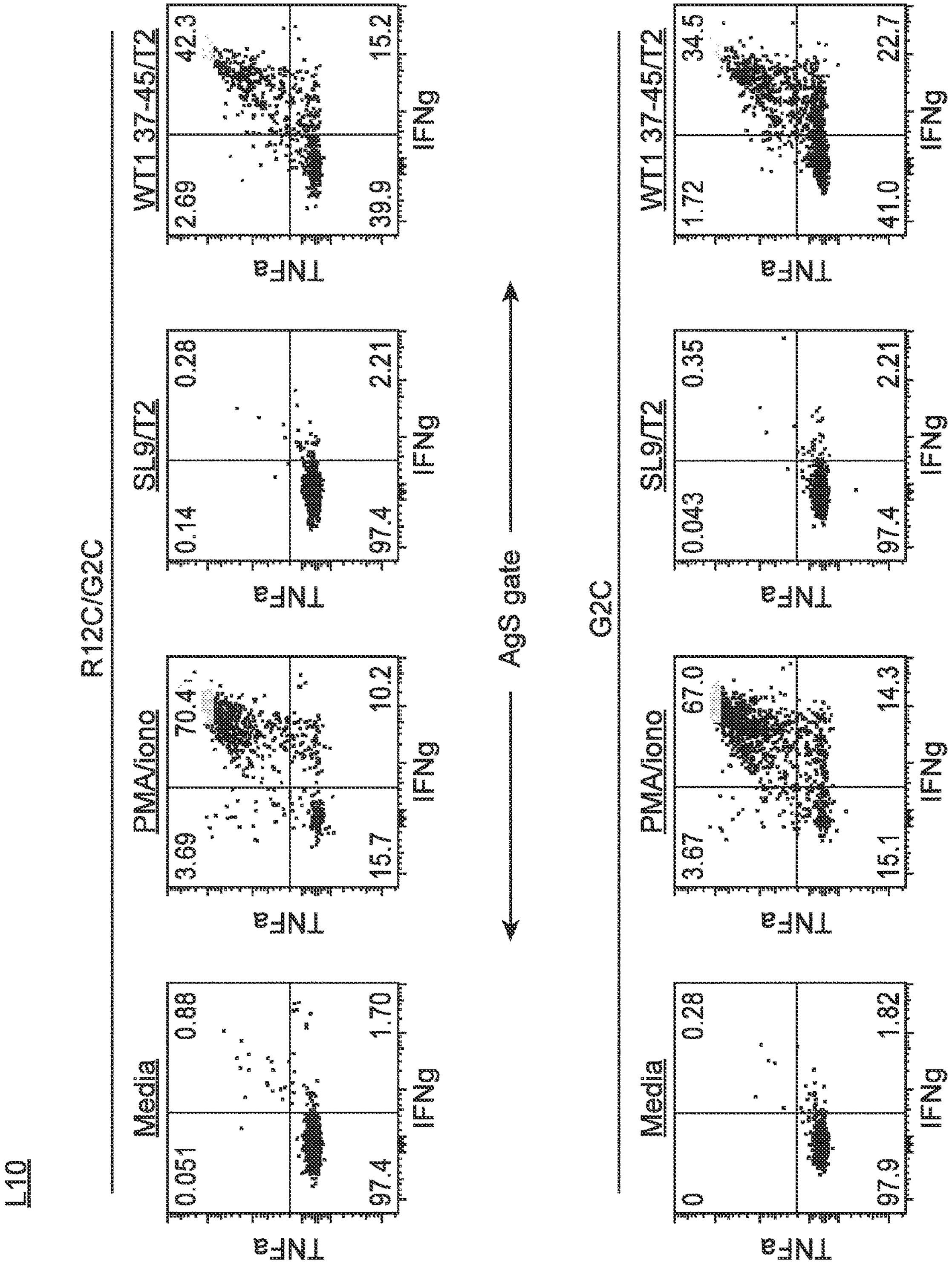
FIG. 23 depicts production of TNF-α and IFN-γ by WT1-specific CD8+ T cells expanded with WT1 37-45 containing TMMPs having either the G2C or R12C/G2C framework.

The data presented in FIG. 23 demonstrate the selective polyfunctionality of the WT1 37-45-specific CD8+ T cells expanded with WT1 37-45 containing TMMPs having either the G2C or R12C/G2C framework. The response measured (TNF-α and IFN-γ production) was observed only upon recognition of target cells presenting the WT1 37-45 peptide but not the SL9 peptide. The positive and negative control wells show that there is no baseline activity in the CD8+ T cells in the absence of stimulation (as seen in the media-only wells) and that both antigen-specific and non-antigen-specific cells are capable of showing functional responses upon strong, antigen-non-specific stimulation (PMA+ionomycin).

Using the same assay, the ability of the CD8 T cells expanded by TMMPs containing the WT1 126-134 peptide ("WT1 126") and containing the R12C and G2C disulfide bonds, to produce TNF-α and IFN-γ in response to target cells (T2 cells) presenting the WT1-126-134 peptide, WT1-126-134 R126Y peptide or an irrelevant peptide (SL9) was tested. The data are shown in FIG. 24.

Figure 24:
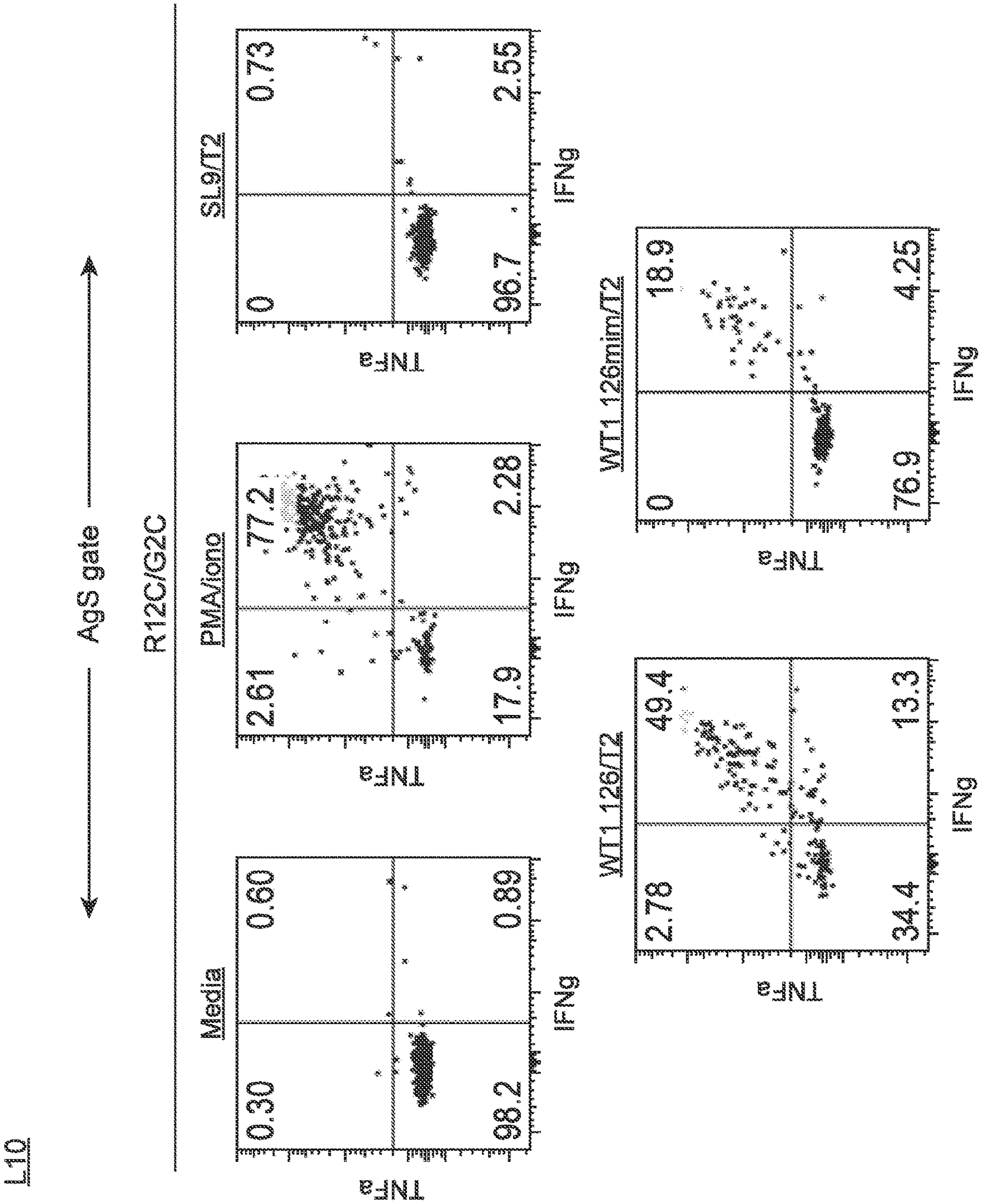
FIG. 24 depicts production of TNF-α and IFN-γ by WT1-specific CD8+ T cells expanded with WT1 126-134 containing TMMPs having the R12C/G2C framework.

The data presented in FIG. 24 demonstrate the selective polyfunctionality of the WT1 126-134-specific CD8+ T cells expanded with WT1 126-134 specific Immuno-STATs on the R12C/G2C framework. The response measured (TNF-α and IFN-γ production) was observed only upon recognition of target cells presenting the WT1 126-134 peptide or the WT1 126-134 R126Y peptide but not the SL9 peptide. The positive and negative control wells show that there is no baseline activity in the CD8+ T cells in the absence of stimulation (as seen in the media-only wells) and that both antigen-specific and non-antigen-specific cells are capable of showing functional responses upon strong, antigen-non-specific stimulation (PMA+ionomycin).

Figure 25:
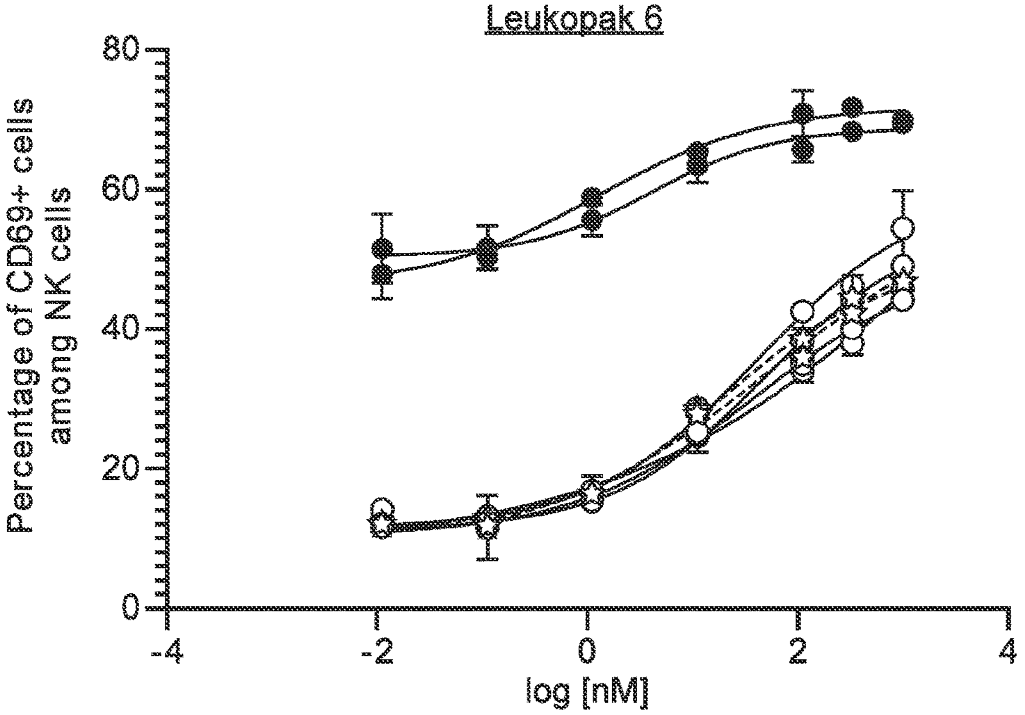
FIG. 25 depicts the effect of disulfide bonds on IL-2-driven immune cell activation.

The effect of disulfide bonds on IL-2-driven immune cell activation was tested. CD69 is an early activation marker on most lymphocytes and some other immune cells. Cells upregulate CD69 upon different types of stimulatory conditions, including IL-2 stimulation. CD69 upregulation on both NK cells, $CD4^+$ T cells, and $CD8^+$ T cells was assessed. CD69 upregulation demonstrates that the IL-2 polypeptides present in the TMMPs are active and that their function is attenuated compared to control (recombinant human IL-2). PBMCs from different human donors were incubated with various TMMPs ("ISTs") set out in the table. TMMPs comprising a CMV epitope or a MART-1 epitope were included as controls. Data from one human donor (Leukopak 6) are shown. The data are shown in FIG. 25. FIG. 25 shows the upregulation of CD69 on NK cells as a relevant and representative example of a cell that readily upregulates CD69 in response to IL-2. Similar data was observed on CD8+ T cell gates and CD4+ T cell gates.

The data presented in FIG. 25 demonstrates the IL-2 immunomodulatory polypeptide engineered on position 1 into HLA-A02-specific Immuno-STATs built on various disulfide frameworks (R12C, G2C and R12C/G2C) is functional (as observed by the induction of CD69 on the surface of a relevant immune cell) and attenuated compared to wild-type recombinant human IL-2.

To evaluate the potency of the variant IL-2 immunomodulatory polypeptides present in the TMMPs, a CTLL-2 proliferation assay was carried out. CTLL-2 cells are dependent on IL-2 for growth; thus, CTLL-2 proliferation is a measure of the amount and/or potency of IL-2 present in the culture medium (e.g., where the IL-2 is produced by T cells contacted with a TMMP). Gillis et al. (1978) *J. Immunol.* 120:2027.

Figure 26:
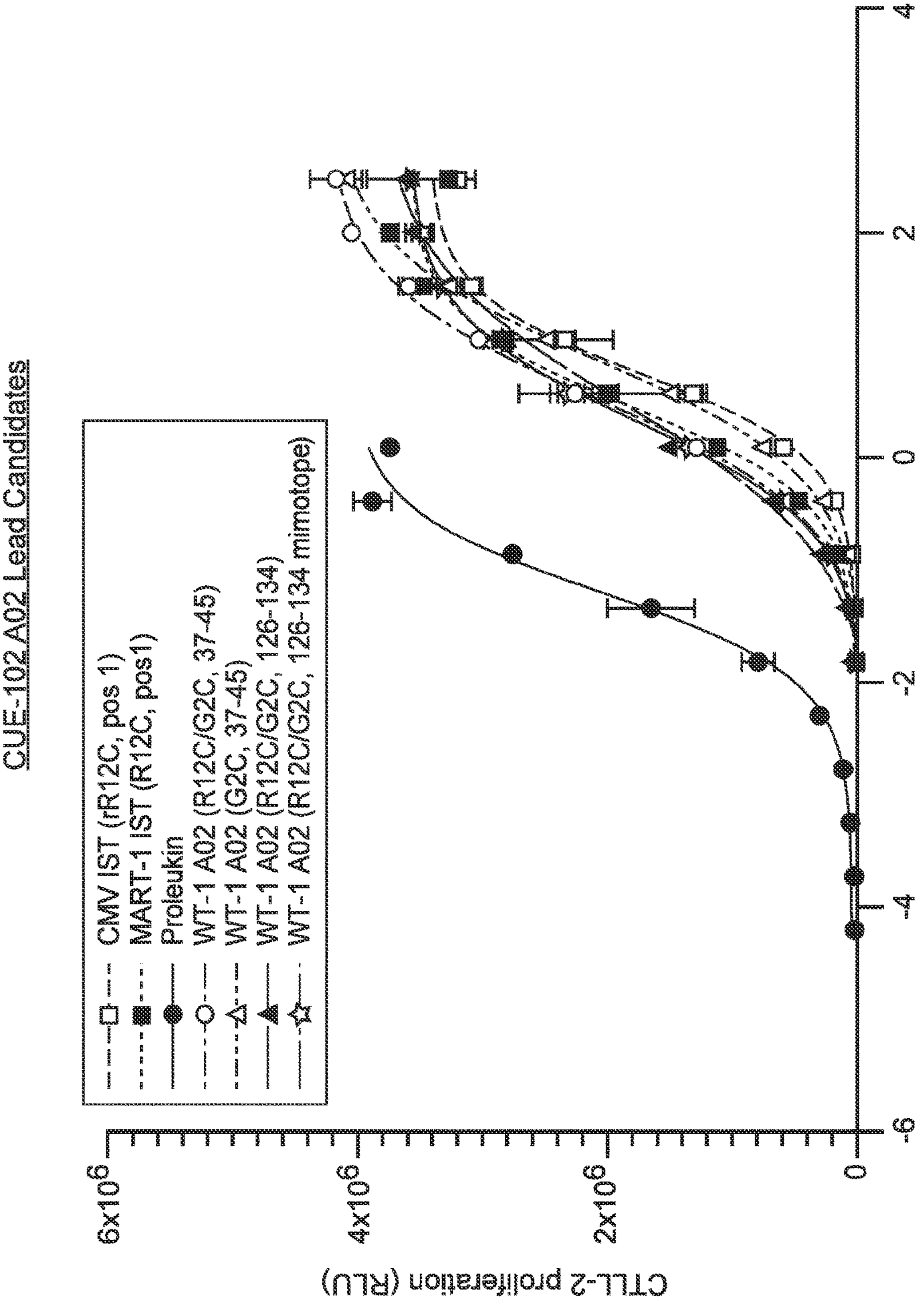
FIG. 26 depicts the effect of TMMP containing variant IL-2 as the immunomodulatory polypeptide on CGLL-2 proliferation, compared to proleukine.

The data are shown in FIG. 26. The data presented in FIG. 26 demonstrate that the IL-2 immunomodulatory polypeptide engineered on position 1 into HLA-A02-specific Immuno-STATs (TMMPs) built on various disulfide frameworks (R12C, G2C and R12C/G2C) is functional (as observed by the induction of CTLL-2 proliferation) and attenuated compared to proleukin.

Figure 27:
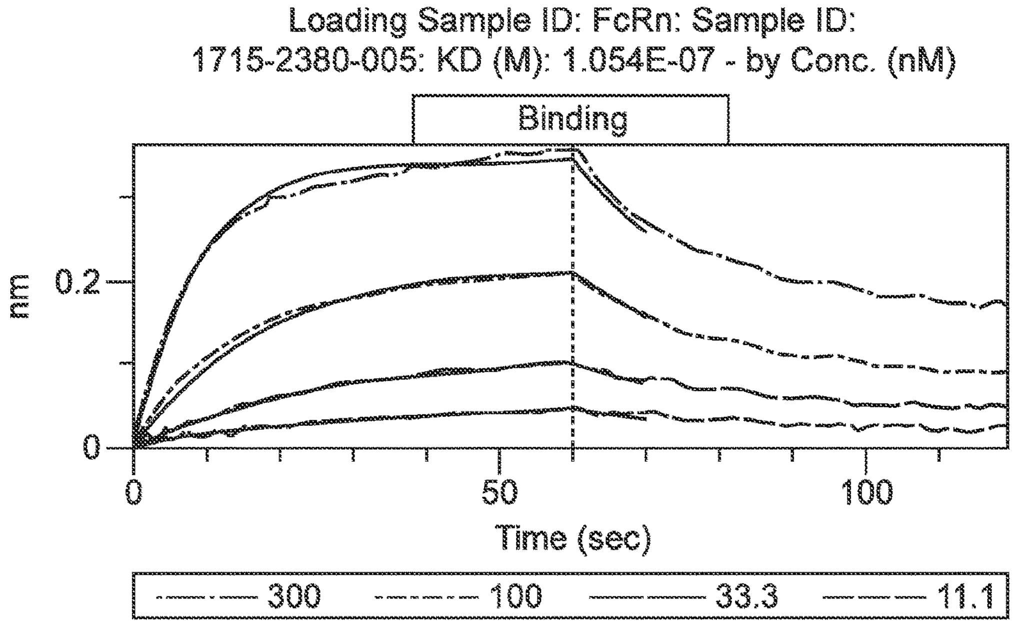
FIG. 27 depicts binding of the "1715+2380" TMPP to various Fc receptors.

The ability of the TMMPs used in these experiments to bind to FcRn was tested. The TMMPs include an Ig Fc region that can bind to FcRn. Binding to FcRn is an indication of prolonged in vivo half-life. Souders et al. (2015) MAbs 7:912. The data for the "1715+2380" TMPP are shown in FIG. 27.

The ability of the "1715+2380" TMPP to bind to other Fc receptors was tested. The "1715+2380" TMPP includes an Ig Fc region with LALA substitutions, which reduce binding of the Ig Fc to FcRI, RIIA, IIB, IIIA-F, and IIIB, thereby reducing Ig Fc-mediated effector functions. The data are shown in FIG. 27.

Materials and Methods

FIG. 21

Leukopaks from two healthy donors were obtained using apheresis machines. Leukopaks were diluted with an equal volume of room temperature phosphate-buffered saline (PBS). PBMCs were isolated from diluted leukopaks by density gradient centrifugation as follows: 30 mL of diluted leukopak was underlayed with 13 mL of Ficoll-Paque in a 50 mL conical tube and centrifugated at 400 g for 30 minutes at room temperature in a swinging bucket rotor without brake. Mononuclear cell layer (lymphocytes, monocytes and thrombocytes) was collected from the plasma-Ficoll interface, transferred to new 50 mL conical tube and washed with 3-fold excess PBS by centrifugation at 300 g for 10 minutes at room temperature. After careful removal of supernatant, cells were resuspended and washed with 50 mL of PBS by centrifugation at 200 g for 10 minutes at room temperature to remove platelets. Upon washing and platelet removal, obtained PBMCs were pooled from the 50 mL tubes, resuspended in PBS, counted, pelleted by centrifugation at 300 g for 10 minutes and resuspended at a final concentration of $50\times10^6$ cells per ml in cell freezing media.

Human healthy donor PBMCs were prepared from two leukopaks as described above. On the day of the experiment, the cells were thawed in A 37° C. water bath and washed in warm ImmunoCult™-XF Cell Expansion Media (Stemcell Technologies) by centrifugation at 350×g for 6 minutes. The supernatant was removed, and the cells were resuspended in ImmunoCult™ media. Live cell count was assessed using the Countess automated cell counter (Invitrogen, CA). The media volume was adjusted to bring the cell concentration to $5\times10^6$ cells/ml and 2 mL of cells (equivalent to $10\times10^6$ cells) were seeded per well in a 6-well plate. PBMCs were stimulated with the indicated amounts of Immuno-STATs or with media alone in a total volume of 4 ml of media. Cells were stimulated for 10 days at 37° C., 5% $CO_2$ with media replacement on days 5 and 7 by aspirating 2 mL of culture supernatant from the wells and adding back 2 mL of fresh media.

Upon culture, the cells were harvested and pelleted by centrifugation at 350×g for 5 minutes, live cell counts were determined by the Countess automated cell counter (Invitrogen, CA), and cells were processed for flow cytometry by staining with: a viability stain, appropriate WT1-peptide-specific HLA-A*0201 tetramers (MBL International) and antibodies against CD69, CD3, CD14, CD19, CD127, CD56, CD4 (Biolegend), CD8, CD25 (BD Biosciences) Stained cells were washed and analyzed by flow cytometry.

Data acquisition was performed using the Attune N×T flow cytometer instrument (Invitrogen). The acquired data was exported as fcs files and analyzed using the Flowjo software (Tree Star, OR).

Based on the frequency of antigen-specific T cells, volumes and events analyzed by flow cytometry and total volume and number of cells harvested at the end of the culture, the number of antigen specific T cells per well was calculated and plotted in the graphs shown.

FIG. 22

PBMCs from two donors were expanded for 10 days with 10 micrograms/ml of the indicated peptides and 50 U/ml of recombinant human IL-2. Expansion was done in 6-well plates with a total of 10 million cells in 4 ml of Immunocult media per well. Cells were stimulated for 10 days at 37° C., 5% $CO_2$ with media replacement on days 5 and 7 by aspirating 2 mL of culture supernatant from the wells and adding back 2 mL of fresh media with 50 U/ml of recombinant human IL-2. Upon culture, the cells were harvested and pelleted by centrifugation at 350 g for 5 minutes, live cell counts were determined by the Countess automated cell counter (Invitrogen, CA). Each stimulation condition was performed in at least 3 wells of a six well plate. PBMCs from one well were used to estimate the frequency/amount of WT1-specific CD8+ T cells in the culture by flow cytometry upon staining with: a viability stain, appropriate WT1-peptide-specific HLA-A*0201 tetramers (MBL International) and antibodies against CD69, CD3, CD14, CD19, CD127, CD56, CD4 (Biolegend), CD8, CD25 (BD Biosciences). Stained cells were washed and analyzed by flow cytometry. At least two wells were used to enrich for CD8+ T cells using a CD8+ T cell negative selection kit from Stem Cell Technologies. The purified CD8+ T cells were restimulated for 8 days with the indicated TMMPs in the presence of autologous PBMCs, previously treated with mitomycin C, in a 1:2 ratio, with a final 5-10 million cells in a volume of 4 ml of Immunocult media per well. TMMPs were used at concentrations previously established to be optimal for the combination of a donor and a particular TMMP.

Upon culture, the cells were harvested and pelleted by centrifugation at 350 g for 5 minutes, live cell counts were determined by the Countess automated cell counter (Invitrogen, CA) and processed for flow cytometry by staining with: a viability stain, appropriate WT1-peptide-specific HLA-A*0201 tetramers (MBL International) and antibodies against CD69, CD3, CD14, CD19, CD127, CD56, CD4 (Biolegend), CD8, CD25 (BD Biosciences) Stained cells were washed and analyzed by flow cytometry.

Data acquisition was performed using the Attune N×T flow cytometer instrument (Invitrogen). The acquired data was exported as fcs files and analyzed using the Flowjo software (Tree Star, OR).

Based on the frequency of antigen-specific T cells, volumes and events analyzed by flow cytometry and total volume and number of cells harvested at the end of the culture, the number of antigen specific T cells per well was calculated and plotted in the graphs shown.

FIG. 23

PBMCs from two donors were expanded for 10 days with 10 micrograms/ml of the WT1 37-45 peptide and 50 U/ml of recombinant human IL-2. Expansion was done in 6-well plates with a total of 10 million cells in 4 ml of Immunocult media per well. Cells were stimulated for 10 days at 37° C., 5% $CO_2$ with media replacement on days 5 and 7 by aspirating 2 mL of culture supernatant from the wells and adding back 2 mL of fresh media with 50 U/ml of recombinant human IL-2. Upon culture, the cells were harvested and pelleted by centrifugation at 350 g for 5 minutes, live cell counts were determined by the Countess automated cell counter (Invitrogen, CA). The stimulation was performed in at least 3 wells of a six well plate. PBMCs from one well were used to estimate the frequency/amount of WT1 37-45 peptide-specific CD8+ T cells in the culture by flow cytometry upon staining with: a viability stain, appropriate WT1 37-45-peptide-specific HLA-A*0201 tetramers (MBL International) and antibodies against CD69, CD3, CD14, CD19, CD127, CD56, CD4 (Biolegend), CD8, CD25 (BD Biosciences). Stained cells were washed and analyzed by flow cytometry. Data acquisition was performed using the Attune N×T flow cytometer instrument (Invitrogen). The acquired data was exported as fcs files and analyzed using the Flowjo software (Tree Star, OR).

At least two wells were used to enrich for CD8+ T cells using a CD8+ T cell negative selection kit from Stem Cell Technologies. The purified CD8+ T cells were restimulated for 8 days with the indicated WT1 37-45 specific Immuno-STATs on either the G2C or the R12C/G2C framework in the presence of autologous PBMCs, previously treated with mitomycin C, in a 1:2 ratio, with a final 5-10 million cells in a volume of 4 ml of Immunocult media per well. WT1 37-45 specific Immuno-STAT on either the G2C or the R12C/G2C framework was used at the concentration previously established to be optimal for that donor.

Upon culture, the cells were harvested and pelleted by centrifugation at 350 g for 5 minutes, live cell counts were determined by the Countess automated cell counter (Invitrogen, CA) and CD8+ T cells were enriched using a CD8+ T cell negative selection kit from Stem Cell Technologies.

Target cells, T2 cells (ATCC), were pulsed with 5 μg/mL of the WT1 37-45 peptide or the human immunodeficiency virus-1 (HIV-1) $Gag_{77-85}$ SL9 peptide for 2 hours at 37° C., 5% $CO_2$. Post-peptide loading, the T2 cells were washed twice and resuspend in ImmunoCult™-XF Cell Expansion Media (Stemcell Technologies).

The enriched $CD8^+$ T cells and the peptide-loaded T2 cells were mixed at a 1:1 ratio ($1\times10^6$ cells each) in a final volume of 200 μL per well in 96-well plates. Media and Phorbol 12-myristate; 13-acetate (PMA)/ionomycin was added to control wells as negative and positive controls, respectively. At 0.5 to 1 hour post-stimulation, the staining antibody against CD107a was added directly to the cells. Cell were stimulated for 5 hours, washed with PBS and stained for viability using the FVS780 for 10 minutes on ice. The cells were washed stained with the WT1 37-45 peptide-specific tetramers (labeled with APC and PE) for 15 minutes at room temperature. Subsequently, the cells were washed and stained antibodies against CD3 and CD8 for 30 minutes on ice. Stained cells were washed twice and resuspended in intracellular (IC) fixation buffer overnight at 4° C. The following day, the cells were washed and resuspended in permeabilization buffer and incubated for 5 minutes at room temperature. Permeabilized cells were washed and stained with antibodies against interferon-γ (IFN-γ), tumor-necrosis factor-α (TNF-α), resuspended in permeabilization buffer, for 30 minutes at room temperature. Stained cells were washed, resuspended in 2 mL of FACS buffer, and transferred to a 96-well deep plate. Data acquisition was performed using the Attune N×T flow cytometer instrument (Thermofisher Scientific, MA). The acquired data was exported as fcs files and analyzed using the Flowjo software (Tree Star, OR).

FIG. 24

PBMCs from two donors were expanded for 10 days with 10 micrograms/ml of the WT1 126-134 peptide and 50 U/ml of recombinant human IL-2. Expansion was done in 6-well plates with a total of 10 million cells in 4 ml of Immunocult media per well. Cells were stimulated for 10 days at 37° C., 5% $CO_2$ with media replacement on days 5 and 7 by aspirating 2 mL of culture supernatant from the wells and adding back 2 mL of fresh media with 50 U/ml of recombinant human IL-2. Upon culture, the cells were harvested and pelleted by centrifugation at 350 g for 5 minutes, live cell counts were determined by the Countess automated cell counter (Invitrogen, CA). The stimulation was performed in at least 3 wells of a six well plate. PBMCs from one well were used to estimate the frequency/amount of WT1 126-134 peptide-specific CD8+ T cells in the culture by flow cytometry upon staining with: a viability stain, appropriate WT1 126-134-peptide-specific HLA-A*0201 tetramers (MBL International) and antibodies against CD69, CD3, CD14, CD19, CD127, CD56, CD4 (Biolegend), CD8, CD25 (BD Biosciences). Stained cells were washed and analyzed by flow cytometry. Data acquisition was performed using the Attune N×T flow cytometer instrument (Invitrogen). The acquired data was exported as fcs files and analyzed using the Flowjo software (Tree Star, OR).

At least two wells were used to enrich for CD8+ T cells using a CD8+ T cell negative selection kit from Stem Cell Technologies. The purified CD8+ T cells were restimulated for 8 days with the WT1 126-134 specific Immuno-STATs on the R12C/G2C framework in the presence of autologous PBMCs, previously treated with mitomycin C, in a 1:2 ratio, with a final 5-10 million cells in a volume of 4 ml of Immunocult media per well. WT1 126-134 specific Immuno-STAT on the R12C/G2C framework was used at the concentration previously established to be optimal for that donor.

Upon culture, the cells were harvested and pelleted by centrifugation at 350 g for 5 minutes, live cell counts were determined by the Countess automated cell counter (Invitrogen, CA) and CD8+ T cells were enriched using a CD8+ T cell negative selection kit from Stem Cell Technologies.

Target cells, T2 cells (ATCC), were pulsed with 5 μg/mL of the WT1 126-134 peptide, the WT1 126-134 R126Y peptide or the human immunodeficiency virus-1 (HIV-1) $Gag_{77-85}$ SL9 peptide for 2 hours at 37° C., 5% $CO_2$. Post-peptide loading, the T2 cells were washed twice and resuspend in ImmunoCult™-XF Cell Expansion Media (Stemcell Technologies).

The enriched $CD8^+$ T cells and the peptide-loaded T2 cells were mixed at a 1:1 ratio ($1\times10^6$ cells each) in a final volume of 200 μL per well in 96-well plates. Media and Phorbol 12-myristate; 13-acetate (PMA)/ionomycin was added to control wells as negative and positive controls, respectively. At 0.5 to 1 hour post-stimulation, the staining antibody against CD107a was added directly to the cells. Cell were stimulated for 5 hours, washed with PBS and stained for viability using the FVS780 for 10 minutes on ice. The cells were washed stained with the WT1 126-134 peptide-specific tetramers (labeled with APC and PE) for 15 minutes at room temperature. Subsequently, the cells were washed and stained antibodies against CD3 and CD8 for 30 minutes on ice. Stained cells were washed twice and resuspended in intracellular (IC) fixation buffer overnight at 4° C. The following day, the cells were washed and resuspended in permeabilization buffer and incubated for 5 minutes at room temperature. Permeabilized cells were washed and stained with antibodies against interferon-γ (IFN-γ), tumor-necrosis factor-α (TNF-α), resuspended in permeabilization buffer, for 30 minutes at room temperature. Stained cells were washed, resuspended in 2 mL of FACS buffer, and transferred to a 96-well deep plate. Data acquisition was performed using the Attune N×T flow cytometer instrument (Thermofisher Scientific, MA). The acquired data was exported as fcs files and analyzed using the Flowjo software (Tree Star, OR).

FIG. 25

Human healthy donor PBMCs were prepared from leukopaks obtained from Hemacare (Northridge, CA) and kept cryopreserved at −150° C. until the day of experiment.

The cells were thawed on the day of the experiment in a water bath for 1 minute, washed with 10 mL of warm ImmunoCult™-XF Cell Expansion Media (Stemcell Technologies, Vancouver, Canada), pelleted by centrifugation (350 g, 5 minutes), and resuspended in 10 mL media. Cells were counted using the Countess automated cell counter (Invitrogen, CA), the media volume was adjusted to bring the cell concentration to $3.8\times10^6$ cell/mL and 237.5 uL of the cell suspensions were added into round bottom 96-well plates.

20× dilution series of the indicated Immuno-STATs and of rh-IL-2, were prepared in Immunocult media. To stimulate the PBMCs, 12.5 μL of the 20× dilution series was added to the wells containing the cells and mixed to obtain the final assay drug concentrations. The PBMCs were incubated at 37° C., 5% $CO_2$ for 20 to 24 hours.

Upon stimulation, the cells were pelleted by centrifugation at 350 g for 5 minutes. Supernatants were collected, frozen and stored at −20° C. until further analysis. Pelleted PBMCs were washed twice with PBS and stained for 10 minutes at 4° C. in 50 μL of Fixable live/dead FVS780 stain. The staining was quenched with 200 μL of stain buffer and the cells were pelleted by centrifugation (350×g, 5 minutes). The cells were stained for 30 minutes at 4° C. with antibodies against CD3, CD4, CD8, CD14, CD19, CD56, and CD69 in 50 μL volume. Upon staining cells were washed with stain buffer, pelleted by centrifugation (350×g, 5 minutes), resuspended in 130 μL of stain buffer and analyzed by Flow Cytometry using the Attune® Flow Cytometer. The acquired data was exported as fcs files and analyzed using the Flowjo software (Tree Star, OR).

CD69 upregulation was assessed on different cell subsets that are sensitive to upregulate CD69 upon IL-2 stimulation. Based on expression levels of the surface markers used in the staining, gates were made to identify NK cells, CD8+ T cells, CD4+ T cells.

FIG. 26

One day before the assay, CTLL-2 cells were washed with media and cultured at $1\times10^5$ cells/ml in a 75-T flask for 24 hours at 37 C, 5% $CO_2$ for IL-2 starvation. After the 24 hour starvation culture, cells were seeded at 5000 cells per well in 100 microliters/well of a 96 well cell culture cluster flat bottom plate with lid (Costar corning, Cat #3599). Cell viability and count were checked before stimulation using Vi cell viability analyzer (Beckman-Coulter).

Dilution series (10 points; 3-fold dilution steps) of the indicated Immuno-STATs (TMMPs) or proleukin (Prometheus Therapeutics) were prepared in complete RPMI supplemented with 10% HI FBS as 2× stocks of the final assay concentrations. 100 μL of this 2× dilution series were added to cells previously seeded in 96 well plates and mixed to obtain the final assay drug concentrations. Each concentration was tested in triplicates. Cells were incubated for three days at 37 C, 5% $CO_2$.

After three days in culture 100 μL of cells from each well was transferred into a flat bottom white tissue culture treated 96 well plate. 100 μL of CellTiter-Glo® Reagent was prepared using CellTiter-Glo Luminescent Cell viability assay kit (Promega cat #G7571) following instructions provided by the manufacturer and were added to the cells. Cells and CellTiter-Glo® Reagent were mixed by placing the plates on an orbital shaker for 2 minutes to induce cell lysis. Then plates were incubated at room temperature for 10 minutes to stabilize luminescent signal. The luminescence was measured and recorded on Biotek synergy neo2 multimode reader, software Gen5 3.04.

FIG. 27

All experiments were performed on the Octet HTX system (ForteBio). Anti-penta-his (HIS1K) kinetic grade biosensors (ForteBio, #18-5122) were hydrated in assay buffer and preconditioned in pH 1.7 glycine. The assay buffer was used for all assays except for FcRn. The buffer used for FcRn was PBS, 0.1% bovine serum albumin (BSA), 0.02% Tween-20, pH 7.2. The assay buffer used for the FcRn reagents was PBS, 0.1% BSA, 0.02% Tween-20, pH 6.

Each His-tagged receptor was immobilized onto HIS biosensors at a concentration of 5 μg/mL (except for FcRI: 10 ug/mL) for 120 seconds. The antigen-loaded HIS biosensors were then dipped into a 7-point, 1:3 dilution series of each individual antibody starting from 300 nM. A well containing only assay buffer was used to test for non-specific binding between the buffer and loaded biosensors. Association was observed for 60 seconds, followed by 60 seconds of dissociation. A short baseline (60 seconds) was established using dissociation buffer after HIS1K loading.

Example 3: Biochemical Characterization of TMMPs Comprising WT1 Epitopes, HLA-A*24 Heavy Chains, Either One or Two Disulfide Bonds Between the 2 Polypeptide Chains of the Heterodimer, and Variant IL-2 Immunomodulatory Polypeptides at Position 1, 3, or 5

The constructs used in this study are summarized in Table 6.

TABLE 6

| Constructs | Epitope | S—S bond(s) | IL-2 position |
|---|---|---|---|
| 3593 + 3192 | WT1 (235-243 (M236Y)) | G2C | 1 |
| 3425 + 3188 | WT1 (235-243 (M236Y)) | R12C + G2C | 3 |
| 3426 + 3192 | WT1 (235-243 (M236Y)) | G2C | 3 |
| 3593 + 3530 | WT1 (239-247 (Q240Y)) | G2C | 1 |
| 3592 + 3529 | WT1 (239-247 (Q240Y)) | R12C + G2C | 1 |
| 3426 + 3530 | WT1 (239-247 (Q240Y)) | G2C | 3 |
| 3425 + 3529 | WT1 (239-247 (Q240Y)) | R12C + G2C | 3 |
| 3426 + 3530 | WT1 (239-247 (Q240Y)) | R12C | 3 |
| 3197 + 3710 | WT1 (239-247 (Q240Y)) | G2C | 5 |
| 3196 + 3709 | WT1 (239-247 (Q240Y)) | R12C + G2C | 5 |
| 2764 + 3708 | WT1 (239-247 (Q240Y)) | R12C | 5 |

Amino acid sequences of the polypeptide chains of the constructs are provided in FIG. 10A-10R.

"G2C" indicates that the TMMP includes a disulfide bond between: i) a Cys in the peptide linker between the peptide epitope and the β2M polypeptide; and ii) a Cys at position 84 of the MHC class I heavy chain, where the MHC class I heavy chain has a Y84C substitution.

"R12C" indicates that the TMMP includes a disulfide bond between: i) a Cys at position 12 in the β2M polypeptide, where the β2M polypeptide has an R12C substitution; and ii) a Cys at position 236 of the MHC class I heavy chain, where the MHC class I heavy chain has an A236C substitution.

"G2C+R12C" indicates that the TMMP includes both the "G2C" disulfide bond and the "R12C" disulfide bond.

WT1 (235-243 (M236Y)) is CYTWNQMNL (SEQ ID NO:262), and is also referred to as "235 mimotope."

WT1 (239-247 (Q240Y)) is NYMNLGATL (SEQ ID NO:263).

IL-2 "position 1," position 3," and "position 5" are depicted schematically in FIG. 19.

Materials and Methods

Effect of TMMP on Number of Antigen-Specific (AgS) $CD8^+$ T Cells

Leukopaks from healthy donors were obtained using apheresis machines. Leukopaks were diluted with an equal volume of room temperature phosphate-buffered saline (PBS). PBMCs were isolated from diluted leukopaks by density gradient centrifugation as follows: 30 mL of diluted leukopak was underlayed with 13 mL of Ficoll-Paque in a 50 mL conical tube and centrifugated at 400 g for 30 minutes at room temperature in a swinging bucket rotor without brake. Mononuclear cell layer (lymphocytes, monocytes and thrombocytes) was collected from the plasma-Ficoll interface, transferred to new 50 mL conical tube and washed with 3-fold excess PBS by centrifugation at 300 g for 10 minutes at room temperature. After careful removal of supernatant, cells were resuspended and washed with 50 mL of PBS by centrifugation at 200 g for 10 minutes at room temperature to remove platelets. Upon washing and platelet removal, obtained PBMCs were pooled from the 50 mL tubes, resuspended in PBS, counted, pelleted by centrifugation at 300 g for 10 minutes and resuspended at a final concentration of $50\times10^6$ cells per ml in cell freezing media.

On the day of the experiment, the cells were thawed in A 37° C. water bath and washed in warm ImmunoCult™-XF Cell Expansion Media (Stemcell Technologies) by centrifugation at 350×g for 6 minutes. The supernatant was removed, and the cells were resuspended in ImmunoCult™ media. Live cell count was assessed using the Countess automated cell counter (Invitrogen, CA). The media volume was adjusted to bring the cell concentration to $5\times10^6$ cells/ml and 2 mL of cells (equivalent to $10\times10^6$ cells) were seeded per well in a 6-well plate. PBMCs were stimulated with the indicated amounts of Immuno-STATs or with media alone in a total volume of 4 ml of media. Cells were stimulated for 10 days at 37° C., 5% $CO_2$ with media replacement on days 5 and 7 by aspirating 2 mL of culture supernatant from the wells and adding back 2 mL of fresh media.

Upon culture, the cells were harvested and pelleted by centrifugation at 350×g for 5 minutes, live cell counts were determined by the Countess automated cell counter (Invitrogen, CA), and cells were processed for flow cytometry by staining with: a viability stain, appropriate WT1-peptide-specific HLA-A*2402 tetramers (MBL International) and antibodies against CD69, CD3, CD14, CD19, CD127, CD56, CD4 (Biolegend), CD8, CD25 (BD Biosciences) Stained cells were washed and analyzed by flow cytometry.

Data acquisition was performed using the Attune N×T flow cytometer instrument (Invitrogen). The acquired data was exported as fcs files and analyzed using the Flowjo software (Tree Star, OR).

Based on the frequency of antigen-specific T cells, volumes and events analyzed by flow cytometry and total volume and number of cells harvested at the end of the culture, the number of antigen specific T cells per well was calculated and plotted in the graphs shown.

Peripheral blood mononuclear cells (PBMCs) obtained from human donors (designated "Leukopak 7", "Leukopak 18", and "Leukopak 6") were incubated in vitro with the TMMPs at various concentrations (0 nM, 10 nM, 100 nM, 300 nM, or 1000 nM) for 10 days. After the 10-day incubation period, the number of cells specific for the epitope was determined.

Effect of Disulfide Bonds on IL-2-Driven Immune Cell Activation

The effect of disulfide bonds on IL-2-driven immune cell activation was tested. CD69 is an early activation marker on most lymphocytes and some other immune cells. Cells upregulate CD69 upon different types of stimulatory conditions, including IL-2 stimulation. CD69 upregulation on both NK cells, $CD4^+$ T cells, and $CD8^+$ T cells was assessed. CD69 upregulation demonstrates that the IL-2 polypeptides present in the TMMPs are active and that their function is attenuated compared to control (recombinant human IL-2). PBMCs from different human donors were incubated with various TMMPs ("ISTs") set out in the table in FIG. 13 and FIG. 14. TMMPs comprising a CMV epitope or a MART-1 epitope were included as controls.

Effect of Variant IL-2 on CTLL-2 Proliferation

To evaluate the potency of the variant IL-2 immunomodulatory polypeptides present in the TMMPs, a CTLL-2 proliferation assay was carried out. CTLL-2 cells are dependent on IL-2 for growth; thus, CTLL-2 proliferation is a measure of the amount and/or potency of IL-2 present in the culture medium (e.g., where the IL-2 is produced by T cells contacted with a TMMP). Gillis et al. (1978) J. Immunol. 120:2027.

One day before the assay, CTLL-2 cells were washed with media and cultured at $1\times10^5$ cells/ml in a 75-T flask for 24 hours at 37 C, 5% $CO_2$ for IL-2 starvation. After the 24 hour starvation culture, cells were seeded at 5000 cells per well in 100 microliters/well of a 96 well cell culture cluster flat bottom plate with lid (Costar corning, Cat #3599). Cell viability and count were checked before stimulation using Vi cell viability analyzer (Beckman-Coulter).

Dilution series (10 points; 3-fold dilution steps) of the indicated Immuno-STATs (TMMPs) or proleukin (Prometheus Therapeutics) were prepared in complete RPMI supplemented with 10% HI FBS as 2× stocks of the final assay concentrations. 100 μL of this 2× dilution series were added to cells previously seeded in 96 well plates and mixed to obtain the final assay drug concentrations. Each concentration was tested in triplicates. Cells were incubated for three days at 37 C, 5% $CO_2$.

After three days in culture 100 μL of cells from each well was transferred into a flat bottom white tissue culture treated 96 well plate. 100 μL of CellTiter-Glo® Reagent was prepared using CellTiter-Glo Luminescent Cell viability assay kit (Promega cat #G7571) following instructions provided by the manufacturer and were added to the cells. Cells and CellTiter-Glo® Reagent were mixed by placing the plates on an orbital shaker for 2 minutes to induce cell lysis. Then plates were incubated at room temperature for 10 minutes to stabilize luminescent signal. The luminescence was measured and recorded on Biotek synergy neo2 multimode reader, software Gen5 3.04.

Binding to Fc Receptors

All experiments were performed on the Octet HTX system (ForteBio). Anti-penta-his (HIS1K) kinetic grade biosensors (ForteBio, #18-5122) were hydrated in assay buffer and preconditioned in pH 1.7 glycine. The assay buffer was used for all assays except for FcRn. The buffer used for FcRn was PBS, 0.1% bovine serum albumin (BSA), 0.02% Tween-20, pH 7.2. The assay buffer used for the FcRn reagents was PBS, 0.1% BSA, 0.02% Tween-20, pH 6.

Each His-tagged receptor was immobilized onto HIS1K biosensors at a concentration of 5 μg/mL (except for FcRI: 10 ug/mL) for 120 seconds. The antigen-loaded HIS1K biosensors were then dipped into a 7-point, 1:3 dilution series of each individual antibody starting from 300 nM. A well containing only assay buffer was used to test for non-specific binding between the buffer and loaded biosensors. Association was observed for 60 seconds, followed by 60 seconds of dissociation. A short baseline (60 seconds) was established using dissociation buffer after HIS1K loading.

Results

The results are shown in FIG. 28-34.

Figure 29:
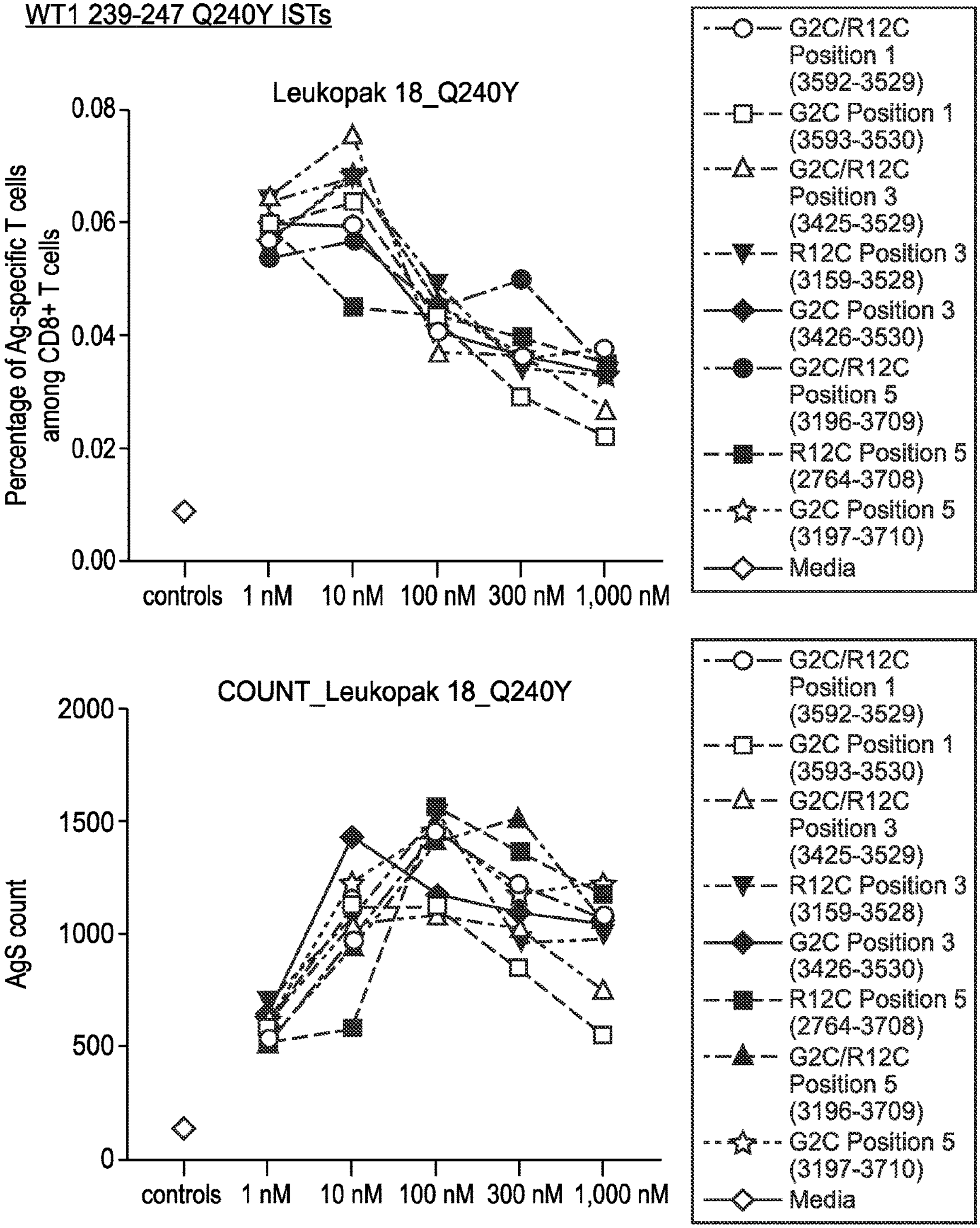
FIG. 29 depicts the effect of TMMPs, containing the WT1 peptide epitope 239-247 (Q240Y) and HLA-A*24 heavy chains, on antigen-specific CD8+ T cell expansion.
Figure 29:
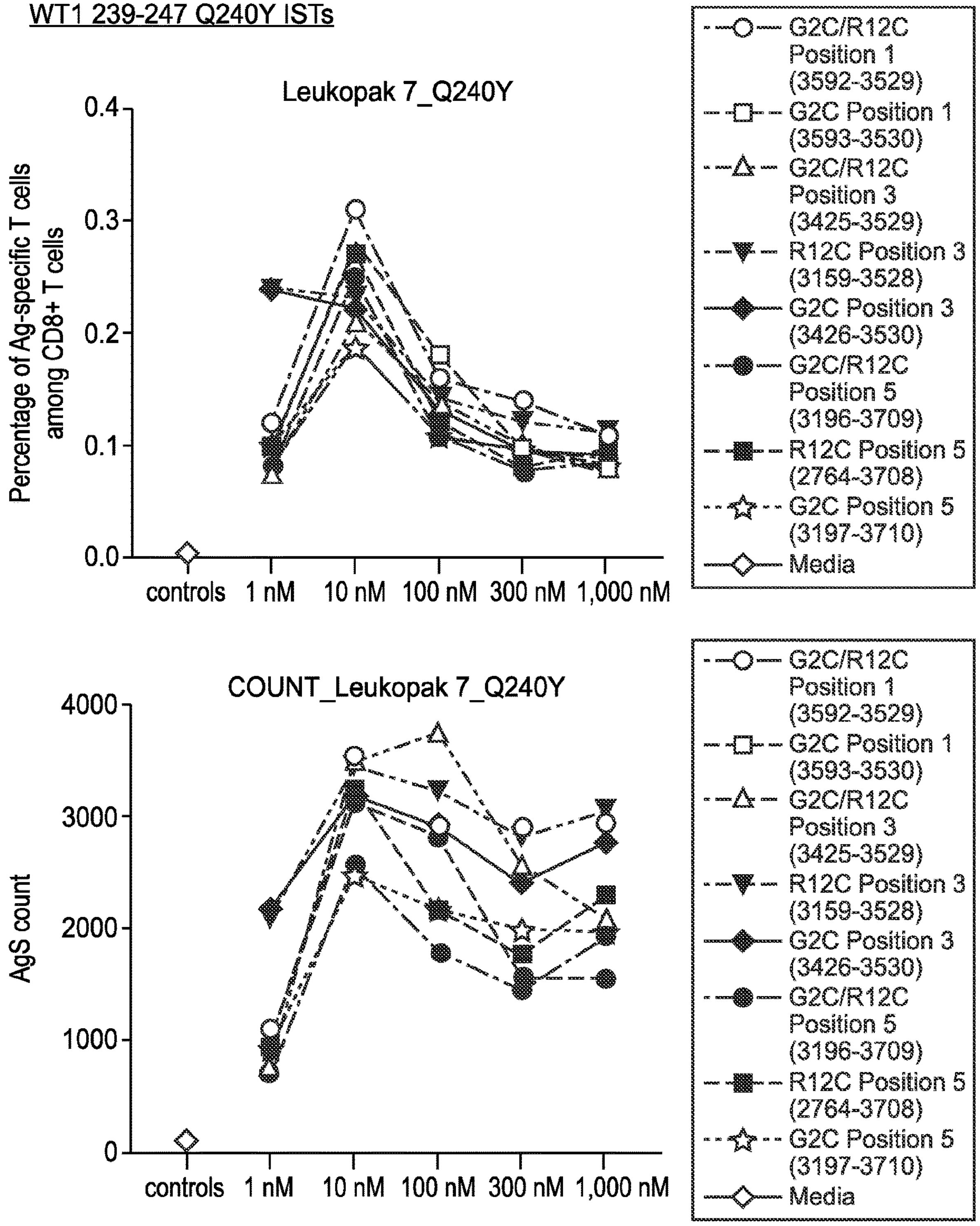

The data presented in FIG. 28 and FIG. 29 demonstrate that TMMPs comprising WT1 235-243 R236Y, with immunomodulatory polypeptides (IL-2) at various positions and with either a single disulfide bond or with two disulfide bonds, can expand WT1-specific CD8+ T cells from total PBMCs over a course of a 10-day stimulation culture. This expansion occurred from PBMCs that have low or no detectable WT1-specific T cell precursors, indicating the ability of these TMMPs to induce antigen-specific responses in donors from an unprimed or naïve repertoire.

Figure 30:
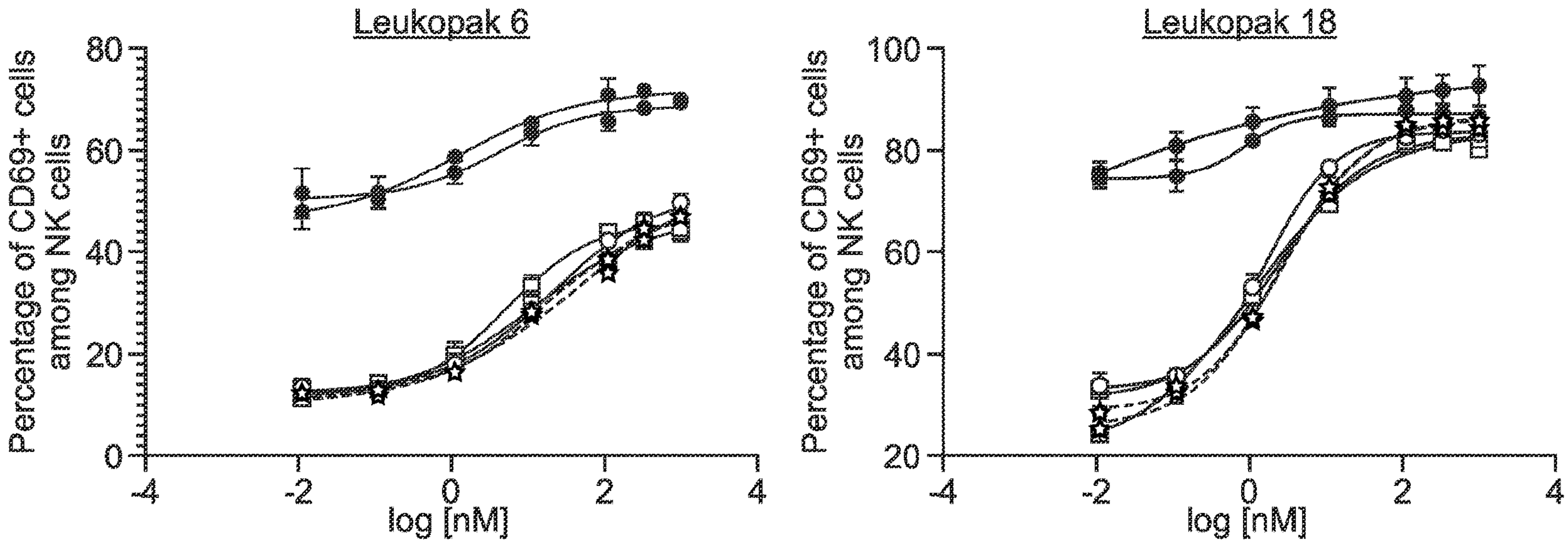
FIG. 30 depicts induction of CD69 expression by TMMPs with IL-2 polypeptide engineered at position 1 or 3, peptide epitope WT1 235-243 (M236Y), HLA-A24 heavy chains, and G2C or R12C/G2C disulfide frameworks.

The data presented in FIG. 30 demonstrate that the IL-2 polypeptide engineered at position 1 or 3 of WT1 235-243 M236Y-specific HLA-A24 TMMPs built on various disulfide frameworks (G2C and R12C/G2C) is functional (as observed by the induction of CD69 on the surface of a relevant immune cell), comparable to the activity of CMV and MART-1 specific HLA-A02 TMMPs and attenuated compared to wild-type recombinant human IL-2.

The data presented in FIG. 31 demonstrate the IL-2 polypeptide engineered at position 1, 3 or 5 of WT1 239-247 Q240Y-specific HLA-A24 TMMPs built on various disulfide frameworks (R12C, G2C and R12C/G2C) is functional (as observed by the induction of CD69 on the surface of a relevant immune cell) comparable to the activity of CMV and MART-1 specific HLA-A02 Immuno-STATs and attenuated compared to wild-type recombinant human IL-2.

Figure 32:
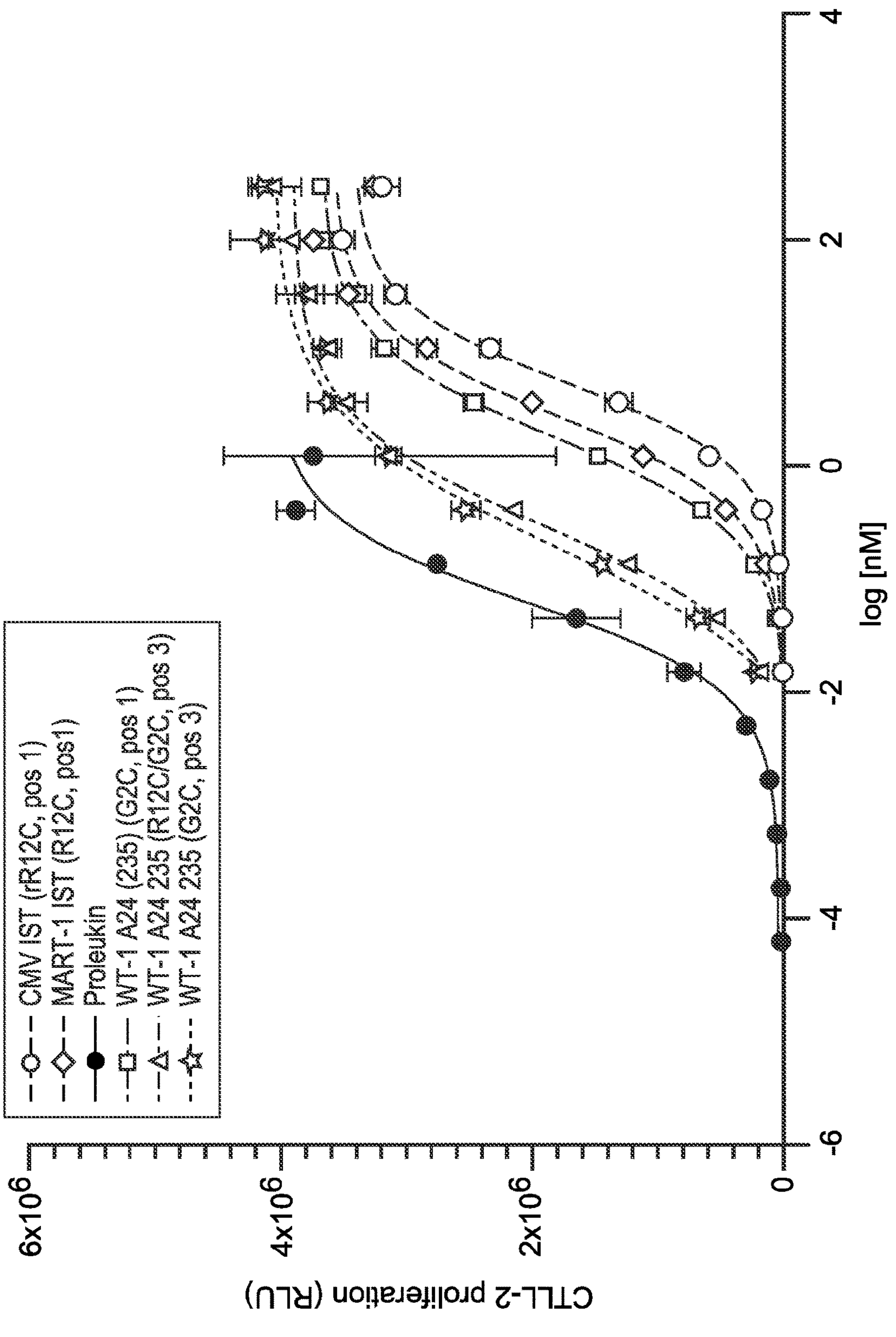
FIG. 32 depicts the effect of TMMPs (with IL-2 polypeptide engineered at position 1 or 3, peptide epitope WT1 235-243 (M236Y), HLA-A24 heavy chains, and G2C or R12C/G2C disulfide frameworks) on CTLL-2 proliferation, compared to proleukine.

The data presented in FIG. 32 demonstrate that the IL-2 polypeptide engineered at position 1 or 3 of WT1 235-243 M236Y-specific HLA-A24 TMMPs built on various disulfide frameworks (G2C and R12C/G2C) is functional (as observed by the induction of CTLL-2 proliferation) and attenuated compared to proleukin and attenuated compared to wild-type recombinant human IL-2.

Figure 33:
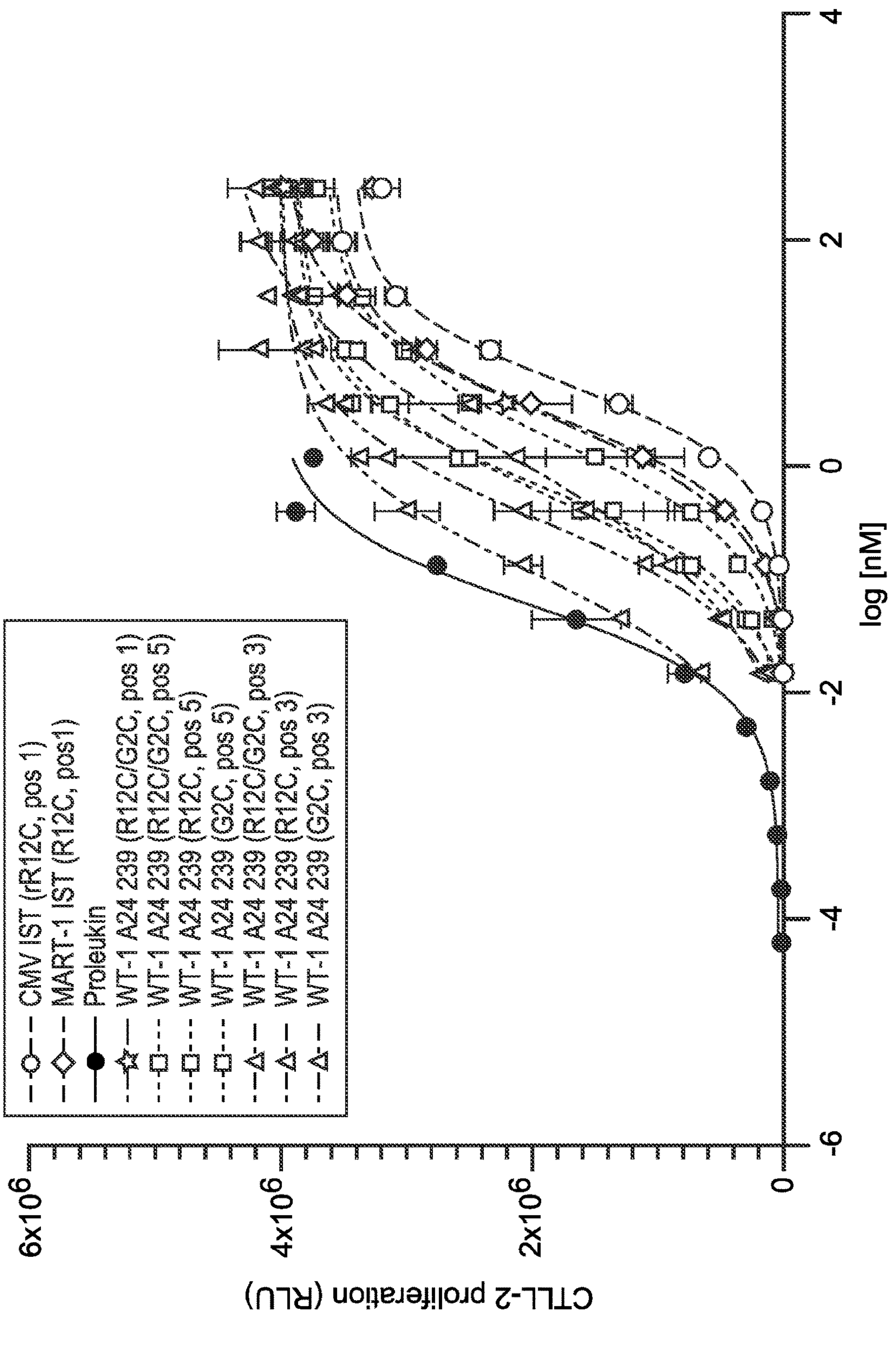
FIG. 33 depicts the effect of TMMPs (with IL-2 polypeptide engineered at position 1 or 3, peptide epitope WT1 239-247 (Q240Y), HLA-A24 heavy chains, and G2C or R12C/G2C disulfide frameworks) on CTLL-2 proliferation, compared to proleukine.

The data presented in FIG. 33 demonstrate that the IL-2 polypeptide engineered at position 1, 3 or 5 of WT1 239-247 Q240Y-specific HLA-A24 TMMPs built on various disulfide frameworks (R12C, G2C and R12C/G2C) is functional (as observed by the induction of CTLL-2 proliferation), and attenuated compared to wild-type recombinant human IL-2.

Figure 34:
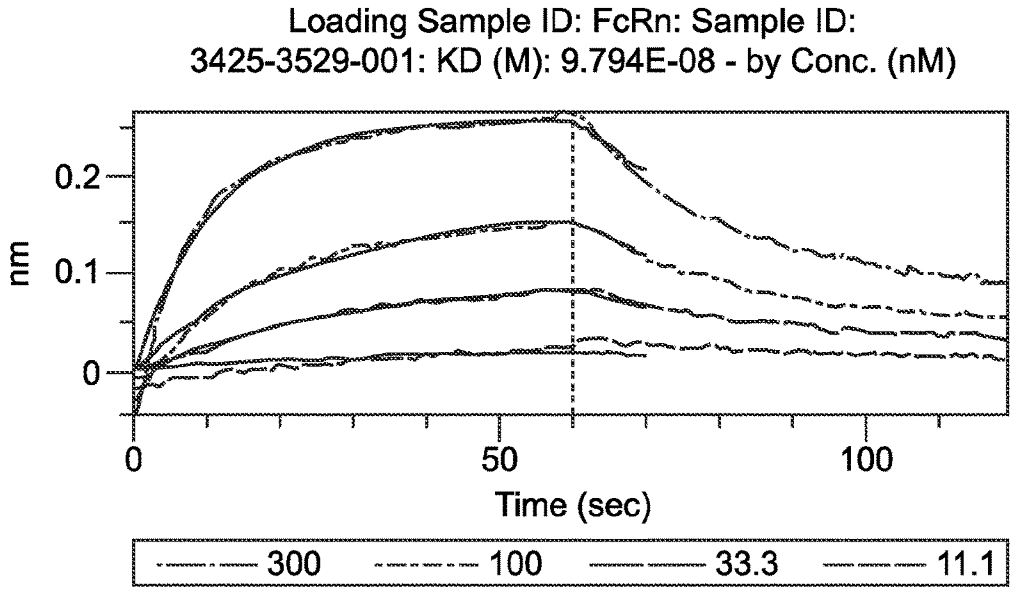
FIG. 34 depicts binding of the "3425+3529" TMPP to various Fc receptors.

The data presented in FIG. 34 demonstrate the ability of the "3425+3529" TMPP to bind to FcRn. The "3425+3529" TMPP includes an Ig Fc region with LALA substitutions. As shown in FIG. 34, the "3425+3529" TMPP exhibits reduced binding of the Ig Fc to FcRI, RIIA, IIB, IIIA-F, and IIIB.

Example 4

A TMMP comprising 1715 (without C-terminal Lys, i.e., 1715A having the sequence set forth in SEQ ID NO:486)+2380 polypeptides was tested. The amino acid sequences of the polypeptide chains are provided in FIG. 14J (1715 without C-terminal lysine, i.e., 1715Δ) and FIG. 14B (2380). The 1715Δ+2380 TMMP includes: i) Class I HLA-A heavy chain polypeptides of the A02:01 allele; and ii) two copies of IL2 (H16A; F42A) immunomodulatory ("MOD") polypeptides. The 2380 polypeptide comprises the WT1 peptide WT1(37-45). The 1715Δ-2380 TMMP is a homodimer of a heterodimer comprising the 1715Δ polypeptide and the 2380 polypeptide. Thus, the TMMP included: i) 2 copies of the 1715Δ+2380 heterodimer, linked by 2 disulfide bonds between the IgFc polypeptide present in the 1715Δ polypeptides.

TMMP 1715Δ+2380 is a double disulfide-linked heterodimer: a) a first disulfide linkage is between: i) the Cys present in the linker between the WT1 peptide and the β2M chain in the 2380 polypeptide; and ii) the Cys introduced by the Y84C substitution in the Class I heavy chain present in the 1715Δ polypeptide; and b) a second disulfide linkages is between: i) the Cys introduced by the R12C substitution in the β2M polypeptide present in the 2380 polypeptide; and ii) the Cys introduced by the A236C substitution in the Class I heavy chain present in the 1715Δ polypeptide.

The effect of TMMP 1715Δ+2380 on PBMCs was tested. The data are shown in FIG. 39-42. TMMP 1715Δ+2380 is also referred to below as "CUE-102/A02 $WT1_{37-45}$ Immuno-STAT," "CUE-102/A02 $WT1_{37-45}$ IST," or simply "CUE-102/A02."

Figure 39:
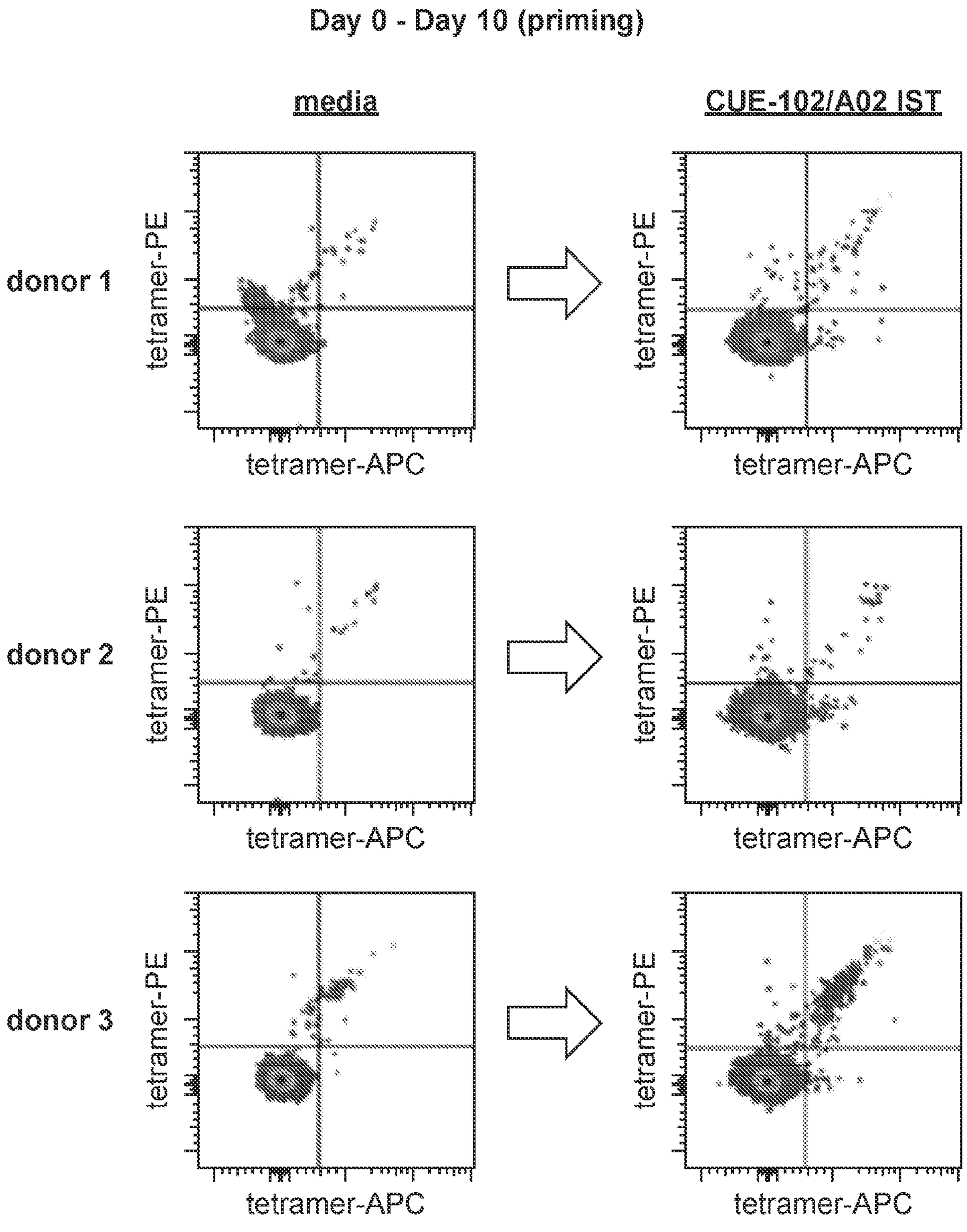
FIG. 39 depicts expansion of $WT1_{37-45}$-specific CD8+ T cells from unprimed PBMCs, in which the expansion was induced by a TMMP of the present disclosure ("CUE-102/A02 $WT1_{37-45}$ IST").
Figure 39:
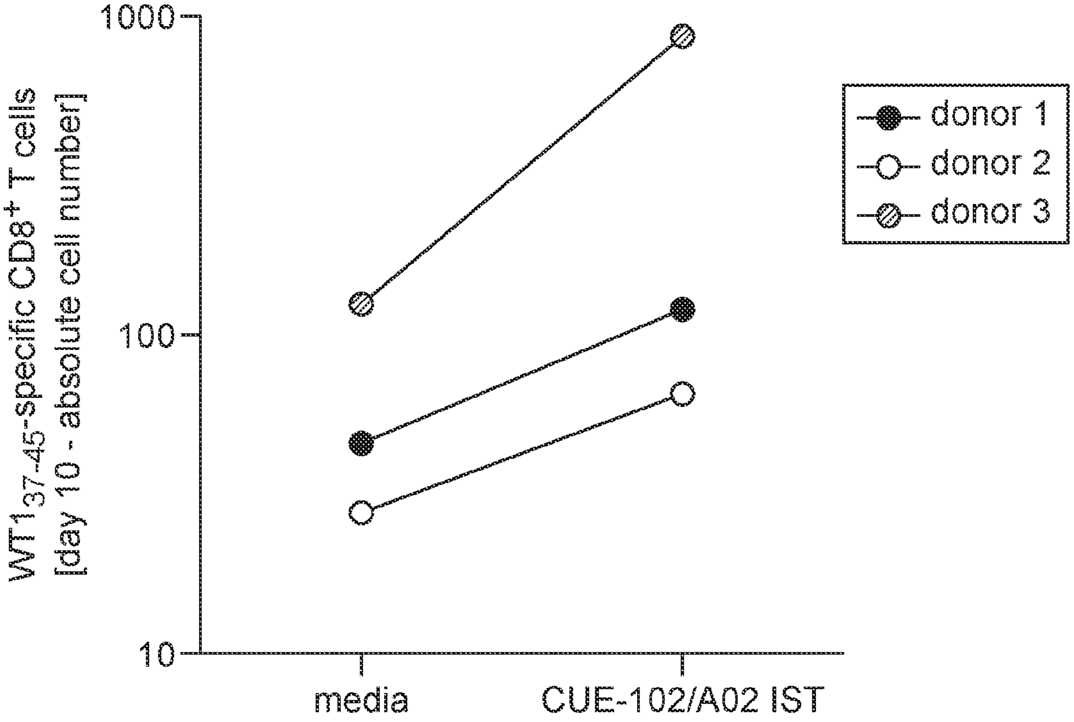

As shown in FIG. 39, CUE-102/A02 $WT1_{37-45}$ IST induces expansion of $WT1_{37-45}$-specific $CD8^+$ T cells from unprimed PBMCs. Healthy donor PBMCs were stimulated for 10 days with the CUE-102/A02 $WT1_{37-45}$ Immuno-STAT (IST) in Immunocult™ media. Cells cultured in the absence of CUE-102/A02 were used as a negative control. Peptide-specific $CD8^+$ T cells were detected by flow cytometry upon staining with $WT1_{37-45}$-specific tetramers.

Figure 40A:
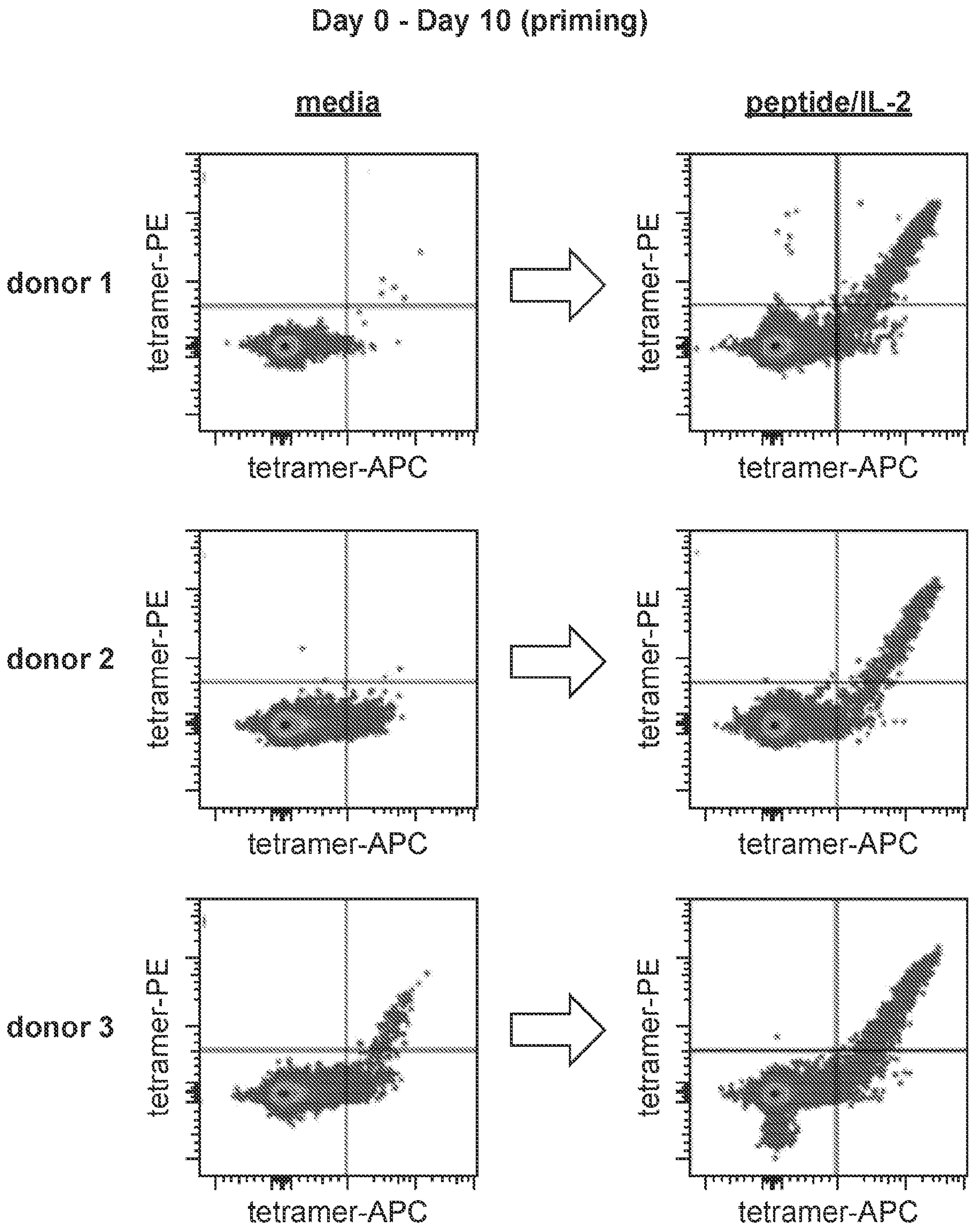
FIG. 40A-40B depict expansion of $WT1_{37-45}$-specific CD8+ T cells from $WT1_{37-45}$ peptide-primed PBMCs, in which the expansion was induced by a TMMP of the present disclosure ("CUE-102/A02 $WT1_{37-45}$ IST").
Figure 40A:
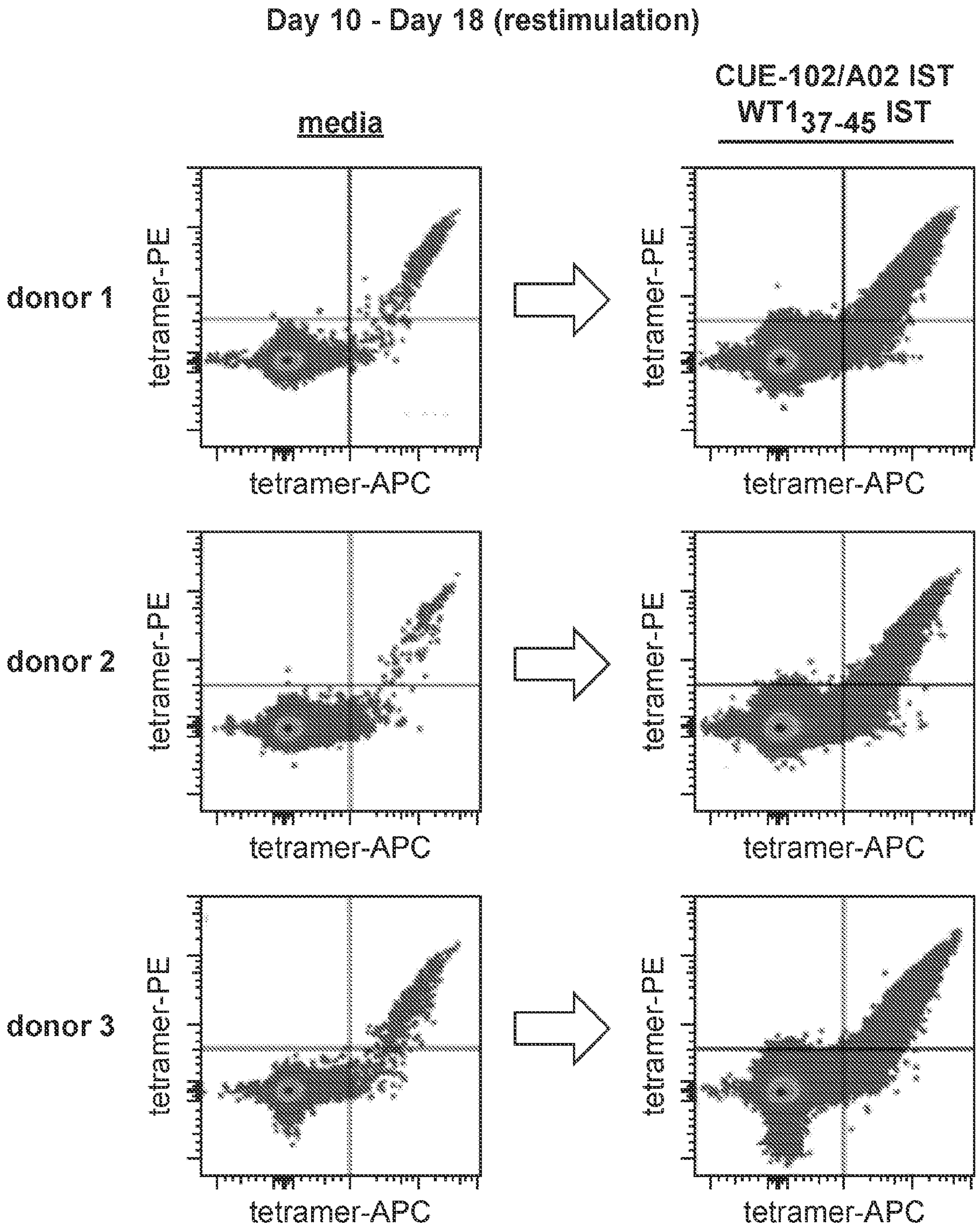
Figure 40B:
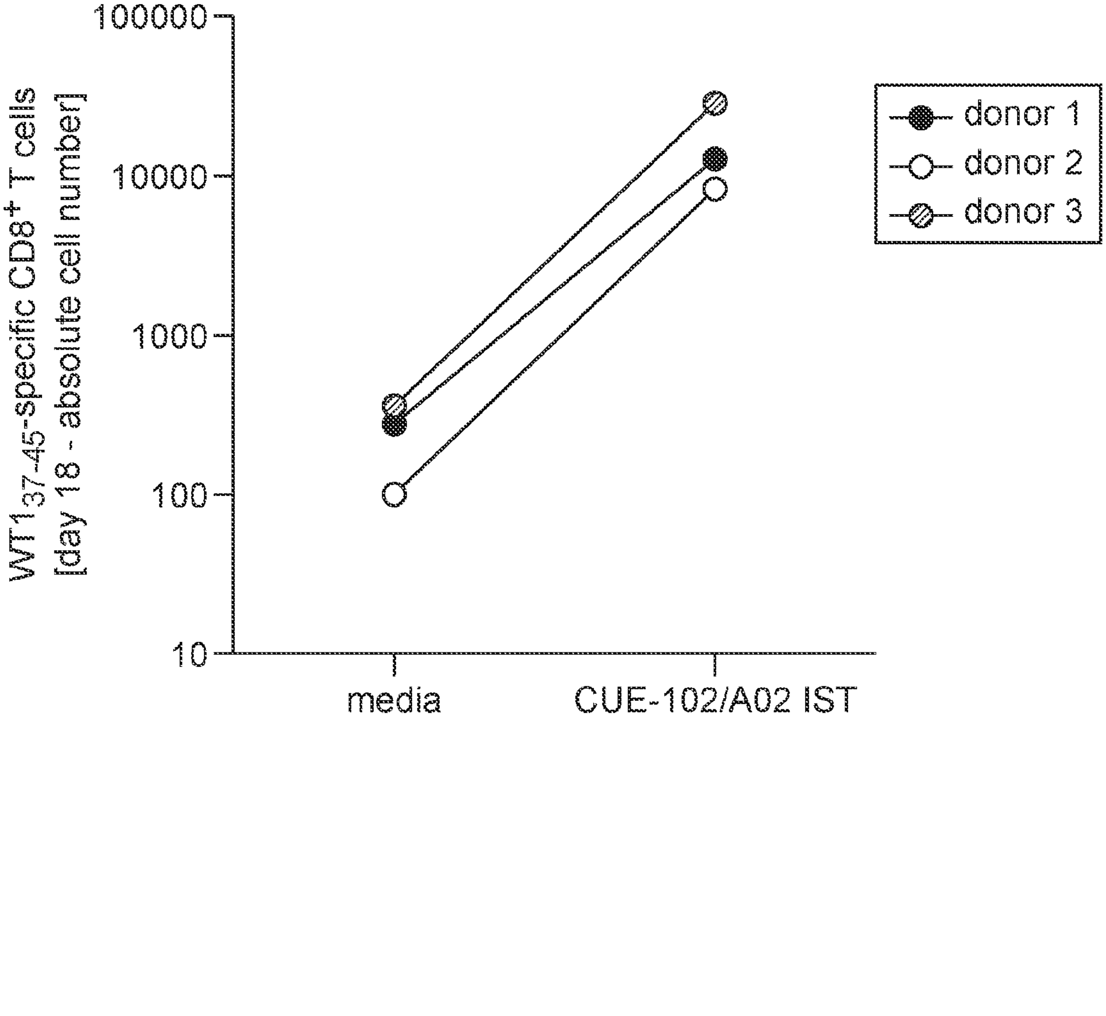

As shown in FIG. 40A-40B, CUE-102/A02 $WT1_{37-45}$ IST induces expansion of $WT1_{37-45}$-specific $CD8^+$ T cells from primed PBMCs. Healthy donor PBMCs were primed for 10 days with $WT1_{37-45}$ peptide in the presence of recombinant human IL-2. $CD8^+$ T cells were then enriched by magnetic separation and restimulated with the CUE-102/A02 $WT1_{37-45}$ IST in Immunocult™ media in the presence of mitomycin C-treated autologous PBMCs for 8 days. Cells restimulated in the absence of CUE-102/A02 were used as a negative control. Peptide-specific $CD8^+$ T cells were detected by flow cytometry upon staining with $WT1_{37-45}$-specific tetramers.

Figure 41A:
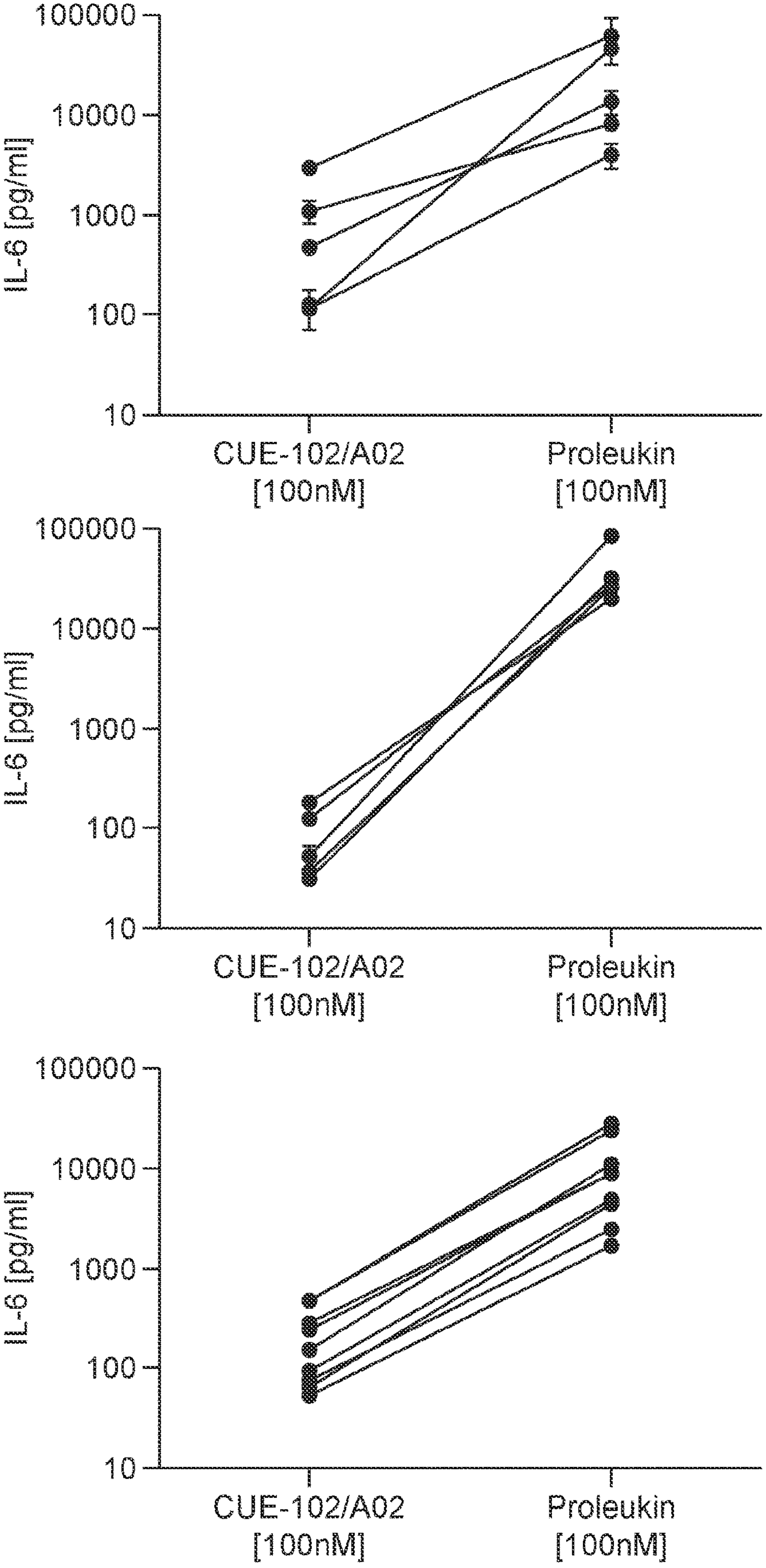
FIG. 41A-41B depict production of TNF-α, IL-6, and IFN-γ, and upregulation of CD69, induced by a TMMP of the present disclosure ("CUE-102/A02 $WT1_{37-45}$ IST") or by wild-type IL-2.
Figure 41B:
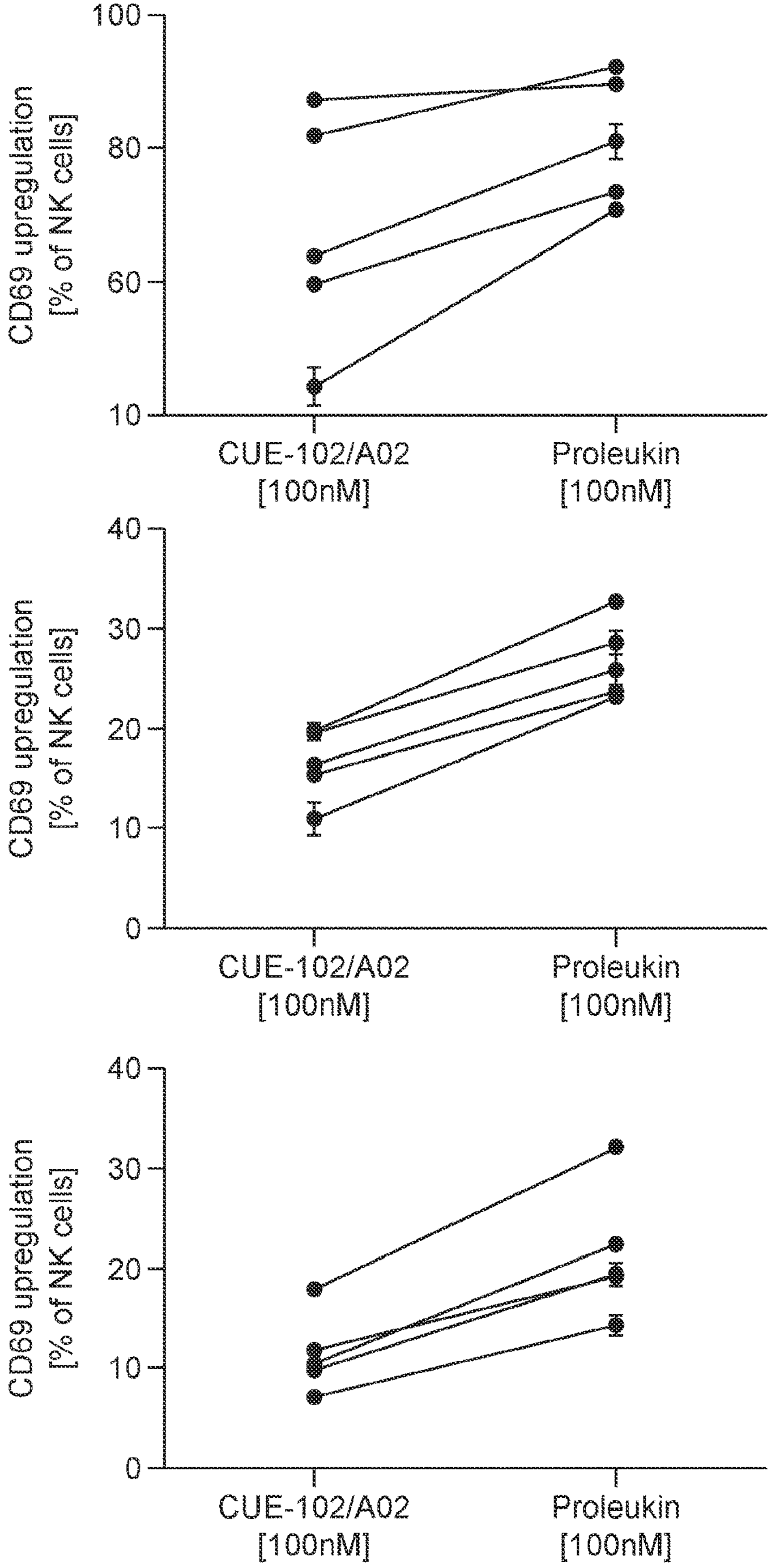

As shown in FIG. 41A-41B, the reduced affinity IL-2-containing CUE-102/A02 $WT1_{37-45}$ IST mitigates the risk associated with systemic IL-2 activation, compared to wild-type IL-2. Five healthy donor PBMCs were stimulated with Proleukin® (IL-2), or CUE-102/A02 $WT1_{37-45}$ IST, in Immunocult™ media for 18 hours. Upon stimulation, supernatants were harvested, and levels of TNF-α, IL-6, and IFN-γ were assessed by immunoassay (FIG. 41A). NK cell, $CD4^+$ T cell, and $CD8^+$ T cell CD69 upregulation was assessed by flow cytometry on cells from the same culture wells (FIG. 41B). Cells cultured in the absence of Proleukin® (IL-2), or CUE-102/A02 $WT1_{37-45}$ IST were used as negative control.

Figure 42A:
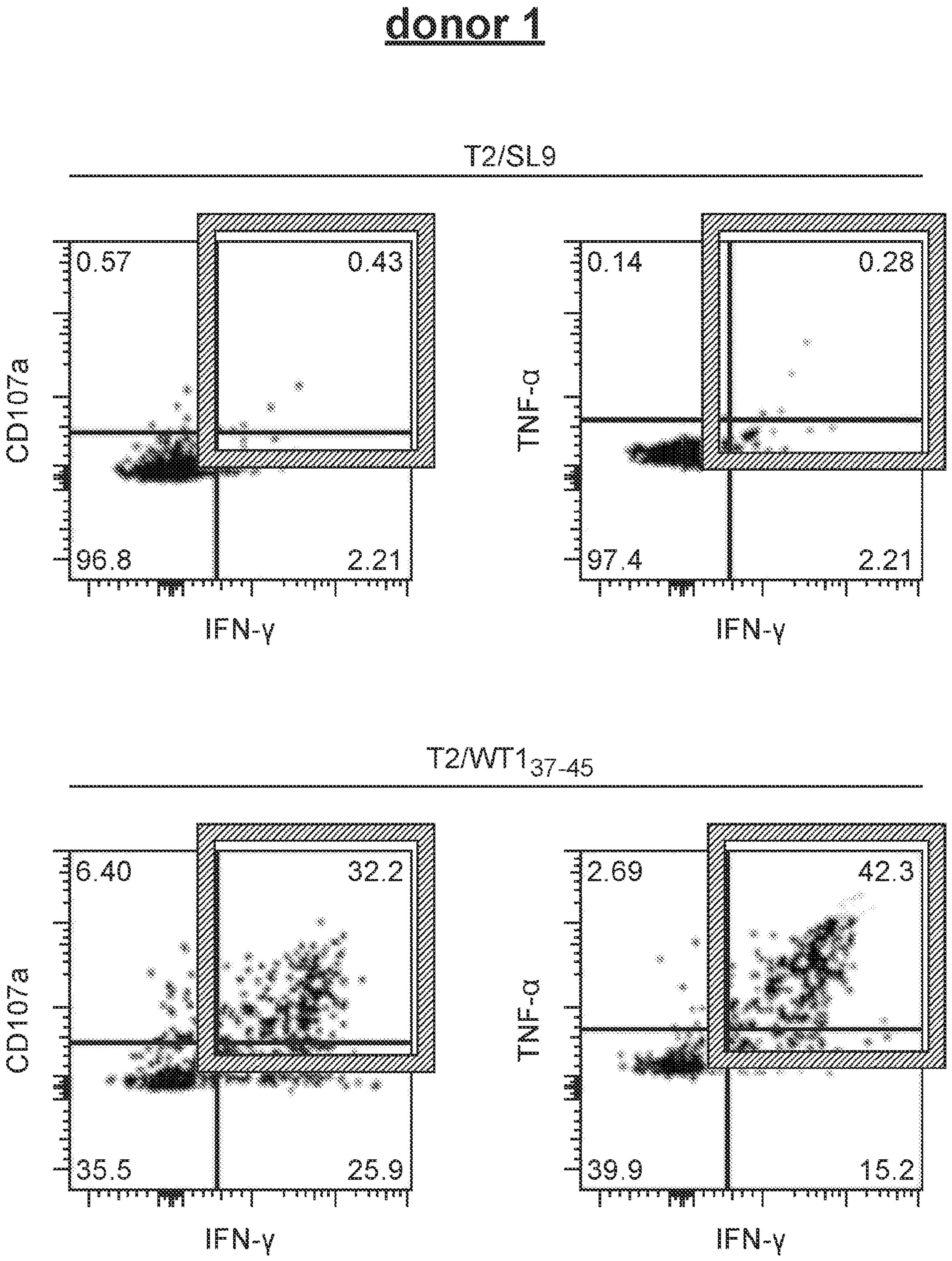
FIG. 42A-42B depict CTL activity, against peptide-presenting target cells, of $WT1_{37-45}$ peptide-specific CD8+ T cells expanded from peptide-primed PBMCs in the presence of a TMMP of the present disclosure ("CUE-102/A02 $WT1_{37-45}$ IST").
Figure 42A:
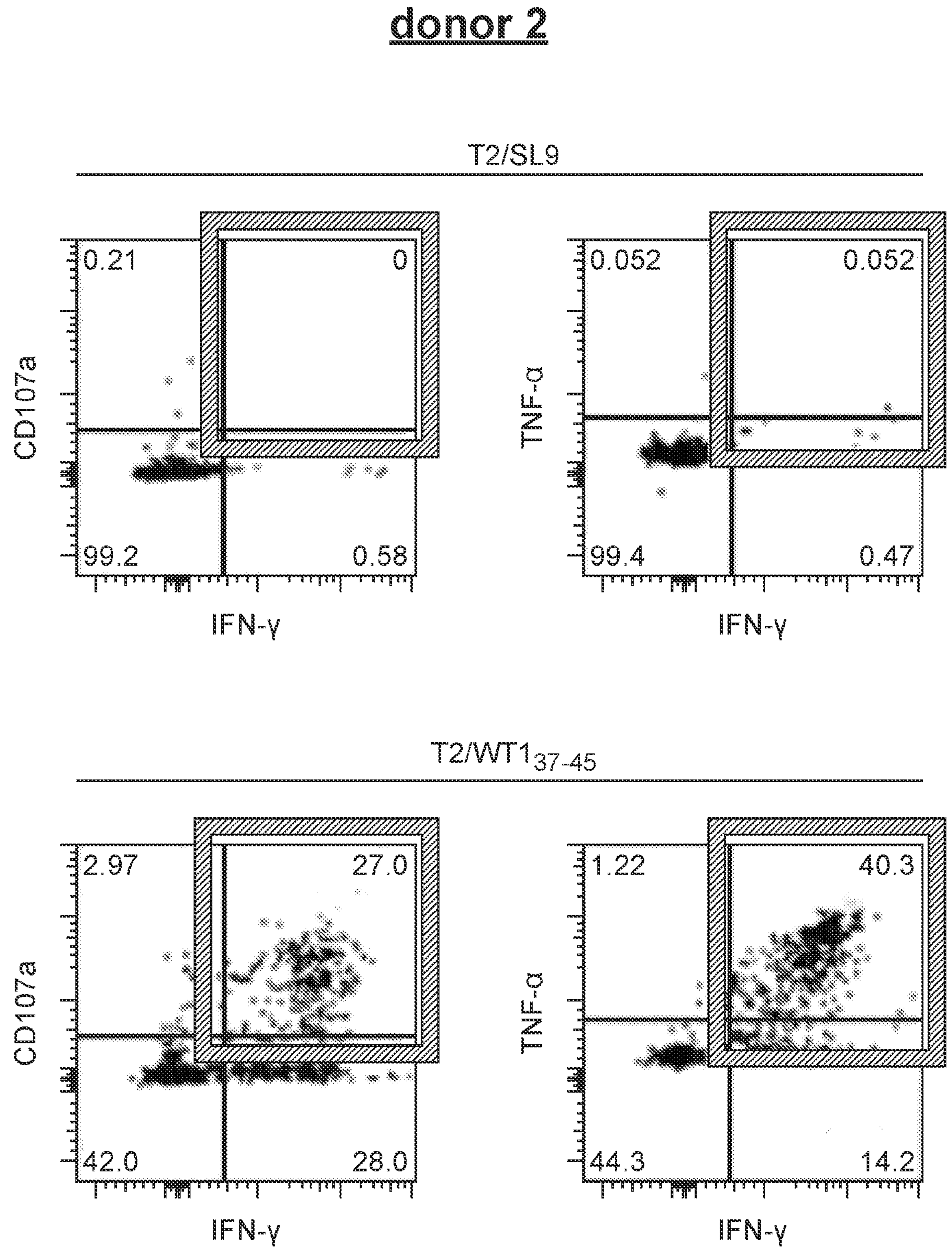
Figure 42B:
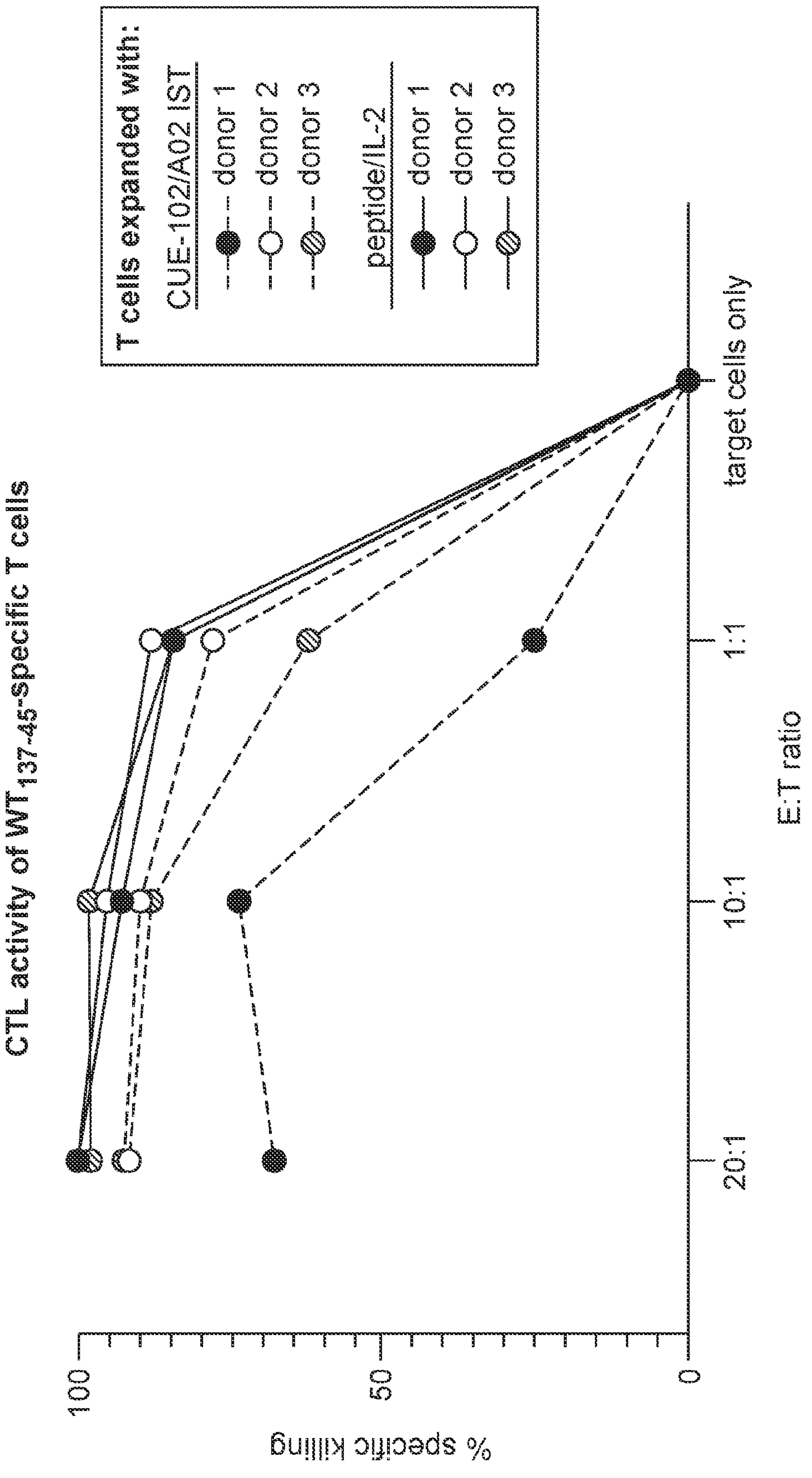

As shown in FIG. 42A-42B, CUE-102/A02 $WT1_{37-45}$ IST-expanded T cells are polyfunctional CTLs that recognize and kill $WT1_{37-45}$ peptide-presenting target cells. Healthy donor PBMCs were primed for 10 days with $WT1_{37-45}$ peptide in the presence of recombinant human IL-2 and expanded for 8 days with $WT1_{37-45}$ peptide or with CUE-102/A02 $WT1_{37-45}$ IST in Immunocult™ media in the presence of mitomycin C-treated autologous PBMCs. $WT1_{37-45}$-specific $CD8^+$ T cells were enriched by magnetic bead-based separation using $WT1_{3745}$-specific PE-labeled tetramers. FIG. 42A: CUE-102/A02 $WT1_{37-45}$ IST-expanded $WT1_{37-45}$-specific T cells expressed effector molecules IFN-γ and TNF-α; and up-regulated the degranulation marker CD107a upon 4 hours of interaction with target T2 cells pulsed with the cognate $WT1_{37-45}$ peptide, but not with a control, irrelevant peptide (SL9). FIG. 42B: Expanded $WT1_{37-45}$-specific T cell killed cognate $WT1_{37-45}$ peptide-pulsed T2 cells, but not control peptide-pulsed T2 cells, in overnight cultures performed at different T cell effector:target cell ratios. Specific killing was assessed by flow cytometry comparing the ratio of viable T2 cell pulsed with cognate peptide vs. control peptide upon overnight culture.

Example 5

The ability of TMMPs to stimulate antigen-specific proliferation of $CD8^+$ T cells was tested. The TMMPs included, as the epitope: i) WT1 235-243(C235S; M236Y); or ii) WT1 239-247(Q240Y). All TMMPs included A24 allele MHC class I heavy chains.

The ability of TMMPs to stimulate antigen-specific proliferation of CD8+ T cells was tested. The TMMPs included, as the epitope: i) WT1 235-243(C235S; M236Y); or ii) WT1 239-247(Q240Y). All TMMPs included A24 allele MHC class I heavy chains. The TMMPs included: a) a "heavy chain" polypeptide comprising: i) a Class I HLA-A heavy chain polypeptide of the A24:02 allele comprising Y84C and A236C substitutions; ii) two copies of IL2 (H16A; F42A) immunomodulatory ("MOD") polypeptides; and iii) IgG1 Fc polypeptide comprising L234A and L235A substitutions; and b) a "light chain" polypeptide construct 3973 (FIG. 37B) or 3529 (FIG. 20M) comprising: i) either WT1 235-243 (C235S; M236Y) or WT1 239-247(Q240Y)); and ii) a beta-2 microglobulin polypeptide comprising an R12C substitution. The heavy and light chain polypeptides were joined by 2 disulfide bonds. The "heavy chain" comprised the amino acid sequence of chain 3425 as depicted in FIG. 20B. The TMMPs comprised homodimers of the "heavy" and "light" chain heterodimers, joined by disulfide bonds formed between the respective IgG1 Fc regions.

Figure 43:
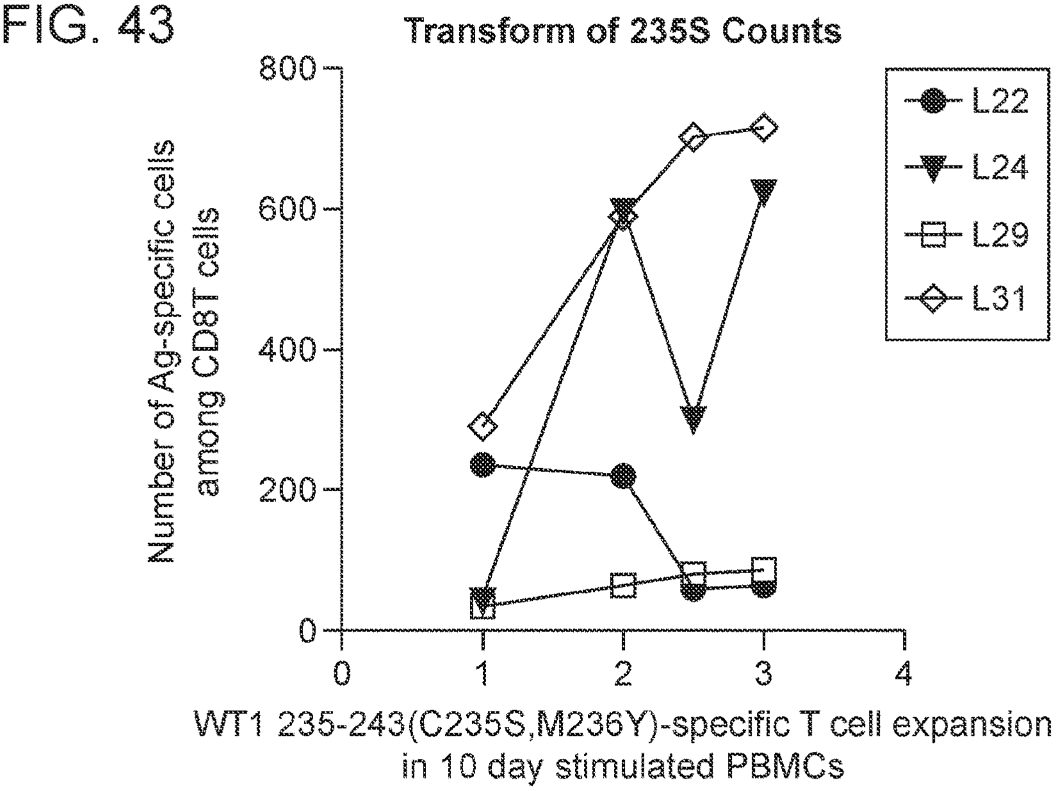
FIG. 43 depicts the effect of TMMPs, containing the WT1 peptide epitope WT1 235-243(C235S; M236Y) and HLA-A*24 heavy chains, on antigen-specific CD8+ T cell expansion.

Peripheral blood mononuclear cells (PBMCs) obtained from human donors were incubated in vitro with the TMMPs at various concentrations (0 nM, 10 nM, 100 nM, 300 nM, or 1000 nM) for 10 days. After the 10-day incubation period, the number of cells specific for the epitope was determined. Data from PBMCs from healthy human donors (Leukopak 22 ("L22"); Leukopak 24 ("L24"); Leukopak 29 ("L29"); and Leukopak 31 ("L31")) are shown in FIG. 43. Data from PBMCs from healthy human donors (Leukopak 24 ("L24"); Leukopak 30 ("L30"); and Leukopak 31 ("L31")) are shown in FIG. 44.

Figure 44:
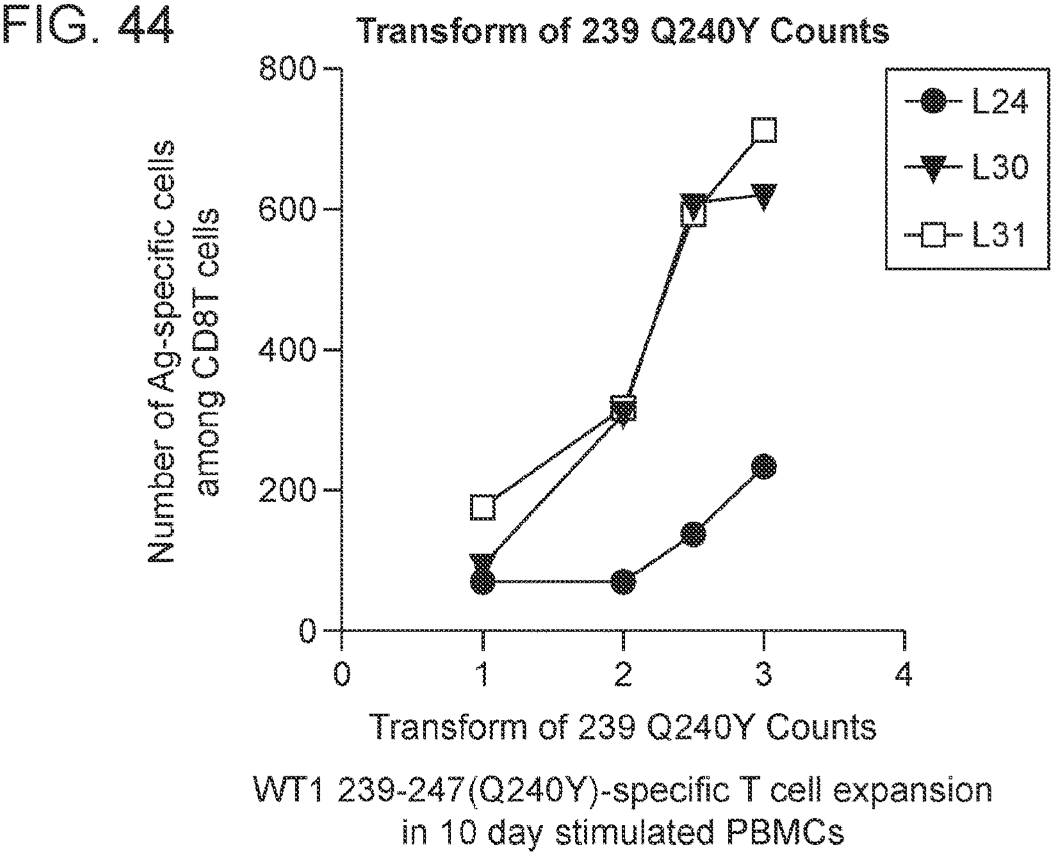
FIG. 44 depicts the effect of TMMPs, containing the WT1 peptide epitope WT1 239-247(Q240Y) and HLA-A*24 heavy chains, on antigen-specific CD8+ T cell expansion.

The data presented in FIG. 43 and FIG. 44 demonstrate that WT1-specific TMMPs can induce expansion of WT1-specific T cells from total PBMCs over a course of a 10-day stimulation culture.

Materials and Methods

Leukopaks from healthy donors were obtained using apheresis machines. Leukopaks were diluted with an equal volume of room temperature phosphate-buffered saline (PBS). PBMCs were isolated from diluted leukopaks by density gradient centrifugation as follows: 30 mL of diluted leukopak was underlayed with 13 mL of Ficoll-Paque in a 50 mL conical tube and centrifugated at 400 g for 30 minutes at room temperature in a swinging bucket rotor without brake. Mononuclear cell layer (lymphocytes, monocytes and thrombocytes) was collected from the plasma-Ficoll interface, transferred to new 50 mL conical tube and washed with 3-fold excess PBS by centrifugation at 300 g for 10 minutes at room temperature. After careful removal of supernatant, cells were resuspended and washed with 50 mL of PBS by centrifugation at 200 g for 10 minutes at room temperature to remove platelets. Upon washing and platelet removal, obtained PBMCs were pooled from the 50 mL tubes, resuspended in PBS, counted, pelleted by centrifugation at 300 g for 10 minutes and resuspended at a final concentration of $50\times10^6$ cells per ml in cell freezing media.

Human healthy donor PBMCs were prepared from two leukopaks as described above. On the day of the experiment, the cells were thawed in A 37° C. water bath and washed in warm ImmunoCult™-XF Cell Expansion Media (Stemcell Technologies) by centrifugation at 350×g for 6 minutes. The supernatant was removed, and the cells were resuspended in ImmunoCult™ media. Live cell count was assessed using the Vi-Cell XR automated cell counter (Beckman-Coulter). The media volume was adjusted to bring the cell concentration to $5\times10^6$ cells/ml and 2 mL of cells (equivalent to $10\times10^6$ cells) were seeded per well in a 6-well plate. PBMCs were stimulated with the indicated amounts of Immuno-STATs, peptide (10 ug/mL) and IL-2 (501U/mL), or with media alone in a total volume of 4 ml of media. Cells were stimulated for 10 days at 37° C., 5% $CO_2$ with media replacement on days 5 and 7 by aspirating 2 mL of culture supernatant from the wells and adding back 2 mL of fresh media.

Upon culture, the cells were harvested and pelleted by centrifugation at 350×g for 5 minutes, live cell counts were determined by the Vi-Cell XR automated cell counter (Beckman-Coulter). and cells were processed for flow cytometry by staining with: a viability stain, appropriate WT1-peptide-specific HLA-A*24:02 tetramers (MBL International) and antibodies against CD3, CD14, CD19, CD56, CD4 (Biolegend), CD8, (BD Biosciences) Stained cells were washed and analyzed by flow cytometry.

Data acquisition was performed using the Attune N×T flow cytometer instrument (Invitrogen). The acquired data was exported as fcs files and analyzed using the Flowjo software (Tree Star, OR).

The absolute number of antigen specific $CD8^+$ T cells was plotted in the graphs shown, depicting expansion of antigen specific cells as a function of Immuno-STAT concentration.

Example 6

Figure 45:
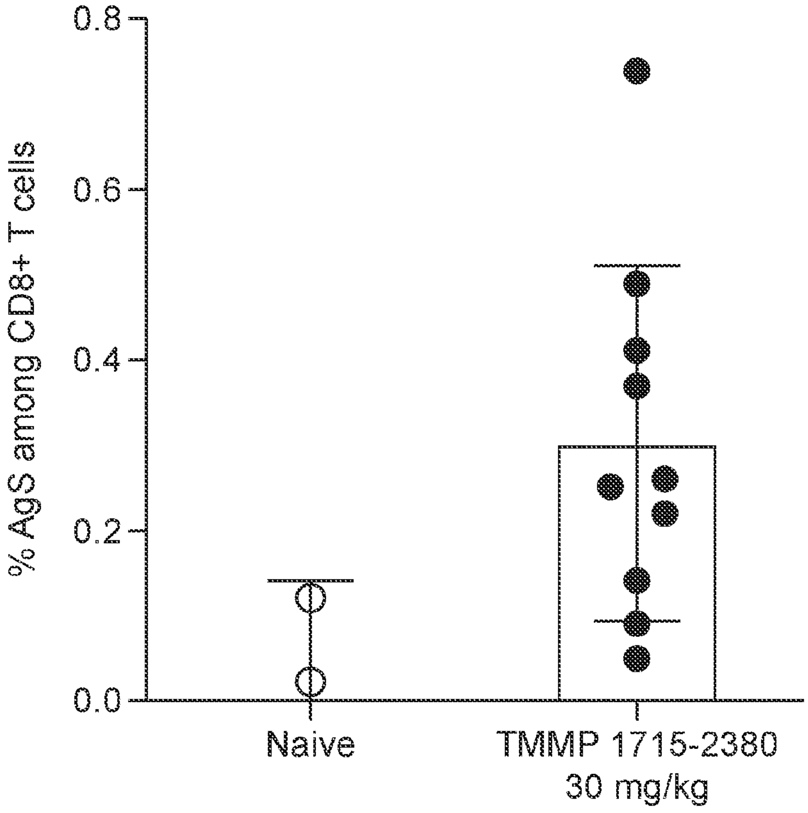
FIG. 45 depicts the effect of TMMPs containing the WT1 peptide epitope 37-45 on antigen-specific CD8+ T cell expansion in naïve HLA-A2 (AAD) transgenic mice.

Naïve HLA-A2 (AAD) transgenic mice were dosed intravenously once weekly with 30 mg/kg of TMMPs comprising homodimers formed from heterodimers 1715-2380 ("TMMP 1715-2380") for a total of three doses. The first dose consisted of a TMMP 1715-2380 generated from a transiently transfected cell line, while the subsequent two doses consisted of TMMP 1715-2380 generated from a stable cell line. The frequency of WT1 37-45-specific CD8+ T cells was then measured in peripheral blood mononuclear cells (PBMCs) 7 days after the last dose. Isolated PBMCs were re-stimulated with WT1 37-45 peptide for 5 hours at 37° C. in the presence of protein transport inhibitors and anti-CD107a antibody to measure degranulation. Cells were then surface stained with WT1 37-45/A02 tetramer, viability dye, and cell surface markers including CD3, CD4, CD8, CD45, CD11b, CD19, and CD44, followed by intracellular staining for IFN-γ, TNF-α, and granzyme B. Antigen-specific cells were detected by analyzing the frequency of tetramer+ cells within the $CD8^+$ T cell population (defined as single, live, CD11b-, CD19-, $CD45^+$, $CD3^+$, CD4−). The frequency of WT1 37-45-specific ("% AgS") CD8+ T cells in treated mice was found to be greater than that observed in naïve mice that were not treated with TMMP 1715-2380 (see FIG. 45).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A composition comprising one or more nucleic acids, wherein the nucleic acids comprise nucleotide sequences encoding a first and second polypeptide, wherein the first polypeptide has the amino acid sequence set forth in SEQ ID NO:423 and the second polypeptide has the amino acid sequence set forth in SEQ ID NO: 486.

* * * * *

SEQUENCE LISTING

```
Sequence total quantity: 499
SEQ ID NO: 1            moltype = AA  length = 245
FEATURE                 Location/Qualifiers
source                  1..245
                        mol_type = protein
                        organism = Homo sapiens
SEQUENCE: 1
MRIFAVFIFM TYWHLLNAFT VTVPKDLYVV EYGSNMTIEC KFPVEKQLDL AALIVYWEME  60
DKNIIQFVHG EEDLKVQHSS YRQRARLLKD QLSLGNAALQ ITDVKLQDAG VYRCMISYGG  120
ADYKRITVKV NAPYNKINQR ILVVDPVTSE HELTCQAEGY PKAEVIWTSS DHQVLSGKTT  180
TTNSKREEKL FNVTSTLRIN TTTNEIFYCT FRRLDPEENH TAELVIPGNI LNVSIKICLT  240
LSPST                                                              245

SEQ ID NO: 2            moltype = AA  length = 219
FEATURE                 Location/Qualifiers
source                  1..219
                        mol_type = protein
                        organism = Homo sapiens
SEQUENCE: 2
FTVTVPKDLY VVEYGSNMTI ECKFPVEKQL DLAALIVYWE MEDKNIIQFV HGEEDLKVQH  60
SSYRQRARLL KDQLSLGNAA LQITDVKLQD AGVYRCMISY GGADYKRITV KVNAPYNKIN  120
QRILVVDPVT SEHELTCQAE GYPKAEVIWT SSDHQVLSGK TTTTNSKREE KLFNVTSTLR  180
INTTTNEIFY CTFRRLDPEE NHTAELVIPG NILNVSIKI                         219

SEQ ID NO: 3            moltype = AA  length = 268
FEATURE                 Location/Qualifiers
source                  1..268
                        mol_type = protein
                        organism = Homo sapiens
SEQUENCE: 3
PGWFLDSPDR PWNPPTFSPA LLVVTEGDNA TFTCSFSNTS ESFVLNWYRM SPSNQTDKLA  60
AFPEDRSQPG QDCRFRVTQL PNGRDFHMSV VRARRNDSGT YLCGAISLAP KAQIKESLRA  120
ELRVTERRAE VPTAHPSPSP RPAGQFQTLV VGVVGGLLGS LVLLVWVLAV ICSRAARGTI  180
GARRTGQPLK EDPSAVPVFS VDYGELDFQW REKTPEPPVP CVPEQTEYAT IVFPSGMGTS  240
SPARRGSADG PRSAQPLRPE DGHCSWPL                                     268

SEQ ID NO: 4            moltype = AA  length = 208
FEATURE                 Location/Qualifiers
source                  1..208
                        mol_type = protein
                        organism = Homo sapiens
SEQUENCE: 4
```

```
VIHVTKEVKE VATLSCGHNV SVEELAQTRI YWQKEKKMVL TMMSGDMNIW PEYKNRTIFD  60
ITNNLSIVIL ALRPSDEGTY ECVVLKYEKD AFKREHLAEV TLSVKADFPT PSISDFEIPT  120
SNIRRIICST SGGFPEPHLS WLENGEELNA INTTVSQDPE TELYAVSSKL DFNMTTNHSF  180
MCLIKYGHLR VNQTFNWNTT KQEHFPDN                                    208

SEQ ID NO: 5            moltype = AA  length = 220
FEATURE                 Location/Qualifiers
source                  1..220
                        mol_type = protein
                        organism = Homo sapiens
SEQUENCE: 5
MLRLLLALNL FPSIQVTGNK ILVKQSPMLV AYDNAVNLSC KYSYNLFSRE FRASLHKGLD  60
SAVEVCVVYG NYSQQLQVYS KTGFNCDGKL GNESVTFYLQ NLYVNQTDIY FCKIEVMYPP  120
PYLDNEKSNG TIIHVKGKHL CPSPLFPGPS KPFWVLVVVG GVLACYSLLV TVAFIIFWVR  180
SKRSRLLHSD YMNMTPRRPG PTRKHYQPYA PPRDFAAYRS                       220

SEQ ID NO: 6            moltype = AA  length = 123
FEATURE                 Location/Qualifiers
source                  1..123
                        mol_type = protein
                        organism = Homo sapiens
SEQUENCE: 6
MLRLLLALNL FPSIQVTGNK ILVKQSPMLV AYDNAVNLSW KHLCPSPLFP GPSKPFWVLV  60
VVGGVLACYS LLVTVAFIIF WVRSKRSRLL HSDYMNMTPR RPGPTRKHYQ PYAPPRDFAA  120
YRS                                                               123

SEQ ID NO: 7            moltype = AA  length = 101
FEATURE                 Location/Qualifiers
source                  1..101
                        mol_type = protein
                        organism = Homo sapiens
SEQUENCE: 7
MLRLLLALNL FPSIQVTGKH LCPSPLFPGP SKPFWVLVVV GGVLACYSLL VTVAFIIFWV  60
RSKRSRLLHS DYMNMTPRRP GPTRKHYQPY APPRDFAAYR S                      101

SEQ ID NO: 8            moltype = AA  length = 224
FEATURE                 Location/Qualifiers
source                  1..224
                        mol_type = protein
                        organism = Homo sapiens
SEQUENCE: 8
APLKIQAYFN ETADLPCQFA NSQNQSLSEL VVFWQDQENL VLNEVYLGKE KFDSVHSKYM  60
NRTSFDSDSW TLRLHNLQIK DKGLYQCIIH HKKPTGMIRI HQMNSELSVL ANFSQPEIVP  120
ISNITENVYI NLTCSSIHGY PEPKKMSVLL RTKNSTIEYD GIMQKSQDNV TELYDVSISL  180
SVSFPDVTSN MTIFCILETD KTRLLSSPFS IELEDPQPPP DHIP                  224

SEQ ID NO: 9            moltype = AA  length = 110
FEATURE                 Location/Qualifiers
source                  1..110
                        mol_type = protein
                        organism = Homo sapiens
SEQUENCE: 9
APLKIQAYFN ETADLPCQFA NSQNQSLSEL VVFWQDQENL VLNEVYLGKE KFDSVHSKYM  60
NRTSFDSDSW TLRLHNLQIK DKGLYQCIIH HKKPTGMIRI HQMNSELSVL             110

SEQ ID NO: 10           moltype = AA  length = 254
FEATURE                 Location/Qualifiers
source                  1..254
                        mol_type = protein
                        organism = Homo sapiens
SEQUENCE: 10
MEYASDASLD PEAPWPPAPR ARACRVLPWA LVAGLLLLLL LAAACAVFLA CPWAVSGARA  60
SPGSAASPRL REGPELSPDD PAGLLDLRQG MFAQLVAQNV LLIDGPLSWY SDPGLAGVSL  120
TGGLSYKEDT KELVVAKAGV YYVFFQLELR RVVAGEGSGS VSLALHLQPL RSAAGAAALA  180
LTVDLPPASS EARNSAFGFQ GRLLHLSAGQ RLGVHLHTEA RARHAWQLTQ GATVLGLFRV  240
TPEIPAGLPS PRSE                                                   254

SEQ ID NO: 11           moltype = AA  length = 174
FEATURE                 Location/Qualifiers
source                  1..174
                        mol_type = protein
                        organism = Homo sapiens
SEQUENCE: 11
PAGLLDLRQG MFAQLVAQNV LLIDGPLSWY SDPGLAGVSL TGGLSYKEDT KELVVAKAGV  60
YYVFFQLELR RVVAGEGSGS VSLALHLQPL RSAAGAAALA LTVDLPPASS EARNSAFGFQ  120
GRLLHLSAGQ RLGVHLHTEA RARHAWQLTQ GATVLGLFRV TPEIPAGLPS PRSE        174

SEQ ID NO: 12           moltype = AA  length = 175
FEATURE                 Location/Qualifiers
```

```
source                  1..175
                        mol_type = protein
                        organism = Homo sapiens
SEQUENCE: 12
DPAGLLDLRQ GMFAQLVAQN VLLIDGPLSW YSDPGLAGVS LTGGLSYKED TKELVVAKAG  60
VYYVFFQLEL RRVVAGEGSG SVSLALHLQP LRSAAGAAAL ALTVDLPPAS SEARNSAFGF  120
QGRLLHLSAG QRLGVHLHTE ARARHAWQLT QGATVLGLFR VTPEIPAGLP SPRSE       175

SEQ ID NO: 13           moltype = AA  length = 167
FEATURE                 Location/Qualifiers
source                  1..167
                        mol_type = protein
                        organism = Homo sapiens
SEQUENCE: 13
DPAGLLDLRQ GMFAQLVAQN VLLIDGPLSW YSDPGLAGVS LTGGLSYKED TKELVVAKAG  60
VYYVFFQLEL RRVVAGEGSG SVSLALHLQP LRSAAGAAAL ALTVDLPPAS SEARNSAFGF  120
QGRLLHLSAG QRLGVHLHTE ARARHAWQLT QGATVLGLFR VTPEIPA                167

SEQ ID NO: 14           moltype = AA  length = 255
FEATURE                 Location/Qualifiers
source                  1..255
                        mol_type = protein
                        organism = Homo sapiens
SEQUENCE: 14
MGNSCYNIVA TLLLVLNFER TRSLQDPCSN CPAGTFCDNN RNQICSPCPP NSFSSAGGQR  60
TCDICRQCKG VFRTRKECSS TSNAECDCTP GFHCLGAGCS MCEQDCKQGQ ELTKKGCKDC  120
CFGTFNDQKR GICRPWTNCS LDGKSVLVNG TKERDVVCGP SPADLSPGAS SVTPPAPARE  180
PGHSPQIISF FLALTSTALL FLLFFLTLRF SVVKRGRKKL LYIFKQPFMR PVQTTQEEDG  240
CSCRFPEEEE GGCEL                                                   255

SEQ ID NO: 15           moltype = AA  length = 133
FEATURE                 Location/Qualifiers
source                  1..133
                        mol_type = protein
                        organism = Homo sapiens
SEQUENCE: 15
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLT                                                     133

SEQ ID NO: 16           moltype = AA  length = 251
FEATURE                 Location/Qualifiers
source                  1..251
                        mol_type = protein
                        organism = Homo sapiens
SEQUENCE: 16
ELCDDDPPEI PHATFKAMAY KEGTMLNCEC KRGFRRIKSG SLYMLCTGNS SHSSWDNQCQ  60
CTSSATRNTT KQVTPQPEEQ KERKTTEMQS PMQPVDQASL PGHCREPPPW ENEATERIYH  120
FVVGQMVYYQ CVQGYRALHR GPAESVCKMT HGKTRWTQPQ LICTGEMETS QFPGEEKPQA  180
SPEGRPESET SCLVTTTDFQ IQTEMAATME TSIFTTEYQV AVAGCVFLLI SVLLLSGLTW  240
QRRQRKSRRT I                                                       251

SEQ ID NO: 17           moltype = AA  length = 524
FEATURE                 Location/Qualifiers
source                  1..524
                        mol_type = protein
                        organism = Homo sapiens
SEQUENCE: 17
VNGTSQFTCF YNSRANISCV WSQDGALQDT SCQVHAWPDR RRWNQTCELL PVSQASWACN  60
LILGAPDSQK LTTVDIVTLR VLCREGVRWR VMAIQDFKPF ENLRLMAPIS LQVVHVETHR  120
CNISWEISQA SHYFERHLEF EARTLSPGHT WEEAPLLTLK QKQEWICLET LTPDTQYEFQ  180
VRVKPLQGEF TTWSPWSQPL AFRTKPAALG KDTIPWLGHL LVGLSGAFGF IILVYLLINC  240
RNTGPWLKKV LKCNTPDPSK FFSQLSSEHG GDVQKWLSSP FPSSSFSPGG LAPEISPLEV  300
LERDKVTQLL LQQDKVPEPA SLSSNHSLTS CFTNQGYFFF HLPDALEIEA CQVYFTYDPY  360
SEEDPDEGVA GAPTGSSPQP LQPLSGEDDA YCTFPSRDDL LLFSPSLLGG PSPPSTAPGG  420
SGAGEERMPP SLQERVPRDW DPQPLGPPTP GVPDLVDFQP PPELVLREAG EEVPDAGPRE  480
GVSFPWSRPP GQGEFRALNA RLPLNTDAYL SLQELQGQDP THLV                   524

SEQ ID NO: 18           moltype = AA  length = 347
FEATURE                 Location/Qualifiers
source                  1..347
                        mol_type = protein
                        organism = Homo sapiens
SEQUENCE: 18
LNTTILTPNG NEDTTADFFL TTMPTDSLSV STLPLPEVQC FVFNVEYMNC TWNSSSEPQP  60
TNLTLHYWYK NSDNDKVQKC SHYLFSEEIT SGCQLQKKEI HLYQTFVVQL QDPREPRRQA  120
TQMLKLQNLV IPWAPENLTL HKLSESQLEL NWNNRFLNHC LEHLVQYRTD WDHSWTEQSV  180
DYRHKFSLPS VDGQKRYTFR VRSRFNPLCG SAQHWSEWSH PIHWGSNTSK ENPFLFALEA  240
VVISVGSMGL IISLLCVYFW LERTMPRIPT LKNLEDLVTE YHGNFSAWSG VSKGLAESLQ  300
```

```
PDYSERLCLV SEIPPKGGAL GEGPGASPCN QHSPYWAPPC YTLKPET              347

SEQ ID NO: 19          moltype = AA  length = 119
FEATURE                Location/Qualifiers
source                 1..119
                       mol_type = protein
                       organism = Homo sapiens
SEQUENCE: 19
MSRSVALAVL ALLSLSGLEA IQRTPKIQVY SRHPAENGKS NFLNCYVSGF HPSDIEVDLL  60
KNGERIEKVE HSDLSFSKDW SFYLLYYTEF TPTEKDEYAC RVNHVTLSQP KIVKWDRDM   119

SEQ ID NO: 20          moltype = AA  length = 119
FEATURE                Location/Qualifiers
source                 1..119
                       mol_type = protein
                       organism = Macaca mulatta
SEQUENCE: 20
MSRSVALAVL ALLSLSGLEA IQRTPKIQVY SRHPPENGKP NFLNCYVSGF HPSDIEVDLL  60
KNGEKMGKVE HSDLSFSKDW SFYLLYYTEF TPNEKDEYAC RVNHVTLSGP RTVKWDRDM   119

SEQ ID NO: 21          moltype = AA  length = 118
FEATURE                Location/Qualifiers
source                 1..118
                       mol_type = protein
                       organism = Bos taurus
SEQUENCE: 21
MARFVALVLL GLLSLSGLDA IQRPPKIQVY SRHPPEDGKP NYLNCYVYGF HPPQIEIDLL  60
KNGEKIKSEQ SDLSFSKDWS FYLLSHAEFT PNSKDQYSCR VKHVTLEQPR IVKWDRDL    118

SEQ ID NO: 22          moltype = AA  length = 119
FEATURE                Location/Qualifiers
source                 1..119
                       mol_type = protein
                       organism = Mus musculus
SEQUENCE: 22
MARSVTLVFL VLVSLTGLYA IQKTPQIQVY SRHPPENGKP NILNCYVTQF HPPHIEIQML  60
KNGKKIPKVE MSDMSFSKDW SFYILAHTEF TPTETDTYAC RVKHASMAEP KTVYWDRDM   119

SEQ ID NO: 23          moltype = AA  length = 365
FEATURE                Location/Qualifiers
source                 1..365
                       mol_type = protein
                       organism = Homo sapiens
SEQUENCE: 23
MAVMAPRTLL LLLSGALALT QTWAGSHSMR YFFTSVSRPG RGEPRFIAVG YVDDTQFVRF  60
DSDAASQKME PRAPWIEQEG PEYWDQETRN MKAHSQTDRA NLGTLRGYYN QSEDGSHTIQ  120
IMYGCDVGPD GRFLRGYRQD AYDGKDYIAL NEDLRSWTAA DMAAQITKRK WEAVHAAEQR  180
RVYLEGRCVD GLRRYLENGK ETLQRTDPPK THMTHHPISD HEATLRCWAL GFYPAEITLT  240
WQRDGEDQTQ DTELVETRPA GDGTFQKWAA VVVPSGEEQR YTCHVQHEGL PKPLTLRWEL  300
SSQPTIPIVG IIAGLVLLGA VITGAVVAAV MWRRKSSDRK GGSYTQAASS DSAQGSDVSL  360
TACKV                                                              365

SEQ ID NO: 24          moltype = AA  length = 365
FEATURE                Location/Qualifiers
source                 1..365
                       mol_type = protein
                       organism = Homo sapiens
SEQUENCE: 24
MAVMAPRTLL LLLSGALALT QTWAGSHSMR YFYTSVSRPG RGEPRFIAVG YVDDTQFVRF  60
DSDAASQRME PRAPWIEQEG PEYWDQETRN VKAQSQTDRV DLGTLRGYYN QSEDGSHTIQ  120
IMYGCDVGPD GRFLRGYRQD AYDGKDYIAL NEDLRSWTAA DMAAQITKRK WEAAHAAEQQ  180
RAYLEGRCVE WLRRYLENGK ETLQRTDPPK THMTHHPISD HEATLRCWAL GFYPAEITLT  240
WQRDGEDQTQ DTELVETRPA GDGTFQKWAA VVVPSGEEQR YTCHVQHEGL PKPLTLRWEL  300
SSQPTIPIVG IIAGLVLLGA VITGAVVAAV MWRRKSSDRK GGSYTQAASS DSAQGSDVSL  360
TACKV                                                              365

SEQ ID NO: 25          moltype = AA  length = 365
FEATURE                Location/Qualifiers
source                 1..365
                       mol_type = protein
                       organism = Homo sapiens
SEQUENCE: 25
MAVMAPRTLV LLLSGALALT QTWAGSHSMR YFSTSVSRPG RGEPRFIAVG YVDDTQFVRF  60
DSDAASQRME PRAPWIEQEG PEYWDEETGK VKAHSQTDRE NLRIALRYYN QSEAGSHTLQ  120
MMFGCDVGSD GRFLRGYHQY AYDGKDYIAL KEDLRSWTAA DMAAQITKRK WEAAHVAEQQ  180
RAYLEGTCVD GLRRYLENGK ETLQRTDPPK THMTHHPISD HEATLRCWAL GFYPAEITLT  240
WQRDGEDQTQ DTELVETRPA GDGTFQKWAA VVVPSGEEQR YTCHVQHEGL PKPLTLRWEP  300
SSQPTVPIVG IIAGLVLLGA VITGAVVAAV MWRRNSSDRK GGSYSQAASS DSAQGSDVSL  360
TACKV                                                              365
```

```
SEQ ID NO: 26           moltype = AA  length = 365
FEATURE                 Location/Qualifiers
source                  1..365
                        mol_type = protein
                        organism = Homo sapiens
SEQUENCE: 26
MAVMAPRTLL LLLLGALALT QTWAGSHSMR YFTTSVSRPG RGEPRFIAVG YVDDTQFVRF  60
DSDAASQRME PRAPWIEQEG PEYWDRNTRN VKAHSQIDRV DLGTLRGYYN QSEAGSHTIQ  120
MMYGCDVGSD GRFLRGYQQD AYDGKDYIAL NEDLRSWTAA DMAAQITQRK WEAARVAEQL  180
RAYLEGTCVE WLRRYLENGK ETLQRTDPPK THMTHHAVSD HEATLRCWAL SFYPAEITLT  240
WQRDGEDQTQ DTELVETRPA GDGTFQKWAS VVVPSGQEQR YTCHVQHEGL PKPLTLRWEP  300
SSQPTIPIVG IIAGLVLFGA VFAGAVVAAV RWRRKSSDRK GGSYSQAASS DSAQGSDMSL  360
TACKV                                                             365

SEQ ID NO: 27           moltype = AA  length = 362
FEATURE                 Location/Qualifiers
source                  1..362
                        mol_type = protein
                        organism = Homo sapiens
SEQUENCE: 27
MLVMAPRTVL LLLSAALALT ETWAGSHSMR YFYTSVSRPG RGEPRFISVG YVDDTQFVRF  60
DSDAASPREE PRAPWIEQEG PEYWDRNTQI YKAQAQTDRE SLRNLRGYYN QSEAGSHTLQ  120
SMYGCDVGPD GRLLRGHDQY AYDGKDYIAL NEDLRSWTAA DTAAQITQRK WEAAREAEQR  180
RAYLEGECVE WLRRYLENGK DKLERADPPK THVTHHPISD HEATLRCWAL GFYPAEITLT  240
WQRDGEDQTQ DTELVETRPA GDRTFQKWAA VVVPSGEEQR YTCHVQHEGL PKPLTLRWEP  300
SSQSTVPIVG IVAGLAVLAV VVIGAVVAAV MCRRKSSGGK GGSYSQAACS DSAQGSDVSL  360
TA                                                                362

SEQ ID NO: 28           moltype = AA  length = 366
FEATURE                 Location/Qualifiers
source                  1..366
                        mol_type = protein
                        organism = Homo sapiens
SEQUENCE: 28
MRVMAPRALL LLLSGGLALT ETWACSHSMR YFDTAVSRPG RGEPRFISVG YVDDTQFVRF  60
DSDAASPRGE PRAPWVEQEG PEYWDRETQN YKRQAQADRV SLRNLRGYYN QSEDGSHTLQ  120
RMYGCDLGPD GRLLRGYDQS AYDGKDYIAL NEDLRSWTAA DTAAQITQRK LEAARAAEQL  180
RAYLEGTCVE WLRRYLENGK ETLQRAEPPK THVTHHPLSD HEATLRCWAL GFYPAEITLT  240
WQRDGEDQTQ DTELVETRPA GDGTFQKWAA VVVPSGQEQR YTCHMQHEGL QEPLTLSWEP  300
SSQPTIPIMG IVAGLAVLVV LAVLGAVVTA MMCRRKSSGG KGGSCSQAAC SNSAQGSDES  360
LITCKA                                                            366

SEQ ID NO: 29           moltype = AA  length = 276
FEATURE                 Location/Qualifiers
SITE                    9
                        note = Xaa is phenylalanine, tyrosine, serine, or threonine
SITE                    44
                        note = Xaa is lysine or arginine
SITE                    62
                        note = Xaa is glutamine, glycine, glutamic acid, or arginine
SITE                    63
                        note = Xaa is asparagine or glutamic acid
SITE                    65
                        note = Xaa is arginine or glycine
SITE                    66
                        note = Xaa is asparagine or lysine
SITE                    67
                        note = Xaa is methionine or valine
SITE                    70
                        note = Xaa is histidine or glutamine
SITE                    73
                        note = Xaa is threonine or isoleucine
SITE                    74
                        note = Xaa is aspartic acid or histidine
SITE                    76
                        note = Xaa is alanine, valine, or glutamic acid
SITE                    77
                        note = Xaa is asparagine or aspartic acid
SITE                    79
                        note = Xaa is glycine or arginine
SITE                    80
                        note = Xaa is threonine or arginine
SITE                    81
                        note = Xaa is leucine or alanine
SITE                    82
                        note = Xaa is arginine or leucine
SITE                    83
                        note = Xaa is glycine ir arginine
```

```
SITE                    90
                        note = Xaa is alanine or aspartic acid
SITE                    95
                        note = Xaa is isoleucine, leucine, or valine
SITE                    97
                        note = Xaa is isoleucine, arginine, or methionine
SITE                    99
                        note = Xaa is phenylalanine or tyrosine
SITE                    105
                        note = Xaa is serine or proline
SITE                    107
                        note = Xaa is tryptophan or glycine
SITE                    114
                        note = Xaa is arginine, histidine, or glutamine
SITE                    116
                        note = Xaa is aspartic acid or tyrosine
SITE                    127
                        note = Xaa is asparagine or lysine
SITE                    142
                        note = Xaa is threonine or isoleucine
SITE                    144
                        note = Xaa is lysine or glutamine
SITE                    145
                        note = Xaa is arginine or histidine
SITE                    149
                        note = Xaa is alanine or threonine
SITE                    150
                        note = Xaa is alanine or valine
SITE                    151
                        note = Xaa is histidine or arginine
SITE                    156
                        note = Xaa is arginine, leucine, glutamine, or tryptophan
SITE                    158
                        note = Xaa is valine or alanine
SITE                    161
                        note = Xaa is aspartic acid or glutamic acid
SITE                    163
                        note = Xaa is arginine or threonine
SITE                    166
                        note = Xaa is aspartic acid or glutamic acid
SITE                    167
                        note = Xaa is tryptophan or glycine
SITE                    184
                        note = Xaa is proline or alanine
SITE                    193
                        note = Xaa is proline or alanine
SITE                    194
                        note = Xaa is valine or isoleucine
SITE                    207
                        note = Xaa is serine or glycine
SITE                    246
                        note = Xaa is alanine or serine
SITE                    253
                        note = Xaa is glutamine or glutamic acid
SITE                    276
                        note = Xaa is proline or leucine
source                  1..276
                        mol_type = protein
                        organism = synthetic construct
SEQUENCE: 29
GSHSMRYFXT SVSRPGRGEP RFIAVGYVDD TQFVRFDSDA ASQXMEPRAP WIEQEGPEYW  60
DXXTXXXKAX SQXXRXXLXX XXXYYNQSEX GSHTXQXMXG CDVGXDXRFL RGYXQXAYDG  120
KDYIALXEDL RSWTAADMAA QXTXXKWEXX XEAEQXRXYL XGXCVXXLRR YLENGKETLQ  180
RTDXPKTHMT HHXXSDHEAT LRCWALXFYP AEITLTWQRD GEDQTQDTEL VETRPAGDGT  240
FQKWAXVVVP SGXEQRYTCH VQHEGLPKPL TLRWEX                            276

SEQ ID NO: 30           moltype = AA  length = 276
FEATURE                 Location/Qualifiers
SITE                    9
                        note = Xaa is histidine, tyrosine, or aspartic acid
SITE                    11
                        note = Xaa is alanine or serine
SITE                    12
                        note = Xaa is methionine or valine
SITE                    24
                        note = Xaa is alanine, serine, or threonine
SITE                    32
                        note = Xaa is glutamine or leucine
SITE                    41
```

```
                      note = Xaa is alanine or threonine
SITE                  45
                      note = Xaa is glutamic acid, methionine, lysine, or
                       threonine
SITE                  46
                      note = Xaa is alanine or threonine
SITE                  63
                      note = Xaa is glutamic acid or asparagine
SITE                  66
                      note = Xaa is isoleucine or lysine
SITE                  67
                      note = Xaa is tyrosine, phenylalanie, serine, or cysteine
SITE                  70
                      note = Xaa is asparagine or glutamine
SITE                  71
                      note = Xaa is alanine or threonine
SITE                  74
                      note = Xaa is aspartic acid or tyrosine
SITE                  76
                      note = Xaa is glutamic acid or valine
SITE                  77
                      note = Xaa is serine or asparagine
SITE                  80
                      note = Xaa is threonine, asparagine, or isoleucine
SITE                  81
                      note = Xaa is alanine or leucine
SITE                  82
                      note = Xaa is leucine or arginine
SITE                  83
                      note = Xaa is arginine or glycine
SITE                  94
                      note = Xaa is threonine or isoleucine
SITE                  95
                      note = Xaa is leucine or isoleucine
SITE                  97
                      note = Xaa is arginine or serine
SITE                  131
                      note = Xaa is arginine or serine
SITE                  143
                      note = Xaa is serine or threonine
SITE                  147
                      note = Xaa is leucine or tryptophan
SITE                  152
                      note = Xaa is glutamic acid OR valine
SITE                  156
                      note = Xaa is arginine, aspartic acid, or leucine
SITE                  158
                      note = Xaa alanine or threonine
SITE                  163
                      note = Xaa is leucine, glutamic acid, or threonine
SITE                  177
                      note = Xaa is glutamic acid or aspartic acid
SITE                  178
                      note = Xaa is lysine or threonine
SITE                  180
                      note = Xaa is glutamic acid or glutamine
SITE                  194
                      note = Xaa is isoleucine or valine
source                1..276
                      mol_type = protein
                      organism = synthetic construct
SEQUENCE: 30
GSHSMRYFXT XXSRPGRGEP RFIXVGYVDD TXFVRFDSDA XSPRXXPRAP WIEQEGPEYW  60
DRXTQXXKTX XTQXYXXNLX XXXYYNQSEA GSHXXQXMYG CDLGPDGRLL RGHDQSAYDG  120
KDYIALNEDL XSWTAADTAA QIXQRKXEAA RXAEQXRXYL EGXCVEWLRR YLENGKXXLX  180
RADPPKTHVT HHPXSDHEAT LRCWALGFYP AEITLTWQRD GEDQTQDTEL VETRPAGDRT  240
FQKWAAVVVP SGEEQRYTCH VQHEGLPKPL TLRWEP                           276

SEQ ID NO: 31         moltype = AA  length = 276
FEATURE               Location/Qualifiers
SITE                  1
                      note = Xaa is cysteine or glycine
SITE                  6
                      note = Xaa is arginine or lysine
SITE                  9
                      note = Xaa is phenylalanine, tyrosine, serine, or aspartic
                       acid
SITE                  14
                      note = Xaa is arginine or tryptophan
```

```
SITE                    21
                        note = Xaa is histidine or arginine
SITE                    24
                        note = Xaa is alanine or serine
SITE                    35
                        note = Xaa is glutamine or arginine
SITE                    49
                        note = Xaa is alanine or arginine
SITE                    66
                        note = Xaa is asparagine, or lysine
SITE                    73
                        note = Xaa is threonine or alanine
SITE                    77
                        note = Xaa is serine or asparagine
SITE                    80
                        note = Xaa is asparagine or lysine
SITE                    90
                        note = Xaa is alanine or aspartic acid
SITE                    91
                        note = Xaa is glycine or arginine
SITE                    94
                        note = Xaa is threonine or isoleucine
SITE                    95
                        note = Xaa is leucine or isoleucine
SITE                    97
                        note = Xaa is tryptophan or arginine
SITE                    99
                        note = Xaa is cysteine, tyrosine, phenylalanine, or serine
SITE                    103
                        note = Xaa is leucine or valine
SITE                    113
                        note = Xaa is tyrosine or histidine
SITE                    114
                        note = Xaa is aspartic acid or asparagine
SITE                    116
                        note = Xaa is tyrosine, phenylalanine, serine, or leucine
SITE                    147
                        note = Xaa is leucine or tryptophan
SITE                    152
                        note = Xaa is glutamic acid, alanine, or threonine
SITE                    156
                        note = Xaa is arginine, leucine, or tryptophan
SITE                    163
                        note = Xaa is leucine or threonine
SITE                    173
                        note = Xaa is glutamic acid or lysine
SITE                    177
                        note = Xaa is glutamic acid or lysine
SITE                    184
                        note = Xaa is histidine or proline
SITE                    194
                        note = Xaa is arginine or valine
SITE                    219
                        note = Xaa is tryptophan or arginine
SITE                    248
                        note = Xaa is valine or methionine
SITE                    253
                        note = Xaa is glutamic acid or lysine
SITE                    261
                        note = Xaa is methionine or valine
SITE                    267
                        note = Xaa is proline or glutamine
SITE                    273
                        note = Xaa is arginine or serine
SITE                    275
                        note = Xaa is proline or glycine
source                  1..276
                        mol_type = protein
                        organism = synthetic construct
SEQUENCE: 31
XSHSMXYFXT AVSXPGRGEP XFIXVGYVDD TQFVXFDSDA ASPRGEPRXP WVEQEGPEYW  60
DRETQXYKRQ AQXDRVXLRX LRGYYNQSEX XSHXXQXMXG CDXGPDGRLL RGXXQXAYDG  120
KDYIALNEDL RSWTAADTAA QITQRKXEAA RXAEQXRAYL EGXCVEWLRR YLXNGKXTLQ  180
RAEXPKTHVT HHPXSDHEAT LRCWALGFYP AEITLTWQXD GEDQTQDTEL VETRPAGDGT  240
FQKWAAVXVP SGXEQRYTCH XQHEGLXEPL TLXWXP                            276

SEQ ID NO: 32           moltype = AA  length = 284
FEATURE                 Location/Qualifiers
SITE                    89
```

```
                       note = Xaa is lysine or glutamic acid
SITE                   107
                       note = Xaa is arginine or glycine
SITE                   157
                       note = Xaa is arginine or glycine
SITE                   158
                       note = Xaa is alanine or valine
SITE                   255
                       note = Xaa is glutamine or proline
SITE                   267
                       note = Xaa is proline or serine
source                 1..284
                       mol_type = protein
                       organism = synthetic construct
SEQUENCE: 32
GSHSLKYFHT SVSRPGRGEP RFISVGYVDD TQFVRFDNDA ASPRMVPRAP WMEQEGSEYW  60
DRETRSARDT AQIFRVNLRT LRGYYNQSXA GSHTLQWMHG CELGPDXRFL RGYEQFAYDG  120
KDYLTLNEDL RSWTAVDTAA QISEQKSNDA SEAEHQXXYL EDTCVEWLHK YLEKGKETLL  180
HLEPPKTHVT HHPISDHEAT LRCWALGFYP AEITLTWQQD GEGHTQDTEL VETRPAGDGT  240
FQKWAAVVVP SGEEXRYTCH VQHEGLXEPV TLRWKPASQP TIPI                  284

SEQ ID NO: 33          moltype = AA  length = 284
FEATURE                Location/Qualifiers
SITE                   7
                       note = Xaa is tyrosine or phenylalanine
SITE                   50
                       note = Xaa is proline or glutamine
SITE                   251
                       note = Xaa is serine or proline
SITE                   278
                       note = Xaa is proline or leucine
source                 1..284
                       mol_type = protein
                       organism = synthetic construct
SEQUENCE: 33
GSHSLRXFST AVSRPGRGEP RYIAVEYVDD TQFLRFDSDA AIPRMEPREX WVEQEGPQYW  60
EWTTGYAKAN AQTDRVALRN LLRRYNQSEA GSHTLQGMNG CDMGPDGRLL RGYHQHAYDG  120
KDYISLNEDL RSWTAADTVA QITQRFYEAE EYAEEFRTYL EGECLELLRR YLENGKETLQ  180
RADPPKAHVA HHPISDHEAT LRCWALGFYP AEITLTWQRD GEEQTQDTEL VETRPAGDGT  240
FQKWAAVVVP XGEEQRYTCH VQHEGLPQPL ILRWEQSXQP TIPI                  284

SEQ ID NO: 34          moltype = AA  length = 284
FEATURE                Location/Qualifiers
SITE                   13
                       note = Xaa is serine or phenylalanine
SITE                   27
                       note = Xaa is tyrosine or histidine
SITE                   31
                       note = Xaa is threonine, serine, or methionine
SITE                   34
                       note = Xaa is leucine or valine
SITE                   54
                       note = Xaa is glutamine or arginine
SITE                   81
                       note = Xaa is proline or leucine
SITE                   100
                       note = Xaa is glycine or aspartic acid
SITE                   104
                       note = Xaa is glycine or valine
SITE                   105
                       note = Xaa is serine or cysteine
SITE                   110
                       note = Xaa is leucine or isoleucine
SITE                   159
                       note = Xaa is tyrosine or histidine
SITE                   169
                       note = Xaa is histidine or arginine
SITE                   171
                       note = Xaa is tyrosine or histidine
SITE                   178
                       note = Xaa is methionine or threonine
SITE                   185
                       note = Xaa is proline or alanine
SITE                   219
                       note = Xaa is arginine, tryptophan, or glutamine
SITE                   258
                       note = Xaa is threonine or methionine
SITE                   275
                       note = Xaa is lysine or glutamic acid
```

```
source                  1..284
                        mol_type = protein
                        organism = synthetic construct
SEQUENCE: 34
GSHSMRYFSA AVXRPGRGEP RFIAMGXVDD XQFXRFDSDS ACPRMEPRAP WVEXEGPEYW  60
EEETRNTKAH AQTDRMNLQT XRGYYNQSEA SSHTLQWMIX CDLXXDGRLX RGYEQYAYDG  120
KDYLALNEDL RSWTAADTAA QISKRKCEAA NVAEQRRAXL EGTCVEWLXR XLENGKEXLQ  180
RADPXKTHVT HHPVFDYEAT LRCWALGFYP AEIILTWQXD GEDQTQDVEL VETRPAGDGT  240
FQKWAAVVVP SGEEQRYXCH VQHEGLPEPL MLRWXQSSLP TIPI                  284

SEQ ID NO: 35           moltype =   length =
SEQUENCE: 35
000

SEQ ID NO: 36           moltype =   length =
SEQUENCE: 36
000

SEQ ID NO: 37           moltype =   length =
SEQUENCE: 37
000

SEQ ID NO: 38           moltype =   length =
SEQUENCE: 38
000

SEQ ID NO: 39           moltype =   length =
SEQUENCE: 39
000

SEQ ID NO: 40           moltype =   length =
SEQUENCE: 40
000

SEQ ID NO: 41           moltype = AA  length = 275
FEATURE                 Location/Qualifiers
source                  1..275
                        mol_type = protein
                        organism = Homo sapiens
SEQUENCE: 41
GSHSMRYFFT SVSRPGRGEP RFIAVGYVDD TQFVRFDSDA ASQKMEPRAP WIEQEGPEYW  60
DQETRNMKAH SQTDRANLGT LRGYYNQSED GSHTIQIMYG CDVGPDGRFL RGYRQDAYDG  120
KDYIALNEDL RSWTAADMAA QITKRKWEAV HAAEQRRVYL EGRCVDGLRR YLENGKETLQ  180
RTDPPKTHMT HHPISDHEAT LRCWALGFYP AEITLTWQRD GEDQTQDTEL VETRPAGDGT  240
FQKWAAVVVP SGEEQRYTCH VQHEGLPKPL TLRWE                             275

SEQ ID NO: 42           moltype = AA  length = 275
FEATURE                 Location/Qualifiers
source                  1..275
                        mol_type = protein
                        organism = Homo sapiens
SEQUENCE: 42
GSHSMRYFYT SVSRPGRGEP RFISVGYVDD TQFVRFDSDA ASPREEPRAP WIEQEGPEYW  60
DRNTQIYKAQ AQTDRESLRN LRGYYNQSEA GSHTLQSMYG CDVGPDGRLL RGHDQYAYDG  120
KDYIALNEDL RSWTAADTAA QITQRKWEAA REAEQRRAYL EGECVEWLRR YLENGKDKLE  180
RADPPKTHVT HHPISDHEAT LRCWALGFYP AEITLTWQRD GEDQTQDTEL VETRPAGDRT  240
FQKWAAVVVP SGEEQRYTCH VQHEGLPKPL TLRWE                             275

SEQ ID NO: 43           moltype = AA  length = 275
FEATURE                 Location/Qualifiers
source                  1..275
                        mol_type = protein
                        organism = Homo sapiens
SEQUENCE: 43
CSHSMRYFDT AVSRPGRGEP RFISVGYVDD TQFVRFDSDA ASPRGEPRAP WVEQEGPEYW  60
DRETQNYKRQ AQADRVSLRN LRGYYNQSED GSHTLQRMYG CDLGPDGRLL RGYDQSAYDG  120
KDYIALNEDL RSWTAADTAA QITQRKLEAA RAAEQLRAYL EGTCVEWLRR YLENGKETLQ  180
RAEPPKTHVT HHPLSDHEAT LRCWALGFYP AEITLTWQRD GEDQTQDTEL VETRPAGDGT  240
FQKWAAVVVP SGQEQRYTCH MQHEGLQEPL TLSWE                             275

SEQ ID NO: 44           moltype = AA  length = 276
FEATURE                 Location/Qualifiers
source                  1..276
                        mol_type = protein
                        organism = Homo sapiens
SEQUENCE: 44
GSHSMRYFFT SVSRPGRGEP RFIAVGYVDD TQFVRFDSDA ASQRMEPRAP WIEQEGPEYW  60
DGETRKVKAH SQTHRVDLGT LRGYYNQSEA GSHTVQRMYG CDVGSDWRFL RGYHQYAYDG  120
KDYIALKEDL RSWTAADMAA QTTKHKWEAA HVAEQLRAYL EGTCVEWLRR YLENGKETLQ  180
```

```
RTDAPKTHMT HHAVSDHEAT LRCWALSFYP AEITLTWQRD GEDQTQDTEL VETRPAGDGT  240
FQKWAAVVVP SGQEQRYTCH VQHEGLPKPL TLRWEP                            276

SEQ ID NO: 45          moltype = AA  length = 274
FEATURE                Location/Qualifiers
source                 1..274
                       mol_type = protein
                       organism = Mus musculus
SEQUENCE: 45
GPHSLRYFVT AVSRPGLGEP RFIAVGYVDD TQFVRFDSDA DNPRFEPRAP WMEQEGPEYW  60
EEQTQRAKSD EQWFRVSLRT AQRYYNQSKG GSHTFQRMFG CDVGSDWRLL RGYQQFAYDG  120
RDYIALNEDL KTWTAADTAA LITRRKWEQA GDAEYYRAYL EGECVEWLRR YLELGNETLL  180
RTDSPKAHVT YHPRSQVDVT LRCWALGFYP ADITLTWQLN GEDLTQDMEL VETRPAGDGT  240
FQKWAAVVVP LGKEQNYTCH VHHKGLPEPL TLRW                              274

SEQ ID NO: 46          moltype = AA  length = 275
FEATURE                Location/Qualifiers
source                 1..275
                       mol_type = protein
                       organism = synthetic construct
SEQUENCE: 46
GSHSMRYFFT SVSRPGRGEP RFIAVGYVDD TQFVRFDSDA ASQRMEPRAP WIEQEGPEYW  60
DGETRKVKAH SQTHRVDLGT LRGAYNQSEA GSHTVQRMYG CDVGSDWRFL RGYHQYAYDG  120
KDYIALKEDL RSWTAADMAA QTTKHKWEAA HVAEQLRAYL EGTCVEWLRR YLENGKETLQ  180
RTDAPKTHMT HHAVSDHEAT LRCWALSFYP AEITLTWQRD GEDQTQDTEL VETRPCGDGT  240
FQKWAAVVVP SGQEQRYTCH VQHEGLPKPL TLRWE                             275

SEQ ID NO: 47          moltype = AA  length = 275
FEATURE                Location/Qualifiers
source                 1..275
                       mol_type = protein
                       organism = synthetic construct
SEQUENCE: 47
GSHSMRYFFT SVSRPGRGEP RFIAVGYVDD TQFVRFDSDA ASQRMEPRAP WIEQEGPEYW  60
DGETRKVKAH SQTHRVDLGT LRGCYNQSEA GSHTVQRMYG CDVGSDWRFL RGYHQYAYDG  120
KDYIALKEDL RSWTAADMCA QTTKHKWEAA HVAEQLRAYL EGTCVEWLRR YLENGKETLQ  180
RTDAPKTHMT HHAVSDHEAT LRCWALSFYP AEITLTWQRD GEDQTQDTEL VETRPCGDGT  240
FQKWAAVVVP SGQEQRYTCH VQHEGLPKPL TLRWE                             275

SEQ ID NO: 48          moltype = AA  length = 276
FEATURE                Location/Qualifiers
source                 1..276
                       mol_type = protein
                       organism = synthetic construct
SEQUENCE: 48
GSHSMRYFFT SVSRPGRGEP RFIAVGYVDD TQFVRFDSDA ASQRMEPRAP WIEQEGPEYW  60
DGETRKVKAH SQTHRVDLGT LRGAYNQSEA GSHTVQRMYG CDVGSDWRFL RGYHQYAYDG  120
KDYIALKEDL RSWTAADMAA QTTKHKWEAA HVAEQLRAYL EGTCVEWLRR YLENGKETLQ  180
RTDAPKTHMT HHAVSDHEAT LRCWALSFYP AEITLTWQRD GEDQTQDTEL VETRPCGDGT  240
FQKWAAVVVP SGQEQRYTCH VQHEGLPKPL TLRWEP                            276

SEQ ID NO: 49          moltype = AA  length = 276
FEATURE                Location/Qualifiers
source                 1..276
                       mol_type = protein
                       organism = Homo sapiens
SEQUENCE: 49
GSHSMRYFYT SVSRPGRGEP RFIAVGYVDD TQFVRFDSDA ASQRMEPRAP WIEQEGPEYW  60
DQETRNVKAQ SQTDRVDLGT LRGYYNQSED GSHTIQIMYG CDVGPDGRFL RGYRQDAYDG  120
KDYIALNEDL RSWTAADMAA QITKRKWEAA HAAEQQRAYL EGRCVEWLRR YLENGKETLQ  180
RTDPPKTHMT HHPISDHEAT LRCWALGFYP AEITLTWQRD GEDQTQDTEL VETRPAGDGT  240
FQKWAAVVVP SGEEQRYTCH VQHEGLPKPL TLRWEL                            276

SEQ ID NO: 50          moltype = AA  length = 276
FEATURE                Location/Qualifiers
source                 1..276
                       mol_type = protein
                       organism = Homo sapiens
SEQUENCE: 50
GSHSMRYFST SVSRPGRGEP RFIAVGYVDD TQFVRFDSDA ASQRMEPRAP WIEQEGPEYW  60
DEETGKVKAH SQTDRENLRI ALRYYNQSEA GSHTLQMMFG CDVGSDGRFL RGYHQYAYDG  120
KDYIALKEDL RSWTAADMAA QITKRKWEAA HVAEQQRAYL EGTCVDGLRR YLENGKETLQ  180
RTDPPKTHMT HHPISDHEAT LRCWALGFYP AEITLTWQRD GEDQTQDTEL VETRPAGDGT  240
FQKWAAVVVP SGEEQRYTCH VQHEGLPKPL TLRWEP                            276

SEQ ID NO: 51          moltype = AA  length = 276
FEATURE                Location/Qualifiers
source                 1..276
                       mol_type = protein
```

```
                         organism = Homo sapiens
SEQUENCE: 51
GSHSMRYFTT SVSRPGRGEP RFIAVGYVDD TQFVRFDSDA ASQRMEPRAP WIEQEGPEYW  60
DRNTRNVKAH SQIDRVDLGT LRGYYNQSEA GSHTIQMMYG CDVGSDGRFL RGYQQDAYDG  120
KDYIALNEDL RSWTAADMAA QITQRKWEAA RVAEQLRAYL EGTCVEWLRR YLENGKETLQ  180
RTDPPKTHMT HHAVSDHEAT LRCWALSFYP AEITLTWQRD GEDQTQDTEL VETRPAGDGT  240
FQKWASVVVP SGQEQRYTCH VQHEGLPKPL TLRWEP                            276

SEQ ID NO: 52            moltype = AA  length = 219
FEATURE                  Location/Qualifiers
SITE                     8
                         note = any amino acid other than aspartic acid
source                   1..219
                         mol_type = protein
                         organism = synthetic construct
SEQUENCE: 52
FTVTVPKXLY VVEYGSNMTI ECKFPVEKQL DLAALIVYWE MEDKNIIQFV HGEEDLKVQH  60
SSYRQRARLL KDQLSLGNAA LQITDVKLQD AGVYRCMISY GGADYKRITV KVNAPYNKIN  120
QRILVVDPVT SEHELTCQAE GYPKAEVIWT SSDHQVLSGK TTTTNSKREE KLFNVTSTLR  180
INTTTNEIFY CTFRRLDPEE NHTAELVIPG NILNVSIKI                         219

SEQ ID NO: 53            moltype = AA  length = 219
FEATURE                  Location/Qualifiers
SITE                     36
                         note = any amino acid other than isoleucine
source                   1..219
                         mol_type = protein
                         organism = synthetic construct
SEQUENCE: 53
FTVTVPKDLY VVEYGSNMTI ECKFPVEKQL DLAALXVYWE MEDKNIIQFV HGEEDLKVQH  60
SSYRQRARLL KDQLSLGNAA LQITDVKLQD AGVYRCMISY GGADYKRITV KVNAPYNKIN  120
QRILVVDPVT SEHELTCQAE GYPKAEVIWT SSDHQVLSGK TTTTNSKREE KLFNVTSTLR  180
INTTTNEIFY CTFRRLDPEE NHTAELVIPG NILNVSIKI                         219

SEQ ID NO: 54            moltype = AA  length = 219
FEATURE                  Location/Qualifiers
SITE                     54
                         note = any amino acid other than glutamine
source                   1..219
                         mol_type = protein
                         organism = synthetic construct
SEQUENCE: 54
FTVTVPKDLY VVEYGSNMTI ECKFPVEKQL DLAALIVYWE MEDKNIIQFV HGEXDLKVQH  60
SSYRQRARLL KDQLSLGNAA LQITDVKLQD AGVYRCMISY GGADYKRITV KVNAPYNKIN  120
QRILVVDPVT SEHELTCQAE GYPKAEVIWT SSDHQVLSGK TTTTNSKREE KLFNVTSTLR  180
INTTTNEIFY CTFRRLDPEE NHTAELVIPG NILNVSIKI                         219

SEQ ID NO: 55            moltype = AA  length = 208
FEATURE                  Location/Qualifiers
SITE                     19
                         note = any amino acid other than asparagine
source                   1..208
                         mol_type = protein
                         organism = synthetic construct
SEQUENCE: 55
VIHVTKEVKE VATLSCGHXV SVEELAQTRI YWQKEKKMVL TMMSGDMNIW PEYKNRTIFD  60
ITNNLSIVIL ALRPSDEGTY ECVVLKYEKD AFKREHLAEV TLSVKADFPT PSISDFEIPT  120
SNIRRIICST SGGFPEPHLS WLENGEELNA INTTVSQDPE TELYAVSSKL DFNMTTNHSF  180
MCLIKYGHLR VNQTFNWNTT KQEHFPDN                                     208

SEQ ID NO: 56            moltype = AA  length = 208
FEATURE                  Location/Qualifiers
SITE                     63
                         note = any amino acid other than asparagine
source                   1..208
                         mol_type = protein
                         organism = synthetic construct
SEQUENCE: 56
VIHVTKEVKE VATLSCGHNV SVEELAQTRI YWQKEKKMVL TMMSGDMNIW PEYKNRTIFD  60
ITXNLSIVIL ALRPSDEGTY ECVVLKYEKD AFKREHLAEV TLSVKADFPT PSISDFEIPT  120
SNIRRIICST SGGFPEPHLS WLENGEELNA INTTVSQDPE TELYAVSSKL DFNMTTNHSF  180
MCLIKYGHLR VNQTFNWNTT KQEHFPDN                                     208

SEQ ID NO: 57            moltype = AA  length = 208
FEATURE                  Location/Qualifiers
SITE                     67
                         note = any amino acid other than isoleucine
source                   1..208
                         mol_type = protein
```

```
                       organism = synthetic construct
SEQUENCE: 57
VIHVTKEVKE VATLSCGHNV SVEELAQTRI YWQKEKKMVL TMMSGDMNIW PEYKNRTIFD  60
ITNNLSXVIL ALRPSDEGTY ECVVLKYEKD AFKREHLAEV TLSVKADFPT PSISDFEIPT  120
SNIRRIICST SGGFPEPHLS WLENGEELNA INTTVSQDPE TELYAVSSKL DFNMTTNHSF  180
MCLIKYGHLR VNQTFNWNTT KQEHFPDN                                    208

SEQ ID NO: 58          moltype = AA  length = 208
FEATURE                Location/Qualifiers
SITE                   86
                       note = any amino acid other than lysine
source                 1..208
                       mol_type = protein
                       organism = synthetic construct
SEQUENCE: 58
VIHVTKEVKE VATLSCGHNV SVEELAQTRI YWQKEKKMVL TMMSGDMNIW PEYKNRTIFD  60
ITNNLSIVIL ALRPSDEGTY ECVVLXYEKD AFKREHLAEV TLSVKADFPT PSISDFEIPT  120
SNIRRIICST SGGFPEPHLS WLENGEELNA INTTVSQDPE TELYAVSSKL DFNMTTNHSF  180
MCLIKYGHLR VNQTFNWNTT KQEHFPDN                                    208

SEQ ID NO: 59          moltype = AA  length = 5
FEATURE                Location/Qualifiers
SITE                   4
                       note = any amino acid other than proline
source                 1..5
                       mol_type = protein
                       organism = synthetic construct
SEQUENCE: 59
VPGXG                                                             5

SEQ ID NO: 60          moltype = AA  length = 208
FEATURE                Location/Qualifiers
SITE                   157
                       note = any amino acid other than glutamine
source                 1..208
                       mol_type = protein
                       organism = synthetic construct
SEQUENCE: 60
VIHVTKEVKE VATLSCGHNV SVEELAQTRI YWQKEKKMVL TMMSGDMNIW PEYKNRTIFD  60
ITNNLSIVIL ALRPSDEGTY ECVVLKYEKD AFKREHLAEV TLSVKADFPT PSISDFEIPT  120
SNIRRIICST SGGFPEPHLS WLENGEELNA INTTVSXDPE TELYAVSSKL DFNMTTNHSF  180
MCLIKYGHLR VNQTFNWNTT KQEHFPDN                                    208

SEQ ID NO: 61          moltype = AA  length = 208
FEATURE                Location/Qualifiers
SITE                   158
                       note = any amino acid other than aspartic acid
source                 1..208
                       mol_type = protein
                       organism = synthetic construct
SEQUENCE: 61
VIHVTKEVKE VATLSCGHNV SVEELAQTRI YWQKEKKMVL TMMSGDMNIW PEYKNRTIFD  60
ITNNLSIVIL ALRPSDEGTY ECVVLKYEKD AFKREHLAEV TLSVKADFPT PSISDFEIPT  120
SNIRRIICST SGGFPEPHLS WLENGEELNA INTTVSQXPE TELYAVSSKL DFNMTTNHSF  180
MCLIKYGHLR VNQTFNWNTT KQEHFPDN                                    208

SEQ ID NO: 62          moltype = AA  length = 208
FEATURE                Location/Qualifiers
SITE                   25
                       note = any amino acid other than leucine
source                 1..208
                       mol_type = protein
                       organism = synthetic construct
SEQUENCE: 62
VIHVTKEVKE VATLSCGHNV SVEEXAQTRI YWQKEKKMVL TMMSGDMNIW PEYKNRTIFD  60
ITNNLSIVIL ALRPSDEGTY ECVVLKYEKD AFKREHLAEV TLSVKADFPT PSISDFEIPT  120
SNIRRIICST SGGFPEPHLS WLENGEELNA INTTVSQDPE TELYAVSSKL DFNMTTNHSF  180
MCLIKYGHLR VNQTFNWNTT KQEHFPDN                                    208

SEQ ID NO: 63          moltype = AA  length = 208
FEATURE                Location/Qualifiers
SITE                   31
                       note = any amino acid other than tyrosine
source                 1..208
                       mol_type = protein
                       organism = synthetic construct
SEQUENCE: 63
VIHVTKEVKE VATLSCGHNV SVEELAQTRI XWQKEKKMVL TMMSGDMNIW PEYKNRTIFD  60
ITNNLSIVIL ALRPSDEGTY ECVVLKYEKD AFKREHLAEV TLSVKADFPT PSISDFEIPT  120
```

```
SNIRRIICST SGGFPEPHLS WLENGEELNA INTTVSQDPE TELYAVSSKL DFNMTTNHSF  180
MCLIKYGHLR VNQTFNWNTT KQEHFPDN                                    208

SEQ ID NO: 64          moltype = AA  length = 208
FEATURE                Location/Qualifiers
SITE                   33
                       note = any amino acid other than glutamine
source                 1..208
                       mol_type = protein
                       organism = synthetic construct
SEQUENCE: 64
VIHVTKEVKE VATLSCGHNV SVEELAQTRI YWXKEKKMVL TMMSGDMNIW PEYKNRTIFD  60
ITNNLSIVIL ALRPSDEGTY ECVVLKYEKD AFKREHLAEV TLSVKADFPT PSISDFEIPT  120
SNIRRIICST SGGFPEPHLS WLENGEELNA INTTVSQDPE TELYAVSSKL DFNMTTNHSF  180
MCLIKYGHLR VNQTFNWNTT KQEHFPDN                                    208

SEQ ID NO: 65          moltype = AA  length = 208
FEATURE                Location/Qualifiers
SITE                   38
                       note = any amino acid other than methionine
source                 1..208
                       mol_type = protein
                       organism = synthetic construct
SEQUENCE: 65
VIHVTKEVKE VATLSCGHNV SVEELAQTRI YWQKEKKXVL TMMSGDMNIW PEYKNRTIFD  60
ITNNLSIVIL ALRPSDEGTY ECVVLKYEKD AFKREHLAEV TLSVKADFPT PSISDFEIPT  120
SNIRRIICST SGGFPEPHLS WLENGEELNA INTTVSQDPE TELYAVSSKL DFNMTTNHSF  180
MCLIKYGHLR VNQTFNWNTT KQEHFPDN                                    208

SEQ ID NO: 66          moltype = AA  length = 208
FEATURE                Location/Qualifiers
SITE                   39
                       note = any amino acid other than valine
source                 1..208
                       mol_type = protein
                       organism = synthetic construct
SEQUENCE: 66
VIHVTKEVKE VATLSCGHNV SVEELAQTRI YWQKEKKMXL TMMSGDMNIW PEYKNRTIFD  60
ITNNLSIVIL ALRPSDEGTY ECVVLKYEKD AFKREHLAEV TLSVKADFPT PSISDFEIPT  120
SNIRRIICST SGGFPEPHLS WLENGEELNA INTTVSQDPE TELYAVSSKL DFNMTTNHSF  180
MCLIKYGHLR VNQTFNWNTT KQEHFPDN                                    208

SEQ ID NO: 67          moltype = AA  length = 208
FEATURE                Location/Qualifiers
SITE                   49
                       note = any amino acid other than isoleucine
source                 1..208
                       mol_type = protein
                       organism = synthetic construct
SEQUENCE: 67
VIHVTKEVKE VATLSCGHNV SVEELAQTRI YWQKEKKMVL TMMSGDMNXW PEYKNRTIFD  60
ITNNLSIVIL ALRPSDEGTY ECVVLKYEKD AFKREHLAEV TLSVKADFPT PSISDFEIPT  120
SNIRRIICST SGGFPEPHLS WLENGEELNA INTTVSQDPE TELYAVSSKL DFNMTTNHSF  180
MCLIKYGHLR VNQTFNWNTT KQEHFPDN                                    208

SEQ ID NO: 68          moltype = AA  length = 208
FEATURE                Location/Qualifiers
SITE                   53
                       note = any amino acid other than tyrosine
source                 1..208
                       mol_type = protein
                       organism = synthetic construct
SEQUENCE: 68
VIHVTKEVKE VATLSCGHNV SVEELAQTRI YWQKEKKMVL TMMSGDMNIW PEXKNRTIFD  60
ITNNLSIVIL ALRPSDEGTY ECVVLKYEKD AFKREHLAEV TLSVKADFPT PSISDFEIPT  120
SNIRRIICST SGGFPEPHLS WLENGEELNA INTTVSQDPE TELYAVSSKL DFNMTTNHSF  180
MCLIKYGHLR VNQTFNWNTT KQEHFPDN                                    208

SEQ ID NO: 69          moltype = AA  length = 208
FEATURE                Location/Qualifiers
SITE                   60
                       note = any amino acid other than aspartic acid
source                 1..208
                       mol_type = protein
                       organism = synthetic construct
SEQUENCE: 69
VIHVTKEVKE VATLSCGHNV SVEELAQTRI YWQKEKKMVL TMMSGDMNIW PEYKNRTIFX  60
ITNNLSIVIL ALRPSDEGTY ECVVLKYEKD AFKREHLAEV TLSVKADFPT PSISDFEIPT  120
SNIRRIICST SGGFPEPHLS WLENGEELNA INTTVSQDPE TELYAVSSKL DFNMTTNHSF  180
```

```
MCLIKYGHLR VNQTFNWNTT KQEHFPDN                                  208

SEQ ID NO: 70          moltype = AA  length = 208
FEATURE                Location/Qualifiers
SITE                   108
                       note = any amino acid other than phenylalanine
source                 1..208
                       mol_type = protein
                       organism = synthetic construct
SEQUENCE: 70
VIHVTKEVKE VATLSCGHNV SVEELAQTRI YWQKEKKMVL TMMSGDMNIW PEYKNRTIFD  60
ITNNLSIVIL ALRPSDEGTY ECVVLKYEKD AFKREHLAEV TLSVKADXPT PSISDFEIPT  120
SNIRRIICST SGGFPEPHLS WLENGEELNA INTTVSQDPE TELYAVSSKL DFNMTTNHSF  180
MCLIKYGHLR VNQTFNWNTT KQEHFPDN                                  208

SEQ ID NO: 71          moltype = AA  length = 208
FEATURE                Location/Qualifiers
SITE                   156
                       note = any amino acid other than serine
source                 1..208
                       mol_type = protein
                       organism = synthetic construct
SEQUENCE: 71
VIHVTKEVKE VATLSCGHNV SVEELAQTRI YWQKEKKMVL TMMSGDMNIW PEYKNRTIFD  60
ITNNLSIVIL ALRPSDEGTY ECVVLKYEKD AFKREHLAEV TLSVKADFPT PSISDFEIPT  120
SNIRRIICST SGGFPEPHLS WLENGEELNA INTTVXQDPE TELYAVSSKL DFNMTTNHSF  180
MCLIKYGHLR VNQTFNWNTT KQEHFPDN                                  208

SEQ ID NO: 72          moltype = AA  length = 208
FEATURE                Location/Qualifiers
SITE                   111
                       note = any amino acid other than proline
source                 1..208
                       mol_type = protein
                       organism = synthetic construct
SEQUENCE: 72
VIHVTKEVKE VATLSCGHNV SVEELAQTRI YWQKEKKMVL TMMSGDMNIW PEYKNRTIFD  60
ITNNLSIVIL ALRPSDEGTY ECVVLKYEKD AFKREHLAEV TLSVKADFPT XSISDFEIPT  120
SNIRRIICST SGGFPEPHLS WLENGEELNA INTTVSQDPE TELYAVSSKL DFNMTTNHSF  180
MCLIKYGHLR VNQTFNWNTT KQEHFPDN                                  208

SEQ ID NO: 73          moltype = AA  length = 224
FEATURE                Location/Qualifiers
SITE                   61
                       note = any amino acid other than asparagine
source                 1..224
                       mol_type = protein
                       organism = synthetic construct
SEQUENCE: 73
APLKIQAYFN ETADLPCQFA NSQNQSLSEL VVFWQDQENL VLNEVYLGKE KFDSVHSKYM  60
XRTSFDSDSW TLRLHNLQIK DKGLYQCIIH HKKPTGMIRI HQMNSELSVL ANFSQPEIVP  120
ISNITENVYI NLTCSSIHGY PEPKKMSVLL RTKNSTIEYD GIMQKSQDNV TELYDVSISL  180
SVSFPDVTSN MTIFCILETD KTRLLSSPFS IELEDPQPPP DHIP                224

SEQ ID NO: 74          moltype = AA  length = 224
FEATURE                Location/Qualifiers
SITE                   66
                       note = any amino acid other than aspartic acid
source                 1..224
                       mol_type = protein
                       organism = synthetic construct
SEQUENCE: 74
APLKIQAYFN ETADLPCQFA NSQNQSLSEL VVFWQDQENL VLNEVYLGKE KFDSVHSKYM  60
NRTSFXSDSW TLRLHNLQIK DKGLYQCIIH HKKPTGMIRI HQMNSELSVL ANFSQPEIVP  120
ISNITENVYI NLTCSSIHGY PEPKKMSVLL RTKNSTIEYD GIMQKSQDNV TELYDVSISL  180
SVSFPDVTSN MTIFCILETD KTRLLSSPFS IELEDPQPPP DHIP                224

SEQ ID NO: 75          moltype = AA  length = 224
FEATURE                Location/Qualifiers
SITE                   70
                       note = any amino acid other than tryptophan
source                 1..224
                       mol_type = protein
                       organism = synthetic construct
SEQUENCE: 75
APLKIQAYFN ETADLPCQFA NSQNQSLSEL VVFWQDQENL VLNEVYLGKE KFDSVHSKYM  60
NRTSFDSDSX TLRLHNLQIK DKGLYQCIIH HKKPTGMIRI HQMNSELSVL ANFSQPEIVP  120
ISNITENVYI NLTCSSIHGY PEPKKMSVLL RTKNSTIEYD GIMQKSQDNV TELYDVSISL  180
SVSFPDVTSN MTIFCILETD KTRLLSSPFS IELEDPQPPP DHIP                224
```

```
SEQ ID NO: 76          moltype = AA  length = 224
FEATURE                Location/Qualifiers
SITE                   91
                       note = any amino acid other than histidine
source                 1..224
                       mol_type = protein
                       organism = synthetic construct
SEQUENCE: 76
APLKIQAYFN ETADLPCQFA NSQNQSLSEL VVFWQDQENL VLNEVYLGKE KFDSVHSKYM  60
NRTSFDSDSW TLRLHNLQIK DKGLYQCIIH XKKPTGMIRI HQMNSELSVL ANFSQPEIVP  120
ISNITENVYI NLTCSSIHGY PEPKKMSVLL RTKNSTIEYD GIMQKSQDNV TELYDVSISL  180
SVSFPDVTSN MTIFCILETD KTRLLSSPFS IELEDPQPPP DHIP                  224

SEQ ID NO: 77          moltype = AA  length = 110
FEATURE                Location/Qualifiers
SITE                   61
                       note = any amino acid other than asparagine
source                 1..110
                       mol_type = protein
                       organism = synthetic construct
SEQUENCE: 77
APLKIQAYFN ETADLPCQFA NSQNQSLSEL VVFWQDQENL VLNEVYLGKE KFDSVHSKYM  60
XRTSFDSDSW TLRLHNLQIK DKGLYQCIIH HKKPTGMIRI HQMNSELSVL             110

SEQ ID NO: 78          moltype = AA  length = 110
FEATURE                Location/Qualifiers
SITE                   66
                       note = any amino acid other than aspartic acid
source                 1..110
                       mol_type = protein
                       organism = synthetic construct
SEQUENCE: 78
APLKIQAYFN ETADLPCQFA NSQNQSLSEL VVFWQDQENL VLNEVYLGKE KFDSVHSKYM  60
NRTSFXSDSW TLRLHNLQIK DKGLYQCIIH HKKPTGMIRI HQMNSELSVL             110

SEQ ID NO: 79          moltype = AA  length = 110
FEATURE                Location/Qualifiers
SITE                   70
                       note = any amino acid other than tryptophan
source                 1..110
                       mol_type = protein
                       organism = synthetic construct
SEQUENCE: 79
APLKIQAYFN ETADLPCQFA NSQNQSLSEL VVFWQDQENL VLNEVYLGKE KFDSVHSKYM  60
NRTSFDSDSX TLRLHNLQIK DKGLYQCIIH HKKPTGMIRI HQMNSELSVL             110

SEQ ID NO: 80          moltype = AA  length = 110
FEATURE                Location/Qualifiers
SITE                   91
                       note = any amino acid other than histidine
source                 1..110
                       mol_type = protein
                       organism = synthetic construct
SEQUENCE: 80
APLKIQAYFN ETADLPCQFA NSQNQSLSEL VVFWQDQENL VLNEVYLGKE KFDSVHSKYM  60
NRTSFDSDSW TLRLHNLQIK DKGLYQCIIH XKKPTGMIRI HQMNSELSVL             110

SEQ ID NO: 81          moltype = AA  length = 224
FEATURE                Location/Qualifiers
SITE                   41
                       note = any amino acid other than valine
source                 1..224
                       mol_type = protein
                       organism = synthetic construct
SEQUENCE: 81
APLKIQAYFN ETADLPCQFA NSQNQSLSEL VVFWQDQENL XLNEVYLGKE KFDSVHSKYM  60
NRTSFDSDSW TLRLHNLQIK DKGLYQCIIH HKKPTGMIRI HQMNSELSVL ANFSQPEIVP  120
ISNITENVYI NLTCSSIHGY PEPKKMSVLL RTKNSTIEYD GIMQKSQDNV TELYDVSISL  180
SVSFPDVTSN MTIFCILETD KTRLLSSPFS IELEDPQPPP DHIP                  224

SEQ ID NO: 82          moltype = AA  length = 110
FEATURE                Location/Qualifiers
SITE                   41
                       note = any amino acid other than valine
source                 1..110
                       mol_type = protein
                       organism = synthetic construct
SEQUENCE: 82
```

```
APLKIQAYFN ETADLPCQFA NSQNQSLSEL VVFWQDQENL XLNEVYLGKE KFDSVHSKYM  60
NRTSFDSDSW TLRLHNLQIK DKGLYQCIIH HKKPTGMIRI HQMNSELSVL             110

SEQ ID NO: 83          moltype = AA  length = 224
FEATURE                Location/Qualifiers
SITE                   35
                       note = any amino acid other than glutamine
source                 1..224
                       mol_type = protein
                       organism = synthetic construct
SEQUENCE: 83
APLKIQAYFN ETADLPCQFA NSQNQSLSEL VVFWXDQENL VLNEVYLGKE KFDSVHSKYM  60
NRTSFDSDSW TLRLHNLQIK DKGLYQCIIH HKKPTGMIRI HQMNSELSVL ANFSQPEIVP  120
ISNITENVYI NLTCSSIHGY PEPKKMSVLL RTKNSTIEYD GIMQKSQDNV TELYDVSISL  180
SVSFPDVTSN MTIFCILETD KTRLLSSPFS IELEDPQPPP DHIP                  224

SEQ ID NO: 84          moltype = AA  length = 110
FEATURE                Location/Qualifiers
SITE                   35
                       note = any amino acid other than glutamine
source                 1..110
                       mol_type = protein
                       organism = synthetic construct
SEQUENCE: 84
APLKIQAYFN ETADLPCQFA NSQNQSLSEL VVFWXDQENL VLNEVYLGKE KFDSVHSKYM  60
NRTSFDSDSW TLRLHNLQIK DKGLYQCIIH HKKPTGMIRI HQMNSELSVL             110

SEQ ID NO: 85          moltype = AA  length = 224
FEATURE                Location/Qualifiers
SITE                   33
                       note = any amino acid other than phenylalanine
source                 1..224
                       mol_type = protein
                       organism = synthetic construct
SEQUENCE: 85
APLKIQAYFN ETADLPCQFA NSQNQSLSEL VVXWQDQENL VLNEVYLGKE KFDSVHSKYM  60
NRTSFDSDSW TLRLHNLQIK DKGLYQCIIH HKKPTGMIRI HQMNSELSVL ANFSQPEIVP  120
ISNITENVYI NLTCSSIHGY PEPKKMSVLL RTKNSTIEYD GIMQKSQDNV TELYDVSISL  180
SVSFPDVTSN MTIFCILETD KTRLLSSPFS IELEDPQPPP DHIP                  224

SEQ ID NO: 86          moltype = AA  length = 110
FEATURE                Location/Qualifiers
SITE                   33
                       note = any amino acid other than phenylalanine
source                 1..110
                       mol_type = protein
                       organism = synthetic construct
SEQUENCE: 86
APLKIQAYFN ETADLPCQFA NSQNQSLSEL VVXWQDQENL VLNEVYLGKE KFDSVHSKYM  60
NRTSFDSDSW TLRLHNLQIK DKGLYQCIIH HKKPTGMIRI HQMNSELSVL             110

SEQ ID NO: 87          moltype = AA  length = 224
FEATURE                Location/Qualifiers
SITE                   72
                       note = any amino acid other than leucine
source                 1..224
                       mol_type = protein
                       organism = synthetic construct
SEQUENCE: 87
APLKIQAYFN ETADLPCQFA NSQNQSLSEL VVFWQDQENL VLNEVYLGKE KFDSVHSKYM  60
NRTSFDSDSW TXRLHNLQIK DKGLYQCIIH HKKPTGMIRI HQMNSELSVL ANFSQPEIVP  120
ISNITENVYI NLTCSSIHGY PEPKKMSVLL RTKNSTIEYD GIMQKSQDNV TELYDVSISL  180
SVSFPDVTSN MTIFCILETD KTRLLSSPFS IELEDPQPPP DHIP                  224

SEQ ID NO: 88          moltype = AA  length = 110
FEATURE                Location/Qualifiers
SITE                   72
                       note = any amino acid other than leucine
source                 1..110
                       mol_type = protein
                       organism = synthetic construct
SEQUENCE: 88
APLKIQAYFN ETADLPCQFA NSQNQSLSEL VVFWQDQENL VLNEVYLGKE KFDSVHSKYM  60
NRTSFDSDSW TXRLHNLQIK DKGLYQCIIH HKKPTGMIRI HQMNSELSVL             110

SEQ ID NO: 89          moltype = AA  length = 224
FEATURE                Location/Qualifiers
SITE                   59
                       note = any amino acid other than tyrosine
```

```
source                  1..224
                        mol_type = protein
                        organism = synthetic construct
SEQUENCE: 89
APLKIQAYFN ETADLPCQFA NSQNQSLSEL VVFWQDQENL VLNEVYLGKE KFDSVHSKXM  60
NRTSFDSDSW TLRLHNLQIK DKGLYQCIIH HKKPTGMIRI HQMNSELSVL ANFSQPEIVP  120
ISNITENVYI NLTCSSIHGY PEPKKMSVLL RTKNSTIEYD GIMQKSQDNV TELYDVSISL  180
SVSFPDVTSN MTIFCILETD KTRLLSSPFS IELEDPQPPP DHIP                  224

SEQ ID NO: 90           moltype = AA  length = 110
FEATURE                 Location/Qualifiers
SITE                    59
                        note = any amino acid other than tyrosine
source                  1..110
                        mol_type = protein
                        organism = synthetic construct
SEQUENCE: 90
APLKIQAYFN ETADLPCQFA NSQNQSLSEL VVFWQDQENL VLNEVYLGKE KFDSVHSKXM  60
NRTSFDSDSW TLRLHNLQIK DKGLYQCIIH HKKPTGMIRI HQMNSELSVL             110

SEQ ID NO: 91           moltype = AA  length = 224
FEATURE                 Location/Qualifiers
SITE                    61
                        note = any amino acid other than asparagine
SITE                    91
                        note = any amino acid other than histidine
source                  1..224
                        mol_type = protein
                        organism = synthetic construct
SEQUENCE: 91
APLKIQAYFN ETADLPCQFA NSQNQSLSEL VVFWQDQENL VLNEVYLGKE KFDSVHSKYM  60
XRTSFDSDSW TLRLHNLQIK DKGLYQCIIH XKKPTGMIRI HQMNSELSVL ANFSQPEIVP  120
ISNITENVYI NLTCSSIHGY PEPKKMSVLL RTKNSTIEYD GIMQKSQDNV TELYDVSISL  180
SVSFPDVTSN MTIFCILETD KTRLLSSPFS IELEDPQPPP DHIP                  224

SEQ ID NO: 92           moltype = AA  length = 110
FEATURE                 Location/Qualifiers
SITE                    61
                        note = any amino acid other than asparagine
SITE                    91
                        note = any amino acid other than histidine
source                  1..110
                        mol_type = protein
                        organism = synthetic construct
SEQUENCE: 92
APLKIQAYFN ETADLPCQFA NSQNQSLSEL VVFWQDQENL VLNEVYLGKE KFDSVHSKYM  60
XRTSFDSDSW TLRLHNLQIK DKGLYQCIIH XKKPTGMIRI HQMNSELSVL             110

SEQ ID NO: 93           moltype = AA  length = 224
FEATURE                 Location/Qualifiers
SITE                    66
                        note = any amino acid other than aspartic acid
SITE                    91
                        note = any amino acid other than histidine
source                  1..224
                        mol_type = protein
                        organism = synthetic construct
SEQUENCE: 93
APLKIQAYFN ETADLPCQFA NSQNQSLSEL VVFWQDQENL VLNEVYLGKE KFDSVHSKYM  60
NRTSFXSDSW TLRLHNLQIK DKGLYQCIIH XKKPTGMIRI HQMNSELSVL ANFSQPEIVP  120
ISNITENVYI NLTCSSIHGY PEPKKMSVLL RTKNSTIEYD GIMQKSQDNV TELYDVSISL  180
SVSFPDVTSN MTIFCILETD KTRLLSSPFS IELEDPQPPP DHIP                  224

SEQ ID NO: 94           moltype = AA  length = 110
FEATURE                 Location/Qualifiers
SITE                    66
                        note = any amino acid other than asparagine
SITE                    91
                        note = Xaa can be any amino acid other than His
source                  1..110
                        mol_type = protein
                        organism = synthetic construct
SEQUENCE: 94
APLKIQAYFN ETADLPCQFA NSQNQSLSEL VVFWQDQENL VLNEVYLGKE KFDSVHSKYM  60
NRTSFXSDSW TLRLHNLQIK DKGLYQCIIH XKKPTGMIRI HQMNSELSVL             110

SEQ ID NO: 95           moltype = AA  length = 224
FEATURE                 Location/Qualifiers
SITE                    61
```

```
                        note = any amino acid other than asparagine
SITE                    66
                        note = any amino acid other than aspartic acid
SITE                    91
                        note = any amino acid other than histidine
source                  1..224
                        mol_type = protein
                        organism = synthetic construct
SEQUENCE: 95
APLKIQAYFN ETADLPCQFA NSQNQSLSEL VVFWQDQENL VLNEVYLGKE KFDSVHSKYM  60
XRTSFXSDSW TLRLHNLQIK DKGLYQCIIH XKKPTGMIRI HQMNSELSVL ANFSQPEIVP  120
ISNITENVYI NLTCSSIHGY PEPKKMSVLL RTKNSTIEYD GIMQKSQDNV TELYDVSISL  180
SVSFPDVTSN MTIFCILETD KTRLLSSPFS IELEDPQPPP DHIP                  224

SEQ ID NO: 96           moltype = AA  length = 110
FEATURE                 Location/Qualifiers
SITE                    61
                        note = any amino acid other than asparagine
SITE                    66
                        note = any amino acid other than aspartic acid
SITE                    91
                        note = any amino acid other than histidine
source                  1..110
                        mol_type = protein
                        organism = synthetic construct
SEQUENCE: 96
APLKIQAYFN ETADLPCQFA NSQNQSLSEL VVFWQDQENL VLNEVYLGKE KFDSVHSKYM  60
XRTSFXSDSW TLRLHNLQIK DKGLYQCIIH XKKPTGMIRI HQMNSELSVL             110

SEQ ID NO: 97           moltype = AA  length = 174
FEATURE                 Location/Qualifiers
SITE                    47
                        note = any amino acid other than lysine
source                  1..174
                        mol_type = protein
                        organism = synthetic construct
SEQUENCE: 97
PAGLLDLRQG MFAQLVAQNV LLIDGPLSWY SDPGLAGVSL TGGLSYXEDT KELVVAKAGV  60
YYVFFQLELR RVVAGEGSGS VSLALHLQPL RSAAGAAALA LTVDLPPASS EARNSAFGFQ  120
GRLLHLSAGQ RLGVHLHTEA RARHAWQLTQ GATVLGLFRV TPEIPAGLPS PRSE        174

SEQ ID NO: 98           moltype = AA  length = 174
FEATURE                 Location/Qualifiers
SITE                    147
                        note = any amino acid other than glutamine
source                  1..174
                        mol_type = protein
                        organism = synthetic construct
SEQUENCE: 98
PAGLLDLRQG MFAQLVAQNV LLIDGPLSWY SDPGLAGVSL TGGLSYKEDT KELVVAKAGV  60
YYVFFQLELR RVVAGEGSGS VSLALHLQPL RSAAGAAALA LTVDLPPASS EARNSAFGFQ  120
GRLLHLSAGQ RLGVHLHTEA RARHAWXLTQ GATVLGLFRV TPEIPAGLPS PRSE        174

SEQ ID NO: 99           moltype = AA  length = 174
FEATURE                 Location/Qualifiers
SITE                    11
                        note = any amino acid other than methionine
source                  1..174
                        mol_type = protein
                        organism = synthetic construct
SEQUENCE: 99
PAGLLDLRQG XFAQLVAQNV LLIDGPLSWY SDPGLAGVSL TGGLSYKEDT KELVVAKAGV  60
YYVFFQLELR RVVAGEGSGS VSLALHLQPL RSAAGAAALA LTVDLPPASS EARNSAFGFQ  120
GRLLHLSAGQ RLGVHLHTEA RARHAWQLTQ GATVLGLFRV TPEIPAGLPS PRSE        174

SEQ ID NO: 100          moltype = AA  length = 174
FEATURE                 Location/Qualifiers
SITE                    12
                        note = any amino acid other than phenylalanine
source                  1..174
                        mol_type = protein
                        organism = synthetic construct
SEQUENCE: 100
PAGLLDLRQG MXAQLVAQNV LLIDGPLSWY SDPGLAGVSL TGGLSYKEDT KELVVAKAGV  60
YYVFFQLELR RVVAGEGSGS VSLALHLQPL RSAAGAAALA LTVDLPPASS EARNSAFGFQ  120
GRLLHLSAGQ RLGVHLHTEA RARHAWQLTQ GATVLGLFRV TPEIPAGLPS PRSE        174

SEQ ID NO: 101          moltype = AA  length = 174
FEATURE                 Location/Qualifiers
```

```
SITE                    14
                        note = any amino acid other than glutamine
source                  1..174
                        mol_type = protein
                        organism = synthetic construct
SEQUENCE: 101
PAGLLDLRQG MFAXLVAQNV LLIDGPLSWY SDPGLAGVSL TGGLSYKEDT KELVVAKAGV  60
YYVFFQLELR RVVAGEGSGS VSLALHLQPL RSAAGAAALA LTVDLPPASS EARNSAFGFQ  120
GRLLHLSAGQ RLGVHLHTEA RARHAWQLTQ GATVLGLFRV TPEIPAGLPS PRSE        174

SEQ ID NO: 102          moltype = AA  length = 174
FEATURE                 Location/Qualifiers
SITE                    15
                        note = any amino acid other than leucine
source                  1..174
                        mol_type = protein
                        organism = synthetic construct
SEQUENCE: 102
PAGLLDLRQG MFAQXVAQNV LLIDGPLSWY SDPGLAGVSL TGGLSYKEDT KELVVAKAGV  60
YYVFFQLELR RVVAGEGSGS VSLALHLQPL RSAAGAAALA LTVDLPPASS EARNSAFGFQ  120
GRLLHLSAGQ RLGVHLHTEA RARHAWQLTQ GATVLGLFRV TPEIPAGLPS PRSE        174

SEQ ID NO: 103          moltype = AA  length = 174
FEATURE                 Location/Qualifiers
SITE                    16
                        note = any amino acid other than valine
source                  1..174
                        mol_type = protein
                        organism = synthetic construct
SEQUENCE: 103
PAGLLDLRQG MFAQLXAQNV LLIDGPLSWY SDPGLAGVSL TGGLSYKEDT KELVVAKAGV  60
YYVFFQLELR RVVAGEGSGS VSLALHLQPL RSAAGAAALA LTVDLPPASS EARNSAFGFQ  120
GRLLHLSAGQ RLGVHLHTEA RARHAWQLTQ GATVLGLFRV TPEIPAGLPS PRSE        174

SEQ ID NO: 104          moltype = AA  length = 174
FEATURE                 Location/Qualifiers
SITE                    18
                        note = any amino acid other than glutamine
source                  1..174
                        mol_type = protein
                        organism = synthetic construct
SEQUENCE: 104
PAGLLDLRQG MFAQLVAXNV LLIDGPLSWY SDPGLAGVSL TGGLSYKEDT KELVVAKAGV  60
YYVFFQLELR RVVAGEGSGS VSLALHLQPL RSAAGAAALA LTVDLPPASS EARNSAFGFQ  120
GRLLHLSAGQ RLGVHLHTEA RARHAWQLTQ GATVLGLFRV TPEIPAGLPS PRSE        174

SEQ ID NO: 105          moltype = AA  length = 174
FEATURE                 Location/Qualifiers
SITE                    19
                        note = any amino acid other than asparagined
source                  1..174
                        mol_type = protein
                        organism = synthetic construct
SEQUENCE: 105
PAGLLDLRQG MFAQLVAQXV LLIDGPLSWY SDPGLAGVSL TGGLSYKEDT KELVVAKAGV  60
YYVFFQLELR RVVAGEGSGS VSLALHLQPL RSAAGAAALA LTVDLPPASS EARNSAFGFQ  120
GRLLHLSAGQ RLGVHLHTEA RARHAWQLTQ GATVLGLFRV TPEIPAGLPS PRSE        174

SEQ ID NO: 106          moltype = AA  length = 174
FEATURE                 Location/Qualifiers
SITE                    20
                        note = any amino acid other than valine
source                  1..174
                        mol_type = protein
                        organism = synthetic construct
SEQUENCE: 106
PAGLLDLRQG MFAQLVAQNX LLIDGPLSWY SDPGLAGVSL TGGLSYKEDT KELVVAKAGV  60
YYVFFQLELR RVVAGEGSGS VSLALHLQPL RSAAGAAALA LTVDLPPASS EARNSAFGFQ  120
GRLLHLSAGQ RLGVHLHTEA RARHAWQLTQ GATVLGLFRV TPEIPAGLPS PRSE        174

SEQ ID NO: 107          moltype = AA  length = 174
FEATURE                 Location/Qualifiers
SITE                    21
                        note = any amino acid other than leucine
source                  1..174
                        mol_type = protein
                        organism = synthetic construct
SEQUENCE: 107
PAGLLDLRQG MFAQLVAQNV XLIDGPLSWY SDPGLAGVSL TGGLSYKEDT KELVVAKAGV  60
```

```
YYVFFQLELR RVVAGEGSGS VSLALHLQPL RSAAGAAALA LTVDLPPASS EARNSAFGFQ  120
GRLLHLSAGQ RLGVHLHTEA RARHAWQLTQ GATVLGLFRV TPEIPAGLPS PRSE        174

SEQ ID NO: 108         moltype = AA  length = 174
FEATURE                Location/Qualifiers
SITE                   22
                       note = any amino acid other than leucine
source                 1..174
                       mol_type = protein
                       organism = synthetic construct
SEQUENCE: 108
PAGLLDLRQG MFAQLVAQNV LXIDGPLSWY SDPGLAGVSL TGGLSYKEDT KELVVAKAGV  60
YYVFFQLELR RVVAGEGSGS VSLALHLQPL RSAAGAAALA LTVDLPPASS EARNSAFGFQ  120
GRLLHLSAGQ RLGVHLHTEA RARHAWQLTQ GATVLGLFRV TPEIPAGLPS PRSE        174

SEQ ID NO: 109         moltype = AA  length = 174
FEATURE                Location/Qualifiers
SITE                   23
                       note = any amino acid other than isoleucine
source                 1..174
                       mol_type = protein
                       organism = synthetic construct
SEQUENCE: 109
PAGLLDLRQG MFAQLVAQNV LLXDGPLSWY SDPGLAGVSL TGGLSYKEDT KELVVAKAGV  60
YYVFFQLELR RVVAGEGSGS VSLALHLQPL RSAAGAAALA LTVDLPPASS EARNSAFGFQ  120
GRLLHLSAGQ RLGVHLHTEA RARHAWQLTQ GATVLGLFRV TPEIPAGLPS PRSE        174

SEQ ID NO: 110         moltype = AA  length = 174
FEATURE                Location/Qualifiers
SITE                   24
                       note = any amino acid other than aspartic acid
source                 1..174
                       mol_type = protein
                       organism = synthetic construct
SEQUENCE: 110
PAGLLDLRQG MFAQLVAQNV LLIXGPLSWY SDPGLAGVSL TGGLSYKEDT KELVVAKAGV  60
YYVFFQLELR RVVAGEGSGS VSLALHLQPL RSAAGAAALA LTVDLPPASS EARNSAFGFQ  120
GRLLHLSAGQ RLGVHLHTEA RARHAWQLTQ GATVLGLFRV TPEIPAGLPS PRSE        174

SEQ ID NO: 111         moltype = AA  length = 174
FEATURE                Location/Qualifiers
SITE                   25
                       note = any amino acid other than glycine
source                 1..174
                       mol_type = protein
                       organism = synthetic construct
SEQUENCE: 111
PAGLLDLRQG MFAQLVAQNV LLIDXPLSWY SDPGLAGVSL TGGLSYKEDT KELVVAKAGV  60
YYVFFQLELR RVVAGEGSGS VSLALHLQPL RSAAGAAALA LTVDLPPASS EARNSAFGFQ  120
GRLLHLSAGQ RLGVHLHTEA RARHAWQLTQ GATVLGLFRV TPEIPAGLPS PRSE        174

SEQ ID NO: 112         moltype = AA  length = 174
FEATURE                Location/Qualifiers
SITE                   26
                       note = any amino acid other than proline
source                 1..174
                       mol_type = protein
                       organism = synthetic construct
SEQUENCE: 112
PAGLLDLRQG MFAQLVAQNV LLIGGXLSWY SDPGLAGVSL TGGLSYKEDT KELVVAKAGV  60
YYVFFQLELR RVVAGEGSGS VSLALHLQPL RSAAGAAALA LTVDLPPASS EARNSAFGFQ  120
GRLLHLSAGQ RLGVHLHTEA RARHAWQLTQ GATVLGLFRV TPEIPAGLPS PRSE        174

SEQ ID NO: 113         moltype = AA  length = 174
FEATURE                Location/Qualifiers
SITE                   27
                       note = any amino acid other than leucine
source                 1..174
                       mol_type = protein
                       organism = synthetic construct
SEQUENCE: 113
PAGLLDLRQG MFAQLVAQNV LLIGGPXSWY SDPGLAGVSL TGGLSYKEDT KELVVAKAGV  60
YYVFFQLELR RVVAGEGSGS VSLALHLQPL RSAAGAAALA LTVDLPPASS EARNSAFGFQ  120
GRLLHLSAGQ RLGVHLHTEA RARHAWQLTQ GATVLGLFRV TPEIPAGLPS PRSE        174

SEQ ID NO: 114         moltype = AA  length = 174
FEATURE                Location/Qualifiers
SITE                   28
                       note = any amino acid other than serine
```

```
source                  1..174
                        mol_type = protein
                        organism = synthetic construct
SEQUENCE: 114
PAGLLDLRQG MFAQLVAQNV LLIGGPLXWY SDPGLAGVSL TGGLSYKEDT KELVVAKAGV  60
YYVFFQLELR RVVAGEGSGS VSLALHLQPL RSAAGAAALA LTVDLPPASS EARNSAFGFQ  120
GRLLHLSAGQ RLGVHLHTEA RARHAWQLTQ GATVLGLFRV TPEIPAGLPS PRSE        174

SEQ ID NO: 115          moltype = AA  length = 174
FEATURE                 Location/Qualifiers
SITE                    29
                        note = any amino acid other than tryptophan
source                  1..174
                        mol_type = protein
                        organism = synthetic construct
SEQUENCE: 115
PAGLLDLRQG MFAQLVAQNV LLIGGPLSXY SDPGLAGVSL TGGLSYKEDT KELVVAKAGV  60
YYVFFQLELR RVVAGEGSGS VSLALHLQPL RSAAGAAALA LTVDLPPASS EARNSAFGFQ  120
GRLLHLSAGQ RLGVHLHTEA RARHAWQLTQ GATVLGLFRV TPEIPAGLPS PRSE        174

SEQ ID NO: 116          moltype = AA  length = 174
FEATURE                 Location/Qualifiers
SITE                    30
                        note = any amino acid other than tyrosine
source                  1..174
                        mol_type = protein
                        organism = synthetic construct
SEQUENCE: 116
PAGLLDLRQG MFAQLVAQNV LLIGGPLSWX SDPGLAGVSL TGGLSYKEDT KELVVAKAGV  60
YYVFFQLELR RVVAGEGSGS VSLALHLQPL RSAAGAAALA LTVDLPPASS EARNSAFGFQ  120
GRLLHLSAGQ RLGVHLHTEA RARHAWQLTQ GATVLGLFRV TPEIPAGLPS PRSE        174

SEQ ID NO: 117          moltype = AA  length = 174
FEATURE                 Location/Qualifiers
SITE                    31
                        note = any amino acid other than serine
source                  1..174
                        mol_type = protein
                        organism = synthetic construct
SEQUENCE: 117
PAGLLDLRQG MFAQLVAQNV LLIGGPLSWY XDPGLAGVSL TGGLSYKEDT KELVVAKAGV  60
YYVFFQLELR RVVAGEGSGS VSLALHLQPL RSAAGAAALA LTVDLPPASS EARNSAFGFQ  120
GRLLHLSAGQ RLGVHLHTEA RARHAWQLTQ GATVLGLFRV TPEIPAGLPS PRSE        174

SEQ ID NO: 118          moltype = AA  length = 174
FEATURE                 Location/Qualifiers
SITE                    32
                        note = any amino acid other than aspartic acid
source                  1..174
                        mol_type = protein
                        organism = synthetic construct
SEQUENCE: 118
PAGLLDLRQG MFAQLVAQNV LLIGGPLSWY SXPGLAGVSL TGGLSYKEDT KELVVAKAGV  60
YYVFFQLELR RVVAGEGSGS VSLALHLQPL RSAAGAAALA LTVDLPPASS EARNSAFGFQ  120
GRLLHLSAGQ RLGVHLHTEA RARHAWQLTQ GATVLGLFRV TPEIPAGLPS PRSE        174

SEQ ID NO: 119          moltype = AA  length = 174
FEATURE                 Location/Qualifiers
SITE                    33
                        note = any amino acid other than proline
source                  1..174
                        mol_type = protein
                        organism = synthetic construct
SEQUENCE: 119
PAGLLDLRQG MFAQLVAQNV LLIGGPLSWY SDXGLAGVSL TGGLSYKEDT KELVVAKAGV  60
YYVFFQLELR RVVAGEGSGS VSLALHLQPL RSAAGAAALA LTVDLPPASS EARNSAFGFQ  120
GRLLHLSAGQ RLGVHLHTEA RARHAWQLTQ GATVLGLFRV TPEIPAGLPS PRSE        174

SEQ ID NO: 120          moltype = AA  length = 174
FEATURE                 Location/Qualifiers
SITE                    34
                        note = any amino acid other than glycine
source                  1..174
                        mol_type = protein
                        organism = synthetic construct
SEQUENCE: 120
PAGLLDLRQG MFAQLVAQNV LLIGGPLSWY SDPXLAGVSL TGGLSYKEDT KELVVAKAGV  60
YYVFFQLELR RVVAGEGSGS VSLALHLQPL RSAAGAAALA LTVDLPPASS EARNSAFGFQ  120
GRLLHLSAGQ RLGVHLHTEA RARHAWQLTQ GATVLGLFRV TPEIPAGLPS PRSE        174
```

```
SEQ ID NO: 121          moltype = AA  length = 174
FEATURE                 Location/Qualifiers
SITE                    35
                        note = any amino acid other than leucine
source                  1..174
                        mol_type = protein
                        organism = synthetic construct
SEQUENCE: 121
PAGLLDLRQG MFAQLVAQNV LLIGGPLSWY SDPGXAGVSL TGGLSYKEDT KELVVAKAGV  60
YYVFFQLELR RVVAGEGSGS VSLALHLQPL RSAAGAAALA LTVDLPPASS EARNSAFGFQ  120
GRLLHLSAGQ RLGVHLHTEA RARHAWQLTQ GATVLGLFRV TPEIPAGLPS PRSE        174

SEQ ID NO: 122          moltype = AA  length = 174
FEATURE                 Location/Qualifiers
SITE                    37
                        note = any amino acid other than glycine
source                  1..174
                        mol_type = protein
                        organism = synthetic construct
SEQUENCE: 122
PAGLLDLRQG MFAQLVAQNV LLIGGPLSWY SDPGLAXVSL TGGLSYKEDT KELVVAKAGV  60
YYVFFQLELR RVVAGEGSGS VSLALHLQPL RSAAGAAALA LTVDLPPASS EARNSAFGFQ  120
GRLLHLSAGQ RLGVHLHTEA RARHAWQLTQ GATVLGLFRV TPEIPAGLPS PRSE        174

SEQ ID NO: 123          moltype = AA  length = 174
FEATURE                 Location/Qualifiers
SITE                    38
                        note = any amino acid other than valine
source                  1..174
                        mol_type = protein
                        organism = synthetic construct
SEQUENCE: 123
PAGLLDLRQG MFAQLVAQNV LLIGGPLSWY SDPGLAGXSL TGGLSYKEDT KELVVAKAGV  60
YYVFFQLELR RVVAGEGSGS VSLALHLQPL RSAAGAAALA LTVDLPPASS EARNSAFGFQ  120
GRLLHLSAGQ RLGVHLHTEA RARHAWQLTQ GATVLGLFRV TPEIPAGLPS PRSE        174

SEQ ID NO: 124          moltype = AA  length = 174
FEATURE                 Location/Qualifiers
SITE                    39
                        note = any amino acid other than serine
source                  1..174
                        mol_type = protein
                        organism = synthetic construct
SEQUENCE: 124
PAGLLDLRQG MFAQLVAQNV LLIGGPLSWY SDPGLAGVXL TGGLSYKEDT KELVVAKAGV  60
YYVFFQLELR RVVAGEGSGS VSLALHLQPL RSAAGAAALA LTVDLPPASS EARNSAFGFQ  120
GRLLHLSAGQ RLGVHLHTEA RARHAWQLTQ GATVLGLFRV TPEIPAGLPS PRSE        174

SEQ ID NO: 125          moltype = AA  length = 174
FEATURE                 Location/Qualifiers
SITE                    40
                        note = any amino acid other than leucine
source                  1..174
                        mol_type = protein
                        organism = synthetic construct
SEQUENCE: 125
PAGLLDLRQG MFAQLVAQNV LLIGGPLSWY SDPGLAGVSX TGGLSYKEDT KELVVAKAGV  60
YYVFFQLELR RVVAGEGSGS VSLALHLQPL RSAAGAAALA LTVDLPPASS EARNSAFGFQ  120
GRLLHLSAGQ RLGVHLHTEA RARHAWQLTQ GATVLGLFRV TPEIPAGLPS PRSE        174

SEQ ID NO: 126          moltype = AA  length = 174
FEATURE                 Location/Qualifiers
SITE                    41
                        note = any amino acid other than threonine
source                  1..174
                        mol_type = protein
                        organism = synthetic construct
SEQUENCE: 126
PAGLLDLRQG MFAQLVAQNV LLIGGPLSWY SDPGLAGVSL XGGLSYKEDT KELVVAKAGV  60
YYVFFQLELR RVVAGEGSGS VSLALHLQPL RSAAGAAALA LTVDLPPASS EARNSAFGFQ  120
GRLLHLSAGQ RLGVHLHTEA RARHAWQLTQ GATVLGLFRV TPEIPAGLPS PRSE        174

SEQ ID NO: 127          moltype = AA  length = 174
FEATURE                 Location/Qualifiers
SITE                    42
                        note = any amino acid other than glycine
source                  1..174
                        mol_type = protein
```

```
                        organism = synthetic construct
SEQUENCE: 127
PAGLLDLRQG MFAQLVAQNV LLIGGPLSWY SDPGLAGVSL TXGLSYKEDT KELVVAKAGV  60
YYVFFQLELR RVVAGEGSGS VSLALHLQPL RSAAGAAALA LTVDLPPASS EARNSAFGFQ  120
GRLLHLSAGQ RLGVHLHTEA RARHAWQLTQ GATVLGLFRV TPEIPAGLPS PRSE        174

SEQ ID NO: 128          moltype = AA  length = 174
FEATURE                 Location/Qualifiers
SITE                    43
                        note = any amino acid other than glycine
source                  1..174
                        mol_type = protein
                        organism = synthetic construct
SEQUENCE: 128
PAGLLDLRQG MFAQLVAQNV LLIGGPLSWY SDPGLAGVSL TGXLSYKEDT KELVVAKAGV  60
YYVFFQLELR RVVAGEGSGS VSLALHLQPL RSAAGAAALA LTVDLPPASS EARNSAFGFQ  120
GRLLHLSAGQ RLGVHLHTEA RARHAWQLTQ GATVLGLFRV TPEIPAGLPS PRSE        174

SEQ ID NO: 129          moltype = AA  length = 174
FEATURE                 Location/Qualifiers
SITE                    44
                        note = any amino acid other than leucine
source                  1..174
                        mol_type = protein
                        organism = synthetic construct
SEQUENCE: 129
PAGLLDLRQG MFAQLVAQNV LLIGGPLSWY SDPGLAGVSL TGGXSYKEDT KELVVAKAGV  60
YYVFFQLELR RVVAGEGSGS VSLALHLQPL RSAAGAAALA LTVDLPPASS EARNSAFGFQ  120
GRLLHLSAGQ RLGVHLHTEA RARHAWQLTQ GATVLGLFRV TPEIPAGLPS PRSE        174

SEQ ID NO: 130          moltype = AA  length = 174
FEATURE                 Location/Qualifiers
SITE                    45
                        note = any amino acid other than serine
source                  1..174
                        mol_type = protein
                        organism = synthetic construct
SEQUENCE: 130
PAGLLDLRQG MFAQLVAQNV LLIGGPLSWY SDPGLAGVSL TGGLXYKEDT KELVVAKAGV  60
YYVFFQLELR RVVAGEGSGS VSLALHLQPL RSAAGAAALA LTVDLPPASS EARNSAFGFQ  120
GRLLHLSAGQ RLGVHLHTEA RARHAWQLTQ GATVLGLFRV TPEIPAGLPS PRSE        174

SEQ ID NO: 131          moltype = AA  length = 174
FEATURE                 Location/Qualifiers
SITE                    46
                        note = any amino acid other than tyrosine
source                  1..174
                        mol_type = protein
                        organism = synthetic construct
SEQUENCE: 131
PAGLLDLRQG MFAQLVAQNV LLIGGPLSWY SDPGLAGVSL TGGLSXKEDT KELVVAKAGV  60
YYVFFQLELR RVVAGEGSGS VSLALHLQPL RSAAGAAALA LTVDLPPASS EARNSAFGFQ  120
GRLLHLSAGQ RLGVHLHTEA RARHAWQLTQ GATVLGLFRV TPEIPAGLPS PRSE        174

SEQ ID NO: 132          moltype = AA  length = 174
FEATURE                 Location/Qualifiers
SITE                    48
                        note = any amino acid other than glutamic acid
source                  1..174
                        mol_type = protein
                        organism = synthetic construct
SEQUENCE: 132
PAGLLDLRQG MFAQLVAQNV LLIGGPLSWY SDPGLAGVSL TGGLSYKXDT KELVVAKAGV  60
YYVFFQLELR RVVAGEGSGS VSLALHLQPL RSAAGAAALA LTVDLPPASS EARNSAFGFQ  120
GRLLHLSAGQ RLGVHLHTEA RARHAWQLTQ GATVLGLFRV TPEIPAGLPS PRSE        174

SEQ ID NO: 133          moltype = AA  length = 174
FEATURE                 Location/Qualifiers
SITE                    49
                        note = any amino acid other than aspartic acid
source                  1..174
                        mol_type = protein
                        organism = synthetic construct
SEQUENCE: 133
PAGLLDLRQG MFAQLVAQNV LLIGGPLSWY SDPGLAGVSL TGGLSYKEXT KELVVAKAGV  60
YYVFFQLELR RVVAGEGSGS VSLALHLQPL RSAAGAAALA LTVDLPPASS EARNSAFGFQ  120
GRLLHLSAGQ RLGVHLHTEA RARHAWQLTQ GATVLGLFRV TPEIPAGLPS PRSE        174

SEQ ID NO: 134          moltype = AA  length = 174
```

```
FEATURE                Location/Qualifiers
SITE                   50
                       note = any amino acid other than threonine
source                 1..174
                       mol_type = protein
                       organism = synthetic construct
SEQUENCE: 134
PAGLLDLRQG MFAQLVAQNV LLIGGPLSWY SDPGLAGVSL TGGLSYKEDX KELVVAKAGV  60
YYVFFQLELR RVVAGEGSGS VSLALHLQPL RSAAGAAALA LTVDLPPASS EARNSAFGFQ  120
GRLLHLSAGQ RLGVHLHTEA RARHAWQLTQ GATVLGLFRV TPEIPAGLPS PRSE        174

SEQ ID NO: 135         moltype = AA  length = 174
FEATURE                Location/Qualifiers
SITE                   51
                       note = any amino acid other than lysine
source                 1..174
                       mol_type = protein
                       organism = synthetic construct
SEQUENCE: 135
PAGLLDLRQG MFAQLVAQNV LLIGGPLSWY SDPGLAGVSL TGGLSYKEDT XELVVAKAGV  60
YYVFFQLELR RVVAGEGSGS VSLALHLQPL RSAAGAAALA LTVDLPPASS EARNSAFGFQ  120
GRLLHLSAGQ RLGVHLHTEA RARHAWQLTQ GATVLGLFRV TPEIPAGLPS PRSE        174

SEQ ID NO: 136         moltype = AA  length = 174
FEATURE                Location/Qualifiers
SITE                   52
                       note = any amino acid other than glutamic acid
source                 1..174
                       mol_type = protein
                       organism = synthetic construct
SEQUENCE: 136
PAGLLDLRQG MFAQLVAQNV LLIGGPLSWY SDPGLAGVSL TGGLSYKEDT KXLVVAKAGV  60
YYVFFQLELR RVVAGEGSGS VSLALHLQPL RSAAGAAALA LTVDLPPASS EARNSAFGFQ  120
GRLLHLSAGQ RLGVHLHTEA RARHAWQLTQ GATVLGLFRV TPEIPAGLPS PRSE        174

SEQ ID NO: 137         moltype = AA  length = 174
FEATURE                Location/Qualifiers
SITE                   64
                       note = any amino acid other than phenylalanine
source                 1..174
                       mol_type = protein
                       organism = synthetic construct
SEQUENCE: 137
PAGLLDLRQG MFAQLVAQNV LLIGGPLSWY SDPGLAGVSL TGGLSYKEDT KELVVAKAGV  60
YYVXFQLELR RVVAGEGSGS VSLALHLQPL RSAAGAAALA LTVDLPPASS EARNSAFGFQ  120
GRLLHLSAGQ RLGVHLHTEA RARHAWQLTQ GATVLGLFRV TPEIPAGLPS PRSE        174

SEQ ID NO: 138         moltype = AA  length = 174
FEATURE                Location/Qualifiers
SITE                   65
                       note = any amino acid other than phenylalanine
source                 1..174
                       mol_type = protein
                       organism = synthetic construct
SEQUENCE: 138
PAGLLDLRQG MFAQLVAQNV LLIGGPLSWY SDPGLAGVSL TGGLSYKEDT KELVVAKAGV  60
YYVFXQLELR RVVAGEGSGS VSLALHLQPL RSAAGAAALA LTVDLPPASS EARNSAFGFQ  120
GRLLHLSAGQ RLGVHLHTEA RARHAWQLTQ GATVLGLFRV TPEIPAGLPS PRSE        174

SEQ ID NO: 139         moltype = AA  length = 174
FEATURE                Location/Qualifiers
SITE                   66
                       note = any amino acid other than glutamine
source                 1..174
                       mol_type = protein
                       organism = synthetic construct
SEQUENCE: 139
PAGLLDLRQG MFAQLVAQNV LLIGGPLSWY SDPGLAGVSL TGGLSYKEDT KELVVAKAGV  60
YYVFFXLELR RVVAGEGSGS VSLALHLQPL RSAAGAAALA LTVDLPPASS EARNSAFGFQ  120
GRLLHLSAGQ RLGVHLHTEA RARHAWQLTQ GATVLGLFRV TPEIPAGLPS PRSE        174

SEQ ID NO: 140         moltype = AA  length = 174
FEATURE                Location/Qualifiers
SITE                   67
                       note = any amino acid other than leucine
source                 1..174
                       mol_type = protein
                       organism = synthetic construct
SEQUENCE: 140
```

```
PAGLLDLRQG MFAQLVAQNV LLIGGPLSWY SDPGLAGVSL TGGLSYKEDT KELVVAKAGV  60
YYVFFQXELR RVVAGEGSGS VSLALHLQPL RSAAGAAALA LTVDLPPASS EARNSAFGFQ  120
GRLLHLSAGQ RLGVHLHTEA RARHAWQLTQ GATVLGLFRV TPEIPAGLPS PRSE        174

SEQ ID NO: 141         moltype = AA  length = 174
FEATURE                Location/Qualifiers
SITE                   68
                       note = any amino acid other than glutamic acid
source                 1..174
                       mol_type = protein
                       organism = synthetic construct
SEQUENCE: 141
PAGLLDLRQG MFAQLVAQNV LLIGGPLSWY SDPGLAGVSL TGGLSYKEDT KELVVAKAGV  60
YYVFFQLXLR RVVAGEGSGS VSLALHLQPL RSAAGAAALA LTVDLPPASS EARNSAFGFQ  120
GRLLHLSAGQ RLGVHLHTEA RARHAWQLTQ GATVLGLFRV TPEIPAGLPS PRSE        174

SEQ ID NO: 142         moltype = AA  length = 174
FEATURE                Location/Qualifiers
SITE                   69
                       note = any amino acid other than leucine
source                 1..174
                       mol_type = protein
                       organism = synthetic construct
SEQUENCE: 142
PAGLLDLRQG MFAQLVAQNV LLIGGPLSWY SDPGLAGVSL TGGLSYKEDT KELVVAKAGV  60
YYVFFQLEXR RVVAGEGSGS VSLALHLQPL RSAAGAAALA LTVDLPPASS EARNSAFGFQ  120
GRLLHLSAGQ RLGVHLHTEA RARHAWQLTQ GATVLGLFRV TPEIPAGLPS PRSE        174

SEQ ID NO: 143         moltype = AA  length = 174
FEATURE                Location/Qualifiers
SITE                   70
                       note = any amino acid other than arginine
source                 1..174
                       mol_type = protein
                       organism = synthetic construct
SEQUENCE: 143
PAGLLDLRQG MFAQLVAQNV LLIGGPLSWY SDPGLAGVSL TGGLSYKEDT KELVVAKAGV  60
YYVFFQLELX RVVAGEGSGS VSLALHLQPL RSAAGAAALA LTVDLPPASS EARNSAFGFQ  120
GRLLHLSAGQ RLGVHLHTEA RARHAWQLTQ GATVLGLFRV TPEIPAGLPS PRSE        174

SEQ ID NO: 144         moltype = AA  length = 174
FEATURE                Location/Qualifiers
SITE                   71
                       note = any amino acid other than arginine
source                 1..174
                       mol_type = protein
                       organism = synthetic construct
SEQUENCE: 144
PAGLLDLRQG MFAQLVAQNV LLIGGPLSWY SDPGLAGVSL TGGLSYKEDT KELVVAKAGV  60
YYVFFQLELR XVVAGEGSGS VSLALHLQPL RSAAGAAALA LTVDLPPASS EARNSAFGFQ  120
GRLLHLSAGQ RLGVHLHTEA RARHAWQLTQ GATVLGLFRV TPEIPAGLPS PRSE        174

SEQ ID NO: 145         moltype = AA  length = 174
FEATURE                Location/Qualifiers
SITE                   72
                       note = any amino acid other than valine
source                 1..174
                       mol_type = protein
                       organism = synthetic construct
SEQUENCE: 145
PAGLLDLRQG MFAQLVAQNV LLIGGPLSWY SDPGLAGVSL TGGLSYKEDT KELVVAKAGV  60
YYVFFQLELR RXVAGEGSGS VSLALHLQPL RSAAGAAALA LTVDLPPASS EARNSAFGFQ  120
GRLLHLSAGQ RLGVHLHTEA RARHAWQLTQ GATVLGLFRV TPEIPAGLPS PRSE        174

SEQ ID NO: 146         moltype = AA  length = 174
FEATURE                Location/Qualifiers
SITE                   73
                       note = any amino acid other than valine
source                 1..174
                       mol_type = protein
                       organism = synthetic construct
SEQUENCE: 146
PAGLLDLRQG MFAQLVAQNV LLIGGPLSWY SDPGLAGVSL TGGLSYKEDT KELVVAKAGV  60
YYVFFQLELR RVXAGEGSGS VSLALHLQPL RSAAGAAALA LTVDLPPASS EARNSAFGFQ  120
GRLLHLSAGQ RLGVHLHTEA RARHAWQLTQ GATVLGLFRV TPEIPAGLPS PRSE        174

SEQ ID NO: 147         moltype = AA  length = 174
FEATURE                Location/Qualifiers
SITE                   75
```

```
                        note = any amino acid other than glycine
source                  1..174
                        mol_type = protein
                        organism = synthetic construct
SEQUENCE: 147
PAGLLDLRQG MFAQLVAQNV LLIGGPLSWY SDPGLAGVSL TGGLSYKEDT KELVVAKAGV  60
YYVFFQLELR RVVAXEGSGS VSLALHLQPL RSAAGAAALA LTVDLPPASS EARNSAFGFQ  120
GRLLHLSAGQ RLGVHLHTEA RARHAWQLTQ GATVLGLFRV TPEIPAGLPS PRSE        174

SEQ ID NO: 148          moltype = AA  length = 174
FEATURE                 Location/Qualifiers
SITE                    76
                        note = any amino acid other than glutamic acid
source                  1..174
                        mol_type = protein
                        organism = synthetic construct
SEQUENCE: 148
PAGLLDLRQG MFAQLVAQNV LLIGGPLSWY SDPGLAGVSL TGGLSYKEDT KELVVAKAGV  60
YYVFFQLELR RVVAGXGSGS VSLALHLQPL RSAAGAAALA LTVDLPPASS EARNSAFGFQ  120
GRLLHLSAGQ RLGVHLHTEA RARHAWQLTQ GATVLGLFRV TPEIPAGLPS PRSE        174

SEQ ID NO: 149          moltype = AA  length = 174
FEATURE                 Location/Qualifiers
SITE                    77
                        note = any amino acid other than glycine
source                  1..174
                        mol_type = protein
                        organism = synthetic construct
SEQUENCE: 149
PAGLLDLRQG MFAQLVAQNV LLIGGPLSWY SDPGLAGVSL TGGLSYKEDT KELVVAKAGV  60
YYVFFQLELR RVVAGEXSGS VSLALHLQPL RSAAGAAALA LTVDLPPASS EARNSAFGFQ  120
GRLLHLSAGQ RLGVHLHTEA RARHAWQLTQ GATVLGLFRV TPEIPAGLPS PRSE        174

SEQ ID NO: 150          moltype = AA  length = 174
FEATURE                 Location/Qualifiers
SITE                    78
                        note = any amino acid other than serine
source                  1..174
                        mol_type = protein
                        organism = synthetic construct
SEQUENCE: 150
PAGLLDLRQG MFAQLVAQNV LLIGGPLSWY SDPGLAGVSL TGGLSYKEDT KELVVAKAGV  60
YYVFFQLELR RVVAGEGXGS VSLALHLQPL RSAAGAAALA LTVDLPPASS EARNSAFGFQ  120
GRLLHLSAGQ RLGVHLHTEA RARHAWQLTQ GATVLGLFRV TPEIPAGLPS PRSE        174

SEQ ID NO: 151          moltype = AA  length = 174
FEATURE                 Location/Qualifiers
SITE                    104
                        note = any amino acid other than aspartic acid
source                  1..174
                        mol_type = protein
                        organism = synthetic construct
SEQUENCE: 151
PAGLLDLRQG MFAQLVAQNV LLIGGPLSWY SDPGLAGVSL TGGLSYKEDT KELVVAKAGV  60
YYVFFQLELR RVVAGEGSGS VSLALHLQPL RSAAGAAALA LTVXLPPASS EARNSAFGFQ  120
GRLLHLSAGQ RLGVHLHTEA RARHAWQLTQ GATVLGLFRV TPEIPAGLPS PRSE        174

SEQ ID NO: 152          moltype = AA  length = 174
FEATURE                 Location/Qualifiers
SITE                    105
                        note = any amino acid other than leucine
source                  1..174
                        mol_type = protein
                        organism = synthetic construct
SEQUENCE: 152
PAGLLDLRQG MFAQLVAQNV LLIGGPLSWY SDPGLAGVSL TGGLSYKEDT KELVVAKAGV  60
YYVFFQLELR RVVAGEGSGS VSLALHLQPL RSAAGAAALA LTVDXPPASS EARNSAFGFQ  120
GRLLHLSAGQ RLGVHLHTEA RARHAWQLTQ GATVLGLFRV TPEIPAGLPS PRSE        174

SEQ ID NO: 153          moltype = AA  length = 174
FEATURE                 Location/Qualifiers
SITE                    106
                        note = any amino acid other than proline
source                  1..174
                        mol_type = protein
                        organism = synthetic construct
SEQUENCE: 153
PAGLLDLRQG MFAQLVAQNV LLIGGPLSWY SDPGLAGVSL TGGLSYKEDT KELVVAKAGV  60
YYVFFQLELR RVVAGEGSGS VSLALHLQPL RSAAGAAALA LTVDLXPASS EARNSAFGFQ  120
```

```
GRLLHLSAGQ RLGVHLHTEA RARHAWQLTQ GATVLGLFRV TPEIPAGLPS PRSE        174

SEQ ID NO: 154          moltype = AA  length = 174
FEATURE                 Location/Qualifiers
SITE                    109
                        note = any amino acid other than serine
source                  1..174
                        mol_type = protein
                        organism = synthetic construct
SEQUENCE: 154
PAGLLDLRQG MFAQLVAQNV LLIGGPLSWY SDPGLAGVSL TGGLSYKEDT KELVVAKAGV  60
YYVFFQLELR RVVAGEGSGS VSLALHLQPL RSAAGAAALA LTVDLPPAXS EARNSAFGFQ  120
GRLLHLSAGQ RLGVHLHTEA RARHAWQLTQ GATVLGLFRV TPEIPAGLPS PRSE        174

SEQ ID NO: 155          moltype = AA  length = 174
FEATURE                 Location/Qualifiers
SITE                    110
                        note = any amino acid other than serine
source                  1..174
                        mol_type = protein
                        organism = synthetic construct
SEQUENCE: 155
PAGLLDLRQG MFAQLVAQNV LLIGGPLSWY SDPGLAGVSL TGGLSYKEDT KELVVAKAGV  60
YYVFFQLELR RVVAGEGSGS VSLALHLQPL RSAAGAAALA LTVDLPPASX EARNSAFGFQ  120
GRLLHLSAGQ RLGVHLHTEA RARHAWQLTQ GATVLGLFRV TPEIPAGLPS PRSE        174

SEQ ID NO: 156          moltype = AA  length = 174
FEATURE                 Location/Qualifiers
SITE                    111
                        note = any amino acid other than glutamic acid
source                  1..174
                        mol_type = protein
                        organism = synthetic construct
SEQUENCE: 156
PAGLLDLRQG MFAQLVAQNV LLIGGPLSWY SDPGLAGVSL TGGLSYKEDT KELVVAKAGV  60
YYVFFQLELR RVVAGEGSGS VSLALHLQPL RSAAGAAALA LTVDLPPASS XARNSAFGFQ  120
GRLLHLSAGQ RLGVHLHTEA RARHAWQLTQ GATVLGLFRV TPEIPAGLPS PRSE        174

SEQ ID NO: 157          moltype = AA  length = 174
FEATURE                 Location/Qualifiers
SITE                    113
                        note = any amino acid other than arginine
source                  1..174
                        mol_type = protein
                        organism = synthetic construct
SEQUENCE: 157
PAGLLDLRQG MFAQLVAQNV LLIGGPLSWY SDPGLAGVSL TGGLSYKEDT KELVVAKAGV  60
YYVFFQLELR RVVAGEGSGS VSLALHLQPL RSAAGAAALA LTVDLPPASS EAXNSAFGFQ  120
GRLLHLSAGQ RLGVHLHTEA RARHAWQLTQ GATVLGLFRV TPEIPAGLPS PRSE        174

SEQ ID NO: 158          moltype = AA  length = 174
FEATURE                 Location/Qualifiers
SITE                    114
                        note = any amino acid other than asparagine
source                  1..174
                        mol_type = protein
                        organism = synthetic construct
SEQUENCE: 158
PAGLLDLRQG MFAQLVAQNV LLIGGPLSWY SDPGLAGVSL TGGLSYKEDT KELVVAKAGV  60
YYVFFQLELR RVVAGEGSGS VSLALHLQPL RSAAGAAALA LTVDLPPASS EARXSAFGFQ  120
GRLLHLSAGQ RLGVHLHTEA RARHAWQLTQ GATVLGLFRV TPEIPAGLPS PRSE        174

SEQ ID NO: 159          moltype = AA  length = 174
FEATURE                 Location/Qualifiers
SITE                    115
                        note = any amino acid other than serine
source                  1..174
                        mol_type = protein
                        organism = synthetic construct
SEQUENCE: 159
PAGLLDLRQG MFAQLVAQNV LLIGGPLSWY SDPGLAGVSL TGGLSYKEDT KELVVAKAGV  60
YYVFFQLELR RVVAGEGSGS VSLALHLQPL RSAAGAAALA LTVDLPPASS EARNXAFGFQ  120
GRLLHLSAGQ RLGVHLHTEA RARHAWQLTQ GATVLGLFRV TPEIPAGLPS PRSE        174

SEQ ID NO: 160          moltype = AA  length = 174
FEATURE                 Location/Qualifiers
SITE                    117
                        note = any amino acid other than phenylalanine
source                  1..174
```

```
                         mol_type = protein
                         organism = synthetic construct
SEQUENCE: 160
PAGLLDLRQG MFAQLVAQNV LLIGGPLSWY SDPGLAGVSL TGGLSYKEDT KELVVAKAGV  60
YYVFFQLELR RVVAGEGSGS VSLALHLQPL RSAAGAAALA LTVDLPPASS EARNSAXGFQ  120
GRLLHLSAGQ RLGVHLHTEA RARHAWQLTQ GATVLGLFRV TPEIPAGLPS PRSE        174

SEQ ID NO: 161           moltype = AA  length = 174
FEATURE                  Location/Qualifiers
SITE                     130
                         note = any amino acid other than glutamine
source                   1..174
                         mol_type = protein
                         organism = synthetic construct
SEQUENCE: 161
PAGLLDLRQG MFAQLVAQNV LLIGGPLSWY SDPGLAGVSL TGGLSYKEDT KELVVAKAGV  60
YYVFFQLELR RVVAGEGSGS VSLALHLQPL RSAAGAAALA LTVDLPPASS EARNSAFGFQ  120
GRLLHLSAGX RLGVHLHTEA RARHAWQLTQ GATVLGLFRV TPEIPAGLPS PRSE        174

SEQ ID NO: 162           moltype = AA  length = 174
FEATURE                  Location/Qualifiers
SITE                     131
                         note = any amino acid other than arginine
source                   1..174
                         mol_type = protein
                         organism = synthetic construct
SEQUENCE: 162
PAGLLDLRQG MFAQLVAQNV LLIGGPLSWY SDPGLAGVSL TGGLSYKEDT KELVVAKAGV  60
YYVFFQLELR RVVAGEGSGS VSLALHLQPL RSAAGAAALA LTVDLPPASS EARNSAFGFQ  120
GRLLHLSAGQ XLGVHLHTEA RARHAWQLTQ GATVLGLFRV TPEIPAGLPS PRSE        174

SEQ ID NO: 163           moltype = AA  length = 174
FEATURE                  Location/Qualifiers
SITE                     132
                         note = any amino acid other than leucine
source                   1..174
                         mol_type = protein
                         organism = synthetic construct
SEQUENCE: 163
PAGLLDLRQG MFAQLVAQNV LLIGGPLSWY SDPGLAGVSL TGGLSYKEDT KELVVAKAGV  60
YYVFFQLELR RVVAGEGSGS VSLALHLQPL RSAAGAAALA LTVDLPPASS EARNSAFGFQ  120
GRLLHLSAGQ RXGVHLHTEA RARHAWQLTQ GATVLGLFRV TPEIPAGLPS PRSE        174

SEQ ID NO: 164           moltype = AA  length = 174
FEATURE                  Location/Qualifiers
SITE                     133
                         note = any amino acid other than glycine
source                   1..174
                         mol_type = protein
                         organism = synthetic construct
SEQUENCE: 164
PAGLLDLRQG MFAQLVAQNV LLIGGPLSWY SDPGLAGVSL TGGLSYKEDT KELVVAKAGV  60
YYVFFQLELR RVVAGEGSGS VSLALHLQPL RSAAGAAALA LTVDLPPASS EARNSAFGFQ  120
GRLLHLSAGQ RLXVHLHTEA RARHAWQLTQ GATVLGLFRV TPEIPAGLPS PRSE        174

SEQ ID NO: 165           moltype = AA  length = 174
FEATURE                  Location/Qualifiers
SITE                     134
                         note = any amino acid other than valine
source                   1..174
                         mol_type = protein
                         organism = synthetic construct
SEQUENCE: 165
PAGLLDLRQG MFAQLVAQNV LLIGGPLSWY SDPGLAGVSL TGGLSYKEDT KELVVAKAGV  60
YYVFFQLELR RVVAGEGSGS VSLALHLQPL RSAAGAAALA LTVDLPPASS EARNSAFGFQ  120
GRLLHLSAGQ RLGXHLHTEA RARHAWQLTQ GATVLGLFRV TPEIPAGLPS PRSE        174

SEQ ID NO: 166           moltype = AA  length = 174
FEATURE                  Location/Qualifiers
SITE                     135
                         note = any amino acid other than histidine
source                   1..174
                         mol_type = protein
                         organism = synthetic construct
SEQUENCE: 166
PAGLLDLRQG MFAQLVAQNV LLIGGPLSWY SDPGLAGVSL TGGLSYKEDT KELVVAKAGV  60
YYVFFQLELR RVVAGEGSGS VSLALHLQPL RSAAGAAALA LTVDLPPASS EARNSAFGFQ  120
GRLLHLSAGQ RLGVXLHTEA RARHAWQLTQ GATVLGLFRV TPEIPAGLPS PRSE        174
```

```
SEQ ID NO: 167          moltype = AA  length = 174
FEATURE                 Location/Qualifiers
SITE                    136
                        note = any amino acid other than leucine
source                  1..174
                        mol_type = protein
                        organism = synthetic construct
SEQUENCE: 167
PAGLLDLRQG MFAQLVAQNV LLIGGPLSWY SDPGLAGVSL TGGLSYKEDT KELVVAKAGV  60
YYVFFQLELR RVVAGEGSGS VSLALHLQPL RSAAGAAALA LTVDLPPASS EARNSAFGFQ  120
GRLLHLSAGQ RLGVHXHTEA RARHAWQLTQ GATVLGLFRV TPEIPAGLPS PRSE        174

SEQ ID NO: 168          moltype = AA  length = 174
FEATURE                 Location/Qualifiers
SITE                    137
                        note = any amino acid other than histidine
source                  1..174
                        mol_type = protein
                        organism = synthetic construct
SEQUENCE: 168
PAGLLDLRQG MFAQLVAQNV LLIGGPLSWY SDPGLAGVSL TGGLSYKEDT KELVVAKAGV  60
YYVFFQLELR RVVAGEGSGS VSLALHLQPL RSAAGAAALA LTVDLPPASS EARNSAFGFQ  120
GRLLHLSAGQ RLGVHLXTEA RARHAWQLTQ GATVLGLFRV TPEIPAGLPS PRSE        174

SEQ ID NO: 169          moltype = AA  length = 174
FEATURE                 Location/Qualifiers
SITE                    138
                        note = any amino acid other than threonine
source                  1..174
                        mol_type = protein
                        organism = synthetic construct
SEQUENCE: 169
PAGLLDLRQG MFAQLVAQNV LLIGGPLSWY SDPGLAGVSL TGGLSYKEDT KELVVAKAGV  60
YYVFFQLELR RVVAGEGSGS VSLALHLQPL RSAAGAAALA LTVDLPPASS EARNSAFGFQ  120
GRLLHLSAGQ RLGVHLHXEA RARHAWQLTQ GATVLGLFRV TPEIPAGLPS PRSE        174

SEQ ID NO: 170          moltype = AA  length = 174
FEATURE                 Location/Qualifiers
SITE                    139
                        note = any amino acid other than glutamic acid
source                  1..174
                        mol_type = protein
                        organism = synthetic construct
SEQUENCE: 170
PAGLLDLRQG MFAQLVAQNV LLIGGPLSWY SDPGLAGVSL TGGLSYKEDT KELVVAKAGV  60
YYVFFQLELR RVVAGEGSGS VSLALHLQPL RSAAGAAALA LTVDLPPASS EARNSAFGFQ  120
GRLLHLSAGQ RLGVHLHTXA RARHAWQLTQ GATVLGLFRV TPEIPAGLPS PRSE        174

SEQ ID NO: 171          moltype = AA  length = 174
FEATURE                 Location/Qualifiers
SITE                    141
                        note = any amino acid other than arginine
source                  1..174
                        mol_type = protein
                        organism = synthetic construct
SEQUENCE: 171
PAGLLDLRQG MFAQLVAQNV LLIGGPLSWY SDPGLAGVSL TGGLSYKEDT KELVVAKAGV  60
YYVFFQLELR RVVAGEGSGS VSLALHLQPL RSAAGAAALA LTVDLPPASS EARNSAFGFQ  120
GRLLHLSAGQ RLGVHLHTEA XARHAWQLTQ GATVLGLFRV TPEIPAGLPS PRSE        174

SEQ ID NO: 172          moltype = AA  length = 174
FEATURE                 Location/Qualifiers
SITE                    143
                        note = any amino acid other than arginine
source                  1..174
                        mol_type = protein
                        organism = synthetic construct
SEQUENCE: 172
PAGLLDLRQG MFAQLVAQNV LLIGGPLSWY SDPGLAGVSL TGGLSYKEDT KELVVAKAGV  60
YYVFFQLELR RVVAGEGSGS VSLALHLQPL RSAAGAAALA LTVDLPPASS EARNSAFGFQ  120
GRLLHLSAGQ RLGVHLHTEA RAXHAWQLTQ GATVLGLFRV TPEIPAGLPS PRSE        174

SEQ ID NO: 173          moltype = AA  length = 174
FEATURE                 Location/Qualifiers
SITE                    144
                        note = any amino acid other than histidine
source                  1..174
                        mol_type = protein
                        organism = synthetic construct
```

```
SEQUENCE: 173
PAGLLDLRQG MFAQLVAQNV LLIGGPLSWY SDPGLAGVSL TGGLSYKEDT KELVVAKAGV  60
YYVFFQLELR RVVAGEGSGS VSLALHLQPL RSAAGAAALA LTVDLPPASS EARNSAFGFQ  120
GRLLHLSAGQ RLGVHLHTEA RARXAWQLTQ GATVLGLFRV TPEIPAGLPS PRSE        174

SEQ ID NO: 174          moltype = AA  length = 174
FEATURE                 Location/Qualifiers
SITE                    146
                        note = any amino acid other than tryptophan
source                  1..174
                        mol_type = protein
                        organism = synthetic construct
SEQUENCE: 174
PAGLLDLRQG MFAQLVAQNV LLIGGPLSWY SDPGLAGVSL TGGLSYKEDT KELVVAKAGV  60
YYVFFQLELR RVVAGEGSGS VSLALHLQPL RSAAGAAALA LTVDLPPASS EARNSAFGFQ  120
GRLLHLSAGQ RLGVHLHTEA RARHAXQLTQ GATVLGLFRV TPEIPAGLPS PRSE        174

SEQ ID NO: 175          moltype = AA  length = 174
FEATURE                 Location/Qualifiers
SITE                    148
                        note = any amino acid other than leucine
source                  1..174
                        mol_type = protein
                        organism = synthetic construct
SEQUENCE: 175
PAGLLDLRQG MFAQLVAQNV LLIGGPLSWY SDPGLAGVSL TGGLSYKEDT KELVVAKAGV  60
YYVFFQLELR RVVAGEGSGS VSLALHLQPL RSAAGAAALA LTVDLPPASS EARNSAFGFQ  120
GRLLHLSAGQ RLGVHLHTEA RARHAWQXTQ GATVLGLFRV TPEIPAGLPS PRSE        174

SEQ ID NO: 176          moltype = AA  length = 174
FEATURE                 Location/Qualifiers
SITE                    149
                        note = any amino acid other than threonine
source                  1..174
                        mol_type = protein
                        organism = synthetic construct
SEQUENCE: 176
PAGLLDLRQG MFAQLVAQNV LLIGGPLSWY SDPGLAGVSL TGGLSYKEDT KELVVAKAGV  60
YYVFFQLELR RVVAGEGSGS VSLALHLQPL RSAAGAAALA LTVDLPPASS EARNSAFGFQ  120
GRLLHLSAGQ RLGVHLHTEA RARHAWQLXQ GATVLGLFRV TPEIPAGLPS PRSE        174

SEQ ID NO: 177          moltype = AA  length = 174
FEATURE                 Location/Qualifiers
SITE                    150
                        note = any amino acid other than glutamine
source                  1..174
                        mol_type = protein
                        organism = synthetic construct
SEQUENCE: 177
PAGLLDLRQG MFAQLVAQNV LLIGGPLSWY SDPGLAGVSL TGGLSYKEDT KELVVAKAGV  60
YYVFFQLELR RVVAGEGSGS VSLALHLQPL RSAAGAAALA LTVDLPPASS EARNSAFGFQ  120
GRLLHLSAGQ RLGVHLHTEA RARHAWQLTX GATVLGLFRV TPEIPAGLPS PRSE        174

SEQ ID NO: 178          moltype = AA  length = 174
FEATURE                 Location/Qualifiers
SITE                    151
                        note = any amino acid other than glycine
source                  1..174
                        mol_type = protein
                        organism = synthetic construct
SEQUENCE: 178
PAGLLDLRQG MFAQLVAQNV LLIGGPLSWY SDPGLAGVSL TGGLSYKEDT KELVVAKAGV  60
YYVFFQLELR RVVAGEGSGS VSLALHLQPL RSAAGAAALA LTVDLPPASS EARNSAFGFQ  120
GRLLHLSAGQ RLGVHLHTEA RARHAWQLTQ XATVLGLFRV TPEIPAGLPS PRSE        174

SEQ ID NO: 179          moltype = AA  length = 174
FEATURE                 Location/Qualifiers
SITE                    153
                        note = any amino acid other than threonine
source                  1..174
                        mol_type = protein
                        organism = synthetic construct
SEQUENCE: 179
PAGLLDLRQG MFAQLVAQNV LLIGGPLSWY SDPGLAGVSL TGGLSYKEDT KELVVAKAGV  60
YYVFFQLELR RVVAGEGSGS VSLALHLQPL RSAAGAAALA LTVDLPPASS EARNSAFGFQ  120
GRLLHLSAGQ RLGVHLHTEA RARHAWQLTQ GAXVLGLFRV TPEIPAGLPS PRSE        174

SEQ ID NO: 180          moltype = AA  length = 174
FEATURE                 Location/Qualifiers
```

```
SITE                    154
                        note = any amino acid other than valine
source                  1..174
                        mol_type = protein
                        organism = synthetic construct
SEQUENCE: 180
PAGLLDLRQG MFAQLVAQNV LLIGGPLSWY SDPGLAGVSL TGGLSYKEDT KELVVAKAGV  60
YYVFFQLELR RVVAGEGSGS VSLALHLQPL RSAAGAAALA LTVDLPPASS EARNSAFGFQ  120
GRLLHLSAGQ RLGVHLHTEA RARHAWQLTQ GATXLGLFRV TPEIPAGLPS PRSE        174

SEQ ID NO: 181          moltype = AA  length = 133
FEATURE                 Location/Qualifiers
SITE                    42
                        note = any amino acid other than phenylalanine
source                  1..133
                        mol_type = protein
                        organism = synthetic construct
SEQUENCE: 181
APTSSSTKKT QLQLEHLLLD LQMILNGINN YKNPKLTRML TXKFYMPKKA TELKHLQCLE  60
EELKPLEEVL NLAQSKNFHL RPRDLISNIN VIVLELKGSE TTFMCEYADE TATIVEFLNR  120
WITFCQSIIS TLT                                                    133

SEQ ID NO: 182          moltype = AA  length = 133
FEATURE                 Location/Qualifiers
SITE                    20
                        note = any amino acid other than aspartic acid
source                  1..133
                        mol_type = protein
                        organism = synthetic construct
SEQUENCE: 182
APTSSSTKKT QLQLEHLLLX LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLT                                                    133

SEQ ID NO: 183          moltype = AA  length = 133
FEATURE                 Location/Qualifiers
SITE                    15
                        note = any amino acid other than glutamic acid
source                  1..133
                        mol_type = protein
                        organism = synthetic construct
SEQUENCE: 183
APTSSSTKKT QLQLXHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLT                                                    133

SEQ ID NO: 184          moltype = AA  length = 133
FEATURE                 Location/Qualifiers
SITE                    16
                        note = any amino acid other than histidine
source                  1..133
                        mol_type = protein
                        organism = synthetic construct
SEQUENCE: 184
APTSSSTKKT QLQLEXLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLT                                                    133

SEQ ID NO: 185          moltype = AA  length = 133
FEATURE                 Location/Qualifiers
SITE                    16
                        note = any amino acid other than histidine
source                  1..133
                        mol_type = protein
                        organism = synthetic construct
SEQUENCE: 185
APTSSSTKKT QLQLEXLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLT                                                    133

SEQ ID NO: 186          moltype = AA  length = 133
FEATURE                 Location/Qualifiers
SITE                    45
                        note = any amino acid other than tyrosine
source                  1..133
                        mol_type = protein
                        organism = synthetic construct
SEQUENCE: 186
APTSSSTKKT QLQLEHLLLD LQMILNGINN YKNPKLTRML TFKFXMPKKA TELKHLQCLE  60
```

```
EELKPLEEVL NLAQSKNFHL RPRDLISNIN VIVLELKGSE TTFMCEYADE TATIVEFLNR  120
WITFCQSIIS TLT                                                    133

SEQ ID NO: 187         moltype = AA  length = 133
FEATURE                Location/Qualifiers
SITE                   126
                       note = any amino acid other than glutamine
source                 1..133
                       mol_type = protein
                       organism = synthetic construct
SEQUENCE: 187
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCXSIIS TLT                                                    133

SEQ ID NO: 188         moltype = AA  length = 133
FEATURE                Location/Qualifiers
SITE                   16
                       note = any amino acid other than histidine
SITE                   42
                       note = any amino acid other than phenylalanine
source                 1..133
                       mol_type = protein
                       organism = synthetic construct
SEQUENCE: 188
APTSSSTKKT QLQLEXLLLD LQMILNGINN YKNPKLTRML TXKFYMPKKA TELKHLQCLE  60
EELKPLEEVL NLAQSKNFHL RPRDLISNIN VIVLELKGSE TTFMCEYADE TATIVEFLNR  120
WITFCQSIIS TLT                                                    133

SEQ ID NO: 189         moltype = AA  length = 133
FEATURE                Location/Qualifiers
SITE                   20
                       note = any amino acid other than aspartic acid
SITE                   42
                       note = any amino acid other than phenylalanine
source                 1..133
                       mol_type = protein
                       organism = synthetic construct
SEQUENCE: 189
APTSSSTKKT QLQLEHLLLX LQMILNGINN YKNPKLTRML TXKFYMPKKA TELKHLQCLE  60
EELKPLEEVL NLAQSKNFHL RPRDLISNIN VIVLELKGSE TTFMCEYADE TATIVEFLNR  120
WITFCQSIIS TLT                                                    133

SEQ ID NO: 190         moltype = AA  length = 133
FEATURE                Location/Qualifiers
SITE                   15
                       note = any amino acid other than glutamic aicd
SITE                   20
                       note = any amino acid other than aspartic acid
SITE                   42
                       note = any amino acid other than phenylalanine
source                 1..133
                       mol_type = protein
                       organism = synthetic construct
SEQUENCE: 190
APTSSSTKKT QLQLXHLLLX LQMILNGINN YKNPKLTRML TXKFYMPKKA TELKHLQCLE  60
EELKPLEEVL NLAQSKNFHL RPRDLISNIN VIVLELKGSE TTFMCEYADE TATIVEFLNR  120
WITFCQSIIS TLT                                                    133

SEQ ID NO: 191         moltype = AA  length = 133
FEATURE                Location/Qualifiers
SITE                   16
                       note = any amino acid other than histidine
SITE                   20
                       note = any amino acid other than aspartic acid
SITE                   42
                       note = any amino acid other than phenylalanine
source                 1..133
                       mol_type = protein
                       organism = synthetic construct
SEQUENCE: 191
APTSSSTKKT QLQLEXLLLX LQMILNGINN YKNPKLTRML TXKFYMPKKA TELKHLQCLE  60
EELKPLEEVL NLAQSKNFHL RPRDLISNIN VIVLELKGSE TTFMCEYADE TATIVEFLNR  120
WITFCQSIIS TLT                                                    133

SEQ ID NO: 192         moltype = AA  length = 133
FEATURE                Location/Qualifiers
SITE                   20
                       note = any amino acid other than aspartic acid
```

```
SITE                    42
                        note = any amino acid other than phenylalanine
SITE                    126
                        note = any amino acid other than glutamine
source                  1..133
                        mol_type = protein
                        organism = synthetic construct
SEQUENCE: 192
APTSSSTKKT QLQLEHLLLX LQMILNGINN YKNPKLTRML TXKFYMPKKA TELKHLQCLE  60
EELKPLEEVL NLAQSKNFHL RPRDLISNIN VIVLELKGSE TTFMCEYADE TATIVEFLNR  120
WITFCXSIIS TLT                                                     133

SEQ ID NO: 193          moltype = AA  length = 133
FEATURE                 Location/Qualifiers
SITE                    20
                        note = any amino acid other than aspartic acid
SITE                    42
                        note = any amino acid other than phenylalanine
SITE                    45
                        note = any amino acid other than tyrosine
source                  1..133
                        mol_type = protein
                        organism = synthetic construct
SEQUENCE: 193
APTSSSTKKT QLQLEHLLLX LQMILNGINN YKNPKLTRML TXKFXMPKKA TELKHLQCLE  60
EELKPLEEVL NLAQSKNFHL RPRDLISNIN VIVLELKGSE TTFMCEYADE TATIVEFLNR  120
WITFCQSIIS TLT                                                     133

SEQ ID NO: 194          moltype = AA  length = 133
FEATURE                 Location/Qualifiers
SITE                    16
                        note = any amino acid other than histidine
SITE                    20
                        note = any amino acid other than aspartic acid
SITE                    42
                        note = any amino acid other than phenylalanine
SITE                    45
                        note = any amino acid other than tyrosine
source                  1..133
                        mol_type = protein
                        organism = synthetic construct
SEQUENCE: 194
APTSSSTKKT QLQLEXLLLX LQMILNGINN YKNPKLTRML TXKFXMPKKA TELKHLQCLE  60
EELKPLEEVL NLAQSKNFHL RPRDLISNIN VIVLELKGSE TTFMCEYADE TATIVEFLNR  120
WITFCQSIIS TLT                                                     133

SEQ ID NO: 195          moltype = AA  length = 133
FEATURE                 Location/Qualifiers
SITE                    20
                        note = any amino acid other than aspartic acid
SITE                    42
                        note = any amino acid other than phenylalanine
SITE                    45
                        note = any amino acid other than tyrosine
SITE                    126
                        note = any amino acid other than glutamine
source                  1..133
                        mol_type = protein
                        organism = synthetic construct
SEQUENCE: 195
APTSSSTKKT QLQLEHLLLX LQMILNGINN YKNPKLTRML TXKFXMPKKA TELKHLQCLE  60
EELKPLEEVL NLAQSKNFHL RPRDLISNIN VIVLELKGSE TTFMCEYADE TATIVEFLNR  120
WITFCXSIIS TLT                                                     133

SEQ ID NO: 196          moltype = AA  length = 133
FEATURE                 Location/Qualifiers
SITE                    16
                        note = any amino acid other than histidine
SITE                    20
                        note = any amino acid other than aspartic acid
SITE                    42
                        note = any amino acid other than phenylalanine
SITE                    45
                        note = any amino acid other than tyrosine
SITE                    126
                        note = any amino acid other than glutamine
source                  1..133
                        mol_type = protein
                        organism = synthetic construct
```

```
SEQUENCE: 196
APTSSSTKKT QLQLEXLLLX LQMILNGINN YKNPKLTRML TXKFXMPKKA TELKHLQCLE  60
EELKPLEEVL NLAQSKNFHL RPRDLISNIN VIVLELKGSE TTFMCEYADE TATIVEFLNR  120
WITFCXSIIS TLT                                                     133

SEQ ID NO: 197          moltype = AA  length = 133
FEATURE                 Location/Qualifiers
SITE                    16
                        note = any amino acid other than histidine
SITE                    42
                        note = any amino acid other than phenylalanine
SITE                    126
                        note = any amino acid other than glutamine
source                  1..133
                        mol_type = protein
                        organism = synthetic construct
SEQUENCE: 197
APTSSSTKKT QLQLEXLLLD LQMILNGINN YKNPKLTRML TXKFYMPKKA TELKHLQCLE  60
EELKPLEEVL NLAQSKNFHL RPRDLISNIN VIVLELKGSE TTFMCEYADE TATIVEFLNR  120
WITFCXSIIS TLT                                                     133

SEQ ID NO: 198          moltype = AA  length = 276
FEATURE                 Location/Qualifiers
source                  1..276
                        mol_type = protein
                        organism = synthetic construct
SEQUENCE: 198
GSHSMRYFFT SVSRPGRGEP RFIAVGYVDD TQFVRFDSDA ASQKMEPRAP WIEQEGPEYW  60
DQETRNMKAH SQTDRANLGT LRGYYNQSED GSHTIQIMYG CDVGPDGRFL RGYRQDAYDG  120
KDYIALNEDL RSWTAADMAA QITKRKWEAV HAAEQRRVYL EGRCVDGLRR YLENGKETLQ  180
RTDPPKTHMT HHPISDHEAT LRCWALGFYP AEITLTWQRD GEDQTQDTEL VETRPAGDGT  240
FQKWAAVVVP SGEEQRYTCH VQHEGLPKPL TLRWEL                            276

SEQ ID NO: 199          moltype = AA  length = 276
FEATURE                 Location/Qualifiers
source                  1..276
                        mol_type = protein
                        organism = synthetic construct
SEQUENCE: 199
GSHSMRYFFT SVSRPGRGEP RFIAVGYVDD TQFVRFDSDA ASQRMEPRAP WIEQEGPEYW  60
DGETRKVKAH SQTHRVDLGT LRGYYNQSEA GSHTVQRMYG CDVGSDWRFL RGYHQYAYDG  120
KDYIALKEDL RSWTAADMAA QTTKHKWEAA HVAEQLRAYL EGTCVEWLRR YLENGKETLQ  180
RTDAPKTHMT HHAVSDHEAT LRCWALSFYP AEITLTWQRD GEDQTQDTEL VETRPAGDGT  240
FQKWAAVVVP SGQEQRYTCH VQHEGLPKPL TLRWEP                            276

SEQ ID NO: 200          moltype = AA  length = 276
FEATURE                 Location/Qualifiers
source                  1..276
                        mol_type = protein
                        organism = synthetic construct
SEQUENCE: 200
GSHSMRYFFT SVSRPGRGEP RFIAVGYVDD TQFVRFDSDA ASQRMEPRAP WIEQEGPEYW  60
DQETRNVKAQ SQTDRVDLGT LRGYYNQSEA GSHTIQIMYG CDVGSDGRFL RGYRQDAYDG  120
KDYIALNEDL RSWTAADMAA QITKRKWEAA HEAEQLRAYL DGTCVEWLRR YLENGKETLQ  180
RTDPPKTHMT HHPISDHEAT LRCWALGFYP AEITLTWQRD GEDQTQDTEL VETRPAGDGT  240
FQKWAAVVVP SGEEQRYTCH VQHEGLPKPL TLRWEL                            276

SEQ ID NO: 201          moltype =   length =
SEQUENCE: 201
000

SEQ ID NO: 202          moltype = AA  length = 276
FEATURE                 Location/Qualifiers
source                  1..276
                        mol_type = protein
                        organism = synthetic construct
SEQUENCE: 202
GSHSMRYFST SVSRPGRGEP RFIAVGYVDD TQFVRFDSDA ASQRMEPRAP WIEQEGPEYW  60
DEETGKVKAH SQTDRENLRI ALRYYNQSEA GSHTLQMMFG CDVGSDGRFL RGYHQYAYDG  120
KDYIALKEDL RSWTAADMAA QITQRKWEAA RVAEQLRAYL EGTCVDGLRR YLENGKETLQ  180
RTDPPKTHMT HHPISDHEAT LRCWALGFYP AEITLTWQRD GEDQTQDTEL VETRPAGDGT  240
FQKWAAVVVP SGEEQRYTCH VQHEGLPKPL TLRWEP                            276

SEQ ID NO: 203          moltype =   length =
SEQUENCE: 203
000

SEQ ID NO: 204          moltype = AA  length = 276
FEATURE                 Location/Qualifiers
```

```
source                 1..276
                       mol_type = protein
                       organism = synthetic construct
SEQUENCE: 204
GSHSMRYFST SVSRPGRGEP RFIAVGYVDD TQFVRFDSDA ASQRMEPRAP WIEQEGPEYW  60
DEETGKVKAQ SQTDRENLRI ALRYYNQSEA GSHTLQMMFG CDVGSDGRFL RGYHQYAYDG  120
KDYIALKEDL RSWTAADMAA QITKRKWEAA HVAEQQRAYL EGTCVDGLRR YLENGKETLQ  180
RTDPPKTHMT HHPISDHEAT LRCWALGFYP AEITLTWQRD GEDQTQDTEL VETRPAGDGT  240
FQKWAAVVVP SGEEQRYTCH VQHEGLPKPL TLRWEP                            276

SEQ ID NO: 205         moltype =   length =
SEQUENCE: 205
000

SEQ ID NO: 206         moltype = AA  length = 276
FEATURE                Location/Qualifiers
source                 1..276
                       mol_type = protein
                       organism = synthetic construct
SEQUENCE: 206
GSHSMRYFYT SVSRPGRGEP RFIAVGYVDD TQFVRFDSDA ASQRMEPRAP WIEQEGPEYW  60
DRNTRKVKAQ SQTDRVDLGT LRGYYNQSED GSHTIQRMYG CDVGPDGRFL RGYQQDAYDG  120
KDYIALNEDL RSWTAADMAA QITQRKWETA HEAEQWRAYL EGTCVEWLRR YLENGKETLQ  180
RTDAPKTHMT HHAVSDHEAT LRCWALSFYP AEITLTWQRD GEDQTQDTEL VETRPAGDGT  240
FQKWASVVVP SGQEQRYTCH VQHEGLPKPL TLRWEP                            276

SEQ ID NO: 207         moltype = AA  length = 276
FEATURE                Location/Qualifiers
source                 1..276
                       mol_type = protein
                       organism = synthetic construct
SEQUENCE: 207
GSHSMRYFYT SVSRPGRGEP RFISVGYVDD TQFVRFDSDA ASPREEPRAP WIEQEGPEYW  60
DRNTQIYKAQ AQTDRESLRN LRGYYNQSEA GSHTLQSMYG CDVGPDGRLL RGHDQYAYDG  120
KDYIALNEDL RSWTAADTAA QITQRKWEAA REAEQRRAYL EGECVEWLRR YLENGKDKLE  180
RADPPKTHVT HHPISDHEAT LRCWALGFYP AEITLTWQRD GEDQTQDTEL VETRPAGDRT  240
FQKWAAVVVP SGEEQRYTCH VQHEGLPKPL TLRWEP                            276

SEQ ID NO: 208         moltype = AA  length = 276
FEATURE                Location/Qualifiers
source                 1..276
                       mol_type = protein
                       organism = synthetic construct
SEQUENCE: 208
GSHSMRYFDT AMSRPGRGEP RFISVGYVDD TQFVRFDSDA ASPREEPRAP WIEQEGPEYW  60
DRNTQIFKTN TQTDRESLRN LRGYYNQSEA GSHTLQSMYG CDVGPDGRLL RGHNQYAYDG  120
KDYIALNEDL RSWTAADTAA QITQRKWEAA RVAEQDRAYL EGTCVEWLRR YLENGKDTLE  180
RADPPKTHVT HHPISDHEAT LRCWALGFYP AEITLTWQRD GEDQTQDTEL VETRPAGDRT  240
FQKWAAVVVP SGEEQRYTCH VQHEGLPKPL TLRWEP                            276

SEQ ID NO: 209         moltype = AA  length = 276
FEATURE                Location/Qualifiers
source                 1..276
                       mol_type = protein
                       organism = synthetic construct
SEQUENCE: 209
GSHSMRYFYT AMSRPGRGEP RFIAVGYVDD TQFVRFDSDA ASPRMAPRAP WIEQEGPEYW  60
DRNTQISKTN TQTYRESLRN LRGYYNQSEA GSHIIQRMYG CDVGPDGRLL RGYDQSAYDG  120
KDYIALNEDL SSWTAADTAA QITQRKWEAA REAEQLRAYL EGLCVEWLRR YLENGKETLQ  180
RADPPKTHVT HHPISDHEAT LRCWALGFYP AEITLTWQRD GEDQTQDTEL VETRPAGDRT  240
FQKWAAVVVP SGEEQRYTCH VQHEGLPKPL TLRWEP                            276

SEQ ID NO: 210         moltype = AA  length = 276
FEATURE                Location/Qualifiers
source                 1..276
                       mol_type = protein
                       organism = synthetic construct
SEQUENCE: 210
GSHSMRYFYT SVSRPGRGEP RFISVGYVDD TQFVRFDSDA ASPREEPRAP WIEQEGPEYW  60
DRNTQICKTN TQTYRENLRT ALRYYNQSEA GSHTLQRMYG CDVGPDGRLL RGHNQFAYDG  120
KDYIALNEDL SSWTAADTAA QITQRKWEAA RVAEQLRTYL EGTCVEWLRR YLENGKETLQ  180
RADPPKTHVT HHPISDHEAT LRCWALGFYP AEITLTWQRD GEDQTQDTEL VETRPAGDRT  240
FQKWAAVVVP SGEEQRYTCH VQHEGLPKPL TLRWEP                            276

SEQ ID NO: 211         moltype = AA  length = 276
FEATURE                Location/Qualifiers
source                 1..276
                       mol_type = protein
                       organism = synthetic construct
```

SEQUENCE: 211
GSHSMRYFHT AMSRPGRGEP RFITVGYVDD TLFVRFDSDA TSPRKEPRAP WIEQEGPEYW 60
DRETQISKTN TQTYRESLRN LRGYYNQSEA GSHTLQRMYG CDVGPDGRLL RGHNQYAYDG 120
KDYIALNEDL RSWTAADTAA QISQRKLEAA RVAEQLRAYL EGECVEWLRR YLENGKDKLE 180
RADPPKTHVT HHPISDHEAT LRCWALGFYP AEITLTWQRD GEDQTQDTEL VETRPAGDRT 240
FQKWAAVVVP SGEEQRYTCH VQHEGLPKPL TLRWEP 276

SEQ ID NO: 212 moltype = AA length = 276
FEATURE Location/Qualifiers
source 1..276
mol_type = protein
organism = synthetic construct
SEQUENCE: 212
GSHSMRYFYT AMSRPGRGEP RFIAVGYVDD TQFVRFDSDA ASPRMAPRAP WIEQEGPEYW 60
DRETQKYKRQ AQTDRVSLRN LRGYYNQSEA GSHTLQRMYG CDVGPDGRLL RGHDQSAYDG 120
KDYIALNEDL SSWTAADTAA QITQRKWEAA REAEQWRAYL EGLCVEWLRR YLENGKETLQ 180
RADPPKTHVT HHPISDHEAT LRCWALGFYP AEITLTWQRD GEDQTQDTEL VETRPAGDRT 240
FQKWAAVVVP SGEEQRYTCH VQHEGLPKPL TLRWEP 276

SEQ ID NO: 213 moltype = AA length = 276
FEATURE Location/Qualifiers
source 1..276
mol_type = protein
organism = synthetic construct
SEQUENCE: 213
GSHSMRYFYT AMSRPGRGEP RFIAVGYVDD TQFVRFDSDA ASPRTEPRAP WIEQEGPEYW 60
DRNTQIFKTN TQTYRENLRI ALRYYNQSEA GSHIIQRMYG CDLGPDGRLL RGHDQSAYDG 120
KDYIALNEDL SSWTAADTAA QITQRKWEAA RVAEQLRAYL EGLCVEWLRR YLENGKETLQ 180
RADPPKTHVT HHPVSDHEAT LRCWALGFYP AEITLTWQRD GEDQTQDTEL VETRPAGDRT 240
FQKWAAVVVP SGEEQRYTCH VQHEGLPKPL TLRWEP 276

SEQ ID NO: 214 moltype = AA length = 276
FEATURE Location/Qualifiers
source 1..276
mol_type = protein
organism = synthetic construct
SEQUENCE: 214
CSHSMKYFFT SVSRPGRGEP RFISVGYVDD TQFVRFDSDA ASPRGEPRAP WVEQEGPEYW 60
DRETQKYKRQ AQTDRVSLRN LRGYYNQSEA GSHTLQWMCG CDLGPDGRLL RGYDQYAYDG 120
KDYIALNEDL RSWTAADTAA QITQRKWEAA REAEQRRAYL EGTCVEWLRR YLENGKETLQ 180
RAEHPKTHVT HHPVSDHEAT LRCWALGFYP AEITLTWQWD GEDQTQDTEL VETRPAGDGT 240
FQKWAAVMVP SGEEQRYTCH VQHEGLPEPL TLRWEP 276

SEQ ID NO: 215 moltype = AA length = 276
FEATURE Location/Qualifiers
source 1..276
mol_type = protein
organism = synthetic construct
SEQUENCE: 215
GSHSMRYFYT AVSRPGRGEP HFIAVGYVDD TQFVRFDSDA ASPRGEPRAP WVEQEGPEYW 60
DRETQKYKRQ AQTDRVSLRN LRGYYNQSEA RSHIIQRMYG CDVGPDGRLL RGYDQYAYDG 120
KDYIALNEDL RSWTAADTAA QITQRKWEAA REAEQLRAYL EGLCVEWLRR YLKNGKETLQ 180
RAEHPKTHVT HHPVSDHEAT LRCWALGFYP AEITLTWQWD GEDQTQDTEL VETRPAGDGT 240
FQKWAAVVVP SGEEQRYTCH VQHEGLPEPL TLRWEP 276

SEQ ID NO: 216 moltype = AA length = 276
FEATURE Location/Qualifiers
source 1..276
mol_type = protein
organism = synthetic construct
SEQUENCE: 216
GSHSMRYFYT AVSRPGRGEP HFIAVGYVDD TQFVRFDSDA ASPRGEPRAP WVEQEGPEYW 60
DRETQKYKRQ AQTDRVSLRN LRGYYNQSEA GSHIIQRMYG CDVGPDGRLL RGYDQYAYDG 120
KDYIALNEDL RSWTAADTAA QITQRKWEAA REAEQLRAYL EGLCVEWLRR YLKNGKETLQ 180
RAEHPKTHVT HHPVSDHEAT LRCWALGFYP AEITLTWQWD GEDQTQDTEL VETRPAGDGT 240
FQKWAAVVVP SGEEQRYTCH VQHEGLPEPL TLRWEP 276

SEQ ID NO: 217 moltype = AA length = 276
FEATURE Location/Qualifiers
source 1..276
mol_type = protein
organism = synthetic construct
SEQUENCE: 217
GSHSMRYFST SVSWPGRGEP RFIAVGYVDD TQFVRFDSDA ASPRGEPREP WVEQEGPEYW 60
DRETQKYKRQ AQADRVNLRK LRGYYNQSED GSHTLQRMFG CDLGPDGRLL RGYNQFAYDG 120
KDYIALNEDL RSWTAADTAA QITQRKWEAA REAEQRRAYL EGTCVEWLRR YLENGKETLQ 180
RAEHPKTHVT HHPVSDHEAT LRCWALGFYP AEITLTWQWD GEDQTQDTEL VETRPAGDGT 240
FQKWAAVVVP SGEEQRYTCH VQHEGLPEPL TLRWKP 276

-continued

```
SEQ ID NO: 218         moltype = AA  length = 276
FEATURE                Location/Qualifiers
source                 1..276
                       mol_type = protein
                       organism = synthetic construct
SEQUENCE: 218
CSHSMRYFDT AVSRPGRGEP RFISVGYVDD TQFVRFDSDA ASPRGEPRAP WVEQEGPEYW  60
DRETQKYKRQ AQADRVNLRK LRGYYNQSED GSHTLQWMYG CDLGPDGRLL RGYDQSAYDG  120
KDYIALNEDL RSWTAADTAA QITQRKWEAA REAEQWRAYL EGTCVEWLRR YLENGKETLQ  180
RAEHPKTHVT HHPVSDHEAT LRCWALGFYP AEITLTWQRD GEDQTQDTEL VETRPAGDGT  240
FQKWAAVVVP SGEEQRYTCH VQHEGLPEPL TLRWEP                            276

SEQ ID NO: 219         moltype = AA  length = 276
FEATURE                Location/Qualifiers
source                 1..276
                       mol_type = protein
                       organism = synthetic construct
SEQUENCE: 219
CSHSMRYFDT AVSRPGRGEP RFISVGYVDD TQFVRFDSDA ASPRGEPRAP WVEQEGPEYW  60
DRETQNYKRQ AQADRVSLRN LRGYYNQSED GSHTLQRMYG CDLGPDGRLL RGYDQSAYDG  120
KDYIALNEDL RSWTAADTAA QITQRKLEAA RAAEQLRAYL EGTCVEWLRR YLENGKETLQ  180
RAEPPKTHVT HHPLSDHEAT LRCWALGFYP AEITLTWQRD GEDQTQDTEL VETRPAGDGT  240
FQKWAAVVVP SGQEQRYTCH MQHEGLQEPL TLSWEP                            276

SEQ ID NO: 220         moltype = AA  length = 276
FEATURE                Location/Qualifiers
source                 1..276
                       mol_type = protein
                       organism = synthetic construct
SEQUENCE: 220
CSHSMRYFDT AVSRPGRGEP RFISVGYVDD TQFVRFDSDA ASPRGEPRAP WVEQEGPEYW  60
DRETQKYKRQ AQADRVSLRN LRGYYNQSED GSHTLQRMSG CDLGPDGRLL RGYDQSAYDG  120
KDYIALNEDL RSWTAADTAA QITQRKLEAA RAAEQLRAYL EGTCVEWLRR YLENGKETLQ  180
RAEPPKTHVT HHPLSDHEAT LRCWALGFYP AEITLTWQRD GEDQTQDTEL VETRPAGDGT  240
FQKWAAVVVP SGQEQRYTCH MQHEGLQEPL TLSWEP                            276

SEQ ID NO: 221         moltype = AA  length = 276
FEATURE                Location/Qualifiers
source                 1..276
                       mol_type = protein
                       organism = synthetic construct
SEQUENCE: 221
CSHSMRYFYT AVSRPGRGEP RFIAVGYVDD TQFVQFDSDA ASPRGEPRAP WVEQEGPEYW  60
DRETQKYKRQ AQTDRVSLRN LRGYYNQSEA GSHTLQRMYG CDLGPDGRLL RGYNQFAYDG  120
KDYIALNEDL RSWTAADTAA QITQRKWEAA RTAEQLRAYL EGTCVEWLRR YLENGKKTLQ  180
RAEHPKTHVT HHPVSDHEAT LRCWALGFYP AEITLTWQRD GEDQTQDTEL VETRPAGDGT  240
FQKWAAVVVP SGEEQRYTCH VQHEGLPEPL TLRWGP                            276

SEQ ID NO: 222         moltype = AA  length = 276
FEATURE                Location/Qualifiers
source                 1..276
                       mol_type = protein
                       organism = synthetic construct
SEQUENCE: 222
CSHSMRYFYT AVSRPGRGEP HFIAVGYVDD TQFVRFDSDA ASPRGEPRAP WVEQEGPEYW  60
DRETQNYKRQ AQTDRVNLRK LRGYYNQSEA GSHIIQRMYG CDLGPDGRLL RGHDQLAYDG  120
KDYIALNEDL RSWTAADTAA QITQRKWEAA REAEQLRAYL EGTCVEWLRR YLENGKETLQ  180
RAEHPKTHVT HHPVSDHEAT LRCWALGFYP AEITLTWQRD GEDQTQDTEL VETRPAGDGT  240
FQKWAAVVVP SGEEQRYTCH VQHEGLPEPL TLRWEP                            276

SEQ ID NO: 223         moltype = AA  length = 15
FEATURE                Location/Qualifiers
source                 1..15
                       mol_type = protein
                       organism = synthetic construct
SEQUENCE: 223
CMTWNQMNLG ATLKG                                                   15

SEQ ID NO: 224         moltype = AA  length = 15
FEATURE                Location/Qualifiers
source                 1..15
                       mol_type = protein
                       organism = synthetic construct
SEQUENCE: 224
WNQMNLGATL KGVAA                                                   15

SEQ ID NO: 225         moltype = AA  length = 15
FEATURE                Location/Qualifiers
source                 1..15
```

```
                        mol_type = protein
                        organism = synthetic construct
SEQUENCE: 225
CMTWNYMNLG ATLKG                                                15

SEQ ID NO: 226          moltype = AA  length = 15
FEATURE                 Location/Qualifiers
source                  1..15
                        mol_type = protein
                        organism = synthetic construct
SEQUENCE: 226
WNYMNLGATL KGVAA                                                15

SEQ ID NO: 227          moltype = AA  length = 15
FEATURE                 Location/Qualifiers
source                  1..15
                        mol_type = protein
                        organism = synthetic construct
SEQUENCE: 227
MTWNQMNLGA TLKGV                                                15

SEQ ID NO: 228          moltype = AA  length = 15
FEATURE                 Location/Qualifiers
source                  1..15
                        mol_type = protein
                        organism = synthetic construct
SEQUENCE: 228
TWNQMNLGAT LKGVA                                                15

SEQ ID NO: 229          moltype = AA  length = 15
FEATURE                 Location/Qualifiers
source                  1..15
                        mol_type = protein
                        organism = synthetic construct
SEQUENCE: 229
CMTWNLMNLG ATLKG                                                15

SEQ ID NO: 230          moltype = AA  length = 15
FEATURE                 Location/Qualifiers
source                  1..15
                        mol_type = protein
                        organism = synthetic construct
SEQUENCE: 230
MTWNLMNLGA TLKGV                                                15

SEQ ID NO: 231          moltype = AA  length = 15
FEATURE                 Location/Qualifiers
source                  1..15
                        mol_type = protein
                        organism = synthetic construct
SEQUENCE: 231
TWNLMNLGAT LKGVA                                                15

SEQ ID NO: 232          moltype = AA  length = 15
FEATURE                 Location/Qualifiers
source                  1..15
                        mol_type = protein
                        organism = synthetic construct
SEQUENCE: 232
WNLMNLGATL KGVAA                                                15

SEQ ID NO: 233          moltype = AA  length = 8
FEATURE                 Location/Qualifiers
source                  1..8
                        mol_type = protein
                        organism = synthetic construct
SEQUENCE: 233
MNLGATLK                                                        8

SEQ ID NO: 234          moltype = AA  length = 15
FEATURE                 Location/Qualifiers
source                  1..15
                        mol_type = protein
                        organism = synthetic construct
SEQUENCE: 234
MTWNYMNLGA TLKGV                                                15

SEQ ID NO: 235          moltype = AA  length = 15
FEATURE                 Location/Qualifiers
```

```
source                  1..15
                        mol_type = protein
                        organism = synthetic construct
SEQUENCE: 235
TWNYMNLGAT LKGVA                                                15

SEQ ID NO: 236          moltype = AA  length = 17
FEATURE                 Location/Qualifiers
source                  1..17
                        mol_type = protein
                        organism = synthetic construct
SEQUENCE: 236
CMTWNQMNLG ATLKGVA                                              17

SEQ ID NO: 237          moltype = AA  length = 17
FEATURE                 Location/Qualifiers
source                  1..17
                        mol_type = protein
                        organism = synthetic construct
SEQUENCE: 237
CMTWNLMNLG ATLKGVA                                              17

SEQ ID NO: 238          moltype = AA  length = 17
FEATURE                 Location/Qualifiers
source                  1..17
                        mol_type = protein
                        organism = synthetic construct
SEQUENCE: 238
CMTWNYMNLG ATLKGVA                                              17

SEQ ID NO: 239          moltype = AA  length = 9
FEATURE                 Location/Qualifiers
source                  1..9
                        mol_type = protein
                        organism = synthetic construct
SEQUENCE: 239
GYLRNPTAC                                                       9

SEQ ID NO: 240          moltype = AA  length = 9
FEATURE                 Location/Qualifiers
source                  1..9
                        mol_type = protein
                        organism = synthetic construct
SEQUENCE: 240
GALRNPTAL                                                       9

SEQ ID NO: 241          moltype = AA  length = 9
FEATURE                 Location/Qualifiers
source                  1..9
                        mol_type = protein
                        organism = synthetic construct
SEQUENCE: 241
YALRNPTAC                                                       9

SEQ ID NO: 242          moltype = AA  length = 9
FEATURE                 Location/Qualifiers
source                  1..9
                        mol_type = protein
                        organism = synthetic construct
SEQUENCE: 242
GLLRNPTAC                                                       9

SEQ ID NO: 243          moltype = AA  length = 9
FEATURE                 Location/Qualifiers
source                  1..9
                        mol_type = protein
                        organism = synthetic construct
SEQUENCE: 243
RYRPHPGAL                                                       9

SEQ ID NO: 244          moltype = AA  length = 9
FEATURE                 Location/Qualifiers
source                  1..9
                        mol_type = protein
                        organism = synthetic construct
SEQUENCE: 244
YQRPHPGAL                                                       9

SEQ ID NO: 245          moltype = AA  length = 9
```

```
FEATURE                 Location/Qualifiers
source                  1..9
                        mol_type = protein
                        organism = synthetic construct
SEQUENCE: 245
RLRPHPGAL                                                   9

SEQ ID NO: 246          moltype = AA  length = 9
FEATURE                 Location/Qualifiers
source                  1..9
                        mol_type = protein
                        organism = synthetic construct
SEQUENCE: 246
RIRPHPGAL                                                   9

SEQ ID NO: 247          moltype = AA  length = 15
FEATURE                 Location/Qualifiers
source                  1..15
                        mol_type = protein
                        organism = synthetic construct
SEQUENCE: 247
QFPNHSFKHE DPMGQ                                            15

SEQ ID NO: 248          moltype = AA  length = 9
FEATURE                 Location/Qualifiers
source                  1..9
                        mol_type = protein
                        organism = synthetic construct
SEQUENCE: 248
HSFKHEDPY                                                   9

SEQ ID NO: 249          moltype = AA  length = 13
FEATURE                 Location/Qualifiers
source                  1..13
                        mol_type = protein
                        organism = synthetic construct
SEQUENCE: 249
QFPNHSFKHE DPM                                              13

SEQ ID NO: 250          moltype = AA  length = 13
FEATURE                 Location/Qualifiers
source                  1..13
                        mol_type = protein
                        organism = synthetic construct
SEQUENCE: 250
QFPNHSFKHE DPY                                              13

SEQ ID NO: 251          moltype = AA  length = 13
FEATURE                 Location/Qualifiers
source                  1..13
                        mol_type = protein
                        organism = synthetic construct
SEQUENCE: 251
KRPFMCAYPG CNK                                              13

SEQ ID NO: 252          moltype = AA  length = 13
FEATURE                 Location/Qualifiers
source                  1..13
                        mol_type = protein
                        organism = synthetic construct
SEQUENCE: 252
KRPFMCAYPG CYK                                              13

SEQ ID NO: 253          moltype = AA  length = 9
FEATURE                 Location/Qualifiers
source                  1..9
                        mol_type = protein
                        organism = synthetic construct
SEQUENCE: 253
FMCAYPGCY                                                   9

SEQ ID NO: 254          moltype = AA  length = 9
FEATURE                 Location/Qualifiers
source                  1..9
                        mol_type = protein
                        organism = synthetic construct
SEQUENCE: 254
FMCAYPGCK                                                   9
```

```
SEQ ID NO: 255          moltype = AA  length = 15
FEATURE                Location/Qualifiers
source                 1..15
                       mol_type = protein
                       organism = synthetic construct
SEQUENCE: 255
KRPFMCAYPG CNKRY                                                   15

SEQ ID NO: 256         moltype = AA  length = 15
FEATURE                Location/Qualifiers
source                 1..15
                       mol_type = protein
                       organism = synthetic construct
SEQUENCE: 256
SEKRPFMCAY PGCNK                                                   15

SEQ ID NO: 257         moltype = AA  length = 15
FEATURE                Location/Qualifiers
source                 1..15
                       mol_type = protein
                       organism = synthetic construct
SEQUENCE: 257
KRPFMCAYPG CYKRY                                                   15

SEQ ID NO: 258         moltype = AA  length = 9
FEATURE                Location/Qualifiers
source                 1..9
                       mol_type = protein
                       organism = synthetic construct
SEQUENCE: 258
NLMNLGATL                                                          9

SEQ ID NO: 259         moltype = AA  length = 9
FEATURE                Location/Qualifiers
source                 1..9
                       mol_type = protein
                       organism = synthetic construct
SEQUENCE: 259
VLDFAPPGA                                                          9

SEQ ID NO: 260         moltype = AA  length = 9
FEATURE                Location/Qualifiers
source                 1..9
                       mol_type = protein
                       organism = synthetic construct
SEQUENCE: 260
RMFPNAPYL                                                          9

SEQ ID NO: 261         moltype = AA  length = 8
FEATURE                Location/Qualifiers
source                 1..8
                       mol_type = protein
                       organism = synthetic construct
SEQUENCE: 261
CMTWNQMN                                                           8

SEQ ID NO: 262         moltype = AA  length = 9
FEATURE                Location/Qualifiers
source                 1..9
                       mol_type = protein
                       organism = synthetic construct
SEQUENCE: 262
CYTWNQMNL                                                          9

SEQ ID NO: 263         moltype = AA  length = 9
FEATURE                Location/Qualifiers
source                 1..9
                       mol_type = protein
                       organism = synthetic construct
SEQUENCE: 263
NYMNLGATL                                                          9

SEQ ID NO: 264         moltype = AA  length = 9
FEATURE                Location/Qualifiers
source                 1..9
                       mol_type = protein
                       organism = synthetic construct
SEQUENCE: 264
YMFPNAPYL                                                          9
```

```
SEQ ID NO: 265          moltype = AA  length = 9
FEATURE                Location/Qualifiers
source                 1..9
                       mol_type = protein
                       organism = synthetic construct
SEQUENCE: 265
SLGEQQYSV                                                                   9

SEQ ID NO: 266          moltype = AA  length = 9
FEATURE                Location/Qualifiers
source                 1..9
                       mol_type = protein
                       organism = synthetic construct
SEQUENCE: 266
CMTWNQMNL                                                                   9

SEQ ID NO: 267          moltype = AA  length = 9
FEATURE                Location/Qualifiers
source                 1..9
                       mol_type = protein
                       organism = synthetic construct
SEQUENCE: 267
NQMNLGATL                                                                   9

SEQ ID NO: 268          moltype =   length =
SEQUENCE: 268
000

SEQ ID NO: 269          moltype =   length =
SEQUENCE: 269
000

SEQ ID NO: 270          moltype =   length =
SEQUENCE: 270
000

SEQ ID NO: 271          moltype = AA  length = 9
FEATURE                Location/Qualifiers
source                 1..9
                       mol_type = protein
                       organism = synthetic construct
SEQUENCE: 271
YPYDVPDYA                                                                   9

SEQ ID NO: 272          moltype = AA  length = 8
FEATURE                Location/Qualifiers
source                 1..8
                       mol_type = protein
                       organism = synthetic construct
SEQUENCE: 272
DYKDDDDK                                                                    8

SEQ ID NO: 273          moltype = AA  length = 10
FEATURE                Location/Qualifiers
source                 1..10
                       mol_type = protein
                       organism = synthetic construct
SEQUENCE: 273
EQKLISEEDL                                                                  10

SEQ ID NO: 274          moltype = AA  length = 5
FEATURE                Location/Qualifiers
source                 1..5
                       mol_type = protein
                       organism = synthetic construct
SEQUENCE: 274
HHHHH                                                                       5

SEQ ID NO: 275          moltype = AA  length = 6
FEATURE                Location/Qualifiers
source                 1..6
                       mol_type = protein
                       organism = synthetic construct
SEQUENCE: 275
HHHHHH                                                                      6

SEQ ID NO: 276          moltype =   length =
SEQUENCE: 276
```

```
000

SEQ ID NO: 277          moltype =   length =
SEQUENCE: 277
000

SEQ ID NO: 278          moltype = AA  length = 8
FEATURE                 Location/Qualifiers
source                  1..8
                        mol_type = protein
                        organism = synthetic construct
SEQUENCE: 278
WSHPQFEK                                                    8

SEQ ID NO: 279          moltype =   length =
SEQUENCE: 279
000

SEQ ID NO: 280          moltype = AA  length = 5
FEATURE                 Location/Qualifiers
source                  1..5
                        mol_type = protein
                        organism = synthetic construct
SEQUENCE: 280
RYIRS                                                       5

SEQ ID NO: 281          moltype = AA  length = 4
FEATURE                 Location/Qualifiers
source                  1..4
                        mol_type = protein
                        organism = synthetic construct
SEQUENCE: 281
FHHT                                                        4

SEQ ID NO: 282          moltype = AA  length = 17
FEATURE                 Location/Qualifiers
source                  1..17
                        mol_type = protein
                        organism = synthetic construct
SEQUENCE: 282
WEAAAREACC RECCARA                                          17

SEQ ID NO: 283          moltype = AA  length = 5
FEATURE                 Location/Qualifiers
source                  1..5
                        mol_type = protein
                        organism = synthetic construct
SEQUENCE: 283
AAAGG                                                       5

SEQ ID NO: 284          moltype = AA  length = 50
FEATURE                 Location/Qualifiers
source                  1..50
                        mol_type = protein
                        organism = synthetic construct
VARIANT                 1..50
                        note = Wherein up to 9 copies of GGGGS can be omitted
SEQUENCE: 284
GGGGSGGGGS GGGGSGGGGS GGGGSGGGGS GGGGSGGGGS GGGGSGGGGS      50

SEQ ID NO: 285          moltype =   length =
SEQUENCE: 285
000

SEQ ID NO: 286          moltype =   length =
SEQUENCE: 286
000

SEQ ID NO: 287          moltype = AA  length = 5
FEATURE                 Location/Qualifiers
source                  1..5
                        mol_type = protein
                        organism = synthetic construct
SEQUENCE: 287
GTLRG                                                       5

SEQ ID NO: 288          moltype = AA  length = 5
FEATURE                 Location/Qualifiers
source                  1..5
```

```
                        mol_type = protein
                        organism = synthetic construct
SEQUENCE: 288
YNQSE                                                                5

SEQ ID NO: 289          moltype = AA  length = 5
FEATURE                 Location/Qualifiers
source                  1..5
                        mol_type = protein
                        organism = synthetic construct
SEQUENCE: 289
TAADM                                                                5

SEQ ID NO: 290          moltype = AA  length = 5
FEATURE                 Location/Qualifiers
source                  1..5
                        mol_type = protein
                        organism = synthetic construct
SEQUENCE: 290
AQTTK                                                                5

SEQ ID NO: 291          moltype = AA  length = 5
FEATURE                 Location/Qualifiers
source                  1..5
                        mol_type = protein
                        organism = synthetic construct
SEQUENCE: 291
VETRP                                                                5

SEQ ID NO: 292          moltype = AA  length = 5
FEATURE                 Location/Qualifiers
source                  1..5
                        mol_type = protein
                        organism = synthetic construct
SEQUENCE: 292
GDGTF                                                                5

SEQ ID NO: 293          moltype = AA  length = 5
FEATURE                 Location/Qualifiers
source                  1..5
                        mol_type = protein
                        organism = synthetic construct
SEQUENCE: 293
RNLRG                                                                5

SEQ ID NO: 294          moltype = AA  length = 5
FEATURE                 Location/Qualifiers
source                  1..5
                        mol_type = protein
                        organism = synthetic construct
SEQUENCE: 294
TAADT                                                                5

SEQ ID NO: 295          moltype = AA  length = 5
FEATURE                 Location/Qualifiers
source                  1..5
                        mol_type = protein
                        organism = synthetic construct
SEQUENCE: 295
AQITQ                                                                5

SEQ ID NO: 296          moltype = AA  length = 5
FEATURE                 Location/Qualifiers
source                  1..5
                        mol_type = protein
                        organism = synthetic construct
SEQUENCE: 296
GDRTF                                                                5

SEQ ID NO: 297          moltype =   length =
SEQUENCE: 297
000

SEQ ID NO: 298          moltype =   length =
SEQUENCE: 298
000

SEQ ID NO: 299          moltype = AA  length = 276
FEATURE                 Location/Qualifiers
```

```
source                  1..276
                        mol_type = protein
                        organism = synthetic construct
SEQUENCE: 299
GSHSMRYFFT SVSRPGRGEP RFIAVGYVDD TQFVRFDSDA ASQRMEPRAP WIEQEGPEYW  60
DGETRKVKAH SQTHRVDLGT LRGCYNQSEA GSHTVQRMYG CDVGSDWRFL RGYHQYAYDG  120
KDYIALKEDL RSWTAADMCA QTTKHKWEAA HVAEQLRAYL EGTCVEWLRR YLENGKETLQ  180
RTDAPKTHMT HHAVSDHEAT LRCWALSFYP AEITLTWQRD GEDQTQDTEL VETRPAGDGT  240
FQKWAAVVVP SGQEQRYTCH VQHEGLPKPL TLRWEP                            276

SEQ ID NO: 300          moltype = AA  length = 275
FEATURE                 Location/Qualifiers
source                  1..275
                        mol_type = protein
                        organism = Homo sapiens
SEQUENCE: 300
GSHSMRYFYT SVSRPGRGEP RFIAVGYVDD TQFVRFDSDA ASQRMEPRAP WIEQEGPEYW  60
DQETRNVKAQ SQTDRVDLGT LRGYYNQSED GSHTIQIMYG CDVGPDGRFL RGYRQDAYDG  120
KDYIALNEDL RSWTAADMAA QITKRKWEAA HAAEQQRAYL EGTCVEWLRR YLENGKETLQ  180
RTDPPKTHMT HHPISDHEAT LRCWALGFYP AEITLTWQRD GEDQTQDTEL VETRPAGDGT  240
FQKWAAVVVP SGEEQRYTCH VQHEGLPKPL TLRWE                             275

SEQ ID NO: 301          moltype = AA  length = 275
FEATURE                 Location/Qualifiers
source                  1..275
                        mol_type = protein
                        organism = synthetic construct
SEQUENCE: 301
GSHSMRYFYT SVSRPGRGEP RFIAVGYVDD TQFVRFDSDA ASQRMEPRAP WIEQEGPEYW  60
DQETRNVKAQ SQTDRVDLGT LRGAYNQSED GSHTIQIMYG CDVGPDGRFL RGYRQDAYDG  120
KDYIALNEDL RSWTAADMAA QITKRKWEAA HAAEQQRAYL EGTCVEWLRR YLENGKETLQ  180
RTDPPKTHMT HHPISDHEAT LRCWALGFYP AEITLTWQRD GEDQTQDTEL VETRPCGDGT  240
FQKWAAVVVP SGEEQRYTCH VQHEGLPKPL TLRWE                             275

SEQ ID NO: 302          moltype = AA  length = 341
FEATURE                 Location/Qualifiers
source                  1..341
                        mol_type = protein
                        organism = Homo sapiens
SEQUENCE: 302
GSHSMRYFST SVSRPGRGEP RFIAVGYVDD TQFVRFDSDA ASQRMEPRAP WIEQEGPEYW  60
DEETGKVKAH SQTDRENLRI ALRYYNQSEA GSHTLQMMFG CDVGSDGRFL RGYHQYAYDG  120
KDYIALKEDL RSWTAADMAA QITKRKWEAA HVAEQQRAYL EGTCVDGLRR YLENGKETLQ  180
RTDPPKTHMT HHPISDHEAT LRCWALGFYP AEITLTWQRD GEDQTQDTEL VETRPAGDGT  240
FQKWAAVVVP SGEEQRYTCH VQHEGLPKPL TLRWEPSSQP TVPIVGIIAG LVLLGAVITG  300
AVVAAVMWRR NSSDRKGGSY SQAASSDSAQ GSDVSLTACK V                      341

SEQ ID NO: 303          moltype = AA  length = 341
FEATURE                 Location/Qualifiers
source                  1..341
                        mol_type = protein
                        organism = Homo sapiens
SEQUENCE: 303
GSHSMRYFTT SVSRPGRGEP RFIAVGYVDD TQFVRFDSDA ASQRMEPRAP WIEQEGPEYW  60
DRNTRNVKAH SQIDRVDLGT LRGYYNQSEA GSHTIQMMYG CDVGSDGRFL RGYQQDAYDG  120
KDYIALNEDL RSWTAADMAA QITQRKWEAA RVAEQLRAYL EGTCVEWLRR YLENGKETLQ  180
RTDPPKTHMT HHAVSDHEAT LRCWALSFYP AEITLTWQRD GEDQTQDTEL VETRPAGDGT  240
FQKWASVVVP SGQEQRYTCH VQHEGLPKPL TLRWEPSSQP TIPIVGIIAG LVLFGAVFAG  300
AVVAAVRWRR KSSDRKGGSY SQAASSDSAQ GSDMSLTACK V                      341

SEQ ID NO: 304          moltype =   length =
SEQUENCE: 304
000

SEQ ID NO: 305          moltype = AA  length = 276
FEATURE                 Location/Qualifiers
source                  1..276
                        mol_type = protein
                        organism = synthetic construct
SEQUENCE: 305
GSHSMRYFYT SVSRPGRGEP RFISVGYVDD TQFVRFDSDA ASPREEPRAP WIEQEGPEYW  60
DRNTQIYKAQ AQTDRESLRN LRGAYNQSEA GSHTLQSMYG CDVGPDGRLL RGHDQYAYDG  120
KDYIALNEDL RSWTAADTAA QITQRKWEAA REAEQRRAYL EGECVEWLRR YLENGKDKLE  180
RADPPKTHVT HHPISDHEAT LRCWALGFYP AEITLTWQRD GEDQTQDTEL VETRPCGDRT  240
FQKWAAVVVP SGEEQRYTCH VQHEGLPKPL TLRWEP                            276

SEQ ID NO: 306          moltype = AA  length = 276
FEATURE                 Location/Qualifiers
source                  1..276
```

```
                       mol_type = protein
                       organism = synthetic construct
SEQUENCE: 306
GSHSMRYFYT SVSRPGRGEP RFISVGYVDD TQFVRFDSDA ASPREEPRAP WIEQEGPEYW  60
DRNTQIYKAQ AQTDRESLRN LRGCYNQSEA GSHTLQSMYG CDVGPDGRLL RGHDQYAYDG  120
KDYIALNEDL RSWTAADTCA QITQRKWEAA REAEQRRAYL EGECVEWLRR YLENGKDKLE  180
RADPPKTHVT HHPISDHEAT LRCWALGFYP AEITLTWQRD GEDQTQDTEL VETRPAGDRT  240
FQKWAAVVVP SGEEQRYTCH VQHEGLPKPL TLRWEP                          276

SEQ ID NO: 307         moltype =   length =
SEQUENCE: 307
000

SEQ ID NO: 308         moltype = AA  length = 276
FEATURE                Location/Qualifiers
source                 1..276
                       mol_type = protein
                       organism = Homo sapiens
SEQUENCE: 308
CSHSMRYFDT AVSRPGRGEP RFISVGYVDD TQFVRFDSDA ASPRGEPRAP WVEQEGPEYW  60
DRETQNYKRQ AQADRVSLRN LRGAYNQSED GSHTLQRMYG CDLGPDGRLL RGYDQSAYDG  120
KDYIALNEDL RSWTAADTAA QITQRKLEAA RAAEQLRAYL EGTCVEWLRR YLENGKETLQ  180
RAEPPKTHVT HHPLSDHEAT LRCWALGFYP AEITLTWQRD GEDQTQDTEL VETRPCGDGT  240
FQKWAAVVVP SGQEQRYTCH MQHEGLQEPL TLSWEP                          276

SEQ ID NO: 309         moltype = AA  length = 276
FEATURE                Location/Qualifiers
SITE                   79..83
                       note = Any one or all of amino acids 79 to 83 can either be
                        present or absent, and each amino acid may include any
                        naturally occuring amino acid
DISULFID               84..139
                       note = where the cysteine residues at positions 84 and 139
                        form a disulfide bond between the alpha1 and alpha2-1
                        helices
SITE                   85..89
                       note = Any one or all of amino acids 85 to 89 can either be
                        present or absent, and each amino acid may include any
                        naturally occuring amino acid
SITE                   134..138
                       note = Any one or all of amino acids 134 to 138 can either
                        be present or absent, and each amino acid may include any
                        naturally occuring amino acid
SITE                   140..144
                       note = Any one or all of amino acids 140 to 144 can either
                        be present or absent, and each amino acid may include any
                        naturally occuring amino acid
SITE                   231..235
                       note = Any one or all of amino acids 231 to 235 can either
                        be present or absent, and each amino acid may include any
                        naturally occuring amino acid
SITE                   237..241
                       note = Any one or all of amino acids 237 to 241 can either
                        be present or absent, and each amino acid may include any
                        naturally occuring amino acid
source                 1..276
                       mol_type = protein
                       organism = synthetic construct
DISULFID               236
                       note = The residue at position 236 forms a disulfide bond
                        with the beta2M polypeptide cysteine at position 12
SEQUENCE: 309
GSHSMRYFFT SVSRPGRGEP RFIAVGYVDD TQFVRFDSDA ASQRMEPRAP WIEQEGPEYW  60
DGETRKVKAH SQTHRVDLXX XXXCXXXXXA GSHTVQRMYG CDVGSDWRFL RGYHQYAYDG  120
KDYIALKEDL RSWXXXXXCX XXXXHKWEAA HVAEQLRAYL EGTCVEWLRR YLENGKETLQ  180
RTDAPKTHMT HHAVSDHEAT LRCWALSFYP AEITLTWQRD GEDQTQDTEL XXXXXCXXXX  240
XQKWAAVVVP SGQEQRYTCH VQHEGLPKPL TLRWEP                          276

SEQ ID NO: 310         moltype = AA  length = 99
FEATURE                Location/Qualifiers
source                 1..99
                       mol_type = protein
                       organism = synthetic construct
SEQUENCE: 310
IQRTPKIQVY SRHPAENGKS NFLNCYVSGF HPSDIEVDLL KNGERIEKVE HSDLSFSKDW  60
SFYLLYYTEF TPTEKDEYAC RVNHVTLSQP KIVKWDRDM                       99

SEQ ID NO: 311         moltype = AA  length = 99
FEATURE                Location/Qualifiers
```

```
source                  1..99
                        mol_type = protein
                        organism = synthetic construct
SEQUENCE: 311
IQRTPKIQVY SCHPAENGKS NFLNCYVSGF HPSDIEVDLL KNGERIEKVE HSDLSFSKDW  60
SFYLLYYTEF TPTEKDEYAC RVNHVTLSQP KIVKWDRDM                         99

SEQ ID NO: 312          moltype = AA  length = 276
FEATURE                 Location/Qualifiers
source                  1..276
                        mol_type = protein
                        organism = synthetic construct
SEQUENCE: 312
GSHSMRYFFT SVSRPGRGEP RFIAVGYVDD TQFVRFDSDA ASQRMEPRAP WIEQEGPEYW  60
DGETRKVKAH SQTHRVDLGT LRGYYNQSEA GSHTVQRMYG CDVGSDWRFL RGYHQYAYDG  120
KDYIALKEDL RSWTAADMAA QTTKHKWEAA HVAEQLRAYL EGTCVEWLRR YLENGKETLQ  180
RTDAPKTHMT HHAVSDHEAT LRCWALSFYP AEITLTWQRD GEDQTQDTEL VETRPCGDGT  240
FQKWAAVVVP SGQEQRYTCH VQHEGLPKPL TLRWEP                            276

SEQ ID NO: 313          moltype =   length =
SEQUENCE: 313
000

SEQ ID NO: 314          moltype =   length =
SEQUENCE: 314
000

SEQ ID NO: 315          moltype = AA  length = 50
FEATURE                 Location/Qualifiers
source                  1..50
                        mol_type = protein
                        organism = synthetic construct
VARIANT                 6..50
                        note = Wherein up to 8 copies of GGGGS may be omitted
SEQUENCE: 315
GCGGSGGGGS GGGGSGGGGS GGGGSGGGGS GGGGSGGGGS GGGGSGGGGS             50

SEQ ID NO: 316          moltype = AA  length = 20
FEATURE                 Location/Qualifiers
source                  1..20
                        mol_type = protein
                        organism = synthetic construct
SEQUENCE: 316
GCGGSGGGGS GGGGSGGGGS                                              20

SEQ ID NO: 317          moltype = AA  length = 15
FEATURE                 Location/Qualifiers
source                  1..15
                        mol_type = protein
                        organism = synthetic construct
SEQUENCE: 317
GCGGSGGGGS GGGGS                                                   15

SEQ ID NO: 318          moltype = AA  length = 5
FEATURE                 Location/Qualifiers
source                  1..5
                        mol_type = protein
                        organism = synthetic construct
SEQUENCE: 318
GCGGS                                                              5

SEQ ID NO: 319          moltype = AA  length = 55
FEATURE                 Location/Qualifiers
source                  1..55
                        mol_type = protein
                        organism = synthetic construct
VARIANT                 6..55
                        note = Wherein up to 9 copies of GGGGS may be omitted
SEQUENCE: 319
GCGGSGGGGS GGGGSGGGGS GGGGSGGGGS GGGGSGGGGS GGGGSGGGGS GGGGS       55

SEQ ID NO: 320          moltype = AA  length = 15
FEATURE                 Location/Qualifiers
source                  1..15
                        mol_type = protein
                        organism = synthetic construct
SEQUENCE: 320
GCGGSGGGGS GGGGS                                                   15
```

```
SEQ ID NO: 321          moltype = AA  length = 20
FEATURE                 Location/Qualifiers
source                  1..20
                        mol_type = protein
                        organism = synthetic construct
SEQUENCE: 321
GCGGSGGGGS GGGGSGGGGS                                             20

SEQ ID NO: 322          moltype = AA  length = 25
FEATURE                 Location/Qualifiers
source                  1..25
                        mol_type = protein
                        organism = synthetic construct
SEQUENCE: 322
GCGGSGGGGS GGGGSGGGGS GGGGS                                       25

SEQ ID NO: 323          moltype = AA  length = 30
FEATURE                 Location/Qualifiers
source                  1..30
                        mol_type = protein
                        organism = synthetic construct
SEQUENCE: 323
GCGGSGGGGS GGGGSGGGGS GGGGSGGGGS                                  30

SEQ ID NO: 324          moltype = AA  length = 35
FEATURE                 Location/Qualifiers
source                  1..35
                        mol_type = protein
                        organism = synthetic construct
SEQUENCE: 324
GCGGSGGGGS GGGGSGGGGS GGGGSGGGGS GGGGS                            35

SEQ ID NO: 325          moltype = AA  length = 40
FEATURE                 Location/Qualifiers
source                  1..40
                        mol_type = protein
                        organism = synthetic construct
SEQUENCE: 325
GCGGSGGGGS GGGGSGGGGS GGGGSGGGGS GGGGSGGGGS                       40

SEQ ID NO: 326          moltype = AA  length = 45
FEATURE                 Location/Qualifiers
source                  1..45
                        mol_type = protein
                        organism = synthetic construct
SEQUENCE: 326
GCGGSGGGGS GGGGSGGGGS GGGGSGGGGS GGGGSGGGGS GGGGS                 45

SEQ ID NO: 327          moltype = AA  length = 50
FEATURE                 Location/Qualifiers
source                  1..50
                        mol_type = protein
                        organism = synthetic construct
SEQUENCE: 327
GCGGSGGGGS GGGGSGGGGS GGGGSGGGGS GGGGSGGGGS GGGGSGGGGS            50

SEQ ID NO: 328          moltype = AA  length = 55
FEATURE                 Location/Qualifiers
source                  1..55
                        mol_type = protein
                        organism = synthetic construct
SEQUENCE: 328
GCGGSGGGGS GGGGSGGGGS GGGGSGGGGS GGGGSGGGGS GGGGSGGGGS GGGGS      55

SEQ ID NO: 329          moltype = AA  length = 5
FEATURE                 Location/Qualifiers
source                  1..5
                        mol_type = protein
                        organism = synthetic construct
SEQUENCE: 329
CGGGS                                                             5

SEQ ID NO: 330          moltype = AA  length = 55
FEATURE                 Location/Qualifiers
source                  1..55
                        mol_type = protein
                        organism = synthetic construct
VARIANT                 6..55
                        note = Wherein up to 9 copies of GGGGS may be omitted
```

SEQUENCE: 330
CGGGSGGGGS GGGGSGGGGS GGGGSGGGGS GGGGSGGGGS GGGGSGGGGS GGGGS 55

SEQ ID NO: 331 moltype = AA length = 10
FEATURE Location/Qualifiers
source 1..10
mol_type = protein
organism = synthetic construct
SEQUENCE: 331
CGGGSGGGGS 10

SEQ ID NO: 332 moltype = AA length = 15
FEATURE Location/Qualifiers
source 1..15
mol_type = protein
organism = synthetic construct
SEQUENCE: 332
CGGGSGGGGS GGGGS 15

SEQ ID NO: 333 moltype = AA length = 20
FEATURE Location/Qualifiers
source 1..20
mol_type = protein
organism = synthetic construct
SEQUENCE: 333
CGGGSGGGGS GGGGSGGGGS 20

SEQ ID NO: 334 moltype = AA length = 25
FEATURE Location/Qualifiers
source 1..25
mol_type = protein
organism = synthetic construct
SEQUENCE: 334
CGGGSGGGGS GGGGSGGGGS GGGGS 25

SEQ ID NO: 335 moltype = AA length = 30
FEATURE Location/Qualifiers
source 1..30
mol_type = protein
organism = synthetic construct
SEQUENCE: 335
CGGGSGGGGS GGGGSGGGGS GGGGSGGGGS 30

SEQ ID NO: 336 moltype = AA length = 35
FEATURE Location/Qualifiers
source 1..35
mol_type = protein
organism = synthetic construct
SEQUENCE: 336
CGGGSGGGGS GGGGSGGGGS GGGGSGGGGS GGGGS 35

SEQ ID NO: 337 moltype = AA length = 40
FEATURE Location/Qualifiers
source 1..40
mol_type = protein
organism = synthetic construct
SEQUENCE: 337
CGGGSGGGGS GGGGSGGGGS GGGGSGGGGS GGGGSGGGGS 40

SEQ ID NO: 338 moltype = AA length = 45
FEATURE Location/Qualifiers
source 1..45
mol_type = protein
organism = synthetic construct
SEQUENCE: 338
CGGGSGGGGS GGGGSGGGGS GGGGSGGGGS GGGGSGGGGS GGGGS 45

SEQ ID NO: 339 moltype = AA length = 50
FEATURE Location/Qualifiers
source 1..50
mol_type = protein
organism = synthetic construct
SEQUENCE: 339
CGGGSGGGGS GGGGSGGGGS GGGGSGGGGS GGGGSGGGGS GGGGSGGGGS 50

SEQ ID NO: 340 moltype = AA length = 55
FEATURE Location/Qualifiers
source 1..55
mol_type = protein

```
                        organism = synthetic construct
SEQUENCE: 340
CGGGSGGGGS GGGGSGGGGS GGGGSGGGGS GGGGSGGGGS GGGGSGGGGS GGGGS        55

SEQ ID NO: 341          moltype = AA  length = 275
FEATURE                 Location/Qualifiers
source                  1..275
                        mol_type = protein
                        organism = synthetic construct
SEQUENCE: 341
GSHSMRYFFT SVSRPGRGEP RFIAVGYVDD TQFVRFDSDA ASQRMEPRAP WIEQEGPEYW  60
DGETRKVKAH SQTHRVDLGT LRGCYNQSEA GSHTVQRMYG CDVGSDWRFL RGYHQYAYDG  120
KDYIALKEDL RSWTAADMAA QTTKHKWEAA HVAEQLRAYL EGTCVEWLRR YLENGKETLQ  180
RTDAPKTHMT HHAVSDHEAT LRCWALSFYP AEITLTWQRD GEDQTQDTEL VETRPCGDGT  240
FQKWAAVVVP SGQEQRYTCH VQHEGLPKPL TLRWE                              275

SEQ ID NO: 342          moltype = AA  length = 276
FEATURE                 Location/Qualifiers
source                  1..276
                        mol_type = protein
                        organism = synthetic construct
SEQUENCE: 342
GSHSMRYFFT SVSRPGRGEP RFIAVGYVDD TQFVRFDSDA ASQRMEPRAP WIEQEGPEYW  60
DGETRKVKAH SQTHRVDLGT LRGCYNQSEA GSHTVQRMYG CDVGSDWRFL RGYHQYAYDG  120
KDYIALKEDL RSWTAADMAA QTTKHKWEAA HVAEQLRAYL EGTCVEWLRR YLENGKETLQ  180
RTDAPKTHMT HHAVSDHEAT LRCWALSFYP AEITLTWQRD GEDQTQDTEL VETRPCGDGT  240
FQKWAAVVVP SGQEQRYTCH VQHEGLPKPL TLRWEP                             276

SEQ ID NO: 343          moltype = AA  length = 275
FEATURE                 Location/Qualifiers
source                  1..275
                        mol_type = protein
                        organism = synthetic construct
SEQUENCE: 343
GSHSMRYFFT SVSRPGRGEP RFIAVGYVDD TQFVRFDSDA ASQKMEPRAP WIEQEGPEYW  60
DQETRNMKAH SQTDRANLGT LRGCYNQSED GSHTIQIMYG CDVGPDGRFL RGYRQDAYDG  120
KDYIALNEDL RSWTAADMAA QITKRKWEAV HAAEQRRVYL EGRCVDGLRR YLENGKETLQ  180
RTDPPKTHMT HHPISDHEAT LRCWALGFYP AEITLTWQRD GEDQTQDTEL VETRPCGDGT  240
FQKWAAVVVP SGEEQRYTCH VQHEGLPKPL TLRWE                              275

SEQ ID NO: 344          moltype = AA  length = 275
FEATURE                 Location/Qualifiers
source                  1..275
                        mol_type = protein
                        organism = synthetic construct
SEQUENCE: 344
GSHSMRYFYT SVSRPGRGEP RFIAVGYVDD TQFVRFDSDA ASQRMEPRAP WIEQEGPEYW  60
DQETRNVKAQ SQTDRVDLGT LRGCYNQSED GSHTIQIMYG CDVGPDGRFL RGYRQDAYDG  120
KDYIALNEDL RSWTAADMAA QITKRKWEAA HAAEQQRAYL EGRCVEWLRR YLENGKETLQ  180
RTDPPKTHMT HHPISDHEAT LRCWALGFYP AEITLTWQRD GEDQTQDTEL VETRPCGDGT  240
FQKWAAVVVP SGEEQRYTCH VQHEGLPKPL TLRWE                              275

SEQ ID NO: 345          moltype = AA  length = 275
FEATURE                 Location/Qualifiers
source                  1..275
                        mol_type = protein
                        organism = synthetic construct
SEQUENCE: 345
GSHSMRYFST SVSRPGRGEP RFIAVGYVDD TQFVRFDSDA ASQRMEPRAP WIEQEGPEYW  60
DEETGKVKAH SQTDRENLRI ALRCYNQSEA GSHTLQMMFG CDVGSDGRFL RGYHQYAYDG  120
KDYIALKEDL RSWTAADMAA QITQRKWEAA RVAEQLRAYL EGTCVDGLRR YLENGKETLQ  180
RTDPPKTHMT HHPISDHEAT LRCWALGFYP AEITLTWQRD GEDQTQDTEL VETRPCGDGT  240
FQKWAAVVVP SGEEQRYTCH VQHEGLPKPL TLRWE                              275

SEQ ID NO: 346          moltype = AA  length = 275
FEATURE                 Location/Qualifiers
source                  1..275
                        mol_type = protein
                        organism = synthetic construct
SEQUENCE: 346
GSHSMRYFST SVSRPGRGEP RFIAVGYVDD TQFVRFDSDA ASQRMEPRAP WIEQEGPEYW  60
DEETGKVKAH SQTDRENLRI ALRCYNQSEA GSHTLQMMFG CDVGSDGRFL RGYHQYAYDG  120
KDYIALKEDL RSWTAADMAA QITKRKWEAA HVAEQQRAYL EGTCVDGLRR YLENGKETLQ  180
RTDPPKTHMT HHPISDHEAT LRCWALGFYP AEITLTWQRD GEDQTQDTEL VETRPCGDGT  240
FQKWAAVVVP SGEEQRYTCH VQHEGLPKPL TLRWE                              275

SEQ ID NO: 347          moltype = AA  length = 275
FEATURE                 Location/Qualifiers
source                  1..275
```

```
                         mol_type = protein
                         organism = synthetic construct
SEQUENCE: 347
GSHSMRYFST SVSRPGRGEP RFIAVGYVDD TQFVRFDSDA ASQRMEPRAP WIEQEGPEYW  60
DEETGKVKAQ SQTDRENLRI ALRCYNQSEA GSHTLQMMFG CDVGSDGRFL RGYHQYAYDG  120
KDYIALKEDL RSWTAADMAA QITKRKWEAA HVAEQQRAYL EGTCVDGLRR YLENGKETLQ  180
RTDPPKTHMT HHPISDHEAT LRCWALGFYP AEITLTWQRD GEDQTQDTEL VETRPCGDGT  240
FQKWAAVVVP SGEEQRYTCH VQHEGLPKPL TLRWE                            275

SEQ ID NO: 348           moltype = AA  length = 275
FEATURE                  Location/Qualifiers
source                   1..275
                         mol_type = protein
                         organism = synthetic construct
SEQUENCE: 348
GSHSMRYFTT SVSRPGRGEP RFIAVGYVDD TQFVRFDSDA ASQRMEPRAP WIEQEGPEYW  60
DRNTRNVKAH SQIDRVDLGT LRGCYNQSEA GSHTIQMMYG CDVGSDGRFL RGYQQDAYDG  120
KDYIALNEDL RSWTAADMAA QITQRKWEAA RVAEQLRAYL EGTCVEWLRR YLENGKETLQ  180
RTDPPKTHMT HHAVSDHEAT LRCWALSFYP AEITLTWQRD GEDQTQDTEL VETRPCGDGT  240
FQKWASVVVP SGQEQRYTCH VQHEGLPKPL TLRWE                            275

SEQ ID NO: 349           moltype = AA  length = 275
FEATURE                  Location/Qualifiers
source                   1..275
                         mol_type = protein
                         organism = synthetic construct
SEQUENCE: 349
GSHSMRYFYT SVSRPGRGEP RFIAVGYVDD TQFVRFDSDA ASQRMEPRAP WIEQEGPEYW  60
DRNTRKVKAQ SQTDRVDLGT LRGCYNQSED GSHTIQRMYG CDVGPDGRFL RGYQQDAYDG  120
KDYIALNEDL RSWTAADMAA QITQRKWETA HEAEQWRAYL EGTCVEWLRR YLENGKETLQ  180
RTDAPKTHMT HHAVSDHEAT LRCWALSFYP AEITLTWQRD GEDQTQDTEL VETRPCGDGT  240
FQKWASVVVP SGQEQRYTCH VQHEGLPKPL TLRWE                            275

SEQ ID NO: 350           moltype = AA  length = 276
FEATURE                  Location/Qualifiers
source                   1..276
                         mol_type = protein
                         organism = synthetic construct
SEQUENCE: 350
GSHSMRYFYT SVSRPGRGEP RFISVGYVDD TQFVRFDSDA ASPREEPRAP WIEQEGPEYW  60
DRNTQIYKAQ AQTDRESLRN LRGCYNQSEA GSHTLQSMYG CDVGPDGRLL RGHDQYAYDG  120
KDYIALNEDL RSWTAADTAA QITQRKWEAA REAEQRRAYL EGECVEWLRR YLENGKDKLE  180
RADPPKTHVT HHPISDHEAT LRCWALGFYP AEITLTWQRD GEDQTQDTEL VETRPCGDRT  240
FQKWAAVVVP SGEEQRYTCH VQHEGLPKPL TLRWEP                           276

SEQ ID NO: 351           moltype = AA  length = 275
FEATURE                  Location/Qualifiers
source                   1..275
                         mol_type = protein
                         organism = synthetic construct
SEQUENCE: 351
GSHSMRYFDT AMSRPGRGEP RFISVGYVDD TQFVRFDSDA ASPREEPRAP WIEQEGPEYW  60
DRNTQIFKTN TQTDRESLRN LRGCYNQSEA GSHTLQSMYG CDVGPDGRLL RGHNQYAYDG  120
KDYIALNEDL RSWTAADTAA QITQRKWEAA RVAEQDRAYL EGTCVEWLRR YLENGKDTLE  180
RADPPKTHVT HHPISDHEAT LRCWALGFYP AEITLTWQRD GEDQTQDTEL VETRPCGDRT  240
FQKWAAVVVP SGEEQRYTCH VQHEGLPKPL TLRWE                            275

SEQ ID NO: 352           moltype = AA  length = 275
FEATURE                  Location/Qualifiers
source                   1..275
                         mol_type = protein
                         organism = synthetic construct
SEQUENCE: 352
GSHSMRYFYT AMSRPGRGEP RFIAVGYVDD TQFVRFDSDA ASPRMAPRAP WIEQEGPEYW  60
DRNTQISKTN TQTYRESLRN LRGCYNQSEA GSHIIQRMYG CDVGPDGRLL RGYDQSAYDG  120
KDYIALNEDL SSWTAADTAA QITQRKWEAA REAEQLRAYL EGLCVEWLRR YLENGKETLQ  180
RADPPKTHVT HHPISDHEAT LRCWALGFYP AEITLTWQRD GEDQTQDTEL VETRPCGDRT  240
FQKWAAVVVP SGEEQRYTCH VQHEGLPKPL TLRWE                            275

SEQ ID NO: 353           moltype = AA  length = 275
FEATURE                  Location/Qualifiers
source                   1..275
                         mol_type = protein
                         organism = synthetic construct
SEQUENCE: 353
GSHSMRYFYT SVSRPGRGEP RFISVGYVDD TQFVRFDSDA ASPREEPRAP WIEQEGPEYW  60
DRNTQICKTN TQTYRENLRT ALRCYNQSEA GSHTLQRMYG CDVGPDGRLL RGHNQFAYDG  120
KDYIALNEDL SSWTAADTAA QITQRKWEAA RVAEQLRTYL EGTCVEWLRR YLENGKETLQ  180
RADPPKTHVT HHPISDHEAT LRCWALGFYP AEITLTWQRD GEDQTQDTEL VETRPCGDRT  240
```

```
FQKWAAVVVP SGEEQRYTCH VQHEGLPKPL TLRWE                         275

SEQ ID NO: 354          moltype = AA  length = 275
FEATURE                 Location/Qualifiers
source                  1..275
                        mol_type = protein
                        organism = synthetic construct
SEQUENCE: 354
GSHSMRYFHT AMSRPGRGEP RFITVGYVDD TLFVRFDSDA TSPRKEPRAP WIEQEGPEYW  60
DRETQISKTN TQTYRESLRN LRGCYNQSEA GSHTLQRMYG CDVGPDGRLL RGHNQYAYDG  120
KDYIALNEDL RSWTAADTAA QISQRKLEAA RVAEQLRAYL EGECVEWLRR YLENGKDKLE  180
RADPPKTHVT HHPISDHEAT LRCWALGFYP AEITLTWQRD GEDQTQDTEL VETRPCGDRT  240
FQKWAAVVVP SGEEQRYTCH VQHEGLPKPL TLRWE                         275

SEQ ID NO: 355          moltype = AA  length = 275
FEATURE                 Location/Qualifiers
source                  1..275
                        mol_type = protein
                        organism = synthetic construct
SEQUENCE: 355
GSHSMRYFYT AMSRPGRGEP RFIAVGYVDD TQFVRFDSDA ASPRMAPRAP WIEQEGPEYW  60
DRETQKYKRQ AQTDRVSLRN LRGCYNQSEA GSHTLQRMYG CDVGPDGRLL RGHDQSAYDG  120
KDYIALNEDL SSWTAADTAA QITQRKWEAA REAEQWRAYL EGLCVEWLRR YLENGKETLQ  180
RADPPKTHVT HHPISDHEAT LRCWALGFYP AEITLTWQRD GEDQTQDTEL VETRPCGDRT  240
FQKWAAVVVP SGEEQRYTCH VQHEGLPKPL TLRWE                         275

SEQ ID NO: 356          moltype = AA  length = 275
FEATURE                 Location/Qualifiers
source                  1..275
                        mol_type = protein
                        organism = synthetic construct
SEQUENCE: 356
GSHSMRYFYT AMSRPGRGEP RFIAVGYVDD TQFVRFDSDA ASPRTEPRAP WIEQEGPEYW  60
DRNTQIFKTN TQTYRENLRI ALRCYNQSEA GSHIIQRMYG CDLGPDGRLL RGHDQSAYDG  120
KDYIALNEDL SSWTAADTAA QITQRKWEAA RVAEQLRAYL EGLCVEWLRR YLENGKETLQ  180
RADPPKTHVT HHPVSDHEAT LRCWALGFYP AEITLTWQRD GEDQTQDTEL VETRPCGDRT  240
FQKWAAVVVP SGEEQRYTCH VQHEGLPKPL TLRWE                         275

SEQ ID NO: 357          moltype = AA  length = 276
FEATURE                 Location/Qualifiers
source                  1..276
                        mol_type = protein
                        organism = synthetic construct
SEQUENCE: 357
CSHSMRYFDT AVSRPGRGEP RFISVGYVDD TQFVRFDSDA ASPRGEPRAP WVEQEGPEYW  60
DRETQNYKRQ AQADRVSLRN LRGCYNQSED GSHTLQRMYG CDLGPDGRLL RGYDQSAYDG  120
KDYIALNEDL RSWTAADTAA QITQRKLEAA RAAEQLRAYL EGTCVEWLRR YLENGKETLQ  180
RAEPPKTHVT HHPLSDHEAT LRCWALGFYP AEITLTWQRD GEDQTQDTEL VETRPCGDGT  240
FQKWAAVVVP SGQEQRYTCH MQHEGLQEPL TLSWEP                        276

SEQ ID NO: 358          moltype = AA  length = 276
FEATURE                 Location/Qualifiers
source                  1..276
                        mol_type = protein
                        organism = synthetic construct
SEQUENCE: 358
CSHSMKYFFT SVSRPGRGEP RFISVGYVDD TQFVRFDSDA ASPRGEPRAP WVEQEGPEYW  60
DRETQKYKRQ AQTDRVSLRN LRGCYNQSEA GSHTLQWMCG CDLGPDGRLL RGYDQYAYDG  120
KDYIALNEDL RSWTAADTAA QITQRKWEAA REAEQRRAYL EGTCVEWLRR YLENGKETLQ  180
RAEHPKTHVT HHPVSDHEAT LRCWALGFYP AEITLTWQWD GEDQTQDTEL VETRPCGDGT  240
FQKWAAVMVP SGEEQRYTCH VQHEGLPEPL TLRWEP                        276

SEQ ID NO: 359          moltype = AA  length = 276
FEATURE                 Location/Qualifiers
source                  1..276
                        mol_type = protein
                        organism = synthetic construct
SEQUENCE: 359
GSHSMRYFYT AVSRPGRGEP HFIAVGYVDD TQFVRFDSDA ASPRGEPRAP WVEQEGPEYW  60
DRETQKYKRQ AQTDRVSLRN LRGCYNQSEA RSHIIQRMYG CDVGPDGRLL RGYDQYAYDG  120
KDYIALNEDL RSWTAADTAA QITQRKWEAA REAEQLRAYL EGLCVEWLRR YLKNGKETLQ  180
RAEHPKTHVT HHPVSDHEAT LRCWALGFYP AEITLTWQWD GEDQTQDTEL VETRPCGDGT  240
FQKWAAVVVP SGEEQRYTCH VQHEGLPEPL TLRWEP                        276

SEQ ID NO: 360          moltype = AA  length = 276
FEATURE                 Location/Qualifiers
source                  1..276
                        mol_type = protein
                        organism = synthetic construct
```

SEQUENCE: 360
GSHSMRYFYT AVSRPGRGEP HFIAVGYVDD TQFVRFDSDA ASPRGEPRAP WVEQEGPEYW 60
DRETQKYKRQ AQTDRVSLRN LRGCYNQSEA GSHIIQRMYG CDVGPDGRLL RGYDQYAYDG 120
KDYIALNEDL RSWTAADTAA QITQRKWEAA REAEQLRAYL EGLCVEWLRR YLKNGKETLQ 180
RAEHPKTHVT HHPVSDHEAT LRCWALGFYP AEITLTWQWD GEDQTQDTEL VETRPCGDGT 240
FQKWAAVVVP SGEEQRYTCH VQHEGLPEPL TLRWEP 276

SEQ ID NO: 361 moltype = AA length = 276
FEATURE Location/Qualifiers
source 1..276
mol_type = protein
organism = synthetic construct
SEQUENCE: 361
GSHSMRYFST SVSWPGRGEP RFIAVGYVDD TQFVRFDSDA ASPRGEPREP WVEQEGPEYW 60
DRETQKYKRQ AQADRVNLRK LRGCYNQSED GSHTLQRMFG CDLGPDGRLL RGYNQFAYDG 120
KDYIALNEDL RSWTAADTAA QITQRKWEAA REAEQRRAYL EGTCVEWLRR YLENGKETLQ 180
RAEHPKTHVT HHPVSDHEAT LRCWALGFYP AEITLTWQWD GEDQTQDTEL VETRPCGDGT 240
FQKWAAVVVP SGEEQRYTCH VQHEGLPEPL TLRWKP 276

SEQ ID NO: 362 moltype = AA length = 276
FEATURE Location/Qualifiers
source 1..276
mol_type = protein
organism = synthetic construct
SEQUENCE: 362
CSHSMRYFDT AVSRPGRGEP RFISVGYVDD TQFVRFDSDA ASPRGEPRAP WVEQEGPEYW 60
DRETQKYKRQ AQADRVNLRK LRGCYNQSED GSHTLQWMYG CDLGPDGRLL RGYDQSAYDG 120
KDYIALNEDL RSWTAADTAA QITQRKWEAA REAEQWRAYL EGTCVEWLRR YLENGKETLQ 180
RAEHPKTHVT HHPVSDHEAT LRCWALGFYP AEITLTWQRD GEDQTQDTEL VETRPCGDGT 240
FQKWAAVVVP SGEEQRYTCH VQHEGLPEPL TLRWEP 276

SEQ ID NO: 363 moltype = AA length = 276
FEATURE Location/Qualifiers
source 1..276
mol_type = protein
organism = synthetic construct
SEQUENCE: 363
CSHSMRYFYT AVSRPGRGEP RFIAVGYVDD TQFVQFDSDA ASPRGEPRAP WVEQEGPEYW 60
DRETQKYKRQ AQTDRVSLRN LRGCYNQSEA GSHTLQRMYG CDLGPDGRLL RGYNQFAYDG 120
KDYIALNEDL RSWTAADTAA QITQRKWEAA RTAEQLRAYL EGTCVEWLRR YLENGKKTLQ 180
RAEHPKTHVT HHPVSDHEAT LRCWALGFYP AEITLTWQRD GEDQTQDTEL VETRPCGDGT 240
FQKWAAVVVP SGEEQRYTCH VQHEGLPEPL TLRWGP 276

SEQ ID NO: 364 moltype = AA length = 276
FEATURE Location/Qualifiers
source 1..276
mol_type = protein
organism = synthetic construct
SEQUENCE: 364
CSHSMRYFYT AVSRPGRGEP HFIAVGYVDD TQFVRFDSDA ASPRGEPRAP WVEQEGPEYW 60
DRETQNYKRQ AQTDRVNLRK LRGCYNQSEA GSHIIQRMYG CDLGPDGRLL RGHDQLAYDG 120
KDYIALNEDL RSWTAADTAA QITQRKWEAA REAEQLRAYL EGTCVEWLRR YLENGKETLQ 180
RAEHPKTHVT HHPVSDHEAT LRCWALGFYP AEITLTWQRD GEDQTQDTEL VETRPCGDGT 240
FQKWAAVVVP SGEEQRYTCH VQHEGLPEPL TLRWEP 276

SEQ ID NO: 365 moltype = AA length = 223
FEATURE Location/Qualifiers
source 1..223
mol_type = protein
organism = synthetic construct
SEQUENCE: 365
PPCPSCPAPE FLGGPSVFLF PPKPKDTLMI SRTPEVTCVV VDVSQEDPEV QFNWYVDGVE 60
VHNAKTKPRE EQFNSTYRVV SVLTVLHQDW LNGKEYKCKV SNKGLPSSIE KTISKAKGQP 120
REPQVYTLPP SQEEMTKNQV SLTCLVKGFY PSDIAVEWES NGQPENNYKT TPPVLDSDGS 180
FFLYSRLTVD KSRWQEGNVF SCSVMHEALH NHYTQKSLSL SPG 223

SEQ ID NO: 366 moltype = AA length = 5
FEATURE Location/Qualifiers
source 1..5
mol_type = protein
organism = synthetic construct
REGION 1..5
note = Wherein the amino acid sequence GSGGS may be
repeated one or more times
SEQUENCE: 366
GSGGS 5

SEQ ID NO: 367 moltype = AA length = 4
FEATURE Location/Qualifiers

```
source                1..4
                      mol_type = protein
                      organism = synthetic construct
REGION                1..4
                      note = Wherein the amino acid sequence GGGS may be repeated
                       one or more times
SEQUENCE: 367
GGGS                                                                        4

SEQ ID NO: 368        moltype = AA  length = 4
FEATURE               Location/Qualifiers
source                1..4
                      mol_type = protein
                      organism = synthetic construct
SEQUENCE: 368
GGSG                                                                        4

SEQ ID NO: 369        moltype = AA  length = 5
FEATURE               Location/Qualifiers
source                1..5
                      mol_type = protein
                      organism = synthetic construct
SEQUENCE: 369
GGSGG                                                                       5

SEQ ID NO: 370        moltype = AA  length = 5
FEATURE               Location/Qualifiers
source                1..5
                      mol_type = protein
                      organism = synthetic construct
SEQUENCE: 370
GSGSG                                                                       5

SEQ ID NO: 371        moltype = AA  length = 5
FEATURE               Location/Qualifiers
source                1..5
                      mol_type = protein
                      organism = synthetic construct
SEQUENCE: 371
GSGGG                                                                       5

SEQ ID NO: 372        moltype = AA  length = 5
FEATURE               Location/Qualifiers
source                1..5
                      mol_type = protein
                      organism = synthetic construct
SEQUENCE: 372
GGGSG                                                                       5

SEQ ID NO: 373        moltype = AA  length = 5
FEATURE               Location/Qualifiers
source                1..5
                      mol_type = protein
                      organism = synthetic construct
SEQUENCE: 373
GSSSG                                                                       5

SEQ ID NO: 374        moltype = AA  length = 50
FEATURE               Location/Qualifiers
source                1..50
                      mol_type = protein
                      organism = synthetic construct
VARIANT               1..50
                      note = Wherein up to 9 copies of GSSSS may be omitted
SEQUENCE: 374
GSSSSGSSSS GSSSSGSSSS GSSSSGSSSS GSSSSGSSSS GSSSSGSSSS             50

SEQ ID NO: 375        moltype = AA  length = 20
FEATURE               Location/Qualifiers
source                1..20
                      mol_type = protein
                      organism = synthetic construct
SEQUENCE: 375
GSSSSGSSSS GSSSSGSSSS                                              20

SEQ ID NO: 376        moltype = AA  length = 25
FEATURE               Location/Qualifiers
source                1..25
                      mol_type = protein
```

```
                        organism = synthetic construct
SEQUENCE: 376
GSSSSGSSSS GSSSSGSSSS GSSSS                                         25

SEQ ID NO: 377          moltype = AA  length = 5
FEATURE                 Location/Qualifiers
source                  1..5
                        mol_type = protein
                        organism = synthetic construct
SEQUENCE: 377
GGGGS                                                               5

SEQ ID NO: 378          moltype = AA  length = 10
FEATURE                 Location/Qualifiers
source                  1..10
                        mol_type = protein
                        organism = synthetic construct
SEQUENCE: 378
GGGGSGGGGS                                                          10

SEQ ID NO: 379          moltype = AA  length = 15
FEATURE                 Location/Qualifiers
source                  1..15
                        mol_type = protein
                        organism = synthetic construct
SEQUENCE: 379
GGGGSGGGGS GGGGS                                                    15

SEQ ID NO: 380          moltype = AA  length = 20
FEATURE                 Location/Qualifiers
source                  1..20
                        mol_type = protein
                        organism = synthetic construct
SEQUENCE: 380
GGGGSGGGGS GGGGSGGGGS                                               20

SEQ ID NO: 381          moltype = AA  length = 25
FEATURE                 Location/Qualifiers
source                  1..25
                        mol_type = protein
                        organism = synthetic construct
SEQUENCE: 381
GGGGSGGGGS GGGGSGGGGS GGGGS                                         25

SEQ ID NO: 382          moltype = AA  length = 30
FEATURE                 Location/Qualifiers
source                  1..30
                        mol_type = protein
                        organism = synthetic construct
SEQUENCE: 382
GGGGSGGGGS GGGGSGGGGS GGGGSGGGGS                                    30

SEQ ID NO: 383          moltype = AA  length = 35
FEATURE                 Location/Qualifiers
source                  1..35
                        mol_type = protein
                        organism = synthetic construct
SEQUENCE: 383
GGGGSGGGGS GGGGSGGGGS GGGGSGGGGS GGGGS                              35

SEQ ID NO: 384          moltype = AA  length = 40
FEATURE                 Location/Qualifiers
source                  1..40
                        mol_type = protein
                        organism = synthetic construct
SEQUENCE: 384
GGGGSGGGGS GGGGSGGGGS GGGGSGGGGS GGGGSGGGGS                         40

SEQ ID NO: 385          moltype = AA  length = 45
FEATURE                 Location/Qualifiers
source                  1..45
                        mol_type = protein
                        organism = synthetic construct
SEQUENCE: 385
GGGGSGGGGS GGGGSGGGGS GGGGSGGGGS GGGGSGGGGS GGGGS                   45

SEQ ID NO: 386          moltype = AA  length = 50
FEATURE                 Location/Qualifiers
source                  1..50
```

```
                        mol_type = protein
                        organism = synthetic construct
SEQUENCE: 386
GGGGSGGGGS GGGGSGGGGS GGGGSGGGGS GGGGSGGGGS GGGGSGGGGS              50

SEQ ID NO: 387          moltype =   length =
SEQUENCE: 387
000

SEQ ID NO: 388          moltype = AA  length = 8
FEATURE                 Location/Qualifiers
source                  1..8
                        mol_type = protein
                        organism = synthetic construct
SEQUENCE: 388
LEVLFQGP                                                            8

SEQ ID NO: 389          moltype = AA  length = 7
FEATURE                 Location/Qualifiers
source                  1..7
                        mol_type = protein
                        organism = synthetic construct
SEQUENCE: 389
ENLYTQS                                                             7

SEQ ID NO: 390          moltype = AA  length = 5
FEATURE                 Location/Qualifiers
source                  1..5
                        mol_type = protein
                        organism = synthetic construct
SEQUENCE: 390
DDDDK                                                               5

SEQ ID NO: 391          moltype = AA  length = 4
FEATURE                 Location/Qualifiers
source                  1..4
                        mol_type = protein
                        organism = synthetic construct
SEQUENCE: 391
LVPR                                                                4

SEQ ID NO: 392          moltype = AA  length = 22
FEATURE                 Location/Qualifiers
source                  1..22
                        mol_type = protein
                        organism = synthetic construct
SEQUENCE: 392
GSGATNFSLL KQAGDVEENP GP                                            22

SEQ ID NO: 393          moltype =   length =
SEQUENCE: 393
000

SEQ ID NO: 394          moltype = AA  length = 6
FEATURE                 Location/Qualifiers
source                  1..6
                        mol_type = protein
                        organism = synthetic construct
SEQUENCE: 394
CHYSEL                                                              6

SEQ ID NO: 395          moltype = AA  length = 9
FEATURE                 Location/Qualifiers
source                  1..9
                        mol_type = protein
                        organism = synthetic construct
SEQUENCE: 395
GILGFVFTL                                                           9

SEQ ID NO: 396          moltype = AA  length = 9
FEATURE                 Location/Qualifiers
source                  1..9
                        mol_type = protein
                        organism = synthetic construct
SEQUENCE: 396
HPVGEADYF                                                           9

SEQ ID NO: 397          moltype = AA  length = 276
FEATURE                 Location/Qualifiers
```

```
source                 1..276
                       mol_type = protein
                       organism = synthetic construct
SEQUENCE: 397
CSHSMRYFDT AVSRPGRGEP RFISVGYVDD TQFVRFDSDA ASPRGEPRAP WVEQEGPEYW  60
DRETQNYKRQ AQADRVSLRN LRGCYNQSED GSHTLQRMYG CDLGPDGRLL RGYDQSAYDG  120
KDYIALNEDL RSWTAADTCA QITQRKLEAA RAAEQLRAYL EGTCVEWLRR YLENGKETLQ  180
RAEPPKTHVT HHPLSDHEAT LRCWALGFYP AEITLTWQRD GEDQTQDTEL VETRPAGDGT  240
FQKWAAVVVP SGQEQRYTCH MQHEGLQEPL TLSWEP                            276

SEQ ID NO: 398         moltype = AA  length = 10
FEATURE                Location/Qualifiers
source                 1..10
                       mol_type = protein
                       organism = synthetic construct
SEQUENCE: 398
GCGGSGGGGS                                                         10

SEQ ID NO: 399         moltype = AA  length = 502
FEATURE                Location/Qualifiers
source                 1..502
                       mol_type = protein
                       organism = Homo sapiens
SEQUENCE: 399
MDFLLLQDPA STCVPEPASQ HTLRSGPGCL QQPEQQGVRD PGGIWAKLGA AEASAERLQG  60
RRSRGASGSE PQQMGSDVRD LNALLPAVPS LGGGGGCALP VSGAAQWAPV LDFAPPGASA  120
YGSLGGPAPP PAPPPPPPPP PHSFIKQEPS WGGAEPHEEQ CLSAFTVHFS GQFTGTAGAC  180
RYGPFGPPPP SQASSGQARM FPNAPYLPSC LESQPAIRNQ GYSTVTFDGT PSYGHTPSHH  240
AAQFPNHSFK HEDPMGQQGS LGEQQYSVPP PVYGCHTPTD SCTGSQALLL RTPYSSDNLY  300
QMTSQLECMT WNQMNLGATL KGHSTGYESD NHTTPILCGA QYRIHTHGVF RGIQDVRRVP  360
GVAPTLVRSA SETSEKRPFM CAYPGCNKRY FKLSHLQMHS RKHTGEKPYQ CDFKDCERRF  420
SRSDQLKRHQ RRHTGVKPFQ CKTCQRKFSR SDHLKTHTRT HTGEKPFSCR WPSCQKKFAR  480
SDELVRHHNM HQRNMTKLQL AL                                           502

SEQ ID NO: 400         moltype = AA  length = 519
FEATURE                Location/Qualifiers
source                 1..519
                       mol_type = protein
                       organism = Homo sapiens
SEQUENCE: 400
MDFLLLQDPA STCVPEPASQ HTLRSGPGCL QQPEQQGVRD PGGIWAKLGA AEASAERLQG  60
RRSRGASGSE PQQMGSDVRD LNALLPAVPS LGGGGGCALP VSGAAQWAPV LDFAPPGASA  120
YGSLGGPAPP PAPPPPPPPP PHSFIKQEPS WGGAEPHEEQ CLSAFTVHFS GQFTGTAGAC  180
RYGPFGPPPP SQASSGQARM FPNAPYLPSC LESQPAIRNQ GYSTVTFDGT PSYGHTPSHH  240
AAQFPNHSFK HEDPMGQQGS LGEQQYSVPP PVYGCHTPTD SCTGSQALLL RTPYSSDNLY  300
QMTSQLECMT WNQMNLGATL KGVAAGSSSS VKWTEGQSNH STGYESDNHT TPILCGAQYR  360
IHTHGVFRGI QDVRRVPGVA PTLVRSASET SEKRPFMCAY PGCNKRYFKL SHLQMHSRKH  420
TGEKPYQCDF KDCERRFSRS DQLKRHQRRH TGVKPFQCKT CQRKFSRSDH LKTHTRTHTG  480
EKPFSCRWPS CQKKFARSDE LVRHHNMHQR NMTKLQLAL                         519

SEQ ID NO: 401         moltype = AA  length = 522
FEATURE                Location/Qualifiers
source                 1..522
                       mol_type = protein
                       organism = Homo sapiens
SEQUENCE: 401
MDFLLLQDPA STCVPEPASQ HTLRSGPGCL QQPEQQGVRD PGGIWAKLGA AEASAERLQG  60
RRSRGASGSE PQQMGSDVRD LNALLPAVPS LGGGGGCALP VSGAAQWAPV LDFAPPGASA  120
YGSLGGPAPP PAPPPPPPPP PHSFIKQEPS WGGAEPHEEQ CLSAFTVHFS GQFTGTAGAC  180
RYGPFGPPPP SQASSGQARM FPNAPYLPSC LESQPAIRNQ GYSTVTFDGT PSYGHTPSHH  240
AAQFPNHSFK HEDPMGQQGS LGEQQYSVPP PVYGCHTPTD SCTGSQALLL RTPYSSDNLY  300
QMTSQLECMT WNQMNLGATL KGVAAGSSSS VKWTEGQSNH STGYESDNHT TPILCGAQYR  360
IHTHGVFRGI QDVRRVPGVA PTLVRSASET SEKRPFMCAY PGCNKRYFKL SHLQMHSRKH  420
TGEKPYQCDF KDCERRFSRS DQLKRHQRRH TGVKPFQCKT CQRKFSRSDH LKTHTRTHTG  480
KTSEKPFSCR WPSCQKKFAR SDELVRHHNM HQRNMTKLQL AL                     522

SEQ ID NO: 402         moltype = AA  length = 302
FEATURE                Location/Qualifiers
source                 1..302
                       mol_type = protein
                       organism = Homo sapiens
SEQUENCE: 402
MEKGYSTVTF DGTPSYGHTP SHHAAQFPNH SFKHEDPMGQ QGSLGEQQYS VPPPVYGCHT  60
PTDSCTGSQA LLLRTPYSSD NLYQMTSQLE CMTWNQMNLG ATLKGVAAGS SSSVKWTEGQ  120
SNHSTGYESD NHTTPILCGA QYRIHTHGVF RGIQDVRRVP GVAPTLVRSA SETSEKRPFM  180
CAYPGCNKRY FKLSHLQMHS RKHTGEKPYQ CDFKDCERRF SRSDQLKRHQ RRHTGVKPFQ  240
CKTCQRKFSR SDHLKTHTRT HTGEKPFSCR WPSCQKKFAR SDELVRHHNM HQRNMTKLQL  300
AL                                                                 302
```

```
SEQ ID NO: 403          moltype = AA  length = 288
FEATURE                 Location/Qualifiers
source                  1..288
                        mol_type = protein
                        organism = Homo sapiens
SEQUENCE: 403
MEKGYSTVTF DGTPSYGHTP SHHAAQFPNH SFKHEDPMGQ QGSLGEQQYS VPPPVYGCHT  60
PTDSCTGSQA LLLRTPYSSD NLYQMTSQLE CMTWNQMNLG ATLKGHSTGY ESDNHTTPIL  120
CGAQYRIHTH GVFRGIQDVR RVPGVAPTLV RSASETSEKR PFMCAYPGCN KRYFKLSHLQ  180
MHSRKHTGEK PYQCDFKDCE RRFSRSDQLK RHQRRHTGVK PFQCKTCQRK FSRSDHLKTH  240
TRTHTGKTSE KPFSCRWPSC QKKFARSDEL VRHHNMHQRN MTKLQLAL                288

SEQ ID NO: 404          moltype = AA  length = 276
FEATURE                 Location/Qualifiers
source                  1..276
                        mol_type = protein
                        organism = synthetic construct
SEQUENCE: 404
CSHSMRYFDT AVSRPGRGEP RFISVGYVDD TQFVRFDSDA ASPRGEPRAP WVEQEGPEYW  60
DRETQKYKRQ AQADRVSLRN LRGCYNQSED GSHTLQRMSG CDLGPDGRLL RGYDQSAYDG  120
KDYIALNEDL RSWTAADTAA QITQRKLEAA RAAEQLRAYL EGTCVEWLRR YLENGKETLQ  180
RAEPPKTHVT HHPLSDHEAT LRCWALGFYP AEITLTWQRD GEDQTQDTEL VETRPCGDGT  240
FQKWAAVVVP SGQEQRYTCH MQHEGLQEPL TLSWEP                            276

SEQ ID NO: 405          moltype = AA  length = 817
FEATURE                 Location/Qualifiers
source                  1..817
                        mol_type = protein
                        organism = synthetic construct
SEQUENCE: 405
GSHSMRYFST SVSRPGRGEP RFIAVGYVDD TQFVRFDSDA ASQRMEPRAP WIEQEGPEYW  60
DEETGKVKAH SQTDRENLRI ALRAYNQSEA GSHTLQMMFG CDVGSDGRFL RGYHQYAYDG  120
KDYIALKEDL RSWTAADMAA QITKRKWEAA HVAEQQRAYL EGTCVDGLRR YLENGKETLQ  180
RTDPPKTHMT HHPISDHEAT LRCWALGFYP AEITLTWQRD GEDQTQDTEL VETRPCGDGT  240
FQKWAAVVVP SGEEQRYTCH VQHEGLPKPL TLRWEGGGGS GGGGSGGGGS APTSSSTKKT  300
QLQLEALLLD LQMILNGINN YKNPKLTRML TAKFYMPKKA TELKHLQCLE EELKPLEEVL  360
NLAQSKNFHL RPRDLISNIN VIVLELKGSE TTFMCEYADE TATIVEFLNR WITFCQSIIS  420
TLTGGGGSGG GGSGGGGSGG GGSAPTSSST KKTQLQLEAL LLDLQMILNG INNYKNPKLT  480
RMLTAKFYMP KKATELKHLQ CLEEELKPLE EVLNLAQSKN FHLRPRDLIS NINVIVLELK  540
GSETTFMCEY ADETATIVEF LNRWITFCQS IISTLTGGGG SGGGGSGGGG SDKTHTCPPC  600
PAPEAAGGPS VFLFPPKPKD TLMISRTPEV TCVVVDVSHE DPEVKFNWYV DGVEVHNAKT  660
KPREEQYNST YRVVSVLTVL HQDWLNGKEY KCKVSNKALP APIEKTISKA KGQPREPQVY  720
TLPPSREEMT KNQVSLTCLV KGFYPSDIAV EWESNGQPEN NYKTTPPVLD SDGSFFLYSK  780
LTVDKSRWQQ GNVFSCSVMH EALHNHYTQK SLSLSPG                           817

SEQ ID NO: 406          moltype = AA  length = 813
FEATURE                 Location/Qualifiers
source                  1..813
                        mol_type = protein
                        organism = synthetic construct
SEQUENCE: 406
APTSSSTKKT QLQLEALLLD LQMILNGINN YKNPKLTRML TAKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTGGGGSGG GGSGGGGSGG GGSAPTSSST KKTQLQLEAL LLDLQMILNG  180
INNYKNPKLT RMLTAKFYMP KKATELKHLQ CLEEELKPLE EVLNLAQSKN FHLRPRDLIS  240
NINVIVLELK GSETTFMCEY ADETATIVEF LNRWITFCQS IISTLTGGGG SGGGGSGGGG  300
SGGGGSGSHS MRYFSTSVSR PGRGEPRFIA VGYVDDTQFV RFDSDAASQR MEPRAPWIEQ  360
EGPEYWDEET GKVKAHSQTD RENLRIALRA YNQSEAGSHT LQMMFGCDVG SDGRFLRGYH  420
QYAYDGKDYI ALKEDLRSWT AADMAAQITK RKWEAAHVAE QQRAYLEGTC VDGLRRYLEN  480
GKETLQRTDP PKTHMTHHPI SDHEATLRCW ALGFYPAEIT LTWQRDGEDQ TQDTELVETR  540
PCGDGTFQKW AAVVVPSGEE QRYTCHVQHE GLPKPLTLRW EAAAGGDKTH TCPPCPAPEA  600
AGGPSVFLFP PKPKDTLMIS RTPEVTCVVV DVSHEDPEVK FNWYVDGVEV HNAKTKPREE  660
QYNSTYRVVS VLTVLHQDWL NGKEYKCKVS NKALPAPIEK TISKAKGQPR EPQVYTLPPS  720
REEMTKNQVS LTCLVKGFYP SDIAVEWESN GQPENNYKTT PPVLDSDGSF FLYSKLTVDK  780
SRWQQGNVFS CSVMHEALHN HYTQKSLSLS PGK                               813

SEQ ID NO: 407          moltype = AA  length = 807
FEATURE                 Location/Qualifiers
source                  1..807
                        mol_type = protein
                        organism = synthetic construct
SEQUENCE: 407
GSHSMRYFST SVSRPGRGEP RFIAVGYVDD TQFVRFDSDA ASQRMEPRAP WIEQEGPEYW  60
DEETGKVKAH SQTDRENLRI ALRAYNQSEA GSHTLQMMFG CDVGSDGRFL RGYHQYAYDG  120
KDYIALKEDL RSWTAADMAA QITKRKWEAA HVAEQQRAYL EGTCVDGLRR YLENGKETLQ  180
RTDPPKTHMT HHPISDHEAT LRCWALGFYP AEITLTWQRD GEDQTQDTEL VETRPCGDGT  240
FQKWAAVVVP SGEEQRYTCH VQHEGLPKPL TLRWEAAAGG DKTHTCPPCP APEAAGGPSV  300
FLFPPKPKDT LMISRTPEVT CVVVDVSHED PEVKFNWYVD GVEVHNAKTK PREEQYNSTY  360
RVVSVLTVLH QDWLNGKEYK CKVSNKALPA PIEKTISKAK GQPREPQVYT LPPSREEMTK  420
```

```
NQVSLTCLVK GFYPSDIAVE WESNGQPENN YKTTPPVLDS DGSFFLYSKL TVDKSRWQQG  480
NVFSCSVMHE ALHNHYTQKS LSLSPGGGGG SGGGGSGGGG SAPTSSSTKK TQLQLEALLL  540
DLQMILNGIN NYKNPKLTRM LTAKFYMPKK ATELKHLQCL EEELKPLEEV LNLAQSKNFH  600
LRPRDLISNI NVIVLELKGS ETTFMCEYAD ETATIVEFLN RWITFCQSII STLTGGGGSG  660
GGGSGGGGSG GGGSAPTSSS TKKTQLQLEA LLLDLQMILN GINNYKNPKL TRMLTAKFYM  720
PKKATELKHL QCLEEELKPL EEVLNLAQSK NFHLRPRDLI SNINVIVLEL KGSETTFMCE  780
YADETATIVE FLNRWITFCQ SIISTLT                                     807

SEQ ID NO: 408         moltype = AA  length = 123
FEATURE                Location/Qualifiers
source                 1..123
                       mol_type = protein
                       organism = synthetic construct
SEQUENCE: 408
CMTWNQMNLG GGGSGGGGSG GGGSIQRTPK IQVYSCHPAE NGKSNFLNCY VSGFHPSDIE  60
VDLLKNGERI EKVEHSDLSF SKDWSFYLLY YTEFTPTEKD EYACRVNHVT LSQPKIVKWD  120
RDM                                                               123

SEQ ID NO: 409         moltype = AA  length = 123
FEATURE                Location/Qualifiers
source                 1..123
                       mol_type = protein
                       organism = synthetic construct
SEQUENCE: 409
CYTWNQMNLG GGGSGGGGSG GGGSIQRTPK IQVYSCHPAE NGKSNFLNCY VSGFHPSDIE  60
VDLLKNGERI EKVEHSDLSF SKDWSFYLLY YTEFTPTEKD EYACRVNHVT LSQPKIVKWD  120
RDM                                                               123

SEQ ID NO: 410         moltype = AA  length = 227
FEATURE                Location/Qualifiers
source                 1..227
                       mol_type = protein
                       organism = Homo sapiens
SEQUENCE: 410
DKTHTCPPCP APELLGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGK               227

SEQ ID NO: 411         moltype = AA  length = 325
FEATURE                Location/Qualifiers
source                 1..325
                       mol_type = protein
                       organism = Homo sapiens
SEQUENCE: 411
STKGPSVFPL APCSRSTSES TAALGCLVKD YFPEPVTVSW NSGALTSGVH TFPAVLQSSG  60
LYSLSSVVTV PSSNFGTQTY TCNVDHKPSN TKVDKTVERK CCVECPPCPA PPVAGPSVFL  120
FPPKPKDTLM ISRTPEVTCV VVDVSHEDPE VQFNWYVDGV EVHNAKTKPR EEQFNSTFRV  180
VSVLTVVHQD WLNGKEYKCK VSNKGLPAPI EKTISKTKGQ PREPQVYTLP PSREEMTKNQ  240
VSLTCLVKGF YPSDIAVEWE SNGQPENNYK TTPPMLDSDG SFFLYSKLTV DKSRWQQGNV  300
FSCSVMHEAL HNHYTQKSLS LSPGK                                       325

SEQ ID NO: 412         moltype = AA  length = 246
FEATURE                Location/Qualifiers
source                 1..246
                       mol_type = protein
                       organism = Homo sapiens
SEQUENCE: 412
HKPSNTKVDK RVELKTPLGD TTHTCPPCPA PELLGGPSVF LFPPKPKDTL MISRTPEVTC  60
VVVDVSHEDP EVKFNWYVDG VEVHNAKTKP REEQYNSTYR VVSVLTVLHQ DWLNGKEYKC  120
KVSNKALPAP IEKTISKAKG QPREPQVYTL PPSRDELTKN QVSLTCLVKG FYPSDIAVEW  180
ESNGQPENNY KTTPPVLDSD GSFFLYSKLT VDKSRWQQGN VFSCSVMHEA LHNHYTQKSL  240
SLSPGK                                                            246

SEQ ID NO: 413         moltype = AA  length = 383
FEATURE                Location/Qualifiers
source                 1..383
                       mol_type = protein
                       organism = Homo sapiens
SEQUENCE: 413
PTKAPDVFPI ISGCRHPKDN SPVVLACLIT GYHPTSVTVT WYMGTQSQPQ RTFPEIQRRD  60
SYYMTSSQLS TPLQQWRQGE YKCVVQHTAS KSKKEIFRWP ESPKAQASSV PTAQPQAEGS  120
LAKATTAPAT TRNTGRGGEE KKKEKEKEEQ EERETKTPEC PSHTQPLGVY LLTPAVQDLW  180
LRDKATFTCF VVGSDLKDAH LTWEVAGKVP TGGVEEGLLE RHSNGSQSQH SRLTLPRSLW  240
NAGTSVTCTL NHPSLPPQRL MALREPAAQA PVKLSLNLLA SSDPPEAASW LLCEVSGFSP  300
PNILLMWLED QREVNTSGFA PARPPPQPRS TTFWAWSVLR VPAPPSPQPA TYTCVVSHED  360
SRTLLNASRS LEVSYVTDHG PMK                                         383

SEQ ID NO: 414         moltype = AA  length = 276
```

```
FEATURE                 Location/Qualifiers
source                  1..276
                        mol_type = protein
                        organism = Homo sapiens
SEQUENCE: 414
VTSTLTIKZS DWLGESMFTC RVDHRGLTFQ QNASSMCVPD QDTAIRVFAI PPSFASIFLT  60
KSTKLTCLVT DLTTYBSVTI SWTREENGAV KTHTNISESH PNATFSAVGE ASICEDBDWS  120
GERFTCTVTH TDLPSPLKQT ISRPKGVALH RPBVYLLPPA RZZLNLRESA TITCLVTGFS  180
PADVFVEWMQ RGEPLSPQKY VTSAPMPEPQ APGRYFAHSI LTVSEEEWNT GGTYTCVVAH  240
EALPNRVTER TVDKSTGKPT LYNVSLVMSD TAGTCY                            276

SEQ ID NO: 415          moltype = AA  length = 353
FEATURE                 Location/Qualifiers
source                  1..353
                        mol_type = protein
                        organism = Homo sapiens
SEQUENCE: 415
ASPTSPKVFP LSLCSTQPDG NVVIACLVQG FFPQEPLSVT WSESGQGVTA RNFPPSQDAS  60
GDLYTTSSQL TLPATQCLAG KSVTCHVKHY TNPSQDVTVP CPVPSTPPTP SPSTPPTPSP  120
SCCHPRLSLH RPALEDLLLG SEANLTCTLT GLRDASGVTF TWTPSSGKSA VQGPPERDLC  180
GCYSVSSVLP GCAEPWNHGK TFTCTAAYPE SKTPLTATLS KSGNTFRPEV HLLPPPSEEL  240
ALNELVTLTC LARGFSPKDV LVRWLQGSQE LPREKYLTWA SRQEPSQGTT TFAVTSILRV  300
AAEDWKKGDT FSCMVGHEAL PLAFTQKTID RLAGKPTHVN VSVVMAEVDG TCY         353

SEQ ID NO: 416          moltype = AA  length = 222
FEATURE                 Location/Qualifiers
source                  1..222
                        mol_type = protein
                        organism = Homo sapiens
SEQUENCE: 416
ADPCDSNPRG VSAYLSRPSP FDLFIRKSPT ITCLVVDLAP SKGTVNLTWS RASGKPVNHS  60
TRKEEKQRNG TLTVTSTLPV GTRDWIEGET YQCRVTHPHL PRALMRSTTK TSGPRAAPEV  120
YAFATPEWPG SRDKRTLACL IQNFMPEDIS VQWLHNEVQL PDARHSTTQP RKTKGSGFFV  180
FSRLEVTRAE WEQKDEFICR AVHEAASPSQ TVQRAVSVNP GK                     222

SEQ ID NO: 417          moltype = AA  length = 327
FEATURE                 Location/Qualifiers
source                  1..327
                        mol_type = protein
                        organism = Homo sapiens
SEQUENCE: 417
ASTKGPSVFP LAPCSRSTSE STAALGCLVK DYFPEPVTVS WNSGALTSGV HTFPAVLQSS  60
GLYSLSSVVT VPSSSLGTKT YTCNVDHKPS NTKVDKRVES KYGPPCPSCP APEFLGGPSV  120
FLFPPKPKDT LMISRTPEVT CVVVDVSQED PEVQFNWYVD GVEVHNAKTK PREEQFNSTY  180
RVVSVLTVLH QDWLNGKEYK CKVSNKGLPS SIEKTISKAK GQPREPQVYT LPPSQEEMTK  240
NQVSLTCLVK GFYPSDIAVE WESNGQPENN YKTTPPVLDS DGSFFLYSRL TVDKSRWQEG  300
NVFSCSVMHE ALHNHYTQKS LSLSLGK                                      327

SEQ ID NO: 418          moltype = AA  length = 227
FEATURE                 Location/Qualifiers
source                  1..227
                        mol_type = protein
                        organism = Homo sapiens
SEQUENCE: 418
DKTHTCPPCP APELLGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVYT LPPSREEMTK NQVSLTCLVK GFYPSDIAVE WESNGQPENN YKTTPPVLDS  180
DGSFFLYSKL TVDKSRWQQG NVFSCSVMHE ALHNHYTQKS LSLSPGK                227

SEQ ID NO: 419          moltype = AA  length = 227
FEATURE                 Location/Qualifiers
source                  1..227
                        mol_type = protein
                        organism = synthetic construct
SEQUENCE: 419
DKTHTCPPCP APEFEGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA SIEKTISKAK  120
GQPREPQVYT LPPSREEMTK NQVSLTCLVK GFYPSDIAVE WESNGQPENN YKTTPPVLDS  180
DGSFFLYSKL TVDKSRWQQG NVFSCSVMHE ALHNHYTQKS LSLSPGK                227

SEQ ID NO: 420          moltype = AA  length = 227
FEATURE                 Location/Qualifiers
source                  1..227
                        mol_type = protein
                        organism = synthetic construct
SEQUENCE: 420
DKTHTCPPCP APELLGGPSV FLFPPKPKDT LMISRTPEVT CVVVDVSHED PEVKFNWYVD  60
GVEVHNAKTK PREEQYASTY RVVSVLTVLH QDWLNGKEYK CKVSNKALPA PIEKTISKAK  120
GQPREPQVYT LPPSREEMTK NQVSLTCLVK GFYPSDIAVE WESNGQPENN YKTTPPVLDS  180
```

```
DGSFFLYSKL TVDKSRWQQG NVFSCSVMHE ALHNHYTQKS LSLSPGK                227

SEQ ID NO: 421          moltype = AA  length = 227
FEATURE                 Location/Qualifiers
source                  1..227
                        mol_type = protein
                        organism = synthetic construct
SEQUENCE: 421
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVYT LPPSREEMTK NQVSLTCLVK GFYPSDIAVE WESNGQPENN YKTTPPVLDS  180
DGSFFLYSKL TVDKSRWQQG NVFSCSVMHE ALHNHYTQKS LSLSPGK                227

SEQ ID NO: 422          moltype = AA  length = 813
FEATURE                 Location/Qualifiers
source                  1..813
                        mol_type = protein
                        organism = synthetic construct
SEQUENCE: 422
APTSSSTKKT QLQLEALLLD LQMILNGINN YKNPKLTRML TAKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTGGGGSGG GGSGGGGSGG GGSAPTSSST KKTQLQLEAL LLDLQMILNG  180
INNYKNPKLT RMLTAKFYMP KKATELKHLQ CLEEELKPLE EVLNLAQSKN FHLRPRDLIS  240
NINVIVLELK GSETTFMCEY ADETATIVEF LNRWITFCQS IISTLTGGGG SGGGGSGGGG  300
SGGGGSGSHS MRYFFTSVSR PGRGEPRFIA VGYVDDTQFV RFDSDAASQR MEPRAPWIEQ  360
EGPEYWDGET RKVKAHSQTH RVDLGTLRGC YNQSEAGSHT VQRMYGCDVG SDWRFLRGYH  420
QYAYDGKDYI ALKEDLRSWT AADMAAQTTK HKWEAAHVAE QLRAYLEGTC VEWLRRYLEN  480
GKETLQRTDA PKTHMTHHAV SDHEATLRCW ALSFYPAEIT LTWQRDGEDQ TQDTELVETR  540
PCGDGTFQKW AAVVVPSGQE QRYTCHVQHE GLPKPLTLRW EAAAGGDKTH TCPPCPAPEA  600
AGGPSVFLFP PKPKDTLMIS RTPEVTCVVV DVSHEDPEVK FNWYVDGVEV HNAKTKPREE  660
QYNSTYRVVS VLTVLHQDWL NGKEYKCKVS NKALPAPIEK TISKAKGQPR EPQVYTLPPS  720
REEMTKNQVS LTCLVKGFYP SDIAVEWESN GQPENNYKTT PPVLDSDGSF FLYSKLTVDK  780
SRWQQGNVFS CSVMHEALHN HYTQKSLSLS PGK                               813

SEQ ID NO: 423          moltype = AA  length = 123
FEATURE                 Location/Qualifiers
source                  1..123
                        mol_type = protein
                        organism = synthetic construct
SEQUENCE: 423
VLDFAPPGAG CGGSGGGGSG GGGSIQRTPK IQVYSCHPAE NGKSNFLNCY VSGFHPSDIE  60
VDLLKNGERI EKVEHSDLSF SKDWSFYLLY YTEFTPTEKD EYACRVNHVT LSQPKIVKWD  120
RDM                                                                123

SEQ ID NO: 424          moltype = AA  length = 123
FEATURE                 Location/Qualifiers
source                  1..123
                        mol_type = protein
                        organism = synthetic construct
SEQUENCE: 424
RMFPNAPYLG CGGSGGGGSG GGGSIQRTPK IQVYSCHPAE NGKSNFLNCY VSGFHPSDIE  60
VDLLKNGERI EKVEHSDLSF SKDWSFYLLY YTEFTPTEKD EYACRVNHVT LSQPKIVKWD  120
RDM                                                                123

SEQ ID NO: 425          moltype = AA  length = 812
FEATURE                 Location/Qualifiers
source                  1..812
                        mol_type = protein
                        organism = synthetic construct
SEQUENCE: 425
APTSSSTKKT QLQLEALLLD LQMILNGINN YKNPKLTRML TAKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTGGGGSGG GGSGGGGSGG GGSAPTSSST KKTQLQLEAL LLDLQMILNG  180
INNYKNPKLT RMLTAKFYMP KKATELKHLQ CLEEELKPLE EVLNLAQSKN FHLRPRDLIS  240
NINVIVLELK GSETTFMCEY ADETATIVEF LNRWITFCQS IISTLTGGGG SGGGGSGGGG  300
SGGGGSGSHS MRYFFTSVSR PGRGEPRFIA VGYVDDTQFV RFDSDAASQR MEPRAPWIEQ  360
EGPEYWDGET RKVKAHSQTH RVDLGTLRGC YNQSEAGSHT VQRMYGCDVG SDWRFLRGYH  420
QYAYDGKDYI ALKEDLRSWT AADMAAQTTK HKWEAAHVAE QLRAYLEGTC VEWLRRYLEN  480
GKETLQRTDA PKTHMTHHAV SDHEATLRCW ALSFYPAEIT LTWQRDGEDQ TQDTELVETR  540
PAGDGTFQKW AAVVVPSGQE QRYTCHVQHE GLPKPLTLRW EAAAGGDKTH TCPPCPAPEA  600
AGGPSVFLFP PKPKDTLMIS RTPEVTCVVV DVSHEDPEVK FNWYVDGVEV HNAKTKPREE  660
QYNSTYRVVS VLTVLHQDWL NGKEYKCKVS NKALPAPIEK TISKAKGQPR EPQVYTLPPS  720
REEMTKNQVS LTCLVKGFYP SDIAVEWESN GQPENNYKTT PPVLDSDGSF FLYSKLTVDK  780
SRWQQGNVFS CSVMHEALHN HYTQKSLSLS PG                                812

SEQ ID NO: 426          moltype = AA  length = 813
FEATURE                 Location/Qualifiers
source                  1..813
                        mol_type = protein
```

```
                          organism = synthetic construct
SEQUENCE: 426
APTSSSTKKT QLQLEALLLD LQMILNGINN YKNPKLTRML TAKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTGGGGSGG GGSGGGGSGG GGSAPTSSST KKTQLQLEAL LLDLQMILNG  180
INNYKNPKLT RMLTAKFYMP KKATELKHLQ CLEEELKPLE EVLNLAQSKN FHLRPRDLIS  240
NINVIVLELK GSETTFMCEY ADETATIVEF LNRWITFCQS IISTLTGGGG SGGGGSGGGG  300
SGGGGSGSHS MRYFFTSVSR PGRGEPRFIA VGYVDDTQFV RFDSDAASQR MEPRAPWIEQ  360
EGPEYWDGET RKVKAHSQTH RVDLGTLRGA YNQSEAGSHT VQRMYGCDVG SDWRFLRGYH  420
QYAYDGKDYI ALKEDLRSWT AADMAAQTTK HKWEAAHVAE QLRAYLEGTC VEWLRRYLEN  480
GKETLQRTDA PKTHMTHHAV SDHEATLRCW ALSFYPAEIT LTWQRDGEDQ TQDTELVETR  540
PCGDGTFQKW AAVVVPSGQE QRYTCHVQHE GLPKPLTLRW EAAAGGDKTH TCPPCPAPEA  600
AGGPSVFLFP PKPKDTLMIS RTPEVTCVVV DVSHEDPEVK FNWYVDGVEV HNAKTKPREE  660
QYNSTYRVVS VLTVLHQDWL NGKEYKCKVS NKALPAPIEK TISKAKGQPR EPQVYTLPPS  720
REEMTKNQVS LTCLVKGFYP SDIAVEWESN GQPENNYKTT PPVLDSDGSF FLYSKLTVDK  780
SRWQQGNVFS CSVMHEALHN HYTQKSLSLS PGK                             813

SEQ ID NO: 427         moltype = AA  length = 123
FEATURE                Location/Qualifiers
source                 1..123
                       mol_type = protein
                       organism = synthetic construct
SEQUENCE: 427
VLDFAPPGAG CGGSGGGGSG GGGSIQRTPK IQVYSRHPAE NGKSNFLNCY VSGFHPSDIE  60
VDLLKNGERI EKVEHSDLSF SKDWSFYLLY YTEFTPTEKD EYACRVNHVT LSQPKIVKWD  120
RDM                                                              123

SEQ ID NO: 428         moltype = AA  length = 123
FEATURE                Location/Qualifiers
source                 1..123
                       mol_type = protein
                       organism = synthetic construct
SEQUENCE: 428
RMFPNAPYLG CGGSGGGGSG GGGSIQRTPK IQVYSRHPAE NGKSNFLNCY VSGFHPSDIE  60
VDLLKNGERI EKVEHSDLSF SKDWSFYLLY YTEFTPTEKD EYACRVNHVT LSQPKIVKWD  120
RDM                                                              123

SEQ ID NO: 429         moltype = AA  length = 123
FEATURE                Location/Qualifiers
source                 1..123
                       mol_type = protein
                       organism = synthetic construct
SEQUENCE: 429
YMFPNAPYLG CGGSGGGGSG GGGSIQRTPK IQVYSCHPAE NGKSNFLNCY VSGFHPSDIE  60
VDLLKNGERI EKVEHSDLSF SKDWSFYLLY YTEFTPTEKD EYACRVNHVT LSQPKIVKWD  120
RDM                                                              123

SEQ ID NO: 430         moltype = AA  length = 123
FEATURE                Location/Qualifiers
source                 1..123
                       mol_type = protein
                       organism = synthetic construct
SEQUENCE: 430
YMFPNAPYLG CGGSGGGGSG GGGSIQRTPK IQVYSRHPAE NGKSNFLNCY VSGFHPSDIE  60
VDLLKNGERI EKVEHSDLSF SKDWSFYLLY YTEFTPTEKD EYACRVNHVT LSQPKIVKWD  120
RDM                                                              123

SEQ ID NO: 431         moltype = AA  length = 812
FEATURE                Location/Qualifiers
source                 1..812
                       mol_type = protein
                       organism = synthetic construct
SEQUENCE: 431
APTSSSTKKT QLQLEALLLD LQMILNGINN YKNPKLTRML TAKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTGGGGSGG GGSGGGGSGG GGSAPTSSST KKTQLQLEAL LLDLQMILNG  180
INNYKNPKLT RMLTAKFYMP KKATELKHLQ CLEEELKPLE EVLNLAQSKN FHLRPRDLIS  240
NINVIVLELK GSETTFMCEY ADETATIVEF LNRWITFCQS IISTLTGGGG SGGGGSGGGG  300
SGGGGSGSHS MRYFSTSVSR PGRGEPRFIA VGYVDDTQFV RFDSDAASQR MEPRAPWIEQ  360
EGPEYWDEET GKVKAHSQTD RENLRIALRC YNQSEAGSHT LQMMFGCDVG SDGRFLRGYH  420
QYAYDGKDYI ALKEDLRSWT AADMAAQITK RKWEAAHVAE QQRAYLEGTC VDGLRRYLEN  480
GKETLQRTDP PKTHMTHHPI SDHEATLRCW ALGFYPAEIT LTWQRDGEDQ TQDTELVETR  540
PCGDGTFQKW AAVVVPSGEE QRYTCHVQHE GLPKPLTLRW EAAAGGDKTH TCPPCPAPEA  600
AGGPSVFLFP PKPKDTLMIS RTPEVTCVVV DVSHEDPEVK FNWYVDGVEV HNAKTKPREE  660
QYNSTYRVVS VLTVLHQDWL NGKEYKCKVS NKALPAPIEK TISKAKGQPR EPQVYTLPPS  720
REEMTKNQVS LTCLVKGFYP SDIAVEWESN GQPENNYKTT PPVLDSDGSF FLYSKLTVDK  780
SRWQQGNVFS CSVMHEALHN HYTQKSLSLS PG                              812

SEQ ID NO: 432         moltype = AA  length = 807
```

```
FEATURE                 Location/Qualifiers
source                  1..807
                        mol_type = protein
                        organism = synthetic construct
SEQUENCE: 432
GSHSMRYFST SVSRPGRGEP RFIAVGYVDD TQFVRFDSDA ASQRMEPRAP WIEQEGPEYW  60
DEETGKVKAH SQTDRENLRI ALRCYNQSEA GSHTLQMMFG CDVGSDGRFL RGYHQYAYDG  120
KDYIALKEDL RSWTAADMAA QITKRKWEAA HVAEQQRAYL EGTCVDGLRR YLENGKETLQ  180
RTDPPKTHMT HHPISDHEAT LRCWALGFYP AEITLTWQRD GEDQTQDTEL VETRPCGDGT  240
FQKWAAVVVP SGEEQRYTCH VQHEGLPKPL TLRWEAAAGG DKTHTCPPCP APEAAGGPSV  300
FLFPPKPKDT LMISRTPEVT CVVVDVSHED PEVKFNWYVD GVEVHNAKTK PREEQYNSTY  360
RVVSVLTVLH QDWLNGKEYK CKVSNKALPA PIEKTISKAK GQPREPQVYT LPPSREEMTK  420
NQVSLTCLVK GFYPSDIAVE WESNGQPENN YKTTPPVLDS DGSFFLYSKL TVDKSRWQQG  480
NVFSCSVMHE ALHNHYTQKS LSLSPGGGGG SGGGGSGGGG SAPTSSSTKK TQLQLEALLL  540
DLQMILNGIN NYKNPKLTRM LTAKFYMPKK ATELKHLQCL EEELKPLEEV LNLAQSKNFH  600
LRPRDLISNI NVIVLELKGS ETTFMCEYAD ETATIVEFLN RWITFCQSII STLTGGGGSG  660
GGGSGGGGSG GGGSAPTSSS TKKTQLQLEA LLLDLQMILN GINNYKNPKL TRMLTAKFYM  720
PKKATELKHL QCLEEELKPL EEVLNLAQSK NFHLRPRDLI SNINVIVLEL KGSETTFMCE  780
YADETATIVE FLNRWITFCQ SIISTLT                                      807

SEQ ID NO: 433          moltype = AA  length = 506
FEATURE                 Location/Qualifiers
source                  1..506
                        mol_type = protein
                        organism = synthetic construct
SEQUENCE: 433
GSHSMRYFST SVSRPGRGEP RFIAVGYVDD TQFVRFDSDA ASQRMEPRAP WIEQEGPEYW  60
DEETGKVKAH SQTDRENLRI ALRCYNQSEA GSHTLQMMFG CDVGSDGRFL RGYHQYAYDG  120
KDYIALKEDL RSWTAADMAA QITKRKWEAA HVAEQQRAYL EGTCVDGLRR YLENGKETLQ  180
RTDPPKTHMT HHPISDHEAT LRCWALGFYP AEITLTWQRD GEDQTQDTEL VETRPCGDGT  240
FQKWAAVVVP SGEEQRYTCH VQHEGLPKPL TLRWEAAAGG DKTHTCPPCP APEAAGGPSV  300
FLFPPKPKDT LMISRTPEVT CVVVDVSHED PEVKFNWYVD GVEVHNAKTK PREEQYNSTY  360
RVVSVLTVLH QDWLNGKEYK CKVSNKALPA PIEKTISKAK GQPREPQVYT LPPSREEMTK  420
NQVSLTCLVK GFYPSDIAVE WESNGQPENN YKTTPPVLDS DGSFFLYSKL TVDKSRWQQG  480
NVFSCSVMHE ALHNHYTQKS LSLSPG                                       506

SEQ ID NO: 434          moltype = AA  length = 507
FEATURE                 Location/Qualifiers
source                  1..507
                        mol_type = protein
                        organism = synthetic construct
SEQUENCE: 434
GSHSMRYFST SVSRPGRGEP RFIAVGYVDD TQFVRFDSDA ASQRMEPRAP WIEQEGPEYW  60
DEETGKVKAH SQTDRENLRI ALRAYNQSEA GSHTLQMMFG CDVGSDGRFL RGYHQYAYDG  120
KDYIALKEDL RSWTAADMAA QITKRKWEAA HVAEQQRAYL EGTCVDGLRR YLENGKETLQ  180
RTDPPKTHMT HHPISDHEAT LRCWALGFYP AEITLTWQRD GEDQTQDTEL VETRPCGDGT  240
FQKWAAVVVP SGEEQRYTCH VQHEGLPKPL TLRWEAAAGG DKTHTCPPCP APEAAGGPSV  300
FLFPPKPKDT LMISRTPEVT CVVVDVSHED PEVKFNWYVD GVEVHNAKTK PREEQYNSTY  360
RVVSVLTVLH QDWLNGKEYK CKVSNKALPA PIEKTISKAK GQPREPQVYT LPPSREEMTK  420
NQVSLTCLVK GFYPSDIAVE WESNGQPENN YKTTPPVLDS DGSFFLYSKL TVDKSRWQQG  480
NVFSCSVMHE ALHNHYTQKS LSLSPGK                                      507

SEQ ID NO: 435          moltype = AA  length = 812
FEATURE                 Location/Qualifiers
source                  1..812
                        mol_type = protein
                        organism = synthetic construct
SEQUENCE: 435
APTSSSTKKT QLQLEALLLD LQMILNGINN YKNPKLTRML TAKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTGGGGSGG GGSGGGGSGG GGSAPTSSST KKTQLQLEAL LLDLQMILNG  180
INNYKNPKLT RMLTAKFYMP KKATELKHLQ CLEEELKPLE EVLNLAQSKN FHLRPRDLIS  240
NINVIVLELK GSETTFMCEY ADETATIVEF LNRWITFCQS IISTLTGGGG SGGGGSGGGG  300
SGGGGSGSHS MRYFSTSVSR PGRGEPRFIA VGYVDDTQFV RFDSDAASQR MEPRAPWIEQ  360
EGPEYWDEET GKVKAHSQTD RENLRIALRC YNQSEAGSHT LQMMFGCDVG SDGRFLRGYH  420
QYAYDGKDYI ALKEDLRSWT AADMAAQITK RKWEAAHVAE QQRAYLEGTC VDGLRRYLEN  480
GKETLQRTDP PKTHMTHHPI SDHEATLRCW ALGFYPAEIT LTWQRDGEDQ TQDTELVETR  540
PAGDGTFQKW AAVVVPSGEE QRYTCHVQHE GLPKPLTLRW EAAAGGDKTH TCPPCPAPEA  600
AGGPSVFLFP PKPKDTLMIS RTPEVTCVVV DVSHEDPEVK FNWYVDGVEV HNAKTKPREE  660
QYNSTYRVVS VLTVLHQDWL NGKEYKCKVS NKALPAPIEK TISKAKGQPR EPQVYTLPPS  720
REEMTKNQVS LTCLVKGFYP SDIAVEWESN GQPENNYKTT PPVLDSDGSF FLYSKLTVDK  780
SRWQQGNVFS CSVMHEALHN HYTQKSLSLS PG                                812

SEQ ID NO: 436          moltype = AA  length = 807
FEATURE                 Location/Qualifiers
source                  1..807
                        mol_type = protein
                        organism = synthetic construct
SEQUENCE: 436
```

```
GSHSMRYFST SVSRPGRGEP RFIAVGYVDD TQFVRFDSDA ASQRMEPRAP WIEQEGPEYW  60
DEETGKVKAH SQTDRENLRI ALRCYNQSEA GSHTLQMMFG CDVGSDGRFL RGYHQYAYDG  120
KDYIALKEDL RSWTAADMAA QITKRKWEAA HVAEQQRAYL EGTCVDGLRR YLENGKETLQ  180
RTDPPKTHMT HHPISDHEAT LRCWALGFYP AEITLTWQRD GEDQTQDTEL VETRPAGDGT  240
FQKWAAVVVP SGEEQRYTCH VQHEGLPKPL TLRWEAAAGG DKTHTCPPCP APEAAGGPSV  300
FLFPPKPKDT LMISRTPEVT CVVVDVSHED PEVKFNWYVD GVEVHNAKTK PREEQYNSTY  360
RVVSVLTVLH QDWLNGKEYK CKVSNKALPA PIEKTISKAK GQPREPQVYT LPPSREEMTK  420
NQVSLTCLVK GFYPSDIAVE WESNGQPENN YKTTPPVLDS DGSFFLYSKL TVDKSRWQQG  480
NVFSCSVMHE ALHNHYTQKS LSLSPGGGGG SGGGGSGGGG SAPTSSSTKK TQLQLEALLL  540
DLQMILNGIN NYKNPKLTRM LTAKFYMPKK ATELKHLQCL EEELKPLEEV LNLAQSKNFH  600
LRPRDLISNI NVIVLELKGS ETTFMCEYAD ETATIVEFLN RWITFCQSII STLTGGGGSG  660
GGGSGGGGSG GGGSAPTSSS TKKTQLQLEA LLLDLQMILN GINNYKNPKL TRMLTAKFYM  720
PKKATELKHL QCLEEELKPL EEVLNLAQSK NFHLRPRDLI SNINVIVLEL KGSETTFMCE  780
YADETATIVE FLNRWITFCQ SIISTLT                                     807

SEQ ID NO: 437          moltype = AA  length = 506
FEATURE                 Location/Qualifiers
source                  1..506
                        mol_type = protein
                        organism = synthetic construct
SEQUENCE: 437
GSHSMRYFST SVSRPGRGEP RFIAVGYVDD TQFVRFDSDA ASQRMEPRAP WIEQEGPEYW  60
DEETGKVKAH SQTDRENLRI ALRCYNQSEA GSHTLQMMFG CDVGSDGRFL RGYHQYAYDG  120
KDYIALKEDL RSWTAADMAA QITKRKWEAA HVAEQQRAYL EGTCVDGLRR YLENGKETLQ  180
RTDPPKTHMT HHPISDHEAT LRCWALGFYP AEITLTWQRD GEDQTQDTEL VETRPAGDGT  240
FQKWAAVVVP SGEEQRYTCH VQHEGLPKPL TLRWEAAAGG DKTHTCPPCP APEAAGGPSV  300
FLFPPKPKDT LMISRTPEVT CVVVDVSHED PEVKFNWYVD GVEVHNAKTK PREEQYNSTY  360
RVVSVLTVLH QDWLNGKEYK CKVSNKALPA PIEKTISKAK GQPREPQVYT LPPSREEMTK  420
NQVSLTCLVK GFYPSDIAVE WESNGQPENN YKTTPPVLDS DGSFFLYSKL TVDKSRWQQG  480
NVFSCSVMHE ALHNHYTQKS LSLSPG                                      506

SEQ ID NO: 438          moltype = AA  length = 123
FEATURE                 Location/Qualifiers
source                  1..123
                        mol_type = protein
                        organism = synthetic construct
SEQUENCE: 438
CYTWNQMNLG CGGSGGGGSG GGGSIQRTPK IQVYSCHPAE NGKSNFLNCY VSGFHPSDIE  60
VDLLKNGERI EKVEHSDLSF SKDWSFYLLY YTEFTPTEKD EYACRVNHVT LSQPKIVKWD  120
RDM                                                               123

SEQ ID NO: 439          moltype = AA  length = 424
FEATURE                 Location/Qualifiers
source                  1..424
                        mol_type = protein
                        organism = synthetic construct
SEQUENCE: 439
CYTWNQMNLG CGGSGGGGSG GGGSIQRTPK IQVYSCHPAE NGKSNFLNCY VSGFHPSDIE  60
VDLLKNGERI EKVEHSDLSF SKDWSFYLLY YTEFTPTEKD EYACRVNHVT LSQPKIVKWD  120
RDMGGGGSGG GGSGGGGSAP TSSSTKKTQL QLEALLLDLQ MILNGINNYK NPKLTRMLTA  180
KFYMPKKATE LKHLQCLEEE LKPLEEVLNL AQSKNFHLRP RDLISNINVI VLELKGSETT  240
FMCEYADETA TIVEFLNRWI TFCQSIISTL TGGGGSGGGG SGGGGSGGGG SAPTSSSTKK  300
TQLQLEALLL DLQMILNGIN NYKNPKLTRM LTAKFYMPKK ATELKHLQCL EEELKPLEEV  360
LNLAQSKNFH LRPRDLISNI NVIVLELKGS ETTFMCEYAD ETATIVEFLN RWITFCQSII  420
STLT                                                              424

SEQ ID NO: 440          moltype = AA  length = 424
FEATURE                 Location/Qualifiers
source                  1..424
                        mol_type = protein
                        organism = synthetic construct
SEQUENCE: 440
CYTWNQMNLG GGGSGGGGSG GGGSIQRTPK IQVYSCHPAE NGKSNFLNCY VSGFHPSDIE  60
VDLLKNGERI EKVEHSDLSF SKDWSFYLLY YTEFTPTEKD EYACRVNHVT LSQPKIVKWD  120
RDMGGGGSGG GGSGGGGSAP TSSSTKKTQL QLEALLLDLQ MILNGINNYK NPKLTRMLTA  180
KFYMPKKATE LKHLQCLEEE LKPLEEVLNL AQSKNFHLRP RDLISNINVI VLELKGSETT  240
FMCEYADETA TIVEFLNRWI TFCQSIISTL TGGGGSGGGG SGGGGSGGGG SAPTSSSTKK  300
TQLQLEALLL DLQMILNGIN NYKNPKLTRM LTAKFYMPKK ATELKHLQCL EEELKPLEEV  360
LNLAQSKNFH LRPRDLISNI NVIVLELKGS ETTFMCEYAD ETATIVEFLN RWITFCQSII  420
STLT                                                              424

SEQ ID NO: 441          moltype = AA  length = 123
FEATURE                 Location/Qualifiers
source                  1..123
                        mol_type = protein
                        organism = synthetic construct
SEQUENCE: 441
CYTWNQMNLG CGGSGGGGSG GGGSIQRTPK IQVYSRHPAE NGKSNFLNCY VSGFHPSDIE  60
VDLLKNGERI EKVEHSDLSF SKDWSFYLLY YTEFTPTEKD EYACRVNHVT LSQPKIVKWD  120
```

```
RDM                                                           123

SEQ ID NO: 442          moltype = AA  length = 424
FEATURE                 Location/Qualifiers
source                  1..424
                        mol_type = protein
                        organism = synthetic construct
SEQUENCE: 442
CYTWNQMNLG CGGSGGGGSG GGGSIQRTPK IQVYSRHPAE NGKSNFLNCY VSGFHPSDIE  60
VDLLKNGERI EKVEHSDLSF SKDWSFYLLY YTEFTPTEKD EYACRVNHVT LSQPKIVKWD  120
RDMGGGGSGG GGSGGGGSAP TSSSTKKTQL QLEALLLDLQ MILNGINNYK NPKLTRMLTA  180
KFYMPKKATE LKHLQCLEEE LKPLEEVLNL AQSKNFHLRP RDLISNINVI VLELKGSETT  240
FMCEYADETA TIVEFLNRWI TFCQSIISTL TGGGGSGGGG SGGGGSGGGG SAPTSSSTKK  300
TQLQLEALLL DLQMILNGIN NYKNPKLTRM LTAKFYMPKK ATELKHLQCL EEELKPLEEV  360
LNLAQSKNFH LRPRDLISNI NVIVLELKGS ETTFMCEYAD ETATIVEFLN RWITFCQSII  420
STLT                                                          424

SEQ ID NO: 443          moltype = AA  length = 123
FEATURE                 Location/Qualifiers
source                  1..123
                        mol_type = protein
                        organism = synthetic construct
SEQUENCE: 443
NYMNLGATLG CGGSGGGGSG GGGSIQRTPK IQVYSCHPAE NGKSNFLNCY VSGFHPSDIE  60
VDLLKNGERI EKVEHSDLSF SKDWSFYLLY YTEFTPTEKD EYACRVNHVT LSQPKIVKWD  120
RDM                                                           123

SEQ ID NO: 444          moltype = AA  length = 424
FEATURE                 Location/Qualifiers
source                  1..424
                        mol_type = protein
                        organism = synthetic construct
SEQUENCE: 444
NYMNLGATLG CGGSGGGGSG GGGSIQRTPK IQVYSCHPAE NGKSNFLNCY VSGFHPSDIE  60
VDLLKNGERI EKVEHSDLSF SKDWSFYLLY YTEFTPTEKD EYACRVNHVT LSQPKIVKWD  120
RDMGGGGSGG GGSGGGGSAP TSSSTKKTQL QLEALLLDLQ MILNGINNYK NPKLTRMLTA  180
KFYMPKKATE LKHLQCLEEE LKPLEEVLNL AQSKNFHLRP RDLISNINVI VLELKGSETT  240
FMCEYADETA TIVEFLNRWI TFCQSIISTL TGGGGSGGGG SGGGGSGGGG SAPTSSSTKK  300
TQLQLEALLL DLQMILNGIN NYKNPKLTRM LTAKFYMPKK ATELKHLQCL EEELKPLEEV  360
LNLAQSKNFH LRPRDLISNI NVIVLELKGS ETTFMCEYAD ETATIVEFLN RWITFCQSII  420
STLT                                                          424

SEQ ID NO: 445          moltype = AA  length = 123
FEATURE                 Location/Qualifiers
source                  1..123
                        mol_type = protein
                        organism = synthetic construct
SEQUENCE: 445
NYMNLGATLG GGGSGGGGSG GGGSIQRTPK IQVYSCHPAE NGKSNFLNCY VSGFHPSDIE  60
VDLLKNGERI EKVEHSDLSF SKDWSFYLLY YTEFTPTEKD EYACRVNHVT LSQPKIVKWD  120
RDM                                                           123

SEQ ID NO: 446          moltype = AA  length = 424
FEATURE                 Location/Qualifiers
source                  1..424
                        mol_type = protein
                        organism = synthetic construct
SEQUENCE: 446
NYMNLGATLG GGGSGGGGSG GGGSIQRTPK IQVYSCHPAE NGKSNFLNCY VSGFHPSDIE  60
VDLLKNGERI EKVEHSDLSF SKDWSFYLLY YTEFTPTEKD EYACRVNHVT LSQPKIVKWD  120
RDMGGGGSGG GGSGGGGSAP TSSSTKKTQL QLEALLLDLQ MILNGINNYK NPKLTRMLTA  180
KFYMPKKATE LKHLQCLEEE LKPLEEVLNL AQSKNFHLRP RDLISNINVI VLELKGSETT  240
FMCEYADETA TIVEFLNRWI TFCQSIISTL TGGGGSGGGG SGGGGSGGGG SAPTSSSTKK  300
TQLQLEALLL DLQMILNGIN NYKNPKLTRM LTAKFYMPKK ATELKHLQCL EEELKPLEEV  360
LNLAQSKNFH LRPRDLISNI NVIVLELKGS ETTFMCEYAD ETATIVEFLN RWITFCQSII  420
STLT                                                          424

SEQ ID NO: 447          moltype = AA  length = 123
FEATURE                 Location/Qualifiers
source                  1..123
                        mol_type = protein
                        organism = synthetic construct
SEQUENCE: 447
NYMNLGATLG CGGSGGGGSG GGGSIQRTPK IQVYSRHPAE NGKSNFLNCY VSGFHPSDIE  60
VDLLKNGERI EKVEHSDLSF SKDWSFYLLY YTEFTPTEKD EYACRVNHVT LSQPKIVKWD  120
RDM                                                           123

SEQ ID NO: 448          moltype = AA  length = 424
FEATURE                 Location/Qualifiers
```

```
source                  1..424
                        mol_type = protein
                        organism = synthetic construct
SEQUENCE: 448
NYMNLGATLG CGGSGGGGSG GGGSIQRTPK IQVYSRHPAE NGKSNFLNCY VSGFHPSDIE  60
VDLLKNGERI EKVEHSDLSF SKDWSFYLLY YTEFTPTEKD EYACRVNHVT LSQPKIVKWD  120
RDMGGGGSGG GGSGGGGSAP TSSSTKKTQL QLEALLLDLQ MILNGINNYK NPKLTRMLTA  180
KFYMPKKATE LKHLQCLEEE LKPLEEVLNL AQSKNFHLRP RDLISNINVI VLELKGSETT  240
FMCEYADETA TIVEFLNRWI TFCQSIISTL TGGGGSGGGG SGGGGSGGGG SAPTSSSTKK  300
TQLQLEALLL DLQMILNGIN NYKNPKLTRM LTAKFYMPKK ATELKHLQCL EEELKPLEEV  360
LNLAQSKNFH LRPRDLISNI NVIVLELKGS ETTFMCEYAD ETATIVEFLN RWITFCQSII  420
STLT                                                               424

SEQ ID NO: 449          moltype = AA  length = 275
FEATURE                 Location/Qualifiers
source                  1..275
                        mol_type = protein
                        organism = synthetic construct
SEQUENCE: 449
GSHSMRYFFT SVSRPGRGEP RFIAVGYVDD TQFVRFDSDA ASQRMEPRAP WIEQEGPEYW  60
DGETRKVKAH SQTHRVDLGT LRGYYNQSEA GSHTVQRMYG CDVGSDWRFL RGYHQYAYDG  120
KDYIALKEDL RSWTAADMAA QTTKHKWEAA HVAEQLRAYL EGTCVEWLRR YLENGKETLQ  180
RTDAPKTHMT HHAVSDHEAT LRCWALSFYP AEITLTWQRD GEDQTQDTEL VETRPAGDGT  240
FQKWAAVVVP SGQEQRYTCH VQHEGLPKPL TLRWE                             275

SEQ ID NO: 450          moltype =   length =
SEQUENCE: 450
000

SEQ ID NO: 451          moltype = AA  length = 9
FEATURE                 Location/Qualifiers
source                  1..9
                        mol_type = protein
                        organism = synthetic construct
SEQUENCE: 451
SMTWNQMNL                                                          9

SEQ ID NO: 452          moltype = AA  length = 10
FEATURE                 Location/Qualifiers
source                  1..10
                        mol_type = protein
                        organism = synthetic construct
SEQUENCE: 452
GCMTWNQMNL                                                         10

SEQ ID NO: 453          moltype = AA  length = 9
FEATURE                 Location/Qualifiers
source                  1..9
                        mol_type = protein
                        organism = synthetic construct
SEQUENCE: 453
SYTWNQMNL                                                          9

SEQ ID NO: 454          moltype = AA  length = 10
FEATURE                 Location/Qualifiers
source                  1..10
                        mol_type = protein
                        organism = synthetic construct
SEQUENCE: 454
GCYTWNQMNL                                                         10

SEQ ID NO: 455          moltype = AA  length = 275
FEATURE                 Location/Qualifiers
source                  1..275
                        mol_type = protein
                        organism = Homo sapiens
SEQUENCE: 455
GSHSMRYFST SVSRPGRGEP RFIAVGYVDD TQFVRFDSDA ASQRMEPRAP WIEQEGPEYW  60
DEETGKVKAH SQTDRENLRI ALRYYNQSEA GSHTLQMMFG CDVGSDGRFL RGYHQYAYDG  120
KDYIALKEDL RSWTAADMAA QITKRKWEAA HVAEQQRAYL EGTCVDGLRR YLENGKETLQ  180
RTDPPKTHMT HHPISDHEAT LRCWALGFYP AEITLTWQRD GEDQTQDTEL VETRPAGDGT  240
FQKWAAVVVP SGEEQRYTCH VQHEGLPKPL TLRWE                             275

SEQ ID NO: 456          moltype = AA  length = 275
FEATURE                 Location/Qualifiers
source                  1..275
                        mol_type = protein
                        organism = Homo sapiens
SEQUENCE: 456
```

```
GSHSMRYFST SVSRPGRGEP RFIAVGYVDD TQFVRFDSDA ASQRMEPRAP WIEQEGPEYW  60
DEETGKVKAH SQTDRENLRI ALRAYNQSEA GSHTLQMMFG CDVGSDGRFL RGYHQYAYDG  120
KDYIALKEDL RSWTAADMAA QITKRKWEAA HVAEQQRAYL EGTCVDGLRR YLENGKETLQ  180
RTDPPKTHMT HHPISDHEAT LRCWALGFYP AEITLTWQRD GEDQTQDTEL VETRPAGDGT  240
FQKWAAVVVP SGEEQRYTCH VQHEGLPKPL TLRWE                            275

SEQ ID NO: 457         moltype = AA  length = 275
FEATURE                Location/Qualifiers
source                 1..275
                       mol_type = protein
                       organism = Homo sapiens
SEQUENCE: 457
GSHSMRYFST SVSRPGRGEP RFIAVGYVDD TQFVRFDSDA ASQRMEPRAP WIEQEGPEYW  60
DEETGKVKAH SQTDRENLRI ALRYYNQSEA GSHTLQMMFG CDVGSDGRFL RGYHQYAYDG  120
KDYIALKEDL RSWTAADMAA QITKRKWEAA HVAEQQRAYL EGTCVDGLRR YLENGKETLQ  180
RTDPPKTHMT HHPISDHEAT LRCWALGFYP AEITLTWQRD GEDQTQDTEL VETRPCGDGT  240
FQKWAAVVVP SGEEQRYTCH VQHEGLPKPL TLRWE                            275

SEQ ID NO: 458         moltype = AA  length = 275
FEATURE                Location/Qualifiers
source                 1..275
                       mol_type = protein
                       organism = Homo sapiens
SEQUENCE: 458
GSHSMRYFST SVSRPGRGEP RFIAVGYVDD TQFVRFDSDA ASQRMEPRAP WIEQEGPEYW  60
DEETGKVKAH SQTDRENLRI ALRAYNQSEA GSHTLQMMFG CDVGSDGRFL RGYHQYAYDG  120
KDYIALKEDL RSWTAADMAA QITKRKWEAA HVAEQQRAYL EGTCVDGLRR YLENGKETLQ  180
RTDPPKTHMT HHPISDHEAT LRCWALGFYP AEITLTWQRD GEDQTQDTEL VETRPCGDGT  240
FQKWAAVVVP SGEEQRYTCH VQHEGLPKPL TLRWE                            275

SEQ ID NO: 459         moltype = AA  length = 275
FEATURE                Location/Qualifiers
source                 1..275
                       mol_type = protein
                       organism = Homo sapiens
SEQUENCE: 459
GSHSMRYFST SVSRPGRGEP RFIAVGYVDD TQFVRFDSDA ASQRMEPRAP WIEQEGPEYW  60
DEETGKVKAH SQTDRENLRI ALRCYNQSEA GSHTLQMMFG CDVGSDGRFL RGYHQYAYDG  120
KDYIALKEDL RSWTAADMAA QITKRKWEAA HVAEQQRAYL EGTCVDGLRR YLENGKETLQ  180
RTDPPKTHMT HHPISDHEAT LRCWALGFYP AEITLTWQRD GEDQTQDTEL VETRPAGDGT  240
FQKWAAVVVP SGEEQRYTCH VQHEGLPKPL TLRWE                            275

SEQ ID NO: 460         moltype = AA  length = 10
FEATURE                Location/Qualifiers
SITE                   1..3
                       note = The amino acids at positions 1 to 3 are
                        independently any amino acid, with the proviso that the
                        N-terminal amino acid is not a Cys
source                 1..10
                       mol_type = protein
                       organism = synthetic construct
SEQUENCE: 460
XXXTWNQMNL                                                        10

SEQ ID NO: 461         moltype = AA  length = 9
FEATURE                Location/Qualifiers
SITE                   1..2
                       note = The amino acids at positions 1 to 2 are
                        independently any amino acid, with the proviso that the
                        N-terminal amino acid is not a Cys
source                 1..9
                       mol_type = protein
                       organism = synthetic construct
SEQUENCE: 461
XXTWNQMNL                                                         9

SEQ ID NO: 462         moltype = AA  length = 123
FEATURE                Location/Qualifiers
source                 1..123
                       mol_type = protein
                       organism = synthetic construct
SEQUENCE: 462
SMTWNQMNLG GGGSGGGGSG GGGSIQRTPK IQVYSCHPAE NGKSNFLNCY VSGFHPSDIE  60
VDLLKNGERI EKVEHSDLSF SKDWSFYLLY YTEFTPTEKD EYACRVNHVT LSQPKIVKWD  120
RDM                                                               123

SEQ ID NO: 463         moltype = AA  length = 123
FEATURE                Location/Qualifiers
source                 1..123
```

```
                        mol_type = protein
                        organism = synthetic construct
SEQUENCE: 463
SMTWNQMNLG CGGSGGGGSG GGGSIQRTPK IQVYSCHPAE NGKSNFLNCY VSGFHPSDIE  60
VDLLKNGERI EKVEHSDLSF SKDWSFYLLY YTEFTPTEKD EYACRVNHVT LSQPKIVKWD  120
RDM                                                              123

SEQ ID NO: 464          moltype = AA  length = 123
FEATURE                 Location/Qualifiers
source                  1..123
                        mol_type = protein
                        organism = synthetic construct
SEQUENCE: 464
SMTWNQMNLG CGGSGGGGSG GGGSIQRTPK IQVYSRHPAE NGKSNFLNCY VSGFHPSDIE  60
VDLLKNGERI EKVEHSDLSF SKDWSFYLLY YTEFTPTEKD EYACRVNHVT LSQPKIVKWD  120
RDM                                                              123

SEQ ID NO: 465          moltype = AA  length = 424
FEATURE                 Location/Qualifiers
source                  1..424
                        mol_type = protein
                        organism = synthetic construct
SEQUENCE: 465
SMTWNQMNLG CGGSGGGGSG GGGSIQRTPK IQVYSRHPAE NGKSNFLNCY VSGFHPSDIE  60
VDLLKNGERI EKVEHSDLSF SKDWSFYLLY YTEFTPTEKD EYACRVNHVT LSQPKIVKWD  120
RDMGGGGSGG GGSGGGGSAP TSSSTKKTQL QLEALLLDLQ MILNGINNYK NPKLTRMLTA  180
KFYMPKKATE LKHLQCLEEE LKPLEEVLNL AQSKNFHLRP RDLISNINVI VLELKGSETT  240
FMCEYADETA TIVEFLNRWI TFCQSIISTL TGGGGSGGGG SGGGGSGGGG SAPTSSSTKK  300
TQLQLEALLL DLQMILNGIN NYKNPKLTRM LTAKFYMPKK ATELKHLQCL EEELKPLEEV  360
LNLAQSKNFH LRPRDLISNI NVIVLELKGS ETTFMCEYAD ETATIVEFLN RWITFCQSII  420
STLT                                                             424

SEQ ID NO: 466          moltype = AA  length = 424
FEATURE                 Location/Qualifiers
source                  1..424
                        mol_type = protein
                        organism = synthetic construct
SEQUENCE: 466
SMTWNQMNLG CGGSGGGGSG GGGSIQRTPK IQVYSCHPAE NGKSNFLNCY VSGFHPSDIE  60
VDLLKNGERI EKVEHSDLSF SKDWSFYLLY YTEFTPTEKD EYACRVNHVT LSQPKIVKWD  120
RDMGGGGSGG GGSGGGGSAP TSSSTKKTQL QLEALLLDLQ MILNGINNYK NPKLTRMLTA  180
KFYMPKKATE LKHLQCLEEE LKPLEEVLNL AQSKNFHLRP RDLISNINVI VLELKGSETT  240
FMCEYADETA TIVEFLNRWI TFCQSIISTL TGGGGSGGGG SGGGGSGGGG SAPTSSSTKK  300
TQLQLEALLL DLQMILNGIN NYKNPKLTRM LTAKFYMPKK ATELKHLQCL EEELKPLEEV  360
LNLAQSKNFH LRPRDLISNI NVIVLELKGS ETTFMCEYAD ETATIVEFLN RWITFCQSII  420
STLT                                                             424

SEQ ID NO: 467          moltype = AA  length = 424
FEATURE                 Location/Qualifiers
source                  1..424
                        mol_type = protein
                        organism = synthetic construct
SEQUENCE: 467
SMTWNQMNLG GGGSGGGGSG GGGSIQRTPK IQVYSCHPAE NGKSNFLNCY VSGFHPSDIE  60
VDLLKNGERI EKVEHSDLSF SKDWSFYLLY YTEFTPTEKD EYACRVNHVT LSQPKIVKWD  120
RDMGGGGSGG GGSGGGGSAP TSSSTKKTQL QLEALLLDLQ MILNGINNYK NPKLTRMLTA  180
KFYMPKKATE LKHLQCLEEE LKPLEEVLNL AQSKNFHLRP RDLISNINVI VLELKGSETT  240
FMCEYADETA TIVEFLNRWI TFCQSIISTL TGGGGSGGGG SGGGGSGGGG SAPTSSSTKK  300
TQLQLEALLL DLQMILNGIN NYKNPKLTRM LTAKFYMPKK ATELKHLQCL EEELKPLEEV  360
LNLAQSKNFH LRPRDLISNI NVIVLELKGS ETTFMCEYAD ETATIVEFLN RWITFCQSII  420
STLT                                                             424

SEQ ID NO: 468          moltype = AA  length = 124
FEATURE                 Location/Qualifiers
source                  1..124
                        mol_type = protein
                        organism = synthetic construct
SEQUENCE: 468
GCMTWNQMNL GGGGSGGGGS GGGGSIQRTP KIQVYSCHPA ENGKSNFLNC YVSGFHPSDI  60
EVDLLKNGER IEKVEHSDLS FSKDWSFYLL YYTEFTPTEK DEYACRVNHV TLSQPKIVKW  120
DRDM                                                             124

SEQ ID NO: 469          moltype = AA  length = 124
FEATURE                 Location/Qualifiers
source                  1..124
                        mol_type = protein
                        organism = synthetic construct
SEQUENCE: 469
GCMTWNQMNL GCGGSGGGGS GGGGSIQRTP KIQVYSCHPA ENGKSNFLNC YVSGFHPSDI  60
```

```
EVDLLKNGER IEKVEHSDLS FSKDWSFYLL YYTEFTPTEK DEYACRVNHV TLSQPKIVKW  120
DRDM                                                               124

SEQ ID NO: 470          moltype = AA  length = 124
FEATURE                 Location/Qualifiers
source                  1..124
                        mol_type = protein
                        organism = synthetic construct
SEQUENCE: 470
GCMTWNQMNL GCGGSGGGGS GGGGSIQRTP KIQVYSRHPA ENGKSNFLNC YVSGFHPSDI  60
EVDLLKNGER IEKVEHSDLS FSKDWSFYLL YYTEFTPTEK DEYACRVNHV TLSQPKIVKW  120
DRDM                                                               124

SEQ ID NO: 471          moltype = AA  length = 425
FEATURE                 Location/Qualifiers
source                  1..425
                        mol_type = protein
                        organism = synthetic construct
SEQUENCE: 471
GCMTWNQMNL GCGGSGGGGS GGGGSIQRTP KIQVYSRHPA ENGKSNFLNC YVSGFHPSDI  60
EVDLLKNGER IEKVEHSDLS FSKDWSFYLL YYTEFTPTEK DEYACRVNHV TLSQPKIVKW  120
DRDMGGGGSG GGGSGGGGSA PTSSSTKKTQ LQLEALLLDL QMILNGINNY KNPKLTRMLT  180
AKFYMPKKAT ELKHLQCLEE ELKPLEEVLN LAQSKNFHLR PRDLISNINV IVLELKGSET  240
TFMCEYADET ATIVEFLNRW ITFCQSIIST LTGGGGSGGG GSGGGGSGGG GSAPTSSSTK  300
KTQLQLEALL LDLQMILNGI NNYKNPKLTR MLTAKFYMPK KATELKHLQC LEEELKPLEE  360
VLNLAQSKNF HLRPRDLISN INVIVLELKG SETTFMCEYA DETATIVEFL NRWITFCQSI  420
ISTLT                                                              425

SEQ ID NO: 472          moltype = AA  length = 425
FEATURE                 Location/Qualifiers
source                  1..425
                        mol_type = protein
                        organism = synthetic construct
SEQUENCE: 472
GCMTWNQMNL GCGGSGGGGS GGGGSIQRTP KIQVYSCHPA ENGKSNFLNC YVSGFHPSDI  60
EVDLLKNGER IEKVEHSDLS FSKDWSFYLL YYTEFTPTEK DEYACRVNHV TLSQPKIVKW  120
DRDMGGGGSG GGGSGGGGSA PTSSSTKKTQ LQLEALLLDL QMILNGINNY KNPKLTRMLT  180
AKFYMPKKAT ELKHLQCLEE ELKPLEEVLN LAQSKNFHLR PRDLISNINV IVLELKGSET  240
TFMCEYADET ATIVEFLNRW ITFCQSIIST LTGGGGSGGG GSGGGGSGGG GSAPTSSSTK  300
KTQLQLEALL LDLQMILNGI NNYKNPKLTR MLTAKFYMPK KATELKHLQC LEEELKPLEE  360
VLNLAQSKNF HLRPRDLISN INVIVLELKG SETTFMCEYA DETATIVEFL NRWITFCQSI  420
ISTLT                                                              425

SEQ ID NO: 473          moltype = AA  length = 425
FEATURE                 Location/Qualifiers
source                  1..425
                        mol_type = protein
                        organism = synthetic construct
SEQUENCE: 473
GCMTWNQMNL GGGGSGGGGS GGGGSIQRTP KIQVYSCHPA ENGKSNFLNC YVSGFHPSDI  60
EVDLLKNGER IEKVEHSDLS FSKDWSFYLL YYTEFTPTEK DEYACRVNHV TLSQPKIVKW  120
DRDMGGGGSG GGGSGGGGSA PTSSSTKKTQ LQLEALLLDL QMILNGINNY KNPKLTRMLT  180
AKFYMPKKAT ELKHLQCLEE ELKPLEEVLN LAQSKNFHLR PRDLISNINV IVLELKGSET  240
TFMCEYADET ATIVEFLNRW ITFCQSIIST LTGGGGSGGG GSGGGGSGGG GSAPTSSSTK  300
KTQLQLEALL LDLQMILNGI NNYKNPKLTR MLTAKFYMPK KATELKHLQC LEEELKPLEE  360
VLNLAQSKNF HLRPRDLISN INVIVLELKG SETTFMCEYA DETATIVEFL NRWITFCQSI  420
ISTLT                                                              425

SEQ ID NO: 474          moltype = AA  length = 123
FEATURE                 Location/Qualifiers
source                  1..123
                        mol_type = protein
                        organism = synthetic construct
SEQUENCE: 474
SYTWNQMNLG GGGSGGGGSG GGGSIQRTPK IQVYSCHPAE NGKSNFLNCY VSGFHPSDIE  60
VDLLKNGERI EKVEHSDLSF SKDWSFYLLY YTEFTPTEKD EYACRVNHVT LSQPKIVKWD  120
RDM                                                                123

SEQ ID NO: 475          moltype = AA  length = 123
FEATURE                 Location/Qualifiers
source                  1..123
                        mol_type = protein
                        organism = synthetic construct
SEQUENCE: 475
SYTWNQMNLG CGGSGGGGSG GGGSIQRTPK IQVYSCHPAE NGKSNFLNCY VSGFHPSDIE  60
VDLLKNGERI EKVEHSDLSF SKDWSFYLLY YTEFTPTEKD EYACRVNHVT LSQPKIVKWD  120
RDM                                                                123

SEQ ID NO: 476          moltype = AA  length = 123
```

```
FEATURE                Location/Qualifiers
source                 1..123
                       mol_type = protein
                       organism = synthetic construct
SEQUENCE: 476
SYTWNQMNLG CGGSGGGGSG GGGSIQRTPK IQVYSRHPAE NGKSNFLNCY VSGFHPSDIE  60
VDLLKNGERI EKVEHSDLSF SKDWSFYLLY YTEFTPTEKD EYACRVNHVT LSQPKIVKWD  120
RDM                                                                 123

SEQ ID NO: 477         moltype = AA  length = 424
FEATURE                Location/Qualifiers
source                 1..424
                       mol_type = protein
                       organism = synthetic construct
SEQUENCE: 477
SYTWNQMNLG CGGSGGGGSG GGGSIQRTPK IQVYSRHPAE NGKSNFLNCY VSGFHPSDIE  60
VDLLKNGERI EKVEHSDLSF SKDWSFYLLY YTEFTPTEKD EYACRVNHVT LSQPKIVKWD  120
RDMGGGGSGG GGSGGGGSAP TSSSTKKTQL QLEALLLDLQ MILNGINNYK NPKLTRMLTA  180
KFYMPKKATE LKHLQCLEEE LKPLEEVLNL AQSKNFHLRP RDLISNINVI VLELKGSETT  240
FMCEYADETA TIVEFLNRWI TFCQSIISTL TGGGGSGGGG SGGGGSGGGG SAPTSSSTKK  300
TQLQLEALLL DLQMILNGIN NYKNPKLTRM LTAKFYMPKK ATELKHLQCL EEELKPLEEV  360
LNLAQSKNFH LRPRDLISNI NVIVLELKGS ETTFMCEYAD ETATIVEFLN RWITFCQSII  420
STLT                                                                424

SEQ ID NO: 478         moltype = AA  length = 424
FEATURE                Location/Qualifiers
source                 1..424
                       mol_type = protein
                       organism = synthetic construct
SEQUENCE: 478
SYTWNQMNLG CGGSGGGGSG GGGSIQRTPK IQVYSCHPAE NGKSNFLNCY VSGFHPSDIE  60
VDLLKNGERI EKVEHSDLSF SKDWSFYLLY YTEFTPTEKD EYACRVNHVT LSQPKIVKWD  120
RDMGGGGSGG GGSGGGGSAP TSSSTKKTQL QLEALLLDLQ MILNGINNYK NPKLTRMLTA  180
KFYMPKKATE LKHLQCLEEE LKPLEEVLNL AQSKNFHLRP RDLISNINVI VLELKGSETT  240
FMCEYADETA TIVEFLNRWI TFCQSIISTL TGGGGSGGGG SGGGGSGGGG SAPTSSSTKK  300
TQLQLEALLL DLQMILNGIN NYKNPKLTRM LTAKFYMPKK ATELKHLQCL EEELKPLEEV  360
LNLAQSKNFH LRPRDLISNI NVIVLELKGS ETTFMCEYAD ETATIVEFLN RWITFCQSII  420
STLT                                                                424

SEQ ID NO: 479         moltype = AA  length = 424
FEATURE                Location/Qualifiers
source                 1..424
                       mol_type = protein
                       organism = synthetic construct
SEQUENCE: 479
SYTWNQMNLG GGGSGGGGSG GGGSIQRTPK IQVYSCHPAE NGKSNFLNCY VSGFHPSDIE  60
VDLLKNGERI EKVEHSDLSF SKDWSFYLLY YTEFTPTEKD EYACRVNHVT LSQPKIVKWD  120
RDMGGGGSGG GGSGGGGSAP TSSSTKKTQL QLEALLLDLQ MILNGINNYK NPKLTRMLTA  180
KFYMPKKATE LKHLQCLEEE LKPLEEVLNL AQSKNFHLRP RDLISNINVI VLELKGSETT  240
FMCEYADETA TIVEFLNRWI TFCQSIISTL TGGGGSGGGG SGGGGSGGGG SAPTSSSTKK  300
TQLQLEALLL DLQMILNGIN NYKNPKLTRM LTAKFYMPKK ATELKHLQCL EEELKPLEEV  360
LNLAQSKNFH LRPRDLISNI NVIVLELKGS ETTFMCEYAD ETATIVEFLN RWITFCQSII  420
STLT                                                                424

SEQ ID NO: 480         moltype = AA  length = 124
FEATURE                Location/Qualifiers
source                 1..124
                       mol_type = protein
                       organism = synthetic construct
SEQUENCE: 480
GCYTWNQMNL GGGGSGGGGS GGGGSIQRTP KIQVYSCHPA ENGKSNFLNC YVSGFHPSDI  60
EVDLLKNGER IEKVEHSDLS FSKDWSFYLL YYTEFTPTEK DEYACRVNHV TLSQPKIVKW  120
DRDM                                                                124

SEQ ID NO: 481         moltype = AA  length = 124
FEATURE                Location/Qualifiers
source                 1..124
                       mol_type = protein
                       organism = synthetic construct
SEQUENCE: 481
GCYTWNQMNL GCGGSGGGGS GGGGSIQRTP KIQVYSCHPA ENGKSNFLNC YVSGFHPSDI  60
EVDLLKNGER IEKVEHSDLS FSKDWSFYLL YYTEFTPTEK DEYACRVNHV TLSQPKIVKW  120
DRDM                                                                124

SEQ ID NO: 482         moltype = AA  length = 124
FEATURE                Location/Qualifiers
source                 1..124
                       mol_type = protein
                       organism = synthetic construct
```

```
SEQUENCE: 482
GCYTWNQMNL GCGGSGGGGS GGGGSIQRTP KIQVYSRHPA ENGKSNFLNC YVSGFHPSDI  60
EVDLLKNGER IEKVEHSDLS FSKDWSFYLL YYTEFTPTEK DEYACRVNHV TLSQPKIVKW  120
DRDM                                                               124

SEQ ID NO: 483         moltype = AA  length = 425
FEATURE                Location/Qualifiers
source                 1..425
                       mol_type = protein
                       organism = synthetic construct
SEQUENCE: 483
GCYTWNQMNL GCGGSGGGGS GGGGSIQRTP KIQVYSRHPA ENGKSNFLNC YVSGFHPSDI  60
EVDLLKNGER IEKVEHSDLS FSKDWSFYLL YYTEFTPTEK DEYACRVNHV TLSQPKIVKW  120
DRDMGGGGSG GGGSGGGGSA PTSSSTKKTQ LQLEALLLDL QMILNGINNY KNPKLTRMLT  180
AKFYMPKKAT ELKHLQCLEE ELKPLEEVLN LAQSKNFHLR PRDLISNINV IVLELKGSET  240
TFMCEYADET ATIVEFLNRW ITFCQSIIST LTGGGGSGGG GSGGGGSGGG GSAPTSSSTK  300
KTQLQLEALL LDLQMILNGI NNYKNPKLTR MLTAKFYMPK KATELKHLQC LEEELKPLEE  360
VLNLAQSKNF HLRPRDLISN INVIVLELKG SETTFMCEYA DETATIVEFL NRWITFCQSI  420
ISTLT                                                              425

SEQ ID NO: 484         moltype = AA  length = 425
FEATURE                Location/Qualifiers
source                 1..425
                       mol_type = protein
                       organism = synthetic construct
SEQUENCE: 484
GCYTWNQMNL GCGGSGGGGS GGGGSIQRTP KIQVYSCHPA ENGKSNFLNC YVSGFHPSDI  60
EVDLLKNGER IEKVEHSDLS FSKDWSFYLL YYTEFTPTEK DEYACRVNHV TLSQPKIVKW  120
DRDMGGGGSG GGGSGGGGSA PTSSSTKKTQ LQLEALLLDL QMILNGINNY KNPKLTRMLT  180
AKFYMPKKAT ELKHLQCLEE ELKPLEEVLN LAQSKNFHLR PRDLISNINV IVLELKGSET  240
TFMCEYADET ATIVEFLNRW ITFCQSIIST LTGGGGSGGG GSGGGGSGGG GSAPTSSSTK  300
KTQLQLEALL LDLQMILNGI NNYKNPKLTR MLTAKFYMPK KATELKHLQC LEEELKPLEE  360
VLNLAQSKNF HLRPRDLISN INVIVLELKG SETTFMCEYA DETATIVEFL NRWITFCQSI  420
ISTLT                                                              425

SEQ ID NO: 485         moltype = AA  length = 425
FEATURE                Location/Qualifiers
source                 1..425
                       mol_type = protein
                       organism = synthetic construct
SEQUENCE: 485
GCYTWNQMNL GGGGSGGGGS GGGGSIQRTP KIQVYSCHPA ENGKSNFLNC YVSGFHPSDI  60
EVDLLKNGER IEKVEHSDLS FSKDWSFYLL YYTEFTPTEK DEYACRVNHV TLSQPKIVKW  120
DRDMGGGGSG GGGSGGGGSA PTSSSTKKTQ LQLEALLLDL QMILNGINNY KNPKLTRMLT  180
AKFYMPKKAT ELKHLQCLEE ELKPLEEVLN LAQSKNFHLR PRDLISNINV IVLELKGSET  240
TFMCEYADET ATIVEFLNRW ITFCQSIIST LTGGGGSGGG GSGGGGSGGG GSAPTSSSTK  300
KTQLQLEALL LDLQMILNGI NNYKNPKLTR MLTAKFYMPK KATELKHLQC LEEELKPLEE  360
VLNLAQSKNF HLRPRDLISN INVIVLELKG SETTFMCEYA DETATIVEFL NRWITFCQSI  420
ISTLT                                                              425

SEQ ID NO: 486         moltype = AA  length = 812
FEATURE                Location/Qualifiers
source                 1..812
                       mol_type = protein
                       organism = synthetic construct
SEQUENCE: 486
APTSSSTKKT QLQLEALLLD LQMILNGINN YKNPKLTRML TAKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTGGGGSGG GGSGGGGSGG GGSAPTSSST KKTQLQLEAL LLDLQMILNG  180
INNYKNPKLT RMLTAKFYMP KKATELKHLQ CLEEELKPLE EVLNLAQSKN FHLRPRDLIS  240
NINVIVLELK GSETTFMCEY ADETATIVEF LNRWITFCQS IISTLTGGGG SGGGGSGGGG  300
SGGGGSGSHS MRYFFTSVSR PGRGEPRFIA VGYVDDTQFV RFDSDAASQR MEPRAPWIEQ  360
EGPEYWDGET RKVKAHSQTH RVDLGTLRGC YNQSEAGSHT VQRMYGCDVG SDWRFLRGYH  420
QYAYDGKDYI ALKEDLRSWT AADMAAQTTK HKWEAAHVAE QLRAYLEGTC VEWLRRYLEN  480
GKETLQRTDA PKTHMTHHAV SDHEATLRCW ALSFYPAEIT LTWQRDGEDQ TQDTELVETR  540
PCGDGTFQKW AAVVVPSGQE QRYTCHVQHE GLPKPLTLRW EAAAGGDKTH TCPPCPAPEA  600
AGGPSVFLFP PKPKDTLMIS RTPEVTCVVV DVSHEDPEVK FNWYVDGVEV HNAKTKPREE  660
QYNSTYRVVS VLTVLHQDWL NGKEYKCKVS NKALPAPIEK TISKAKGQPR EPQVYTLPPS  720
REEMTKNQVS LTCLVKGFYP SDIAVEWESN GQPENNYKTT PPVLDSDGSF FLYSKLTVDK  780
SRWQQGNVFS CSVMHEALHN HYTQKSLSLS PG                                812

SEQ ID NO: 487         moltype = AA  length = 226
FEATURE                Location/Qualifiers
source                 1..226
                       mol_type = protein
                       organism = Homo sapiens
SEQUENCE: 487
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
```

```
GQPREPQVYT LPPSREEMTK NQVSLTCLVK GFYPSDIAVE WESNGQPENN YKTTPPVLDS  180
DGSFFLYSKL TVDKSRWQQG NVFSCSVMHE ALHNHYTQKS LSLSPG                 226

SEQ ID NO: 488          moltype = AA  length = 275
FEATURE                 Location/Qualifiers
source                  1..275
                        mol_type = protein
                        organism = synthetic construct
SEQUENCE: 488
GSHSMRYFFT SVSRPGRGEP RFIAVGYVDD TQFVRFDSDA ASQRMEPRAP WIEQEGPEYW  60
DGETRKVKAH SQTHRVDLGT LRGCYNQSEA GSHTVQRMYG CDVGSDWRFL RGYHQYAYDG  120
KDYIALKEDL RSWTAADMAA QTTKHKWEAA HVAEQLRAYL EGTCVEWLRR YLENGKETLQ  180
RTDAPKTHMT HHAVSDHEAT LRCWALSFYP AEITLTWQRD GEDQTQDTEL VETRPCGDGT  240
FQKWAAVVVP SGQEQRYTCH VQHEGLPKPL TLRWE                             275

SEQ ID NO: 489          moltype = AA  length = 226
FEATURE                 Location/Qualifiers
source                  1..226
                        mol_type = protein
                        organism = synthetic construct
SEQUENCE: 489
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVYT LPPSREEMTK NQVSLTCLVK GFYPSDIAVE WESNGQPENN YKTTPPVLDS  180
DGSFFLYSKL TVDKSRWQQG NVFSCSVMHE ALHNHYTQKS LSLSPG                 226

SEQ ID NO: 490          moltype = AA  length = 133
FEATURE                 Location/Qualifiers
source                  1..133
                        mol_type = protein
                        organism = synthetic construct
SEQUENCE: 490
APTSSSTKKT QLQLEALLLD LQMILNGINN YKNPKLTRML TAKFYMPKKA TELKHLQCLE  60
EELKPLEEVL NLAQSKNFHL RPRDLISNIN VIVLELKGSE TTFMCEYADE TATIVEFLNR  120
WITFCQSIIS TLT                                                     133

SEQ ID NO: 491          moltype = AA  length = 133
FEATURE                 Location/Qualifiers
source                  1..133
                        mol_type = protein
                        organism = synthetic construct
SEQUENCE: 491
APTSSSTKKT QLQLETLLLD LQMILNGINN YKNPKLTRML TAKFYMPKKA TELKHLQCLE  60
EELKPLEEVL NLAQSKNFHL RPRDLISNIN VIVLELKGSE TTFMCEYADE TATIVEFLNR  120
WITFCQSIIS TLT                                                     133

SEQ ID NO: 492          moltype = AA  length = 275
FEATURE                 Location/Qualifiers
source                  1..275
                        mol_type = protein
                        organism = Homo sapiens
SEQUENCE: 492
GSHSLKYFHT SVSRPGRGEP RFISVGYVDD TQFVRFDNDA ASPRMVPRAP WMEQEGSEYW  60
DRETRSARDT AQIFRVNLRT LRGYYNQSEA GSHTLQWMHG CELGPDRRFL RGYEQFAYDG  120
KDYLTLNEDL RSWTAVDTAA QISEQKSNDA SEAEHQRAYL EDTCVEWLHK YLEKGKETLL  180
HLEPPKTHVT HHPISDHEAT LRCWALGFYP AEITLTWQQD GEGHTQDTEL VETRPAGDGT  240
FQKWAAVVVP SGEEQRYTCH VQHEGLPEPV TLRWK                             275

SEQ ID NO: 493          moltype = AA  length = 275
FEATURE                 Location/Qualifiers
source                  1..275
                        mol_type = protein
                        organism = synthetic construct
SEQUENCE: 493
GSHSLKYFHT SVSRPGRGEP RFISVGYVDD TQFVRFDNDA ASPRMVPRAP WMEQEGSEYW  60
DRETRSARDT AQIFRVNLRT LRGCYNQSEA GSHTLQWMHG CELGPDRRFL RGYEQFAYDG  120
KDYLTLNEDL RSWTAVDTAA QISEQKSNDA SEAEHQRAYL EDTCVEWLHK YLEKGKETLL  180
HLEPPKTHVT HHPISDHEAT LRCWALGFYP AEITLTWQQD GEGHTQDTEL VETRPCGDGT  240
FQKWAAVVVP SGEEQRYTCH VQHEGLPEPV TLRWK                             275

SEQ ID NO: 494          moltype = AA  length = 275
FEATURE                 Location/Qualifiers
source                  1..275
                        mol_type = protein
                        organism = Homo sapiens
SEQUENCE: 494
GSHSLKYFHT SVSRPGRGEP RFISVGYVDD TQFVRFDNDA ASPRMVPRAP WMEQEGSEYW  60
DRETRSARDT AQIFRVNLRT LRGYYNQSEA GSHTLQWMHG CELGPDGRFL RGYEQFAYDG  120
KDYLTLNEDL RSWTAVDTAA QISEQKSNDA SEAEHQRAYL EDTCVEWLHK YLEKGKETLL  180
```

-continued

```
HLEPPKTHVT HHPISDHEAT LRCWALGFYP AEITLTWQQD GEGHTQDTEL VETRPAGDGT  240
FQKWAAVVVP SGEEQRYTCH VQHEGLPEPV TLRWK                             275

SEQ ID NO: 495         moltype = AA  length = 275
FEATURE                Location/Qualifiers
source                 1..275
                       mol_type = protein
                       organism = synthetic construct
SEQUENCE: 495
GSHSLKYFHT SVSRPGRGEP RFISVGYVDD TQFVRFDNDA ASPRMVPRAP WMEQEGSEYW  60
DRETRSARDT AQIFRVNLRT LRGCYNQSEA GSHTLQWMHG CELGPDGRFL RGYEQFAYDG  120
KDYLTLNEDL RSWTAVDTAA QISEQKSNDA SEAEHQRAYL EDTCVEWLHK YLEKGKETLL  180
HLEPPKTHVT HHPISDHEAT LRCWALGFYP AEITLTWQQD GEGHTQDTEL VETRPCGDGT  240
FQKWAAVVVP SGEEQRYTCH VQHEGLPEPV TLRWK                             275

SEQ ID NO: 496         moltype = AA  length = 275
FEATURE                Location/Qualifiers
source                 1..275
                       mol_type = protein
                       organism = Homo sapiens
SEQUENCE: 496
GSHSMRYFSA AVSRPGRGEP RFIAMGYVDD TQFVRFDSDS ACPRMEPRAP WVEQEGPEYW  60
EEETRNTKAH AQTDRMNLQT LRGYYNQSEA SSHTLQWMIG CDLGSDGRLL RGYEQYAYDG  120
KDYLALNEDL RSWTAADTAA QISKRKCEAA NVAEQRRAYL EGTCVEWLHR YLENGKEMLQ  180
RADPPKTHVT HHPVFDYEAT LRCWALGFYP AEIILTWQRD GEDQTQDVEL VETRPAGDGT  240
FQKWAAVVVP SGEEQRYTCH VQHEGLPEPL MLRWK                             275

SEQ ID NO: 497         moltype = AA  length = 275
FEATURE                Location/Qualifiers
source                 1..275
                       mol_type = protein
                       organism = synthetic construct
SEQUENCE: 497
GSHSMRYFSA AVSRPGRGEP RFIAMGYVDD TQFVRFDSDS ACPRMEPRAP WVEQEGPEYW  60
EEETRNTKAH AQTDRMNLQT LRGCYNQSEA SSHTLQWMIG CDLGSDGRLL RGYEQYAYDG  120
KDYLALNEDL RSWTAADTAA QISKRKCEAA NVAEQRRAYL EGTCVEWLHR YLENGKEMLQ  180
RADPPKTHVT HHPVFDYEAT LRCWALGFYP AEIILTWQRD GEDQTQDVEL VETRPCGDGT  240
FQKWAAVVVP SGEEQRYTCH VQHEGLPEPL MLRWK                             275

SEQ ID NO: 498         moltype = AA  length = 275
FEATURE                Location/Qualifiers
source                 1..275
                       mol_type = protein
                       organism = Homo sapiens
SEQUENCE: 498
GSHSMRYFSA AVSRPGRGEP RFIAMGYVDD TQFVRFDSDS ACPRMEPRAP WVEQEGPEYW  60
EEETRNTKAH AQTDRMNLQT LRGYYNQSEA SSHTLQWMIG CDLGSDGRLI RGYEQYAYDG  120
KDYLALNEDL RSWTAADTAA QISKRKCEAA NVAEQRRAYL EGTCVEWLHR YLENGKEMLQ  180
RADPPKTHVT HHPVFDYEAT LRCWALGFYP AEIILTWQRD GEDQTQDVEL VETRPAGDGT  240
FQKWAAVVVP SGEEQRYTCH VQHEGLPEPL MLRWK                             275

SEQ ID NO: 499         moltype = AA  length = 275
FEATURE                Location/Qualifiers
source                 1..275
                       mol_type = protein
                       organism = synthetic construct
SEQUENCE: 499
GSHSMRYFSA AVSRPGRGEP RFIAMGYVDD TQFVRFDSDS ACPRMEPRAP WVEQEGPEYW  60
EEETRNTKAH AQTDRMNLQT LRGCYNQSEA SSHTLQWMIG CDLGSDGRLI RGYEQYAYDG  120
KDYLALNEDL RSWTAADTAA QISKRKCEAA NVAEQRRAYL EGTCVEWLHR YLENGKEMLQ  180
RADPPKTHVT HHPVFDYEAT LRCWALGFYP AEIILTWQRD GEDQTQDVEL VETRPCGDGT  240
FQKWAAVVVP SGEEQRYTCH VQHEGLPEPL MLRWK                             275
```